United States Patent
Yoshida et al.

Patent Number: 5,534,529
Date of Patent: Jul. 9, 1996

[54] SUBSTITUTED AROMATIC AMIDES AND UREAS DERIVATIVES HAVING ANTI-HYPERCHOLESTEREMIC ACTIVITY, THEIR PREPARATION AND THEIR THERAPEUTIC USES

[75] Inventors: Akira Yoshida; Koza Oda; Sadao Ishihara; Takashi Kasai; Fujio Saito; Hiroyuki Koike; Teiichiro Koga; Eiichi Kitazawa; Hiroshi Kogen; Ichiro Hayakawa, all of Tokyo, Japan

[73] Assignee: Sankyo Company, Limited, Tokyo, Japan

[21] Appl. No.: 267,124

[22] Filed: Jun. 28, 1994

[30] Foreign Application Priority Data

Jun. 30, 1993 [JP] Japan ................................ 5-162572

[51] Int. Cl.$^6$ ................ C07C 275/28; C07C 275/30; A61K 31/17; A61K 31/24; C07D 311/82; C07D 513/04

[52] U.S. Cl. .............. 514/357; 514/500; 514/585; 514/586; 514/587; 514/588; 514/589; 514/597; 514/598; 514/596; 514/399; 514/400; 548/338.1; 549/388; 549/390; 564/48; 564/49; 564/52

[58] Field of Search ..................... 564/48, 49, 52; 548/338.1; 549/388, 390; 514/596, 585, 586, 587, 588, 589, 597, 598, 357, 500, 399, 400

[56] References Cited

U.S. PATENT DOCUMENTS

| | | | |
|---|---|---|---|
| 4,623,662 | 11/1986 | De Vries | 514/596 |
| 4,716,175 | 12/1987 | Hoefle et al. | 514/357 |
| 5,015,644 | 5/1991 | Roth et al. | 514/247 |
| 5,258,405 | 11/1993 | Ito et al. | 514/597 |

FOREIGN PATENT DOCUMENTS

| | | | |
|---|---|---|---|
| 0335375 | 10/1989 | European Pat. Off. | 514/247 |
| 0384320 | 8/1990 | European Pat. Off. | 514/247 |
| 0497201 | 8/1992 | European Pat. Off. | 514/247 |
| 90-15048 | 12/1990 | WIPO | 564/48 |
| WO9203413 | 3/1992 | WIPO | 514/247 |
| WO9306096 | 4/1993 | WIPO | 514/247 |

OTHER PUBLICATIONS

Bridge, Chemical Abstracts, vol. 115, #71152e (1991).
Kimura et al, Chemical Abstracts, vol. 117, #47920z (1992).
Kumazawa, et al, Chemical Abstracts, vol. 117, #233877z (1992).
Lythgoe, Chemical Abstracts, vol. 117, #69592w (1992).
Sekiya et al, Chemical Abstracts, vol. 116, #6541n (1992).
Yoshida et al, Chemical Abstracts, vol. 119, #180658c (1993).

*Primary Examiner*—Floyd D. Higel
*Attorney, Agent, or Firm*—Frishauf, Holtz, Goodman, Langer & Chick

[57] ABSTRACT

Compounds of formula (I) are provided:

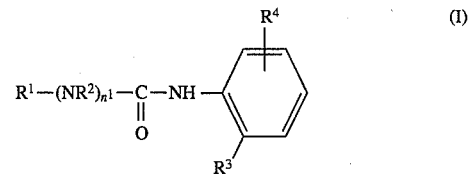

wherein: $R^1$ represents an alkyl group; or a group of formula (II), (III), (IV) or (V):

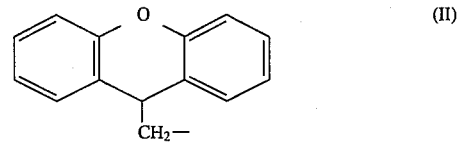

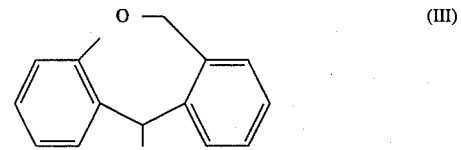

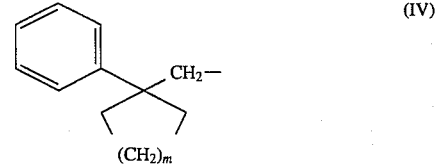

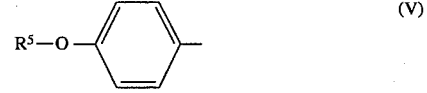

and wherein the groups $R^2$, $R^3$, $R^4$ and $R^5$ are hydrogen or various organic groups; and pharmaceutically acceptable salts thereof; as well as methods for the preparation of such compounds and their use in the treatment and prophylaxis of hypercholesteremia and arteriosclerosis.

66 Claims, No Drawings

SUBSTITUTED AROMATIC AMIDES AND UREAS DERIVATIVES HAVING ANTI-HYPERCHOLESTEREMIC ACTIVITY, THEIR PREPARATION AND THEIR THERAPEUTIC USES

BACKGROUND TO THE INVENTION

The present invention relates to a series of new amide and urea compounds having anti-hypercholesteremic activities and which can therefore be used in the treatment and prophylaxis of hypercholesteremia, arteriosclerosis and like disorders. The invention also provides methods and compositions using such compounds as well as processes for their preparation.

Among the causes of ischemic cardiac insufficiency (which may result in angina, myocardial infarction and the like) atherosclerosis is thought to be most important. It is believed that the foam cells under the endodermis cell layer of blood vessels accumulate cholesterol esters, and that this is a major cause of arteriosclerosis.

Inhibitors of acyl-CoA: cholesterol acyl transferase (hereinafter referred as ACAT) inhibit the synthesis of cholesterol esters in the foam cells, diminish the accumulation of cholesterol esters and inhibit the formation and development of atherosclerosis due to the accumulation of cholesterol esters.

Additionally, it has been established that there is a correlation between arterioselerosis and hypercholesterolemia. Cholesterols in food are absorbed as free cholesterol in the intestinal mucosal cell tract. They are then esterified by ACAT, and get into blood. Therefore, an ACAT inhibitor inhibits a rise in the cholesterol concentration in blood by inhibiting the absorption of food cholesterol into the blood.

For this reason, compounds having the ability to inhibit the activity of ACAT are useful for the treatment and prophylaxis of atheroscleosis.

The compounds of the present invention have a (9H-xanthen-9-yl)methyl group, a 6,11-dihydrodibenz-[b.e]oxepine-11-yl group, a (1-phenylcycloalkyl)methyl group, a p-alkoxyphenyl group or an alkyl group attached to an amido or ureido group. Compounds containing a (9H-xanthen-9-yl)methyl group are disclosed in Publications WO 93/06096 and EP 337375. Compounds containing a 6,11-dihydrodibenz[b.e]oxepine-11-yl group are disclosed in Publication EP 497201. Compounds containing a (1-phenylcycloalkyl)methyl group are disclosed in Publication EP 293880. Compounds containing a p-alkoxyphenyl group are disclosed in Publication EP 424194. Compounds containing an alkyl group are disclosed in Publication EP 283742. Diphenylurea compounds are disclosed in WO 92/03413. Other somewhat similar compounds are disclosed in EP Publications 439059 and 477778.

The compounds of the present invention, and especially those containing a (9H-xanthen-9-yl)methyl group, have surprisingly been found to have a much better inhibitory activity against ACAT than do the prior art compounds referred to above and/or have a much better oral absorbability.

BRIEF SUMMARY OF INVENTION

It is, accordingly, an object of the present invention to provide a series of novel amide and urea derivatives.

It is a further, and more specific, advantage of the present invention to provide such compounds having useful anti-hypercholesteremic activity.

Other objects and advantages of the present invention will become apparent as the description proceeds.

Thus, the present invention provides compounds of formula (I):

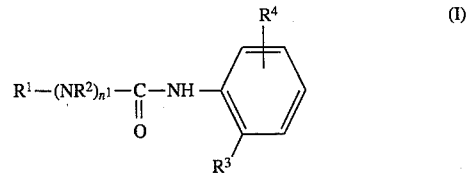

wherein:
R$^1$ represents an alkyl group having from 1 to 20 carbon atoms, or a group of formula (II), (III), (IV) or (V):

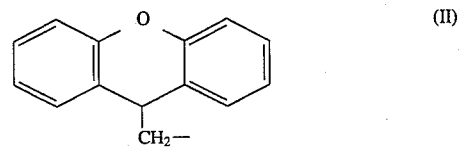

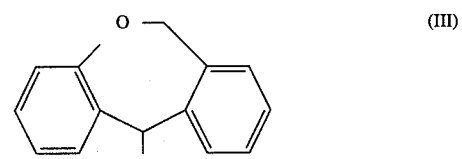

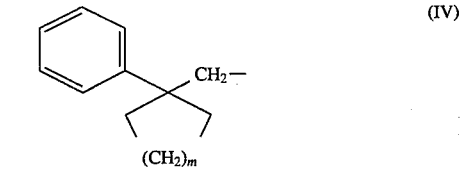

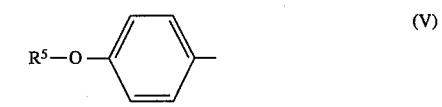

where R$^5$ represents an alkyl group having from 1 to 15 carbon atoms; m is an integer of from 1 to 4; and, any aromatic ring in said group represented by R$^1$ is unsubstituted or is substituted by at least one substituent selected from the group consisting of substituents α, defined below;
R$^2$ represents a hydrogen atom or an alkyl group having from 1 to 10 carbon atoms;
R$^3$ represents
an alkyl group having from 1 to 10 carbon atoms,
an alkoxy group having from 1 to 10 carbon atoms,
an alkylthio group having from 1 to 10 carbon atoms,
an alkylsulfinyl group having from 1 to 10 carbon atoms,
an alkylsulfonyl group having from 1 to 10 carbon atoms,
a phenylthio group in which the phenyl part is unsubstituted or is substituted by at least one substituent selected from the group consisting of substituents α, defined below,
a phenylsulfinyl group in which the phenyl part is unsubstituted or is substituted by at least one substituent selected from the group consisting of substituents α, defined below,
a phenylsulfonyl group in which the phenyl part is unsubstituted or is substituted by at least one substituent selected from the group consisting of substituents α, defined below, or
an alkoxyalkyl group in which the alkoxy part has from 1 to 6 carbon atoms and the alkyl part has from 1 to 4 carbon atoms;

$R^4$ represents a group of formula (VI), (VII), (VIII), (IX), (X) or (XI):

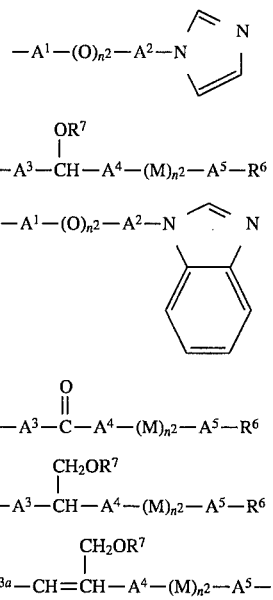

$$-A^1-(O)_{n2}-A^2-N\underset{\diagdown}{\overset{\diagup}{\text{N}}} \quad \text{(VI)}$$

$$-A^3-\underset{\underset{OR^7}{|}}{CH}-A^4-(M)_{n2}-A^5-R^6 \quad \text{(VII)}$$

$$-A^1-(O)_{n2}-A^2-N\diagdown\text{N} \quad \text{(VIII)}$$

(with benzimidazolyl ring)

$$-A^3-\overset{O}{\underset{\|}{C}}-A^4-(M)_{n2}-A^5-R^6 \quad \text{(IX)}$$

$$-A^3-\underset{\underset{CH_2OR^7}{|}}{CH}-A^4-(M)_{n2}-A^5-R^6 \quad \text{(X)}$$

$$-A^{3a}-\underset{\underset{CH_2OR^7}{|}}{CH}=CH-A^4-(M)_{n2}-A^5-R^6 \quad \text{(XI)}$$

where $A^1$ represents a single bond or an alkylene group having from 1 to 4 carbon atoms, $A^2$ represents a single bond or an alkylene group having from 1 to 6 carbon atoms, $A^3, A^{3a}, A^4$ and $A^5$ are independently selected from the group consisting of single bonds and alkylene groups having from 1 to 10 carbon atoms which may be saturated or may include a carbon-carbon double bond, provided that the total number of carbon atoms in $A^3$, $A^4$ and $A^5$ and that in $A^{3a}$, $A^4$ and $A^5$ does not exceed 10;

$R^6$ represents an alkyl group having from 1 to 6 carbon atoms, a cycloalkyl group having from 3 to 9 carbon atoms in one or more aliphatic carbocyclic rings, said rings being unsubstituted or being substituted by at least one substituent selected from the group consisting of substituents α, defined below, or an aryl group, as defined below; and in the groups of formulae (VI) and (VIII), the imidazolyl and benzimidazolyl groups may be unsubstituted or may be substituted by at least one substituent selected from the group consisting of substituents β, defined below;

$R^7$ represents a hydrogen atom, a benzyl group, a phosphono group or a group of formula (XII):

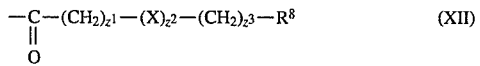

$$-\underset{\underset{O}{\|}}{C}-(CH_2)_{z1}-(X)_{z2}-(CH_2)_{z3}-R^8 \quad \text{(XII)}$$

where:
$z^1$ is 0 or 1;
$z^2$ is 0, 1 or 2;
X is an oxygen or sulfur atom or a sulfinyl, sulfonyl or phenylene group, provided that, when $z^2$ is 2, at least one X is a phenylene group;
$z^3$ is 0 or an integer from 1 to 4; and
$R^8$ is a carboxy group, a phenyl group, a group of formula $-NR^9R^{10}$,
where $R^9$ and $R^{10}$ are independently selected from the group consisting of hydrogen atoms and alkyl groups having from 1 to 4 carbon atoms,
or a heterocyclic group having 5 or 6 ring atoms of which 1 or 2 are hetero-atoms selected from the group consisting of oxygen and nitrogen atoms, said heterocyclic group being unsubstituted or being substituted on a carbon atom by an oxygen atom or by an alkyl group having from 1 to 4 carbon atoms; and said groups of formula $(CH_2)_z1$ and $(CH_2)_z3$ being unsubstituted or being substituted on a carbon atom by an alkyl group having from 1 to 4 carbon atoms or by a group of formula $-NR^9R^{10}$, where $R^9$ and $R^{10}$ are as defined above;
$n^1$ is 0 or 1;
$n^2$ is 0 or 1;
M represents an oxygen atom, a sulfur atom, a sulfinyl group or a sulfonyl group;
said substituents α are selected from the group consisting of alkyl groups having from 1 to 4 carbon atoms, alkoxy groups having from 1 to 4 carbon atoms and halogen atoms; and
said substituents β are selected from the group consisting of alkyl groups having from 1 to 4 carbon atoms and phenyl groups which are unsubstituted or are substituted by at least one substituent selected from the group consisting of said substituents α;
said aryl groups are aromatic carbocyclic groups having from 6 to 10 ring carbon atoms and are unsubstituted or are substituted by at least one substituent selected from the group consisting of substituents α, defined above;
PROVIDED THAT, where $R^4$ represents said group of formula (VII), (IX), (X) or (XI), $R^1$ does not represent said alkyl group and that, where $n^2$ is 1, $A^4$ does not represent a single bond, and that, where $n^1$ is 0, $R^3$ is ethyl and $R^4$ is 2-acetyl, $R^1$ does not represent a methyl group;
and pharmaceutically acceptable salts thereof.

The invention also provides a composition for the treatment and prophylaxis of hypercholesteremia or arteriosclerosis, which comprises an effective amount of a compound of formula (I) or a pharmaceutically acceptable salt thereof in admixture with a pharmaceutically acceptable carrier or diluent.

The invention still further provides a method for the treatment and prophylaxis of hypercholesteremia or arteriosclerosis in a mammal, which may be human, which comprises administering to said mammal an effective amount of a compound of formula (I) or a pharmaceutically acceptable salt thereof.

Processes for preparing these compounds and salts thereof also form part of the present invention and are described in more detail hereafter.

DETAILED DESCRIPTION OF INVENTION

In the compounds of the present invention, where $R^1$ represents an alkyl group, this may be a straight or branched chain alkyl group having from 1 to 20 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 2,2-dimethylheptyl, decyl, 1-methylnonyl, 3-methylnonyl, 8-methylnonyl, 3-ethyloctyl, 1,1-dimethyloctyl, 2,2-dimethyloctyl, undecyl, 4,8-dimethylnonyl, dodecyl, tridecyl, 1,1-dimethylundecyl, tetradecyl, 2,2-dimethyldodecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl and 3,7,11,15-tetramethylhexadecyl groups. Of these, we prefer those groups having from 3 to 20 carbon atoms, particularly from 4 to 20 carbon atoms, more preferably those having from 10 to 16 carbon atoms, and still more preferably those having from 11 to 14 carbon atoms, particularly the undecyl, 1,1-dimethylundecyl and 2,2-dimethyldodecyl groups.

Where $R^1$ represents a group of formula (II), (III), (IV) or (V):

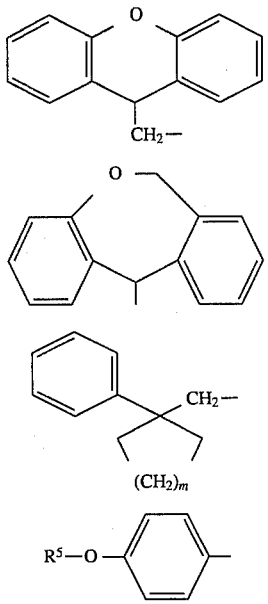

any of the aromatic rings may be unsubstituted or they may be substituted by one or more of the substituents α, for example:

alkyl groups having from 1 to 4 carbon atoms, such as the methyl, ethyl, propyl, isopropyl, butyl, isobutyl, sec-butyl and t-butyl groups, of which the methyl, ethyl, propyl and isopropyl groups are preferred;

alkoxy groups having from 1 to 4 carbon atoms, such as the methoxy, ethoxy, propoxy, isopropoxy, butoxy, isobutoxy, sec-butoxy and t-butoxy groups, of which the methoxy and ethoxy groups are preferred; and halogen atoms, such as the fluorine, chlorine, bromine and iodine atoms, of which the fluorine, chlorine and bromine atoms are preferred.

In the case of the groups of formula (II), preferred substituents are the alkyl and alkoxy groups having 1 or 2 carbon atoms and the halogen atoms, especially the methyl and methoxy groups and the chlorine and bromine atoms, more preferably the methoxy group and the chlorine and bromine atoms. Any of these substituents, particularly the preferred and more preferred substituents, may be on any substitutable carbon atom of the (9H-xanthen-9-yl)methyl group represented by the formula (II), but are preferably present on the 2- or 3-carbon atoms. There is no specific restriction on the number of substituents except such as may be imposed by the number of substitutable positions and possibly by steric constraints, however, where the group is substituted, from 1 to 3 substituents are preferred and a single substituent is more preferred. However, the group is more preferably unsubstituted.

In the case of the groups of formula (III), preferred substituents are the alkyl and alkoxy groups having 1 or 2 carbon atoms and the halogen atoms, especially the methyl and methoxy groups and the chlorine and bromine atoms. Any of these substituents, particularly the preferred substituents, may be on any substitutable carbon atom of the 6,11-dihydrodibenz-[b.e]oxepin-11-yl group represented by the formula (III), but are preferably present on the 2-carbon atom. There is no specific restriction on the number of substituents except such as may be imposed by the number of substitutable positions and possibly by steric constraints, however, where the group is substituted, from 1 to 3 substituents are preferred and a single substituent is more preferred. However, the group is more preferably unsubstituted.

In the case of the groups of formula (IV), preferred substituents are the alkyl and alkoxy groups having 1 or 2 carbon atoms and the halogen atoms, especially the methyl and methoxy groups and the chlorine and bromine atoms, more preferably the methoxy group and the chlorine and bromine atoms. Any of these substituents, particularly the preferred and more preferred substituents, may be on any substitutable carbon atom of the benzene ring of the group represented by the formula (IV), but are preferably present on the 2-, 3- or 4-carbon atoms. There is no specific restriction on the number of substituents except such as may be imposed by the number of substitutable positions and possibly by steric constraints, however, where the group is substituted, from 1 to 3 substituents are preferred and a single substituent is more preferred. However, the group is more preferably unsubstituted. In the group of formula (IV), m is preferably 2 or 3.

In the case of the groups of formula (V), preferred substituents are the alkyl and alkoxy groups having 1 or 2 carbon atoms and the halogen atoms, but the group preferably has no further substituent on the benzene ring in addition to the group of formula $R^5$—O—. $R^5$ represents an alkyl group which may be a straight or branched chain alkyl group having from 1 to 15 carbon atoms, and examples include the methyl, ethyl, propyl, isopropyl, butyl, isobutyl, sec-butyl, t-butyl, pentyl, isopentyl, 2-metylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl and 3,7,11-trimethyldodecyl groups. Of these, we prefer those groups having from 4 to 15 carbon atoms, more preferably those having 8 to 12 carbon atoms.

Of all of the options for $R^1$, we prefer those compounds where $R^1$ represents a group of formula (II).

Where $R^2$ or $R^3$ represents an alkyl group, this may be a straight or branched chain alkyl group having from 1 to 10 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, 1,1-dimethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 1,1-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 1,1-dimethylhexyl, nonyl, 1-methyloctyl, 2-methyloctyl, 3-methyloctyl, 6-methyloctyl, 1-propylhexyl, 1-ethylheptyl, 1,1-dimethylheptyl, decyl, 1-methylnonyl, 3-methylnonyl, 8-methylnonyl, 3-ethyloctyl, 1,1-dimethyloctyl and 7,7-dimethyloctyl groups. Of which we prefer, in the case of $R^2$, those having from 4 to 8, more preferably from 5 to 8, carbon atoms, and of these groups, the straight chain groups are especially preferred. Alternatively, $R^2$ is preferably a hydrogen atom. Preferred groups for $R^3$ are those having from 1 to 8, more preferably from 1 to 6, carbon atoms, which may be straight or branched chain groups, for example the methyl, ethyl, isopropyl, isobutyl, t-butyl, 1,1-dimethylpropyl, 1,1-dimethylbutyl, 1,1-dimethylpentyl and 1,1-dimethylhexyl groups, most preferably the isopropyl and t-butyl groups.

Where $R^3$ represents an alkoxy group, this may be a straight or branched chain alkoxy group having from 1 to 10 carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, 1,1-dimethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, heptyloxy, 1-methylhexyloxy, 2-methylhexyloxy, 3-methylhexyloxy, 4-methylhexyloxy, 5-methylhexyloxy, 1-propylbutoxy, 1,1-dimethylpentyloxy, octyloxy, 1-methylheptyloxy, 2-methylheptyloxy, 3-methylheptyloxy, 4-methylheptyloxy, 5-methylheptyloxy, 6-methylheptyloxy, 1-propylpentyloxy, 2-ethylhexyloxy, 1,1-dimethylhexyloxy, nonyloxy, 1-methyloctyloxy, 2-methyloctyloxy, 3-methyloctyloxy, 6-methyloctyloxy, 1-propylhexyloxy, 1-ethylheptyloxy, 1,1-dimethylheptyloxy, decyloxy, 1-methylnonyloxy, 3-methylnonyloxy, 8-methylnonyloxy, 3-ethyloctyloxy, 1,1-dimethyloctyloxy and 7,7-dimethyloctyloxy groups, of which we prefer those having from 3 to 8 carbon atoms. Of these groups, the isopropoxy and t-butoxy groups are especially preferred.

Where $R^3$ represents an alkylthio group, this may be a straight or branched chain alkylthio group having from 1 to 10 carbon atoms, and examples include the methylthio, ethylthio, propylthio, isopropylthio, butylthio, isobutylthio, sec-butylthio, t-butylthio, pentylthio, isopentylthio, 2-methylbutylthio, neopentylthio, 1-ethylpropylthio, 1,1-dimethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, heptylthio, 1-methylhexylthio, 2-methylhexylthio, 3-methylhexylthio, 4-methylhexylthio, 5-methylhexylthio, 1-propylbutylthio, 1,1-dimethylpentylthio, octylthio, 1-methylheptylthio, 2-methylheptylthio, 3-methylheptylthio, 4-methylheptylthio, 5-methylheptylthio, 6-methylheptylthio, 1-propylpentylthio, 2-ethylhexylthio, 1,1-dimethylhexylthio, nonylthio, 1-methyloctylthio, 2-methyloctylthio, 3-methyloctylthio, 6-methyloctylthio, 1-propylhexylthio, 1-ethylheptylthio, 1,1-dimethylheptylthio, decylthio, 1-methylnonylthio, 3-methylnonylthio, 8-methylnonylthio, 3-ethyloctylthio, 1,1-dimethyloctylthio and 7,7-dimethyloctylthio groups, of which we prefer those having from 1 to 4 carbon atoms. Of these groups, the methylthio, isopropylthio and t-butylthio groups are especially preferred.

Where $R^3$ represents an alkylsulfinyl group, this may be a straight or branched chain alkylsulfinyl group having from 1 to 10 carbon atoms, and examples include the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, 2-methylbutylsulfinyl, neopentylsulfinyl, 1-ethylpropylsulfinyl, 1,1-dimethylpropylsulfinyl, hexylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl, 2-ethylbutylsulfinyl, heptylsulfinyl, 1-methylhexylsulfinyl, 2-methylhexylsulfinyl, 3-methylhexylsulfinyl, 4-methylhexylsulfinyl, 5-methylhexylsulfinyl, 1-propylbutylsulfinyl, 1,1-dimethylpentylsulfinyl, octylsulfinyl, 1-methylheptylsulfinyl, 2-methylheptylsulfinyl, 3-methylheptylsulfinyl, 4-methylheptylsulfinyl, 5-methylheptylsulfinyl, 6-methylheptylsulfinyl, 1-propylpentylsulfinyl, 2-ethylhexylsulfinyl, 1,1-dimethylhexylsulfinyl, nonylsulfinyl, 1-methyloctylsulfinyl, 2-methyloctylsulfinyl, 3-methyloctylsulfinyl, 6-methyloctylsulfinyl, 1-propylhexylsulfinyl, 1-ethylheptylsulfinyl, 1,1-dimethylheptylsulfinyl, decylsulfinyl, 1-methylnonylsulfinyl, 3-methylnonylsulfinyl, 8-methylnonylsulfinyl, 3-ethyloctylsulfinyl, 1,1-dimethyloctylsulfinyl and 7,7-dimethyloctylsulfinyl groups, of which we prefer those having from 1 to 4 carbon atoms. Of these groups, the methylsulfinyl, isopropylsulfinyl and t-butylsulfinyl groups are especially preferred.

Where $R^3$ represents an alkylsulfonyl group, this may be a straight or branched chain alkylsulfonyl group having from 1 to 10 carbon atoms, and examples include the methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, 2-methylbutylsulfonyl, neopentylsulfonyl, 1-ethylpropylsulfonyl, 1,1-dimethylpropylsulfonyl, hexylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl, 2-ethylbutylsulfonyl, heptylsulfonyl, 1-methylhexylsulfonyl, 2-methylhexylsulfonyl, 3-methylhexylsulfonyl, 4-methylhexylsulfonyl, 5-methylhexylsulfonyl, 1-propylbutylsulfonyl, 1,1-dimethylpentylsulfonyl, octylsulfonyl, 1-methylheptylsulfonyl, 2-methylheptylsulfonyl, 3-methylheptylsulfonyl, 4-methylheptylsulfonyl, 5-methylheptylsulfonyl, 6-methylheptylsulfonyl, 1-propylpentylsulfonyl, 2-ethylhexylsulfonyl, 1,1-dimethylhexylsulfonyl, nonylsulfonyl, 1-methyloctylsulfonyl, 2-methyloctylsulfonyl, 3-methyloctylsulfonyl, 6-methyloctylsulfonyl, 1-propylhexylsulfonyl, 1-ethylheptylsulfonyl, 1,1-dimethylheptylsulfonyl, decylsulfonyl, 1-methylnonylsulfonyl, 3-methylnonylsulfonyl, 8-methylnonylsulfonyl, 3-ethyloctylsulfonyl, 1,1-dimethyloctylsulfonyl and 7,7-dimethyloctylsulfonyl groups, of which we prefer those having from 1 to 4 carbon atoms. Of these groups, the methylsulfonyl, isopropylsulfonyl and t-butylsulfonyl groups are especially preferred.

Where $R^3$ represents a phenylthio, phenylsulfinyl or phenylsulfonyl group, the phenyl part may be unsubstituted or it may be substituted by one or more substituents selected from the group consisting of substituents α, defined and exemplified above. There is no specific restriction on the number of substituents except such as may be imposed by the number of substitutable positions and possibly by steric constraints, however, where the group is substituted, from 1 to 3 substituents are preferred and a single substituent is more preferred. Specific examples of substituted and unsubstituted groups include the phenylthio, 4-methylphenylthio, 2-methylphenylthio, 3-ethylphenylthio, 4-propylphenylthio, 2-methoxyphenylthio, 3-methoxyphenylthio, 4-ethoxyphenylthio, 3-fluorophenylthio, 4-chlorophenylthio, 3-bromophenylthio, phenylsulfinyl, 4-methylphenylsulfinyl, 2-methylphenylsulfinyl, 3-ethylphenylsulfinyl, 4-propylphenylsulfinyl, 2-methoxyphenylsulfinyl, 3-methoxyphenylsulfinyl, 4-ethoxyphenylsulfinyl, 3-fluorophenylsulfinyl, 4-chlorophenylsulfinyl, 3-bromophenylsulfinyl, phenylsulfonyl, 4-methylphenylsulfonyl, 2-methylphenylsulfonyl, 3-ethylphenylsulfonyl, 4-propylphenylsulfonyl, 2-methoxyphenylsulfonyl, 3-methoxyphenylsulfonyl, 4-ethoxyphenylsulfonyl, 3-fluorophenylsulfonyl, 4-chlorophenylsulfonyl and 3-bromophenylsulfonyl groups, preferably the phenylthio, 4-methylphenylthio, 2-methylphenylthio, 4-chlorophenylthio, phenylsulfonyl, 4-methylphenylsulfonyl, 2-methylphenylsulfonyl and 4-chlorophenylsulfonyl groups.

Where $R^3$ represents an alkoxyalkyl group, this consists of an alkoxy group having 1 to 6, preferably from 1 to 4, carbon atoms which is a substituent on an alkyl group having 1 to 4 carbon atoms. Examples of such groups include the alkoxy groups having from 1 to 6 carbon atoms included in the groups which may be represented by $R^3$ and the alkyl groups having from 1 to 4 carbon atoms included, inter alia, in the groups which may be represented by $R^1$. Specific examples of such alkoxyalkyl groups include the methoxymethyl, ethoxymethyl, isopropoxymethyl, t-butoxymethyl, 1-methoxyethyl, 2-methoxyethyl, 1-ethoxyethyl, 2-ethoxyethyl, 1-isopropoxyethyl, 2-isopropoxyethyl, 1-t-butoxyethyl, 2-t-butoxyethyl, 1-methoxypropyl, 2-methoxypropyl, 3-methoxypropyl, 1-ethoxypropyl, 2-ethoxypropyl, 3-ethoxypropyl, 1-isopropoxybutyl, 2-isopropoxybutyl, 3-isopropoxybutyl, 4-isopropoxybutyl, 1-t-butoxybutyl, 2-t-butoxybutyl, 3-t-butoxybutyl, 4-t-butoxybutyl and 1,1-dimethyl-2-methoxyethyl groups. Of these, more preferred groups are those in which an alkoxy group having from 1 to 4 carbon atoms is a substituent on a methyl group, preferably the methoxymethyl, ethoxymethyl, isopropoxymethyl and t-butoxymethyl groups, and the most preferred groups are the methoxymethyl and isopropoxymethyl groups.

$R^4$ represents a group of formula (VI), (VII), (VIII), (IX), (X) or (XI):

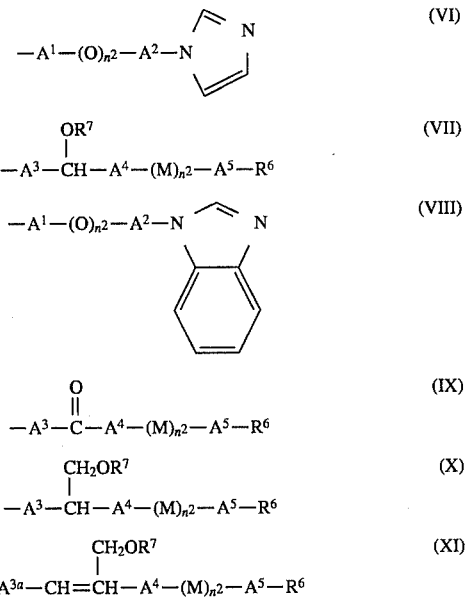

In the case of the groups (VI) and (VIII), where $A^1$ represents an alkylene group having from 1 to 4 carbon atoms, this may be a straight or branched chain group, preferably having from 1 to 3 carbon atoms. The two "free" valencies may be on the same carbon atom (in which case, the group is sometimes called an "alkylidene" group) or, where there are 2 or more carbon atoms, on different carbon atoms. The straight chain groups are preferred. Examples of such groups include the methylene, ethylene, propylene, 1-methylethylene, trimethylene and tetramethylene groups, of which the methylene, ethylene and propylene groups are preferred, the methylene group being most preferred. Alternatively, $A^1$ may represent a single bond, however, we prefer those compounds where $A^1$ represents an alkylene group, preferably a methylene group.

In the case of the groups of formula (VI) and (VIII), $A^2$ represents a single bond or an alkylene group having from 1 to 6 carbon atoms. This may be a straight or branched chain group, preferably having from 2 to 4 carbon atoms. The two "free" valencies may be on the same carbon atom or on different carbon atoms. The straight chain groups are preferred. Examples of such groups include the ethylene, trimethylene, 1-methylethylene, tetramethylene, 1-methyltrimethylene, 2-methyltri- methylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene and 4,4-dimethyltetramethylene groups. Of these, we prefer the ethylene, trimethylene, 1-methylethylene and tetramethylene groups. In the compounds in which $n^2$ is 1, it is preferred that $A^2$ is not a single bond and is an alkylene group other than methylene.

Also in the case of the groups of formulae (VI) and (VIII), the imidazolyl and benzimidazolyl groups may be unsubstituted or may be substituted by at least one substituent selected from the group consisting of substituents β, defined above. Examples of such substituents β include:

alkyl groups having from 1 to 4 carbon atoms, such as those defined and exemplified above in relation to substituents α, preferably the methyl and ethyl groups, and phenyl groups which are unsubstituted or are substituted by at least one substituent selected from the group consisting of said substituents α (which substituents may be as defined and exemplified above), for example the phenyl, 2-chlorophenyl, 4-chlorophenyl, 2-methoxyphenyl, 3-methoxyphenyl and 2-methylphenyl groups, more preferably the phenyl and 2-chlorophenyl groups.

However, the unsubstituted imidazolyl and benzimidazolyl groups and those substituted by a methyl or ethyl group are preferred.

Also in the case of the groups of formulae (VII), (IX), (X) and (XI), $A^3$, $A^{3a}$, $A^4$ and $A^5$ may each represent an alkylene group having 1 to 10 carbon atoms which may be interrupted by at least one double bond. Where a group contains 2 or more of these, the groups represented by $A^3$, $A^{3a}$, $A^4$ and $A^5$ may be the same as or different from each other. Examples of such groups include such saturated alkylene groups having from 1 to 10 carbon atoms as the methylene, methylmethylene, ethylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2- dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentamethylene, 3-ethyl-2-methylpentamethylene, nonamethylene, 2-methyloctamethylene, 7-methyloctamethylene, 4-ethylheptamethylene, 3-ethyl-2-methylhexanethylene, 2-ethyl-1-methylhexamethylene, decamethylene, 2-methylnonamethylene, 8-methylnonamethylene, 5-ethyloctamethylene, 3-ethyl-2-methylheptamethylene and 3,3-diethylhexamethylene groups; and straight or branched chain alkenylene groups having from 2 to 10 carbon atoms such as the 2-propenylene, 1-methyl-2-propenylene, 2-methyl-2-propenylene, 2-ethyl-2-propenylene, 2-butenylene, 1-methyl-2-butenylene, 2-methyl-2-butenylene, 1-ethyl-2-butenylene, 2-pentenylene, 1-methyl-2-pentenylene, 2-methyl-2-pentenylene, 3-pentenylene, 1-methyl-3-pentenylene, 2-methyl-3-pentenylene, 1-methyl-4-pentenylene, 2-methyl-4-pentenylene, 2-hexenylene, 3-hexenylene, 4-hexenylene, 5-hexenylene, heptenylene, octenylene, nonylene and decene groups. Alternatively, any one or more of these groups may represent a single bond.

$A^3$ and $A^{3a}$ each preferably represents a single bond or an alkylene or alkenylene group having from 1 to 7 carbon atoms, more preferably from 1 to 4 carbon atom, and most preferably an alkylene group having from 1 to 7, more preferably from 1 to 4, carbon atoms; whilst $A^4$ preferably represents a single bond or an alkylene or alkenylene group having from 1 to 7 carbon atoms. Further, $A^3$ is most preferably a single bond, or a methylene or an ethylene group.

$A^5$ preferably represents a single bond or an alkylene group having from 1 to 6 carbon atoms, which may be unsubstituted or may be substituted with an alkyl group having from 1 to 4 carbon atoms, and examples include the methylene, methylmethylene, ethylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene and 4,4-dimethyltetramethylene groups, of which we prefer the methylene, ethylene and propylene groups.

In those cases where a group of formula (VII), (IX), (X) or (XI) includes two or more of the groups represented by $A^3$, $A^{3a}$, $A^4$ and $A^5$, the total number of carbon atoms provided by these groups should not exceed 10.

Also in the case of the groups of formulae (VII), (IX), (X) and (XI), where $R^6$ represents an alkyl group, this may be a straight or branched chain group having from 1 to 4 carbon atoms, and examples include the methyl, ethyl, propyl, isopropyl, butyl, isobutyl, sec-butyl and t-butyl groups, of which we prefer the methyl, isopropyl and t-butyl groups.

Where $R^6$ represents a cycloalkyl group, this has from 3 to 9 ring carbon atoms in one or more, preferably one or two and more preferably one, carbocyclic ring, and examples include the cyclopropyl, cyclobutyl, cyclopentyl, cyclohexyl, cycloheptyl, cyclooctyl, cyclononyl, norpinanyl and norbornyl groups, preferably the cyclobutyl, cyclopentyl, cyclohexyl and cycloheptyl groups, and more preferably the cyclopentyl and cyclohexyl groups. These cycloalkyl group may be unsubstituted or they may have on their ring at least one substituent selected from the group consisting of substituents α, defined and exemplified above. Examples of such substituted groups include the cyclopentyl, cyclohexyl, cycloheptyl, 4-methylcyclohexyl, 4-ethylcyclohexyl, 4-propylcyclohexyl, 4-t-butylcyclohexyl, 4-methoxycyclohexyl, 4-ethoxycyclohexyl and bornyl groups.

Where $R^6$ represents an aryl group, this has from 6 to 10 carbon atoms, more preferably 6 or 10 carbon atoms, in one or more, preferably one or two and more preferably one, carbocyclic ring, and examples of the unsubstituted groups include the phenyl, 1-naphthyl and 2-naphthyl groups, preferably the phenyl group. Such groups may be unsubstituted or they may have on the ring at least one substituent selected from the group consisting of substituents α, defined and exemplified above. Examples of such substituted groups include the phenyl, 2-methylphenyl, 2-methoxyphenyl, 2-chlorophenyl and 3-chlorophenyl groups.

In the definition of $R^7$, $R^9$ and $R^{10}$ may be hydrogen atoms or alkyl groups having from 1 to 4 carbon atoms. In the case of the alkyl groups, these may be straight or branched chain alkyl groups and examples include the methyl, ethyl, propyl, isopropyl, butyl, isobutyl, sec-butyl and t-butyl groups. Of these, we prefer those alkyl groups having 1 or 2 carbon atoms, and most preferably the methyl group. Alternatively, we prefer that $R^9$ and $R^{10}$ should each represent a hydrogen atom. Of the combinations of $R^9$ and $R^{10}$ in the group of formula $-NR^9R^{10}$, we prefer that both $R^9$ and $R^{10}$ should represent hydrogen atoms or methyl groups.

The heterocyclic group which may be represented by $R^8$ may have 5 or 6 ring atoms, of which 1 or 2 are hetero-atoms selected from the group consisting of nitrogen and oxygen atoms. Examples of such groups include the furyl, pyranyl, tetrahydrofuryl, tetrahydropyranyl, pyrrolyl, imidazolyl, pyridyl, pyrazinyl, pyrimidinyl, pyrrolidinyl, imidazolidinyl, imidazolinyl, pyrazolidinyl, piperidyl, piperazinyl, dioxolenyl and morpholinyl (especially morpholino) groups. Preferred are the morpholino, imidazolyl and dioxolenyl groups. Such groups may be unsubstituted or may be substituted on a carbon atom by an oxygen atom or by an alkyl group having from 1 to 4 carbon atoms. Examples of alkyl substituents are as described above. Of the substituted groups, we especially prefer the optionally alkyl-substituted 2-oxo-1,3-dioxolen-4-yl groups and most especially the 5-methyl-2-oxo-1,3-dioxolen-4-yl.

Examples of groups which may be represented by $R^7$ include a hydrogen atom, and the carbamoyl, benzyl, benzoyl and phosphono [-PO(OH)$_2$] groups, and groups of formulae (XIII) to (XXXV):

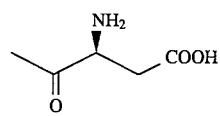
(XIII)

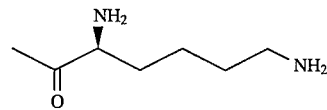
(XIV)

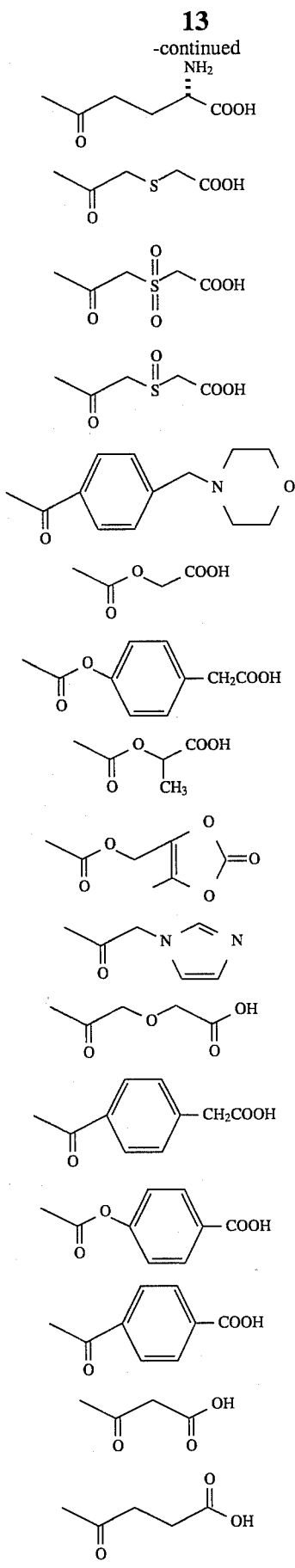
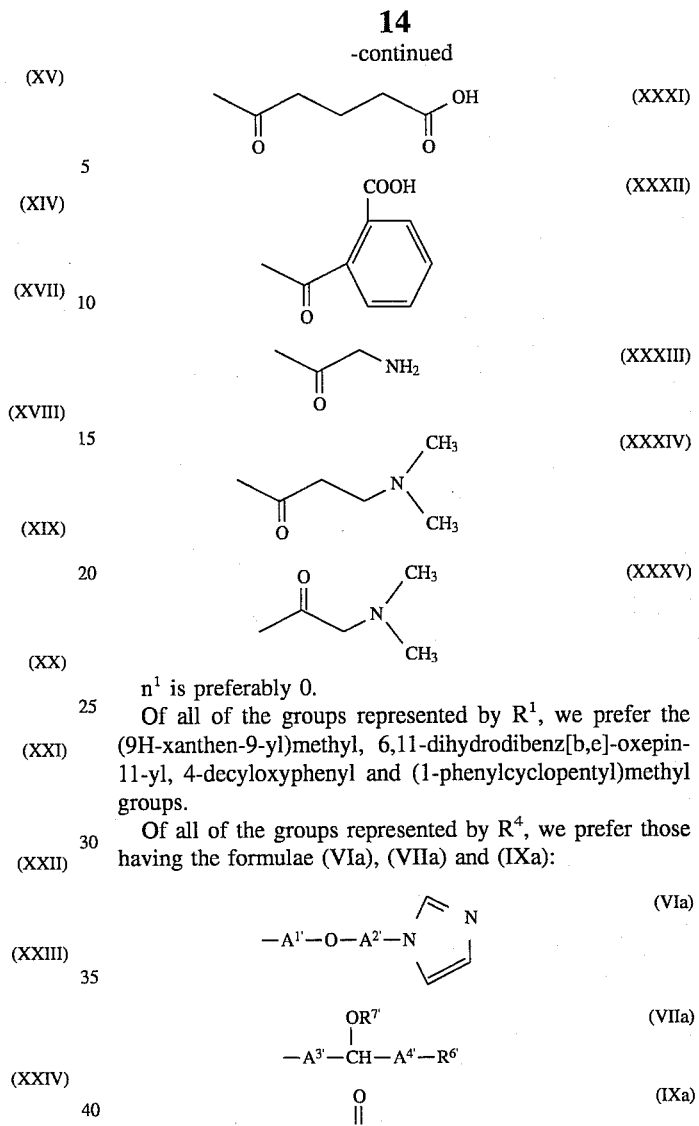

$n^1$ is preferably 0.

Of all of the groups represented by $R^1$, we prefer the (9H-xanthen-9-yl)methyl, 6,11-dihydrodibenz[b,e]-oxepin-11-yl, 4-decyloxyphenyl and (1-phenylcyclopentyl)methyl groups.

Of all of the groups represented by $R^4$, we prefer those having the formulae (VIa), (VIIa) and (IXa):

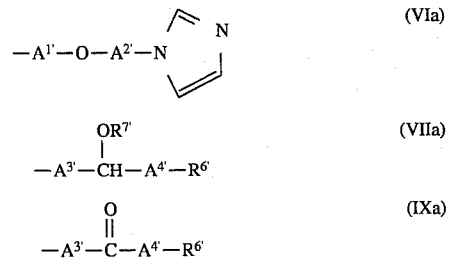

in which:

$R^{6'}$ represents a cyclopentyl group, a cyclohexyl group, a cycloheptyl group, a phenyl group, a 2-methylphenyl group, a 2-chlorophenyl group or a 4-chlorophenyl group;

$R^{7'}$ represents a 3-carboxypropionyl group, a 2-carboxybenzoyl group or an 2-aminoacetyl group;

$A^{1'}$ represents a methylene group;

$A^{2'}$ represents an alkylene group having from 2 to 4 carbon atoms;

$A^{3'}$ represents a single bond or an alkylene group having from 1 to 3 carbon atoms which may be interrupted by a double bond (particularly a methylene or ethylene group);

$A^{4'}$ represents a single bond or an alkylene group having from 1 to 5 carbon atoms which may be interrupted by a double bond.

Of all of the groups represented by $R^7$, we prefer the 3-carboxypropionyl, 2-carboxybenzoyl and 2-aminoacetyl groups.

Of all of the groups included in substituents α, the methyl and methoxy groups, and the fluorine, chlorine and bromine atoms are preferred.

Of all of the groups included in substituents β, the methyl, ethyl, propyl and phenyl groups are preferred.

$R^2$ preferably represents a hydrogen atom or a hexyl or heptyl group.

$R^3$ preferably represents a methyl, ethyl, isopropyl, t-butyl, methoxymethyl, isopropoxymethyl, t-butylthio, isopropylthio, methylthio or phenylthio groups.

$R^4$ may be at any position on the benzene ring forming part of the compound of formula (I). However, we particularly prefer that it should be at the ortho-position with respect to the amino group and the meta-position with respect to $R^3$, or at the meta-position with respect to the amino group and the para-position with respect to $R^3$.

Preferred classes of compounds of the present invention are:
(A) those compounds of formula (I) and salts thereof, defined above, in which $R^1$ represents a group of formula (II) or (IV):

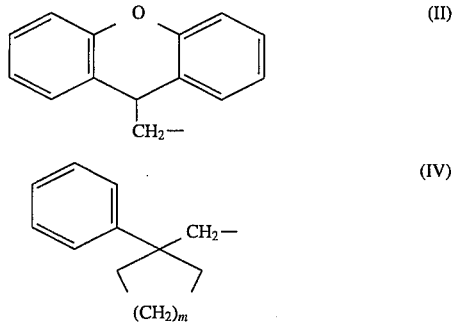

(in which the aromatic rings are unsubstituted or substituted by at least one substituent selected from the group consisting of substituents α, defined above, and m is as defined above) and $n^1$ is 0, and more preferably
(B) those compounds of formula (I) and salts thereof, defined above, in which $R^1$ represents a group of formula (II) and the aromatic rings are unsubstituted.

We also prefer those classes of compounds of formula (I) and salts thereof, defined above, in which:
(C) $R^3$ represents an alkyl group having from 1 to 10 carbon atoms, an alkylthio group having from 1 to 10 carbon atoms or an alkoxy group having from 1 to 10 carbon atoms, more preferably
(D) $R^3$ represents an alkyl group having from 1 to 6 carbon atoms, an alkylthio group having from 1 to 6 carbon atoms or an alkoxy group having from 1 to 6 carbon atoms.

We also prefer those classes of compounds of formula (I) and salts thereof, defined above, in which:
(E) $R^4$ represents a group of formula (VI), (VII) or (X), as defined above, in which M represents an oxygen atom, more preferably
(F) in the case where $n^2$ is 1, $R^4$ represents a group of formula (VI), in which the total number of carbon atoms in $A^1$ and $A^2$ is from 2 to 4, or
(F') in the case where $n^2$ is 0, $R^4$ represents a group of formula (VI), in which the total number of carbon atoms in $A^1$ and $A^2$ is from 1 to 3, or
(G) $R^4$ represents a group of formula (VII), in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms, more preferably
(H) $R^4$ is as defined in (G) above and $R^7$ represents a hydrogen atom or a group of formula (XVI), (XXIV), (XXV) or (XXX), defined above, and still more preferably
(I) $R^4$ is as defined in (H) above and $R^6$ represents an unsubstituted cyclohexyl group, or
(J) $R^4$ represents a group of formula (X), in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms, more preferably
(K) $R^4$ is as defined in (J) above and $R^7$ represents a hydrogen atom or a group of formula (XVI), (XXIV), (XXV) or (XXX), defined above, and still more preferably
(L) $R^4$ is as defined in (K) above and $R^6$ represents an unsubstituted cyclohexyl group.

Particularly preferred are those compounds of formula (I) and salts thereof as previously defined in which any combination of definitions (A) to (I) is also applied. For example, we prefer those in which $R^1$ is as in (A) or (B) and $R^3$ is as in (C) or (D), especially (A)+(C) or (B)+(D), and more especially (B)+(D)+(E) and still more especially (B)+(D)+(E)+[(F) or (F')] or (G) or (J)]. Even more preferred are (B)+(D)+(E)+[(F) or (F')] and (B)+(D)+(E) +(H) and (B)+(D)+(E)+(K). Of these, the most preferred are (B)+(D)+(E)+[(F) or (F')] and (B)+(D)+(E)+(I) and (B)+(D)+(E)+(L).

In the most preferred compounds of the present invention:
$R^1$ represents a (9H-xanthen-9-yl)methyl group;
$n^1$ is 0;
$R^3$ represents a methylthio isopropylthio, isopropyl or t-butyl group;
$R^4$ represents a group of formula (VIa), (VIIa) or (IXa), in which
$R^{6'}$ represents a cyclopentyl group, a cyclohexyl group, a cycloheptyl group, a phenyl group, a 2-methylphenyl group, a 2-chlorophenyl group or a 4-chlorophenyl group;
$R^{7'}$ represents a 3-carboxypropionyl group, a 2-carboxybenzoyl group or an aminoacetyl group;
$A^{1'}$ represents a methylene group;
$A^{2'}$ represents an alkylene group having from 2 to 4 carbon atoms;
$A^{3'}$ represents a single bond or an alkylene group having from 1 to 3 carbon atoms which may be interrupted by a double bond (particularly a methylene group or an ethylene group);
$A^{4'}$ represents a single bond or an alkylene group having from 1 to 5 carbon atoms which may be interrupted by a double bond;
the bonding site of $R^4$ on the benzene ring in the compound of formula (I) is the ortho-position with respect to the amino group and the meta-position with respect to $R^3$, or the meta-position with respect to the amino group and the para-position with respect to $R^3$.

Where the compound of the present invention contains a basic group in its molecule, for example an amino group or an imidazolyl group, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

Specific examples of compounds of the present invention are given in the following formulae (I-1) to (I-5), in which the substituent groups are as defined in the corresponding one of Tables 1 to 5, i.e. Table 1 relates to formula (I-1), Table 2 relates to formula (I-2) and so on to Table 5, which relates to formula (I-5). In the formulae, where appropriate, peripheral positional numbering is shown:

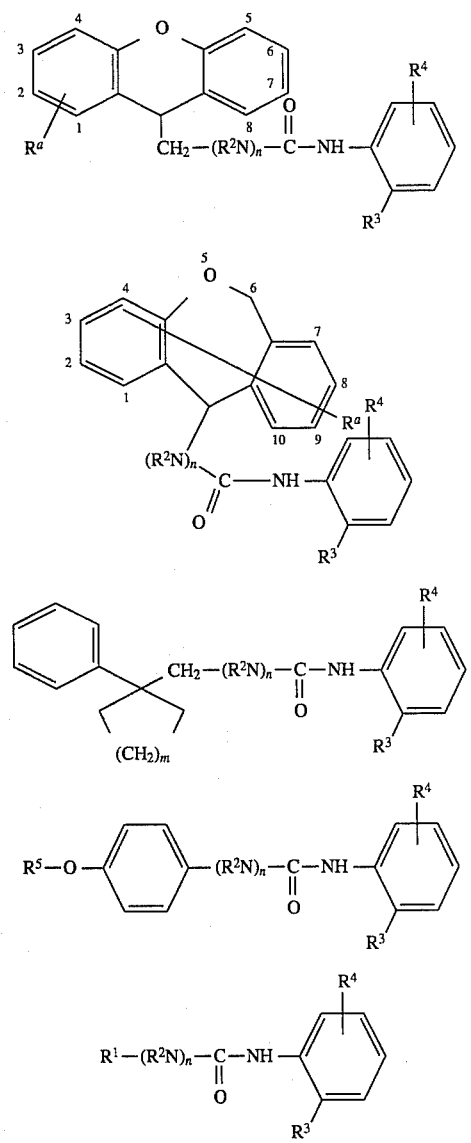
In these Tables, the following abbreviations are used:
| Bimd | benzimidazolyl |
|---|---|
| Bu | butyl |
| cBu | cyclobutyl |
| iBu | isobutyl |
| tBu | t-butyl |
| Bz | benzyl |
| Et | ethyl |
| Hp | heptyl |
| cHp | cycloheptyl |
| Hx | hexyl |
| cHx | cyclohexyl |
| Imd | imidazolyl |
| Me | methyl |
| cOc | cyclooctyl |
| Ph | phenyl |
| Pn | pentyl |
| cPn | cyclopentyl |
| Pr | propyl |
| cPr | cyclopropyl |
| iPr | isopropyl |
| G | 1,1-dimethylundecyl |
| J | undecyl |
| K | 2,2-dimethyldodecyl |
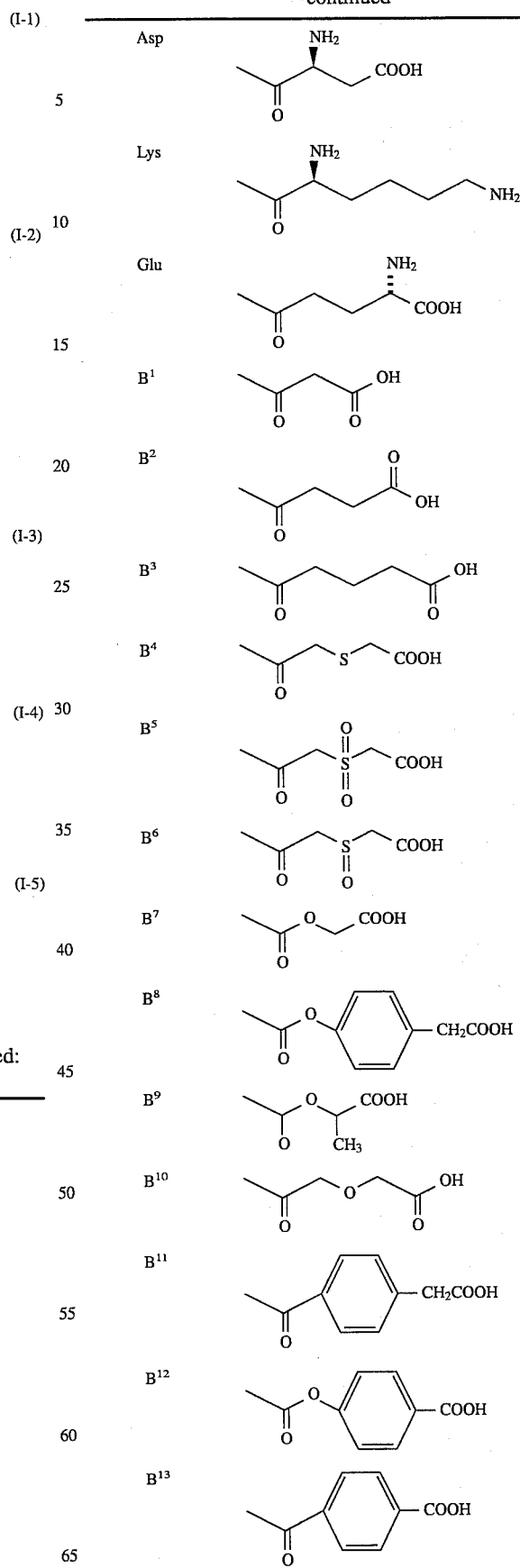

19
-continued

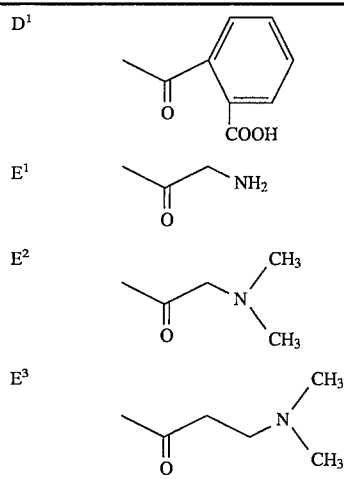

| | |
|---|---|
| D¹ | 2-acetylbenzoic acid (COOH) |
| E¹ | CH₃C(O)CH₂NH₂ |
| E² | CH₃C(O)CH₂N(CH₃)₂ |
| E³ | CH₃C(O)CH₂CH₂N(CH₃)₂ |

20
-continued

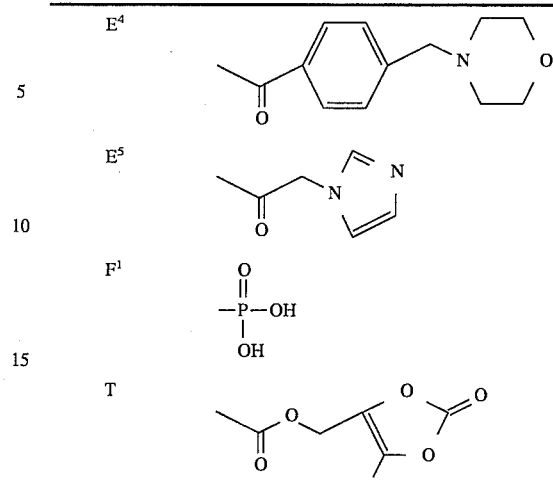

| | |
|---|---|
| E⁴ | 4-(morpholinomethyl)acetophenone |
| E⁵ | 1-(imidazol-1-yl)propan-2-one |
| F¹ | H₃PO₃ (phosphonic acid) |
| T | (carbonate ester structure) |

TABLE 1

| Cpd. No. | $R^a$ | $R^2$ | $R^3$ | n | $R^4$ |
|---|---|---|---|---|---|
| 1-1 | H | — | tBu | 0 | 5-(CH₂)₂CH(OH)(CH₂)₂cHx |
| 1-2 | H | — | iPr | 0 | 5-(CH₂)₂CH(OH)(CH₂)₂cHx |
| 1-3 | H | — | iBu | 0 | 5-(CH₂)₂CH(OH)(CH₂)₂-cHx |
| 1-4 | H | — | Et | 0 | 5-(CH₂)₂CH(OH)(CH₂)₂-cHx |
| 1-5 | H | — | MeOCH₂CMe₂ | 0 | 5-(CH₂)₂CH(OH)(CH₂)₂-cHx |
| 1-6 | H | — | EtCMe₂ | 0 | 5-(CH₂)₂CH(OH)(CH₂)₂-cHx |
| 1-7 | H | — | PrCMe₂ | 0 | S-(CH₂)₂CH(OH)(CH₂)₂-cHx |
| 1-8 | H | — | BuCMe₂ | 0 | 5-(CH₂)₂CH(OH)(CH₂)₂-cHx |
| 1-9 | H | — | PnCMe₂ | 0 | 5-(CH₂)₂CH(OH)(CH₂)₂-cHx |
| 1-10 | H | — | CH₃OCH₂ | 0 | 5-(CH₂)₂CH(OH)(CH₂)₂-cHx |
| 1-11 | H | — | EtOCH₂ | 0 | 5-(CH₂)₂CH(OH)(CH₂)₂-cHx |
| 1-12 | H | — | S-tBu | 0 | 5-(CH₂)₂CH(OH)(CH₂)₂-cHx |
| 1-13 | H | — | S-iPr | 0 | 5-(CH₂)₂CH(OH)(CH₂)₂-cHx |
| 1-14 | H | — | S-Ph | 0 | S-(CH₂)₂CH(OH)(CH₂)₂-cHx |
| 1-15 | H | H | tBu | 1 | S-(CH₂)₂CH(OH)(CH₂)₂-cHx |
| 1-16 | H | H | iPr | 1 | 5-(CH₂)₂CH(OH)(CH₂)₂-cHx |
| 1-17 | H | Bu | tBu | 1 | 5-(CH₂)₂CH(OH)(CH₂)₂-cHx |
| 1-18 | H | Pn | tBu | 1 | 5-(CH₂)₂CH(OH)(CH₂)₂-cHx |
| 1-19 | H | Hx | tBu | 1 | 5-(CH₂)₂CH(OH)(CH₂)₂-cHx |
| 1-20 | H | Hp | tBu | 1 | 5-(CH₂)₂CH(OH)(CH₂)₂-cHx |
| 1-21 | 3-Cl | Hp | tBu | 1 | 5-(CH₂)₂CH(OH)(CH₂)₂-cHx |
| 1-22 | 3-Br | Hp | tBu | 1 | 5-(CH₂)₂CH(OH)(CH₂)₂-cHx |
| 1-23 | 3-OMe | Hp | tBu | 1 | 5-(CH₂)₂CH(OH)(CH₂)₂-cHx |
| 1-24 | 2-OMe | Hp | tBu | 1 | 5-(CH₂)₂CH(OH)(CH₂)₂-cHx |
| 1-25 | H | — | tBu | 0 | 5-(CH₂)₂CH(OH)(CH₂)-cHx |
| 1-26 | H | — | iPr | 0 | 5-(CH₂)₂CH(OH)(CH₂)-cHx |
| 1-27 | H | — | iBu | 0 | 5-(CH₂)₂CH(OH)(CH₂)-cHx |
| 1-28 | H | — | Et | 0 | 5-(CH₂)₂CH(OH)(CH₂)-cHx |
| 1-29 | H | — | MeOCH₂CMe₂ | 0 | 5-(CH₂)₂CH(OH)(CH₂)-cHx |
| 1-30 | H | — | EtCMe₂ | 0 | 5-(CH₂)₂CH(OH)(CH₂)-cHx |
| 1-31 | H | — | PrCMe₂ | 0 | 5-(CH₂)₂CH(OH)(CH₂)-cHx |
| 1-32 | H | — | BuCMe₂ | 0 | 5-(CH₂)₂CH(OH)(CH₂)-cHx |
| 1-33 | H | — | PnCMe₂ | 0 | 5-(CH₂)₂CH(OH)(CH₂)-cHx |
| 1-34 | H | — | CH₃OCH₂ | 0 | 5-(CH₂)₂CH(OH)(CH₂)-cHx |
| 1-35 | H | — | EtOCH₂ | 0 | 5-(CH₂)₂CH(OH)(CH₂)-cHx |
| 1-36 | H | — | S-tBu | 0 | 5-(CH₂)₂CH(OH)(CH₂)-cHx |
| 1-37 | H | — | S-iPr | 0 | 5-(CH₂)₂CH(OH)(CH₂)-cHx |
| 1-38 | H | — | S-Ph | 0 | 5-(CH₂)₂CH(OH)(CH₂)-cHx |
| 1-39 | H | H | tBu | 1 | 5-(CH₂)₂CH(OH)(CH₂)-cHx |
| 1-40 | H | H | iPr | 1 | 5-(CH₂)₂CH(OH)(CH₂)-cHx |
| 1-41 | H | Bu | tBu | 1 | 5-(CH₂)₂CH(OH)(CH₂)-cHx |
| 1-42 | H | Pn | tBu | 1 | 5-(CH₂)₂CH(OH)(CH₂)-cHx |
| 1-43 | H | Hx | tBu | 1 | 5-(CH₂)₂CH(OH)(CH₂)-cHx |
| 1-44 | H | Hp | tBu | 1 | 5-(CH₂)₂CH(OH)(CH₂)-cHx |
| 1-45 | 3-Cl | Hp | tBu | 1 | 5-(CH₂)₂CH(OH)(CH₂)-cHx |
| 1-46 | 3-Br | Hp | tBu | 1 | 5-(CH₂)₂CH(OH)(CH₂)-cHx |
| 1-47 | 3-OMe | Hp | tBu | 1 | 5-(CH₂)₂CH(OH)(CH₂)-cHx |
| 1-48 | 2-OMe | Hp | tBu | 1 | 5-(CH₂)₂CH(OH)(CH₂)-cHx |
| 1-49 | H | — | tBu | 0 | 5-(CH₂)₂CH(OH)(CH 2)₃-cHx |

TABLE 1-continued

| Cpd. No. | $R^a$ | $R^2$ | $R^3$ | n | $R^4$ |
|---|---|---|---|---|---|
| 1-50 | H | — | iPr | 0 | 5-$(CH_2)_2CH(OH)(CH_2)_3$-cHx |
| 1-51 | H | — | iBu | 0 | 5-$(CH_2)_2CH(OH)(CH_2)_3$-cHx |
| 1-52 | H | — | Et | 0 | 5-$(CH_2)_2CH(OH)(CH_2)_3$-cHx |
| 1-53 | H | — | $MeOCH_2CMe_2$ | 0 | 5-$(CH_2)_2CH(OH)(CH_2)_3$-cHx |
| 1-54 | H | — | $EtCMe_2$ | 0 | 5-$(CH_2)_2CH(OH)(CH_2)_3$-cHx |
| 1-55 | H | — | $PrCMe_2$ | 0 | 5-$(CH_2)_2CH(OH)(CH_2)_3$-cHx |
| 1-56 | H | — | $BuCMe_2$ | 0 | 5-$(CH_2)_2CH(OH)(CH_2)_3$-cHx |
| 1-57 | H | — | PnCMe | 0 | 5-$(CH_2)_2CH(OH)(CH_2)_3$-cHx |
| 1-58 | H | — | $CH_3OCH_2$ | 0 | 5-$(CH_2)_2CH(OH)(CH_2)_3$-cHx |
| 1-59 | H | — | $EtOCH_2$ | 0 | 5-$(CH_2)_2CH(OH)(CH_2)_3$-cHx |
| 1-60 | H | — | S-tBu | 0 | 5-$(CH_2)_2CH(OH)(CH_2)_3$-cHx |
| 1-61 | H | — | S-iPr | 0 | 5-$(CH_2)_2CH(OH)(CH_2)_3$-cHx |
| 1-62 | H | — | S-Ph | 0 | 5-$(CH_2)_2CH(OH)(CH_2)_3$-cHx |
| 1-63 | H | H | tBu | 1 | 5-$(CH_2)_2CH(OH)(CH_2)_3$-cHx |
| 1-64 | H | H | iPr | 1 | 5-$(CH_2)_2CH(OH)(CH_2)_3$-cHx |
| 1-65 | H | Bu | tBu | 1 | 5-$(CH_2)_2CH(OH)(CH_2)_3$-cHx |
| 1-66 | H | Pn | tBu | 1 | 5-$(CH_2)_2CH(OH)(CH_2)_3$-cHx |
| 1-67 | H | Hx | tBu | 1 | 5-$(CH_2)_2CH(OH)(CH_2)_3$-cHx |
| 1-68 | H | Hp | tBu | 1 | 5-$(CH_2)_2CH(OH)(CH_2)_3$-cHx |
| 1-69 | 3-Cl | Hp | tBu | 1 | 5-$(CH_2)_2CH(OH)(CH_2)_3$-cHx |
| 1-70 | 3-Br | Hp | tBu | 1 | 5-$(CH_2)_2CH(OH)(CH_2)_3$-cHx |
| 1-71 | 3-OMe | Hp | tBu | 1 | 5-$(CH_2)_2CH(OH)(CH_2)_3$-cHx |
| 1-72 | 2-OMe | Hp | tBu | 1 | 5-$(CH_2)_2CH(OH)(CH_2)_3$-cHx |
| 1-73 | H | — | tBu | 0 | 5-$(CH_2)_2CH(OH)(CH_2)_4$-cHx |
| 1-74 | H | — | iPr | 0 | 5-$(CH_2)_2CH(OH)(CH_2)_4$-cHx |
| 1-75 | H | — | iBu | 0 | 5-$(CH_2)_2CH(OH)(CH_2)_4$-cHx |
| 1-76 | H | — | Et | 0 | 5-$(CH_2)_2CH(OH)(CH_2)_4$-cHx |
| 1-77 | H | — | $MeOCH_2CMe_2$ | 0 | 5-$(CH_2)_2CH(OH)(CH_2)_4$-cHx |
| 1-78 | H | — | $EtCMe_2$ | 0 | 5-$(CH_2)_2CH(OH)(CH_2)_4$-cHx |
| 1-79 | H | — | $PrCMe_2$ | 0 | 5-$(CH_2)_2CH(OH)(CH_2)_4$-cHx |
| 1-80 | H | — | $BuCMe_2$ | 0 | 5-$(CH_2)_2CH(OH)(CH_2)_4$-cHx |
| 1-81 | H | — | $PnCMe_2$ | 0 | 5-$(CH_2)_2CH(OH)(CH_2)_4$-cHx |
| 1-82 | H | — | $CH_3OCH_2$ | 0 | 5-$(CH_2)_2CH(OH)(CH_2)_4$-cHx |
| 1-83 | H | — | $EtOCH_2$ | 0 | 5-$(CH_2)_2CH(OH)(CH_2)_4$-cHx |
| 1-84 | H | — | S-tBu | 0 | 5-$(CH_2)_2CH(OH)(CH_2)_4$-cHx |
| 1-85 | H | — | S-iPr | 0 | 5-$(CH_2)_2CH(OH)(CH_2)_4$-cHx |
| 1-86 | H | — | S-Ph | 0 | 5-$(CH_2)_2CH(OH)(CH_2)_4$-cHx |
| 1-87 | H | H | tBu | 1 | 5-$(CH_2)_2CH(OH)(CH_2)_4$-cHx |
| 1-88 | H | H | iPr | 1 | 5-$(CH_2)_2CH(OH)(CH_2)_4$-cHx |
| 1-89 | H | Bu | tBu | 1 | 5-$(CH_2)_2CH(OH)(CH_2)_4$-cHx |
| 1-90 | H | Pn | tBu | 1 | 5-$(CH_2)_2CH(OH)(CH_2)_4$-cHx |
| 1-91 | H | Hx | tBu | 1 | 5-$(CH_2)_2CH(OH)(CH_2)_4$-cHx |
| 1-92 | H | Hp | tBu | 1 | 5-$(CH_2)_2CH(OH)(CH_2)_4$-cHx |
| 1-93 | 3-Cl | Hp | tBu | 1 | 5-$(CH_2)_2CH(OH)(CH_2)_4$-cHx |
| 1-94 | 3-Br | Hp | tBu | 1 | 5-$(CH_2)_2CH(OH)(CH_2)_4$-cHx |
| 1-95 | 3-OMe | Hp | tBu | 1 | 5-$(CH_2)_2CH(OH)(CH_2)_4$-cHx |
| 1-96 | 2-OMe | Hp | tBu | 1 | 5-$(CH_2)_2CH(OH)(CH_2)_4$-cHx |
| 1-97 | H | — | tBu | 0 | 5-$(CH_2)_2CH(OH)(CH_2)_5$-cHx |
| 1-98 | H | — | iPr | 0 | 5-$(CH_2)_2CH(OH)(CH_2)_5$-cHx |
| 1-99 | H | — | iBu | 0 | 5-$(CH_2)_2CH(OH)(CH_2)_5$-cHx |
| 1-100 | H | — | Et | 0 | 5-$(CH_2)_2CH(OH)(CH_2)_5$-cHx |
| 1-101 | H | — | $MeOCH_2CMe_2$ | 0 | 5-$(CH_2)_2CH(OH)(CH_2)_5$-cHx |
| 1-102 | H | — | $EtCMe_2$ | 0 | 5-$(CH_2)_2CH(OH)(CH_2)_5$-cHx |
| 1-103 | H | — | $PrCMe_2$ | 0 | 5-$(CH_2)_2CH(OH)(CH_2)_5$-cHx |
| 1-104 | H | — | $BuCMe_2$ | 0 | 5-$(CH_2)_2CH(OH)(CH_2)_5$-cHx |
| 1-105 | H | — | $PnCMe_2$ | 0 | 5-$(CH_2)_2CH(OH)(CH_2)_5$-cHx |
| 1-106 | H | — | $CH_3OCH_2$ | 0 | 5-$(CH_2)_2CH(OH)(CH_2)_5$-cHx |
| 1-107 | H | — | $EtOCH_2$ | 0 | 5-$(CH_2)_2CH(OH)(CH_2)_5$-cHx |
| 1-108 | H | — | S-tBu | 0 | 5-$(CH_2)_2CH(OH)(CH_2)_5$-cHx |
| 1-109 | H | — | S-iPr | 0 | 5-$(CH_2)_2CH(OH)(CH_2)_5$-cHx |
| 1-110 | H | — | S-Ph | 0 | 5-$(CH_2)_2CH(OH)(CH_2)_5$-cHx |
| 1-111 | H | H | tBu | 1 | 5-$(CH_2)_2CH(OH)(CH_2)_5$-cHx |
| 1-112 | H | H | iPr | 1 | 5-$(CH_2)_2CH(OH)(CH_2)_5$-cHx |
| 1-113 | H | Bu | tBu | 1 | 5-$(CH_2)_2CH(OH)(CH_2)_5$-cHx |
| 1-114 | H | Pn | tBu | 1 | 5-$(CH_2)_2CH(OH)(CH_2)_5$-cHx |
| 1-115 | H | Hx | tBu | 1 | 5-$(CH_2)_2CH(OH)(CH_2)_5$-cHx |
| 1-116 | H | Hp | tBu | 1 | 5-$(CH_2)_2CH(OH)(CH_2)_5$-cHx |
| 1-117 | 3-Cl | Hp | tBu | 1 | 5-$(CH_2)_2CH(OH)(CH_2)_5$-cHx |
| 1-118 | 3-Br | Hp | tBu | 1 | 5-$(CH_2)_2CH(OH)(CH_2)_5$-cHx |
| 1-119 | 3-OMe | Hp | tBu | 1 | 5-$(CH_2)_2CH(OH)(CH_2)_5$-cHx |
| 1-120 | H | — | tBu | 0 | 5-$(CH_2)_2CH(OH)(CH_2)_6$-cHx |
| 1-121 | H | — | iPr | 0 | 5-$(CH_2)_2CH(OH)(CH_2)_6$-cHx |
| 1-122 | H | — | iBu | 0 | 5-$(CH_2)_2CH(OH)(CH_2)_6$-cHx |
| 1-123 | H | — | Et | 0 | 5-$(CH_2)_2CH(OH)(CH_2)_6$-cHx |
| 1-124 | H | — | $MeOCH_2CMe_2$ | 0 | 5-$(CH_2)_2CH(OH)(CH_2)_6$-cHx |
| 1-125 | H | — | $CH_3OCH_2$ | 0 | 5-$(CH_2)_2CH(OH)(CH_2)_6$-cHx |

TABLE 1-continued

| Cpd. No. | $R^a$ | $R^2$ | $R^3$ | n | $R^4$ |
|---|---|---|---|---|---|
| 1-126 | H | — | EtOCH$_2$ | 0 | 5-(CH$_2$)$_2$CH(OH)(CH$_2$)$_6$-cHx |
| 1-127 | H | — | S-tBu | 0 | 5-(CH$_2$)$_2$CH(OH)(CH$_2$)$_6$-cHx |
| 1-128 | H | — | S-iPr | 0 | 5-(CH$_2$)$_2$CH(OH)(CH$_2$)$_6$-cHx |
| 1-129 | H | — | S-Ph | 0 | 5-(CH$_2$)$_2$CH(OH)(CH$_2$)$_6$-cHx |
| 1-130 | H | H | tBu | 1 | 5-(CH$_2$)$_2$CH(OH)(CH$_2$)$_6$-cHx |
| 1-131 | H | — | tBu | 0 | 5-(CH$_2$)$_2$CH(OH)-cHx |
| 1-132 | H | — | iPr | 0 | 5-(CH$_2$)$_2$CH(OH)-cHx |
| 1-133 | H | — | iBu | 0 | 5-(CH$_2$)$_2$CH(OH)-cHx |
| 1-134 | H | — | Et | 0 | 5-(CH$_2$)$_2$CH(OH)-cHx |
| 1-135 | H | — | MeOCH$_2$CMe$_2$ | 0 | 5-(CH$_2$)$_2$CH(OH)-cHx |
| 1-136 | H | — | EtCMe$_2$ | 0 | 5-(CH$_2$)$_2$CH(OH)-cHx |
| 1-137 | H | — | PrCMe$_2$ | 0 | 5-(CH$_2$)$_2$CH(OH)-cHx |
| 1-138 | H | — | BuCMe$_2$ | 0 | 5-(CH$_2$)$_2$CH(OH)-cHx |
| 1-139 | H | — | PnCMe$_2$ | 0 | 5-(CH$_2$)$_2$CH(OH)-cHx |
| 1-140 | H | — | CH$_3$OCH$_2$ | 0 | 5-(CH$_2$)$_2$CH(OH)-cHx |
| 1-141 | H | — | EtOCH$_2$ | 0 | 5-(CH$_2$)$_2$CH(OH)-cHx |
| 1-142 | H | — | S-tBu | 0 | 5-(CH$_2$)$_2$CH(OH)-cHx |
| 1-143 | H | — | S-iPr | 0 | 5-(CH$_2$)$_2$CH(OH)-cHx |
| 1-144 | H | — | S-Ph | 0 | 5-(CH$_2$)$_2$CH(OH)-cHx |
| 1-145 | H | H | tBu | 1 | 5-(CH$_2$)$_2$CH(OH)-cHx |
| 1-146 | H | H | iPr | 1 | 5-(CH$_2$)$_2$CH(OH)-cHx |
| 1-147 | H | Bu | tBu | 1 | 5-(CH$_2$)$_2$CH(OH)-cHx |
| 1-148 | H | Pn | tBu | 1 | 5-(CH$_2$)$_2$CH(OH)-cHx |
| 1-149 | H | Hx | tBu | 1 | 5-(CH$_2$)$_2$CH(OH)-cHx |
| 1-150 | H | Hp | tBu | 1 | 5-(CH$_2$)$_2$CH(OH)-cHx |
| 1-151 | 3-Cl | Hp | tBu | 1 | 5-(CH$_2$)$_2$CH(OH)-cHx |
| 1-152 | 3-Br | Hp | tBu | 1 | 5-(CH$_2$)$_2$CH(OH)-cHx |
| 1-153 | 3-Ome | Hp | tBu | 1 | 5-(CH$_2$)$_2$CH(OH)-cHx |
| 1-154 | 2-OMe | Hp | tBu | 1 | 5-(CH$_2$)$_2$CH(OH)-cHx |
| 1-155 | H | — | tBu | 0 | 5-CH(OH)-cHx |
| 1-156 | H | — | iPr | 0 | 5-CH(OH)-cHx |
| 1-157 | H | — | iBu | 0 | 5-CH(OH)-cHx |
| 1-158 | H | — | Et | 0 | 5-CH(OH)-cHx |
| 1-159 | H | — | MeOCH$_2$CMe$_2$ | 0 | 5-CH(OH)-cHx |
| 1-160 | H | — | EtCMe$_2$ | 0 | 5-CH(OH)-cHx |
| 1-161 | H | — | PrCMe$_2$ | 0 | 5-CH(OH)-cHx |
| 1-162 | H | — | BuCMe$_2$ | 0 | 5-CH(OH)-cHx |
| 1-163 | H | — | PnCMe$_2$ | 0 | 5-CH(OH)-cHx |
| 1-164 | H | — | CH$_3$OCH$_2$ | 0 | 5-CH(OH)-cHx |
| 1-165 | H | — | EtOCH$_2$ | 0 | 5-CH(OH)-cHx |
| 1-166 | H | — | S-tBu | 0 | 5-CH(OH)-cHx |
| 1-167 | H | — | S-iPr | 0 | 5-CH(OH)-cHx |
| 1-168 | H | — | S-Ph | 0 | 5-CH(OH)-cHx |
| 1-169 | H | H | tBu | 1 | 5-CH(OH)-cHx |
| 1-170 | H | H | iPr | 1 | 5-CH(OH)-cHx |
| 1-171 | H | Bu | tBu | 1 | 5-CH(OH)-cHx |
| 1-172 | H | Pn | tBu | 1 | 5-CH(OH)-cHx |
| 1-173 | H | Hx | tBu | 1 | 5-CH(OH)-cHx |
| 1-174 | H | Hp | tBu | 1 | 5-CH(OH)-cHx |
| 1-175 | 3-Cl | Hp | tBu | 1 | 5-CH(OH)-cHx |
| 1-176 | 3-Br | Hp | tBu | 1 | 5-CH(OH)-cHx |
| 1-177 | 3-OMe | Hp | tBu | 1 | 5-CH(OH)-cHx |
| 1-178 | 2-OMe | Hp | tBu | 1 | 5-CH(OH)-cHx |
| 1-179 | H | — | tBu | 0 | 5-CH(OH)(CH$_2$)-cHx |
| 1-180 | H | — | iPr | 0 | 5-CH(OH)(CH$_2$)-cHx |
| 1-181 | H | — | iBu | 0 | 5-CH(OH)(CH$_2$)-cHx |
| 1-182 | H | — | Et | 0 | 5-CH(OH)(CH$_2$)-cHx |
| 1-183 | H | — | MeOCH$_2$CMe$_2$ | 0 | 5-CH(OH)(CH$_2$)-cHx |
| 1-184 | H | — | EtCMe$_2$ | 0 | 5-CH(OH)(CH$_2$)-cHx |
| 1-185 | H | — | PrCHc$_2$ | 0 | 5-CH(OH)(CH$_2$)-cHx |
| 1-186 | H | — | BuCMe$_2$ | 0 | 5-CH(OH)(CH$_2$)-cHx |
| 1-187 | H | — | PnCMe$_2$ | 0 | 5-CH(OH)(CH$_2$)-cHx |
| 1-188 | H | — | CH$_3$OCH$_2$ | 0 | 5-CH(OH)(CH$_2$)-cHx |
| 1-189 | H | — | EtOCH$_2$ | 0 | 5-CH(OH)(CH$_2$)-cHx |
| 1-190 | H | — | S-tBu | 0 | 5-CH(OH)(CH$_2$)-cHx |
| 1-191 | H | — | S-iPr | 0 | 5-CH(OH)(CH$_2$)-cHx |
| 1-192 | H | — | S-Ph | 0 | 5-CH(OH)(CH$_2$)-cHx |
| 1-193 | H | H | tBu | 1 | 5-CH(OH)(CH$_2$)-cHx |
| 1-194 | H | H | iPr | 1 | 5-CH(OH)(CH$_2$)-cHx |
| 1-196 | H | Pn | tBu | 1 | 5-CH(OH)(CH$_2$)-cHx |
| 1-197 | H | Hx | tBu | 1 | 5-CH(OH)(CH$_2$)-cHx |
| 1-198 | H | Hp | tBu | 1 | 5-CH(OH)(CH$_2$)-cHx |
| 1-199 | 3-Cl | Hp | tBu | 1 | 5-CH(OH)(CH$_2$)-cHx |
| 1-200 | 3-Br | Hp | tBu | 1 | 5-CH(OH)(CH$_2$)-cHx |
| 1-201 | 3-OMe | Hp | tBu | 1 | 5-CH(OH)(CH$_2$)-cHx |
| 1-202 | 2-OMe | Hp | tBu | 1 | 5-CH(OH)(CH$_2$)-cHx |

TABLE 1-continued

| Cpd. No. | $R^a$ | $R^2$ | $R^3$ | n | $R^4$ |
|---|---|---|---|---|---|
| 1-203 | H | — | tBu | 0 | 5-CH(OH)(CH$_2$)$_2$-cHx |
| 1-204 | H | — | iPr | 0 | 5-CH(OH)(CH$_2$)$_2$-cHx |
| 1-205 | H | — | iBu | 0 | 5-CH(OH)(CH$_2$)$_2$-cHx |
| 1-206 | H | — | Et | 0 | 5-CH(OH)(CH$_2$)$_2$-cHx |
| 1-207 | H | — | MeOCH$_2$CMe$_2$ | 0 | 5-CH(OH)(CH$_2$)$_2$-cHx |
| 1-208 | H | — | EtCMe$_2$ | 0 | 5-CH(OH)(CH$_2$)$_2$-cHx |
| 1-209 | H | — | PrCMe$_2$ | 0 | 5-CH(OH)(CH$_2$)$_2$-cHx |
| 1-210 | H | — | BuCMe$_2$ | 0 | 5-CH(OH)(CH$_2$)$_2$-cHx |
| 1-211 | H | — | PnCMe$_2$ | 0 | 5-CH(OH)(CH$_2$)$_2$-cHx |
| 1-212 | H | — | CH$_3$OCH$_2$ | 0 | 5-CH(OH)(CH$_2$)$_2$-cHx |
| 1-213 | H | — | EtOCH$_2$ | 0 | 5-CH(OH)(CH$_2$)$_2$-cHx |
| 1-214 | H | — | S-tBu | 0 | 5-CH(OH)(CH$_2$)$_2$-cHx |
| 1-215 | H | — | S-iPr | 0 | 5-CH(OH)(CH$_2$)$_2$-cHx |
| 1-216 | H | — | S-Ph | 0 | 5-CH(OH)(CH$_2$)$_2$-cHx |
| 1-217 | H | H | tBu | 1 | 5-CH(OH)(CH$_2$)$_2$-cHx |
| 1-218 | H | H | iPr | 1 | 5-CH(OH)(CH$_2$)$_2$-cHx |
| 1-219 | H | Bu | tBu | 1 | 5-CH(OH)(CH$_2$)$_2$-cHx |
| 1-220 | H | Pn | tBu | 1 | 5-CH(OH)(CH$_2$)$_2$-cHx |
| 1-221 | H | Hx | tBu | 1 | 5-CH(OH)(CH$_2$)$_2$-cHx |
| 1-222 | H | Hp | tBu | 1 | 5-CH(OH)(CH$_2$)$_2$-cHx |
| 1-223 | 3-Cl | Hp | tBu | 1 | 5-CH(OH)(CH$_2$)$_2$-cHx |
| 1-224 | 3-Br | Hp | tBu | 1 | 5-CH(OH)(CH$_2$)$_2$-cHx |
| 1-225 | 3-OMe | Hp | tBu | 1 | 5-CH(OH)(CH$_2$)$_2$-cHx |
| 1-226 | 2-OMe | Hp | tBu | 1 | 5-CH(OH)(CH$_2$)$_2$-cHx |
| 1-227 | H | — | tBu | 0 | 5-CH(OH)(CH$_2$)$_3$-cHx |
| 1-228 | H | — | iPr | 0 | 5-CH(OH)(CH$_2$)$_3$-cHx |
| 1-229 | H | — | iBu | 0 | 5-CH(OH)(CH$_2$)$_3$-cHx |
| 1-230 | H | — | Et | 0 | 5-CH(OH)(CH$_2$)$_3$-cHx |
| 1-231 | H | — | MeOCH$_2$CMe$_2$ | 0 | 5-CH(OH)(CH$_2$)$_3$-cHx |
| 1-232 | H | — | EtCMe$_2$ | 0 | 5-CH(OH)(CH$_2$)$_3$-cHx |
| 1-233 | H | — | PrCMe$_2$ | 0 | 5-CH(OH)(CH$_2$)$_3$-cHx |
| 1-234 | H | — | BuCMe$_2$ | 0 | 5-CH(OH)(CH$_2$)$_3$-cHx |
| 1-235 | H | — | PnCMe$_2$ | 0 | 5-CH(OH)(CH$_2$)$_3$-cHx |
| 1-236 | H | — | CH$_3$OCH$_2$ | 0 | 5-CH(OH)(CH$_2$)$_3$-cHx |
| 1-237 | H | — | EtOCH$_2$ | 0 | 5-CH(OH)(CH$_2$)$_3$-cHx |
| 1-238 | H | — | S-tBu | 0 | 5-CH(OH)(CH$_2$)$_3$-cHx |
| 1-239 | H | — | S-iPr | 0 | 5-CH(OH)(CH$_2$)$_3$-cHx |
| 1-240 | H | — | S-Ph | 0 | 5-CH(OH)(CH$_2$)$_3$-cHx |
| 1-241 | H | H | tBu | 1 | 5-CH(OH)(CH$_2$)$_3$-cHx |
| 1-242 | H | H | iPr | 1 | 5-CH(OH)(CH$_2$)$_3$-cHx |
| 1-243 | H | Bu | tBu | 1 | 5-CH(OH)(CH$_2$)$_3$-cHx |
| 1-244 | H | Pn | tBu | 1 | 5-CH(OH)(CH$_2$)$_3$-cHx |
| 1-245 | H | Hx | tBu | 1 | 5-CH(OH)(CH$_2$)$_3$-cHx |
| 1-246 | H | Hp | tBu | 1 | 5-CH(OH)(CH$_2$)$_3$-cHx |
| 1-247 | 3-Cl | Hp | tBu | 1 | 5-CH(OH)(CH$_2$)$_3$-cHx |
| 1-248 | 3-Br | Hp | tBu | 1 | 5-CH(OH)(CH$_2$)$_3$-cHx |
| 1-249 | 3-OMe | Hp | tBu | 1 | 5-CH(OH)(CH$_2$)$_3$-cHx |
| 1-250 | 2-OMe | Hp | tBu | 1 | 5-CH(OH)(CH$_2$)$_3$-cHx |
| 1-251 | H | — | tBu | 0 | 5-CH(OH)(CH$_2$)$_4$-cHx |
| 1-252 | H | — | iPr | 0 | 5-CH(OH)(CH$_2$)$_4$-cHx |
| 1-253 | H | — | iBu | 0 | 5-CH(OH)(CH$_2$)$_4$-cHx |
| 1-254 | H | — | Et | 0 | 5-CH(OH)(CH$_2$)$_4$-cHx |
| 1-255 | H | — | MeOCH$_2$CMe$_2$ | 0 | 5-CH(OH)(CH$_2$)$_4$-cHx |
| 1-256 | H | — | EtCMe$_2$ | 0 | 5-CH(OH)(CH$_2$)$_4$-cHx |
| 1-257 | H | — | PrCMe$_2$ | 0 | 5-CH(OH)(CH$_2$)$_4$-cHx |
| 1-258 | H | — | BuCMe$_2$ | 0 | 5-CH(OH)(CH$_2$)$_4$-cHx |
| 1-259 | H | — | PnCMe$_2$ | 0 | 5-CH(OH)(CH$_2$)$_4$-cHx |
| 1-260 | H | — | CH$_3$OCH$_2$ | 0 | 5-CH(OH)(CH$_2$)$_4$-cHx |
| 1-261 | H | — | EtOCH$_2$ | 0 | 5-CH(OH)(CH$_2$)$_4$-cHx |
| 1-262 | H | — | S-tBu | 0 | 5-CH(OH)(CH$_2$)$_4$-cHx |
| 1-263 | H | — | S-iPr | 0 | 5-CH(OH)(CH$_2$)$_4$-cHx |
| 1-264 | H | — | S-Ph | 0 | 5-CH(OH)(CH$_2$)$_4$-cHx |
| 1-265 | H | H | tBu | 1 | 5-CH(OH)(CH$_2$)$_4$-cHx |
| 1-266 | H | H | iPr | 1 | 5-CH(OH)(CH$_2$)$_4$-cHx |
| 1-267 | H | Bu | tBu | 1 | 5-CH(OH)(CH$_2$)$_4$-cHx |
| 1-268 | H | Pn | tBu | 1 | 5-CH(OH)(CH$_2$)$_4$-cHx |
| 1-269 | H | Hx | tBu | 1 | 5-CH(OH)(CH$_2$)$_4$-cHx |
| 1-270 | H | Hp | tBu | 1 | 5-CH(OH)(CH$_2$)$_4$-cHx |
| 1-271 | 3-Cl | Hp | tBu | 1 | 5-CH(OH)(CH$_2$)$_4$-cHx |
| 1-272 | 3-Br | Hp | tBu | 1 | 5-CH(OH)(CH$_2$)$_4$-cHx |
| 1-273 | 3-OMe | Hp | tBu | 1 | 5-CH(OH)(CH$_2$)$_4$-cHx |
| 1-274 | 2-OMe | Hp | tBu | 1 | 5-CH(OH)(CH$_2$)$_4$-cHx |
| 1-275 | H | — | tBu | 0 | 5-CH(OH)(CH$_2$)$_5$-cHx |
| 1-276 | H | — | iPr | 0 | 5-CH(OH)(CH$_2$)$_5$-cHx |
| 1-277 | H | — | iBu | 0 | 5-CH(OH)(CH$_2$)$_5$-cHx |
| 1-278 | H | — | Et | 0 | 5-CH(OH)(CH$_2$)$_5$-cHx |

TABLE 1-continued

| Cpd. No. | $R^a$ | $R^2$ | $R^3$ | n | $R^4$ |
|---|---|---|---|---|---|
| 1-279 | H | — | MeOCH$_2$CMe$_2$ | 0 | 5-CH(OH)(CH$_2$)$_5$-cHx |
| 1-280 | H | — | EtCMe$_2$ | 0 | 5-CH(OH)(CH$_2$)$_5$-cHx |
| 1-281 | H | — | PrCMe$_2$ | 0 | 5-CH(OH)(CH$_2$)$_5$-cHx |
| 1-282 | H | — | BuCMe$_2$ | 0 | 5-CH(OH)(CH$_2$)$_5$-cHx |
| 1-283 | H | — | PnCMe$_2$ | 0 | 5-CH(OH)(CH$_2$)$_5$-cHx |
| 1-284 | H | — | CH$_3$OCH$_2$ | 0 | 5-CH(OH)(CH$_2$)$_5$-cHx |
| 1-285 | H | — | EtOCH$_2$ | 0 | 5-CH(OH)(CH$_2$)$_5$-cHx |
| 1-286 | H | — | S-tBu | 0 | 5-CH(OH)(CH$_2$)$_5$-cHx |
| 1-287 | H | — | S-iPr | 0 | 5-CH(OH)(CH$_2$)$_5$-cHx |
| 1-288 | H | — | S-Ph | 0 | 5-CH(OH)(CH$_2$)$_5$-cHx |
| 1-289 | H | H | tBu | 1 | 5-CH(OH)(CH$_2$)$_5$-cHx |
| 1-290 | H | H | iPr | 1 | 5-CH(OH)(CH$_2$)$_5$-cHx |
| 1-291 | H | Bu | tBu | 1 | 5-CH(OH)(CH$_2$)$_5$-cHx |
| 1-292 | H | Pn | tBu | 1 | 5-CH(OH)(CH$_2$)$_5$-cHx |
| 1-293 | H | Hx | tBu | 1 | 5-CH(OH)(CH$_2$)$_5$-cHx |
| 1-294 | H | Hp | tBu | 1 | 5-CH(OH)(CH$_2$)$_5$-cHx |
| 1-295 | 3-Cl | Hp | tBu | 1 | 5-CH(OH)(CH$_2$)$_5$-cHx |
| 1-296 | 3-Br | Hp | tBu | 1 | 5-CH(OH)(CH$_2$)$_5$-cHx |
| 1-297 | 3-OMe | Hp | tBu | 1 | 5-CH(OH)(CH$_2$)$_5$-cHx |
| 1-298 | 2-OMe | Hp | tBu | 1 | 5-CH(OH)(CH$_2$)$_5$-cHx |
| 1-299 | H | — | tBu | 0 | 5-CH(OH)(CH$_2$)$_6$-cHx |
| 1-300 | H | — | iPr | 0 | 5-CH(OH)(CH$_2$)$_6$-cHx |
| 1-301 | H | — | iBu | 0 | 5-CH(OH)(CH$_2$)$_6$-cHx |
| 1-302 | H | — | Et | 0 | 5-CH(OH)(CH$_2$)$_6$-cHx |
| 1-303 | H | — | MeOCH$_2$CMe$_2$ | 0 | 5-CH(OH)(CH$_2$)$_6$-cHx |
| 1-304 | H | — | EtCMe$_2$ | 0 | 5-CH(OH)(CH$_2$)$_6$-cHx |
| 1-305 | H | — | PrCMe$_2$ | 0 | 5-CH(OH)(CH$_2$)$_6$-cHx |
| 1-306 | H | — | BuCMe$_2$ | 0 | 5-CH(OH)(CH$_2$)$_6$-cHx |
| 1-307 | H | — | PnCMe$_2$ | 0 | 5-CH(OH)(CH$_2$)$_6$-cHx |
| 1-308 | H | — | CH$_3$OCH$_2$ | 0 | 5-CH(OH)(CH$_2$)$_6$-cHx |
| 1-309 | H | — | EtOCH$_2$ | 0 | 5-CH(OH)(CH$_2$)$_6$-cHx |
| 1-310 | H | — | S-tBu | 0 | 5-CH(OH)(CH$_2$)$_6$-cHx |
| 1-311 | H | — | S-iPr | 0 | 5-CH(OH)(CH$_2$)$_6$-cHx |
| 1-312 | H | — | S-Ph | 0 | 5-CH(OH)(CH$_2$)$_6$-cHx |
| 1-313 | H | H | tBu | 1 | 5-CH(OH)(CH$_2$)$_6$-cHx |
| 1-314 | H | H | iPr | 1 | 5-CH(OH)(CH$_2$)$_6$-cHx |
| 1-315 | H | Bu | tBu | 1 | 5-CH(OH)(CH$_2$)$_6$-cHx |
| 1-316 | H | Pn | tBu | 1 | 5-CH(OH)(CH$_2$)$_6$-cHx |
| 1-317 | H | Hx | tBu | 1 | 5-CH(OH)(CH$_2$)$_6$-cHx |
| 1-318 | H | Hp | tBu | 1 | 5-CH(OH)(CH$_2$)$_6$-cHx |
| 1-319 | 3-Cl | Hp | tBu | 1 | 5-CH(OH)(CH$_2$)$_6$-cHx |
| 1-320 | 3-Br | Hp | tBu | 1 | 5-CH(OH)(CH$_2$)$_6$-cHx |
| 1-321 | 3-OMe | Hp | tBu | 1 | 5-CH(OH)(CH$_2$)$_6$-cHx |
| 1-322 | 2-OMe | Hp | tBu | 1 | 5-CH(OH)(CH$_2$)$_6$-cHx |
| 1-323 | H | — | tBu | 0 | 5-CH(OH)(CH$_2$)$_7$-cHx |
| 1-324 | H | — | tBu | 0 | 5-(CH$_2$)CH(OH)-cHx |
| 1-325 | H | — | tBu | 0 | 5-(CH$_2$)CH(OH)-cHx |
| 1-326 | H | — | iPr | 0 | 5-(CH$_2$)CH(OH)-cHx |
| 1-327 | H | — | iBu | 0 | 5-(CH$_2$)CH(OH)-cHx |
| 1-328 | H | — | Et | 0 | 5-(CH$_2$)CH(OH)-cHx |
| 1-329 | H | — | MeOCH$_2$CMe$_2$ | 0 | 5-(CH$_2$)CH(OH)-cHx |
| 1-330 | H | — | EtCMe$_2$ | 0 | 5-(CH$_2$)CH(OH)-cHx |
| 1-331 | H | — | PrCMe$_2$ | 0 | 5-(CH$_2$)CH(OH)-cHx |
| 1-332 | H | — | BuCMe$_2$ | 0 | 5-(CH$_2$)CH(OH)-cHx |
| 1-333 | H | — | PnCMe$_2$ | 0 | 5-(CH$_2$)CH(OH)-cHx |
| 1-334 | H | — | CH$_3$OCH$_2$ | 0 | 5-(CH$_2$)CH(OH)-cHx |
| 1-335 | H | — | EtOCH$_2$ | 0 | 5-(CH$_2$)CH(OH)-cHx |
| 1-336 | H | — | S-tBu | 0 | 5-(CH$_2$)CH(OH)-cHx |
| 1-337 | H | — | S-iPr | 0 | 5-(CH$_2$)CH(OH)-cHx |
| 1-338 | H | — | S-Ph | 0 | 5-(CH$_2$)CH(OH)-cHx |
| 1-339 | H | H | tBu | 1 | 5-(CH$_2$)CH(OH)-cHx |
| 1-340 | H | H | iPr | 1 | 5-(CH$_2$)CH(OH)-cHx |
| 1-341 | H | Bu | tBu | 1 | 5-(CH$_2$)CH(OH)-cHx |
| 1-342 | H | Pn | tBu | 1 | 5-(CH$_2$)CH(OH)-cHx |
| 1-343 | H | Hx | tBu | 1 | 5-(CH$_2$)CH(OH)-cHx |
| 1-344 | H | Hp | tBu | 1 | 5-(CH$_2$)CH(OH)-cHx |
| 1-345 | 3-Cl | Hp | tBu | 1 | 5-(CH$_2$)CH(OH)-cHx |
| 1-346 | 3-Br | Hp | tBu | 1 | 5-(CH$_2$)CH(OH)-cHx |
| 1-347 | 3-OMe | Hp | tBu | 1 | 5-(CH$_2$)CH(OH)-cHx |
| 1-348 | 2-OMe | Hp | tBu | 1 | 5-(CH$_2$)CH(OH)-cHx |
| 1-349 | H | — | tBu | 0 | 5-(CH$_2$)CH(OH)(CH$_2$)-cHx |
| 1-350 | H | — | iPr | 0 | 5-(CH$_2$)CH(OH)(CH$_2$)-cHx |
| 1-351 | H | — | tBu | 0 | 5-(CH$_2$)CH(OH)(CH$_2$)-cHx |
| 1-352 | H | — | Et | 0 | 5-(CH$_2$)CH(OH)(CH$_2$)-cHx |
| 1-353 | H | — | MeOCH$_2$CMe$_2$ | 0 | 5-(CH$_2$)CH(OH)(CH$_2$)-cHx |
| 1-354 | H | — | EtCMe$_2$ | 0 | 5-(CH$_2$)CH(OH)(CH$_2$)-cHx |

TABLE 1-continued

| Cpd. No. | R$^a$ | R$^2$ | R$^3$ | n | R$^4$ |
|---|---|---|---|---|---|
| 1-355 | H | — | PrCMe$_2$ | 0 | 5-(CH$_2$)CH(OH)(CH$_2$)-cHx |
| 1-356 | H | — | BuCMe$_2$ | 0 | 5-(CH$_2$)CH(OH)(CH$_2$)-cHx |
| 1-357 | H | — | PnCMe$_2$ | 0 | 5-(CH$_2$)CH(OH)(CH$_2$)-cHx |
| 1-358 | H | — | CH$_3$OCH$_2$ | 0 | 5-(CH$_2$)CH(OH)(CH$_2$)-cHx |
| 1-359 | H | — | EtOCH$_2$ | 0 | 5-(CH$_2$)CH(OH)(CH$_2$)-cHx |
| 1-360 | H | — | S-tBu | 0 | 5-(CH$_2$)CH(OH)(CH$_2$)-cHx |
| 1-361 | H | — | S-iPr | 0 | 5-(CH$_2$)CH(OH)(CH$_2$)-cHx |
| 1-362 | H | — | S-Ph | 0 | 5-(CH$_2$)CH(OH)(CH$_2$)-cHx |
| 1-363 | H | H | tBu | 1 | 5-(CH$_2$)CH(OH)(CH$_2$)-cHx |
| 1-364 | H | H | iPr | 1 | 5-(CH$_2$)CH(OH)(CH$_2$)-cHx |
| 1-365 | H | Bu | tBu | 1 | 5-(CH$_2$)CH(OH)(CH$_2$)-cHx |
| 1-366 | H | Pn | tBu | 1 | 5-(CH$_2$)CH(OH)(CH$_2$)-cHx |
| 1-367 | H | Hx | tBu | 1 | 5-(CH$_2$)CH(OH)(CH$_2$)-cHx |
| 1-368 | H | Hp | tBu | 1 | 5-(CH$_2$)CH(OH)(CH$_2$)-cHx |
| 1-369 | 3-Cl | Hp | tBu | 1 | 5-(CH$_2$)CH(OH)(CH$_2$)-cHx |
| 1-370 | 3-Br | Hp | tBu | 1 | 5-(CH$_2$)CH(OH)(CH$_2$)-cHx |
| 1-371 | 3-OMe | Hp | tBu | 1 | 5-(CH$_2$)CH(OH)(CH$_2$)-cHx |
| 1-372 | 2-OMe | Hp | tBu | 1 | 5-(CH$_2$)CH(OH)(CH$_2$)-cHx |
| 1-373 | H | — | tBu | 0 | 5-(CH$_2$)CH(OH)(CH$_2$)$_2$-cHx |
| 1-374 | H | — | iPr | 0 | 5-(CH$_2$)CH(OH)(CH$_2$)$_2$-cHx |
| 1-375 | H | — | iBu | 0 | 5-(CH$_2$)CH(OH)(CH$_2$)$_2$-cHx |
| 1-376 | H | — | Et | 0 | 5-(CH$_2$)CH(OH)(CH$_2$)$_2$-cHx |
| 1-377 | H | — | MeOCH$_2$CMe$_2$ | 0 | 5-(CH$_2$)CH(OH)(CH$_2$)$_2$-cHx |
| 1-378 | H | — | EtCMe$_2$ | 0 | 5-(CH$_2$)CH(OH)(CH$_2$)$_2$-cHx |
| 1-379 | H | — | PrCMe$_2$ | 0 | 5-(CH$_2$)CH(OH)(CH$_2$)$_2$-cHx |
| 1-380 | H | — | BuCMe$_2$ | 0 | 5-(CH$_2$)CH(OH)(CH$_2$)$_2$-cHx |
| 1-381 | H | — | PnCMe$_2$ | 0 | 5-(CH$_2$)CH(OH)(CH$_2$)$_2$-cHx |
| 1-382 | H | — | CH$_3$OCH$_2$ | 0 | 5-(CH$_2$)CH(OH)(CH$_2$)$_2$-cHx |
| 1-383 | H | — | EtOCH$_2$ | 0 | 5-(CH$_2$)CH(OH)(CH$_2$)$_2$-cHx |
| 1-384 | H | — | S-tBu | 0 | 5-(CH$_2$)CH(OH)(CH$_2$)$_2$-cHx |
| 1-385 | H | — | S-iPr | 0 | 5-(CH$_2$)CH(OH)(CH$_2$)$_2$-cHx |
| 1-386 | H | — | S-Ph | 0 | 5-(CH$_2$)CH(OH)(CH$_2$)$_2$-cHx |
| 1-387 | H | H | tBu | 1 | 5-(CH$_2$)CH(OH)(CH$_2$)$_2$-cHx |
| 1-388 | H | H | iPr | 1 | 5-(CH$_2$)CH(OH)(CH$_2$)$_2$-cHx |
| 1-389 | H | Bu | tBu | 1 | 5-(CH$_2$)CH(OH)(CH$_2$)$_2$-cHx |
| 1-390 | H | Pn | tBu | 1 | 5-(CH$_2$)CH(OH)(CH$_2$)$_2$-cHx |
| 1-391 | H | Hx | tBu | 1 | 5-(CH$_2$)CH(OH)(CH$_2$)$_2$-cHx |
| 1-392 | H | Hp | tBu | 1 | 5-(CH$_2$)CH(OH)(CH$_2$)$_2$-cHx |
| 1-393 | 3-Cl | Hp | tBu | 1 | 5-(CH$_2$)CH(OH)(CH$_2$)$_2$-cHx |
| 1-394 | 3-Br | Hp | tBu | 1 | 5-(CH$_2$)CH(OH)(CH$_2$)$_2$-cHx |
| 1-395 | 3-OMe | Hp | tBu | 1 | 5-(CH$_2$)CH(OH)(CH$_2$)$_2$-cHx |
| 1-396 | 2-OMe | Hp | tBu | 1 | 5-(CH$_2$)CH(OH)(CH$_2$)$_2$-cHx |
| 1-397 | H | — | tBu | 0 | 5-(CH$_2$)CH(OH)(CH$_2$)$_3$-cHx |
| 1-398 | H | — | iPr | 0 | 5-(CH$_2$)CH(OH)(CH$_2$)$_3$-cHx |
| 1-399 | H | — | iBu | 0 | 5-(CH$_2$)CH(OH)(CH$_2$)$_3$-cHx |
| 1-400 | H | — | Et | 0 | 5-(CH$_2$)CH(OH)(CH$_2$)$_3$-cHx |
| 1-401 | H | — | MeOCH$_2$CMe$_2$ | 0 | 5-(CH$_2$)CH(OH)(CH$_2$)$_3$-cHx |
| 1-402 | H | — | EtCMe$_2$ | 0 | 5-(CH$_2$)CH(OH)(CH$_2$)$_3$-cHx |
| 1-403 | H | — | PrCMe$_2$ | 0 | 5-(CH$_2$)CH(OH)(CH$_2$)$_3$-cHx |
| 1-404 | H | — | BuCMe$_2$ | 0 | 5-(CH$_2$)CH(OH)(CH$_2$)$_3$-cHx |
| 1-405 | H | — | PnCMe$_2$ | 0 | 5-(CH$_2$)CH(OH)(CH$_2$)$_3$-cHx |
| 1-406 | H | — | CH$_3$OCH$_2$ | 0 | 5-(CH$_2$)CH(OH)(CH$_2$)$_3$-cHx |
| 1-407 | H | — | EtOCH$_2$ | 0 | 5-(CH$_2$)CH(OH)(CH$_2$)$_3$-cHx |
| 1-408 | H | — | S-tBu | 0 | 5-(CH$_2$)CH(OH)(CH$_2$)$_3$-cHx |
| 1-409 | H | — | S-iPr | 0 | 5-(CH$_2$)CH(OH)(CH$_2$)$_3$-cHx |
| 1-410 | H | — | S-Ph | 0 | 5-(CH$_2$)CH(OH)(CH$_2$)$_3$-cHx |
| 1-411 | H | H | tBu | 1 | 5-(CH$_2$)CH(OH)(CH$_2$)$_3$-cHx |
| 1-412 | H | H | iPr | 1 | 5-(CH$_2$)CH(OH)(CH$_2$)$_3$-cHx |
| 1-413 | H | Bu | tBu | 1 | 5-(CH$_2$)CH(OH)(CH$_2$)$_3$-cHx |
| 1-414 | H | Pn | tBu | 1 | 5-(CH$_2$)CH(OH)(CH$_2$)$_3$-cHx |
| 1-415 | H | Hx | tBu | 1 | 5-(CH$_2$)CH(OH)(CH$_2$)$_3$-cHx |
| 1-416 | H | Hp | tBu | 1 | 5-(CH$_2$)CH(OH)(CH$_2$)$_3$-cHx |
| 1-417 | 3-Cl | Hp | tBu | 1 | 5-(CH$_2$)CH(OH)(CH$_2$)$_3$-cHx |
| 1-418 | 3-Br | Hp | tBu | 1 | 5-(CH$_2$)CH(OH)(CH$_2$)$_3$-cHx |
| 1-419 | 3-OMe | Hp | tBu | 1 | 5-(CH$_2$)CH(OH)(CH$_2$)$_3$-cHx |
| 1-420 | 2-OMe | Hp | tBu | 1 | 5-(CH$_2$)CH(OH)(CH$_2$)$_3$-cHx |
| 1-421 | H | — | tBu | 0 | 5-(CH$_2$)CH(OH)(CH$_2$)$_4$-cHx |
| 1-422 | H | — | iPr | 0 | 5-(CH$_2$)CH(OH)(CH$_2$)$_4$-cHx |
| 1-423 | H | — | iBu | 0 | 5-(CH$_2$)CH(OH)(CH$_2$)$_4$-cHx |
| 1-424 | H | — | Et | 0 | 5-(CH$_2$)CH(OH)(CH$_2$)$_4$-cHx |
| 1-425 | H | — | MeOCH$_2$CMe$_2$ | 0 | 5-(CH$_2$)CH(OH)(CH$_2$)$_4$-cHx |
| 1-426 | H | — | EtCMe$_2$ | 0 | 5-(CH$_2$)CH(OH)(CH$_2$)$_4$-cHx |
| 1-427 | H | — | PrCMe$_2$ | 0 | 5-(CH$_2$)CH(OH)(CH$_2$)$_4$-cHx |
| 1-428 | H | — | BuCMe$_2$ | 0 | 5-(CH$_2$)CH(OH)(CH$_2$)$_4$-cHx |
| 1-429 | H | — | PnCMe$_2$ | 0 | 5-(CH$_2$)CH(OH)(CH$_2$)$_4$-cHx |
| 1-430 | H | — | CH$_3$OCH$_2$ | 0 | 5-(CH$_2$)CH(OH)(CH$_2$)$_4$-cHx |

TABLE 1-continued

| Cpd. No. | Rᵃ | R² | R³ | n | R⁴ |
|---|---|---|---|---|---|
| 1-431 | H | — | EtOCH₂ | 0 | 5-(CH₂)CH(OH)(CH₂)₄-cHx |
| 1-432 | H | — | S-tBu | 0 | 5-(CH₂)CH(OH)(CH₂)₄-cHx |
| 1-433 | H | — | S-iPr | 0 | 5-(CH₂)CH(OH)(CH₂)₄-cHx |
| 1-434 | H | — | S-Ph | 0 | 5-(CH₂)CH(OH)(CH₂)₄-cHx |
| 1-435 | H | H | tBu | 1 | 5-(CH₂)CH(OH)(CH₂)₄-cHx |
| 1-436 | H | H | iPr | 1 | 5-(CH₂)CH(OH)(CH₂)₄-cHx |
| 1-437 | H | Bu | tBu | 1 | 5-(CH₂)CH(OH)(CH₂)₄-cHx |
| 1-438 | H | Pn | tBu | 1 | 5-(CH₂)CH(OH)(CH₂)₄-cHx |
| 1-439 | H | Hx | tBu | 1 | 5-(CH₂)CH(OH)(CH₂)₄-cHx |
| 1-440 | H | Hp | tBu | 1 | 5-(CH₂)CH(OH)(CH₂)₄-cHx |
| 1-441 | 3-Cl | Hp | tBu | 1 | 5-(CH₂)CH(OH)(CH₂)₄-cHx |
| 1-442 | 3-Br | Hp | tBu | 1 | 5-(CH₂)CH(OH)(CH₂)₄-cHx |
| 1-443 | 3-OMe | Hp | tBu | 1 | 5-(CH₂)CH(OH)(CH₂)₄-cHx |
| 1-444 | 2-OMe | Hp | tBu | 1 | 5-(CH₂)CH(OH)(CH₂)₄-cHx |
| 1-445 | H | — | tBu | 0 | 5-(CH₂)CH(OH)(CH₂)₅-cHx |
| 1-446 | H | — | iPr | 0 | 5-(CH₂)CH(OH)(CH₂)₅-cHx |
| 1-447 | H | — | iBu | 0 | 5-(CH₂)CH(OH)(CH₂)₅-cHx |
| 1-448 | H | — | Et | 0 | 5-(CH₂)CH(OH)(CH₂)₅-cHx |
| 1-449 | H | — | MeOCH₂CMe₂ | 0 | 5-(CH₂)CH(OH)(CH₂)₅-cHx |
| 1-450 | H | — | EtCMe₂ | 0 | 5-(CH₂)CH(OH)(CH₂)₅-cHx |
| 1-451 | H | — | PrCMe₂ | 0 | 5-(CH₂)CH(OH)(CH₂)₅-cHx |
| 1-452 | H | — | BuCMe₂ | 0 | 5-(CH₂)CH(OH)(CH₂)₅-cHx |
| 1-453 | H | — | PnCMe₂ | 0 | 5-(CH₂)CH(OH)(CH₂)₅-cHx |
| 1-454 | H | — | CH₃OCH₂ | 0 | 5-(CH₂)CH(OH)(CH₂)₅-cHx |
| 1-455 | H | — | EtOCH₂ | 0 | 5-(CH₂)CH(OH)(CH₂)₅-cHx |
| 1-456 | H | — | S-tBu | 0 | 5-(CH₂)CH(OH)(CH₂)₅-cHx |
| 1-457 | H | — | S-iPr | 0 | 5-(CH₂)CH(OH)(CH₂)₅-cHx |
| 1-458 | H | — | S-Ph | 0 | 5-(CH₂)CH(OH)(CH₂)₅-cHx |
| 1-459 | H | H | tBu | 1 | 5-(CH₂)CH(OH)(CH₂)₅-cHx |
| 1-460 | H | H | iPr | 1 | 5-(CH₂)CH(OH)(CH₂)₅-cHx |
| 1-461 | H | Bu | tBu | 1 | 5-(CH₂)CH(OH)(CH₂)₅-cHx |
| 1-462 | H | Pn | tBu | 1 | 5-(CH₂)CH(OH)(CH₂)₅-cHx |
| 1-463 | H | Hx | tBu | 1 | 5-(CH₂)CH(OH)(CH₂)₅-cHx |
| 1-464 | H | Hp | tBu | 1 | 5-(CH₂)CH(OH)(CH₂)₅-cHx |
| 1-465 | 3-Cl | Hp | tBu | 1 | 5-(CH₂)CH(OH)(CH₂)₅-cHx |
| 1-466 | 3-Br | Hp | tBu | 1 | 5-(CH₂)CH(OH)(CH₂)₅-cHx |
| 1-467 | 3-OMe | Hp | tBu | 1 | 5-(CH₂)CH(OH)(CH₂)₅-cHx |
| 1-468 | 2-OMe | Hp | tBu | 1 | 5-(CH₂)CH(OH)(CH₂)₅-cHx |
| 1-469 | H | — | tBu | 0 | 5-CH₂CH(OH)(CH₂)₆-cHx |
| 1-470 | H | — | tBu | 0 | 5-CH₂CH(OH)(CH₂)₇-cHx |
| 1-471 | H | — | tBu | 0 | 5-(CH₂)₃CH(OH)-cHx |
| 1-472 | H | — | iPr | 0 | 5-(CH₂)₃CH(OH)-cHx |
| 1-473 | H | — | tBu | 0 | 5-(CH₂)₃CH(OH)-cHx |
| 1-474 | H | — | Et | 0 | 5-(CH₂)₃CH(OH)-cHx |
| 1-475 | H | — | MeOCH₂CMe₂ | 0 | 5-(CH₂)₃CH(OH)-cHx |
| 1-476 | H | — | EtCMe₂ | 0 | 5-(CH₂)₃CH(OH)-cHx |
| 1-477 | H | — | PrCMe₂ | 0 | 5-(CH₂)₃CH(OH)-cHx |
| 1-478 | H | — | BuCMe₂ | 0 | 5-(CH₂)₃CH(OH)-cHx |
| 1-479 | H | — | PnCMe₂ | 0 | 5-(CH₂)₃CH(OH)-cHx |
| 1-480 | H | — | CH₃OCH₂ | 0 | 5-(CH₂)₃CH(OH)-cHx |
| 1-481 | H | — | EtOCH₂ | 0 | 5-(CH₂)₃CH(OH)-cHx |
| 1-482 | H | — | S-tBu | 0 | 5-(CH₂)₃CH(OH)-cHx |
| 1-483 | H | — | S-iPr | 0 | 5-(CH₂)₃CH(OH)-cHx |
| 1-484 | H | — | S-Pr | 0 | 5-(CH₂)₃CH(OH)-cHx |
| 1-485 | H | H | tBu | 1 | 5-(CH₂)₃CH(OH)-cHx |
| 1-486 | H | H | iPr | 1 | 5-(CH₂)₃CH(OH)-cHx |
| 1-487 | H | Bu | tBu | 1 | 5-(CH₂)₃CH(OH)-cHx |
| 1-488 | H | Pn | tBu | 1 | 5-(CH₂)₃CH(OH)-cHx |
| 1-489 | H | Hx | tBu | 1 | 5-(CH₂)₃CH(OH)-cHx |
| 1-490 | H | Hp | tBu | 1 | 5-(CH₂)₃CH(OH)-cHx |
| 1-491 | 3-Cl | — | tBu | 0 | 5-(CH₂)₃CH(OH)-cHx |
| 1-492 | 3-Br | — | tBu | 0 | 5-(CH₂)₃CH(OH)-cHx |
| 1-493 | 3-OMe | — | tBu | 0 | 5-(CH₂)₃CH(OH)-cHx |
| 1-494 | 2-OMe | — | tBu | 0 | 5-(CH₂)₃CH(OH)-cHx |
| 1-495 | H | — | tBu | 0 | 5-(CH₂)₃CH(OH)(CH₂)-cHx |
| 1-496 | H | — | iPr | 0 | 5-(CH₂)₃CH(OH)(CH₂)-cHx |
| 1-497 | H | — | iBu | 0 | 5-(CH₂)₃CH(OH)(CH₂)-cHx |
| 1-498 | H | — | Et | 0 | 5-(CH₂)₃CH(OH)(CH₂)-cHx |
| 1-499 | H | — | MeOCH₂CMe₂ | 0 | 5-(CH₂)₃CH(OH)(CH₂)-cHx |
| 1-500 | H | — | EtCMe₂ | 0 | 5-(CH₂)₃CH(OH)(CH₂)-cHx |
| 1-501 | H | — | PrCMe₂ | 0 | 5-(CH₂)₃CH(OH)(CH₂)-cHx |
| 1-502 | H | — | BuCMe₂ | 0 | 5-(CH₂)₃CH(OH)(CH₂)-cHx |
| 1-503 | H | — | PnCMe₂ | 0 | 5-(CH₂)₃CH(OH)(CH₂)-cHx |
| 1-504 | H | — | CH₃OCH₂ | 0 | 5-(CH₂)₃CH(OH)(CH₂)-cHx |
| 1-505 | H | — | EtOCH₂ | 0 | 5-(CH₂)₃CH(OH)(CH₂)-cHx |
| 1-506 | H | — | S-tBu | 0 | 5-(CH₂)₃CH(OH)(CH₂)-cHx |

TABLE 1-continued

| Cpd. No. | $R^a$ | $R^2$ | $R^3$ | n | $R^4$ |
|---|---|---|---|---|---|
| 1-507 | H | — | S-iPr | 0 | 5-(CH$_2$)$_3$CH(OH)(CH$_2$)-cHx |
| 1-508 | H | — | S-Pr | 0 | 5-(CH$_2$)$_3$CH(OH)(CH$_2$)-cHx |
| 1-509 | H | — | tBu | 0 | 5-(CH$_2$)$_3$CH(OH)(CH$_2$)-cHx |
| 1-510 | H | — | iPr | 0 | 5-(CH$_2$)$_3$CH(OH)(CH$_2$)-cHx |
| 1-511 | H | Bu | tBu | 1 | 5-(CH$_2$)$_3$CH(OH)(CH$_2$)-cHx |
| 1-512 | H | Pn | tBu | 1 | 5-(CH$_2$)$_3$CH(OH)(CH$_2$)-cHx |
| 1-513 | H | Hx | tBu | 1 | 5-(CH$_2$)$_3$CH(OH)(CH$_2$)-cHx |
| 1-514 | H | Hp | tBu | 1 | 5-(CH$_2$)$_3$CH(OH)(CH$_2$)-cHx |
| 1-515 | 3-Cl | — | tBu | 0 | 5-(CH$_2$)$_3$CH(OH)(CH$_2$)-cHx |
| 1-516 | 3-Br | — | tBu | 0 | 5-(CH$_2$)$_3$CH(OH)(CH$_2$)-cHx |
| 1-517 | 3-OMe | — | tBu | 0 | 5-(CH$_2$)$_3$CH(OH)(CH$_2$)-cHx |
| 1-518 | 2-OMe | — | tBu | 0 | 5-(CH$_2$)$_3$CH(OH)(CH$_2$)-cHx |
| 1-519 | H | — | tBu | 0 | 5-(CH$_2$)$_3$CH(OH)(CH$_2$)$_2$-cHx |
| 1-520 | H | — | iPr | 0 | 5-(CH$_2$)$_3$CH(OH)(CH$_2$)$_2$-cHx |
| 1-521 | H | — | iBu | 0 | 5-(CH$_2$)$_3$CH(OH)(CH$_2$)$_2$-cHx |
| 1-522 | H | — | Et | 0 | 5-(CH$_2$)$_3$CH(OH)(CH$_2$)$_2$-cHx |
| 1-523 | H | — | MeOCH$_2$CMe$_2$ | 0 | 5-(CH$_2$)$_3$CH(OH)(CH$_2$)$_2$-cHx |
| 1-524 | H | — | EtCMe$_2$ | 0 | 5-(CH$_2$)$_3$CH(OH)(CH$_2$)$_2$-cHx |
| 1-525 | H | — | PrCMe$_2$ | 0 | 5-(CH$_2$)$_3$CH(OH)(CH$_2$)$_2$-cHx |
| 1-526 | H | — | BuCMe$_2$ | 0 | 5-(CH$_2$)$_3$CH(OH)(CH$_2$)$_2$-cHx |
| 1-527 | H | — | PnCMe$_2$ | 0 | 5-(CH$_2$)$_3$CH(OH)(CH$_2$)$_2$-cHx |
| 1-528 | H | — | CH$_3$OCH$_2$ | 0 | 5-(CH$_2$)$_3$CH(OH)(CH$_2$)$_2$-cHx |
| 1-529 | H | — | EtOCH$_2$ | 0 | 5-(CH$_2$)$_3$CH(OH)(CH$_2$)$_2$-cHx |
| 1-530 | H | — | S-tBu | 0 | 5-(CH$_2$)$_3$CH(OH)(CH$_2$)$_2$-cHx |
| 1-531 | H | — | S-iPr | 0 | 5-(CH$_2$)$_3$CH(OH)(CH$_2$)$_2$-cHx |
| 1-532 | H | — | S-Ph | 0 | 5-(CH$_2$)$_3$CH(OH)(CH$_2$)$_2$-cHx |
| 1-533 | H | H | tBu | 1 | 5-(CH$_2$)$_3$CH(OH)(CH$_2$)$_2$-cHx |
| 1-534 | H | H | iPr | 1 | 5-(CH$_2$)$_3$CH(OH)(CH$_2$)$_2$-cHx |
| 1-535 | H | Bu | tBu | 1 | 5-(CH$_2$)$_3$CH(OH)(CH$_2$)$_2$-cHx |
| 1-536 | H | Pn | tBu | 1 | 5-(CH$_2$)$_3$CH(OH)(CH$_2$)$_2$-cHx |
| 1-537 | H | Hx | tBu | 1 | 5-(CH$_2$)$_3$CH(OH)(CH$_2$)$_2$-cHx |
| 1-538 | H | Hp | tBu | 1 | 5-(CH$_2$)$_3$CH(OH)(CH$_2$)$_2$-cHx |
| 1-539 | 3-Cl | — | tBu | 0 | 5-(CH$_2$)$_3$CH(OH)(CH$_2$)$_2$-cHx |
| 1-540 | 3-Br | — | tBu | 0 | 5-(CH$_2$)$_3$CH(OH)(CH$_2$)$_2$-cHx |
| 1-541 | 3-OMe | — | tBu | 0 | 5-(CH$_2$)$_3$CH(OH)(CH$_2$)$_2$-cHx |
| 1-542 | 2-OMe | — | tBu | 0 | 5-(CH$_2$)$_3$CH(OH)(CH$_2$)$_2$-cHx |
| 1-543 | H | — | tBu | 0 | 5-(CH$_2$)$_3$CH(OH)(CH$_2$)$_3$-cHx |
| 1-544 | H | — | iPr | 0 | 5-(CH$_2$)$_3$CH(OH)(CH$_2$)$_3$-cHx |
| 1-545 | H | — | iBu | 0 | 5-(CH$_2$)$_3$CH(OH)(CH$_2$)$_3$-cHx |
| 1-546 | H | — | Et | 0 | 5-(CH$_2$)$_3$CH(OH)(CH$_2$)$_3$-cHx |
| 1-547 | H | — | MeOCH$_2$CMe$_2$ | 0 | 5-(CH$_2$)$_3$CH(OH)(CH$_2$)$_3$-cHx |
| 1-548 | H | — | EtCMe$_2$ | 0 | 5-(CH$_2$)$_3$CH(OH)(CH$_2$)$_3$-cHx |
| 1-549 | H | — | PrCMe$_2$ | 0 | 5-(CH$_2$)$_3$CH(OH)(CH$_2$)$_3$-cHx |
| 1-550 | H | — | BuCMe$_2$ | 0 | 5-(CH$_2$)$_3$CH(OH)(CH$_2$)$_3$-cHx |
| 1-551 | H | — | PnCMe$_2$ | 0 | 5-(CH$_2$)$_3$CH(OH)(CH$_2$)$_3$-cHx |
| 1-552 | H | — | CH$_3$OCH$_2$ | 0 | 5-(CH$_2$)$_3$CH(OH)(CH$_2$)$_3$-cHx |
| 1-553 | H | — | EtOCH$_2$ | 0 | 5-(CH$_2$)$_3$CH(OH)(CH$_2$)$_3$-cHx |
| 1-554 | H | — | S-tBu | 0 | 5-(CH$_2$)$_3$CH(OH)(CH$_2$)$_3$-cHx |
| 1-555 | H | — | S-iPr | 0 | 5-(CH$_2$)$_3$CH(OH)(CH$_2$)$_3$-cHx |
| 1-556 | H | — | S-Ph | 0 | 5-(CH$_2$)$_3$CH(OH)(CH$_2$)$_3$-cHx |
| 1-557 | H | H | tBu | 0 | 5-(CH$_2$)$_3$CH(OH)(CH$_2$)$_3$-cHx |
| 1-558 | H | H | iPr | 1 | 5-(CH$_2$)$_3$CH(OH)(CH$_2$)$_3$-cHx |
| 1-559 | H | Bu | tBu | 1 | 5-(CH$_2$)$_3$CH(OH)(CH$_2$)$_3$-cHx |
| 1-560 | H | Pn | tBu | 1 | 5-(CH$_2$)$_3$CH(OH)(CH$_2$)$_3$-cHx |
| 1-561 | H | Hx | tBu | 1 | 5-(CH$_2$)$_3$CH(OH)(CH$_2$)$_3$-cHx |
| 1-562 | H | Hp | tBu | 1 | 5-(CH$_2$)$_3$CH(OH)(CH$_2$)$_3$-cHx |
| 1-563 | 3-Cl | — | tBu | 0 | 5-(CH$_2$)$_3$CH(OH)(CH$_2$)$_3$-cHx |
| 1-564 | 3-Br | — | tBu | 0 | 5-(CH$_2$)$_3$CH(OH)(CH$_2$)$_3$-cHx |
| 1-565 | 3-OMe | — | tBu | 0 | 5-(CH$_2$)$_3$CH(OH)(CH$_2$)$_3$-cHx |
| 1-566 | 2-OMe | — | tBu | 0 | 5-(CH$_2$)$_3$CH(OH)(CH$_2$)$_3$-cHx |
| 1-567 | H | — | tBu | 0 | 5-(CH$_2$)$_3$CH(OH)(CH$_2$)$_4$-cHx |
| 1-568 | H | — | iPr | 0 | 5-(CH$_2$)$_3$CH(OH)(CH$_2$)$_4$-cHx |
| 1-569 | H | — | iBu | 0 | 5-(CH$_2$)$_3$CH(OH)(CH$_2$)$_4$-cHx |
| 1-570 | H | — | MeOCH$_2$CMe$_2$ | 0 | 5-(CH$_2$)$_3$CH(OH)(CH$_2$)$_4$-cHx |
| 1-571 | H | — | EtCMe$_2$ | 0 | 5-(CH$_2$)$_3$CH(OH)(CH$_2$)$_4$-cHx |
| 1-572 | H | — | PrCMe$_2$ | 0 | 5-(CH$_2$)$_3$CH(OH)(CH$_2$)$_4$-cHx |
| 1-573 | H | — | BuCMe$_2$ | 0 | 5-(CH$_2$)$_3$CH(OH)(CH$_2$)$_4$-cHx |
| 1-574 | H | — | PnCMe$_2$ | 0 | 5-(CH$_2$)$_3$CH(OH)(CH$_2$)$_4$-cHx |
| 1-575 | H | H | tBu | 1 | 5-(CH$_2$)$_3$CH(OH)(CH$_2$)$_4$-cHx |
| 1-576 | H | — | tBu | 0 | 5-(CH$_2$)$_3$CH(OH)(CH$_2$)$_4$-cHx |
| 1-577 | H | — | tBu | 0 | 5-(CH$_2$)$_4$CH(OH)-cHx |
| 1-578 | H | — | iPr | 0 | 5-(CH$_2$)$_4$CH(OH)-cHx |
| 1-579 | H | — | iBu | 0 | 5-(CH$_2$)$_4$CH(OH)-cHx |
| 1-580 | H | — | Et | 0 | 5-(CH$_2$)$_4$CH(OH)-cHx |
| 1-581 | H | — | MeOCH$_2$CMe$_2$ | 0 | 5-(CH$_2$)$_4$CH(OH)-cHx |
| 1-582 | H | — | EtCMe$_2$ | 0 | 5-(CH$_2$)$_4$CH(OH)-cHx |

TABLE 1-continued

| Cpd. No. | $R^a$ | $R^2$ | $R^3$ | n | $R^4$ |
|---|---|---|---|---|---|
| 1-583 | H | — | PrCMe$_2$ | 0 | 5-(CH$_2$)$_4$CH(OH)-cHx |
| 1-584 | H | — | BuCMe$_2$ | 0 | 5-(CH$_2$)$_4$CH(OH)-cHx |
| 1-585 | H | — | EtOCH$_2$ | 0 | 5-(CH$_2$)$_4$CH(OH)-cHx |
| 1-586 | H | H | tBu | 1 | 5-(CH$_2$)$_4$CH(OH)-cHx |
| 1-587 | H | — | tBu | 0 | 5-(CH$_2$)$_4$CH(OH)(CH$_2$)-cHx |
| 1-588 | H | — | iPr | 0 | 5-(CH$_2$)$_4$CH(OH)(CH$_2$)-cHx |
| 1-589 | H | — | iBu | 0 | 5-(CH$_2$)$_4$CH(OH)(CH$_2$)-cHx |
| 1-590 | H | — | Et | 0 | 5-(CH$_2$)$_4$CH(OH)(CH$_2$)-cHx |
| 1-591 | H | — | MeOCH$_2$CMe$_2$ | 0 | 5-(CH$_2$)$_4$CH(OH)(CH$_2$)-cHx |
| 1-592 | H | — | EtCMe$_2$ | 0 | 5-(CH$_2$)$_4$CH(OH)(CH$_2$)-cHx |
| 1-593 | H | — | PrCMe$_2$ | 0 | 5-(CH$_2$)$_4$CH(OH)(CH$_2$)-cHx |
| 1-594 | H | — | BuCMe$_2$ | 0 | 5-(CH$_2$)$_4$CH(OH)(CH$_2$)-cHx |
| 1-595 | H | — | EtOCH$_2$ | 0 | 5-(CH$_2$)$_4$CH(OH)(CH$_2$)-cHx |
| 1-596 | H | H | tBu | 1 | 5-(CH$_2$)$_4$CH(OH)(CH$_2$)$_2$-cHx |
| 1-597 | H | — | tBu | 0 | 5-(CH$_2$)$_4$CH(OH)(CH$_2$)$_2$-cHx |
| 1-598 | H | — | iPr | 0 | 5-(CH$_2$)$_4$CH(OH)(CH$_2$)$_2$-cHx |
| 1-599 | H | — | iBu | 0 | 5-(CH$_2$)$_4$CH(OH)(CH$_2$)$_2$-cHx |
| 1-600 | H | — | EtCMe$_2$ | 0 | 5-(CH$_2$)$_4$CH(OH)(CH$_2$)$_2$-cHx |
| 1-601 | H | — | PrCMe$_2$ | 0 | 5-(CH$_2$)$_4$CH(OH)(CH$_2$)$_2$-cHx |
| 1-602 | H | — | BuCMe$_2$ | 0 | 5-(CH$_2$)$_4$CH(OH)(CH$_2$)$_2$-cHx |
| 1-603 | H | — | EtOCH$_2$ | 0 | 5-(CH$_2$)$_4$CH(OH)(CH$_2$)$_2$-cHx |
| 1-604 | H | H | tBu | 1 | 5-(CH$_2$)$_4$CH(OH)(CH$_2$)$_2$-cHx |
| 1-605 | H | — | tBu | 0 | 5-(CH$_2$)$_4$CH(OH)(CH$_2$)$_2$-cHx |
| 1-606 | H | — | iPr | 0 | 5-(CH$_2$)$_4$CH(OH)(CH$_2$)$_2$-cHx |
| 1-607 | H | — | iBu | 0 | 5-(CH$_2$)$_4$CH(OH)(CH$_2$)$_2$-cHx |
| 1-608 | H | H | tBu | 1 | 5-(CH$_2$)$_4$CH(OH)(CH$_2$)$_2$-cHx |
| 1-609 | H | — | iBu | 0 | 5-(CH$_2$)$_4$CH(OH)(CH$_2$)$_2$-cHx |
| 1-610 | H | — | iPr | 0 | 5-(CH$_2$)$_4$CH(OH)(CH$_2$)$_2$-cHx |
| 1-611 | H | — | iBu | 0 | 5-(CH$_2$)$_4$CH(OH)(CH$_2$)$_2$-cHx |
| 1-612 | H | H | tBu | 1 | 5-(CH$_2$)$_4$CH(OH)(CH$_2$)$_2$-cHx |
| 1-613 | H | — | tBu | 0 | 5-(CH$_2$)$_5$CH(OH)-cHx |
| 1-614 | H | — | iPr | 0 | 5-(CH$_2$)$_5$CH(OH)-cHx |
| 1-615 | H | — | iBu | 0 | 5-(CH$_2$)$_5$CH(OH)-cHx |
| 1-616 | H | H | tBu | 1 | 5-(CH$_2$)$_5$CH(OH)-cHx |
| 1-617 | H | — | tBu | 0 | 5-(CH$_2$)$_5$CH(OH)(CH$_2$)-cHx |
| 1-618 | H | — | iPr | 0 | 5-(CH$_2$)$_5$CH(OH)(CH$_2$)-cHx |
| 1-619 | H | — | iBu | 0 | 5-(CH$_2$)$_5$CH(OH)(CH$_2$)-cHx |
| 1-620 | H | — | Et | 0 | 5-(CH$_2$)$_5$CH(OH)(CH$_2$)-cHx |
| 1-621 | H | — | tBu | 0 | 5-(CH$_2$)$_5$CH(OH)(CH$_2$)$_2$-cHx |
| 1-622 | H | — | iPr | 0 | 5-(CH$_2$)$_5$CH(OH)(CH$_2$)$_2$-cHx |
| 1-623 | H | — | iBu | 0 | 5-(CH$_2$)$_5$CH(OH)(CH$_2$)$_2$-cHx |
| 1-624 | H | H | tBu | 1 | 5-(CH$_2$)$_5$CH(OH)(CH$_2$)$_2$-cHx |
| 1-625 | H | — | tBu | 0 | 5-(CH$_2$)$_5$CH(OH)(CH$_2$)$_2$-cHx |
| 1-626 | H | H | tBu | 1 | 5-(CH$_2$)$_5$CH(OH)(CH$_2$)$_2$-cHx |
| 1-627 | H | H | tBu | 1 | 5-(CH$_2$)$_6$CH(OH)-cHx |
| 1-628 | H | — | tBu | 0 | 5-CH(OH)-cPn |
| 1-629 | H | — | iPr | 0 | 5-CH(OH)-cPn |
| 1-630 | H | — | iBu | 0 | 5-CH(OH)-cPn |
| 1-631 | H | — | Et | 0 | 5-CH(OH)-cPn |
| 1-632 | H | — | MeOCH$_2$CMe$_2$ | 0 | 5-CH(OH)-cPn |
| 1-633 | H | — | EtCMe$_2$ | 0 | 5-CH(OH)-cPn |
| 1-634 | H | — | PrCMe$_2$ | 0 | 5-CH(OH)-cPn |
| 1-635 | H | — | BuCMe$_2$ | 0 | 5-CH(OH)-cPn |
| 1-636 | H | — | PnCMe$_2$ | 0 | 5-CH(OH)-cPn |
| 1-637 | H | — | CH$_3$OCH$_2$ | 0 | 5-CH(OH)-cPn |
| 1-638 | H | — | EtOCH$_2$ | 0 | 5-CH(OH)-cPn |
| 1-639 | H | — | S-tBu | 0 | 5-CH(OH)-cPn |
| 1-640 | H | — | S-iPr | 0 | 5-CH(OH)-cPn |
| 1-641 | H | — | S-Ph | 0 | 5-CH(OH)-cPn |
| 1-642 | H | H | tBu | 1 | 5-CH(OH)-cPn |
| 1-643 | H | H | iPr | 1 | 5-CH(OH)-cPn |
| 1-644 | H | Bu | tBu | 1 | 5-CH(OH)-cPn |
| 1-645 | H | Pn | tBu | 1 | 5-CH(OH)-cPn |
| 1-646 | H | Hx | tBu | 1 | 5-CH(OH)-cPn |
| 1-647 | H | Hp | tBu | 1 | 5-CH(OH)-cPn |
| 1-648 | 3-Cl | — | tBu | 0 | 5-CH(OH)-cPn |
| 1-649 | 3-Br | — | tBu | 0 | 5-CH(OH)-cPn |
| 1-650 | 3-OMe | — | tBu | 0 | 5-CH(OH)-cPn |
| 1-651 | 2-OMe | — | tBu | 0 | 5-CH(OH)-cPn |
| 1-652 | H | — | tBu | 0 | 5-CH(OH)(CH$_2$)-cPn |
| 1-653 | H | — | iPr | 0 | 5-CH(OH)(CH$_2$)-cPn |
| 1-654 | H | — | iBu | 0 | 5-CH(OH)(CH$_2$)-cPn |
| 1-655 | H | — | Et | 0 | 5-CH(OH)(CH$_2$)-cPn |
| 1-656 | H | — | MeOCH$_2$CMe$_2$ | 0 | 5-CH(OH)(CH$_2$)-cPn |
| 1-657 | H | — | EtOCH$_2$ | 0 | 5-CH(OH)(CH$_2$)-cPn |
| 1-658 | H | — | S-tBu | 0 | 5-CH(OH)(CH$_2$)-cPn |

TABLE 1-continued

| Cpd. No. | $R^a$ | $R^2$ | $R^3$ | n | $R^4$ |
|---|---|---|---|---|---|
| 1-659 | H | — | S-iPr | 0 | 5-CH(OH)(CH$_2$)-cPn |
| 1-660 | H | — | S-Ph | 0 | 5-CH(OH)(CH$_2$)-cPn |
| 1-661 | H | H | tBu | 1 | 5-CH(OH)(CH$_2$)-cPn |
| 1-662 | H | — | tBu | 0 | 5-CH(OH)(CH$_2$)2-cPn |
| 1-663 | H | — | iPr | 0 | 5-CH(OH)(CH$_2$)$_2$-cPn |
| 1-664 | H | — | iBu | 0 | 5-CH(OH)(CH$_2$)$_2$cPn |
| 1-665 | H | — | PrCMe$_2$ | 0 | 5-CH(OH)(CH$_2$)$_2$cPn |
| 1-666 | H | — | BuCMe$_2$ | 0 | 5-CH(OH)(CH$_2$)$_2$-cPn |
| 1-667 | H | — | PnCMe$_2$ | 0 | 5-CH(OH)(CH$_2$)$_2$-cPn |
| 1-668 | H | — | S-tBu | 0 | 5-CH(OH)(CH$_2$)$_2$-cPn |
| 1-669 | H | H | tBu | 1 | 5-CH(OH)(CH$_2$)$_2$-cPn |
| 1-670 | H | — | tBu | 0 | 5-CH(OH)(CH$_2$)$_3$-cPn |
| 1-671 | H | — | iPr | 0 | 5-CH(OH)(CH$_2$)$_3$-cPn |
| 1-672 | H | — | iBu | 0 | 5-CH(OH)(CH$_2$)$_3$-cPn |
| 1-673 | H | — | PnCMe$_2$ | 0 | 5-CH(OH)(CH$_2$)$_3$-cPn |
| 1-674 | H | — | CH$_3$OCH$_2$ | 0 | 5-CH(OH)(CH$_2$)$_3$-cPn |
| 1-675 | H | — | S-iPr | 0 | 5-CH(OH)(CH$_2$)$_3$-cPn |
| 1-676 | H | H | tBu | 1 | 5-CH(OH)(CH$_2$)$_3$-cPn |
| 1-677 | H | — | tBu | 0 | 5-CH(OH)(CH$_2$)$_4$-cPn |
| 1-678 | H | — | iPr | 0 | 5-CH(OH)(CH$_2$)$_4$-cPn |
| 1-679 | H | — | iBu | 0 | 5-CH(OH)(CH$_2$)$_4$-cPn |
| 1-680 | H | — | PrCMe$_2$ | 0 | 5-CH(OH)(CH$_2$)$_4$-cPn |
| 1-681 | H | — | CH$_3$OCH$_2$ | 0 | 5-CH(OH)(CH$_2$)$_4$-cPn |
| 1-682 | H | — | S-tBu | 0 | 5-CH(OH)(CH$_2$)$_4$-cPn |
| 1-683 | H | H | tBu | 1 | 5-CH(OH)(CH$_2$)$_4$-cPn |
| 1-684 | H | — | tBu | 0 | 5-CH(OH)(CH$_2$)$_5$-cPn |
| 1-685 | H | — | iPr | 0 | 5-CH(OH)(CH$_2$)$_5$-cPn |
| 1-686 | H | — | iBu | 0 | 5-CH(OH)(CH$_2$)$_5$-cPn |
| 1-687 | H | — | CH$_3$OCH$_2$ | 0 | 5-CH(OH)(CH$_2$)$_5$-cPn |
| 1-688 | H | — | S-Ph | 0 | 5-CH(OH)(CH$_2$)$_5$-cPn |
| 1-689 | H | H | tBu | 1 | 5-CH(OH)(CH$_2$)$_5$-cPn |
| 1-690 | H | — | tBu | 0 | 5-CH(OH)(CH$_2$)$_6$-cPn |
| 1-691 | H | — | iPr | 0 | 5-CH(OH)(CH$_2$)$_6$-cPn |
| 1-692 | H | — | iBu | 0 | 5-CH(OH)(CH$_2$)$_6$-cPn |
| 1-693 | H | — | CH$_3$OCH$_2$ | 0 | 5-CH(OH)(CH$_2$)$_6$-cPn |
| 1-694 | H | — | S-tBu | 0 | 5-CH(OH)(CH$_2$)$_6$-cPn |
| 1-695 | H | H | tBu | 1 | 5-CH(OH)(CH$_2$)$_6$-cPn |
| 1-696 | H | — | tBu | 0 | 5-(CH$_2$)CH(OH)-cPn |
| 1-697 | H | — | iPr | 0 | 5-(CH$_2$)CH(OH)-cPn |
| 1-698 | H | — | Et | 0 | 5-(CH$_2$)CH(OH)-cPn |
| 1-699 | H | — | MeOCH$_2$CMe$_2$ | 0 | 5-(CH$_2$)CH(OH)-cPn |
| 1-700 | H | — | S-Ph | 0 | 5-(CH$_2$)CH(OH)-cPn |
| 1-701 | H | H | tBu | 1 | 5-(CH$_2$)CH(OH)-cPn |
| 1-702 | H | — | tBu | 0 | 5-(CH$_2$)CH(OH)(CH$_2$)-cPn |
| 1-703 | H | — | tBu | 0 | 5-(CH$_2$)CH(OH)(CH$_2$)$_2$-cPn |
| 1-704 | H | — | EtOCH$_2$ | 0 | 5-(CH$_2$)CH(OH)(CH$_2$)$_2$-cPn |
| 1-705 | H | — | S-iPr | 0 | 5-(CH$_2$)CH(OH)(CH$_2$)$_2$-cPn |
| 1-706 | H | H | tBu | 1 | 5-(CH$_2$)CH(OH)(CH$_2$)$_2$-cPn |
| 1-707 | H | — | tBu | 0 | 5-(CH$_2$)CH(OH)(CH$_2$)$_3$-cPn |
| 1-708 | H | — | iPr | 0 | 5-(CH$_2$)CH(OH)(CH$_2$)$_3$-cPn |
| 1-709 | H | — | Et | 0 | 5-(CH$_2$)CH(OH)(CH$_2$)$_3$-cPn |
| 1-710 | H | — | BuCMe$_2$ | 0 | 5-(CH$_2$)CH(OH)(CH$_2$)$_3$-cPn |
| 1-711 | H | — | EtOCH$_2$ | 0 | 5-(CH$_2$)CH(OH)(CH$_2$)$_3$-cPn |
| 1-712 | H | H | tBu | 1 | 5-(CH$_2$)CH(OH)(CH$_2$)$_3$-cPn |
| 1-713 | H | — | tBu | 0 | 5-(CH$_2$)CH(OH)(CH$_2$)$_4$-cPn |
| 1-714 | H | — | iPr | 0 | 5-(CH$_2$)CH(OH)(CH$_2$)$_4$-cPn |
| 1-715 | H | — | EtOCH$_2$ | 0 | 5-(CH$_2$)CH(OH)(CH$_2$)$_4$-cPn |
| 1-716 | H | — | S-tBu | 0 | 5-(CH$_2$)CH(OH)(CH$_2$)$_4$-cPn |
| 1-717 | H | H | tBu | 1 | 5-(CH$_2$)CH(OH)(CH$_2$)$_4$-cPn |
| 1-718 | H | — | tBu | 0 | 5-(CH$_2$)CH(OH)(CH$_2$)$_5$-cPn |
| 1-719 | H | — | iPr | 0 | 5-(CH$_2$)CH(OH)(CH$_2$)$_5$-cPn |
| 1-720 | H | — | PnCMe$_2$ | 0 | 5-(CH$_2$)CH(OH)(CH$_2$)$_5$-cPn |
| 1-721 | H | — | S-iPr | 0 | 5-(CH$_2$)CH(OH)(CH$_2$)$_5$-cPn |
| 1-722 | H | H | tBu | 1 | 5-(CH$_2$)CH(OH)(CH$_2$)$_5$-cPn |
| 1-723 | H | — | tBu | 0 | 5-(CH$_2$)CH(OH)-cPn |
| 1-724 | H | — | iPr | 0 | 5-(CH$_2$)CH(OH)-cPn |
| 1-725 | H | — | iBu | 0 | 5-(CH$_2$)CH(OH)-cPn |
| 1-726 | H | — | Et | 0 | 5-(CH$_2$)CH(OH)-cPn |
| 1-727 | H | — | MeOCH$_2$CMe$_2$ | 0 | 5-(CH$_2$)CH(OH)-cPn |
| 1-728 | H | — | EtCMe$_2$ | 0 | 5-(CH$_2$)CH(OH)-cPn |
| 1-729 | H | — | PrCMe$_2$ | 0 | 5-(CH$_2$)$_2$CH(OH)-cPn |
| 1-730 | H | — | BuCMe$_2$ | 0 | 5-(CH$_2$)$_2$CH(OH)-cPn |
| 1-731 | H | — | PnCMe$_2$ | 0 | 5-(CH$_2$)$_2$CH(OH)-cPn |
| 1-732 | H | — | CH$_3$OCH$_2$ | 0 | 5-(CH$_2$)$_2$CH(OH)-cPn |
| 1-733 | H | — | EtOCH$_2$ | 0 | 5-(CH$_2$)$_2$CH(OH)-cPn |
| 1-734 | H | — | S-tBu | 0 | 5-(CH$_2$)$_2$CH(OH)-cPn |

TABLE 1-continued

| Cpd. No. | R$^a$ | R$^2$ | R$^3$ | n | R$^4$ |
|---|---|---|---|---|---|
| 1-735 | H | — | S-iPr | 0 | 5-(CH$_2$)$_2$CH(OH)-cPn |
| 1-736 | H | — | S-Ph | 0 | 5-(CH$_2$)$_2$CH(OH)-cPn |
| 1-737 | H | H | tBu | 1 | 5-(CH$_2$)$_2$CH(OH)-cPn |
| 1-738 | H | H | iPr | 1 | 5-(CH$_2$)$_2$CH(OH)-cPn |
| 1-739 | H | Bu | tBu | 1 | 5-(CH$_2$)$_2$CH(OH)-cPn |
| 1-740 | H | Pn | tBu | 1 | 5-(CH$_2$)$_2$CH(OH)-cPn |
| 1-741 | H | Hx | tBu | 1 | 5-(CH$_2$)$_2$CH(OH)-cPn |
| 1-742 | H | Hp | tBu | 1 | 5-(CH$_2$)$_2$CH(OH)-cPn |
| 1-743 | 3-Cl | — | tBu | 0 | 5-(CH$_2$)$_2$CH(OH)-cPn |
| 1-744 | 3-Br | — | tBu | 0 | 5-(CH$_2$)$_2$CH(OH)-cPn |
| 1-745 | 3-OMe | — | tBu | 0 | 5-(CH$_2$)$_2$CH(OH)-cPn |
| 1-746 | 2-OMe | — | tBu | 0 | 5-(CH$_2$)$_2$CH(OH)-cPn |
| 1-747 | H | — | tBu | 0 | 5-(CH$_2$)$_2$CH(OH)(CH$_2$)-cPn |
| 1-748 | H | — | iPr | 0 | 5-(CH$_2$)$_2$CH(OH)(CH$_2$)-cPn |
| 1-749 | H | — | iBu | 0 | 5-(CH$_2$)$_2$CH(OH)(CH$_2$)-cPn |
| 1-750 | H | — | Et | 0 | 5-(CH$_2$)$_2$CH(OH)(CH$_2$)-cPn |
| 1-751 | H | — | MeOCH$_2$CMe$_2$ | 0 | 5-(CH$_2$)$_2$CH(OH)(CH$_2$)-cPn |
| 1-752 | H | — | EtCMe$_2$ | 0 | 5-(CH$_2$)$_2$CH(OH)(CH$_2$)-cPn |
| 1-753 | H | — | PrCMe$_2$ | 0 | 5-(CH$_2$)$_2$CH(OH)(CH$_2$)-cPn |
| 1-754 | H | — | BuCMe$_2$ | 0 | 5-(CH$_2$)$_2$CH(OH)(CH$_2$)-cPn |
| 1-755 | H | — | PnCMe$_2$ | 0 | 5-(CH$_2$)$_2$CH(OH)(CH$_2$)-cPn |
| 1-756 | H | — | CH$_3$OCH$_2$ | 0 | 5-(CH$_2$)$_2$CH(OH)(CH$_2$)-cPn |
| 1-757 | H | — | EtOCH$_2$ | 0 | 5-(CH$_2$)$_2$CH(OH)(CH$_2$)-cPn |
| 1-758 | H | — | S-tBu | 0 | 5-(CH$_2$)$_2$CH(OH)(CH$_2$)-cPn |
| 1-759 | H | — | S-iPr | 0 | 5-(CH$_2$)$_2$CH(OH)(CH$_2$)-cPn |
| 1-760 | H | — | S-Ph | 0 | 5-(CH$_2$)$_2$CH(OH)(CH$_2$)-cPn |
| 1-761 | H | H | tBu | 1 | 5-(CH$_2$)$_2$CH(OH)(CH$_2$)-cPn |
| 1-762 | H | H | iPr | 1 | 5-(CH$_2$)$_2$CH(OH)(CH$_2$)-cPn |
| 1-763 | H | Bu | tBu | 1 | 5-(CH$_2$)$_2$CH(OH)(CH$_2$)-cPn |
| 1-764 | H | Pn | tBu | 1 | 5-(CH$_2$)$_2$CH(OH)(CH$_2$)-cPn |
| 1-765 | H | Hx | tBu | 1 | 5-(CH$_2$)$_2$CH(OH)(CH$_2$)-cPn |
| 1-766 | H | Hp | tBu | 1 | 5-(CH$_2$)$_2$CH(OH)(CH$_2$)-cPn |
| 1-767 | 3-Cl | — | tBu | 0 | 5-(CH$_2$)$_2$CH(OH)(CH$_2$)-cPn |
| 1-768 | 3-Br | — | tBu | 0 | 5-(CH$_2$)$_2$CH(OH)(CH$_2$)-cPn |
| 1-769 | 3-OMe | — | tBu | 0 | 5-(CH$_2$)$_2$CH(OH)(CH$_2$)-cPn |
| 1-770 | 2-OMe | — | tBu | 0 | 5-(CH$_2$)$_2$CH(OH)(CH$_2$)-cPn |
| 1-771 | H | — | tBu | 0 | 5-(CH$_2$)$_2$CH(OH)(CH$_2$)$_2$-cPn |
| 1-772 | H | — | iPr | 0 | 5-(CH$_2$)$_2$CH(OH)(CH$_2$)$_2$-cPn |
| 1-773 | H | — | iBu | 0 | 5-(CH$_2$)$_2$CH(OH)(CH$_2$)$_2$-cPn |
| 1-774 | H | — | MeOCH$_2$CHe$_2$ | 0 | 5-(CH$_2$)$_2$CH(OH)(CH$_2$)$_2$-cPn |
| 1-775 | H | — | EtCMe$_2$ | 0 | 5-(CH$_2$)$_2$CH(OH)(CH$_2$)$_2$-cPn |
| 1-776 | H | — | PrCMe$_2$ | 0 | 5-(CH$_2$)$_2$CH(OH)(CH$_2$)$_2$-cPn |
| 1-777 | H | — | BuCMe$_2$ | 0 | 5-(CH$_2$)$_2$CH(OH)(CH$_2$)$_2$-cPn |
| 1-778 | H | — | PnCMe$_2$ | 0 | 5-(CH$_2$)$_2$CH(OH)(CH$_2$)$_2$-cPn |
| 1-779 | H | — | CH$_3$OCH$_2$ | 0 | 5-(CH$_2$)$_2$CH(OH)(CH$_2$)$_2$-cPn |
| 1-780 | H | — | EtOCH$_2$ | 0 | 5-(CH$_2$)$_2$CH(OH)(CH$_2$)$_2$-cPn |
| 1-781 | H | — | S-tBu | 0 | 5-(CH$_2$)$_2$CH(OH)(CH$_2$)$_2$-cPn |
| 1-782 | H | — | S-iPr | 0 | 5-(CH$_2$)$_2$CH(OH)(CH$_2$)$_2$-cPn |
| 1-783 | H | H | tBu | 1 | 5-(CH$_2$)$_2$CH(OH)(CH$_2$)$_2$-cPn |
| 1-784 | H | H | iPr | 1 | 5-(CH$_2$)$_2$CH(OH)(CH$_2$)$_2$-cPn |
| 1-785 | H | Bu | tBu | 1 | 5-(CH$_2$)$_2$CH(OH)(CH$_2$)$_2$-cPn |
| 1-786 | H | Hx | tBu | 1 | 5-(CH$_2$)$_2$CH(OH)(CH$_2$)$_2$-cPn |
| 1-787 | 3-Cl | — | tBu | 0 | 5-(CH$_2$)$_2$CH(OH)(CH$_2$)$_2$-cPn |
| 1-788 | H | — | tBu | 0 | 5-(CH$_2$)$_2$CH(OH)(CH$_2$)$_3$-cPn |
| 1-789 | H | — | iPr | 0 | 5-(CH$_2$)$_2$CH(OH)(CH$_2$)$_3$-cPn |
| 1-790 | H | — | MeOCH$_2$CMe$_2$ | 0 | 5-(CH$_2$)$_2$CH(OH)(CH$_2$)$_3$-cPn |
| 1-791 | H | — | PnCMe$_2$ | 0 | 5-(CH$_2$)$_2$CH(OH)(CH$_2$)$_3$-cPn |
| 1-792 | H | — | EtOCH$_2$ | 0 | 5-(CH$_2$)$_2$CH(OH)(CH$_2$)$_3$-cPn |
| 1-793 | H | — | S-Ph | 0 | 5-(CH$_2$)$_2$CH(OH)(CH$_2$)$_3$-cPn |
| 1-794 | H | H | tBu | 1 | 5-(CH$_2$)$_2$CH(OH)(CH$_2$)$_3$-cPn |
| 1-795 | H | Pn | tBu | 1 | 5-(CH$_2$)$_2$CH(OH)(CH$_2$)$_3$-cPn |
| 1-796 | H | Hp | tBu | 1 | 5-(CH$_2$)$_2$CH(OH)(CH$_2$)$_3$-cPn |
| 1-797 | 3-Cl | — | tBu | 0 | 5-(CH$_2$)$_2$CH(OH)(CH$_2$)$_3$-cPn |
| 1-798 | 2-OMe | — | tBu | 0 | 5-(CH$_2$)$_2$CH(OH)(CH$_2$)$_3$-cPn |
| 1-799 | H | — | tBu | 0 | 5-(CH$_2$)$_2$CH(OH)(CH$_2$)$_4$-cPn |
| 1-800 | H | — | iPr | 0 | 5-(CH$_2$)$_2$CH(OH)(CH$_2$)$_4$-cPn |
| 1-801 | H | — | EtOCH$_2$ | 0 | 5-(CH$_2$)$_2$CH(OH)(CH$_2$)$_4$-cPn |
| 1-802 | H | — | S-iPr | 0 | 5-(CH$_2$)$_2$CH(OH)(CH$_2$)$_4$-cPn |
| 1-803 | H | H | tBu | 1 | 5-(CH$_2$)$_2$CH(OH)(CH$_2$)$_4$-cPn |
| 1-804 | H | — | tBu | 0 | 5-(CH$_2$)$_2$CH(OH)(CH$_2$)$_5$-cPn |
| 1-805 | H | — | iPr | 0 | 5-(CH$_2$)$_2$CH(OH)(CH$_2$)$_5$-cPn |
| 1-806 | H | — | PnCMe$_2$ | 0 | 5-(CH$_2$)$_2$CH(OH)(CH$_2$)$_5$-cPn |
| 1-807 | H | — | EtOCH$_2$ | 0 | 5-(CH$_2$)$_2$CH(OH)(CH$_2$)$_5$-cPn |
| 1-808 | H | — | S-Ph | 0 | 5-(CH$_2$)$_2$CH(OH)(CH$_2$)$_5$-cPn |
| 1-809 | H | H | tBu | 1 | 5-(CH$_2$)$_2$CH(OH)(CH$_2$)$_5$-cPn |
| 1-810 | H | — | tBu | 0 | 5-(CH$_2$)$_3$CH(OH)-cPn |

TABLE 1-continued

| Cpd. No. | $R^a$ | $R^2$ | $R^3$ | n | $R^4$ |
|---|---|---|---|---|---|
| 1-811 | H | — | iPr | 0 | 5-(CH$_2$)$_3$CH(OH)-cPn |
| 1-812 | H | — | PrCMe$_2$ | 0 | 5-(CH$_2$)$_3$CH(OH)-cPn |
| 1-813 | H | — | PnCMe$_2$ | 0 | 5-(CH$_2$)$_3$CH(OH)-cPn |
| 1-814 | H | — | EtOCH$_2$ | 0 | 5-(CH$_2$)$_3$CH(OH)-cPn |
| 1-815 | H | — | S-tBu | 0 | 5-(CH$_2$)$_3$CH(OH)-cPn |
| 1-816 | H | — | S-iPr | 0 | 5-(CH$_2$)$_3$CH(OH)-cPn |
| 1-817 | H | — | S-Ph | 0 | 5-(CH$_2$)$_3$CH(OH)-cPn |
| 1-818 | H | H | tBu | 1 | 5-(CH$_2$)$_3$CH(OH)-cPn |
| 1-819 | H | — | tBu | 0 | 5-(CH$_2$)$_3$CH(OH)(CH$_2$)-cPn |
| 1-820 | H | — | iPr | 0 | 5-(CH$_2$)$_3$CH(OH)(CH$_2$)-cPn |
| 1-821 | H | — | PnCMe$_2$ | 0 | 5-(CH$_2$)$_3$CH(OH)(CH$_2$)-cPn |
| 1-822 | H | — | CH$_3$OCH$_2$ | 0 | 5-(CH$_2$)$_3$CH(OH)(CH$_2$)-cPn |
| 1-823 | H | — | S-iPr | 0 | 5-(CH$_2$)$_3$CH(OH)(CH$_2$)-cPn |
| 1-824 | H | H | tBu | 1 | 5-(CH$_2$)$_3$CH(OH)(CH$_2$)-cPn |
| 1-825 | H | — | tBu | 0 | 5-(CH$_2$)$_3$CH(OH)(CH$_2$)$_2$-cPn |
| 1-826 | H | — | PrCMe$_2$ | 0 | 5-(CH$_2$)$_3$CH(OH)(CH$_2$)$_2$-cPn |
| 1-827 | H | — | PnCMe$_2$ | 0 | 5-(CH$_2$)$_3$CH(OH)(CH$_2$)$_2$-cPn |
| 1-828 | H | — | EtOCH$_2$ | 0 | 5-(CH$_2$)$_3$CH(OH)(CH$_2$)$_2$-cPn |
| 1-829 | H | — | S-iPr | 0 | 5-(CH$_2$)$_3$CH(OH)(CH$_2$)$_2$-cPn |
| 1-830 | H | H | tBu | 1 | 5-(CH$_2$)$_3$CH(OH)(CH$_2$)$_2$-cPn |
| 1-831 | H | — | tBu | 0 | 5-(CH$_2$)$_3$CH(OH)(CH$_2$)$_3$-cPn |
| 1-832 | H | — | BuCMe$_2$ | 0 | 5-(CH$_2$)$_3$CH(OH)(CH$_2$)$_3$-cPn |
| 1-833 | H | — | S-Ph | 0 | 5-(CH$_2$)$_3$CH(OH)(CH$_2$)$_3$-cPn |
| 1-834 | H | H | tBu | 1 | 5-(CH$_2$)$_3$CH(OH)(CH$_2$)$_3$-cPn |
| 1-835 | H | — | tBu | 0 | 5-(CH$_2$)$_2$CH(OH)(CH$_2$)$_6$-cPn |
| 1-836 | H | — | tBu | 0 | 5-(CH$_2$)$_3$CH(OH)(CH$_2$)$_4$-cPn |
| 1-837 | H | H | tBu | 1 | 5-(CH$_2$)$_3$CH(OH)(CH$_2$)$_4$-cPn |
| 1-838 | H | — | tBu | 0 | 5-(CH$_2$)$_4$CH(OH)-cPn |
| 1-839 | H | — | tBu | 0 | 5-(CH$_2$)$_4$CH(OH)-CH$_2$-cPn |
| 1-840 | H | — | tBu | 0 | 5-(CH$_2$)$_4$CH(OH)(CH$_2$)$_2$-cPn |
| 1-841 | H | — | tBu | 0 | 5-(CH$_2$)$_4$CH(OH)(CH$_2$)$_3$-cPn |
| 1-842 | H | H | tBu | 1 | 5-(CH$_2$)$_4$CH(OH)CH$_2$-cPn |
| 1-843 | H | — | tBu | 0 | 5-(CH$_2$)$_5$CH(OH)CH$_2$-cPn |
| 1-844 | H | — | tBu | 0 | 5-(CH$_2$)$_5$CH(OH)-cPn |
| 1-845 | H | — | tBu | 0 | 5-CH(OH)-cHp |
| 1-846 | H | — | iPr | 0 | 5-CH(OH)-cHp |
| 1-847 | H | — | EtOCH$_2$ | 0 | 5-CH(OH)-cHp |
| 1-848 | H | — | S-Pr | 0 | 5-CH(OH)-cHp |
| 1-849 | H | H | tBu | 1 | 5-CH(OH)-cHp |
| 1-850 | 3-Cl | — | tBu | 0 | 5-CH(OH)-cHp |
| 1-851 | 3-Br | — | tBu | 0 | 5-CH(OH)-cHp |
| 1-852 | 3-OMe | — | tBu | 0 | 5-CH(OH)-cHp |
| 1-853 | 2-OMe | — | tBu | 0 | 5-CH(OH)-cHp |
| 1-854 | H | — | tBu | 0 | 5-CH(OH)(CH$_2$)-cHp |
| 1-855 | H | — | iPr | 0 | 5-CH(OH)(CH$_2$)-cHp |
| 1-856 | H | — | PnCMe$_2$ | 0 | 5-CH(OH)(CH$_2$)-cHp |
| 1-857 | H | — | EtOCH$_2$ | 0 | 5-CH(OH)(CH$_2$)-cHp |
| 1-858 | H | — | S-tBu | 0 | 5-CH(OH)(CH$_2$)-cHp |
| 1-859 | H | H | tBu | 1 | 5-CH(OH)(CH$_2$)-cHp |
| 1-860 | H | Bu | tBu | 1 | 5-CH(OH)(CH$_2$)-cHp |
| 1-861 | if | Hp | tBu | 1 | 5-CH(OH)(CH$_2$)-cHp |
| 1-862 | 3-Br | — | tBu | 0 | 5-CH(OH)(CH$_2$)-cHp |
| 1-863 | 2-OMe | — | tBu | 0 | 5-CH(OH)(CH$_2$)-cHp |
| 1-864 | H | — | tBu | 0 | 5-CH(OH)(CH$_2$)$_2$-cHp |
| 1-865 | H | — | iPr | 0 | 5-CH(OH)(CH$_2$)$_2$-cHp |
| 1-866 | H | — | EtOCH$_2$ | 0 | 5-CH(OH)(CH$_2$)$_2$-cHp |
| 1-867 | H | — | S-Ph | 0 | 5-CH(OH)(CH$_2$)$_2$-cHp |
| 1-868 | H | H | tBu | 1 | 5-CH(OH)(CH$_2$)$_2$-cHp |
| 1-869 | H | Bu | tBu | 1 | 5-CH(OH)(CH$_2$)$_2$-cHp |
| 1-870 | H | Hp | tBu | 1 | 5-CH(OH)(CH$_2$)$_2$-cHp |
| 1-871 | 3-Cl | — | tBu | 0 | 5-CH(OH)(CH$_2$)$_2$-cHp |
| 1-872 | 3-OMe | — | tBu | 0 | 5-CH(OH)(CH$_2$)$_2$-cHp |
| 1-873 | H | — | tBu | 0 | 5-CH(OH)(CH$_2$)$_3$-cHp |
| 1-874 | H | — | iPr | 0 | 5-CH(OH)(CH$_2$)$_3$-cHp |
| 1-875 | H | — | PnCMe$_2$ | 0 | 5-CH(OH)(CH$_2$)$_3$-cHp |
| 1-876 | H | — | EtOCH$_2$ | 0 | 5-CH(OH)(CH$_2$)$_3$-cHp |
| 1-877 | H | — | S-Ph | 0 | 5-CH(OH)(CH$_2$)$_3$-cHp |
| 1-878 | H | H | tBu | 1 | 5-CH(OH)(CH$_2$)$_3$-cHp |
| 1-879 | H | Hp | tBu | 1 | 5-CH(OH)(CH$_2$)$_3$-cHp |
| 1-880 | 3-Br | — | tBu | 0 | 5-CH(OH)(CH$_2$)$_3$-cHp |
| 1-881 | H | — | tBu | 0 | 5-CH(OH)(CH$_2$)$_4$-cHp |
| 1-882 | H | — | iPr | 0 | 5-CH(OH)(CH$_2$)$_4$-cHp |
| 1-883 | H | — | PnCMe$_2$ | 0 | 5-CH(OH)(CH$_2$)$_4$-cHp |
| 1-884 | H | — | EtOCH$_2$ | 0 | 5-CH(OH)(CH$_2$)$_4$-cHp |
| 1-885 | H | — | S-iPr | 0 | 5-CH(OH)(CH$_2$)$_4$-cHp |
| 1-886 | H | H | tBu | 1 | 5-CH(OH)(CH$_2$)$_4$-cHp |

TABLE 1-continued

| Cpd. No. | $R^a$ | $R^2$ | $R^3$ | n | $R^4$ |
|---|---|---|---|---|---|
| 1-887 | H | Pn | tBu | 1 | 5-CH(OH)(CH$_2$)$_4$-cHp |
| 1-888 | H | Hp | tBu | 1 | 5-CH(OH)(CH$_2$)$_4$-cHp |
| 1-889 | 3-Br | — | tBu | 0 | 5-CH(OH)(CH$_2$)$_4$-cHp |
| 1-890 | 2-OMe | — | tBu | 0 | 5-CH(OH)(CH$_2$)$_4$-cHp |
| 1-891 | H | — | tBu | 0 | 5-CH(OH)(CH$_2$)$_5$-cHp |
| 1-892 | H | — | PnCMe$_2$ | 0 | 5-CH(OH)(CH$_2$)$_5$-cHp |
| 1-893 | H | — | EtOCH$_2$ | 0 | 5-CH(OH)(CH$_2$)$_5$-cHp |
| 1-894 | H | H | tBu | 1 | 5-CH(OH)(CH$_2$)$_5$-cHp |
| 1-895 | H | Pn | tBu | 1 | 5-CH(OH)(CH$_2$)$_5$-cHp |
| 1-896 | 3-OMe | — | tBu | 0 | 5-CH(OH)(CH$_2$)$_5$-cHp |
| 1-897 | H | — | tBu | 0 | 5-CH(OH)(CH$_2$)$_6$-cHp |
| 1-898 | H | — | tBu | 0 | 5-CH(OH)(CH$_2$)$_6$-cHp |
| 1-899 | H | — | tBu | 0 | 5-(CH$_2$)CH(OH)-cHp |
| 1-900 | H | — | PrCMe$_2$ | 0 | 5-(CH$_2$)CH(OH)-cHp |
| 1-901 | H | — | S-Ph | 0 | 5-(CH$_2$)CH(OH)-cHp |
| 1-902 | H | H | tBu | 1 | 5-(CH$_2$)CH(OH)-cHp |
| 1-903 | H | Pn | tBu | 1 | 5-(CH$_2$)CH(OH)-cHp |
| 1-904 | H | Hx | tBu | 1 | 5-(CH$_2$)CH(OH)-cHp |
| 1-905 | 3-Cl | — | tBu | 0 | 5-(CH$_2$)CH(OH)-cHp |
| 1-906 | 3-OMe | — | tBu | 0 | 5-(CH$_2$)CH(OH)-cHp |
| 1-907 | H | — | tBu | 0 | 5-(CH$_2$)CH(OH)(CH$_2$)-cHp |
| 1-908 | H | — | iPr | 0 | 5-(CH$_2$)CH(OH)(CH$_2$)-cHp |
| 1-909 | H | — | BuCMe$_2$ | 0 | 5-(CH$_2$)CH(OH)(CH$_2$)-cHp |
| 1-910 | H | — | EtOCH$_2$ | 0 | 5-(CH$_2$)CH(OH)(CH$_2$)-cHp |
| 1-911 | H | — | S-iPr | 0 | 5-(CH$_2$)CH(OH)(CH$_2$)-cHp |
| 1-912 | H | H | tBu | 1 | 5-(CH$_2$)CH(OH)(CH$_2$)-cHp |
| 1-913 | H | Hp | tBu | 1 | 5-(CH$_2$)CH(OH)(CH$_2$)-cHp |
| 1-914 | 3-Br | — | tBu | 0 | 5-(CH$_2$)CH(OH)(CH$_2$)-cHp |
| 1-915 | H | — | tBu | 0 | 5-(CH$_2$)CH(OH)(CH$_2$)$_2$-cHp |
| 1-916 | H | — | iPr | 0 | 5-(CH$_2$)CH(OH)(CH$_2$)$_2$-cHp |
| 1-917 | H | — | PnCMe$_2$ | 0 | 5-(CH$_2$)CH(OH)(CH$_2$)$_2$-cHp |
| 1-918 | H | — | EtOCH$_2$ | 0 | 5-(CH$_2$)CH(OH)(CH$_2$)$_2$-cHp |
| 1-919 | H | — | S-iPr | 0 | 5-(CH$_2$)CH(OH)(CH$_2$)$_2$-cHp |
| 1-920 | H | H | tBu | 1 | 5-(CH$_2$)CH(OH)(CH$_2$)$_2$-cHp |
| 1-921 | H | Pn | tBu | 1 | 5-(CH$_2$)CH(OH)(CH$_2$)$_2$-cHp |
| 1-922 | 3-OMe | — | tBu | 0 | 5-(CH$_2$)CH(OH)(CH$_2$)$_2$-cHp |
| 1-923 | H | — | tBu | 0 | 5-(CH$_2$)CH(OH)(CH$_2$)$_3$-cHp |
| 1-924 | H | — | BuCMe$_2$ | 0 | 5-(CH$_2$)CH(OH)(CH$_2$)$_3$-cHp |
| 1-925 | H | — | EtOCH$_2$ | 0 | 5-(CH$_2$)CH(OH)(CH$_2$)$_3$-cHp |
| 1-926 | H | H | tBu | 1 | 5-(CH$_2$)CH(OH)(CH$_2$)$_3$-cHp |
| 1-927 | H | Hx | tBu | 1 | 5-(CH$_2$)CH(OH)(CH$_2$)$_3$-cHp |
| 1-928 | 2-OMe | — | tBu | 0 | 5-(CH$_2$)CH(OH)(CH$_2$)$_3$-cHp |
| 1-929 | H | — | tBu | 0 | 5-(CH$_2$)CH(OH)(CH$_2$)$_4$-cHp |
| 1-930 | H | — | EtOCH$_2$ | 0 | 5-(CH$_2$)CH(OH)(CH$_2$)$_4$-cHp |
| 1-931 | H | — | S-iPr | 0 | 5-(CH$_2$)CH(OH)(CH$_2$)$_4$-cHp |
| 1-932 | H | H | tBu | 1 | 5-(CH$_2$)CH(OH)(CH$_2$)$_4$-cHp |
| 1-933 | H | Pn | tBu | 1 | 5-(CH$_2$)CH(OH)(CH$_2$)$_4$-cHp |
| 1-934 | 3-Br | Hp | tBu | 1 | 5-(CH$_2$)CH(OH)(CH$_2$)$_4$-cHp |
| 1-935 | H | — | tBu | 0 | 5-(CH$_2$)CH(OH)(CH$_2$)$_5$-cHp |
| 1-936 | H | — | PnCMe$_2$ | 0 | 5-(CH$_2$)CH(OH)(CH$_2$)$_5$-cHp |
| 1-937 | H | — | EtOCH$_2$ | 0 | 5-(CH$_2$)CH(OH)(CH$_2$)$_5$-cHp |
| 1-938 | H | — | S-Ph | 0 | 5-(CH$_2$)CH(OH)(CH$_2$)$_5$-cHp |
| 1-939 | H | H | tBu | 1 | 5-(CH$_2$)CH(OH)(CH$_2$)$_5$-cHp |
| 1-940 | H | Hp | tBu | 1 | 5-(CH$_2$)CH(OH)(CH$_2$)$_5$-cHp |
| 1-941 | 3-Cl | Hp | tBu | 1 | 5-(CH$_2$)CH(OH)(CH$_2$)$_5$-cHp |
| 1-942 | H | — | tBu | 0 | 5-(CH$_2$)CH(OH)(CH$_2$)$_6$-cHp |
| 1-943 | H | — | tBu | 0 | 5-(CH$_2$)CH(OH)$_2$CH(OH)-cHp |
| 1-944 | H | — | EtOCH$_2$ | 0 | 5-(CH$_2$)CH(OH)$_2$CH(OH)-cHp |
| 1-945 | H | — | S-iPr | 0 | 5-(CH$_2$)CH(OH)$_2$CH(OH)-cHp |
| 1-946 | H | H | tBu | 1 | 5-(CH$_2$)CH(OH)$_2$CH(OH)-cHp |
| 1-947 | H | Pn | tBu | 1 | 5-(CH$_2$)CH(OH)$_2$CH(OH)-cHp |
| 1-948 | 2-OMe | Hp | tBu | 1 | 5-(CH$_2$)CH(OH)$_2$CH(OH)(CH$_2$)-cHp |
| 1-949 | H | — | tBu | 0 | 5-(CH$_2$)CH(OH)$_2$CH(OH)(CH$_2$)-cHp |
| 1-950 | H | — | PrCMe$_2$ | 0 | 5-(CH$_2$)CH(OH)$_2$CH(OH)(CH$_2$)-cHp |
| 1-952 | H | — | EtOCH$_2$ | 0 | 5-(CH$_2$)CH(OH)$_2$CH(OH)(CH$_2$)-cHp |
| 1-953 | H | — | S-Ph | 0 | 5-(CH$_2$)$_2$CH(OH)(CH$_2$)-cHp |
| 1-954 | H | H | tBu | 1 | 5-(CH$_2$)$_2$CH(OH)(CH$_2$)-cHp |
| 1-955 | H | Bu | tBu | 1 | 5-(CH$_2$)$_2$CH(OH)(CH$_2$)-cHp |
| 1-956 | H | Pn | tBu | 1 | 5-(CH$_2$)$_2$CH(OH)(CH$_2$)-cHp |
| 1-957 | H | Hp | tBu | 1 | 5-(CH$_2$)$_2$CH(OH)(CH$_2$)-cHp |
| 1-958 | 3-Cl | Hp | tBu | 1 | 5-(CH$_2$)$_2$CH(OH)(CH$_2$)-cHp |
| 1-959 | H | - | tBu | 0 | 5-(CH$_2$)$_2$CH(OH)(CH$_2$)$_2$-cHp |
| 1-960 | H | - | iPr | 0 | 5-(CH$_2$)$_2$CH(OH)(CH$_2$)$_2$-cHp |
| 1-961 | H | - | PnCMe$_2$ | 0 | 5-(CH$_2$)$_2$CH(OH)(CH$_2$)$_2$-cHp |
| 1-962 | H | - | EtOCH$_2$ | 0 | 5-(CH$_2$)$_2$CH(OH)(CH$_2$)$_2$-cHp |
| 1-963 | H | - | S-Ph | 0 | 5-(CH$_2$)$_2$CH(OH)(CH$_2$)$_2$-cHp |

TABLE 1-continued

| Cpd. No. | $R^a$ | $R^2$ | $R^3$ | n | $R^4$ |
|---|---|---|---|---|---|
| 1-964 | H | H | tBu | 1 | 5-$(CH_2)_2CH(OH)(CH_2)_2$-cHp |
| 1-965 | H | Hp | tBu | 1 | 5-$(CH_2)_2CH(OH)(CH_2)_2$-cHp |
| 1-966 | 3-Br | Hp | tBu | 1 | 5-$(CH_2)_2CH(OH)(CH_2)_2$-cHp |
| 1-967 | H | — | tBu | 0 | 5-$(CH_2)_2CH(OH)(CH_2)_3$-cHp |
| 1-968 | H | — | iPr | 0 | 5-$(CH_2)_2CH(OH)(CH_2)_3$-cHp |
| 1-969 | H | — | $BuCMe_2$ | 0 | 5-$(CH_2)_2CH(OH)(CH_2)_3$-cHp |
| 1-970 | H | — | $CH_3OCH_2$ | 0 | 5-$(CH_2)_2CH(OH)(CH_2)_3$-cHp |
| 1-971 | H | — | S-iPr | 0 | 5-$(CH_2)_2CH(OH)(CH_2)_3$-cHp |
| 1-972 | H | H | tBu | 1 | 5-$(CH_2)_2CH(OH)(CH_2)_3$-cHp |
| 1-973 | H | Pn | tBu | 1 | 5-$(CH_2)_2CH(OH)(CH_2)_3$-cHp |
| 1-974 | 3-Cl | Hp | tBu | 1 | 5-$(CH_2)_2CH(OH)(CH_2)_3$-cHp |
| 1-975 | 2-OMe | Hp | tBu | 1 | 5-$(CH_2)_2CH(OH)(CH_2)_3$-cHp |
| 1-976 | H | — | tBu | 0 | 5-$(CH_2)_2CH(OH)(CH_2)_4$-cHp |
| 1-977 | H | — | $EtOCH_2$ | 0 | 5-$(CH_2)_2CH(OH)(CH_2)_4$-cHp |
| 1-978 | H | — | S-iPr | 0 | 5-$(CH_2)_2CH(OH)(CH_2)_4$-cHp |
| 1-979 | H | H | tBu | 1 | 5-$(CH_2)_2CH(OH)(CH_2)_4$-cHp |
| 1-980 | H | Pn | tBu | 1 | 5-$(CH_2)_2CH(OH)(CH_2)_4$-cHp |
| 1-981 | 3-Cl | Hp | tBu | 1 | 5-$(CH_2)_2CH(OH)(CH_2)_4$-cHp |
| 1-982 | H | — | tBu | 0 | 5-$(CH_2)_2CH(OH)(CH_2)_5$-cHp |
| 1-983 | H | — | tBu | 0 | 5-$(CH_2)_2CH(OH)(CH_2)_6$-cHp |
| 1-984 | H | — | tBu | 0 | 5-$(CH_2)_3CH(OH)$-cHp |
| 1-985 | H | — | $EtOCH_2$ | 0 | 5-$(CH_2)_3CH(OH)$-cHp |
| 1-986 | H | — | S-Ph | 0 | 5-$(CH_2)_3CH(OH)$-cHp |
| 1-987 | H | H | tBu | 1 | 5-$(CH_2)_3CH(OH)$-cHp |
| 1-988 | H | Hx | tBu | 1 | 5-$(CH_2)_3CH(OH)$-cHp |
| 1-989 | 3-Br | Hp | tBu | 1 | 5-$(CH_2)_3CH(OH)$-cHp |
| 1-990 | H | — | tBu | 0 | 5-$(CH_2)_3CH(OH)(CH_2)$-cHp |
| 1-991 | H | — | $EtOCH_2$ | 0 | 5-$(CH_2)_3CH(OH)(CH_2)$-cHp |
| 1-992 | H | — | S-Ph | 0 | 5-$(CH_2)_3CH(OH)(CH_2)$-cHp |
| 1-993 | H | H | tBu | 1 | 5-$(CH_2)_3CH(OH)(CH_2)$-cHp |
| 1-994 | H | Hp | tBu | 1 | 5-$(CH_2)_3CH(OH)(CH_2)$-cHp |
| 1-995 | 3-Br | Hp | tBu | 1 | 5-$(CH_2)_3CH(OH)(CH_2)$-cHp |
| 1-996 | H | — | tBu | 0 | 5-$(CH_2)_3CH(OH)(CH_2)_2$-cHp |
| 1-997 | H | — | iPr | 0 | 5-$(CH_2)_3CH(OH)(CH_2)_2$-cHp |
| 1-998 | H | — | S-iPr | 0 | 5-$(CH_2)_3CH(OH)(CH_2)_2$-cHp |
| 1-999 | H | H | tBu | 1 | 5-$(CH_2)_3CH(OH)(CH_2)_2$-cHp |
| 1-1000 | H | Hx | tBu | 1 | 5-$(CH_2)_3CH(OH)(CH_2)_2$-cHp |
| 1-1001 | 3-Cl | Hp | tBu | 1 | 5-$(CH_2)_3CH(OH)(CH_2)_2$-cHp |
| 1-1002 | H | — | tBu | 0 | 5-$(CH_2)_3CH(OH)(CH_2)_3$-cHp |
| 1-1003 | H | — | $EtOCH_2$ | 0 | 5-$(CH_2)_3CH(OH)(CH_2)_3$-cHp |
| 1-1004 | H | — | S-iPr | 0 | 5-$(CH_2)_3CH(OH)(CH_2)_3$-cHp |
| 1-1005 | 3-Cl | — | tBu | 0 | 5-$(CH_2)_3CH(OH)(CH_2)_3$-cHp |
| 1-1006 | H | — | tBu | 0 | 5-$(CH_2)_3CH(OH)(CH_2)_4$-cHp |
| 1-1007 | H | H | tBu | 1 | 5-$(CH_2)_3CH(OH)(CH_2)_4$-cHp |
| 1-1008 | H | H | tBu | 1 | 5-$(CH_2)_3CH(OH)(CH_2)_3$-cHp |
| 1-1009 | H | — | tBu | 0 | 5-$(CH_2)_4CH(OH)$-cHp |
| 1-1010 | H | H | tBu | 1 | 5-$(CH_2)_4CH(OH)$-cHp |
| 1-1011 | H | — | tBu | 0 | 5-$(CH_2)_4CH(OH)CH_2$-cHp |
| 1-1012 | H | H | tBu | 1 | 5-$(CH_2)_4CH(OH)CH_2$-cHp |
| 1-1013 | H | — | tBu | 0 | 5-$(CH_2)_4CH(OH)(CH_2)_2$-cHp |
| 1-1014 | H | H | tBu | 1 | 5-$(CH_2)_4CH(OH)(CH_2)_2$-cHp |
| 1-1015 | H | — | tBu | 0 | 5-$(CH_2)_4CH(OH)(CH_2)_3$-cHp |
| 1-1016 | H | — | tBu | 0 | 5-$(CH_2)_5CH(OH)$-cHp |
| 1-1017 | H | H | tBu | 1 | 5-$(CH_2)_5CH(OH)$-cHp |
| 1-1018 | H | — | tBu | 0 | 5-$(CH_2)_5CH(OH)(CH_2)$-cHp |
| 1-1019 | H | — | tBu | 0 | 5-$(CH_2)_5CH(OH)(CH_2)_2$-cHp |
| 1-1020 | H | — | tBu | 0 | 5-$(CH_2)_6CH(OH)$-cHp |
| 1-1021 | H | — | tBu | 0 | 5-$CH(OB^2)$-cHx |
| 1-1022 | H | — | tBu | 0 | 5-$CH(OB^2)CH_2$-cHx |
| 1-1023 | H | — | tBu | 0 | 5-$CH(OB^2)CH_2$-cHx<br>Na salt |
| 1-1024 | H | — | tBu | 0 | 5-$CH(OB^3)CH_2$-cHx<br>Na salt |
| 1-1025 | H | — | tBu | 0 | 5-$CH(OE^1)CH_2$-cHx<br>HCl salt |
| 1-1026 | H | — | tBu | 0 | 5-$CH(OB^2)(CH_2)_2$-cHx<br>Na salt |
| 1-1027 | H | — | tBu | 0 | 5-$CH(OB^3)(CH_2)_2$-cHx<br>Na salt |
| 1-1028 | H | — | tBu | 0 | 5-$CH(OE^3)(CH_2)_2$-cHx<br>HCl salt |
| 1-1029 | H | — | tBu | 0 | 5-$CH(OB^1)(CH_2)_3$-cHx<br>Na salt |
| 1-1030 | H | — | tBu | 0 | 5-$CH(OB^2)(CH_2)_3$-cHx<br>Na salt |
| 1-1031 | H | — | tBu | 0 | 5-$CH(OB^3)(CH_2)_3$-cHx |

TABLE 1-continued

| Cpd. No. | R$^a$ | R$^2$ | R$^3$ | n | R$^4$ |
|---|---|---|---|---|---|
| 1-1032 | H | — | tBu | 0 | 5-CH(OD$^1$)(CH$_2$)$_3$-cHx Na salt |
| 1-1033 | H | — | tBu | 0 | 5-CH(OE$^1$)(CH$_2$)$_3$-cHx HCl salt |
| 1-1034 | H | — | tBu | 0 | 5-CH(OE$^2$)(CH$_2$)$_3$-cHx HCl salt |
| 1-1035 | H | — | tBu | 0 | 5-CH(OB$^2$)(CH$_2$)$_3$-cHx |
| 1-1036 | H | — | tBu | 0 | 5-CH(OB$^1$)(CH$_2$)$_4$-cHx Na salt |
| 1-1037 | H | — | tBu | 0 | 5-CH(OB$^2$)(CH$_2$)$_4$-cHx Na salt |
| 1-1038 | H | — | tBu | 0 | 5-CH(OB$^3$)(CH$_2$)$_4$-cHx Na salt |
| 1-1039 | H | — | tBu | 0 | 5-CH(OD$^1$)(CH$_2$)$_4$-cHx Na salt |
| 1-1040 | H | — | tBu | 0 | 5-CH(OE$^1$)(CH$_2$)$_4$-cHx HCl salt |
| 1-1041 | H | — | tBu | 0 | 5-CH(OE$^2$)(CH$_2$)$_4$-cHx HCl salt |
| 1-1042 | H | — | tBu | 0 | 5-CH(OE$^3$)(CH$_2$)$_4$-cHx HCl salt |
| 1-1043 | H | — | tBu | 0 | 5-CH(OF$^1$)(CH$_2$)$_4$-cHx Na salt |
| 1-1044 | H | — | tBu | 0 | 5-CH(OB$^2$)(CH$_2$)$_4$-cHx |
| 1-1045 | H | — | tBu | 0 | 5-CH(OB$^1$)(CH$_2$)$_5$-cHx Na salt |
| 1-1046 | H | — | tBu | 0 | 5-CH(OB$^2$)(CH$_2$)$_5$-cHx Na salt |
| 1-1047 | H | — | tBu | 0 | 5-CH(OB$_3$)(CH$_2$)$_5$-cHx Na salt |
| 1-1048 | H | — | tBu | 0 | 5-CH(OD$^1$)(CH$_2$)$_5$-cHx Na salt |
| 1-1049 | H | — | tBu | 0 | 5-CH(OE$^1$)(CH$_2$)$_5$-cHx HCl salt |
| 1-1050 | H | — | tBu | 0 | 5-CH(OE$^2$)(CH$_2$)$_5$-cHx HCl salt |
| 1-1051 | H | — | tBu | 0 | 5-CH(OE$^3$)(CH$_2$)$_5$-cHx HCl salt |
| 1-1052 | H | — | tBu | 0 | 5-CH(OF$^1$)(CH$_2$)$_5$-cHx Na salt |
| 1-1053 | H | — | tBu | 0 | 5-CH(OB$^2$)(CH$_2$)$_5$-cHx |
| 1-1054 | H | — | tBu | 0 | 5-CH(OB$^2$)(CH$_2$)$_6$-cHx Na salt |
| 1-1055 | H | — | tBu | 0 | 5-CH(OD$^1$)(CH$_2$)-cHx Na salt |
| 1-1056 | H | — | tBu | 0 | 5-CH(OF$^1$)(CH$_2$)-cHx Na salt |
| 1-1057 | H | H | tBu | 1 | 5-CH(OB$^2$)CH$_2$-cHx Na salt |
| 1-1058 | H | H | tBu | 1 | 5-CH(OB$^2$)(CH$_2$)$_2$-cHx Na salt |
| 1-1059 | H | H | tBu | 1 | 5-CH(OB$^2$)(CH$_2$)$_3$-cHx Na salt |
| 1-1060 | H | H | tBu | 1 | 5-CH(OB$^2$)(CH$_2$)$_4$-cHx Na salt |
| 1-1061 | H | H | tBu | 1 | 5-CH(OB$^2$)(CH$_2$)$_5$-cHx Na salt |
| 1-1062 | H | H | tBu | 1 | 5-(CH$_2$)CH(OB$^2$)CH$_2$-cHx Na salt |
| 1-1063 | H | H | tBu | 1 | 5-(CH$_2$)CH(OB$^2$)(CH$_2$)$_2$-cHx Na salt |
| 1-1064 | H | H | tBu | 1 | 5-(CH$_2$)$_2$CH(OB$^2$)(CH$_2$)$_4$-cHx Na salt |
| 1-1065 | H | H | tBu | 1 | 5-(CH$_2$)CH(OB$^2$)(CH$_2$)$_4$-cHx Na salt |
| 1-1066 | H | H | tBu | 1 | 5-(CH$_2$)CH(OB$^2$)(CH$_2$)$_5$-cHx Na salt |
| 1-1067 | H | H | tBu | 1 | 5-(CH$_2$)$_2$CH(OB$^2$)-cHx Na salt |
| 1-1068 | H | H | tBu | 1 | 5-(CH$_2$)$_2$CH(OB$^2$)(CH$_2$)$_2$-cHx Na salt |
| 1-1069 | H | H | tBu | 1 | 5-(CH$_2$)$_2$CH(OB$^2$)(CH$_2$)$_3$-cHx Na salt |
| 1-1070 | H | H | tBu | 1 | 5-(CH$_2$)$_3$CH(OB$^2$)(CH$_2$)-cHx Na salt |

TABLE 1-continued

| Cpd. No. | R$^a$ | R$^2$ | R$^3$ | n | R$^4$ |
|---|---|---|---|---|---|
| 1-1071 | H | H | tBu | 1 | 5-(CH$_2$)$_3$CH(OB$^2$)(CH$_2$)$_2$-cHx Na salt |
| 1-1072 | H | H | tBu | 1 | 5-(CH$_2$)$_3$CH(OB$^2$)(CH$_2$)$_3$-cHx Na salt |
| 1-1073 | H | H | tBu | 1 | 5-(CH$_2$)$_3$CH(OB$^2$)(CH$_2$)$_4$-cHx Na salt |
| 1-1074 | H | H | tBu | 1 | 5-(CH$_2$)$_4$CH(OB$^2$)(CH$_2$)-cHx Na salt |
| 1-1075 | H | H | tBu | 1 | 5-(CH$_2$)$_4$CH(OB$^2$)-cHx Na salt |
| 1-1076 | H | H | tBu | 1 | 5-(CH$_2$)$_4$CH(OB$^2$)(CH$_2$)-cHx Na salt |
| 1-1077 | H | H | tBu | 1 | 5-(CH$_2$)$_4$CH(OB$^2$)(CH$_2$)$_2$-cHx |
| 1-1078 | H | — | tBu | 0 | 5-(CH$_2$)CH(OB$^2$)-cHx Na salt |
| 1-1079 | H | — | tBu | 0 | 5-(CH$_2$)CH(OB$^2$)(CH$_2$)-cHx Na salt |
| 1-1080 | H | — | tBu | 0 | 5-(CH$_2$)CH(OD$^1$)(CH$_2$)-cHx Na salt |
| 1-1081 | H | — | tBu | 0 | 5-(CH$_2$)CH(OE$^1$)(CH$_2$)-cHx HCl salt |
| 1-1082 | H | — | tBu | 0 | 5-(CH$_2$)CH(OF$^1$)(CH$_2$)-cHx Na salt |
| 1-1083 | H | — | tBu | 0 | 5-(CH$_2$)CH(OB$^2$)(CH$_2$)-cHx |
| 1-1084 | H | — | tBu | 0 | 5-(CH$_2$)CH(OB$^2$)(CH$_2$)$_2$-cHx Na salt |
| 1-1085 | H | — | tBu | 0 | 5-(CH$_2$)CH(OD$^1$)(CH$_2$)$_2$-cHx Na salt |
| 1-1086 | H | — | tBu | 0 | 5-(CH$_2$)CH(OE$^1$)(CH$_2$)$_2$-cHx HCl salt |
| 1-1087 | H | — | tBu | 0 | 5-(CH$_2$)CH(OF$^1$)(CH$_2$)$_2$-cHx Na salt |
| 1-1088 | H | — | tBu | 0 | 5-(CH$_2$)CH(OB$^2$)(CH$_2$)$_2$-cHx |
| 1-1089 | H | — | tBu | 0 | 5-(CH$_2$)CH(OB$^2$)(CH$_2$)$_3$-cHx Na salt |
| 1-1090 | H | — | tBu | 0 | 5-(CH$_2$)CH(OB$^2$)(CH$_2$)$_4$-cHx Na salt |
| 1-1091 | H | — | tBu | 0 | 5-(CH$_2$)CH(OB$^2$)(CH$_2$)$_5$-cHx Na salt |
| 1-1092 | H | — | tBu | 0 | 5-(CH$_2$)$_2$CH(OB$^1$)-cHx Na salt |
| 1-1093 | H | — | tBu | 0 | 5-(CH$_2$)$_2$CH(OB$^2$)-cHx Na salt |
| 1-1094 | H | — | tBu | 0 | 5-(CH$_2$)$_2$CH(OB$^3$)-cHx Na salt |
| 1-1095 | H | — | tBu | 0 | 5-(CH$_2$)$_2$CH(OD$^1$)-cHx Na salt |
| 1-1096 | H | — | tBu | 0 | 5-(CH$_2$)$_2$CH(OE$^1$)-cHx HCl salt |
| 1-1097 | H | — | tBu | 0 | 5-(CH$_2$)$_2$CH(OE$^2$)-cHx HCl salt |
| 1-1098 | H | — | tBu | 0 | 5-(CH$_2$)$_2$CH(OE$^3$)-cHx HCl salt |
| 1-1099 | H | — | tBu | 0 | 5-(CH$_2$)$_2$CH(OF$^1$)-cHx Na salt |
| 1-1100 | H | — | tBu | 0 | 5-(CH$_2$)$_2$CH(OB$^2$)-cHx |
| 1-1101 | H | — | tBu | 0 | 5-(CH$_2$)$_2$CH(OB$^1$)(CH$_2$)-cHx Na salt |
| 1-1102 | H | — | tBu | 0 | 5-(CH$_2$)$_2$CH(OB$^2$)(CH$_2$)-cHx Na salt |
| 1-1103 | H | — | tBu | 0 | 5-(CH$_2$)$_2$CH(OB$^3$)(CH$_2$)-cHx Na salt |
| 1-1104 | H | — | tBu | 0 | 5-(CH$_2$)$_2$CH(OD$^1$)(CH$_2$)-cHx Na salt |
| 1-1105 | H | — | tBu | 0 | 5-(CH$_2$)$_2$CH(OE$^1$)(CH$_2$)-cHx HCl salt |
| 1-1106 | H | — | tBu | 0 | 5-(CH$_2$)$_2$CH(OE$^2$)(CH$_2$)-cHx HCl salt |
| 1-1107 | H | — | tBu | 0 | 5-(CH$_2$)$_2$CH(OE$^3$)(CH$_2$)-cHx HCl salt |
| 1-1108 | H | — | tBu | 0 | 5-(CH$_2$)$_2$CH(OF$^1$)(CH$_2$)-cHx Na salt |
| 1-1109 | H | — | tBu | 0 | 5-(CH$_2$)$_2$CH(OB$^2$)(CH$_2$)-cHx |
| 1-1110 | H | — | tBu | 0 | 5-(CH$_2$)$_2$CH(OB$^1$)(CH$_2$)$_2$-cHx Na salt |
| 1-1111 | H | — | tBu | 0 | 5-(CH$_2$)$_2$CH(OB$^2$)(CH$_2$)$_2$-cHx |

TABLE 1-continued

| Cpd. No. | R$^a$ | R$^2$ | R$^3$ | n | R$^4$ |
|---|---|---|---|---|---|
| 1-1112 | H | — | tBu | 0 | 5-(CH$_2$)CH(OB$^3$)(CH$_2$)$_2$-cHx<br>Na salt |
| 1-1113 | H | — | tBu | 0 | 5-(CH$_2$)$_2$CH(OD$^1$)(CH$_2$)$_2$-cHx<br>Na salt |
| 1-1114 | H | — | tBu | 0 | 5-(CH$_2$)$_2$CH(OE$^1$)(CH$_2$)$_2$-cHx<br>HCl salt |
| 1-1115 | H | — | tBu | 0 | 5-(CH$_2$)$_2$CH(OE$^2$)(CH$_2$)$_2$-cHx<br>HCl salt |
| 1-1116 | H | — | tBu | 0 | 5-(CH$_2$)$_2$CH(OE$^3$)(CH$_2$)$_2$-cHx<br>HCl salt |
| 1-1117 | H | — | tBu | 0 | 5-(CH$_2$)$_2$CH(OF$^1$)(CH$_2$)$_2$-cHx<br>Na salt |
| 1-1118 | H | — | tBu | 0 | 5-(CH$_2$)$_2$CH(OB$^2$)(CH$_2$)$_2$-cHx |
| 1-1119 | H | — | tBu | 0 | 5-(CH$_2$)$_2$CH(OB$^1$)(CH$_2$)$_3$-cHx<br>Na salt |
| 1-1120 | H | — | tBu | 0 | 5-(CH$_2$)$_2$CH(OB$^2$)(CH$_2$)$_3$-cHx<br>Na salt |
| 1-1121 | H | — | tBu | 0 | 5-(CH$_2$)$_2$CH(OB$^3$)(CH$_2$)$_3$-cHx<br>Na salt |
| 1-1122 | H | — | tBu | 0 | 5-(CH$_2$)$_2$CH(OD$^1$)(CH$_2$)$_3$-cHx<br>Na salt |
| 1-1123 | H | — | tBu | 0 | 5-(CH$_2$)$_2$CH(OE$^1$)(CH$_2$)$_3$-cHx<br>HCl salt |
| 1-1124 | H | — | tBu | 0 | 5-(CH$_2$)$_2$CH(OE$^2$)(CH$_2$)$_3$-cHx<br>HCl salt |
| 1-1125 | H | — | tBu | 0 | 5-(CH$_2$)$_2$CH(OE$^3$)(CH$_2$)$_3$-cHx<br>HCl salt |
| 1-1126 | H | — | tBu | 0 | 5-(CH$_2$)$_2$CH(OF$^1$)(CH$_2$)$_3$-cHx<br>Na salt |
| 1-1127 | H | — | tBu | 0 | 5-(CH$_2$)$_2$CH(OB$^2$)(CH$_2$)$_3$-cHx |
| 1-1128 | H | — | tBu | 0 | 5-(CH$_2$)$_2$CH(OB$^1$)(CH$_2$)$_4$-cHx<br>Na salt |
| 1-1129 | H | — | tBu | 0 | 5-(CH$_2$)$_2$CH(OB$^2$)(CH$_2$)$_4$-cHx<br>Na salt |
| 1-1130 | H | — | tBu | 0 | 5-(CH$_2$)$_2$CH(OB$^3$)(CH$_2$)$_4$-cHx<br>Na salt |
| 1-1131 | H | — | tBu | 0 | 5-(CH$_2$)$_2$CH(OD$^1$)(CH$_2$)$_4$-cHx<br>Na salt |
| 1-1132 | H | — | tBu | 0 | 5-(CH$_2$)$_2$CH(OE$^1$)(CH$_2$)$_4$-cHx<br>HCl salt |
| 1-1133 | H | — | tBu | 0 | 5-(CH$_2$)$_2$CH(OE$^2$)(CH$_2$)$_4$-cHx<br>HCl salt |
| 1-1134 | H | — | tBu | 0 | 5-(CH$_2$)$_2$CH(OE$^3$)(CH$_2$)$_4$-cHx<br>HCl salt |
| 1-1135 | H | — | tBu | 0 | 5-(CH$_2$)$_2$CH(OF$^1$)(CH$_2$)$_4$-cHx<br>Na salt |
| 1-1136 | H | — | tBu | 0 | 5-(CH$_2$)$_2$CH(OB$^2$)(CH$_2$)$_4$-cHx |
| 1-1137 | H | — | tBu | 0 | 5-(CH$_2$)$_2$CH(OB$^2$)(CH$_2$)$_5$-cHx<br>Na salt |
| 1-1138 | H | — | tBu | 0 | 5-(CH$_2$)$_2$CH(OD$^1$)(CH$_2$)$_5$-cHx<br>Na salt |
| 1-1139 | H | — | tBu | 0 | 5-(CH$_2$)$_2$CH(OE$^1$)(CH$_2$)$_5$-cHx<br>HCl salt |
| 1-1140 | -H | — | tBu | 0 | 5-(CH$_2$)$_2$CH(OF$^1$)(CH$_2$)$_5$-cHx<br>Na salt |
| 1-1141 | H | — | tBu | 0 | 5-(CH$_2$)$_2$CH(OB$^2$)(CH$_2$)$_5$-cHx |
| 1-1142 | H | — | tBu | 0 | 5-(CH$_2$)$_3$CH(OB$^2$)cHx<br>Na salt |
| 1-1143 | H | — | tBu | 0 | 5-(CH$_2$)$_3$CH(OB$^2$)(CH$_2$)-cHx<br>Na salt |
| 1-1144 | H | — | tBu | 0 | 5-(CH$_2$)$_3$CH(OB$^2$)(CH$_2$)$_2$-cHx<br>Na salt |
| 1-1145 | H | — | tBu | 0 | 5-(CH$_2$)$_3$CH(OB$^2$)(CH$_2$)$_3$-cHx<br>Na salt |
| 1-1146 | H | — | tBu | 0 | 5-(CH$_2$)$_3$CH(OB$^2$)(CH$_2$)$_4$-cHx<br>Na salt |
| 1-1147 | H | — | tBu | 0 | 5-(CH$_2$)$_3$CH(OD$^1$)(CH$_2$)-cHx<br>Na salt |
| 1-1148 | H | — | tBu | 0 | 5-(CH$_2$)$_3$CH(OE$^1$)(CH$_2$)$_2$-cHx<br>HCl salt |
| 1-1149 | H | — | tBu | 0 | 5-(CH$_2$)$_4$CH(OB$^2$)-cHx<br>Na salt |
| 1-1150 | H | — | tBu | 0 | 5-(CH$_2$)$_4$CH(OB$^3$)(CH$_2$)-cHx<br>Na salt |
| 1-1151 | H | — | tBu | 0 | 5-(CH$_2$)$_4$CH(OB$^2$)(CH$_2$)$_2$-cHx |

TABLE 1-continued

| Cpd. No. | R$^a$ | R$^2$ | R$^3$ | n | R$^4$ |
|---|---|---|---|---|---|
| 1-1152 | H | — | tBu | 0 | 5-(CH$_2$)$_4$CH(OF$^1$)(CH$_2$)$_3$-cHx Na salt |
| 1-1153 | H | — | tBu | 0 | 5-(CH$_2$)$_5$CH(OB$^2$)-cHx Na salt |
| 1-1154 | H | — | tBu | 0 | 5-(CH$_2$)$_5$CH(OB$^3$)(CH$_2$)-cHx Na salt |
| 1-1155 | H | — | tBu | 0 | 5-CH(OB$^2$)-cPn Na salt |
| 1-1156 | H | — | tBu | 0 | 5-CH(OB$^2$)(CH$_2$)-cPn Na salt |
| 1-1157 | H | — | tBu | 0 | 5-CH(OB$^2$)(CH$_2$)$_2$-cPn Na salt |
| 1-1158 | H | — | tBu | 0 | 5-CH(OB$^2$)(CH$_2$)$_3$-cPn Na salt |
| 1-1159 | H | — | tBu | 0 | 5-CH(OB$^2$)(CH$_2$)$_4$-cPn Na salt |
| 1-1160 | H | — | tBu | 0 | 5-CH(OB$^2$)(CH$_2$)$_5$-cPn Na salt |
| 1-1161 | H | — | tBu | 0 | 5-CH(OD$^1$)(CH$_2$)$_6$-cPn Na salt |
| 1-1162 | H | — | tBu | 0 | 5-CH(OE$^3$)(CH$_2$)$_2$-cPn HCl salt |
| 1-1163 | H | — | tBu | 0 | 5-(CH$_2$)CH(OB$^2$)-cPn Na salt |
| 1-1164 | H | — | tBu | 0 | 5-(CH$_2$)CH(OB$^2$)(CH$_2$)-cPn Na salt |
| 1-1165 | H | — | tBu | 0 | 5-(CH$_2$)CH(OB$^2$)(CH$_2$)$_2$-cPn Na salt |
| 1-1166 | H | — | tBu | 0 | 5-(CH$_2$)CH(OB$^2$)(CH$_2$)$_3$-cPn Na salt |
| 1-1167 | H | — | tBu | 0 | 5-(CH$_2$)CH(OB$^2$)(CH$_2$)$_4$-cPn Na salt |
| 1-1168 | H | — | tBu | 0 | 5-(CH$_2$)CH(OB$^2$)(CH$_2$)$_5$-cPn Na salt |
| 1-1169 | H | — | tBu | 0 | 5-CH$_2$CH(OD$^1$)(CH$_2$)-cPn Na salt |
| 1-1170 | H | — | tBu | 0 | 5-CH$_2$CH(OE$^1$)(CH$_2$)$_2$-cPn HCl salt |
| 1-1171 | H | — | tBu | 0 | 5-CH$_2$CH(OF$^1$)(CH$_2$)$_3$-cPn Na salt |
| 1-1172 | H | — | tBu | 0 | 5-(CH$_2$)$_2$CH(OB$^2$)-cPn Na salt |
| 1-1173 | H | — | tBu | 0 | 5-(CH$_2$)$_2$CH(OE$^1$)-cPn HCl salt |
| 1-1174 | H | — | tBu | 0 | 5-(CH$_2$)$_2$CH(OD$^1$)-cPn Na salt |
| 1-1175 | H | — | tBu | 0 | 5-(CH$_2$)$_2$CH(OB$^1$)(CH$_2$)-cPn Na salt |
| 1-1176 | H | — | tBu | 0 | 5-(CH$_2$)$_2$CH(OB$^2$)(CH$_2$)-cPn Na salt |
| 1-1177 | H | — | tBu | 0 | 5-(CH$_2$)$_2$CH(OB$^3$)(CH$_2$)-cPn Na salt |
| 1-1178 | H | — | tBu | 0 | 5-(CH$_2$)$_2$CH(OD$^1$)(CH$_2$)-cPn Na salt |
| 1-1179 | H | — | tBu | 0 | 5-(CH$_2$)$_2$CH(OE$^1$)(CH$_2$)-cPn HCl salt |
| 1-1180 | H | — | tBu | 0 | 5-(CH$_2$)$_2$CH(OE$^2$)(CH$_2$)-cPn HCl salt |
| 1-1181 | H | — | tBu | 0 | 5-(CH$_2$)$_2$CH(OE$^3$)(CH$_2$)-cPn HCl salt |
| 1-1182 | H | — | tBu | 0 | 5-(CH$_2$)$_2$CH(OF$^1$)(CH$_2$)-cPn Na salt |
| 1-1183 | H | — | tBu | 0 | 5-(CH$_2$)$_2$CH(OB$^2$)(CH$_2$)-cPn |
| 1-1184 | H | H | tBu | 1 | 5-(CH$_2$)$_2$CH(OB$^2$)-cPn Na salt |
| 1-1185 | H | H | tBu | 1 | 5-(CH$_2$)$_2$CH(OB$^2$)(CH$_2$)-cPn Na salt |
| 1-1186 | H | H | tBu | 1 | 5-(CH$_2$)$_2$CH(OB$^2$)(CH$_2$)$_2$-cPn Na salt |
| 1-1187 | H | H | tBu | 1 | 5-(CH$_2$)$_2$CH(OB$^2$)(CH$_2$)$_3$-cPn Na salt |
| 1-1188 | H | H | tBu | 1 | 5-(CH$_2$)$_2$CH(OB$^2$)(CH$_2$)$_4$-cPn Na salt |
| 1-1189 | H | H | tBu | 1 | 5-(CH$_2$)$_2$CH(OE$^1$)(CH$_2$)-cPn HCl salt |
| 1-1190 | H | H | tBu | 1 | 5-(CH$_2$)$_2$CH(OF$^1$)(CH$_2$)$_2$-cPn Na salt |

TABLE 1-continued

| Cpd. No. | R$^a$ | R$^2$ | R$^3$ | n | R$^4$ |
|---|---|---|---|---|---|
| 1-1191 | H | — | tBu | 0 | 5-(CH$_2$)$_3$CH(OB$^2$)-cPn Na salt |
| 1-1192 | H | — | tBu | 0 | 5-(CH$_2$)$_3$CH(OB$^2$)(CH$_2$)-cPn Na salt |
| 1-1193 | H | — | tBu | 0 | 5-(CH$_2$)$_3$CH(OB$^2$)(CH$_2$)$_2$-cPn Na salt |
| 1-1194 | H | — | tBu | 0 | 5-(CH$_2$)$_3$CH(OB$^2$)(CH$_2$)$_3$-cPn Na salt |
| 1-1195 | H | — | tBu | 0 | 5-(CH$_2$)$_3$CH(OD$^1$)(CH$_2$)$_4$-cPn Na salt |
| 1-1196 | H | — | tBu | 1 | 5-(CH$_2$)$_3$CH(OE$^3$)(CH$_2$)-cPn HCl salt |
| 1-1197 | H | — | tBu | 0 | 5-(CH$_2$)$_3$CH(OB$^2$)(CH$_2$)-cPn |
| 1-1198 | H | — | tBu | 0 | 5-(CH$_2$)$_4$CH(OE$^2$)-cPn HCl salt |
| 1-1199 | H | — | tBu | 0 | 5-(CH$_2$)$_4$CH(OB$^2$)(CH$_2$)-cPn Na salt |
| 1-1200 | H | — | tBu | 0 | 5-(CH$_2$)$_4$CH(OE$^1$)(CH$_2$)$_2$-cPn HCl salt |
| 1-1201 | H | — | tBu | 0 | 5-(CH$_2$)$_5$CH(OB$^2$)-cPn Na salt |
| 1-1202 | H | — | tBu | 0 | 5-(CH$_2$)$_5$CH(OB$^2$)(CH$_2$)-cPn Na salt |
| 1-1203 | H | — | tBu | 0 | 5-CH(OB$^2$)-cHp Na salt |
| 1-1204 | H | — | tBu | 0 | 5-CH(OB$^2$)(CH$_2$)-cHp Na salt |
| 1-1205 | H | — | tBu | 0 | 5-CH(OB$^2$)(CH$_2$)$_2$-cHp Na salt |
| 1-1206 | H | — | tBu | 0 | 5-CH(OB$^2$)(CH$_2$)$_3$-cHp Na salt |
| 1-1207 | H | — | tBu | 0 | 5-CH(OB$^2$)(CH$_2$)$_4$-cHp Na salt |
| 1-1208 | H | — | tBu | 0 | 5-CH(OB$^2$)(CH$_2$)$_5$-cHp Na salt |
| 1-1209 | H | — | tBu | 0 | 5-CH(OD$^1$)(CH$_2$)$_6$-cHp Na salt |
| 1-1210 | H | — | tBu | 0 | 5-CH(OE$^1$)(CH$_2$)-cHp HCl salt |
| 1-1211 | H | — | tBu | 0 | 5-CH$_2$CH(OB$^2$)-cHp Na salt |
| 1-1212 | H | — | tBu | 0 | 5-CH$_2$CH(OB$^2$)(CH$_2$)-cHp Na salt |
| 1-1213 | H | — | tBu | 0 | 5-CH$_2$CH(OB$^2$)(CH$_2$)$_2$-cHp Na salt |
| 1-1214 | H | — | tBu | 0 | 5-CH$_2$CH(OB$^2$)(CH$_2$)$_3$-cHp Na salt |
| 1-1215 | H | — | tBu | 0 | 5-CH$_2$CH(OB$^2$)(CH$_2$)$_4$-cHp Na salt |
| 1-1216 | H | — | tBu | 0 | 5-CH$_2$CH(OB$^2$)(CH$_2$)$_5$-cHp Na salt |
| 1-1217 | H | — | tBu | 0 | 5-CH$_2$CH(OE$^1$)(CH$_2$)-cHp HCl salt |
| 1-1218 | H | — | tBu | 0 | 5-CH$_2$CH(OF$^1$)(CH$_2$)-cHp Na salt |
| 1-1219 | H | — | tBu | 0 | 5-(CH$_2$)$_2$CH(OB$^2$)-cHp Na salt |
| 1-1220 | H | — | tBu | 0 | 5-(CH$_2$)$_2$CH(OB$^2$)(CH$_2$)-cHp Na salt |
| 1-1221 | H | — | tBu | 0 | 5-(CH$_2$)$_2$CH(OB$^2$)(CH$_2$)-cHp |
| 1-1222 | H | — | tBu | 0 | 5-(CH$_2$)$_2$CH(OB$^2$)(CH$_2$)$_2$-cHp Na salt |
| 1-1223 | H | — | tBu | 0 | 5-(CH$_2$)$_2$CH(OB$^2$)(CH$_2$)$_3$-cHp Na salt |
| 1-1224 | H | — | tBu | 0 | 5-(CH$_2$)$_2$CH(OB$^2$)(CH$_2$)$_4$-cHp Na salt |
| 1-1225 | H | — | tBu | 0 | 5-(CH$_2$)$_2$CH(OB$^2$)(CH$_2$)$_5$-cHp Na salt |
| 1-1226 | H | — | tBu | 0 | 5-(CH$_2$)$_2$CH(OE$^1$)(CH$_2$)-cHp HCl salt |
| 1-1227 | H | — | tBu | 0 | 5-(CH$_2$)$_2$CH(OD$^1$)(CH$_2$)$_2$-cHp Na salt |
| 1-1228 | H | — | tBu | 0 | 5-(CH$_2$)$_2$CH(OF$^1$)(CH$_2$)$_2$-cHp Na salt |
| 1-1229 | H | — | tBu | 0 | 5-(CH$_2$)$_3$CH(OB$^2$)(CH$_2$)-cHp Na salt |
| 1-1230 | H | — | tBu | 0 | 5-(CH$_2$)$_3$CH(OB$^2$)(CH$_2$)$_2$-cHp |

TABLE 1-continued

| Cpd. No. | $R^a$ | $R^2$ | $R^3$ | n | $R^4$ |
|---|---|---|---|---|---|
| 1-1231 | H | — | tBu | 0 | 5-(CH$_2$)$_3$CH(OB$^2$)(CH$_2$)$_3$-cHp Na salt |
| 1-1232 | H | — | tBu | 0 | 5-(CH$_2$)$_4$CH(OB$^2$)-cHp Na salt |
| 1-1233 | H | — | tBu | 0 | 5-(CH$_2$)$_4$CH(OB$^2$)CH$_2$-cHp Na salt |
| 1-1234 | H | — | tBu | 0 | 5-CH=CH—CH(OH)(CH$_2$)-cHx |
| 1-1235 | H | — | tBu | 0 | 5-CH=CH—CH(OH)(CH$_2$)$_2$-cHp |
| 1-1236 | H | — | tBu | 0 | 5-CH=CH—CH(OH)(CH$_2$)$_3$-cPN |
| 1-1237 | H | — | tBu | 0 | 5-CH=CH—CH(OH)(CH$_2$)-cHp |
| 1-1238 | H | H | tBu | 1 | 5-CH=CH—CH(OH)(CH$_2$)-cHx |
| 1-1239 | H | H | tBu | 1 | 5-CH=CH—CH(OH)-cHx |
| 1-1240 | H | — | tBu | 0 | 5-CH=CH—CH(OB$^2$)(CH$_2$)-cHx Na salt |
| 1-1241 | H | — | tBu | 0 | 5-CH=CH—CH(OB$^2$)(CH$_2$)-cHp Na salt |
| 1-1242 | H | — | tBu | 0 | 5-(CH$_2$)$_2$CH(OH)-cOc |
| 1-1243 | H | — | tBu | 0 | 5-(CH$_2$)$_2$CH(OH)-cBu |
| 1-1244 | H | — | tBu | 0 | 5-(CH$_2$)$_2$CH(OH)-cPr |
| 1-1245 | H | — | tBu | 0 | 5-(CH$_2$)CH(OH)-cBu |
| 1-1246 | H | — | tBu | 0 | 5-(CH$_2$)CH(OH)-cOc |
| 1-1247 | H | — | tBu | 0 | 5-(CH$_2$)CH(OH)-cPr |
| 1-1248 | H | — | tBu | 0 | 5-(CH$_2$)CH(OH)(CH$_2$)-cPr |
| 1-1249 | H | — | tBu | 0 | 5-(CH$_2$)CH(OH)(CH$_2$)$_2$-cPr |
| 1-1250 | H | — | tBu | 0 | 5-(CH$_2$)$_3$CH(OH)(CH$_2$)-cPr |
| 1-1251 | H | — | tBu | 0 | 5-CH(OH)(CH$_2$)-cPr |
| 1-1252 | H | — | tBu | 0 | 5-CH(OH)(CH$_2$)-cOc |
| 1-1253 | H | — | tBu | 0 | 5-CH(OH)(CH$_2$)$_2$-tBu |
| 1-1254 | H | — | tBu | 0 | 5-CH(OH)(CH$_2$)-iPr |
| 1-1255 | H | — | tBu | 0 | 5-(CH$_2$)CH(OH)-iPr |
| 1-1256 | H | — | tBu | 0 | 5-(CH$_2$)CH(OH)(CH$_2$)$_5$-iPr |
| 1-1257 | H | — | tBu | 0 | 5-(CH$_2$)CH(OH)(CH$_2$)$_2$-iPr |
| 1-1258 | H | — | tBu | 0 | 5-(CH$_2$)$_2$CH(OH)(CH$_2$)-iPr |
| 1-1259 | H | — | tBu | 0 | 5-(CH$_2$)$_2$CH(OH)(CH$_2$)$_2$-iPr |
| 1-1260 | H | — | tBu | 0 | 5-(CH$_2$)$_2$CH(OH)(CH$_2$)$_4$CH$_3$ |
| 1-1261 | H | — | tBu | 0 | 5-(CH$_2$)$_2$CH(OH)(CH$_2$)$_4$-tBu |
| 1-1262 | H | — | tBu | 0 | 5-C(=O)(CH$_2$)$_5$-cHx |
| 1-1263 | H | — | tBu | 0 | 5-(CH$_2$)$_2$C(=O)CH$_2$-cHx |
| 1-1264 | H | — | tBu | 0 | 5-(CH$_2$)$_2$C(=O)(CH$_2$)$_2$-cHx |
| 1-1265 | H | — | tBu | 0 | 5-(CH$_2$)C(=O)(CH$_2$)$_2$-cHx |
| 1-1266 | H | — | tBu | 0 | 5-(CH$_2$)C(=O)(CH$_2$)$_3$-cHx |
| 1-1267 | H | — | tBu | 0 | 5-(CH$_2$)C(=O)(CH$_2$)$_4$-cHx |
| 1-1268 | H | — | tBu | 0 | 5-(CH$_2$)$_4$C(=O)(CH$_2$)-cHx |
| 1-1269 | H | — | tBu | 0 | 5-(CH$_2$)$_3$C(=O)(CH$_2$)-cHx |
| 1-1270 | H | — | tBu | 0 | 5-(CH$_2$)$_2$C(=O)(CH$_2$)-cHx |
| 1-1271 | H | — | tBu | 0 | 5-(CH$_2$)$_4$C(=O)(CH$_2$)$_2$-cHx |
| 1-1272 | H | — | tBu | 0 | 5-C(=O)-cHx |
| 1-1273 | H | — | tBu | 0 | 5-C(=O)(CH$_2$)-cPn |
| 1-1274 | H | — | tBu | 0 | 5-C(=O)(CH$_2$)$_2$-cHp |
| 1-1275 | H | — | tBu | 0 | 5-C(=O)(CH$_2$)$_3$-cHx |
| 1-1276 | H | — | tBu | 0 | 5-C(=O)(CH$_2$)$_4$-cPn |
| 1-1277 | H | — | tBu | 0 | 5-C(=O)(CH$_2$)$_5$-cHp |
| 1-1278 | H | — | tBu | 0 | 5-CH(OH)Ph |
| 1-1279 | H | — | tBu | 0 | t-CH(OH)(CH$_2$)Ph |
| 1-1280 | H | — | tBu | 0 | 5-CH(OH)(CH$_2$)$_2$Ph |
| 1-1281 | H | — | tBu | 0 | 5-CH(OH)(CH$_2$)$_3$Ph |
| 1-1282 | H | — | tBu | 0 | 5-CH(OH)(CH$_2$)$_4$Ph |
| 1-1283 | H | — | tBu | 0 | 5-CH(OH)(CH$_2$)$_5$Ph |
| 1-1284 | H | — | tBu | 0 | 5-CH(OH)(4-MePh) |
| 1-1285 | H | — | tBu | 0 | 5-CH(OH)CH$_2$(2-MeOPh) |
| 1-1286 | H | H | tBu | 1 | 5-CH(OH)(CH$_2$)$_2$(2-MePh) |
| 1-1287 | H | H | tBu | 1 | 5-CH(OH)(CH$_2$)$_3$(3-ClPh) |
| 1-1288 | H | H | tBu | 1 | 5-CH(OH)(CH$_2$)$_4$(2-BrPh) |
| 1-1289 | H | H | tBu | 1 | 5-CH(OH)(CH$_2$)$_4$(2-MePh) |
| 1-1290 | H | — | tBu | 0 | 5-CH$_2$CH(OH)Ph |
| 1-1291 | H | — | tBu | 0 | 5-CH$_2$CH(OH)CH$_2$Ph |
| 1-1292 | H | — | tBu | 0 | 5-CH$_2$CH(OH)(CH$_2$)$_3$Ph |
| 1-1293 | H | — | tBu | 0 | 5-CH$_2$CH(OH)(CH$_2$)$_4$Ph |
| 1-1294 | H | — | tBu | 0 | 5-CH$_2$CH(OH)(CH$_2$)$_5$Ph |
| 1-1295 | H | — | tBu | 0 | 5-CH$_2$CH(OH)(2-ClPh) |
| 1-1296 | H | — | tBu | 0 | 5-CH$_2$CH(OH)(CH$_2$)(2-MePh) |
| 1-1297 | H | H | tBu | 1 | 5-CH$_2$CH(OH)(CH$_2$)$_2$(4-MePh) |
| 1-1298 | H | H | tBu | 1 | 5-CH$_2$CH(OH)(CH$_2$)$_3$(4-ClPh) |
| 1-1299 | H | H | tBu | 1 | 5-CH$_2$CH(OH)(CH$_2$)$_4$(3-MePh) |
| 1-1300 | H | — | tBu | 0 | 5-(CH$_2$)$_2$CH(OH)Ph |

TABLE 1-continued

| Cpd. No. | R$^a$ | R$^2$ | R$^3$ | n | R$^4$ |
|---|---|---|---|---|---|
| 1-1301 | H | — | tBu | 0 | 5-(CH$_2$)$_2$CH(OH)CH$_2$Ph |
| 1-1302 | H | — | tBu | 0 | 5-(CH$_2$)$_2$CH(OH)(CH$_2$)$_2$(2-FPh) |
| 1-1303 | H | — | tBu | 0 | 5-(CH$_2$)$_2$CH(OH)(CH$_2$)$_3$Ph |
| 1-1304 | H | — | tBu | 0 | 5-(CH$_2$)$_2$CH(OH)(CH$_2$)$_4$Ph |
| 1-1305 | H | — | tBu | 0 | 5-(CH$_2$)$_2$CH(OH)(CH$_2$)(4-MePh) |
| 1-1306 | H | H | tBu | 1 | 5-(CH$_2$)$_2$CH(OH)(CH$_2$)$_2$(4-MePh) |
| 1-1307 | H | — | tBu | 0 | 5-(CH$_2$)$_2$CH(OH)(CH$_2$)$_3$(4-MeOPh) |
| 1-1308 | H | H | tBu | 1 | 5-(CH$_2$)$_2$CH(OH)(CH$_2$)$_4$(2-MeOPh) |
| 1-1309 | H | — | tBu | 0 | 5-(CH$_2$)$_3$CH(OH)Ph |
| 1-1310 | H | — | tBu | 0 | 5-(CH$_2$)$_3$CH(OH)CH$_2$Ph |
| 1-1311 | H | — | tBu | 0 | 5-(CH$_2$)$_3$CH(OH)(CH$_2$)$_2$Ph |
| 1-1312 | H | — | tBu | 0 | 5-(CH$_2$)$_3$CH(OH)(CH$_2$)$_3$(2-MePh) |
| 1-1313 | H | H | tBu | 1 | 5-(CH$_2$)$_3$CH(OH)(CH$_2$)(2-MeOPh) |
| 1-1314 | H | — | tBu | 0 | 5-(CH$_2$)$_4$CH(OH)Ph |
| 1-1315 | H | — | tBu | 0 | 5-(CH$_2$)$_4$CH(OH)CH$_2$(2-MePh) |
| 1-1316 | H | H | tBu | 1 | 5-(CH$_2$)$_4$CH(OH)(4-MePh) |
| 1-1317 | H | — | tBu | 0 | 5-CH=CH—CH(OH)Ph |
| 1-1318 | H | — | tBu | 0 | 5-(CH$_2$)$_2$CH(OH)(CH$_2$)$_2$(4-FPh) |
| 1-1319 | H | — | tBu | 0 | 5-CH=CH—CH(OH)(CH$_2$)$_2$(4-FPh) |
| 1-1320 | H | — | tBu | 0 | 5-C(=O)Ph |
| 1-1321 | H | — | tBu | 0 | 5-C(=O)CH$_2$Ph |
| 1-1322 | H | — | tBu | 0 | 5-C(=O)(CH$_2$)$_2$Ph |
| 1-1323 | H | — | tBu | 0 | 5-C(=O)(CH$_2$)$_3$Ph |
| 1-1324 | H | — | tBu | 0 | 5-C(=O)(CH$_2$)$_4$Ph |
| 1-1325 | H | — | tBu | 0 | 5-C(=O)(CH$_2$)$_5$Ph |
| 1-1326 | H | — | tBu | 0 | 5-(CH$_2$)$_2$—CO—Ph |
| 1-1327 | H | — | tBu | 0 | 5-(CH$_2$)$_2$—CO—CH$_2$Ph |
| 1-1328 | H | — | tBu | 0 | 5-(CH$_2$)$_3$—CO—CH$_2$Ph |
| 1-1329 | H | H | tBu | 1 | 5-(CH$_2$)$_2$—CO—CH$_2$Ph |
| 1-1330 | H | H | tBu | 1 | 5-(CH$_2$)$_2$—CO—CH$_2$(2-MePh) |
| 1-1331 | H | — | tBu | 0 | 5-CH(OB$^2$)Ph Na salt |
| 1-1332 | H | — | tBu | 0 | 5-CH(OB$^2$)CH$_2$Ph Na salt |
| 1-1333 | H | — | tBu | 0 | 5-CH(OB$^2$)(CH$_2$)(4-MePh) Na salt |
| 1-1334 | H | — | tBu | 0 | 5-CH(OB$^2$)(CH$_2$)$_3$(4-MePh) Na salt |
| 1-1335 | H | — | tBu | 0 | 5-CH(OE$^1$)(CH$_2$)$_4$(4-MePh) HCl salt |
| 1-1336 | H | — | tBu | 0 | 5-CH(OB$^2$)(CH$_2$)$_5$Ph Na salt |
| 1-1337 | H | — | tBu | 0 | 5-CH(OB$^2$)(CH$_2$)$_5$Ph Na salt |
| 1-1338 | H | — | tBu | 0 | 5-(CH$_2$)CH(OB$^1$)CH$_2$Ph Na salt |
| 1-1339 | H | — | tBu | 0 | 5-(CH$_2$)CH(OD$^1$)(CH$_2$)$_2$Ph Na salt |
| 1-1340 | H | — | tBu | 0 | 5-(CH$_2$)CH(OE$^1$)(CH$_2$)$_3$Ph HCl salt |
| 1-1341 | H | H | tBu | 1 | 5-(CH$_2$)CH(OE$^1$)(CH$_2$)$_4$Ph Na salt |
| 1-1342 | H | — | tBu | 0 | 5-(CH$_2$)$_2$CH(OB$^2$)Ph Na salt |
| 1-1343 | H | — | tBu | 0 | 5-(CH$_2$)$_2$CH(OB$^2$)CH$_2$Ph Na salt |
| 1-1344 | H | — | tBu | 0 | 5-(CH$_2$)$_2$CH(OB$^2$)(CH$_2$)$_2$Ph Na salt |
| 1-1345 | H | — | tBu | 0 | 5-(CH$_2$)$_2$CH(OB$^2$)(CH$_2$)$_3$Ph Na salt |
| 1-1346 | H | — | tBu | 0 | 5-(CH$_2$)$_2$CH(OE$^1$)CH$_2$Ph HCl salt |
| 1-1347 | H | — | tBu | 0 | 5-(CH$_2$)$_3$CH(OE$^1$)CH$_2$Ph HCl salt |
| 1-1348 | Pi | — | tBu | 0 | 5-(CH$_2$)$_3$CH(OB$^2$)Ph Na salt |
| 1-1349 | H | — | tBu | 0 | 5-(CH$_2$)$_3$CH(OB$^2$)CH$_2$(4-MePh) Na salt |
| 1-1350 | H | — | tBu | 0 | 5-(CH$_2$)$_3$CH(OB$^3$)(CH$_2$)$_3$(2-ClPh) Na salt |
| 1-1351 | H | — | tBu | 0 | 5-(CH$_2$)$_3$CH(OB$^2$)CH$_2$Ph Na salt |
| 1-1352 | H | — | tBu | 0 | 5-(CH$_2$)$_4$CH(OB$^2$)Ph Na salt |
| 1-1353 | H | — | tBu | 0 | 5-(CH$_2$)$_4$CH(OB$^2$)CH$_2$Ph Na salt |
| 1-1354 | H | — | tBu | 0 | 5-(CH$_2$)$_5$CH(OD$^1$)Ph Na salt |
| 1-1355 | H | — | iPr | 0 | 6-CH(OH)-cHx |

TABLE 1-continued

| Cpd. No. | R$^a$ | R$^2$ | R$^3$ | n | R$^4$ |
|---|---|---|---|---|---|
| 1-1356 | H | — | Et | 0 | 6-CH(OH)-cHx |
| 1-1357 | H | — | tBu | 0 | 6-CH(OH)—CH$_2$-cHx |
| 1-1358 | H | — | iPr | 0 | 6-CH(OH)—CH$_2$-cHx |
| 1-1359 | H | — | Et | 0 | 6-CH(OH)—CH$_2$-cHx |
| 1-1360 | H | — | tBu | 0 | 6-CH(OH)(CH$_2$)$_2$-cHx |
| 1-1361 | H | — | tBu | 0 | 6-CH(OH)(CH$_2$)$_2$-cHx |
| 1-1362 | H | — | tBu | 0 | 6-CH(OH)(CH$_2$)$_2$-cHx |
| 1-1363 | H | — | tBu | 0 | 6-CH(OH)(CH$_2$)$_3$-cHx |
| 1-1364 | H | — | iPr | 0 | 6-CH(OH)(CH$_2$)$_3$-cHx |
| 1-1365 | H | — | Et | 0 | 6-CH(OH)(CH$_2$)$_3$-cHx |
| 1-1366 | H | — | tBu | 0 | 6-CH(OH)(CH$_2$)$_4$-cHx |
| 1-1367 | H | — | iPr | 0 | 6-CH(OH)(CH$_2$)$_4$-cHx |
| 1-1368 | H | — | Et | 0 | 6-CH(OH)(CH$_2$)$_4$-cHx |
| 1-1369 | H | — | tBu | 0 | 6-CH(OH)(CH$_2$)$_5$-cHx |
| 1-1370 | H | — | iPr | 0 | 6-CH(OH)(CH$_2$)$_5$-cHx |
| 1-1371 | H | — | Et | 0 | 6-CH(OH)(CH$_2$)$_4$-cHx |
| 1-1372 | H | H | tBu | 1 | 6-CH(OH)CH$_2$-cHx |
| 1-1373 | 3-Br | H | iPr | 1 | 6-CH(OH)(CH$_2$)$_3$-cHx |
| 1-1374 | H | H | iPr | 1 | 6-CH(OH)(CH$_2$)$_4$-cHx |
| 1-1375 | H | H | iPr | 1 | 6-CH(OH)(CH$_2$)$_5$-cHx |
| 1-1376 | 2-MeO | H | iPr | 1 | 6-CH(OH)(CH$_2$)$_3$-cHx |
| 1-1377 | H | — | iPr | 0 | 6-CH$_2$CH(OH)-cHx |
| 1-1378 | H | — | tBu | 0 | 6-CH$_2$CH(OH)(CH$_2$)-cHx |
| 1-1379 | H | — | tBu | 0 | 6-CH$_2$CH(OH)(CH$_2$)$_2$-cHx |
| 1-1380 | H | — | tBu | 0 | 6-CH$_2$CH(OH)(CH$_2$)$_3$-cHx |
| 1-1381 | H | — | tBu | 0 | 6-CH$_2$CH(OH)(CH$_2$)$_4$-cHx |
| 1-1382 | H | — | tBu | 0 | 6-(CH$_2$)$_2$CH(OH)-cHx |
| 1-1383 | H | — | tBu | 0 | 6-(CH$_2$)$_2$CH(OH)(CH$_2$)-cHx |
| 1-1384 | H | H | tBu | 1 | 6-(CH$_2$)$_2$CH(OH)(CH$_2$)-cHx |
| 1-1385 | H | — | iPr | 0 | 6-(CH$_2$)$_2$CH(OH)(CH$_2$)-cHx |
| 1-1386 | H | — | iPr | 0 | 6-(CH$_2$)$_2$CH(OH)(CH$_2$)$_2$-cHx |
| 1-1387 | H | — | iPr | 0 | 6-(CH$_2$)$_2$CH(OH)(CH$_2$)$_3$-cHx |
| 1-1388 | 2-MeO | H | iPr | 1 | 6-(CH$_2$)$_2$CH(OH)(CH$_2$)$_4$-cHx |
| 1-1389 | H | — | tBu | 0 | 6-(CH$_2$)$_3$CH(OH)-cHx |
| 1-1390 | H | — | tBu | 0 | 6-(CH$_2$)$_3$CH(OH)(CH$_2$)-cHx |
| 1-1391 | H | — | tBu | 0 | 6-(CH$_2$)$_3$CH(OH)(CH$_2$)$_2$-cHx |
| 1-1392 | H | — | iPr | 0 | 6-(CH$_2$)$_3$CH(OH)(CH$_2$)$_3$-cHx |
| 1-1393 | H | — | iPr | 0 | 6-(CH$_2$)$_4$CH(OH)-cHx |
| 1-1394 | H | H | ipr | 1 | 6-(CH$_2$)$_4$CH(OH)(CH$_2$)-cHx |
| 1-1395 | H | — | tBu | 0 | 6-(CH$_2$)$_4$CH(OH)(CH$_2$)$_2$-cHx |
| 1-1396 | H | — | iPr | 0 | 6-CH(OH)-cPn |
| 1-1397 | H | — | iPr | 0 | 6-CH(OH)(CH$_2$)-cHp |
| 1-1398 | H | H | iPr | 1 | 6-CH(OH)(CH$_2$)$_2$-cOc |
| 1-1399 | H | — | tBu | 0 | 6-CH(OH)(CH$_2$)$_2$-cPn |
| 1-1400 | H | — | iPr | 0 | 6-CH(OH)(CH$_2$)$_4$-cHp |
| 1-1401 | H | — | iPr | 0 | 6-CH(OH)(CH$_2$)$_5$-cPn |
| 1-1402 | H | — | iPr | 0 | 6-(CH$_2$)CH(OH)-cHp |
| 1-1403 | H | — | iPr | 0 | 6-(CH$_2$)CH(OH)(CH$_2$)-cPn |
| 1-1404 | H | H | iPr | 1 | 6-(CH$_2$)CH(OH)(CH$_2$)$_2$-cOc |
| 1-1405 | 2-MeO | H | iPr | 1 | 6-(CH$_2$)CH(OH)(CH$_2$)$_3$-cOc |
| 1-1406 | 2-Cl | H | iPr | 1 | 6-(CH$_2$)CH(OH)(CH$_2$)$_4$-cPn |
| 1-1407 | 2-Br | H | iPr | 1 | 6-(CH$_2$)CH(OH)-cPn |
| 1-1408 | H | — | iPr | 0 | 6-(CH$_2$)$_2$CH(OH)(CH$_2$)-cPn |
| 1-1409 | H | — | iPr | 0 | 6-(CH$_2$)$_2$CH(OH)(CH$_2$)-cHp |
| 1-1410 | H | — | iPr | 0 | 6-(CH$_2$)$_2$CH(OH)(CH$_2$)$_3$-cHp |
| 1-1411 | H | — | iPr | 0 | 6-(CH$_2$)$_2$CH(OH)(CH$_2$)$_4$-cHp |
| 1-1412 | H | — | iPr | 0 | 6-(CH$_2$)$_2$CH(OH)(CH$_2$)$_5$-cPn |
| 1-1413 | H | — | iLPr | 0 | 6-(CH$_2$)$_3$CH(OH)-cPn |
| 1-1414 | H | H | iPr | 1 | 6-(CH$_2$)$_3$CH(OH)(CH$_2$)-cHp |
| 1-1415 | H | — | iPr | 0 | 6-(CH$_2$)$_3$CH(OH)(CH$_2$)$_2$-cPn |
| 1-1416 | H | — | iPr | 0 | 6-(CH$_2$)$_4$CH(OH)-cPn |
| 1-1417 | 2-Cl | — | iPr | 0 | 6-(CH$_2$)$_4$CH(OH)(CH$_2$)-cHp |
| 1-1418 | H | — | iPr | 0 | 6-C(=C)-cHx |
| 1-1419 | H | — | iPr | 0 | 6-C(≡O)(CH$_2$)-cHp |
| 1-1420 | H | — | tBu | 0 | 6-C(≡O)(CH$_2$)$_2$-cPn |
| 1-1421 | H | — | tBu | 0 | 6-C(≡O)(CH$_2$)$_3$-cHx |
| 1-1422 | H | — | iPr | 0 | 6-C(≡O)(CH$_2$)$_4$-cHx |
| 1-1423 | H | — | tBu | 0 | 6-C(≡O)(CH$_2$)$_5$-cHx |
| 1-1424 | H | — | iPr | 0 | 6-CH=CH—CH(OH)-cHx |
| 1-1425 | H | — | iPr | 0 | 6-CH=CH—CH(OH)(CH$_2$)-cHp |
| 1-1426 | H | — | iPr | 0 | 6-CH=CH—CH(OH)(CH$_2$)$_2$-cHx |
| 1-1427 | H | — | iPr | 0 | 6-CH=CH—CH(OH)(CH$_2$)$_3$-cHp |
| 1-1428 | H | — | iPr | 0 | 6-CH=CH—CH(OH)(CH$_2$)$_4$-cHx |
| 1-1429 | H | — | iPr | 0 | 6-CH(OH)(CH$_2$)-iPr |
| 1-1430 | H | — | iPr | 0 | 6-CH(OH)(CH$_2$)$_2$-tBu |
| 1-1431 | H | — | iPr | 0 | 6-CH(OH)(CH$_2$)$_3$-iPr |

TABLE 1-continued

| Cpd. No. | $R^a$ | $R^2$ | $R^3$ | n | $R^4$ |
|---|---|---|---|---|---|
| 1-1432 | H | — | iPr | 0 | 6-CH(OH)(CH$_2$)$_4$-iPr |
| 1-1433 | H | — | iLPr | 0 | 6-CH(OH)(CH$_2$)$_5$-iPr |
| 1-1434 | H | — | Et | 0 | 6-CH(OH)Et |
| 1-1435 | H | — | CH3 | 0 | 6-(CH$_2$)$_2$CH(OH)CH$_3$ |
| 1-1436 | H | — | CH3 | 0 | 6-(CH$_2$)$_2$C(=O)CH$_3$ |
| 1-1437 | H | — | CH3 | 0 | 6-(CH$_2$)$_2$C(=O)Ph |
| 1-1438 | H | — | CH3 | 0 | 6-(CH$_2$)$_2$CH(OH)Ph |
| 1-1439 | H | — | CH3 | 0 | 6-(CH$_2$)$_2$C(=O)Ph |
| 1-1440 | H | — | Et | 0 | 6-(CH$_2$)$_2$CH(OH)Ph |
| 1-1441 | H | — | Et | 0 | 6-CH(OH)(CH$_2$)$_2$Ph |
| 1-1442 | H | — | S-tBu | 0 | 6-(CH$_2$)$_2$CH(OH)Ph |
| 1-1443 | H | — | MEOCH 2 | 0 | 6-CH=CH—CH(OH)Ph |
| 1-1444 | H | — | MEOCH 2 | 0 | 6-(CH$_2$)$_2$CH(OH)Ph |
| 1-1445 | H | — | Et | 0 | 6-(CH$_2$)$_2$C(=O)(CH$_2$)$_3$Ph |
| 1-1446 | H | — | Et | 0 | 6-(CH$_2$)$_2$CH(OH)(CH$_2$)$_3$Ph |
| 1-1447 | H | — | Et | 0 | 6-CH=CH—C(=O)(CH$_2$)$_3$Ph |
| 1-1448 | H | — | MeOCMe 2 | 0 | 6-CH(OH)(CH$_2$)-cHx |
| 1-1449 | H | — | MeOCMe 2 | 0 | 6-CH(OH)(CH$_2$)$_2$-Hp |
| 1-1450 | H | — | MeOCMe 2 | 0 | 6-CH(OH)(CH$_2$)$_3$-cPn |
| 1-1451 | H | — | MeOCHe 2 | 0 | 6-CH(OH)(CH$_2$)$_4$-cHp |
| 1-1452 | H | H | MeOCMe | I | 6-CH(OH)(CH$_2$)$_5$cOc |
| 1-1453 | H | — | MeOCMe 2 | 0 | 6-(CH$_2$)$_2$CH(OH)(CH$_2$)-cHx |
| 1-1454 | H | — | MeOCMe 2 | 0 | 6-(CH$_2$)$_2$CH(OH)-cHx |
| 1-1455 | H | — | Sph | 0 | 6-CH(OH)CH$_2$-cHx |
| 1-1456 | H | — | Sph | 0 | 6-CH(OH)(CH$_2$)$_2$-cHx |
| 1-1457 | H | — | S-(2-ClPh) | 0 | 6-CH(OH)(CH$_2$)$_3$-cHx |
| 1-1458 | H | — | S-(2-BrPh) | 0 | 6-CH(OH)CH$_2$-cHx |
| 1-1459 | H | — | S-(2-MePh) | 0 | 6-(CH$_2$)$_2$CH(OH)(CH$_2$)$_2$-cHx |
| 1-1460 | H | — | iLPr | 0 | 6-CH(OB$^2$)-cHx Na salt |
| 1-1461 | H | — | tBu | 0 | 6-CH(OB$^2$)(CH$_2$)-cHx Na salt |
| 1-1462 | H | — | iPr | 0 | 6-CH(OB$^2$)(CH$_2$)$_2$-cHx Na salt |
| 1-1463 | H | — | iPr | 0 | 6-CH(OB$^2$)(CH$_2$)$_3$-cHx Na salt |
| 1-1464 | H | — | iPr | 0 | 6-CH(OD$^2$)(CH$_2$)$_4$-cHx Na salt |
| 1-1465 | H | — | iPr | 0 | 6-CH(OE$^1$)(CH$_2$)$_5$-cHx Na salt |
| 1-1466 | H | — | iPr | 0 | 6-(CH$_2$)$_2$CH(OB$^2$)-cHx HCl salt |
| 1-1467 | H | — | iPr | 0 | 6-(CH$_2$)$_2$CH(OB$^2$)(CH$_2$)-cHp Na salt |
| 1-1468 | H | — | iPr | 0 | 6-(CH$_2$)$_2$CH(OB$^2$)(CH$_2$)$_2$-cHp Na salt |
| 1-1469 | H | — | iPr | 0 | 6-(CH$_2$)$_2$CH(OB$^2$)(CH$_2$)$_3$-cHp Na salt |
| 1-1470 | H | — | iPr | 0 | 6-(CH$_2$)$_2$CH(OB$^2$)(CH$_2$)$_4$-cHx Na salt |
| 1-1471 | H | — | iPr | 0 | 6-(CH$_2$)$_3$CH(OB$^2$)(CH$_2$)-cHx Na salt |
| 1-1472 | H | — | iPr | 0 | 6-(CH$_2$)$_3$CH(OB$^2$)(CH$_2$)$_2$-cHx |
| 1-1473 | H | — | iPr | 0 | 6-(CH$_2$)$_4$CH(OE$^1$)(CH$_2$)-cHx HCl salt |
| 1-1474 | H | — | SCH$_3$ | 0 | 6-CH$_2$O(CH$_2$)$_3$Imd HCl salt |
| 1-1475 | H | — | SCH$_3$ | 0 | 6-CH$_2$O(CH$_2$)$_3$-Imd |
| 1-1476 | H | — | SCH$_3$ | 0 | 5-CH$_2$O(CH$_2$)$_3$Imd HCl salt |
| 1-1477 | H | — | SCH$_3$ | 0 | 5-CH$_2$O(CH$_2$)$_3$Imd |
| 1-1478 | H | — | SCH$_3$ | 0 | 5-O(CH$_2$)$_3$Imd HCl salt |
| 1-1479 | H | — | SCH$_3$ | 0 | 5-O(CH$_2$)$_3$Imd |
| 1-1480 | H | — | tBu | 0 | 6-CH$_2$O(CH$_2$)$_3$Imd HCl salt |
| 1-1481 | H | — | iPr | 0 | 6-CH$_2$O(CH$_2$)$_3$Imd HCl salt |
| 1-1482 | H | H | tBu | 1 | 6-CH$_2$O(CH$_2$)$_3$Imd HCl salt |
| 1-1483 | H | H | tBu | 1 | 6-CH$_2$O(CH$_2$)$_3$Imd HCl salt |
| 1-1484 | H | — | tBu | 0 | 6-CH$_2$O(CH$_2$)$_2$Imd HCl salt |
| 1-1485 | H | — | tBu | 0 | 6-CH$_2$O(CH$_2$)$_4$Imd HCl salt |
| 1-1486 | H | — | iPr | 0 | 6-CH$_2$O(CH$_2$)$_4$Imd |

TABLE 1-continued

| Cpd. No. | $R^a$ | $R^2$ | $R^3$ | n | $R^4$ |
|---|---|---|---|---|---|
| 1-1487 | H | — | iPr | 0 | 6-$CH_2O(CH_2)_5$Imd<br>HCl salt |
| 1-1488 | H | — | iPr | 0 | 6-$CH_2O(CH_2)_5$Imd<br>HCl salt |
| 1-1489 | H | — | iPr | 0 | 6-$CH_2O(CH_2)_3$-(4-Ph-5-Et-Imd) |
| 1-1490 | H | — | iPr | 0 | 6-$CH_2O(CH_2)_3$-(4-Ph-5-Et-Imd)<br>HCl salt |
| 1-1491 | H | H | iPr | 1 | 6-$CH_2O(CH_2)_3$-(4-Ph-5-Et-Imd)<br>HCl salt |
| 1-1492 | H | — | tBu | 0 | 5-$(CH_2)_2C(=O)(CH_2)$—$SO_2$cHx |
| 1-1493 | H | — | tBu | 0 | 5-$(CH_2)_2C(=O)(CH_2)_2$—$SO_2$cHx |
| 1-1494 | H | — | tBu | 0 | 5-$(CH_2)C(=O)(CH_2)$—$SO_2$cHx |
| 1-1495 | H | — | tBu | 0 | 5-$(CH_2)C(=O)(CH_2)_2$—$SO_2$cHx |
| 1-1496 | H | — | tBu | 0 | 5-$C(=O)(CH_2)$—$SO_2$cHx |
| 1-1497 | H | — | tBu | 0 | 5-$C(=O)(CH_2)_2$—$SO_2$cHx |
| 1-1498 | H | — | tBu | 0 | 5-$(CH_2)_2C(=O)(CH_2)$—$SO_2(CH_2)$cHx |
| 1-1499 | H | — | tBu | 0 | 5-$(CH_2)_2C(=O)(CH_2)_2$—$SO_2(CH_2)$cHx |
| 1-1500 | H | — | tBu | 0 | 5-$(CH_2)C(=O)(CH_2)$—$SO_2(CH_2)$cHx |
| 1-1501 | H | — | tBu | 0 | 5-$(CH_2)_2C(=O)(CH_2)_2$—$SO_2(CH_2)$cHx |
| 1-1502 | H | — | tBu | 0 | 5-$C(=O)(CH_2)$—$SO_2(CH_2)$cHx |
| 1-1503 | H | — | tBu | 0 | 5-$C(=O)(CH_2)_2$—$SO_2(CH_2)$cHx |
| 1-1534 | H | — | tBu | 0 | 5-$(CH_2)_2C(=O)(CH_2)$—$SO_2(CH_2)_2$cHx |
| 1-1505 | H | — | tBu | 0 | 5-$(CH_2)_2C(=O)(CH_2)_2$—$SO_2(CH_2)_2$cHx |
| 1-1506 | H | — | tBu | 0 | 5-$(CH_2)C(=O)(CH_2)$—$SO_2(CH_2)_2$cHx |
| 1-1507 | H | — | tBu | 0 | 5-$(CH_2)C(=O)(CH_2)_2$—$SO_2(CH_2)_2$cHx |
| 1-1508 | H | — | tBu | 0 | 5-$C(=O)(CH_2)$—$SO_2(CH_2)_2$cHx |
| 1-1509 | H | — | tBu | 0 | 5-$C(=O)(CH_2)_2$—$SO_2(CH_2)_2$cHx |
| 1-1510 | H | — | tBu | 0 | 5-$(CH_2)_2C(=O)(CH_2)$—$SO_2(CH_2)_3$cHx |
| 1-1511 | H | — | tBu | 0 | 5-$(CH_2)_2C(=O)(CH_2)_2$—$SO_2(CH_2)_3$cHx |
| 1-1512 | H | — | tBu | 0 | 5-$(CH_2)C(=O)(CH_2)$—$SO_2(CH_2)_3$cHx |
| 1-1513 | H | — | tBu | 0 | 5-$(CH_2)C(=O)(CH_2)_2$—$SO_2(CH_2)_3$cHx |
| 1-1514 | H | — | tBu | 0 | 5-$C(=O)(CH_2)$—$SO_2(CH_2)_3$cHx |
| 1-1515 | H | — | tBu | 0 | 5-$C(=O)(CH_2)_2$—$SO_2(CH_2)_3$cHx |
| 1-1516 | H | — | tBu | 0 | 5-$(CH_2)_2CH(OH)(CH_2)$—$SO_2$cHx |
| 1-1517 | H | — | tBu | 0 | 5-$(CH_2)CH(OH)(CH_2)_2$—$SO_2$cHx |
| 1-1518 | H | — | tBu | 0 | 5-$(CH_2)CH(OH)(CH_2)$—$SO_2$cHx |
| 1-1519 | H | — | tBu | 0 | 5-$(CH_2)CH(OH)(CH_2)_2$—$SO_2$cHx |
| 1-1520 | H | — | tBu | 0 | 5-$CH(OH)(CH_2)$—$SO_2$cHx |
| 1-1521 | H | — | tBu | 0 | 5-$CH(OH)(CH_2)_2$—$SO_2$cHx |
| 1-1522 | H | — | tBu | 0 | 5-$(CH_2)_2CH(OH)(CH_2)$—$SO_2(CH_2)$cHx |
| 1-1523 | H | — | tBu | 0 | 5-$(CH_2)_2CH(OH)(CH_2)_2$—$SO_2(CH_2)$cHx |
| 1-1524 | H | — | tBu | 0 | 5-$(CH_2)_2CH(OH)(CH_2)_2$—ScHx |
| 1-1525 | H | — | tBu | 0 | 6-$(CH_2)_2CH(OH)(CH_2)_2$—ScHx |
| 1-1526 | H | — | tBu | 0 | 6-$(CH_2)_2CH(OH)(CH_2)_2$—$SO_2$cHx |
| 1-1527 | H | — | tBu | 0 | 5-$(CH_2)_2CH(OE^5)(CH_2)_2$—ScHx |
| 1-1528 | H | — | tBu | 0 | 5-$(CH_2)_2CH(OB^2)(CH_2)_2$—$SO_2$cHx<br>Na salt |
| 1-1529 | H | — | tBu | 0 | 5-$(CH_2)_2CH(OB^{10})(CH_2)_2$—S-cHx<br>Na salt |
| 1-1530 | H | — | tBu | 0 | 5-$(CH_2)_2CH(OH)(CH_2)_2$—$SO_2$Ph |
| 1-1531 | H | — | tBu | 0 | 5-$(CH_2)CH(OH)(CH_2)$—$SO_2(CH_2)$cHx |
| 1-1532 | H | — | tBu | 0 | 5-$(CH_2)CH(OH)(CH_2)_2$—$SO_2(CH_2)$cHx |
| 1-1533 | H | — | tBu | 0 | 5-$CH(OH)(CH_2)$—$SO_2(CH_2)$cHx |
| 1-1534 | H | — | tBu | 0 | 5-$CH(OH)(CH_2)_2$—$SO_2(CH_2)$cHx |
| 1-1535 | H | — | tBu | 0 | 5-$(CH_2)_2CH(OH)(CH_2)$—$SO_2(CH_2)_2$cHx |
| 1-1536 | H | — | tBu | 0 | 5-$(CH_2)_2CH(OH)(CH_2)_2$—$SO_2(CH_2)_2$cHx |
| 1-1537 | H | — | tBu | 0 | 5-$(CH_2)CH(OH)(CH_2)$—$SO_2(CH_2)_2$cHx |
| 1-1538 | H | — | tBu | 0 | 5-$(CH_2)CH(OH)(CH_2)_2$—$SO_2(CH_2)_2$-cHx |
| 1-1539 | H | — | tBu | 0 | 5-$CH(OH)(CH_2)$—$SO_2(CH_2)_2$cHx |
| 1-1540 | H | — | tBu | 0 | 5-$CH(OH)(CH_2)_2$—$SO_2(CH_2)_2$cHx |
| 1-1541 | H | — | tBu | 0 | 5-$(CH_2)_2CH(OH)(CH_2)$—$SO_2(CH_2)_3$cHx |
| 1-1542 | H | — | tBu | 0 | 5-$(CH_2)_2CH(OH)(CH_2)_2$—$SO_2(CH_2)_3$cHx |
| 1-1543 | H | — | tBu | 0 | 5-$(CH_2)CH(OH)(CH_2)$—$SO_2(CH_2)_3$cHx |
| 1-1544 | H | — | tBu | 0 | 5-$(CH_2)CH(OH)(CH_2)_2$—$SO_2(CH_2)_3$cHx |
| 1-1545 | H | — | tBu | 0 | 5-$CH(OH)(CH_2)$—$SO_2(CH_2)_3$cHx |
| 1-1546 | H | — | tBu | 0 | 5-$CH(OH)(CH_2)_{22}$—$SO_2(CH_2)_3$cHx |
| 1-1547 | H | — | tBu | 0 | 5-$(CH_2)_2CH(OB_z)(CH_2)$-cHx |
| 1-1548 | H | — | tBu | 0 | 5-$(CH_2)_2CH(OA_{sp})(CH_2)$-cHx<br>HCl |
| 1-1549 | H | — | tBu | 0 | 5-$(CH_2)_2CH(OLys)(CH_2)$-cHx<br>2HCl |
| 1-1550 | H | — | tBu | 0 | 5-$(CH_2)_2CH(OGlu)(CH_2)$-cHx<br>Hcl |
| 1-1551 | H | — | tBu | 0 | 5-$(CH_2)_2CH(OB^4)(CH_2)$-cHx |
| 1-1552 | H | — | tBu | 0 | 5-$(CH_2)_2CH(OB^4)(CH_2)$-cHx |

TABLE 1-continued

| Cpd. No. | R$^a$ | R$^2$ | R$^3$ | n | R$^4$ |
|---|---|---|---|---|---|
| 1-1553 | H | — | tBu | 0 | Na salt |
| 1-1554 | H | — | tBu | 0 | 5-(CH$_2$)$_2$CH(OB$^5$)(CH$_2$)-cHx |
| | | | | | 5-(CH$_2$)$_2$CH(OB$^5$)(CH$_2$)-cHx Na salt |
| 1-1555 | H | — | tBu | 0 | 5-(CH$_2$)$_2$CH(OB$^6$)(CH$_2$)-cHx |
| 1-1556 | H | — | tBu | 0 | 5-(CH$_2$)$_2$CH(OB$^6$)(CH$_2$)-cHx Na salt |
| 1-1557 | H | — | tBu | 0 | 5-(CH$_2$)$_2$CH(OE$^4$)(CH$_2$)-cHx |
| 1-1558 | H | — | tBu | 0 | 5-(CH$_2$)$_2$CH(OB$^7$)(CH$_2$)-cHx |
| 1-1559 | H | — | tBu | 0 | 5-(CH$_2$)$_2$CH(OB$^7$)(CH$_2$)-cHx Na salt |
| 1-1560 | H | — | tBu | 0 | 5-(CH$_2$)$_2$CH(OB$^8$)(CH$_2$)-cHx |
| 1-1561 | H | — | tBu | 0 | 5-(CH$_2$)$_2$CH(OB$^8$)(CH$_2$)-cHx Na salt |
| 1-1562 | H | — | tBu | 0 | 5-(CH$_2$)$_2$CH(OB$^9$)(CH$_2$)-cHx |
| 1-1563 | H | — | tBu | 0 | 5-(CH$_2$)$_2$CH(OB$^9$)(CH$_2$)-cHx Na salt |
| 1-1564 | H | — | tBu | 0 | 5-(CH$_2$)$_2$CH(OT)(CH$_2$)-cHx |
| 1-1565 | H | — | tBu | 0 | 5-(CH$_2$)$_2$CH(OE$^5$)(CH$_2$)-cHx HCl |
| 1-1566 | H | — | tBu | 0 | 5-(CH$_2$)$_2$CH(OB$^{10}$)(CH$_2$)-cHx |
| 1-1567 | H | — | tBu | 0 | 5-(CH$_2$)$_2$CH(OB$^{10}$)(CH$_2$)-cHx Na salt |
| 1-1568 | H | — | tBu | 0 | 5-(CH$_2$)$_2$CH(OB$^{11}$)(CH$_2$)-cHx |
| 1-1569 | H | — | tBu | 0 | 5-(CH$_2$)$_2$CH(OB$^{11}$)(CH$_2$)-cHx Na salt |
| 1-1570 | H | — | tBu | 0 | 5-(CH$_2$)$_2$CH(OB$^{12}$)(CH$_2$)-cHx |
| 1-1571 | H | — | tBu | 0 | 5-(CH$_2$)$_2$CH(OB$^{12}$)(CH$_2$)-cHx Na salt |
| 1-1572 | H | — | tBu | 0 | 5-(CH$_2$)$_2$CH(OCONH2)(CH$_2$)-cHx |
| 1-1573 | H | — | tBu | 0 | 5-(CH$_2$)$_2$CH(OB$^{13}$)(CH$_2$)-cHx |
| 1-1574 | Et | — | tBu | 0 | 5-(CH$_2$)$_2$CH(OB$^{13}$)(CH$_2$)-cHx Na salt |
| 1-1575 | H | — | tBu | 0 | 5-(CH$_2$)$_2$CH(OB$^{10}$)(CH$_2$)-cHx |
| 1-1576 | H | — | tBu | 0 | 5-(CH$_2$)$_2$CH(OB$^{10}$)(CH$_2$)-cHx Na salt |
| 1-1577 | H | — | tBu | 0 | 5-CH(OBz)-cHx |
| 1-1578 | H | — | tBu | 0 | 5-CH(OAsp)-cHx HCl |
| 1-1579 | H | — | tBu | 0 | 5-CH(OLys)-cHx 2HCl |
| 1-1580 | H | — | tBu | 0 | 5-CH(OGlu)-cHx HCl |
| 1-1581 | H | — | tBu | 0 | 5-CH(OB$^4$)-cHx |
| 1-1582 | H | — | tBu | 0 | 5-CH(OB$^4$)-cHx Na salt |
| 1-1583 | H | — | tBu | 0 | 5-CH(OB$^5$)-cHx |
| 1-1584 | H | — | tBu | 0 | 5-CH(OB$^5$)-cHx Na salt |
| 1-1585 | H | — | tBu | 0 | 5-CH(OB$^6$)-cHx |
| 1-1586 | H | — | tBu | 0 | 5-CH(OB$^6$)-cHx Na salt |
| 1-1587 | H | — | tBu | 0 | 5-CH(OE$^4$)-cHx |
| 1-1588 | H | — | tBu | 0 | 5-CH(OB$^7$)-cHx |
| 1-1589 | H | — | tBu | 0 | 5-CH(OB$^7$)-cHx Na salt |
| 1-1590 | H | — | tBu | 0 | 5-CH(OB$^8$)-cHx |
| 1-1591 | H | — | tBu | 0 | 5-CH(OB$^8$)-cHx Na salt |
| 1-1592 | H | — | tBu | 0 | 5-CH(OB$^9$)-cHx |
| 1-1593 | H | — | tBu | 0 | 5-CH(OB$^9$)-cHx Na salt |
| 1-1594 | H | — | tBu | 0 | 5-CH(OT)-cHx |
| 1-1595 | H | — | tBu | 0 | 5-CH(OE$^5$)-cHx HCl |
| 1-1596 | H | — | tBu | 0 | 5-CH(OB$^{10}$)-cHx |
| 1-1597 | H | — | tBu | 0 | 5-CH(OB$^{10}$)-cHx Na salt |
| 1-1598 | H | — | tBu | 0 | 5-CH(OB$^{11}$)-cHx |
| 1-1599 | H | — | tBu | 0 | 5-CH(OB$^{11}$)-cHx Na salt |
| 1-1600 | H | — | tBu | 0 | 5-CH(OB$^{12}$)-cHx |
| 1-1601 | H | — | tBu | 0 | 5-CH(OB$^{12}$)-cHx Na salt |
| 1-1602 | H | — | tBu | 0 | 5-CH(OCONH$_2$)-cHx |
| 1-1603 | H | — | tBu | 0 | 5-CH(OB$^{13}$)-cHx |

TABLE 1-continued

| Cpd. No. | R$^a$ | R$^2$ | R$^3$ | n | R$^4$ |
|---|---|---|---|---|---|
| 1-1604 | H | — | tBu | 0 | 5-CH(OB$^{13}$)-cHx Na salt |
| 1-1605 | H | — | tBu | 0 | 5-CH(OBz)(CH$_2$)-cHx |
| 1-1606 | H | — | tBu | 0 | 5-CH(OAsp)(CH$_2$)-cHx HCl |
| 1-1607 | H | — | tBu | 0 | 5-CH(OLys)(CH$_2$)-cHx 2HCl |
| 1-1608 | H | — | tBu | 0 | 5-CH(OGlu)(CH$_2$)-cHx Hcl |
| 1-1609 | H | — | tBu | 0 | 5-CH(OB$^4$)(CH$_2$)-cHx |
| 1-1610 | H | — | tBu | 0 | 5-CH(OB$^4$)(CH$_2$)-cHx Na salt |
| 1-1611 | H | — | tBu | 0 | 5-CH(OB$^5$)(CH$_2$)-cHx |
| 1-1612 | H | — | tBu | 0 | 5-CH(OB$^5$)(CH$_2$)-cHx Na salt |
| 1-1613 | H | — | tBu | 0 | 5-CH(OB$^6$)(CH$_2$)-cHx |
| 1-1614 | H | — | tBu | 0 | 5-CH(OB$^6$)(CH$_2$)-cHx Na salt |
| 1-1615 | H | — | tBu | 0 | 5-CH(OE$^4$)(CH$_2$)-cHx |
| 1-1616 | H | — | tBu | 0 | 5-CH(OB$^7$)(CH$_2$)-cHx |
| 1-1617 | H | — | tBu | 0 | 5-CH(OB$^7$)(CH$_2$)-cHx |
| 1-1618 | H | — | tBu | 0 | 5-CH(OB$^8$)(CH$_2$)-cHx |
| 1-1619 | H | — | tBu | 0 | 5-CH(OB$^8$)(CH$_2$)-cHx Na salt |
| 1-1620 | H | — | tBu | 0 | 5-CH(OB$^9$)(CH$_2$)-cHx |
| 1-1621 | H | — | tBu | 0 | 5-CH(OB$^9$)(CH$_2$)-cHx Na salt |
| 1-1622 | H | — | tBu | 0 | 5-CH(OT)(CH$_2$)(-cHx |
| 1-1623 | H | — | tBu | 0 | 5-CH(OE$^5$)(CH$_2$)-cHx HCl |
| 1-1624 | H | — | tBu | 0 | 5-CH(OB$^{10}$)(CH$_2$)-cHx |
| 1-1625 | H | — | tBu | 0 | 5-CH(OB$^{10}$)(CH$_2$)-cHx Na salt |
| 1-1626 | H | — | tBu | 0 | 5-CH(OB$^{11}$)(CH$_2$)-cHx |
| 1-1627 | H | — | tBu | 0 | 5-CH(OB$^{11}$)(CH$_2$)-cHx Na salt |
| 1-1628 | H | — | tBu | 0 | 5-CH(OB$^{12}$)(CH$_2$)-cHx |
| 1-1629 | H | — | tBu | 0 | 5-CH(OB$^{12}$)(CH$_2$)-cHx Na salt |
| 1-1630 | H | — | tBu | 0 | 5-CH(OCONH$_2$)(CH$_2$)-cHx |
| 1-1631 | H | — | tBu | 0 | 5-CH(OB$^{13}$)(CH$_2$)-cHx |
| 1-1632 | H | — | tBu | 0 | 5-CH(OB$^{13}$)(CH$_2$)-cHx Na salt |
| 1-1633 | H | — | tBu | 0 | 5-CH(OBz)(CH$_2$)$_2$-cHc |
| 1-1634 | H | — | tBu | 0 | 5-CH(OAsp)(CH$_2$)$_2$-cHx HCl |
| 1-1635 | H | — | tBu | 0 | 5-CH(OLys)(CH$_2$)$_2$-cHz 2HCl |
| 1-1636 | H | — | tBu | 0 | 5-CH(OGlu)(CH$_2$)$_2$-cHx HCl |
| 1-1637 | H | — | tBu | 0 | 5-CH(OB$^4$)(CH$_2$)$_2$-cHx |
| 1-1638 | H | — | tBu | 0 | 5-CH(OB$^4$)(CH$_2$)$_2$-cHx Na salt |
| 1-1639 | H | — | tBu | 0 | 5-CH(OB$^5$)(CH$_2$)$_2$-cHx |
| 1-1640 | H | — | tBu | 0 | 5-CH(OB$^5$)(CH$_2$)$_2$-cHx Na salt |
| 1-1641 | H | — | tBu | 0 | 5-CH(OB$^6$)(CH$_2$)$_2$-cHx |
| 1-1642 | H | — | tBu | 0 | 5-CH(OB$^6$)(CH$_2$)$_2$-cHx Na salt |
| 1-1643 | H | — | tBu | 0 | 5-CH(OE$^4$)(CH$_2$)$_2$-cHx |
| 1-1644 | H | — | tBu | 0 | 5-CH(OB$^7$)(CH$_2$)$_2$-cHx |
| 1-1645 | H | — | tBu | 0 | 5-CH(OB$^7$)(CH$_2$)$_2$-cHx Na salt |
| 1-1646 | H | — | tBu | 0 | 5-CH(OB$^8$)(CH$_2$)$_2$-cHx |
| 1-1647 | H | — | tBu | 0 | 5-CH(OB$^8$)(CH$_2$)$_2$-cHx Na salt |
| 1-1648 | H | — | tBu | 0 | 5-CH(OB$^9$)(CH$_2$)$_2$-cHx |
| 1-1649 | H | — | tBu | 0 | 5-CH(OB$^9$)(CH$_2$)$_2$-cHx Na salt |
| 1-1650 | H | — | tBu | 0 | 5-CH(OT)(CH$_2$)$_2$-cHx |
| 1-1651 | H | — | tBu | 0 | 5-CH(OE$^5$)(CH$_2$)$_2$-cHx HCl |
| 1-1652 | H | — | tBu | 0 | 5-CH(OB$^{10}$)(CH$_2$)$_2$-cHx |
| 1-1653 | H | — | tBu | 0 | 5-CH(OB$^{10}$)(CH$_2$)$_2$-cHx Na salt |
| 1-1654 | H | — | tBu | 0 | 5-CH(OB$^{11}$)(CH$_2$)$_2$-cHx |

TABLE 1-continued

| Cpd. No. | R$^a$ | R$^2$ | R$^3$ | n | R$^4$ |
|---|---|---|---|---|---|
| 1-1655 | H | — | tBu | 0 | 5-CH(OB$^{11}$)(CH$_2$)$_2$-cHx Na salt |
| 1-1656 | H | — | tBu | 0 | 5-CH(OB$^{12}$)(CH$_2$)$_2$-cHx |
| 1-1657 | H | — | tBu | 0 | 5-CH(OB$^{12}$)(CH$_2$)$_2$-cHx Na salt |
| 1-1658 | H | — | tBu | 0 | 5-CH(OCONH$_2$)(CH$_2$)$_2$-cHx |
| 1-1659 | H | — | tBu | 0 | 5-CH(OB$^{13}$)(CH$_2$)$_2$-cHx |
| 1-1660 | H | — | tBu | 0 | 5-CH(OB$^{13}$)(CH$_2$)$_2$-cHx Na salt |
| 1-1661 | H | — | tBu | 0 | 5-CH(OBz)(CH$_2$)$_3$-cHx |
| 1-1662 | H | — | tBu | 0 | 5-CH(OAsp)(CH$_2$)$_3$-cHx HCl |
| 1-1663 | H | — | tBu | 0 | 5-CH(OLys)(CH$_2$)$_3$-cHx 2HCl |
| 1-1664 | H | — | tBu | 0 | 5-CH(OGlu)(CH$_2$)$_3$-cHx HCl |
| 1-1665 | H | — | tBu | 0 | 5-CH(OB$^4$)(CH$_2$)$_3$-cHx |
| 1-1666 | H | — | tBu | 0 | 5-CH(OB$^4$)(CH$_2$)$_3$-cHx Na salt |
| 1-1667 | H | — | tBu | 0 | 5-CH(OB$^5$)(CH$_2$)$_3$-cHx |
| 1-1668 | H | — | tBu | 0 | 5-CH(OB$^5$)(CH$_2$)$_3$-cHx Na salt |
| 1-1669 | H | — | tBu | 0 | 5-CH(OB$^6$)(CH$_2$)$_3$-cHx |
| 1-1670 | H | — | tBu | 0 | 5-CH(OB$^6$)(CH$_2$)$_3$-cHx Na salt |
| 1-1671 | H | — | tBu | 0 | 5-CH(OE$^4$)(CH$_2$)$_3$-cHx |
| 1-1672 | H | — | tBu | 0 | 5-CH(OB$^7$)(CH$_2$)$_3$-cHx |
| 1-1673 | H | — | tBu | 0 | 5-CH(OB$^7$)(CH$_2$)$_3$-cHx Na salt |
| 1-1674 | H | — | tBu | 0 | 5-CH(OB$^8$)(CH$_2$)$_3$-cHx |
| 1-1675 | H | — | tBu | 0 | 5-CH(OB$^8$)(CH$_2$)$_3$-cHx Na salt |
| 1-1676 | H | — | tBu | 0 | 5-CH(OB$^9$)(CH$_2$)$_3$-cHx |
| 1-1677 | H | — | tBu | 0 | 5-CH(OB$^9$)(CH$_2$)$_3$-cHx Na salt |
| 1-1678 | H | — | tBu | 0 | 5-CH(OT)(CH$_2$)$_3$-cHx |
| 1-1679 | H | — | tBu | 0 | 5-CH(OE$^5$)(CH$_2$)$_3$-cHx HCl |
| 1-1680 | H | — | tBu | 0 | 5-CH(OB$^{10}$)(CH$_2$)$_3$-cHx |
| 1-1681 | H | — | tBu | 0 | 5-CH(OB$^{10}$)(CH$_2$)$_3$-cHx Na salt |
| 1-1682 | H | — | tBu | 0 | 5-CH(OB$^{11}$)(CH$_2$)$_3$-cHx |
| 1-1683 | H | — | tBu | 0 | 5-CH(OB$^{11}$)(CH$_2$)$_3$-cHx Na salt |
| 1-1684 | H | — | tBu | 0 | 5-CH(OB$^{12}$)(CH$_2$)$_3$-cHx |
| 1-1685 | H | — | tBu | 0 | 5-CH(OB$^{12}$)(CH$_2$)$_3$-cHx Na salt |
| 1-1686 | H | — | tBu | 0 | 5-CH(OCONH$_2$)(CH$_2$)$_3$-cHx |
| 1-1687 | H | — | tBu | 0 | 5-CH(OB$^{13}$)(CH$_2$)$_3$-cHx |
| 1-1688 | H | — | tBu | 0 | 5-CH(OB$^{13}$)(CH$_2$)$_3$-cHx Na salt |
| 1-1689 | H | — | tBu | 0 | 5-CH(OBz)(CH$_2$)$_4$-cHx |
| 1-1690 | H | — | tBu | 0 | 5-CH(OAsp)(CH$_2$)$_4$-cHx HCl |
| 1-1691 | H | — | tBu | 0 | 5-CH(OLys)(CH$_2$)$_4$cHx 2HCl |
| 1-1692 | H | — | tBu | 0 | 5-CH(OGlu)(CH$_2$)$_4$-cHx HCl |
| 1-1693 | H | — | tBu | 0 | 5-CH(OB$^4$)(CH$_2$)$_4$-cHx |
| 1-1694 | H | — | tBu | 0 | 5-CH(OB$^4$)(CH$_2$)$_4$-cHx Na salt |
| 1-1695 | H | — | tBu | 0 | 5-CH(OB$^5$)(CH$_2$)$_4$-cHx |
| 1-1696 | H | — | tBu | 0 | 5-CH(OB$^5$)(CH$_2$)$_4$-cHx Na salt |
| 1-1697 | H | — | tBu | 0 | 5-CH(OB$^6$)(CH$_2$)$_4$-cHx |
| 1-1698 | H | — | tBu | 0 | 5-CH(OB$^6$)(CH$_2$)$_4$-cHx Na salt |
| 1-1699 | H | — | tBu | 0 | 5-CH(OE$^4$)(CH$_2$)$_4$-cHx |
| 1-1700 | H | — | tBu | 0 | 5-CH(OB$^7$)(CH$_2$)$_4$-cHx |
| 1-1701 | H | — | tBu | 0 | 5-CH(OB$^7$)(CH$_2$)$_4$-cHx Na salt |
| 1-1702 | H | — | tBu | 0 | 5-CH(OB$^8$)(CH$_2$)$_4$-cHx |
| 1-1703 | H | — | tBu | 0 | 5-CH(OB$^8$)(CH$_2$)$_4$-cHx Na salt |
| 1-1704 | H | — | tBu | 0 | 5-CH(OB$^9$)(CH$_2$)$_4$-cHx |
| 1-1705 | H | — | tBu | 0 | 5-CH(OB$^9$)(CH$_2$)$_4$-cHx |

TABLE 1-continued

| Cpd. No. | R$^a$ | R$^2$ | R$^3$ | n | R$^4$ |
|---|---|---|---|---|---|
| 1-1706 | H | — | tBu | 0 | 5-CH(OT)(CH$_2$)$_4$-cHx Na salt |
| 1-1707 | H | — | tBu | 0 | 5-CH(OE$^5$)(CH$_2$)$_4$-cHx HCl |
| 1-1708 | H | — | tBu | 0 | 5-CH(OB$^{10}$)(CH$_2$)$_4$-cHx |
| 1-1709 | H | — | tBu | 0 | 5-CH(OB$^{10}$)(CH$_2$)$_4$-cHx Na salt |
| 1-1710 | H | — | tBu | 0 | 5-CH(OB$^{11}$)(CH$_2$)$_4$-cHx |
| 1-1711 | H | — | tBu | 0 | 5-CH(OB$^{11}$)(CH$_2$)$_4$-cHx Na salt |
| 1-1712 | H | — | tBu | 0 | 5-CH(OB$^{12}$)(CH$_2$)$_4$-cHx |
| 1-1713 | H | — | tBu | 0 | 5-CH(OB$^{12}$)(CH$_2$)$_4$-cHx Na salt |
| 1-1714 | H | — | tBu | 0 | 5-CH(OCONH$_2$)(CH$_2$)$_4$-cHx |
| 1-1715 | H | — | tBu | 0 | 5-CH(OB$^{13}$)(CH$_2$)$_4$-cHx |
| 1-1716 | H | — | tBu | 0 | 5-CH(OB$^{13}$)(CH$_2$)$_4$-cHx Na salt |
| 1-1717 | H | — | tBu | 0 | 5-(CH$_2$)CH(OBz)-cHx |
| 1-1718 | H | — | tBu | 0 | 5-(CH$_2$)CH(OAsp)-cHx HCl |
| 1-1719 | H | — | tBu | 0 | 5-(CH$_2$)CH(OLys)-cHx 2HCl |
| 1-1720 | H | — | tBu | 0 | 5-(CH$_2$)CH(OGlu)-cHx HCl |
| 1-1721 | H | — | tBu | 0 | 5-(CH$_2$)CH(OB$^4$)-cHx |
| 1-1722 | H | — | tBu | 0 | 5-(CH$_2$)CH(OB$^4$)-cHx Na salt |
| 1-1723 | H | — | tBu | 0 | 5-(CH$_2$)CH(OB$^5$)-cHx |
| 1-1724 | H | — | tBu | 0 | 5-(CH$_2$)CH(OB$^5$)-cHx Na salt |
| 1-1725 | H | — | tBu | 0 | 5-(CH$_2$)CH(OB$^6$)-cHx |
| 1-1726 | H | — | tBu | 0 | 5-(CH$_2$)CH(OB$^6$)-cHx Na salt |
| 1-1727 | H | — | tBu | 0 | 5-(CH$_2$)CH(OE$^4$)-cHx |
| 1-1728 | H | — | tBu | 0 | 5-(CH$_2$)CH(OB$^7$)-cHx |
| 1-1729 | H | — | tBu | 0 | 5-(CH$_2$)CH(OB$^7$)-cHx Na salt |
| 1-1730 | H | — | tBu | 0 | 5-(CH$_2$)CH(OB$^8$)-cHx |
| 1-1731 | H | — | tBu | 0 | 5-(CH$_2$)CH(OB$^8$)-cHx Na salt |
| 1-1732 | H | — | tBu | 0 | 5-(CH$_2$)CH(OB$^9$)-cHx |
| 1-1733 | H | — | tBu | 0 | 5-(CH$_2$)CH(OB$^9$)-cHx Na salt |
| 1-1734 | H | — | tBu | 0 | 5-(CH$_2$)CH(OT)-cHx |
| 1-1735 | H | — | tBu | 0 | 5-(CH$_2$)CH(OE$^5$)-cHx HCl |
| 1-1736 | H | — | tBu | 0 | 5-(CH$_2$)CH(OB$^{10}$)-cHx |
| 1-1737 | H | — | tBu | 0 | 5-(CH$_2$)CH(OB$^{10}$)-cHx Na salt |
| 1-1738 | H | — | tBu | 0 | 5-(CH$_2$)CH(OB$^{11}$)-cHx |
| 1-1739 | H | — | tBu | 0 | 5-(CH$_2$)CH(OB$^{11}$)-cHx Na salt |
| 1-1740 | H | — | tBu | 0 | 5-(CH$_2$)CH(OB$^{12}$)-cHx |
| 1-1741 | H | — | tBu | 0 | 5-(CH$_2$)CH(OB$^{12}$)-cHx Na salt |
| 1-1742 | H | — | tBu | 0 | 5-(CH$_2$)CH(OCONH$_2$)-cHx |
| 1-1743 | H | — | tBu | 0 | 5-(CH$_2$)CH(OB$^{13}$)-cHx |
| 1-1744 | H | — | tBu | 0 | 5-(CH$_2$)CH(OB$^{13}$)-cHx Na salt |
| 1-1745 | H | — | tBu | 0 | 5-(CH$_2$)CH(OBz)(CH$_2$)-cHx |
| 1-1746 | H | — | tBu | 0 | 5-(CH$_2$)CH(OAsp)(CH$_2$)-cHx HCl |
| 1-1747 | H | — | tBu | 0 | 5-(CH$_2$)CH(OLys)(CH$_2$)-cHx 2HCl |
| 1-1748 | H | — | tBu | 0 | 5-(CH$_2$)CH(OGlu)(CH$_2$)-cHx HCl |
| 1-1749 | H | — | tBu | 0 | 5-(CH$_2$)CH(OB$^4$)(CH$_2$)-cHx |
| 1-1750 | H | — | tBu | 0 | 5-(CH$_2$)CH(OB$^4$)(CH$_2$)-cHx Na salt |
| 1-1751 | H | — | tBu | 0 | 5-(CH$_2$)CH(OB$^5$)(CH$_2$)-cHx |
| 1-1752 | H | — | tBu | 0 | 5-(CH$_2$)CH(OB$^5$)(CH$_2$)-cHx Na salt |
| 1-1753 | H | — | tBu | 0 | 5-(CH$_2$)CH(OB$^6$)(CH$_2$)-cHx |
| 1-1754 | H | — | tBu | 0 | 5-(CH$_2$)CH(OB$^6$)(CH$_2$)-cHx Na salt |
| 1-1755 | H | — | tBu | 0 | 5-(CH$_2$)CH(OE$^4$)(CH$_2$)-cHx |

TABLE 1-continued

| Cpd. No. | $R^a$ | $R^2$ | $R^3$ | n | $R^4$ |
|---|---|---|---|---|---|
| 1-1756 | H | — | tBu | 0 | 5-(CH$_2$)CH(OB$^7$)(CH$_2$)-cHx |
| 1-1757 | H | — | tBu | 0 | 5-(CH$_2$)CH(OB$^7$)(CH$_2$)-cHx Na salt |
| 1-1758 | H | — | tBu | 0 | 5-(CH$_2$)CH(OB$^8$)(CH$_2$)-cHx |
| 1-1759 | H | — | tBu | 0 | 5-(CH$_2$)CH(OB$^8$)(CH$_2$)-cHx Na salt |
| 1-1760 | H | — | tBu | 0 | 5-(CH$_2$)CH(OB$^9$)(CH$_2$)-cHx |
| 1-1761 | H | — | tBu | 0 | 5-(CH$_2$)CH(OB$^9$)(CH$_2$)-cHx Na salt |
| 1-1762 | H | — | tBu | 0 | 5-(CH$_2$)CH(OT)(CH$_2$)-cHx |
| 1-1763 | H | — | tBu | 0 | 5-(CH$_2$)CH(OE$^5$)(CH$_2$)-cHx HCl |
| 1-1764 | H | — | tBu | 0 | 5-(CH$_2$)CH(OB$^{10}$)(CH$_2$)-cHx |
| 1-1765 | H | — | tBu | 0 | 5-(CH$_2$)CH(OB$^{10}$)(CH$_2$)-cHx Na salt |
| 1-1766 | H | — | tBu | 0 | 5-(CH$_2$)CH(OB$^{11}$)(CH$_2$)-cHx |
| 1-1767 | H | — | tBu | 0 | 5-(CH$_2$)CH(OB$^{11}$)(CH$_2$)-cHx Na salt |
| 1-1768 | H | — | tBu | 0 | 5-(CH$_2$)CH(OB$^{12}$)(CH$_2$)-cHx |
| 1-1769 | H | — | tBu | 0 | 5-(CH$_2$)CH(OB$^{12}$)(CH$_2$)-cHx Na salt |
| 1-1770 | H | — | tBu | 0 | 5-(CH$_2$)CH(OCONH$_2$)(CH$_2$)-cHx |
| 1-1771 | H | — | tBu | 0 | 5-(CH$_2$)CH(OB$^{13}$)(CH$_2$)-cHx |
| 1-1772 | H | — | tBu | 0 | 5-(CH$_2$)CH(OB$^{13}$)(CH$_2$)-cHx Na salt |
| 1-1773 | H | — | tBu | 0 | 5-(CH$_2$)CH(OBz)(CH$_2$)$_2$-cHx |
| 1-1774 | H | — | tBu | 0 | 5-(CH$_2$)CH(OAsp)(CH$_2$)$_2$-cHx HCl |
| 1-1775 | H | — | tBu | 0 | 5-(CH$_2$)CH(OLys)(CH$_2$)$_2$-cHx 2HCl |
| 1-1776 | H | — | tBu | 0 | 5-(CH$_2$)CH(OGlu)(CH$_2$)$_2$-cHx HCl |
| 1-1777 | H | — | tBu | 0 | 5-(CH$_2$)CH(OB$^4$)(CH$_2$)$_2$-cHx |
| 1-1778 | H | — | tBu | 0 | 5-(CH$_2$)CH(OB$^4$)(CH$_2$)$_2$-cHx Na salt |
| 1-1779 | H | — | tBu | 0 | 5-(CH$_2$)CH(OB$^5$)(CH$_2$)$_2$-cHx |
| 1-1780 | H | — | tBu | 0 | 5-(CH$_2$)CH(OB$^5$)(CH$_2$)$_2$-cHx Na salt |
| 1-1781 | H | — | tBu | 0 | 5-(CH$_2$)CH(OB$^6$)(CH$_2$)$_2$-cHx |
| 1-1782 | H | — | tBu | 0 | 5-(CH$_2$)CH(OB$^6$)(CH$_2$)$_2$-cHx Na salt |
| 1-1783 | H | — | tBu | 0 | 5-(CH$_2$)CH(OE$^4$)(CH$_2$)$_2$-cHx |
| 1-1784 | H | — | tBu | 0 | 5-(CH$_2$)CH(OB$^7$)(CH$_2$)$_2$-cHx |
| 1-1785 | H | — | tBu | 0 | 5-(CH$_2$)CH(OB$^7$)(CH$_2$)$_2$-cHx Na salt |
| 1-1786 | H | — | tBu | 0 | 5-(CH$_2$)CH(OB$^8$)(CH$_2$)$_2$-cHx |
| 1-1787 | H | — | tBu | 0 | 5-(CH$_2$)CH(OB$^8$)(CH$_2$)$_2$-cHx Na salt |
| 1-1788 | H | — | tBu | 0 | 5-(CH$_2$)CH(OB$^9$)(CH$_2$)$_2$-cHx |
| 1-1789 | H | — | tBu | 0 | 5-(CH$_2$)CH(OB$^9$)(CH$_2$)$_2$-cHx Na salt |
| 1-1790 | H | — | tBu | 0 | 5-(CH$_2$)CH(OT)(CH$_2$)$_2$-cHx |
| 1-1791 | H | — | tBu | 0 | 5-(CH$_2$)CH(OE$^5$)(CH$_2$)$_2$-cHx HCl |
| 1-1792 | H | — | tBu | 0 | 5-(CH$_2$)CH(OB$^{10}$)(CH$_2$)$_2$-cHx |
| 1-1793 | H | — | tBu | 0 | 5-(CH$_2$)CH(OB$^{10}$)(CH$_2$)$_2$-cHx Na salt |
| 1-1794 | H | — | tBu | 0 | 5-(CH$_2$)CH(OB$^{11}$)(CH$_2$)$_2$-cHx |
| 1-1795 | H | — | tBu | 0 | 5-(CH$_2$)CH(OB$^{11}$)(CH$_2$)$_2$-cHx Na salt |
| 1-1796 | H | — | tBu | 0 | 5-(CH$_2$)CH(OB$^{12}$)(CH$_2$)$_2$-cHx |
| 1-1797 | H | — | tBu | 0 | 5-(CH$_2$)CH(OB$^{12}$)(CH$_2$)$_2$-cHx Na salt |
| 1-1798 | H | — | tBu | 0 | 5-(CH$_2$)CH(OCONH$^2$)(CH$_2$)$_2$-cHx |
| 1-1799 | H | — | tBu | 0 | 5-(CH$_2$)CH(OB$^{13}$)(CH$_2$)$_2$-cHx |
| 1-1800 | H | — | tBu | 0 | 5-(CH$_2$)CH(OB$^{13}$)(CH$_2$)$_2$-cHx Na salt |
| 1-1801 | H | — | tBu | 0 | 5-(CH$_2$)CH(OBz)(CH$_2$)$_3$-cHx |
| 1-1802 | H | — | tBu | 0 | 5-(CH$_2$)CH(OAsp)(CH$_2$)$_3$-cHx HCl |
| 1-1803 | H | — | tBu | 0 | 5-(CH$_2$)CH(OLys)(CH$_2$)$_3$-cHx 2HCl |
| 1-1804 | H | — | tBu | 0 | 5-(CH$_2$)CH(OGlu)(CH$_2$)$_3$-cHx HCl |
| 1-1805 | H | — | tBu | 0 | 5-(CH$_2$)CH(OB$^4$)(CH$_2$)$_3$-cHx |
| 1-1806 | H | — | tBu | 0 | 5-(CH$_2$)CH(OB$^4$)(CH$_2$)$_3$-cHx |

TABLE 1-continued

| Cpd. No. | $R^a$ | $R^2$ | $R^3$ | n | $R^4$ |
|---|---|---|---|---|---|
| 1-1807 | H | — | tBu | 0 | 5-$(CH_2)CH(OB^5)(CH_2)_3$-cHx Na salt |
| 1-1808 | H | — | tBu | 0 | 5-$(CH_2)CH(OB^5)(CH_2)_3$-cHx Na salt |
| 1-1809 | H | — | tBu | 0 | 5-$(CH_2)CH(OB^6)(CH_2)_3$-cHx |
| 1-1810 | H | — | tBu | 0 | 5-$(CH_2)CH(OB^6)(CH_2)_3$-cHx Na salt |
| 1-1811 | H | — | tBu | 0 | 5-$(CH_2)CH(OE^4)(CH_2)_3$-cHx |
| 1-1812 | H | — | tBu | 0 | 5-$(CH_2)CH(OB^7)(CH_2)_3$-cHx |
| 1-1813 | H | — | tBu | 0 | 5-$(CH_2)CH(OB^7)(CH_2)_3$-cHx Na salt |
| 1-1814 | H | — | tBu | 0 | 5-$(CH_2)CH(OB^8)(CH_2)_3$-cHx |
| 1-1815 | H | — | tBu | 0 | 5-$(CH_2)CH(OB^8)(CH_2)_3$-cHx Na salt |
| 1-1816 | H | — | tBu | 0 | 5-$(CH_2)CH(OB^9)(CH_2)_3$-cHx |
| 1-1817 | H | — | tBu | 0 | 5-$(CH_2)CH(OB^9)(CH_2)_3$-cHx Na salt |
| 1-1818 | H | — | tBu | 0 | 5-$(CH_2)CH(OT)(CH_2)_3$-cHx |
| 1-1819 | H | — | tBu | 0 | 5-$(CH_2)CH(OE^5)(CH_2)_3$-cHx HCl |
| 1-1820 | H | — | tBu | 0 | 5-$(CH_2)CH(OB^{10})(CH_2)_3$-cHx |
| 1-1821 | H | — | tBu | 0 | 5-$(CH_2)CH(OB^{10})(CH_2)_3$-cHx Na salt |
| 1-1822 | H | — | tBu | 0 | 5-$(CH_2)CH(OB^{11})(CH_2)_3$-cHx |
| 1-1823 | H | — | tBu | 0 | 5-$(CH_2)CH(OB^{11})(CH_2)_3$-cHx Na salt |
| 1-1824 | H | — | tBu | 0 | 5-$(CH_2)CH(OB^{12})(CH_2)_3$-cHx |
| 1-1825 | H | — | tBu | 0 | 5-$(CH_2)CH(OB^{12})(CH_2)_3$-cHx Na salt |
| 1-1826 | H | — | tBu | 0 | 5-$(CH_2)CH(OCONH_2)(CH_2)_3$-cHx |
| 1-1827 | H | — | tBu | 0 | 5-$(CH_2)CH(OB^{13})(CH_2)_3$-cHx |
| 1-1828 | H | — | tBu | 0 | 5-$(CH_2)CH(OB^{13})(CH_2)_3$-cHx Na salt |
| 1-1829 | H | — | tBu | 0 | 5-$(CH_2)CH(OBz)(CH_2)_4$-cHx |
| 1-1830 | H | — | tBu | 0 | 5-$(CH_2)CH(OAsp)(CH_2)_4$-cHx HCl |
| 1-1831 | H | — | tBu | 0 | 5-$(CH_2)CH(OLys)(CH_2)_4$-cHx 2HCl |
| 1-1832 | H | — | tBu | 0 | 5-$(CH_2)CH(OGlu)(CH_2)_4$-cHx HCl |
| 1-1833 | H | — | tBu | 0 | 5-$(CH_2)CH(OB^4)(CH_2)_4$-cHx |
| 1-1834 | H | — | tBu | 0 | 5-$(CH_2)CH(OB^4)(CH_2)_4$-cHx Na salt |
| 1-1835 | H | — | tBu | 0 | 5-$(CH_2)CH(OB^5)(CH_2)_4$-cHx |
| 1-1836 | H | — | tBu | 0 | 5-$(CH_2)CH(OB^5)(CH_2)_4$-cHx Na salt |
| 1-1837 | H | — | tBu | 0 | 5-$(CH_2)CH(OB^6)(CH_2)_4$-cHx |
| 1-1838 | H | — | tBu | 0 | 5-$(CH_2)CH(OB^6)(CH_2)_4$-cHx Na salt |
| 1-1839 | H | — | tBu | 0 | 5-$(CH_2)CH(OE^4)(CH_2)_4$-cHx |
| 1-1840 | H | — | tBu | 0 | 5-$(CH_2)CH(OB^7)(CH_2)_4$-cHx |
| 1-1841 | H | — | tBu | 0 | 5-$(CH_2)CH(OB^7)(CH_2)_4$-cHx Na salt |
| 1-1842 | H | — | tBu | 0 | 5-$(CH_2)CH(OB^8)(CH_2)_4$-cHx |
| 1-1843 | H | — | tBu | 0 | 5-$(CH_2)CH(OB^8)(CH_2)_4$-cHx Na salt |
| 1-1844 | H | — | tBu | 0 | 5-$(CH_2)CH(OB^9)(CH_2)_4$-cHx |
| 1-1845 | H | — | tBu | 0 | 5-$(CH_2)CH(OB^9)(CH_2)_4$-cHx Na salt |
| 1-1846 | H | — | tBu | 0 | 5-$(CH_2)CH(OT)(CH_2)_4$-cHx |
| 1-1847 | H | — | tBu | 0 | 5-$(CH_2)CH(OE^5)(CH_2)_4$-cHx HCl |
| 1-1848 | H | — | tBu | 0 | 5-$(CH_2)CH(OB^{10})(CH_2)_4$-cHx |
| 1-1849 | H | — | tBu | 0 | 5-$(CH_2)CH(OB^{10})(CH_2)_4$-cHx Na salt |
| 1-1850 | H | — | tBu | 0 | 5-$(CH_2)CH(OB^{11})(CH_2)_4$-cHx |
| 1-1851 | H | — | tBu | 0 | 5-$(CH_2)CH(OB^{11})(CH_2)_4$-cHx Na salt |
| 1-1852 | H | — | tBu | 0 | 5-$(CH_2)CH(OB^{12})(CH_2)_4$-cHx |
| 1-1853 | H | — | tBu | 0 | 5-$(CH_2)CH(OB^{12})(CH_2)_4$-cHx Na salt |
| 1-1854 | H | — | tBu | 0 | 5-$(CH_2)CH(OCONH_2)(CH_2)_4$-cHx |
| 1-1855 | H | — | tBu | 0 | 5-$(CH_2)CH(OB^{13})(CH_2)_4$-cHx |
| 1-1856 | H | — | tBu | 0 | 5-$(CH_2)CH(OB^{13})(CH_2)_4$-cHx Na salt |
| 1-1857 | H | — | tBu | 0 | 5-$(CH_2)_2CH(OBz)(CH_2)_2$-cHx |

TABLE 1-continued

| Cpd. No. | R$^a$ | R$^2$ | R$^3$ | n | R$^4$ |
|---|---|---|---|---|---|
| 1-1858 | H | — | tBu | 0 | 5-(CH$_2$)$_2$CH(OAsp)(CH$_2$)$_2$-cHx HCl |
| 1-1859 | H | — | tBu | 0 | 5-(CH$_2$)$_2$CH(OLys)(CH$_2$)$_2$-cHx 2HCl |
| 1-1860 | H | — | tBu | 0 | 5-(CH$_2$)$_2$CH(OGlu)(CH$_2$)$_2$-cHx HCl |
| 1-1861 | H | — | tBu | 0 | 5-(CH$_2$)$_2$CH(OB$^4$)(CH$_2$)$_2$-cHx |
| 1-1862 | H | — | tBu | 0 | 5-(CH$_2$)$_2$CH(OB$^4$)(CH$_2$)$_2$-cHx Na salt |
| 1-1863 | H | — | tBu | 0 | 5-(CH$_2$)$_2$CH(OB$^5$)(CH$_2$)$_2$-cHx |
| 1-1864 | H | — | tBu | 0 | 5-(CH$_2$)$_2$CH(OB$^5$)(CH$_2$)$_2$-cHx Na salt |
| 1-1865 | H | — | tBu | 0 | 5-(CH$_2$)$_2$CH(OB$^6$)(CH$_2$)$_2$-cHx |
| 1-1866 | H | — | tBu | 0 | 5-(CH$_2$)$_2$CH(OB$^6$)(CH$_2$)$_2$-cHx Na salt |
| 1-1867 | H | — | tBu | 0 | 5-(CH$_2$)$_2$CH(OE$^4$)(CH$_2$)$_2$-cHx |
| 1-1868 | H | — | tBu | 0 | 5-(CH$_2$)$_2$CH(OB$^7$)(CH$_2$)$_2$-cHx |
| 1-1869 | H | — | tBu | 0 | 5-(CH$_2$)$_2$CH(OB$^7$)(CH$_2$)$_2$-cHx Na salt |
| 1-1870 | H | — | tBu | 0 | 5-(CH$_2$)$_2$CH(OB$^8$)(CH$_2$)$_2$-cHx |
| 1-1871 | H | — | tBu | 0 | 5-(CH$_2$)$_2$CH(OB$^8$)(CH$_2$)$_2$-cHx Na salt |
| 1-1872 | H | — | tBu | 0 | 5-(CH$_2$)$_2$CH(OB$^9$)(CH$_2$)$_2$-cHx |
| 1-1873 | H | — | tBu | 0 | 5-(CH$_2$)$_2$CH(OB$^9$)(CH$_2$)$_2$-cHx Na salt |
| 1-1874 | H | — | tBu | 0 | 5-(CH$_2$)$_2$CH(OT)(CH$_2$)$_2$-cHx |
| 1-1875 | H | — | tBu | 0 | 5-(CH$_2$)$_2$CH(OE$^5$)(CH$_2$)$_2$-cHx HCl |
| 1-1876 | H | — | tBu | 0 | 5-(CH$_2$)$_2$CH(OB$^{10}$)(CH$_2$)$_2$-cHx |
| 1-1877 | H | — | tBu | 0 | 5-(CH$_2$)$_2$CH(OB$^{10}$)(CH$_2$)$_2$-cHx Na salt |
| 1-1878 | H | — | tBu | 0 | 5-(CH$_2$)$_2$CH(OB$^{11}$)(CH$_2$)$_2$-cHx |
| 1-1879 | H | — | tBu | 0 | 5-(CH$_2$)$_2$CH(OB$^{11}$)(CH$_2$)$_2$-cHx Na salt |
| 1-1880 | H | — | tBu | 0 | 5-(CH$_2$)$_2$CH(OB$^{12}$)(CH$_2$)$_2$-cHx |
| 1-1881 | H | — | tBu | 0 | 5-(CH$_2$)$_2$CH(OB$^{12}$)(CH$_2$)$_2$-cHx Na salt |
| 1-1882 | H | — | tBu | 0 | 5-(CH$_2$)$_2$CH(OCONH$_2$)(CH$_2$)$_2$-cHx |
| 1-1883 | H | — | tBu | 0 | 5-(CH$_2$)$_2$CH(OB$^{13}$)(CH$_2$)$_2$-cHx |
| 1-1884 | H | — | tBu | 0 | 5-(CH$_2$)$_2$CH(OB$^{13}$)(CH$_2$)$_2$-cHx Na salt |
| 1-1885 | H | — | tBu | 0 | 5-(CH$_2$)$_2$CH(OBz)(CH$_2$)$_3$-cHx |
| 1-1886 | H | — | tBu | 0 | 5-(CH$_2$)$_2$CH(OAsp)(CH$_2$)$_3$-cHx HCl |
| 1-1887 | H | — | tBu | 0 | 5-(CH$_2$)$_2$CH(OLys)(CH$_2$)$_3$-cHx 2HCl |
| 1-1888 | H | — | tBu | 0 | 5-(CH$_2$)$_2$CH(OGlu)(CH$_2$)$_3$-cHx 2HCl |
| 1-1889 | H | — | tBu | 0 | 5-(CH$_2$)$_2$CH(OB$^4$)(CH$_2$)$_3$-cHx |
| 1-1890 | H | — | tBu | 0 | 5-(CH$_2$)$_2$CH(OB$^4$)(CH$_2$)$_3$-cHx Na salt |
| 1-1891 | H | — | tBu | 0 | 5-(CH$_2$)$_2$CH(OB$^5$)(CH$_2$)$_3$-cHx |
| 1-1892 | H | — | tBu | 0 | 5-(CH$_2$)$_2$CH(OB$^5$)(CH$_2$)$_3$-cHx Na salt |
| 1-1893 | H | — | tBu | 0 | 5-(CH$_2$)$_2$CH(OB$^6$)(CH$_2$)$_3$-cHx |
| 1-1894 | H | — | tBu | 0 | 5-(CH$_2$)$_2$CH(OB$^6$)(CH$_2$)$_3$-cHx Na salt |
| 1-1895 | H | — | tBu | 0 | 5-(CH$_2$)$_2$CH(OE$^4$)(CH$_2$)$_3$-cHx |
| 1-1896 | H | — | tBu | 0 | 5-(CH$_2$)$_2$CH(OB$^7$)(CH$_2$)$_3$-cHx |
| 1-1897 | H | — | tBu | 0 | 5-(CH$_2$)$_2$CH(OB$^7$)(CH$_2$)$_3$-cHx Na salt |
| 1-1898 | H | — | tBu | 0 | 5-(CH$_2$)$_2$CH(OB$^8$)(CH$_2$)$_3$-cHx |
| 1-1899 | H | — | tBu | 0 | 5-(CH$_2$)$_2$CH(OB$^8$)(CH$_2$)$_3$-cHx Na salt |
| 1-1900 | H | — | tBu | 0 | 5-(CH$_2$)$_2$CH(OB$^9$)(CH$_2$)$_3$-cHx |
| 1-1901 | H | — | tBu | 0 | 5-(CH$_2$)$_2$CH(OB$^9$)(CH$_2$)$_3$-cHx Na salt |
| 1-1902 | H | — | tBu | 0 | 5-(CH$_2$)$_2$CH(OT)(CH$_2$)$_3$-cHx |
| 1-1903 | H | — | tBu | 0 | 5-(CH$_2$)$_2$CH(OE$^5$)(CH$_2$)$_3$-cHx HCl |
| 1-1904 | H | — | tBu | 0 | 5-(CH$_2$)$_2$CH(OB$^{10}$)(CH$_2$)$_3$-cHx |
| 1-1905 | H | — | tBu | 0 | 5-(CH$_2$)$_2$CH(OB$^{10}$)(CH$_2$)$_3$-cHx Na salt |
| 1-1906 | H | — | tBu | 0 | 5-(CH$_2$)$_2$CH(OB$^{11}$)(CH$_2$)$_3$-cHx |
| 1-1907 | H | — | tBu | 0 | 5-(CH$_2$)$_2$CH(OB$^{11}$)(CH$_2$)$_3$-cHx Na salt |

TABLE 1-continued

| Cpd. No. | $R^a$ | $R^2$ | $R^3$ | n | $R^4$ |
|---|---|---|---|---|---|
| 1-1908 | H | — | tBu | 0 | 5-$(CH_2)_2CH(OB^{12})(CH_2)_3$-cHx |
| 1-1909 | H | — | tBu | 0 | 5-$(CH_2)_2CH(OB^{12})(CH_2)_3$-cHx Na salt |
| 1-1910 | H | — | tBu | 0 | 5-$(CH_2)_2CH(OCONH_2)(CH_2)_3$-cHx |
| 1-1911 | H | — | tBu | 0 | 5-$(CH_2)_2CH(OB^{13})(CH_2)_3$-cHx |
| 1-1912 | H | — | tBu | 0 | 5-$(CH_2)_2CH(OB^{13})(CH_2)_3$-cHx Na salt |
| 1-1913 | H | — | tBu | 0 | 5-$(CH_2)_2CH(OBz)(CH_2)_4$-cHx |
| 1-1914 | H | — | tBu | 0 | 5-$(CH_2)_2CH(OAsp)(CH_2)_4$-cHx HCl |
| 1-1915 | H | — | tBu | 0 | 5-$(CH_2)_2CH(OLys)(CH_2)_4$-cHx 2HCl |
| 1-1916 | H | — | tBu | 0 | 5-$(CH_2)_2CH(OGlu)(CH_2)_4$-cHx HCl |
| 1-1917 | H | — | tBu | 0 | 5-$(CH_2)_2CH(OB^4)(CH_2)_4$-cHx |
| 1-1918 | H | — | tBu | 0 | 5-$(CH_2)_2CH(OB^4)(CH_2)_4$-cHx Na salt |
| 1-1919 | H | — | tBu | 0 | 5-$(CH_2)_2CH(OB^5)(CH_2)_4$-cHx |
| 1-1920 | H | — | tBu | 0 | 5-$(CH_2)_2CH(OB^5)(CH_2)_4$-cHx Na salt |
| 1-1921 | H | — | tBu | 0 | 5-$(CH_2)_2CH(OB^6)(CH_2)_4$-cHx |
| 1-1922 | H | — | tBu | 0 | 5-$(CH_2)_2CH(OB^6)(CH_2)_4$-cHx Na salt |
| 1-1923 | H | — | tBu | 0 | 5-$(CH_2)_2CH(OE^4)(CH_2)_4$-cHx |
| 1-1924 | H | — | tBu | 0 | 5-$(CH_2)_2CH(OB^7)(CH_2)_4$-cHx |
| 1-1925 | H | — | tBu | 0 | 5-$(CH_2)_2CH(OB^7)(CH_2)_4$-cHx Na salt |
| 1-1926 | H | — | tBu | 0 | 5-$(CH_2)_2CH(OB^8)(CH_2)_4$-cHx |
| 1-1927 | H | — | tBu | 0 | 5-$(CH_2)_2CH(OB^8)(CH_2)_4$-cHx Na salt |
| 1-1928 | H | — | tBu | 0 | 5-$(CH_2)_2CH(OB^9)(CH_2)_4$-cHx |
| 1-1929 | H | — | tBu | 0 | 5-$(CH_2)_2CH(OB^9)(CH_2)_4$-cHx Na salt |
| 1-1930 | H | — | tBu | 0 | 5-$(CH_2)_2CH(OT)(CH_2)_4$-cHx |
| 1-1931 | H | — | tBu | 0 | 5-$(CH_2)_2CH(OE^4)(CH_2)_4$-cHx HCl |
| 1-1932 | H | — | tBu | 0 | 5-$(CH_2)_2CH(OB^{10})(CH_2)_4$-cHx |
| 1-1933 | H | — | tBu | 0 | 5-$(CH_2)_2CH(OB^{10})(CH_2)_4$-cHx Na salt |
| 1-1934 | H | — | tBu | 0 | 5-$(CH_2)_2CH(OB^{11})(CH_2)_4$-cHx |
| 1-1935 | H | — | tBu | 0 | 5-$(CH_2)_2CH(OB^{11})(CH_2)_4$-cHx Na salt |
| 1-1936 | H | — | tBu | 0 | 5-$(CH_2)_2CH(OB^{12})(CH_2)_4$-cHx |
| 1-1937 | H | — | tBu | 0 | 5-$(CH_2)_2CH(OB^{12})(CH_2)_4$-cHx Na salt |
| 1-1938 | H | — | tBu | 0 | 5-$(CH_2)_2CH(OCONH_2)(CH_2)_4$-cHx |
| 1-1939 | H | — | tBu | 0 | 5-$(CH_2)_2CH(OB^{13})(CH_2)_4$-cHx |
| 1-1940 | H | — | tBu | 0 | 5-$(CH_2)_2CH(OB^{13})(CH_2)_4$-cHx Na salt |
| 1-1941 | H | — | tBu | 0 | 5-$(CH_2)_2CH(OB^{10})(CH_2)5$-cHx |
| 1-1942 | H | — | tBu | 0 | 5-$(CH_2)_2CH(OB^{10})(CH_2)5$-cHx Na salt |
| 1-1943 | H | — | tBu | 0 | 5-CH=CH—CH(OCH$_2$Ph)O-cHx |
| 1-1944 | H | — | tBu | 0 | 5-CH=CH—CH(OCH$_2$Ph)(CH$_2$)O-cHx |
| 1-1945 | H | — | tBu | 0 | 5-CH=CH—CH(OCH$_2$Ph)(CH$_2$)$_2$O-cHx |
| 1-1946 | H | — | tBu | 0 | 5-CH=CH—CH(OCH$_2$Ph)(CH$_2$)$_3$O-cHx |
| 1-1947 | H | — | tBu | 0 | 5-CH=CH—CH(OCH$_2$Ph)(CH$_2$)$_4$O-cHx |
| 1-1948 | H | — | tBu | 0 | 5-CH=CH—CH(OCH$_2$Ph)O-cPn |
| 1-1949 | H | — | tBu | 0 | 5-CH=CH—CH(OCH$_2$Ph)(CH$_2$)O-cPn |
| 1-1950 | H | — | tBu | 0 | 5-CH=CH—CH(OCH$_2$Ph)(CH$_2$)$_2$O-cPn |
| 1-1951 | H | — | tBu | 0 | 5-CH=CH—CH(OCH$_2$Ph)(CH$_2$)$_3$O-cPn |
| 1-1952 | H | — | tBu | 0 | 5-CH=CH—CH(OCH$_2$Ph)(CH$_2$)$_4$O-cPn |
| 1-1953 | H | — | tBu | 0 | 5-CH=C(CH$_2$OCH$_2$Ph)(CH$_2$)-cHx |
| 1-1954 | H | — | tBu | 0 | 5-CH=C(CH$_2$OCH$_2$Ph)(CH$_2$)$_2$-cHx |
| 1-1955 | H | — | tBu | 0 | 5-CH=C(CH$_2$OCH$_2$Ph)(CH$_2$)$_3$-cHx |
| 1-1956 | H | — | tBu | 0 | 5-CH=C(CH$_2$OCH$_2$Ph)(CH$_2$)$_4$-cHx |
| 1-1957 | H | — | tBu | 0 | 5-CH=C(CH$_2$OCH$_2$Ph)(CH$_2$)$_5$-cHx |
| 1-1958 | H | — | tBu | 0 | 5-CH=C(CH$_2$OCH$_2$Ph)(CH$_2$)$_6$-cHx |
| 1-1959 | H | — | tBu | 0 | 5-CH=C(CH$_2$OCH$_2$Ph)(CH$_2$)$_7$-cHx |
| 1-1960 | H | — | tBu | 0 | 5-CH=C(CH$_2$OCH$_2$Ph)(CH$_2$)-cPn |
| 1-1961 | H | — | tBu | 0 | 5-CH=C(CH$_2$OCH$_2$Ph)(CH$_2$)$_2$-cPn |
| 1-1962 | H | — | tBu | 0 | 5-CH=C(CH$_2$OCH$_2$Ph)(CH$_2$)$_3$-cPn |
| 1-1963 | H | — | tBu | 0 | 5-CH=C(CH$_2$OCH$_2$Ph)(CH$_2$)$_4$-cPn |
| 1-1964 | H | — | tBu | 0 | 5-CH=C(CH$_2$OCH$_2$Ph)(CH$_2$)$_5$-cPn |
| 1-1965 | H | — | tBu | 0 | 5-CH=C(CH$_2$OCH$_2$Ph)(CH$_2$)$_6$-cPn |
| 1-1966 | H | — | tBu | 0 | 5-CH=C(CH$_2$OCH$_2$Ph)(CH$_2$)$_7$-cPn |

TABLE 1-continued

| Cpd. No. | R$^a$ | R$^2$ | R$^3$ | n | R$^4$ |
|---|---|---|---|---|---|
| 1-1967 | H | — | tBu | 0 | 5-CH(CH$_2$OH)-cHx |
| 1-1968 | H | — | tBu | 0 | 5-CH(CH$_2$OH)(CH$_2$)-cHx |
| 1-1969 | H | — | tBu | 0 | 5-CH(CH$_2$OH)(CH$_2$)$_2$-cHx |
| 1-1970 | H | — | tBu | 0 | 5-CH(CH$_2$OH)(CH$_2$)$_3$-cHx |
| 1-1971 | H | — | tBu | 0 | 5-CH(CH$_2$OH)(CH$_2$)$_3$-cPn |
| 1-1972 | H | — | tBu | 0 | 5-CH(CH$_2$OH)(CH$_2$)$_4$-cHx |
| 1-1973 | H | — | tBu | 0 | 5-CH(CH$_2$OH)(CH$_2$)$_4$-cPn |
| 1-1974 | H | — | tBu | 0 | 5-CH(CH$_2$OH)(CH$_2$)$_5$-cHx |
| 1-1975 | H | — | tBu | 0 | 5-(CH$_2$)CH(CH$_2$OH)-cHx |
| 1-1976 | H | — | tBu | 0 | 5-(CH$_2$)CH(CH$_2$OH)(CH$_2$)-cHx |
| 1-1977 | H | — | tBu | 0 | 5-(CH$_2$)CH(CH$_2$OH)(CH$_2$)$_2$-cHx |
| 1-1978 | H | — | tBu | 0 | 5-(CH$_2$)CH(CH$_2$OH)(CH$_2$)$_2$-cPn |
| 1-1979 | H | — | tBu | 0 | 5-(CH$_2$)CH(CH$_2$OH)(CH$_2$)$_3$-cHx |
| 1-1980 | H | — | tBu | 0 | 5-(CH$_2$)CH(CH$_2$OH)(CH$_2$)$_3$-cPn |
| 1-1981 | H | — | tBu | 0 | 5-(CH$_2$)CH(CH$_2$OH)(CH$_2$)$_4$-cHx |
| 1-1982 | H | — | tBu | 0 | 5-(CH$_2$)CH(CH$_2$OH)(CH$_2$)$_5$-cHx |
| 1-1983 | H | — | tBu | 0 | 5-(CH$_2$)$_2$CH(CH$_2$OH)-cHx |
| 1-1984 | H | — | tBu | 0 | 5-(CH$_2$)$_2$CH(CH$_2$OH)(CH$_2$)-cHx |
| 1-1985 | H | — | tBu | 0 | 5-(CH$_2$)$_2$CH(CH$_2$OH)(CH$_2$)$_2$-cHx |
| 1-1986 | H | — | tBu | 0 | 5-(CH$_2$)$_2$CH(CH$_2$OH)(CH$_2$)$_3$-cHx |
| 1-1987 | H | — | tBu | 0 | 5-(CH$_2$)$_2$CH(CH$_2$OH)(CH$_2$)$_4$-cHx |
| 1-1988 | H | — | tBu | 0 | 5-(CH$_2$)$_2$CH(CH$_2$OH)(CH$_2$)$_5$-cHx |
| 1-1989 | H | — | SO$_2$CH$_3$ | 0 | 6-(CH$_2$)O(CH$_2$)$_3$-Imd |
| 1-1990 | H | — | SOCH$_3$ | 0 | 6-(CH$_2$)O(CH$_2$)$_3$-Imd |
| 1-1991 | H | — | SOCH$_3$ | 0 | 6-(CH$_2$)O(CH$_2$)$_2$-Imd |
| 1-1992 | H | — | SO$_2$CH$_3$ | 0 | 6-(CH$_2$)O(CH$_2$)$_2$-Imd |
| 1-1993 | H | — | SO$_2$CH$_3$ | 0 | 6-(CH$_2$)O(CH$_2$)$_4$-Imd |
| 1-1994 | H | — | SOCH$_3$ | 0 | 6-(CH$_2$)O(CH$_2$)$_4$-Imd |
| 1-1995 | H | — | SOCH$_3$ | 0 | 6-(CH$_2$)-Imd |
| 1-1996 | H | — | SO$_2$ | 0 | 6-(CH$_2$)-Imd |
| 1-1997 | H | — | SO$_2$ | 0 | 6-(CH$_2$)$_3$-Imd |
| 1-1998 | H | — | SOCH$_3$ | 0 | 6-(CH$_2$)$_3$-Imd |
| 1-1999 | H | — | SO$_2$CH$_3$ | 0 | 5-(CH$_2$)O(CH$_2$)$_3$-Imd |
| 1-2000 | H | — | SOCH$_3$ | 0 | 5-(CH$_2$)O(CH$_2$)$_3$-Imd |
| 1-2001 | H | — | iPr | 0 | 6-(CH$_2$)-Bimd |
| 1-2002 | H | — | iPr | 0 | 6-(CH$_2$)-Bimd HCl |
| 1-2003 | H | — | tBu | 0 | 6-(CH$_2$)-Bimd |
| 1-2004 | H | — | tBu | 0 | 6-(CH$_2$)$_3$-Bimd |
| 1-2005 | H | — | tBu | 0 | 5-(CH$_2$)O(CH$_2$)$_3$-Bimd |
| 1-2006 | H | — | tBu | 0 | 5-(CH$_2$)O(CH$_2$)$_2$-Bimd |
| 1-2007 | H | — | iPr | 0 | 6-(CH$_2$)O(CH$_2$)$_3$-Bimd |
| 1-2008 | H | — | iPr | 0 | 6-(CH$_2$)O(CH$_2$)$_3$-Bimd |
| 1-2009 | H | — | iPr | 0 | 6-(CH$_2$)O(CH$_2$)$_4$-Iimd HCl |
| 1-2010 | H | — | iPr | 0 | 6-(CH$_2$)O(CH$_2$)$_4$-Imd |
| 1-2011 | H | — | iPr | 0 | 5-(CH$_2$)$_2$O(CH$_2$)$_2$-Imd HCl |
| 1-2012 | H | — | iPr | 0 | 5-(CH$_2$)$_2$O(CH$_2$)$_2$-Imd |
| 1-2013 | H | — | iPr | 0 | 6-(CH$_2$)$_2$O(CH$_2$)$_3$-Imd HCl |
| 1-2014 | H | — | iPr | 0 | 6-(CH$_2$)$_2$O(CH$_2$)$_3$-Imd |
| 1-2015 | H | — | iPr | 0 | 6-(CH$_2$)$_2$O(CH$_2$)$_4$-Imd HCl |
| 1-2016 | H | — | iPr | 0 | 6-(CH$_2$)$_2$O(CH$_2$)$_4$-Imd |
| 1-2017 | H | — | iPr | 0 | 6-(CH$_2$)$_3$O(CH$_2$)$_2$-Imd HCl |
| 1-2018 | H | — | iPr | 0 | 6-(CH$_2$)$_3$O(CH$_2$)$_2$-Imd |
| 1-2019 | H | — | iPr | 0 | 6-(CH$_2$)$_3$O(CH$_2$)$_3$-Imd HCl |
| 1-2020 | H | — | iPr | 0 | 6-(CH$_2$)$_3$O(CH$_2$)$_3$-Imd |
| 1-2021 | H | — | iPr | 0 | 6-(CH$_2$)$_3$O(CH$_2$)$_4$-Imd HCl |
| 1-2022 | H | — | iPr | 0 | 6-(CH$_2$)$_3$O(CH$_2$)$_4$-Imd |
| 1-2023 | H | — | iPr | 0 | 6-(CH$_2$)-Imd HCl |
| 1-2024 | H | — | iPr | 0 | 6-(CH$_2$)-Imd |
| 1-2025 | H | — | iPr | 0 | 6-(CH$_2$)$_2$-Imd HCl |
| 1-2026 | H | — | iPr | 0 | 6-(CH$_2$)$_2$-Imd |
| 1-2027 | H | — | iPr | 0 | 6-(CH$_2$)$_3$-Imd HCl |
| 1-2028 | H | — | iPr | 0 | 6-(CH$_2$)$_3$-Imd |
| 1-2029 | H | — | iPr | 0 | 6-(CH$_2$)$_4$-Imd HCl |
| 1-2030 | H | — | iPr | 0 | 6-(CH$_2$)$_4$-Imd |

TABLE 1-continued

| Cpd. No. | $R^a$ | $R^2$ | $R^3$ | n | $R^4$ |
|---|---|---|---|---|---|
| 1-2031 | H | — | iPr | 0 | 6-$(CH_2)_5$-Imd HCl |
| 1-2032 | H | — | iPr | 0 | 6-$(CH_2)_5$-Imd |
| 1-2033 | H | — | iPr | 0 | 6-$(CH_2)_6$-Imd HCl |
| 1-2034 | H | — | iPr | 0 | 6-$(CH_2)_6$-Imd |
| 1-2035 | H | — | iPr | 0 | 6-$(CH_2)_7$-Imd HCl |
| 1-2036 | H | — | iPr | 0 | 6-$(CH_2)_7$-Imd |
| 1-2037 | H | — | tBu | 0 | 6-$(CH_2)O(CH_2)_2$-Imd |
| 1-2038 | H | — | tBu | 0 | 6-$(CH_2)O(CH_2)_3$-Imd |
| 1-2039 | H | — | tBu | 0 | 6-$(CH_2)O(CH_2)_4$-Imd HCl |
| 1-2040 | H | — | tBu | 0 | 6-$(CH_2)O(CH_2)_4$-Imd |
| 1-2041 | H | — | tBu | 0 | 5-$(CH_2)_2O(CH_2)_2$-Imd |
| 1-2042 | H | — | tBu | 0 | 6-$(CH_2)_2O(CH_2)_2$-Imd HCl |
| 1-2043 | H | — | tBu | 0 | 6-$(CH_2)_2O(CH_2)_2$-Imd |
| 1-2044 | H | — | tBu | 0 | 5-$(CH_2)_2O(CH_2)_3$-Imd HCl |
| 1-2045 | H | — | tBu | 0 | 6-$(CH_2)_2O(CH_2)_3$-Imd HCl |
| 1-2046 | H | — | tBu | 0 | 6-$(CH_2)_2O(CH_2)_3$-Imd |
| 1-2047 | H | — | tBu | 0 | 5-$(CH_2)_2O(CH_2)_4$-Imd HCl |
| 1-2048 | H | — | tBu | 0 | 6-$(CH_2)_2O(CH_2)_4$-Imd HCl |
| 1-2049 | H | — | tBu | 0 | 6-$(CH_2)_2O(CH_2)_4$-Imd |
| 1-2050 | H | — | tBu | 0 | 6-$(CH_2)_3O(CH_2)_2$-Imd HCl |
| 1-2051 | H | — | tBu | 0 | 6-$(CH_2)_3O(CH_2)_2$-Imd |
| 1-2052 | H | — | tBu | 0 | 6-$(CH_2)_3O(CH_2)_3$-Imd HCl |
| 1-2053 | H | — | tBu | 0 | 6-$(CH_2)_3O(CH_2)_3$-Imd |
| 1-2054 | H | — | tBu | 0 | 6-$(CH_2)_3O(CH_2)_4$-Imd HCl |
| 1-2055 | H | — | tBu | 0 | 5-$(CH_2)_2O(CH_2)_4$-Imd |
| 1-2056 | H | — | tBu | 0 | 6-$(CH_2)$-Imd HCl |
| 1-2057 | H | — | tBu | 0 | 5-$(CH_2)$-Imd |
| 1-2058 | H | — | tBu | 0 | 6-$(CH_2)$-Imd |
| 1-2059 | H | — | tBu | 0 | 6-$(CH_2)_2$-Imd HCl |
| 1-2060 | H | — | tBu | 0 | 5-$(CH_2)_2$-Imd |
| 1-2061 | H | — | tBu | 0 | 6-$(CH_2)_2$-Imd |
| 1-2062 | H | — | tBu | 0 | 6-$(CH_2)_3$-Imd HCl |
| 1-2063 | H | — | tBu | 0 | 5-$(CH_2)_3$-Imd |
| 1-2064 | H | — | tBu | 0 | 6-$(CH_2)_3$-Imd |
| 1-2065 | H | — | tBu | 0 | 6-$(CH_2)_4$-Imd HCl |
| 1-2066 | H | — | tBu | 0 | 6-$(CH_2)_4$-Imd |
| 1-2067 | H | — | tBu | 0 | 6-$(CH_2)_5$-Imd HCl |
| 1-2068 | H | — | tBu | 0 | 5-$(CH_2)_5$-Imd |
| 1-2069 | H | — | tBu | 0 | 6-$(CH_2)_5$-Imd |
| 1-2070 | H | — | tBu | 0 | 6-$(CH_2)_6$-Imd HCl |
| 1-2071 | H | — | tBu | 0 | 6-$(CH_2)_6$-Imd |
| 1-2072 | H | — | tBu | 0 | 6-$(CH_2)_7$-Imd HCl |
| 1-2073 | H | — | tBu | 0 | 6-$(CH_2)_7$-Imd |
| 1-2074 | H | — | $OCH_3$ | 0 | 6-$(CH_2)O(CH_2)_2$-Imd HCl |
| 1-2075 | H | — | $OCH_3$ | 0 | 6-$(CH_2)O(CH_2)_2$-Imd |
| 1-2076 | H | — | $OCH_3$ | 0 | 6-$(CH_2)O(CH_2)_3$-Imd HCl |
| 1-2077 | H | — | $OCH_3$ | 0 | 6-$(CH_2)O(CH_2)_3$-Imd |
| 1-2078 | H | — | $OCH_3$ | 0 | 6-$(CH_2)O(CH_2)_4$-Imd HCl |
| 1-2079 | H | — | $OCH_3$ | 0 | 6-$(CH_2)O(CH_2)_4$-Imd |
| 1-2080 | H | — | $OCH_3$ | 0 | 6-$(CH_2)_2O(CH_2)_2$-Imd HCl |
| 1-2081 | H | — | $OCH_3$ | 0 | 6-$(CH_2)_2O(CH_2)_2$-Imd |
| 1-2082 | H | — | $OCH_3$ | 0 | 6-$(CH_2)_2O(CH_2)_3$-Imd |

TABLE 1-continued

| Cpd. No. | R$^a$ | R$^2$ | R$^3$ | n | R$^4$ |
|---|---|---|---|---|---|
| 1-2083 | H | — | OCH$_3$ | 0 | 6-(CH$_2$)$_2$O(CH$_2$)$_3$-Imd HCl |
| 1-2084 | H | — | OCH$_3$ | 0 | 6-(CH$_2$)$_2$O(CH$_2$)$_4$-Imd |
| 1-2085 | H | — | OCH$_3$ | 0 | 6-(CH$_2$)$_2$O(CH$_2$)$_4$-Imd HCl |
| 1-2086 | H | — | OCH$_3$ | 0 | 6-(CH$_2$)$_3$O(CH$_2$)$_2$-Imd |
| 1-2087 | H | — | OCH$_3$ | 0 | 6-(CH$_2$)$_3$O(CH$_2$)$_2$-Imd HCl |
| 1-2088 | H | — | OCH$_3$ | 0 | 6-(CH$_2$)$_3$O(CH$_2$)$_3$-Imd |
| 1-2089 | H | — | OCH$_3$ | 0 | 6-(CH$_2$)$_3$O(CH$_2$)$_3$-Imd HCl |
| 1-2090 | H | — | OCH$_3$ | 0 | 6-(CH$_2$)$_3$O(CH$_2$)$_4$-Imd |
| 1-2091 | H | — | OCH$_3$ | 0 | 6-(CH$_2$)$_3$O(CH$_2$)$_4$-Imd HCl |
| 1-2092 | H | — | OCH$_3$ | 0 | 6-(CH$_2$)-Imd |
| 1-2093 | H | — | OCH$_3$ | 0 | 6-(CH$_2$)-Imd HCl |
| 1-2094 | H | — | OCH$_3$ | 0 | 6-(CH$_2$)$_2$-Imd |
| 1-2095 | H | — | OCH$_3$ | 0 | 6-(CH$_2$)$_2$-Imd HCl |
| 1-2096 | H | — | OCH$_3$ | 0 | 6-(CH$_2$)$_3$-Imd |
| 1-2097 | H | — | OCH$_3$ | 0 | 6-(CH$_2$)$_3$-Imd HCl |
| 1-2098 | H | — | OCH$_3$ | 0 | 6-(CH$_2$)$_4$-Imd |
| 1-2099 | H | — | OCH$_3$ | 0 | 6-(CH$_2$)$_4$-Imd HCl |
| 1-2100 | H | — | OCH$_3$ | 0 | 6-(CH$_2$)$_5$-Imd |
| 1-2101 | H | — | OCH$_3$ | 0 | 6-(CH$_2$)$_5$-Imd HCl |
| 1-2102 | H | — | OCH$_3$ | 0 | 6-(CH$_2$)$_6$-Imd |
| 1-2103 | H | — | OCH$_3$ | 0 | 6-(CH$_2$)$_6$-Imd HCl |
| 1-2104 | H | — | OCH$_3$ | 0 | 6-(CH$_2$)$_7$-Imd |
| 1-2105 | H | — | OCH$_3$ | 0 | 6-(CH$_2$)$_7$-Imd HCl |
| 1-2106 | H | — | SCH$_3$ | 0 | 6-(CH$_2$)O(CH$_2$)$_2$-Imd |
| 1-2107 | H | — | SCH$_3$ | 0 | 5-(CH$_2$)O(CH$_2$)$_2$-Imd |
| 1-2108 | H | — | SCH$_3$ | 0 | 6-(CH$_2$)O(CH$_2$)$_2$-Imd |
| 1-2109 | H | — | SCH$_3$ | 0 | 6-(CH$_2$)O(CH$_2$)$_4$-Imd HCl |
| 1-2110 | H | — | SCH$_3$ | 0 | 5-(CH$_2$)O(CH$_2$)$_4$-Imd HCl |
| 1-2111 | H | — | SCH$_3$ | 0 | 6-(CH$_2$)O(CH$_2$)$_4$-Imd |
| 1-2112 | H | — | SCH$_3$ | 0 | 6-(CH$_2$)$_2$O(CH$_2$)$_2$-Imd HCl |
| 1-2113 | H | — | SCH$_3$ | 0 | 5-(CH$_2$)$_2$O(CH$_2$)$_2$-Imd HCl |
| 1-2114 | H | — | SCH$_3$ | 0 | 6-(CH$_2$)$_2$O(CH$_2$)$_2$-Imd |
| 1-2115 | H | — | SCH$_3$ | 0 | 6-(CH$_2$)$_2$O(CH$_2$)$_3$-Imd HCl |
| 1-2116 | H | — | SCH$_3$ | 0 | 5-(CH$_2$)$_2$O(CH$_2$)$_3$-Imd HCl |
| 1-2117 | H | — | SCH$_3$ | 0 | 6-(CH$_2$)$_2$O(CH$_2$)$_3$-Imd |
| 1-2118 | H | — | SCH$_3$ | 0 | 6-(CH$_2$)$_2$O(CH$_2$)$_4$-Imd HCl |
| 1-2119 | H | — | SCH$_3$ | 0 | 5-(CH$_2$)$_2$O(CH$_2$)$_4$-Imd HCl |
| 1-2120 | H | — | SCH$_3$ | 0 | 6-(CH$_2$)$_2$O(CH$_2$)$_4$-Imd |
| 1-2121 | H | — | SCH$_3$ | 0 | 6-(CH$_2$)$_2$O(CH$_2$)$_2$-Imd HCl |
| 1-2122 | H | — | SCH$_3$ | 0 | 6-(CH$_2$)$_2$O(CH$_2$)$_2$-Imd |
| 1-2123 | H | — | SCH$_3$ | 0 | 6-(CH$_2$)$_2$O(CH$_2$)$_3$-Imd HCl |
| 1-2124 | H | — | SCH$_3$ | 0 | 6-(CH$_2$)$_2$O(CH$_2$)$_3$-Imd |
| 1-2125 | H | — | SCH$_3$ | 0 | 6-(CH$_2$)$_2$O(CH$_2$)$_4$-Imd HCl |
| 1-2126 | H | — | SCH$_3$ | 0 | 6-(CH$_2$)$_2$O(CH$_2$)$_4$-Imd |
| 1-2127 | H | — | SCH$_3$ | 0 | 6-(CH$_2$)-Imd HCl |
| 1-2128 | H | — | SCH$_3$ | 0 | 6-(CH$_2$)-Imd |
| 1-2129 | H | — | SCH$_3$ | 0 | 6-(CH$_2$)$_2$-Imd HCl |
| 1-2130 | H | — | SCH$_3$ | 0 | 6-(CH$_2$)$_2$-Imd |
| 1-2131 | H | — | SCH$_3$ | 0 | 6-(CH$_2$)$_3$-Imd HCl |

TABLE 1-continued

| Cpd. No. | $R^a$ | $R^2$ | $R^3$ | n | $R^4$ |
|---|---|---|---|---|---|
| 1-2132 | H | — | $SCH_3$ | 0 | 6-$(CH_2)_3$-Imd |
| 1-2133 | H | — | $SCH_3$ | 0 | 6-$(CH_2)_4$-Imd HCl |
| 1-2134 | H | — | $SCH_3$ | 0 | 6-$(CH_2)_4$-Imd |
| 1-2135 | H | — | $SCH_3$ | 0 | 6-$(CH_2)_5$-Imd HCl |
| 1-2136 | H | — | $SCH_3$ | 0 | 6-$(CH_2)_5$-Imd |
| 1-2137 | H | — | $SCH_3$ | 0 | 6-$(CH_2)_6$-Imd HCl |
| 1-2138 | H | — | $SCH_3$ | 0 | 6-$(CH_2)_6$-Imd |
| 1-2139 | H | — | $SCH_3$ | 0 | 6-$(CH_2)_7$-Imd HCl |
| 1-2140 | H | — | $SCH_3$ | 0 | 6-$(CH_2)_7$-Imd |
| 1-2141 | H | — | O-iPr | 0 | 5-$(CH_2)O(CH_2)_2$-Imd HCl |
| 1-2142 | H | — | O-iPr | 0 | 6-$(CH_2)O(CH_2)_2$-Imd HCl |
| 1-2143 | H | — | O-iPr | 0 | 6-$(CH_2)O(CH_2)_2$-Imd |
| 1-2144 | H | — | O-iPr | 0 | 5-$(CH_2)O(CH_2)_3$-Imd HCl |
| 1-2145 | H | — | O-iPr | 0 | 6-$(CH_2)O(CH_2)_3$-Imd HCl |
| 1-2146 | H | — | O-iPr | 0 | 6-$(CH_2)O(CH_2)_3$-Imd |
| 1-2147 | H | — | O-iPr | 0 | 5-$(CH_2)O(CH_2)_4$-Imd HCl |
| 1-2148 | H | — | O-iPr | 0 | 6-$(CH_2)O(CH_2)_4$-Imd HCl |
| 1-2149 | H | — | O-iPr | 0 | 6-$(CH_2)O(CH_2)_4$-Imd |
| 1-2150 | H | — | O-iPr | 0 | 6-$(CH_2)_2O(CH_2)_2$-Imd HCl |
| 1-2151 | H | — | O-iPr | 0 | 6-$(CH_2)_2O(CH_2)_2$-Imd |
| 1-2152 | H | — | O-iPr | 0 | 6-$(CH_2)_2O(CH_2)_3$-Imd HCl |
| 1-2153 | H | — | O-iPr | 0 | 6-$(CH_2)_2O(CH_2)_3$-Imd |
| 1-2154 | H | — | O-iPr | 0 | 6-$(CH_2)_2O(CH_2)_4$-Imd HCl |
| 1-2155 | H | — | O-iPr | 0 | 6-$(CH_2)_2O(CH_2)_4$-Imd |
| 1-2156 | H | — | O-iPr | 0 | 6-$(CH_2)_3O(CH_2)_2$-Imd HCl |
| 1-2157 | H | — | O-iPr | 0 | 6-$(CH_2)_3O(CH_2)_2$-Imd |
| 1-2158 | H | — | O-iPr | 0 | 6-$(CH_2)_3O(CH_2)_3$-Imd HCl |
| 1-2159 | H | — | O-iPr | 0 | 6-$(CH_2)_3O(CH_2)_3$-Imd |
| 1-2160 | H | — | O-iPr | 0 | 6-$(CH_2)_3O(CH_2)_4$-Imd HCl |
| 1-2161 | H | — | O-iPr | 0 | 6-$(CH_2)_3O(CH_2)_4$-Imd |
| 1-2162 | H | — | O-iPr | 0 | 6-$(CH_2)$-Imd HCl |
| 1-2163 | H | — | O-iPr | 0 | 6-$(CH_2)$-Imd |
| 1-2164 | H | — | O-iPr | 0 | 6-$(CH_2)_2$-Imd HCl |
| 1-2165 | H | — | O-iPr | 0 | 6-$(CH_2)_2$-Imd |
| 1-2166 | H | — | O-iPr | 0 | 6-$(CH_2)_3$-Imd HCl |
| 1-2167 | H | — | O-iPr | 0 | 6-$(CH_2)_3$-Imd |
| 1-2168 | H | — | O-iPr | 0 | 6-$(CH_2)_4$-Imd HCl |
| 1-2169 | H | — | O-iPr | 0 | 6-$(CH_2)_4$-Imd |
| 1-2170 | H | — | O-iPr | 0 | 6-$(CH_2)_5$-Imd |
| 1-2171 | H | — | O-iPr | 0 | 6-$(CH_2)_5$-Imd |
| 1-2172 | H | — | O-iPr | 0 | 6-$(CH_2)_6$-Imd HCl |
| 1-2173 | H | — | O-iPr | 0 | 6-$(CH_2)_6$-Imd |
| 1-2174 | H | — | O-iPr | 0 | 6-$(CH_2)_7$-Imd HCl |
| 1-2175 | H | — | O-iPr | 0 | 6-$(CH_2)_7$-Imd |
| 1-2176 | H | — | tBu | 0 | 5-$(CH_2OH)O(CH_2)$-cHx |
| 1-2177 | H | — | tBu | 0 | 5-$CH(CH_2OH)O(CH_2)$-cHx |
| 1-2178 | H | — | tBu | 0 | 5-$CH(CH_2OH)(CH_2)O$-cHx |
| 1-2179 | H | — | tBu | 0 | 5-$CH(CH_2OH)(CH_2)O(CH_2)$-cHx |
| 1-2180 | H | — | tBu | 0 | 5-$CH(CH_2OH)(CH_2)_2O$-cHx |
| 1-2181 | H | — | tBu | 0 | 5-$CH(CH_2OH)(CH_2)_2O(CH_2)$-cHx |
| 1-2182 | H | — | tBu | 0 | 5-$(CH_2)CH(CH_2OH)O$-cHx |
| 1-2183 | H | — | tBu | 0 | 5-$(CH_2)CH(CH_2OH)O(CH_2)$-cHx |
| 1-2184 | H | — | tBu | 0 | 5-$(CH_2)CH(CH_2OH)(CH_2)O$-cHx |

TABLE 1-continued

| Cpd. No. | $R^a$ | $R^2$ | $R^3$ | n | $R^4$ |
|---|---|---|---|---|---|
| 1-2185 | H | — | tBu | 0 | 5-(CH$_2$)CH(CH$_2$OH)(CH$_2$)O(CH$_2$)-cHx |
| 1-2186 | H | — | tBu | 0 | 5-(CH$_2$)CH(CH$_2$OH)(CH$_2$)$_2$O-cHx |
| 1-2187 | H | — | tBu | 0 | 5-(CH$_2$)CH(CH$_2$OH)(CH$_2$)$_2$O(CH$_2$)-cHx |
| 1-2188 | H | — | tBu | 0 | 5-(CH$_2$)$_2$CH(CH$_2$OH)O-cHx |
| 1-2189 | H | — | tBu | 0 | 5-(CH$_2$)$_2$CH(CH$_2$OH)O(CH$_2$)-cHx |
| 1-2190 | H | — | tBu | 0 | 5-(CH$_2$)$_2$CH(CH$_2$OH)(CH$_2$)O-cHx |
| 1-2191 | H | — | tBu | 0 | 5-(CH$_2$)$_2$CH(CH$_2$OH)(CH$_2$)O(CH$_2$)-cHx |
| 1-2192 | H | — | tBu | 0 | 5-(CH$_2$)$_2$CH(CH$_2$OH)(CH$_2$)$_2$O-cHx |
| 1-2193 | H | — | tBu | 0 | 5-(CH$_2$)$_2$CH(CH$_2$OH)(CH$_2$)$_2$O(CH$_2$)-cHx |
| 1-2194 | H | — | tBu | 0 | 5-CH(CH$_2$OB$^{10}$O-cHx |
| 1-2195 | H | — | tBu | 0 | 5-CH(CH$_2$OB$^{10}$)O(CH$_2$)-cHx |
| 1-2196 | H | — | tBu | 0 | 5-CH(CH$_2$OB$^{10}$)(CH$_2$)O-cHx |
| 1-2197 | H | — | tBu | 0 | 5-CH(CH$_2$OB$^{10}$)(CH$_2$)O(CH$_2$)-cHx |
| 1-2198 | H | — | tBu | 0 | 5-CH(CH$_2$OB$^{10}$)(CH$_2$)$_2$O-cHx |
| 1-2199 | H | — | tBu | 0 | 5-CH(CH$_2$OB$^{10}$)(CH$_2$)$_2$O(CH$_2$)-cHx |
| 1-2200 | H | — | tBu | 0 | 5-(CH$_2$)CH(CH$_2$OB$^{10}$)O-cHx |
| 1-2201 | H | — | tBu | 0 | 5-(CH$_2$)CH(CH$_2$OB$^{10}$)O(CH$_2$)-cHx |
| 1-2202 | H | — | tBu | 0 | 5-(CH$_2$)CH(CH$_2$OB$^{10}$)(CH$_2$)O-cHx |
| 1-2203 | H | — | tBu | 0 | 5-(CH$_2$)CH(CH$_2$OB$^{10}$)(CH$_2$)O(CH$_2$)-cHx |
| 1-2204 | H | — | tBu | 0 | 5-(CH$_2$)CH(CH$_2$OB$^{10}$)(CH$_2$)$_2$O-cHx |
| 1-2205 | H | — | tBu | 0 | 5-(CH$_2$)CH(CH$_2$OB$^{10}$)(CH$_2$)$_2$O(CH$_2$)-cHx |
| 1-2206 | H | — | tBu | 0 | 5-(CH$_2$)$_2$CH(CH$_2$OB$^{10}$)O-cHx |
| 1-2207 | H | — | tBu | 0 | 5-(CH$_2$)$_2$CH(CH$_2$OB$^{10}$)O(CH$_2$)-cHx |
| 1-2208 | H | — | tBu | 0 | 5-(CH$_2$)$_2$CH(CH$_2$OB$^{10}$)(CH$_2$)O-cHx |
| 1-2209 | H | — | tBu | 0 | 5-(CH$_2$)$_2$CH(CH$_2$OB$^{10}$)(CH$_2$)O(CH$_2$)-cHx |
| 1-2210 | H | — | tBu | 0 | 5-(CH$_2$)$_2$CH(CH$_2$OB$^{10}$)(CH$_2$)$_2$O-cHx |
| 1-2211 | H | — | tBu | 0 | 5-(CH$_2$)$_2$CH(CH$_2$OB$^{10}$)(CH$_2$)$_2$O(CH$_2$)-cHx |
| 1-2212 | H | — | tBu | 0 | 5-CH(CH$_2$OB$^4$)O-cHx |
| 1-2213 | H | — | tBu | 0 | 5-CH(CH$_2$OB$^4$)O(CH$_2$)-cHx |
| 1-2214 | H | — | tBu | 0 | 5-CH(CH$_2$OB$^4$)(CH$_2$)O-cHx |
| 1-2215 | H | — | tBu | 0 | 5-CH(CH$_2$OB$^4$)(CH$_2$)O(CH$_2$)-cHx |
| 1-2216 | H | — | tBu | 0 | 5-CH(CH$_2$OB$^4$)(CH$_2$)$_2$O-cHx |
| 1-2217 | H | — | tBu | 0 | 5-CH(CH$_2$OB$^4$)(CH$_2$)$_2$O(CH$_2$)-cHx |
| 1-2218 | H | — | tBu | 0 | 5-(CH$_2$)CH(CH$_2$OB$^4$)O-cHx |
| 1-2219 | H | — | tBu | 0 | 5-(CH$_2$)CH(CH$_2$OB$^4$)O(CH$_2$)-cHx |
| 1-2220 | H | — | tBu | 0 | 5-(CH$_2$)CH(CH$_2$OB$^4$)(CH$_2$)O-cHx |
| 1-2221 | H | — | tBu | 0 | 5-(CH$_2$)CH(CH$_2$OB$^4$)(CH$_2$)O(CH$_2$)-cHx |
| 1-2222 | H | — | tBu | 0 | 5-(CH$_2$)CH(CH$_2$OB$^4$)(CH$_2$)$_2$O-cHx |
| 1-2223 | H | — | tBu | 0 | 5-(CH$_2$)CH(CH$_2$OB$^4$)(CH$_2$)$_2$O(CH$_2$)-cHx |
| 1-2224 | H | — | tBu | 0 | 5-(CH$_2$)$_2$CH(CH$_2$OB$^4$)O-cHx |
| 1-2225 | H | — | tBu | 0 | 5-(CH$_2$)$_2$CH(CH$_2$OB$^4$)O(CH$_2$)-cHx |
| 1-2226 | H | — | tBu | 0 | 5-(CH$_2$)$_2$CH(CH$_2$OB$^4$)(CH$_2$)O-cHx |
| 1-2227 | H | — | tBu | 0 | 5-(CH$_2$)$_2$CH(CH$_2$OB$^4$)(CH$_2$)O(CH$_2$)-cHx |
| 1-2228 | H | — | tBu | 0 | 5-(CH$_2$)$_2$CH(CH$_2$OB$^4$)(CH$_2$)$_2$O-cHx |
| 1-2229 | H | — | tBu | 0 | 5-(CH$_2$)$_2$CH(CH$_2$OB$^4$)(CH$_2$)$_2$O(CH$_2$)-cHx |
| 1-2230 | H | — | tBu | 0 | 5-CH(CH$_2$OE$^5$)O-cHx |
| 1-2231 | H | — | tBu | 0 | 5-CH(CH$_2$OE$^5$)O(CH$_2$)-cHx |
| 1-2232 | H | — | tBu | 0 | 5-CH(CH$_2$OE$^5$)(CH$_2$)O-cHx |
| 1-2233 | H | — | tBu | 0 | 5-CH(CH$_2$OE$^5$)(CH$_2$)O(CH$_2$)-cHx |
| 1-2234 | H | — | tBu | 0 | 5-CH(CH$_2$OE$^5$)(CH$_2$)$_2$O-cHx |
| 1-2235 | H | — | tBu | 0 | 5-CH(CH$_2$OE$^5$)(CH$_2$)$_2$O(CH$_2$)-cHx |
| 1-2236 | H | — | tBu | 0 | 5-(CH$_2$)CH(CH$_2$OE$^5$)O-cHx |
| 1-2237 | H | — | tBu | 0 | 5-(CH$_2$)CH(CH$_2$OE$^5$)O(CH$_2$)-cHx |
| 1-2238 | H | — | tBu | 0 | 5-(CH$_2$)CH(CH$_2$OE$^5$)(CH$_2$)O-cHx |
| 1-2239 | H | — | tBu | 0 | 5-(CH$_2$)CH(CH$_2$OE$^5$)(CH$_2$)O(CH$_2$)-cHx |
| 1-2240 | H | — | tBu | 0 | 5-(CH$_2$)CH(CH$_2$OE$^5$)(CH$_2$)$_2$O-cHx |
| 1-2241 | H | — | tBu | 0 | 5-(CH$_2$)CH(CH$_2$OE$^5$)(CH$_2$)$_2$O(CH$_2$)-cHx |
| 1-2242 | H | — | tBu | 0 | 5-(CH$_2$)$_2$CH(CH$_2$OE$^5$)O-cHx |
| 1-2243 | H | — | tBu | 0 | 5-(CH$_2$)$_2$CH(CH$_2$OE$^5$)O(CH$_2$)-cHx |
| 1-2244 | H | — | tBu | 0 | 5-(CH$_2$)$_2$CH(CH$_2$OE$^5$)(CH$_2$)O-cHx |
| 1-2245 | H | — | tBu | 0 | 5-(CH$_2$)$_2$CH(CH$_2$OE$^5$)(CH$_2$)O(CH$_2$)-cHx |
| 1-2246 | H | — | tBu | 0 | 5-(CH$_2$)$_2$CH(CH$_2$OE$^5$)(CH$_2$)$_2$O-cHx |
| 1-2247 | H | — | tBu | 0 | 5-(CH$_2$)$_2$CH(CH$_2$OE$^5$)(CH$_2$)$_2$O(CH$_2$)-cHx |
| 1-2248 | H | — | tBu | 0 | 5-CH(CH$_2$OB$^2$)O-cHx |
| 1-2249 | H | — | tBu | 0 | 5-CH(CH$_2$OB$^2$)O(CH$_2$)-cHx |
| 1-2250 | H | — | tBu | 0 | 5-CH(CH$_2$OB$^2$)(CH$_2$)O-cHx |
| 1-2251 | H | — | tBu | 0 | 5-CH(CH$_2$OB$^2$)(CH$_2$)O(CH$_2$)-cHx |
| 1-2252 | H | — | tBu | 0 | 5-CH(CH$_2$OB$^4$)(CH$_2$)$_2$O-cHx |
| 1-2253 | H | — | tBu | 0 | 5-CH(CH$_2$OB$^4$)(CH$_2$)$_2$O(CH$_2$)-cHx |
| 1-2254 | H | — | tBu | 0 | 5-CH(CH$_2$OB$^2$)O-cHx |
| 1-2255 | H | — | tBu | 0 | 5-(CH$_2$)CH(CH$_2$OB$^2$)O(CH$_2$)-cHx |
| 1-2256 | H | — | tBu | 0 | 5-(CH$_2$)CH(CH$_2$OB$^2$)(CH$_2$)O-cHx |
| 1-2257 | H | — | tBu | 0 | 5-(CH$_2$)CH(CH$_2$OB$^2$)(CH$_2$)O(CH$_2$)-cHx |
| 1-2258 | H | — | tBu | 0 | 5-(CH$_2$)CH(CH$_2$OB$^2$)(CH$_2$)$_2$O-cHx |
| 1-2259 | H | — | tBu | 0 | 5-(CH$_2$)CH(CH$_2$OB$^2$)(CH$_2$)$_2$O(CH$_2$)-cHx |
| 1-2260 | H | — | tBu | 0 | 5-(CH$_2$)$_2$CH(CH$_2$OB$^2$)O-cHx |

TABLE 1-continued

| Cpd. No. | $R^a$ | $R^2$ | $R^3$ | n | $R^4$ |
|---|---|---|---|---|---|
| 1-2261 | H | — | tBu | 0 | 5-$(CH_2)_2CH(CH_2OB^2)O(CH_2)$-cHx |
| 1-2262 | H | — | tBu | 0 | 5-$(CH_2)_2CH(CH_2OB^2)(CH_2)O$-cHx |
| 1-2263 | H | — | tBu | 0 | 5-$(CH_2)_2CH(CH_2OB^2)(CH_2)O(CH_2)$-cHx |
| 1-2264 | H | — | tBu | 0 | 5-$(CH_2)_2CH(CH_2OB^2)(CH_2)_2O$-cHx |
| 1-2265 | H | — | tBu | 0 | 5-$(CH_2)_2CH(CH_2OB^2)(CH_2)_2O(CH_2)$-cHx |
| 1-2266 | H | — | tBu | 0 | 5-$CH(CH_2OB^{10})O$-cHx Na salt |
| 1-2267 | H | — | tBu | 0 | 5-$CH(CH_2OB^{10})O(CH_2)$-cHx Na salt |
| 1-2268 | H | — | tBu | 0 | 5-$CH(CH_2OB^{10})(CH_2)O$-cHx Na salt |
| 1-2269 | H | — | tBu | 0 | 5-$CH(CH_2OB^{10})(CH_2)O(CH_2)$-cHx Na salt |
| 1-2270 | H | — | tBu | 0 | 5-$CH(CH_2OB^{10})(CH_2)_2O$-cHx Na salt |
| 1-2271 | H | — | tBu | 0 | 5-$CH(CH_2OB^{10})(CH_2)_2O(CH_2)$-cHx Na salt |
| 1-2272 | H | — | tBu | 0 | 5-$(CH_2)CH(CH_2OB^{10})O$-cHx Na salt |
| 1-2273 | H | — | tBu | 0 | 5-$(CH_2)CH(CH_2OB^{10})O(CH_2)$-cHx Na salt |
| 1-2274 | H | — | tBu | 0 | 5-$(CH_2)CH(CH_2OB^{10})(CH_2)O$-cHx Na salt |
| 1-2275 | H | — | tBu | 0 | 5-$(CH_2)CH(CH_2OB^{10})(CH_2)O(CH_2)$-cHx Na salt |
| 1-2276 | H | — | tBu | 0 | 5-$(CH_2)CH(CH_2OB^{10})(CH_2)_2O$-cHx Na salt |
| 1-2277 | H | — | tBu | 0 | 5-$(CH_2)CH(CH_2OB^{10})(CH_2)_2O(CH_2)$-cHx Na salt |
| 1-2278 | H | — | tBu | 0 | 5-$(CH_2)_2CH(CH_2OB^{10})O$-cHx Na salt |
| 1-2279 | H | — | tBu | 0 | 5-$(CH_2)_2CH(CH_2OB^{10})O(CH_2)$-cHx Na salt |
| 1-2280 | H | — | tBu | 0 | 5-$(CH_2)_2CH(CH_2OB^{10})(CH_2)O$-cHx Na salt |
| 1-2281 | H | — | tBu | 0 | 5-$(CH_2)_2CH(CH_2OB^{10})(CH_2)O(CH_2)$-cHx Na salt |
| 1-2282 | H | — | tBu | 0 | 5-$(CH_2)_2CH(CH_2OB^{10})(CH_2)_2O$-cHx Na salt |
| 1-2283 | H | — | tBu | 0 | 5-$(CH_2)_2CH(CH_2OB^{10})(CH_2)_2O(CH_2)$-cHx Na salt |
| 1-2284 | H | — | tBu | 0 | 5-$CH(CH_2OB^4)O$-cHx Na salt |
| 1-2285 | H | — | tBu | 0 | 5-$CH(CH_2OB^4)O(CH_2)$-cHx Na salt |
| 1-2286 | H | — | tBu | 0 | 5-$CH(CH_2OB^4)(CH_2)O$-cHx Na salt |
| 1-2287 | H | — | tBu | 0 | 5-$CH(CH_2OB^4)(CH_2)O(CH_2)$-cHx |
| 1-2288 | H | — | tBu | 0 | 5-$CH(CH_2OB^4)(CH_2)_2O$-cHx |
| 1-2289 | H | — | tBu | 0 | 5-$CH(CH_2OB^4)(CH_2)_2O(CH_2)$-cHx |
| 1-2290 | H | — | tBu | 0 | 5-$(CH_2)CH(CH_2OB^4)O$-cHx |
| 1-2291 | H | — | tBu | 0 | 5-$(CH_2)CH(CH_2OB^4)O(CH_2)$-cHx |
| 1-2292 | H | — | tBu | 0 | 5-$(CH_2)CH(CH_2OB^4)(CH_2)O$-cHx |
| 1-2293 | H | — | tBu | 0 | 5-$(CH_2)CH(CH_2OB^4)(CH_2)O(CH_2)$-cHx |
| 1-2294 | H | — | tBu | 0 | 5-$(CH_2)CH(CH_2OB^4)(CH_2)_2O$-cHx |
| 1-2295 | H | — | tBu | 0 | 5-$(CH_2)CH(CH_2OB^4)(CH_2)_2O(CH_2)$-cHx |
| 1-2296 | H | — | tBu | 0 | 5-$(CH_2)_2CH(CH_2OB^4)O$-cHx |
| 1-2297 | H | — | tBu | 0 | 5-$(CH_2)_2CH(CH_2OB^4)O(CH_2)$-cHx |
| 1-2298 | H | — | tBu | 0 | 5-$(CH_2)_2CH(CH_2OB^4)(CH_2)O$-cHx |
| 1-2299 | H | — | tBu | 0 | 5-$(CH_2)_2CH(CH_2OB^4)(CH_2)O(CH_2)$-cHx |
| 1-2300 | H | — | tBu | 0 | 5-$(CH_2)_2CH(CH_2OB^4)(CH_2)_2O$-cHx |
| 1-2301 | H | — | tBu | 0 | 5-$(CH_2)_2CH(CH_2OB^4)(CH_2)_2O(CH_2)$-cHx |
| 1-2302 | H | — | tBu | 0 | 5-$CH(CH_2OE^5)O$-cHx |
| 1-2303 | H | — | tBu | 0 | 5-$CH(CH_2OE^5)O(CH_2)$-cHx |
| 1-2304 | H | — | tBu | 0 | 5-$CH(CH_2OE^5)(CH_2)O$-cHx |
| 1-2305 | H | — | tBu | 0 | 5-$CH(CH_2OE^5)(CH_2)O(CH_2)$-cHx |
| 1-2306 | H | — | tBu | 0 | 5-$CH(CH_2OE^5)(CH_2)_2O$-cHx |
| 1-2307 | H | — | tBu | 0 | 5-$CH(CH_2OE^5)(CH_2)_2O(CH_2)$-cHx |
| 1-2308 | H | — | tBu | 0 | 5-$(CH_2)CH(CH_2OE^5)O$-cHx |
| 1-2309 | H | — | tBu | 0 | 5-$(CH_2)CH(CH_2OE^5)O(CH_2)$-cHx |
| 1-2310 | H | — | tBu | 0 | 5-$(CH_2)CH(CH_2OE^5)(CH_2)O$-cHx |
| 1-2311 | H | — | tBu | 0 | 5-$(CH_2)CH(CH_2OE^5)(CH_2)O(CH_2)$-cHx |
| 1-2312 | H | — | tBu | 0 | 5-$(CH_2)CH(CH_2OEhu\ 5)(CH_2)_2O$-cHx |
| 1-2313 | H | — | tBu | 0 | 5-$(CH_2)CH(CH_2OE^5)(CH_2)_2O(CH_2)$-cHx |
| 1-2314 | H | — | tBu | 0 | 5-$(CH_2)_2CH(CH_2OE^5)O$-cHx |
| 1-2315 | H | — | tBu | 0 | 5-$(CH_2)_2CH(CH_2OE^5)O(CH_2)$-cHx |

TABLE 1-continued

| Cpd. No. | R$^a$ | R$^2$ | R$^3$ | n | R$^4$ |
|---|---|---|---|---|---|
| 1-2316 | H | — | tBu | 0 | 5-(CH$_2$)$_2$CH(CH$_2$OE$^5$)(CH$_2$)O-cHx |
| 1-2317 | H | — | tBu | 0 | 5-(CH$_2$)$_2$CH(CH$_2$OE$^5$)(CH$_2$)O(CH$_2$)-cHx |
| 1-2318 | H | — | tBu | 0 | 5-(CH$_2$)$_2$CH(CH$_2$OE$^5$)(CH$_2$)$_2$O-cHx |
| 1-2319 | H | — | tBu | 0 | 5-(CH$_2$)$_2$CH(CH$_2$OE$^5$)(CH$_2$)$_2$O(CH$_2$)-cHx |
| 1-2320 | H | — | tBu | 0 | 5-CH(CH$_2$OB$^2$)O-cHx |
| 1-2321 | H | — | tBu | 0 | 5-CH(CH$_2$OB$^2$)O(CH$_2$)-cHx |
| 1-2322 | H | — | tBu | 0 | 5-CH(CH$_2$OB$^2$)(CH$_2$)O-cHx |
| 1-2323 | H | — | tBu | 0 | 5-CH(CH$_2$OB$^2$)(CH$_2$)O(CH$_2$)-cHx |
| 1-2324 | H | — | tBu | 0 | 5-CH(CH$_2$OB$^2$)(CH$_2$)$_2$O-cHx |
| 1-2325 | H | — | tBu | 0 | 5-CH(CH$_2$OB$^2$)(CH$_2$)$_2$O(CH$_2$)-cHx |
| 1-2326 | H | — | tBu | 0 | 5-(CH$_2$)CH(CH$_2$OB$^2$)O-cHx |
| 1-2327 | H | — | tBu | 0 | 5-(CH$_2$)CH(CH$_2$OB$^2$)O(CH$_2$)-cHx |
| 1-2328 | H | — | tBu | 0 | 5-(CH$_2$)CH(CH$_2$OB$^2$)(CH$_2$)O-cHx |
| 1-2329 | H | — | tBu | 0 | 5-(CH$_2$)CH(CH$_2$OB$^2$)(CH$_2$)O(CH$_2$)-cHx |
| 1-2330 | H | — | tBu | 0 | 5-(CH$_2$)CH(CH$_2$OB$^2$)(CH$_2$)$_2$O-cHx |
| 1-2331 | H | — | tBu | 0 | 5-(CH$_2$)CH(CH$_2$OB$^2$)(CH$_2$)$_2$O(CH$_2$)-cHx |
| 1-2332 | H | — | tBu | 0 | 5-(CH$_2$)$_2$CH(CH$_2$OB$^2$)O-cHx |
| 1-2333 | H | — | tBu | 0 | 5-(CH$_2$)$_2$CH(CH$_2$OB$^2$)O(CH$_2$)-cHx |
| 1-2334 | H | — | tBu | 0 | 5-(CH$_2$)$_2$CH(CH$_2$OB$^2$)(CH$_2$)O-cHx |
| 1-2335 | H | — | tBu | 0 | 5-(CH$_2$)$_2$CH(CH$_2$OB$^2$)(CH$_2$)O(CH$_2$)-cHx |
| 1-2336 | H | — | tBu | 0 | 5-(CH$_2$)$_2$CH(CH$_2$OB$^2$)(CH$_2$)$_2$O-cHx |
| 1-2337 | H | — | tBu | 0 | 5-(CH$_2$)$_2$CH(CH$_2$OB$^2$)(CH$_2$)$_2$O(CH$_2$)-cHx |
| 1-2338 | H | — | tBu | 0 | 5-(CH$_2$)$_2$CH(CH$_2$OB$^2$)(CH$_2$)$_3$O(CH$_2$)-cHx |
| 1-2339 | H | — | tBu | 0 | 5-CH(CH$_2$OB$^2$)-cHx |
| 1-2340 | H | — | tBu | 0 | 5-CH(CH$_2$OB$^2$)(CH$_2$)-cHx |
| 1-2341 | H | — | tBu | 0 | 5-CH(CH$_2$OB$^2$)(CH$_2$)$_2$-cHx |
| 1-2342 | H | — | tBu | 0 | 5-(CH$_2$)CH(CH$_2$OB$^2$)-cHx |
| 1-2343 | H | — | tBu | 0 | 5-(CH$_2$)CH(CH$_2$OB$^2$)(CH$_2$)-cHx |
| 1-2344 | H | — | tBu | 0 | 5-(CH$_2$)CH(CH$_2$OB$^2$)(CH$_2$)$_2$-cHx |
| 1-2345 | H | — | tBu | 0 | 5-(CH$_2$)CH(CH$_2$OB$^2$)(CH$_2$)$_3$-cHx |
| 1-2346 | H | — | tBu | 0 | 5-(CH$_2$)CH(CH$_2$OB$^2$)(CH$_2$)$_4$-cHx |
| 1-2347 | H | — | tBu | 0 | 5-(CH$_2$)CH(CH$_2$OB$^2$)(CH$_2$)$_5$-cHx |
| 1-2348 | H | — | tBu | 0 | 5-(CH$_2$)$_2$CH(CH$_2$OB$^2$)-cHx |
| 1-2349 | H | — | tBu | 0 | 5-(CH$_2$)$_2$CH(CH$_2$OB$^2$)(CH$_2$)-cHx |
| 1-2350 | H | — | tBu | 0 | 5-(CH$_2$)$_2$CH(CH$_2$OB$^2$)(CH$_2$)$_2$-cHx |
| 1-2351 | H | — | tBu | 0 | 5-CH(CH$_2$OB$^2$)-cHx |
| 1-2352 | H | — | tBu | 0 | 5-CH(CH$_2$OB$^2$)(CH$_2$)-cHx |
| 1-2353 | H | — | tBu | 0 | 5-CH(CH$_2$OB$^2$)(CH$_2$)$_2$-cHx |
| 1-2354 | H | — | tBu | 0 | 5-(CH$_2$)CH(CH$_2$OB$^2$)-cHx |
| 1-2355 | H | — | tBu | 0 | 5-(CH$_2$)CH(CH$_2$OB$^2$)(CH$_2$)-cHx |
| 1-2356 | H | — | tBu | 0 | 5-(CH$_2$)CH(CH$_2$OB$^4$)(CH$_2$)-cHx |
| 1-2357 | H | — | tBu | 0 | 5-(CH$_2$)CH(CH$_2$OB$^{10}$)(CH$_2$)-cHx |
| 1-2358 | H | — | tBu | 0 | 5-(CH$_2$)CH(CH$_2$OE$^5$)(CH$_2$)-cHx |
| 1-2359 | H | — | tBu | 0 | 5-(CH$_2$)CH(CH$_2$OB$^2$)(CH$_2$)$_2$-cHx |
| 1-2360 | H | — | tBu | 0 | 5-(CH$_2$)CH(CH$_2$OB$^4$)(CH$_2$)$_2$-cHx |
| 1-2361 | H | — | tBu | 0 | 5-(CH$_2$)CH(CH$_2$OB$^{10}$)(CH$_2$)$_2$-cHx |
| 1-2362 | H | — | tBu | 0 | 5-(CH$_2$)CH(CH$_2$OE$^5$)(CH$_2$)$_2$-cHx |
| 1-2363 | H | — | tBu | 0 | 5-(CH$_2$)CH(CH$_2$OB$^2$)(CH$_2$)$_3$-cHx |
| 1-2364 | H | — | tBu | 0 | 5-(CH$_2$)CH(CH$_2$OB$^2$)(CH$_2$)$_4$-cHx |
| 1-2365 | H | — | tBu | 0 | 5-(CH$_2$)CH(CH$_2$OB$^2$)(CH$_2$)$_5$-cHx |
| 1-2366 | H | — | tBu | 0 | 5-(CH$_2$)$_2$CH(CH$_2$OB$^2$)-cHx |
| 1-2367 | H | — | tBu | 0 | 5-(CH$_2$)$_2$CH(CH$_2$OB$^2$)(CH$_2$)-cHx |
| 1-2368 | H | — | tBu | 0 | 5-(CH$_2$)$_2$CH(CH$_2$OB$^2$)(CH$_2$)$_2$-cHx |
| 1-2369 | H | — | tBu | 0 | 5-CH(OH)(CH$_2$)O-cHx |
| 1-2370 | H | — | tBu | 0 | 5-CH(OH)(CH$_2$)O(CH$_2$)-cHx |
| 1-2371 | H | — | tBu | 0 | 5-CH(OH)(CH$_2$)O(CH$_2$)$_2$-cHx |
| 1-2372 | H | — | tBu | 0 | 5-CH(OH)(CH$_2$)$_2$O-cHx |
| 1-2373 | H | — | tBu | 0 | 5-CH(OH)(CH$_2$)$_2$O(CH$_2$)-cHx |
| 1-2374 | H | — | tBu | 0 | 5-CH(OH)(CH$_2$)$_2$O(CH$_2$)$_2$-cHx |
| 1-2375 | H | — | tBu | 0 | 5-CH(OH)(CH$_2$)$_3$O-cHx |
| 1-2376 | H | — | tBu | 0 | 5-CH(OH)(CH$_2$)$_3$O(CH$_2$)-cHx |
| 1-2377 | H | — | tBu | 0 | 5-CH(OH)(CH$_2$)$_3$O(CH$_2$)$_2$-cHx |
| 1-2378 | H | — | tBu | 0 | 5-(CH$_2$)CH(OH)(CH$_2$)O-cHx |
| 1-2379 | H | — | tBu | 0 | 5-(CH$_2$)CH(OH)(CH$_2$)O(CH$_2$)-cHx |
| 1-2380 | H | — | tBu | 0 | 5-(CH$_2$)CH(OH)(CH$_2$)O(CH$_2$)$_2$-cHx |
| 1-2381 | H | — | tBu | 0 | 5-(CH$_2$)CH(OH)(CH$_2$)$_2$O-cHx |
| 1-2382 | H | — | tBu | 0 | 5-(CH$_2$)CH(OH)(CH$_2$)$_2$O(CH$_2$)-cHx |
| 1-2383 | H | — | tBu | 0 | 5-(CH$_2$)CH(OH)(CH$_2$)$_2$O(CH$_2$)$_2$-cHx |
| 1-2384 | H | — | tBu | 0 | 5-(CH$_2$)CH(OH)(CH$_2$)$_3$O-cHx |
| 1-2385 | H | — | tBu | 0 | 5-(CH$_2$)CH(OH)(CH$_2$)$_3$O(CH$_2$)-cHx |
| 1-2386 | H | — | tBu | 0 | 5-(CH$_2$)CH(OH)(CH$_2$)$_3$O(CH$_2$)$_2$-cHx |
| 1-2387 | H | — | tBu | 0 | 5-(CH$_2$)$_2$CH(OH)(CH$_2$)O-cHx |
| 1-2388 | H | — | tBu | 0 | 5-(CH$_2$)$_2$CH(OH)(CH$_2$)O(CH$_2$)-cHx |
| 1-2389 | H | — | tBu | 0 | 5-(CH$_2$)$_2$CH(OH)(CH$_2$)O(CH$_2$)$_2$-cHx |
| 1-2390 | H | — | tBu | 0 | 5-(CH$_2$)$_2$CH(OH)(CH$_2$)$_2$O-cHx |
| 1-2391 | H | — | tBu | 0 | 5-(CH$_2$)$_2$CH(OH)(CH$_2$)$_2$O(CH$_2$)-cHx |

TABLE 1-continued

| Cpd. No. | $R^a$ | $R^2$ | $R^3$ | n | $R^4$ |
|---|---|---|---|---|---|
| 1-2392 | H | — | tBu | 0 | 5-$(CH_2)_2CH(OH)(CH_2)_2O(CH_2)_2$-cHx |
| 1-2393 | H | — | tBu | 0 | 5-$(CH_2)_2CH(OH)(CH_2)_3O$-cHx |
| 1-2394 | H | — | tBu | 0 | 5-$(CH_2)_2CH(OH)(CH_2)_3O(CH_2)$-cHx |
| 1-2395 | H | — | tBu | 0 | 5-$(CH_2)_2CH(OH)(CH_2)_3O(CH_2)_2$-cHx |
| 1-2396 | H | — | tBu | 0 | 5-$CH(OH)(CH_2)O$-cPn |
| 1-2397 | H | — | tBu | 0 | 5-$CH(OH)(CH_2)O(CH_2)$-cPn |
| 1-2398 | H | — | tBu | 0 | 5-$CH(OH)(CH_2)O(CH_2)_2$-cPn |
| 1-2399 | H | — | tBu | 0 | 5-$CH(OH)(CH_2)_2O$-cPn |
| 1-2400 | H | — | tBu | 0 | 5-$CH(OH)(CH_2)_2O(CH_2)$-cPn |
| 1-2401 | H | — | tBu | 0 | 5-$CH(OH)(CH_2)_2O(CH_2)_2$-cPn |
| 1-2402 | H | — | tBu | 0 | 5-$CH(OH)(CH_2)_3O$-cPn |
| 1-2403 | H | — | tBu | 0 | 5-$CH(OH)(CH_2)_3O(CH_2)$-cPn |
| 1-2404 | H | — | tBu | 0 | 5-$CH(OH)(CH_2)_3O(CH_2)_2$-cPn |
| 1-2405 | H | — | tBu | 0 | 5-$(CH_2)CH(OH)(CH_2)O$-cPn |
| 1-2406 | H | — | tBu | 0 | 5-$(CH_2)CH(OH)(CH_2)O(CH_2)$-cPn |
| 1-2407 | H | — | tBu | 0 | 5-$(CH_2)CH(OH)(CH_2)O(CH_2)_2$-cPn |
| 1-2408 | H | — | tBu | 0 | 5-$(CH_2)CH(OH)(CH_2)_2O$-cPn |
| 1-2409 | H | — | tBu | 0 | 5-$(CH_2)CH(OH)(CH_2)_2O(CH_2)$-cPn |
| 1-2410 | H | — | tBu | 0 | 5-$(CH_2)CH(OH)(CH_2)_2O(CH_2)_2$-cPn |
| 1-2411 | H | — | tBu | 0 | 5-$(CH_2)CH(OH)(CH_2)_3O$-cPn |
| 1-2412 | H | — | tBu | 0 | 5-$(CH_2)CH(OH)(CH_2)_3O(CH_2)$-cPn |
| 1-2413 | H | — | tBu | 0 | 5-$(CH_2)CH(OH)(CH_2)_3O(CH_2)_2$-cPn |
| 1-2414 | H | — | tBu | 0 | 5-$(CH_2)_2CH(OH)(CH_2)O$-cPn |
| 1-2415 | H | — | tBu | 0 | 5-$(CH_2)_2CH(OH)(CH_2)O(CH_2)$-cPn |
| 1-2416 | H | — | tBu | 0 | 5-$(CH_2)_2CH(OH)(CH_2)O(CH_2)_2$-cPn |
| 1-2417 | H | — | tBu | 0 | 5-$(CH_2)_2CH(OH)(CH_2)_2O$-cPn |
| 1-2418 | H | — | tBu | 0 | 5-$(CH_2)_2CH(OH)(CH_2)_2O(CH_2)$-cPn |
| 1-2419 | H | — | tBu | 0 | 5-$(CH_2)_2CH(OH)(CH_2)_2O(CH_2)_2$-cPn |
| 1-2420 | H | — | tBu | 0 | 5-$(CH_2)_2CH(OH)(CH_2)_3O$-cPn |
| 1-2421 | H | — | tBu | 0 | 5-$(CH_2)_2CH(OH)(CH_2)_3O(CH_2)$-cPn |
| 1-2422 | H | — | tBu | 0 | 5-$(CH_2)_2CH(OH)(CH_2)_3O(CH_2)_2$-cPn |
| 1-2423 | H | — | tBu | 0 | 5-$CH(OB^5)(CH_2)O$-cHx |
| 1-2424 | H | — | tBu | 0 | 5-$CH(OB^5)(CH_2)O(CH_2)$-cHx |
| 1-2425 | H | — | tBu | 0 | 5-$CH(OB^5)(CH_2)O(CH_2)_2$-cHx |
| 1-2426 | H | — | tBu | 0 | 5-$CH(OB^2)(CH_2)_2O$-cHx |
| 1-2427 | H | — | tBu | 0 | 5-$CH(OB^2)(CH_2)_2O(CH_2)$-cHx |
| 1-2428 | H | — | tBu | 0 | 5-$CH(OB^2)(CH_2)_2O(CH_2)_2$-cHx |
| 1-2429 | H | — | tBu | 0 | 5-$CH(OB^2)(CH_2)_3O$-cHx |
| 1-2430 | H | — | tBu | 0 | 5-$CH(OB^2)(CH_2)_3O(CH_2)$-cHx |
| 1-2431 | H | — | tBu | 0 | 5-$CH(OB^2)(CH_2)_3O(CH_2)_2$-cHx |
| 1-2432 | H | — | tBu | 0 | 5-$(CH_2)CH(OB^2)(CH_2)O$-cHx |
| 1-2433 | H | — | tBu | 0 | 5-$(CH_2)CH(OB^2)(CH_2)O(CH_2)$-cHx |
| 1-2434 | H | — | tBu | 0 | 5-$(CH_2)CH(OB^2)(CH_2)O(CH_2)_2$-cHx |
| 1-2435 | H | — | tBu | 0 | 5-$(CH_2)CH(OB^2)(CH_2)_2O$-cHx |
| 1-2436 | H | — | tBu | 0 | 5-$(CH_2)CH(OB^2)(CH_2)_2O(CH_2)$-cHx |
| 1-2437 | H | — | tBu | 0 | 5-$(CH_2)CH(OB^2)(CH_2)_2O(CH_2)_2$-cHx |
| 1-2438 | H | — | tBu | 0 | 5-$(CH_2)CH(OB^2)(CH_2)_3O$-cHx |
| 1-2439 | H | — | tBu | 0 | 5-$(CH_2)CH(OB^2)(CH_2)_3O(CH_2)$-cHx |
| 1-2440 | H | — | tBu | 0 | 5-$(CH_2)CH(OB^2)(CH_2)_3O(CH_2)_2$-cHx |
| 1-2441 | H | — | tBu | 0 | 5-$(CH_2)_2CH(OB^2)(CH_2)O$-cHx |
| 1-2442 | H | — | tBu | 0 | 5-$(CH_2)_2CH(OB^2)(CH_2)O(CH_2)$-cHx |
| 1-2443 | H | — | tBu | 0 | 5-$(CH_2)_2CH(OB^2)(CH_2)O(CH_2)_2$-cHx |
| 1-2444 | H | — | tBu | 0 | 5-$(CH_2)_2CH(OB^2)(CH_2)_2O$-cHx |
| 1-2445 | H | — | tBu | 0 | 5-$(CH_2)_2CH(OB^2)(CH_2)_2O(CH_2)$-cHx |
| 1-2446 | H | — | tBu | 0 | 5-$(CH_2)_2CH(OB^2)(CH_2)_2O(CH_2)_2$-cHx |
| 1-2447 | H | — | tBu | 0 | 5-$(CH_2)_2CH(OB^2)(CH_2)_3O$-cHx |
| 1-2448 | H | — | tBu | 0 | 5-$(CH_2)_2CH(OB^2)(CH_2)_3O(CH_2)$-cHx |
| 1-2449 | H | — | tBu | 0 | 5-$(CH_2)_2CH(OB^2)(CH_2)_3O(CH_2)_2$-cHx |
| 1-2450 | H | — | tBu | 0 | 5-$CH(OB^2)(CH_2)O$-cPn |
| 1-2451 | H | — | tBu | 0 | 5-$CH(OB^2)(CH_2)O(CH_2)$-cPn |
| 1-2452 | H | — | tBu | 0 | 5-$CH(OB^2)(CH_2)O(CH_2)_2$-cPn |
| 1-2453 | H | — | tBu | 0 | 5-$CH(OB^2)(CH_2)_2O$-cPn |
| 1-2454 | H | — | tBu | 0 | 5-$CH(OB^2)(CH_2)_2O(CH_2)$-cPn |
| 1-2455 | H | — | tBu | 0 | 5-$CH(OB^2)(CH_2)_2O(CH_2)_2$-cPn |
| 1-2456 | H | — | tBu | 0 | 5-$CH(OB^2)(CH_2)_3O$-cPn |
| 1-2457 | H | — | tBu | 0 | 5-$CH(OB^2)(CH_2)_3O(CH_2)$-cPn |
| 1-2458 | H | — | tBu | 0 | 5-$CH(OB^2)(CH_2)_3O(CH_2)_2$-cPn |
| 1-2459 | H | — | tBu | 0 | 5-$(CH_2)CH(OB^2)(CH_2)O$-cPn |
| 1-2460 | H | — | tBu | 0 | 5-$(CH_2)CH(OB^2)(CH_2)O(CH_2)$-cPn |
| 1-2461 | H | — | tBu | 0 | 5-$(CH_2)CH(OB^2)(CH_2)O(CH_2)_2$-cPn |
| 1-2462 | H | — | tBu | 0 | 5-$(CH_2)CH(OB^2)(CH_2)_2O$-cPn |
| 1-2463 | H | — | tBu | 0 | 5-$(CH_2)CH(OB^2)(CH_2)_2O(CH_2)$-cPn |
| 1-2464 | H | — | tBu | 0 | 5-$(CH_2)CH(OB^2)(CH_2)_2O(CH_2)_2$-cPn |
| 1-2465 | H | — | tBu | 0 | 5-$(CH_2)CH(OB^2)(CH_2)_3O$-cPn |
| 1-2466 | H | — | tBu | 0 | 5-$(CH_2)CH(OB^2)(CH_2)_3O(CH_2)$-cPn |
| 1-2467 | H | — | tBu | 0 | 5-$(CH_2)CH(OB^2)(CH_2)_3O(CH_2)_2$-cPn |

TABLE 1-continued

| Cpd. No. | $R^a$ | $R^2$ | $R^3$ | n | $R^4$ |
|---|---|---|---|---|---|
| 1-2468 | H | — | tBu | 0 | 5-$(CH_2)_2CH(OB^2)(CH_2)O$-cPn |
| 1-2469 | H | — | tBu | 0 | 5-$(CH_2)_2CH(OB^2)(CH_2)O(CH_2)$-cPn |
| 1-2470 | H | — | tBu | 0 | 5-$(CH_2)_2CH(OB^2)(CH_2)O(CH_2)_2$-cPn |
| 1-2471 | H | — | tBu | 0 | 5-$(CH_2)_2CH(OB^2)(CH_2)_2O$-cPn |
| 1-2472 | H | — | tBu | 0 | 5-$(CH_2)_2CH(OB^2)(CH_2)_2O(CH_2)$-cPn |
| 1-2473 | H | — | tBu | 0 | 5-$(CH_2)_2CH(OB^2)(CH_2)_2O(CH_2)_2$-cPn |
| 1-2474 | H | — | tBu | 0 | 5-$(CH_2)_2CH(OB^2)(CH_2)_3O$-cPn |
| 1-2475 | H | — | tBu | 0 | 5-$(CH_2)_2CH(OB^2)(CH_2)_3O(CH_2)$-cPn |
| 1-2476 | H | — | tBu | 0 | 5-$(CH_2)_2CH(OB^2)(CH_2)_3O(CH_2)_2$-cPn |
| 1-2477 | H | — | tBu | 0 | 5-$CH(OE^5)(CH_2)O$-cHx |
| 1-2478 | H | — | tBu | 0 | 5-$CH(OE^5)(CH_2)O(CH_2)$-cHx |
| 1-2479 | H | — | tBu | 0 | 5-$CH(OE^5)(CH_2)O(CH_2)_2$-cHx |
| 1-2480 | H | — | tBu | 0 | 5-$CH(OE^5)(CH_2)_2O$-cHx |
| 1-2481 | H | — | tBu | 0 | 5-$CH(OE^5)(CH_2)_2O(CH_2)$-cHx |
| 1-2482 | H | — | tBu | 0 | 5-$CH(OE^5)(CH_2)_2O(CH_2)_2$-cHx |
| 1-2483 | H | — | tBu | 0 | 5-$CH(OE^5)(CH_2)_3O$-cHx |
| 1-2484 | H | — | tBu | 0 | 5-$CH(OE^5)(CH_2)_3O(CH_2)$-cHx |
| 1-2485 | H | — | tBu | 0 | 5-$CH(OE^5)(CH_2)_3O(CH_2)_2$-cHx |
| 1-2486 | H | — | tBu | 0 | 5-$(CH_2)CH(OE^5)(CH_2)O$-cHx |
| 1-2487 | H | — | tBu | 0 | 5-$(CH_2)CH(OE^5)(CH_2)O(CH_2)$-cHx |
| 1-2488 | H | — | tBu | 0 | 5-$(CH_2)CH(OE^5)(CH_2)O(CH_2)_2$-cHx |
| 1-2489 | H | — | tBu | 0 | 5-$(CH_2)CH(OE^5)(CH_2)_2O$-cHx |
| 1-2490 | H | — | tBu | 0 | 5-$(CH_2)CH(OE^5)(CH_2)_2O(CH_2)$-cHx |
| 1-2491 | H | — | tBu | 0 | 5-$(CH_2)CH(OE^5)(CH_2)_2O(CH_2)_2$-cHx |
| 1-2492 | H | — | tBu | 0 | 5-$(CH_2)CH(OE^5)(CH_2)_3O$-cHx |
| 1-2493 | H | — | tBu | 0 | 5-$(CH_2)CH(OE^5)(CH_2)_3O(CH_2)$-cHx |
| 1-2494 | H | — | tBu | 0 | 5-$(CH_2)CH(OE^5)(CH_2)_3O(CH_2)_2$-cHx |
| 1-2495 | H | — | tBu | 0 | 5-$(CH_2)_2CH(OE^5)(CH_2)O$-cHx |
| 1-2496 | H | — | tBu | 0 | 5-$(CH_2)_2CH(OE^5)(CH_2)O(CH_2)$-cHx |
| 1-2497 | H | — | tBu | 0 | 5-$(CH_2)_2CH(OE^5)(CH_2)O(CH_2)_2$-cHx |
| 1-2498 | H | — | tBu | 0 | 5-$(CH_2)_2CH(OE^5)(CH_2)_2O$-cHx |
| 1-2499 | H | — | tBu | 0 | 5-$(CH_2)_2CH(OE^5)(CH_2)_2O(CH_2)$-cHx |
| 1-2500 | H | — | tBu | 0 | 5-$(CH_2)_2CH(OE^5)(CH_2)_2O(CH_2)_2$-cHx |
| 1-2501 | H | — | tBu | 0 | 5-$(CH_2)_2CH(OE^5)(CH_2)_3O$-cHx |
| 1-2502 | H | — | tBu | 0 | 5-$(CH_2)_2CH(OE^5)(CH_2)_3O(CH_2)$-cHx |
| 1-2503 | H | — | tBu | 0 | 5-$(CH_2)_2CH(OE^5)(CH_2)_3O(CH_2)_2$-cHx |
| 1-2504 | H | — | tBu | 0 | 5-$CH(OE^5)(CH_2)O$-cPn |
| 1-2505 | H | — | tBu | 0 | 5-$CH(OE^5)(CH_2)O(CH_2)$-cPn |
| 1-2506 | H | — | tBu | 0 | 5-$CH(OE^5)(CH_2)O(CH_2)_2$-cPn |
| 1-2507 | H | — | tBu | 0 | 5-$CH(OE^5)(CH_2)_2O$-cPn |
| 1-2508 | H | — | tBu | 0 | 5-$CH(OE^5)(CH_2)_2O(CH_2)$-cPn |
| 1-2509 | H | — | tBu | 0 | 5-$CH(OE^5)(CH_2)_2O(CH_2)_2$-cPn |
| 1-2510 | H | — | tBu | 0 | 5-$CH(OE^5)(CH_2)_3O$-cPn |
| 1-2511 | H | — | tBu | 0 | 5-$CH(OE^5)(CH_2)_3O(CH_2)$-cPn |
| 1-2512 | H | — | tBu | 0 | 5-$CH(OE^5)(CH_2)_3O(CH_2)_2$-cPn |
| 1-2513 | H | — | tBu | 0 | 5-$(CH_2)CH(OE^5)(CH_2)O$-cPn |
| 1-2514 | H | — | tBu | 0 | 5-$(CH_2)CH(OE^5)(CH_2)O(CH_2)$-cPn |
| 1-2515 | H | — | tBu | 0 | 5-$(CH_2)CH(OE^5)(CH_2)O(CH_2)_2$-cPn |
| 1-2516 | H | — | tBu | 0 | 5-$(CH_2)CH(OE^5)(CH_2)_2O$-cPn |
| 1-2517 | H | — | tBu | 0 | 5-$(CH_2)CH(OE^5)(CH_2)_2O(CH_2)$-cPn |
| 1-2518 | H | — | tBu | 0 | 5-$(CH_2)CH(OE^5)(CH_2)_2O(CH_2)_2$-cPn |
| 1-2519 | H | — | tBu | 0 | 5-$(CH_2)CH(OE^5)(CH_2)_3O$-cPn |
| 1-2520 | H | — | tBu | 0 | 5-$(CH_2)CH(OE^5)(CH_2)_3O(CH_2)$-cPn |
| 1-2521 | H | — | tBu | 0 | 5-$(CH_2)CH(OE^5)(CH_2)_3O(CH_2)_2$-cPn |
| 1-2522 | H | — | tBu | 0 | 5-$(CH_2)_2CH(OE^5)(CH_2)O$-cPn |
| 1-2523 | H | — | tBu | 0 | 5-$(CH_2)_2CH(OE^5)(CH_2)O(CH_2)$-cPn |
| 1-2524 | H | — | tBu | 0 | 5-$(CH_2)_2CH(OE^5)(CH_2)O(CH_2)_2$-cPn |
| 1-2525 | H | — | tBu | 0 | 5-$(CH_2)_2CH(OE^5)(CH_2)_2O$-cPn |
| 1-2526 | H | — | tBu | 0 | 5-$(CH_2)_2CH(OE^5)(CH_2)_2O(CH_2)$-cPn |
| 1-2527 | H | — | tBu | 0 | 5-$(CH_2)_2CH(OE^5)(CH_2)_2O(CH_2)_2$-cPn |
| 1-2528 | H | — | tBu | 0 | 5-$(CH_2)_2CH(OE^5)(CH_2)_3O$-cPn |
| 1-2529 | H | — | tBu | 0 | 5-$(CH_2)_2CH(OE^5)(CH_2)_3O(CH_2)$-cPn |
| 1-2530 | H | — | tBu | 0 | 5-$(CH_2)_2CH(OE^5)(CH_2)_3O(CH_2)_2$-cPn |
| 1-2531 | H | — | tBu | 0 | 5-$CH(OB^{10})(CH_2)O$-cHx |
| 1-2532 | H | — | tBu | 0 | 5-$CH(OB^{10})(CH_2)O(CH_2)$-cHx |
| 1-2533 | H | — | tBu | 0 | 5-$CH(OB^{10})(CH_2)O(CH_2)_2$-cHx |
| 1-2534 | H | — | tBu | 0 | 5-$CH(OB^{10})(CH_2)_2O$-cHx |
| 1-2535 | H | — | tBu | 0 | 5-$CH(OB^{10})(CH_2)_2O(CH_2)$-cHx |
| 1-2536 | H | — | tBu | 0 | 5-$CH(OB^{10})(CH_2)_2O(CH_2)_2$-cHx |
| 1-2537 | H | — | tBu | 0 | 5-$CH(OB^{10})(CH_2)_3O$-cHx |
| 1-2538 | H | — | tBu | 0 | 5-$CH(OB^{10})(CH_2)_3O(CH_2)$-cHx |
| 1-2539 | H | — | tBu | 0 | 5-$CH(OB^{10})(CH_2)_3O(CH_2)_2$-cHx |
| 1-2540 | H | — | tBu | 0 | 5-$(CH_2)CH(OB^{10})(CH_2)O$-cHx |
| 1-2541 | H | — | tBu | 0 | 5-$(CH_2)CH(OB^{10})(CH_2)O(CH_2)$-cHx |
| 1-2542 | H | — | tBu | 0 | 5-$(CH_2)CH(OB^{10})(CH_2)O(CH_2)_2$-cHx |
| 1-2543 | H | — | tBu | 0 | 5-$(CH_2)CH(OB^{10})(CH_2)_2O$-cHx |

TABLE 1-continued

| Cpd. No. | $R^a$ | $R^2$ | $R^3$ | n | $R^4$ |
|---|---|---|---|---|---|
| 1-2544 | H | — | tBu | 0 | 5-$(CH_2)CH(OB^{10})(CH_2)_2O(CH_2)$-cHx |
| 1-2545 | H | — | tBu | 0 | 5-$(CH_2)CH(OB^{10})(CH_2)_2O(CH_2)_2$-cHx |
| 1-2546 | H | — | tBu | 0 | 5-$(CH_2)CH(OB^{10})(CH_2)_3O$-cHx |
| 1-2547 | H | — | tBu | 0 | 5-$(CH_2)CH(OB^{10})(CH_2)_3O(CH_2)$-cHx |
| 1-2548 | H | — | tBu | 0 | 5-$(CH_2)CH(OB^{10})(CH_2)_3O(CH_2)_2$-cHx |
| 1-2549 | H | — | tBu | 0 | 5-$(CH_2)_2CH(OB^{10})(CH_2)O$-cHx |
| 1-2550 | H | — | tBu | 0 | 5-$(CH_2)_2CH(OB^{10})(CH_2)O(CH_2)$-cHx |
| 1-2551 | H | — | tBu | 0 | 5-$(CH_2)_2CH(OB^{10})(CH_2)O(CH_2)_2$-cHx |
| 1-2552 | H | — | tBu | 0 | 5-$(CH_2)_2CH(OB^{10})(CH_2)_2O$-cHx |
| 1-2553 | H | — | tBu | 0 | 5-$(CH_2)_2CH(OB^{10})(CH_2)_2O(CH_2)$-cHx |
| 1-2554 | H | — | tBu | 0 | 5-$(CH_2)_2CH(OB^{10})(CH_2)_2O(CH_2)_2$-cHx |
| 1-2555 | H | — | tBu | 0 | 5-$(CH_2)_2CH(OB^{10})(CH_2)_3O$-cHx |
| 1-2556 | H | — | tBu | 0 | 5-$(CH_2)_2CH(OB^{10})(CH_2)_3O(CH_2)$-cHx |
| 1-2557 | H | — | tBu | 0 | 5-$(CH_2)_2CH(OB^{10})(CH_2)_3O(CH_2)_2$-cHx |
| 1-2558 | H | — | tBu | 0 | 5-$CH(OB^{10})(CH_2)O$-cPn |
| 1-2559 | H | — | tBu | 0 | 5-$CH(OB^{10})(CH_2)O(CH_2)$-cPn |
| 1-2560 | H | — | tBu | 0 | 5-$CH(OB^{10})(CH_2)O(CH_2)_2$-cPn |
| 1-2561 | H | — | tBu | 0 | 5-$CH(OB^{10})(CH_2)_2O$-cPn |
| 1-2562 | H | — | tBu | 0 | 5-$CH(OB^{10})(CH_2)_2O(CH_2)$-cPn |
| 1-2563 | H | — | tBu | 0 | 5-$CH(OB^{10})(CH_2)_2O(CH_2)_2$-cPn |
| 1-2564 | H | — | tBu | 0 | 5-$CH(OB^{10})(CH_2)_3O$-cPn |
| 1-2565 | H | — | tBu | 0 | 5-$CH(OB^{10})(CH_2)_3O(CH_2)$-cPn |
| 1-2566 | H | — | tBu | 0 | 5-$CH(OB^{10})(CH_2)_3O(CH_2)_2$-cPn |
| 1-2567 | H | — | tBu | 0 | 5-$(CH_2)CH(OB^{10})(CH_2)O$-cPn |
| 1-2568 | H | — | tBu | 0 | 5-$(CH_2)CH(OB^{10})(CH_2)O(CH_2)$-cPn |
| 1-2569 | H | — | tBu | 0 | 5-$(CH_2)CH(OB^{10})(CH_2)O(CH_2)_2$-cPn |
| 1-2570 | H | — | tBu | 0 | 5-$(CH_2)CH(OB^{10})(CH_2)_2O$-cPn |
| 1-2571 | H | — | tBu | 0 | 5-$(CH_2)CH(OB^{10})(CH_2)_2O(CH_2)$-cPn |
| 1-2572 | H | — | tBu | 0 | 5-$(CH_2)CH(OB^{10})(CH_2)_2O(CH_2)_2$-cPn |
| 1-2573 | H | — | tBu | 0 | 5-$(CH_2)CH(OB^{10})(CH_2)_3O$-cPn |
| 1-2574 | H | — | tBu | 0 | 5-$(CH_2)CH(OB^{10})(CH_2)_3O(CH_2)$-cPn |
| 1-2575 | H | — | tBu | 0 | 5-$(CH_2)CH(OB^{10})(CH_2)_3O(CH_2)_2$-cPn |
| 1-2576 | H | — | tBu | 0 | 5-$(CH_2)_2CH(OB^{10})(CH_2)O$-cPn |
| 1-2577 | H | — | tBu | 0 | 5-$(CH_2)_2CH(OB^{10})(CH_2)O(CH_2)$-cPn |
| 1-2578 | H | — | tBu | 0 | 5-$(CH_2)_2CH(OB^{10})(CH_2)O(CH_2)_2$-cPn |
| 1-2579 | H | — | tBu | 0 | 5-$(CH_2)_2CH(OB^{10})(CH_2)_2O$-cPn |
| 1-2580 | H | — | tBu | 0 | 5-$(CH_2)_2CH(OB^{10})(CH_2)_2O(CH_2)$-cPn |
| 1-2581 | H | — | tBu | 0 | 5-$(CH_2)_2CH(OB^{10})(CH_2)_2O(CH_2)_2$-cPn |
| 1-2582 | H | — | tBu | 0 | 5-$(CH_2)_2CH(OB^{10})(CH_2)_3O$-cPn |
| 1-2583 | H | — | tBu | 0 | 5-$(CH_2)_2CH(OB^{10})(CH_2)_3O(CH_2)$-cPn |
| 1-2584 | H | — | tBu | 0 | 5-$(CH_2)_2CH(OB^{10})(CH_2)_3O(CH_2)_2$-cPn |
| 1-2585 | H | — | tBu | 0 | 5-$CH(OB^4)(CH_2)O$-cHx |
| 1-2586 | H | — | tBu | 0 | 5-$CH(OB^4)(CH_2)O(CH_2)$-cHx |
| 1-2587 | H | — | tBu | 0 | 5-$CH(OB^4)(CH_2)O(CH_2)_2$-cHx |
| 1-2588 | H | — | tBu | 0 | 5-$CH(OB^4)(CH_2)_2O$-cHx |
| 1-2589 | H | — | tBu | 0 | 5-$CH(OB^4)(CH_2)_2O(CH_2)$-cHx |
| 1-2590 | H | — | tBu | 0 | 5-$CH(OB^4)(CH_2)_2O(CH_2)_2$-cHx |
| 1-2591 | H | — | tBu | 0 | 5-$CH(OB^4)(CH_2)_3O$-cHx |
| 1-2592 | H | — | tBu | 0 | 5-$CH(OB^4)(CH_2)_3O(CH_2)$-cHx |
| 1-2593 | H | — | tBu | 0 | 5-$CH(OB^4)(CH_2)_3O(CH_2)_2$-cHx |
| 1-2594 | H | — | tBu | 0 | 5-$(CH_2)CH(OB^4)(CH_2)O$-cHx |
| 1-2595 | H | — | tBu | 0 | 5-$(CH_2)CH(OB^4)(CH_2)OCH2$-cHx |
| 1-2596 | H | — | tBu | 0 | 5-$(CH_2)CH(OB^4)(CH_2)O(CH_2)_2$-cHx |
| 1-2597 | H | — | tBu | 0 | 5-$(CH_2)CH(OB^4)(CH_2)_2O$-cHx |
| 1-2598 | H | — | tBu | 0 | 5-$(CH_2)CH(OB^4)(CH_2)_2O(CH_2)$-cHx |
| 1-2599 | H | — | tBu | 0 | 5-$(CH_2)CH(OB^4)(CH_2)_2O(CH_2)_2$-cHx |
| 1-2600 | H | — | tBu | 0 | 5-$(CH_2)CH(OB^4)(CH_2)_3O$-cHx |
| 1-2601 | H | — | tBu | 0 | 5-$(CH_2)CH(OB^4)(CH_2)_3O(CH_2)$-cHx |
| 1-2602 | H | — | tBu | 0 | 5-$(CH_2)CH(OB^4)(CH_2)_3O(CH_2)_2$-cHx |
| 1-2603 | H | — | tBu | 0 | 5-$(CH_2)_2CH(OB^4)(CH_2)O$-cHx |
| 1-2604 | H | — | tBu | 0 | 5-$(CH_2)_2CH(OB^4)(CH_2)O(CH_2)$-cHx |
| 1-2605 | H | — | tBu | 0 | 5-$(CH_2)_2CH(OB^4)(CH_2)O(CH_2)_2$-cHx |
| 1-2606 | H | — | tBu | 0 | 5-$(CH_2)_2CH(OB^4)(CH_2)_2O$-cHx |
| 1-2607 | H | — | tBu | 0 | 5-$(CH_2)_2CH(OB^4)(CH_2)_2O(CH_2)$-cHx |
| 1-2608 | H | — | tBu | 0 | 5-$(CH_2)_2CH(OB^4)(CH_2)_2O(CH_2)_2$-cHx |
| 1-2609 | H | — | tBu | 0 | 5-$(CH_2)_2CH(OB^4)(CH_2)_3O$-cHx |
| 1-2610 | H | — | tBu | 0 | 5-$(CH_2)_2CH(OB^4)(CH_2)_3O(CH_2)$-cHx |
| 1-2611 | H | — | tBu | 0 | 5-$(CH_2)_2CH(OB^4)(CH_2)_3O(CH_2)_2$-cHx |
| 1-2612 | H | — | tBu | 0 | 5-$CH(OB^4)(CH_2)O$-cPn |
| 1-2613 | H | — | tBu | 0 | 5-$CH(OB^4)(CH_2)O(CH_2)$-cPn |
| 1-2614 | H | — | tBu | 0 | 5-$CH(OB^4)(CH_2)O(CH_2)_2$-cPn |
| 1-2615 | H | — | tBu | 0 | 5-$CH(OB^4)(CH_2)_2O$-cPn |
| 1-2616 | H | — | tBu | 0 | 5-$CH(OB^4)(CH_2)_2O(CH_2)$-cPn |
| 1-2617 | H | — | tBu | 0 | 5-$CH(OB^4)(CH_2)_2O(CH_2)_2$-cPn |
| 1-2618 | H | — | tBu | 0 | 5-$CH(OB^4)(CH_2)_3O$-cPn |
| 1-2619 | H | — | tBu | 0 | 5-$CH(OB^4)(CH_2)_3O(CH_2)$-cPn |

TABLE 1-continued

| Cpd. No. | R$^a$ | R$^2$ | R$^3$ | n | R$^4$ |
|---|---|---|---|---|---|
| 1-2620 | H | — | tBu | 0 | 5-CH(OB$^4$)(CH$_2$)$_3$O(CH$_2$)$_2$-cPn |
| 1-2621 | H | — | tBu | 0 | 5-(CH$_2$)CH(OB$^4$)(CH$_2$)O-cHx |
| 1-2622 | H | — | tBu | 0 | 5-(CH$_2$)CH(OB$^4$)(CH$_2$)O(CH$_2$)-cHx |
| 1-2623 | H | — | tBu | 0 | 5-(CH$_2$)CH(OB$^4$)(CH$_2$)O(CH$_2$)$_2$-cHx |
| 1-2624 | H | — | tBu | 0 | 5-(CH$_2$)CH(OB$^4$)(CH$_2$)$_2$O-cHx |
| 1-2625 | H | — | tBu | 0 | 5-(CH$_2$)CH(OB$^4$)(CH$_2$)$_2$O(CH$_2$)-cHx |
| 1-2626 | H | — | tBu | 0 | 5-(CH$_2$)CH(OB$^4$)(CH$_2$)$_2$O(CH$_2$)$_2$-cHx |
| 1-2627 | H | — | tBu | 0 | 5-(CH$_2$)CH(OB$^4$)(CH$_2$)$_3$O-cHx |
| 1-2628 | H | — | tBu | 0 | 5-(CH$_2$)CH(OB$^4$)(CH$_2$)$_3$O(CH$_2$)-cHx |
| 1-2629 | H | — | tBu | 0 | 5-(CH$_2$)CH(OB$^4$)(CH$_2$)$_3$O(CH$_2$)$_2$-cHx |
| 1-2630 | H | — | tBu | 0 | 5-(CH$_2$)$_2$CH(OB$^4$)(CH$_2$)O-cPn |
| 1-2631 | H | — | tBu | 0 | 5-(CH$_2$)$_2$CH(OB$^4$)(CH$_2$)O(CH$_2$)-cPn |
| 1-2632 | H | — | tBu | 0 | 5-(CH$_2$)$_2$CH(OB$^4$)(CH$_2$)O(CH$_2$)$_2$-cPn |
| 1-2633 | H | — | tBu | 0 | 5-(CH$_2$)$_2$CH(OB$^4$)(CH$_2$)$_2$O-cPn |
| 1-2634 | H | — | tBu | 0 | 5-(CH$_2$)$_2$CH(OB$^4$)(CH$_2$)$_2$O(CH$_2$)-cPn |
| 1-2635 | H | — | tBu | 0 | 5-(CH$_2$)$_2$CH(OB$^4$)(CH$_2$)$_2$O(CH$_2$)$_2$-cPn |
| 1-2636 | H | — | tBu | 0 | 5-(CH$_2$)$_2$CH(OB$^4$)(CH$_2$)$_3$O-cPn |
| 1-2637 | H | — | tBu | 0 | 5-(CH$_2$)$_2$CH(OB$^4$)(CH$_2$)$_3$O(CH$_2$)-cPn |
| 1-2638 | H | — | tBu | 0 | 5-(CH$_2$)$_2$CH(OB$^4$)(CH$_2$)$_3$O(CH$_2$)$_2$-cPn |
| 1-2639 | H | — | tBu | 0 | 5-CH(OB$^2$)(CH$_2$)O-cHx |
| 1-2640 | H | — | tBu | 0 | 5-CH(OB$^2$)(CH$_2$)O(CH$_2$)-cHx |
| 1-2641 | H | — | tBu | 0 | 5-CH(OB$^2$)(CH$_2$)O(CH$_2$)$_2$-cHx |
| 1-2642 | H | — | tBu | 0 | 5-CH(OB$^2$)(CH$_2$)$_2$O-cHx |
| 1-2643 | H | — | tBu | 0 | 5-CH(OB$^2$)(CH$_2$)$_2$O(CH$_2$)-cHx |
| 1-2644 | H | — | tBu | 0 | 5-CH(OB$^2$)(CH$_2$)$_2$O(CH$_2$)$_2$-cHx |
| 1-2645 | H | — | tBu | 0 | 5-CH(OB$^2$)(CH$_2$)$_3$O-cHx |
| 1-2646 | H | — | tBu | 0 | 5-CH(OB$^2$)(CH$_2$)$_3$O(CH$_2$)-cHx |
| 1-2647 | H | — | tBu | 0 | 5-CH(OB$^2$)(CH$_2$)$_3$O(CH$_2$)$_2$-cHx |
| 1-2648 | H | — | tBu | 0 | 5-(CH$_2$)CH(OB$^2$)(CH$_2$)O-cHx |
| 1-2649 | H | — | tBu | 0 | 5-(CH$_2$)CH(OB$^2$)(CH$_2$)O(CH$_2$)-cHx |
| 1-2650 | H | — | tBu | 0 | 5-(CH$_2$)CH(OB$^2$)(CH$_2$)O(CH$_2$)$_2$-cHx |
| 1-2651 | H | — | tBu | 0 | 5-(CH$_2$)CH(OB$^2$)(CH$_2$)$_2$O-cHx |
| 1-2652 | H | — | tBu | 0 | 5-(CH$_2$)CH(OB$^2$)(CH$_2$)$_2$O(CH$_2$)-cHx |
| 1-2653 | H | — | tBu | 0 | 5-(CH$_2$)CH(OB$^2$)(CH$_2$)$_2$O(CH$_2$)$_2$-cHx |
| 1-2654 | H | — | tBu | 0 | 5-(CH$_2$)CH(OB$^2$)(CH$_2$)$_3$O-cHx |
| 1-2655 | H | — | tBu | 0 | 5-(CH$_2$)CH(OB$^2$)(CH$_2$)$_3$O(CH$_2$)-cHx |
| 1-2656 | H | — | tBu | 0 | 5-(CH$_2$)CH(OB$^2$)(CH$_2$)$_3$O(CH$_2$)$_2$-cHx |
| 1-2657 | H | — | tBu | 0 | 5-(CH$_2$)$_2$CH(OB$^2$)(CH$_2$)O-cHx |
| 1-2658 | H | — | tBu | 0 | 5-(CH$_2$)$_2$CH(OB$^2$)(CH$_2$)O(CH$_2$)-cHx |
| 1-2659 | H | — | tBu | 0 | 5-(CH$_2$)$_2$CH(OB$^2$)(CH$_2$)O(CH$_2$)$_2$-cHx |
| 1-2660 | H | — | tBu | 0 | 5-(CH$_2$)$_2$CH(OB$^2$)(CH$_2$)$_2$O-cHx |
| 1-2661 | H | — | tBu | 0 | 5-(CH$_2$)$_2$CH(OB$^2$)(CH$_2$)$_2$O(CH$_2$)-cHx |
| 1-2662 | H | — | tBu | 0 | 5-(CH$_2$)$_2$CH(OB$^2$)(CH$_2$)$_2$O(CH$_2$)$_2$-cHx |
| 1-2663 | H | — | tBu | 0 | 5-(CH$_2$)$_2$CH(OB$^2$)(CH$_2$)$_3$O-cHx |
| 1-2664 | H | — | tBu | 0 | 5-(CH$_2$)$_2$CH(OB$^2$)(CH$_2$)$_3$O(CH$_2$)-cHx |
| 1-2665 | H | — | tBu | 0 | 5-(CH$_2$)$_2$CH(OB$^2$)(CH$_2$)$_3$O(CH$_2$)$_2$-cHx |
| 1-2666 | H | — | tBu | 0 | 5-CH(OB$^2$)(CH$_2$)O-cPn |
| 1-2667 | H | — | tBu | 0 | 5-CH(OB$^2$)(CH$_2$)O(CH$_2$)-cPn |
| 1-2668 | H | — | tBu | 0 | 5-CH(OB$^2$)(CH$_2$)O(CH$_2$)$_2$-cPn |
| 1-2669 | H | — | tBu | 0 | 5-CH(OB$^2$)(CH$_2$)$_2$O-cPn |
| 1-2670 | H | — | tBu | 0 | 5-CH(OB$^2$)(CH$_2$)$_2$O(CH$_2$)-cPn |
| 1-2671 | H | — | tBu | 0 | 5-CH(OB$^2$)(CH$_2$)$_2$O(CH$_2$)$_2$-cPn |
| 1-2672 | H | — | tBu | 0 | 5-CH(OB$^2$)(CH$_2$)$_3$O-cPn |
| 1-2673 | H | — | tBu | 0 | 5-CH(OB$^2$)(CH$_2$)$_3$O(CH$_2$)-cPn |
| 1-2674 | H | — | tBu | 0 | 5-CH(OB$^2$)(CH$_2$)$_3$O(CH$_2$)$_2$-cPn |
| 1-2675 | H | — | tBu | 0 | 5-(CH$_2$)CH(OB$^2$)(CH$_2$)O-cPn |
| 1-2676 | H | — | tBu | 0 | 5-(CH$_2$)CH(OB$^2$)(CH$_2$)O(CH$_2$)-cPn |
| 1-2677 | H | — | tBu | 0 | 5-(CH$_2$)CH(OB$^2$)(CH$_2$)O(CH$_2$)$_2$-cPn |
| 1-2678 | H | — | tBu | 0 | 5-(CH$_2$)CH(OB$^2$)(CH$_2$)$_2$O-cPn |
| 1-2679 | H | — | tBu | 0 | 5-(CH$_2$)CH(OB$^2$)(CH$_2$)$_2$O(CH$_2$)-cPn |
| 1-2680 | H | — | tBu | 0 | 5-(CH$_2$)CH(OB$^2$)(CH$_2$)$_2$O(CH$_2$)$_2$-cPn |
| 1-2681 | H | — | tBu | 0 | 5-(CH$_2$)CH(OB$^2$)(CH$_2$)$_3$O-cPn |
| 1-2682 | H | — | tBu | 0 | 5-(CH$_2$)CH(OB$^2$)(CH$_2$)$_3$O(CH$_2$)-cPn |
| 1-2683 | H | — | tBu | 0 | 5-(CH$_2$)CH(OB$^2$)(CH$_2$)$_3$O(CH$_2$)$_2$-cPn |
| 1-2684 | H | — | tBu | 0 | 5-(CH$_2$)$_2$CH(OB$^2$)(CH$_2$)O-cPn |
| 1-2685 | H | — | tBu | 0 | 5-(CH$_2$)$_2$CH(OB$^2$)(CH$_2$)O(CH$_2$)-cPn |
| 1-2686 | H | — | tBu | 0 | 5-(CH$_2$)$_2$CH(OB$^2$)(CH$_2$)O(CH$_2$)$_2$-cPn |
| 1-2687 | H | — | tBu | 0 | 5-(CH$_2$)$_2$CH(OB$^2$)(CH$_2$)$_2$O-cPn |
| 1-2688 | H | — | tBu | 0 | 5-(CH$_2$)$_2$CH(OB$^2$)(CH$_2$)$_2$O(CH$_2$)-cPn |
| 1-2689 | H | — | tBu | 0 | 5-(CH$_2$)$_2$CH(OB$^2$)(CH$_2$)$_2$O(CH$_2$)$_2$-cPn |
| 1-2690 | H | — | tBu | 0 | 5-(CH$_2$)$_2$CH(OB$^2$)(CH$_2$)$_3$O-cPn |
| 1-2691 | H | — | tBu | 0 | 5-(CH$_2$)$_2$CH(OB$^2$)(CH$_2$)$_3$O(CH$_2$)-cPn |
| 1-2692 | H | — | tBu | 0 | 5-(CH$_2$)$_2$CH(OB$^2$)(CH$_2$)$_3$O(CH$_2$)$_2$-cPn |
| 1-2693 | H | — | tBu | 0 | 5-CH(OE$^5$)(CH$_2$)O-cHx |
| 1-2694 | H | — | tBu | 0 | 5-CH(OE$^5$)(CH$_2$)O(CH$_2$)-cHx |
| 1-2695 | H | — | tBu | 0 | 5-CH(OE$^5$)(CH$_2$)O(CH$_2$)$_2$-cHx |

TABLE 1-continued

| Cpd. No. | $R^a$ | $R^2$ | $R^3$ | n | $R^4$ |
|---|---|---|---|---|---|
| 1-2696 | H | — | tBu | 0 | 5-CH(OE$^5$)(CH$_2$)$_2$O-cHx |
| 1-2697 | H | — | tBu | 0 | 5-CH(OE$^5$)(CH$_2$)$_2$O(CH$_2$)-cHx |
| 1-2698 | H | — | tBu | 0 | 5-CH(OE$^5$)(CH$_2$)$_2$O(CH$_2$)$_2$-cHx |
| 1-2699 | H | — | tBu | 0 | 5-CH(OE$^5$)(CH$_2$)$_3$O-cHx |
| 1-2700 | H | — | tBu | 0 | 5-CH(OE$^5$)(CH$_2$)$_3$O(CH$_2$)-cHx |
| 1-2701 | H | — | tBu | 0 | 5-CH(OE$^5$)(CH$_2$)$_3$O(CH$_2$)$_2$-cHx |
| 1-2702 | H | — | tBu | 0 | 5-(CH$_2$)CH(OE$^5$)(CH$_2$)O-cHx |
| 1-2703 | H | — | tBu | 0 | 5-(CH$_2$)CH(OE$^5$)(CH$_2$)O(CH$_2$)-cHx |
| 1-2704 | H | — | tBu | 0 | 5-(CH$_2$)CH(OE$^5$)(CH$_2$)O(CH$_2$)$_2$-cHx |
| 1-2705 | H | — | tBu | 0 | 5-(CH$_2$)CH(OE$^5$)(CH$_2$)$_2$O-cHx |
| 1-2706 | H | — | tBu | 0 | 5-(CH$_2$)CH(OE$^5$)(CH$_2$)$_2$O(CH$_2$)-cHx |
| 1-2707 | H | — | tBu | 0 | 5-(CH$_2$)CH(OE$^5$)(CH$_2$)$_2$O(CH$_2$)$_2$-cHx |
| 1-2708 | H | — | tBu | 0 | 5-(CH$_2$)CH(OE$^5$)(CH$_2$)$_3$O-cHx |
| 1-2709 | H | — | tBu | 0 | 5-(CH$_2$)CH(OE$^5$)(CH$_2$)$_3$O(CH$_2$)-cHx |
| 1-2710 | H | — | tBu | 0 | 5-(CH$_2$)CH(OE$^5$)(CH$_2$)$_3$O(CH$_2$)$_2$-cHx |
| 1-2711 | H | — | tBu | 0 | 5-(CH$_2$)$_2$CH(OE$^5$)(CH$_2$)O-cHx |
| 1-2712 | H | — | tBu | 0 | 5-(CH$_2$)$_2$CH(OE$^5$)(CH$_2$)O(CH$_2$)-cHx |
| 1-2713 | H | — | tBu | 0 | 5-(CH$_2$)$_2$CH(OE$^5$)(CH$_2$)O(CH$_2$)$_2$-cHx |
| 1-2714 | H | — | tBu | 0 | 5-(CH$_2$)$_2$CH(OE$^5$)(CH$_2$)$_2$O-cHx |
| 1-2715 | H | — | tBu | 0 | 5-(CH$_2$)$_2$CH(OE$^5$)(CH$_2$)$_2$O(CH$_2$)-cHx |
| 1-2716 | H | — | tBu | 0 | 5-(CH$_2$)$_2$CH(OE$^5$)(CH$_2$)$_2$O(CH$_2$)$_2$-cHx |
| 1-2717 | H | — | tBu | 0 | 5-(CH$_2$)$_2$CH(OE$^5$)(CH$_2$)$_3$O-cHx |
| 1-2718 | H | — | tBu | 0 | 5-(CH$_2$)$_2$CH(OE$^5$)(CH$_2$)$_3$O(CH$_2$)-cHx |
| 1-2719 | H | — | tBu | 0 | 5-(CH$_2$)$_2$CH(OE$^5$)(CH$_2$)$_3$O(CH$_2$)$_2$-cHx |
| 1-2720 | H | — | tBu | 0 | 5-CH(OE$^5$)(CH$_2$)O-cPn |
| 1-2721 | H | — | tBu | 0 | 5-CH(OE$^5$)(CH$_2$)O(CH$_2$)-cPn |
| 1-2722 | H | — | tBu | 0 | 5-CH(OE$^5$)(CH$_2$)O(CH$_2$)$_2$-cPn |
| 1-2723 | H | — | tBu | 0 | 5-CH(OE$^5$)(CH$_2$)$_2$O-cPn |
| 1-2724 | H | — | tBu | 0 | 5-CH(OE$^5$)(CH$_2$)$_2$O(CH$_2$)-cPn |
| 1-2725 | H | — | tBu | 0 | 5-CH(OE$^5$)(CH$_2$)$_2$O(CH$_2$)$_2$-cPn |
| 1-2726 | H | — | tBu | 0 | 5-CH(OE$^5$)(CH$_2$)$_3$O-cPn |
| 1-2727 | H | — | tBu | 0 | 5-CH(OE$^5$)(CH$_2$)$_3$O(CH$_2$)-cPn |
| 1-2728 | H | — | tBu | 0 | 5-CH(OE$^5$)(CH$_2$)$_3$O(CH$_2$)$_2$-cPn |
| 1-2729 | H | — | tBu | 0 | 5-(CH$_2$)CH(OE$^5$)(CH$_2$)O-cPn |
| 1-2730 | H | — | tBu | 0 | 5-(CH$_2$)CH(OE$^5$)(CH$_2$)O(CH$_2$)-cPn |
| 1-2731 | H | — | tBu | 0 | 5-(CH$_2$)CH(OE$^5$)(CH$_2$)O(CH$_2$)$_2$-cPn |
| 1-2732 | H | — | tBu | 0 | 5-(CH$_2$)CH(OE$^5$)(CH$_2$)$_2$O-cPn |
| 1-2733 | H | — | tBu | 0 | 5-(CH$_2$)CH(OE$^5$)(CH$_2$)$_2$O(CH$_2$)-cPn |
| 1-2734 | H | — | tBu | 0 | 5-(CH$_2$)CH(OE$^5$)(CH$_2$)$_2$O(CH$_2$)$_2$-cPn |
| 1-2735 | H | — | tBu | 0 | 5-(CH$_2$)CH(OE$^5$)(CH$_2$)$_3$O-cPn |
| 1-2736 | H | — | tBu | 0 | 5-(CH$_2$)CH(OE$^5$)(CH$_2$)$_3$O(CH$_2$)-cPn |
| 1-2737 | H | — | tBu | 0 | 5-(CH$_2$)CH(OE$^5$)(CH$_2$)$_3$O(CH$_2$)$_2$-cPn |
| 1-2738 | H | — | tBu | 0 | 5-(CH$_2$)$_2$CH(OE$^5$)(CH$_2$)O-cPn |
| 1-2739 | H | — | tBu | 0 | 5-(CH$_2$)$_2$CH(OE$^5$)(CH$_2$)O(CH$_2$)-cPn |
| 1-2740 | H | — | tBu | 0 | 5-(CH$_2$)$_2$CH(OE$^5$)(CH$_2$)O(CH$_2$)$_2$-cPn |
| 1-2741 | H | — | tBu | 0 | 5-(CH$_2$)$_2$CH(OE$^5$)(CH$_2$)$_2$O-cPn |
| 1-2742 | H | — | tBu | 0 | 5-(CH$_2$)$_2$CH(OE$^5$)(CH$_2$)$_2$O(CH$_2$)-cPn |
| 1-2743 | H | — | tBu | 0 | 5-(CH$_2$)$_2$CH(OE$^5$)(CH$_2$)$_2$O(CH$_2$)$_2$-cPn |
| 1-2744 | H | — | tBu | 0 | 5-(CH$_2$)$_2$CH(OE$^5$)(CH$_2$)$_3$O-cPn |
| 1-2745 | H | — | tBu | 0 | 5-(CH$_2$)$_2$CH(OE$^5$)(CH$_2$)$_3$O(CH$_2$)-cPn |
| 1-2746 | H | — | tBu | 0 | 5-(CH$_2$)$_2$CH(OE$^5$)(CH$_2$)$_3$O(CH$_2$)$_2$-cPn |
| 1-2747 | H | — | tBu | 0 | 5-CH(OB$^{10}$)(CH$_2$)O-cHx |
| 1-2748 | H | — | tBu | 0 | 5-CH(OB$^{10}$)(CH$_2$)O(CH$_2$)-cHx |
| 1-2750 | H | — | tBu | 0 | 5-CH(OB$^{10}$)(CH$_2$)O(CH$_2$)$_2$-cHx |
| 1-2751 | H | — | tBu | 0 | 5-CH(OB$^{10}$)(CH$_2$)$_2$O-cHx |
| 1-2752 | H | — | tBu | 0 | 5-CH(OB$^{10}$)(CH$_2$)$_2$O(CH$_2$)-cHx |
| 1-2753 | H | — | tBu | 0 | 5-CH(OB$^{10}$)(CH$_2$)$_2$O(CH$_2$)$_2$-cHx |
| 1-2754 | H | — | tBu | 0 | 5-CH(OB$^{10}$)(CH$_2$)$_3$O-cHx |
| 1-2755 | H | — | tBu | 0 | 5-CH(OB$^{10}$)(CH$_2$)$_3$O(CH$_2$)-cHx |
| 1-2756 | H | — | tBu | 0 | 5-CH(OB$^{10}$)(CH$_2$)$_3$O(CH$_2$)$_2$-cHx |
| 1-2757 | H | — | tBu | 0 | 5-(CH$_2$)CH(OB$^{10}$)(CH$_2$)O(CH$_2$)-cHx |
| 1-2758 | H | — | tBu | 0 | 5-(CH$_2$)CH(OB$^{10}$)(CH$_2$)O(CH$_2$)$_2$-cHx |
| 1-2759 | H | — | tBu | 0 | 5-(CH$_2$)CH(OB$^{10}$)(CH$_2$)$_2$O-cHx |
| 1-2760 | H | — | tBu | 0 | 5-(CH$_2$)CH(OB$^{10}$)(CH$_2$)$_2$O(CH$_2$)-cHx |
| 1-2761 | H | — | tBu | 0 | 5-(CH$_2$)CH(OB$^{10}$)(CH$_2$)$_2$O(CH$_2$)$_2$-cHx |
| 1-2762 | H | — | tBu | 0 | 5-(CH$_2$)CH(OB$^{10}$)(CH$_2$)$_3$O-cHx |
| 1-2763 | H | — | tBu | 0 | 5-(CH$_2$)CH(OB$^{10}$)(CH$_2$)$_3$O(CH$_2$)-cHx |
| 1-2764 | H | — | tBu | 0 | 5-(CH$_2$)CH(OB$^{10}$)(CH$_2$)$_3$O(CH$_2$)$_2$-cHx |
| 1-2765 | H | — | tBu | 0 | 5-(CH$_2$)$_2$CH(OB$^{10}$)(CH$_2$)O-cHx |
| 1-2766 | H | — | tBu | 0 | 5-(CH$_2$)$_2$CH(OB$^{10}$)(CH$_2$)O(CH$_2$)-cHx |
| 1-2767 | H | — | tBu | 0 | 5-(CH$_2$)$_2$CH(OB$^{10}$)(CH$_2$)O(CH$_2$)$_2$-cHx |
| 1-2768 | H | — | tBu | 0 | 5-(CH$_2$)$_2$CH(OB$^{10}$)(CH$_2$)$_2$O-cHx |
| 1-2769 | H | — | tBu | 0 | 5-(CH$_2$)$_2$CH(OB$^{10}$)(CH$_2$)$_2$O(CH$_2$)-cHx |
| 1-2770 | H | — | tBu | 0 | 5-(CH$_2$)$_2$CH(OB$^{10}$)(CH$_2$)$_2$O(CH$_2$)$_2$-cHx |
| 1-2771 | H | — | tBu | 0 | 5-(CH$_2$)$_2$CH(OB$^{10}$)(CH$_2$)$_3$O-cHx |
| 1-2772 | H | — | tBu | 0 | 5-(CH$_2$)$_2$CH(OB$^{10}$)(CH$_2$)$_3$O(CH$_2$)-cHx |

TABLE 1-continued

| Cpd. No. | R$^a$ | R$^2$ | R$^3$ | n | R$^4$ |
|---|---|---|---|---|---|
| 1-2773 | H | — | tBu | 0 | 5-(CH$_2$)$_2$CH(OB$^{10}$)(CH$_2$)$_3$O(CH$_2$)$_2$-cHx |
| 1-2774 | H | — | tBu | 0 | 5-CH(OB$^{10}$)(CH$_2$)O-cPn |
| 1-2775 | H | — | tBu | 0 | 5-CH(OB$^{10}$)(CH$_2$)O(CH$_2$)-cPn |
| 1-2776 | H | — | tBu | 0 | 5-CH(OB$^{10}$)(CH$_2$)O(CH$_2$)$_2$-cPn |
| 1-2777 | H | — | tBu | 0 | 5-CH(OB$^{10}$)(CH$_2$)$_2$O-cPn |
| 1-2778 | H | — | tBu | 0 | 5-CH(OB$^{10}$)(CH$_2$)$_2$O(CH$_2$)-cPn |
| 1-2779 | H | — | tBu | 0 | 5-CH(OB$^{10}$)(CH$_2$)$_2$O(CH$_2$)$_2$-cPn |
| 1-2780 | H | — | tBu | 0 | 5-CH(OB$^{10}$)(CH$_2$)$_3$O-cPn |
| 1-2781 | H | — | tBu | 0 | 5-CH(OB$^{10}$)(CH$_2$)$_3$O(CH$_2$)-cPn |
| 1-2782 | H | — | tBu | 0 | 5-CH(OB$^{10}$)(CH$_2$)$_3$O(CH$_2$)$_2$-cPn |
| 1-2783 | H | — | tBu | 0 | 5-(CH$_2$)CH(OB$^{10}$)(CH$_2$)O-cPn |
| 1-2784 | H | — | tBu | 0 | 5-(CH$_2$)CH(OB$^{10}$)(CH$_2$)O(CH$_2$)-cPn |
| 1-2785 | H | — | tBu | 0 | 5-(CH$_2$)CH(OB$^{10}$)(CH$_2$)O(CH$_2$)$_2$-cPn |
| 1-2786 | H | — | tBu | 0 | 5-(CH$_2$)CH(OB$^{10}$)(CH$_2$)$_2$O-cPn |
| 1-2787 | H | — | tBu | 0 | 5-(CH$_2$)CH(OB$^{10}$)(CH$_2$)$_2$O(CH$_2$)-cPn |
| 1-2788 | H | — | tBu | 0 | 5-(CH$_2$)CH(OB$^{10}$)(CH$_2$)$_2$O(CH$_2$)$_2$-cPn |
| 1-2789 | H | — | tBu | 0 | 5-(CH$_2$)CH(OB$^{10}$)(CH$_2$)$_3$O-cPn |
| 1-2790 | H | — | tBu | 0 | 5-(CH$_2$)CH(OB$^{10}$)(CH$_2$)$_3$O(CH$_2$)-cPn |
| 1-2791 | H | — | tBu | 0 | 5-(CH$_2$)CH(OB$^{10}$)(CH$_2$)$_3$O(CH$_2$)$_2$-cPn |
| 1-2792 | H | — | tBu | 0 | 5-(CH$_2$)$_2$CH(OB$^{10}$)(CH$_2$)O-cPn |
| 1-2793 | H | — | tBu | 0 | 5-(CH$_2$)$_2$CH(OB$^{10}$)(CH$_2$)O(CH$_2$)-cPn |
| 1-2794 | H | — | tBu | 0 | 5-(CH$_2$)$_2$CH(OB$^{10}$)(CH$_2$)O(CH$_2$)$_2$-cPn |
| 1-2795 | H | — | tBu | 0 | 5-(CH$_2$)$_2$CH(OB$^{10}$)(CH$_2$)$_2$O-cPn |
| 1-2796 | H | — | tBu | 0 | 5-(CH$_2$)$_2$CH(OB$^{10}$)(CH$_2$)$_2$O(CH$_2$)-cPn |
| 1-2797 | H | — | tBu | 0 | 5-(CH$_2$)$_2$CH(OB$^{10}$)(CH$_2$)$_2$O(CH$_2$)$_2$-cPn |
| 1-2798 | H | — | tBu | 0 | 5-(CH$_2$)$_2$CH(OB$^{10}$)(CH$_2$)$_3$O-cPn |
| 1-2799 | H | — | tBu | 0 | 5-(CH$_2$)$_2$CH(OB$^{10}$)(CH$_2$)$_3$O(CH$_2$)-cPn |
| 1-2800 | H | — | tBu | 0 | 5-(CH$_2$)$_2$CH(OB$^{10}$)(CH$_2$)$_3$O(CH$_2$)$_2$-cPn |
| 1-2801 | H | — | tBu | 0 | 5-CH(OB$^4$)(CH$_2$)O-cHx |
| 1-2802 | H | — | tBu | 0 | 5-CH(OB$^4$)(CH$_2$)O(CH$_2$)-cHx |
| 1-2803 | H | — | tBu | 0 | 5-CH(OB$^4$)(CH$_2$)O(CH$_2$)$_2$-cHx |
| 1-2804 | H | — | tBu | 0 | 5-CH(OB$^4$)(CH$_2$)$_2$O-cHx |
| 1-2805 | H | — | tBu | 0 | 5-CH(OB$^4$)(CH$_2$)$_2$O(CH$_2$)-cHx |
| 1-2806 | H | — | tBu | 0 | 5-CH(OB$^4$)(CH$_2$)$_2$O(CH$_2$)$_2$-cHx |
| 1-2807 | H | — | tBu | 0 | 5-CH(OB$^4$)(CH$_2$)$_3$O-cHx |
| 1-2808 | H | — | tBu | 0 | 5-CH(OB$^4$)(CH$_2$)$_3$O(CH$_2$)-cHx |
| 1-2809 | H | — | tBu | 0 | 5-CH(OB$^4$)(CH$_2$)$_3$O(CH$_2$)$_2$-cHx |
| 1-2810 | H | — | tBu | 0 | 5-(CH$_2$)CH(OB$^4$)(CH$_2$)O-cHx |
| 1-2811 | H | — | tBu | 0 | 5-(CH$_2$)CH(OB$^4$)(CH$_2$)O(CH$_2$)-cHx |
| 1-2813 | H | — | tBu | 0 | 5-(CH$_2$)CH(OB$^4$)(CH$_2$)O(CH$_2$)$_2$-cHx |
| 1-2814 | H | — | tBu | 0 | 5-(CH$_2$)CH(OB$^4$)(CH$_2$)$_2$O-cHx |
| 1-2815 | H | — | tBu | 0 | 5-(CH$_2$)CH(OB$^4$)(CH$_2$)$_2$O(CH$_2$)-cHx |
| 1-2816 | H | — | tBu | 0 | 5-(CH$_2$)CH(OB$^4$)(CH$_2$)$_2$O(CH$_2$)$_2$-cHx |
| 1-2817 | H | — | tBu | 0 | 5-(CH$_2$)CH(OB$^4$)(CH$_2$)$_3$O-cHx |
| 1-2818 | H | — | tBu | 0 | 5-(CH$_2$)CH(OB$^4$)(CH$_2$)$_3$O(CH$_2$)-cHx |
| 1-2819 | H | — | tBu | 0 | 5-(CH$_2$)CH(OB$^4$)(CH$_2$)$_3$O(CH$_2$)$_2$-cHx |
| 1-2820 | H | — | tBu | 0 | 5-(CH$_2$)$_2$CH(OB$^4$)(CH$_2$)O(CH$_2$)-cHx |
| 1-2821 | H | — | tBu | 0 | 5-(CH$_2$)$_2$CH(OB$^4$)(CH$_2$)O(CH$_2$)$_2$-cHx |
| 1-2822 | H | — | tBu | 0 | 5-(CH$_2$)$_2$CH(OB$^4$)(CH$_2$)$_2$O-cHx |
| 1-2823 | H | — | tBu | 0 | 5-(CH$_2$)$_2$CH(OB$^4$)(CH$_2$)$_2$O(CH$_2$)-cHx |
| 1-2824 | H | — | tBu | 0 | 5-(CH$_2$)$_2$CH(OB$^4$)(CH$_2$)$_2$O(CH$_2$)$_2$-cHx |
| 1-2825 | H | — | tBu | 0 | 5-(CH$_2$)$_2$CH(OB$^4$)(CH$_2$)$_3$O-cHx |
| 1-2826 | H | — | tBu | 0 | 5-(CH$_2$)$_2$CH(OB$^4$)(CH$_2$)$_3$O(CH$_2$)-cHx |
| 1-2827 | H | — | tBu | 0 | 5-(CH$_2$)$_2$CH(OB$^4$)(CH$_2$)$_3$O(CH$_2$)$_2$-cHx |
| 1-2828 | H | — | tBu | 0 | 5-CH(OB$^4$)(CH$_2$)O-cPn |
| 1-2829 | H | — | tBu | 0 | 5-CH(OB$^4$)(CH$_2$)O(CH$_2$)-cPn |
| 1-2830 | H | — | tBu | 0 | 5-CH(OB$^4$)(CH$_2$)O(CH$_2$)$_2$-cPn |
| 1-2831 | H | — | tBu | 0 | 5-CH(OB$^4$)(CH$_2$)$_2$O-cPn |
| 1-2832 | H | — | tBu | 0 | 5-CH(OB$^4$)(CH$_2$)$_2$O(CH$_2$)-cPn |
| 1-2833 | H | — | tBu | 0 | 5-CH(OB$^4$)(CH$_2$)$_2$O(CH$_2$)$_2$-cPn |
| 1-2834 | H | — | tBu | 0 | 5-CH(OB$^4$)(CH$_2$)$_3$O-cPn |
| 1-2835 | H | — | tBu | 0 | 5-CH(OB$^4$)(CH$_2$)$_3$O(CH$_2$)-cPn |
| 1-2836 | H | — | tBu | 0 | 5-CH(OB$^4$)(CH$_2$)$_3$O(CH$_2$)$_2$-cPn |
| 1-2837 | H | — | tBu | 0 | 5-(CH$_2$)CH(OB$^4$)O-cPn |
| 1-2838 | H | — | tBu | 0 | 5-(CH$_2$)CH(OB$^4$)(CH$_2$)O(CH$_2$)-cPn |
| 1-2839 | H | — | tBu | 0 | 5-(CH$_2$)CH(OB$^4$)(CH$_2$)O(CH$_2$)$_2$-cPn |
| 1-2840 | H | — | tBu | 0 | 5-(CH$_2$)CH(OB$^4$)(CH$_2$)$_2$O-cPn |
| 1-2841 | H | — | tBu | 0 | 5-(CH$_2$)CH(OB$^4$)(CH$_2$)$_2$O(CH$_2$)-cPn |
| 1-2842 | H | — | tBu | 0 | 5-(CH$_2$)CH(OB$^4$)(CH$_2$)$_2$O(CH$_2$)$_2$-cPn |
| 1-2843 | H | — | tBu | 0 | 5-(CH$_2$)CH(OB$^4$)(CH$_2$)$_3$O-cPn |
| 1-2844 | H | — | tBu | 0 | 5-(CH$_2$)CH(OB$^4$)(CH$_2$)$_3$O(CH$_2$)-cPn |
| 1-2845 | H | — | tBu | 0 | 5-(CH$_2$)CH(OB$^4$)(CH$_2$)$_3$O(CH$_2$)$_2$-cPn |
| 1-2846 | H | — | tBu | 0 | 5-(CH$_2$)$_2$CH(OB$^4$)(CH$_2$)O-cPn |
| 1-2847 | H | — | tBu | 0 | 5-(CH$_2$)$_2$CH(OB$^4$)(CH$_2$)O(CH$_2$)-cPn |
| 1-2848 | H | — | tBu | 0 | 5-(CH$_2$)$_2$CH(OB$^4$)(CH$_2$)O(CH$_2$)$_2$-cPn |
| 1-2849 | H | — | tBu | 0 | 5-(CH$_2$)$_2$CH(OB$^4$)(CH$_2$)$_2$O-cPn |

TABLE 1-continued

| Cpd. No. | $R^a$ | $R^2$ | $R^3$ | n | $R^4$ |
|---|---|---|---|---|---|
| 1-2850 | H | — | tBu | 0 | 5-$(CH_2)_2CH(OB^4)(CH_2)_2O(CH_2)$-cPn |
| 1-2851 | H | — | tBu | 0 | 5-$(CH_2)_2CH(OB^4)(CH_2)_2O(CH_2)_2$-cPn |
| 1-2852 | H | — | tBu | 0 | 5-$(CH_2)_2CH(OB^4)(CH_2)_3O$-cPn |
| 1-2853 | H | — | tBu | 0 | 5-$(CH_2)_2CH(OB^4)(CH_2)_3O(CH_2)$-cPn |
| 1-2854 | H | — | tBu | 0 | 5-$(CH_2)_2CH(OB^4)(CH_2)_3O(CH_2)_2$-cPn |
| 1-2855 | H | — | $SCH_3$ | 0 | 6-$(CH_2)O(CH_2)_3$-Imd |
| 1-2856 | H | — | $SCH_3$ | 0 | 6-$(CH_2)O(CH_2)_3$-Imd |
| 1-2857 | H | — | $SCH_3$ | 0 | 6-$(CH_2)O(CH_2)_3$-Imd |
| 1-2858 | H | — | $SCH_3$ | 0 | 6-$(CH_2)O(CH_2)_3$-Imd |
| 1-2859 | H | — | $SCH_3$ | 0 | 6-$(CH_2)O(CH_2)_3$-Imd |
| 1-2860 | H | — | $SCH_3$ | 0 | 6-$(CH_2)O(CH_2)_3$-Imd |
| 1-2861 | H | — | $SCH_3$ | 0 | 6-$(CH_2)O(CH_2)_3$-Imd |
| 1-2862 | H | — | tBu | 0 | 5-$(CH_2)_2CH(OB1)(CH_2)_2$-cHx |
| 1-2863 | H | — | tBu | 0 | 5-$(CH_2)_2CH(OB1)(CH_2)_4$-cHx |
| 1-2864 | H | — | tBu | 0 | 5-$(CH_2)_2CH(OB1)(CH_2)_5$-cHx |
| 1-2865 | H | — | tBu | 0 | 5-$CH(OB^4)(CH_2)_2$-cHx |
| 1-2866 | H | — | iPr | 0 | 6-$(CH_2)_2CH(OB^2)(CH_2)_3$-cHx |
| 1-2867 | H | — | iPr | 0 | 6-$(CH_2)_2CH(OB^2)(CH_2)_3$-cHx |
| 1-2868 | H | — | tBu | 0 | 5-$(CH_2)_4C(=O)(CH_2)_2$-cHp |
| 1-2869 | H | — | tBu | 0 | 5-$(CH_2)_2C(=O)$-cHp |
| 1-2870 | H | — | $C(CH_3)_2CH_2OMe$ | 0 | 6-$(CH_2)_2CH(OH)(CH_2)$-cHx |
| 1-2871 | H | — | tBu | 0 | 5-$(CH_2)_2CH(OF^1)(CH_2)$-cHx |
| 1-2872 | H | — | tBu | 0 | 5-$(CH_2)_2CH(OD^1)(CH_2)$-cHx |
| 1-2873 | H | — | tBu | 0 | 5-$(CH_2)_2CH(OB^1)(CH_2)$-cHx |
| 1-2874 | H | — | tBu | 0 | 5-$(CH_2)_2CH(OE^2)(CH_2)$-cHx |
| 1-2875 | H | — | tBu | 0 | 5-$(CH_2)_2CH(OB^3)(CH_2)$-cHx |
| 1-2876 | H | — | iPr | 0 | 6-CH=CH—$C(=O)(CH_2)_3$-cHx |
| 1-2877 | H | — | tBu | 0 | 5-$(CH_2)_2C(=O)(CH_2)_3$—Ph |
| 1-2878 | H | — | tBu | 0 | 5-$(CH_2)C(=O)(CH_2)_2$—Ph |
| 1-2879 | H | — | tBu | 0 | 5-$(CH_2)_2C(=O)(CH_2)_2$-cPn |
| 1-2880 | H | — | tBu | 0 | 5-$(CH_2)_4C(=O)(CH_2)_2$-cPn |
| 1-2881 | H | — | tBu | 0 | 5-$(CH_2)C(=O)(CH_2)_3$-cPn |
| 1-2882 | H | — | tBu | 0 | 5-$(CH_2)_2C(=O)$-cPn |
| 1-2883 | H | — | tBu | 0 | 5-$(CH_2)C(=O)(CH_2)_2$-cPn |
| 1-2884 | H | — | tBu | 0 | 5-$(CH_2)_4C(=O)$-cPn |
| 1-2885 | H | — | tBu | 0 | 5-$(CH_2)_3C(=O)(CH_2)_2$-cPn |
| 1-2886 | H | — | tBu | 0 | 5-$(CH_2)_3C(=O)(CH_2)$-cPn |
| 1-2887 | H | — | tBu | 0 | 5-$(CH_2)_3C(=O)(CH_2)_3$-cPn |
| 1-2888 | H | — | tBu | 0 | 5-$(CH_2)C(=O)$-cPn |
| 1-2889 | H | — | tBu | 0 | 5-$(CH_2)_2C(=O)(CH_2)_3$-cPn |
| 1-2890 | H | — | tBu | 0 | 5-$(CH_2)_4C(=O)(CH_2)_3$-cPn |
| 1-2891 | H | — | tBu | 0 | 5-$(CH_2)C(=O)(CH_2)$-cPn |
| 1-2892 | H | — | tBu | 0 | 5-$(CH_2)_2C(=O)(CH_2)_4$-cPn |
| 1-2893 | H | — | tBu | 0 | 5-$(CH_2)_4C(=O)(CH_2)_4$-cPn |
| 1-2894 | H | — | tBu | 0 | 5-$(CH_2)_3C(=O)$-cPn |
| 1-2895 | H | — | tBu | 0 | 5-$(CH_2)C(=O)(CH_2)_5$-cPn |
| 1-2896 | H | — | tBu | 0 | 5-$(CH_2)_3C(=O)(CH_2)_4$-cPn |
| 1-2897 | H | — | tBu | 0 | 5-$(CH_2)_2C(=O)(CH_2)_5$-cPn |
| 1-2898 | H | — | tBu | 0 | 5-$(CH_2)_3C(=O)(CH_2)_5$-cPn |
| 1-2899 | H | — | tBu | 0 | 5-$(CH_2)C(=O)(CH_2)_4$-cPn |
| 1-2900 | H | — | tBu | 0 | 5-$(CH_2)_4C(=O)(CH_2)_5$-cPn |
| 1-2901 | H | — | tBu | 0 | 5-$(CH_2)CH(OH)(CH_2)_2$—Ph |
| 1-2902 | H | — | tBu | 0 | 5-$(CH_2)_4CH(OH)(CH_2)_2$-cPn |
| 1-2903 | H | — | tBu | 0 | 5-$(CH_2)_4CH(OH)(CH_2)_4$-cPn |
| 1-2904 | H | — | tBu | 0 | 5-$(CH_2)_3CH(OH)(CH_2)_5$-cPn |
| 1-2905 | H | — | tBu | 0 | 5-$(CH_2)_4CH(OH)(CH_2)_5$-cPn |
| 1-2906 | H | — | $SCH_3$ | 0 | 6-$(CH_2)O(CH_2)_3$-Imd(2-Et) |
| 1-2907 | H | — | iPr | 0 | 6-$(CH_2)O(CH_2)_3$-Imd |
| 1-2908 | H | — | iPr | 0 | 6-$(CH_2)O(CH_2)_2$-Imd |
| 1-2909 | H | — | $CH_3$ | 0 | 6-$(CH_2)O(CH_2)_3$-Imd |
| 1-2910 | H | — | tBu | 0 | 5-$(CH_2)_2CH(OH)(CH_2)_8CH_3$ |
| 1-2911 | H | — | tBu | 0 | 5-$(CH_2)_2CH(OH)(CH_2)_{10}CH_3$ |
| 1-2912 | H | — | tBu | 0 | 5-$(CH_2)_2CH(OB^2)(CH_2)_8CH_3$ |
| 1-2913 | H | — | tBu | 0 | 5-$(CH_2)_2CH(OB^4)(CH_2)_8CH_3$ |
| 1-2914 | H | — | tBu | 0 | 5-$(CH_2)_2CH(OB^{10})(CH_2)_8CH_3$ |
| 1-2915 | H | — | tBu | 0 | 5-$(CH_2)_2CH(OE^5)(CH_2)_8CH_3$ |
| 1-2916 | H | — | tBu | 0 | 5-$CH(OH)(CH_2)_{10}CH_3$ |
| 1-2917 | H | — | tBu | 0 | 6-$(CH_2)_2CH(OH)(CH_2)_8CH_3$ |
| 1-2918 | H | — | OtBu | 0 | 6-$(CH_2)O(CH_2)_3$-Imd |
| 1-2919 | H | — | tBu | 0 | 5-$CH_2$-Imd |
| 1-2920 | H | — | tBu | 0 | 5-$CH_2$-(2-EtImd) |
| 1-2921 | H | — | tBu | 0 | 5-$CH_2$-(2-EtImd) |
| 1-2922 | H | — | tBu | 0 | 5-$CH_2$-Imd |
| 1-2923 | H | — | tBu | 0 | 5-$CH_2$-(2-MeImd) |
| 1-2924 | H | — | tBu | 0 | 5-$CH_2$-(4,5-diMeImd) |
| 1-2925 | H | — | tBu | 0 | 5-$(CH_2)_2$-Imd |

TABLE 1-continued

| Cpd. No. | $R^a$ | $R^2$ | $R^3$ | n | $R^4$ |
|---|---|---|---|---|---|
| 1-2926 | H | — | tBu | 0 | 5-(CH$_2$)$_3$-Imd |

TABLE 2

| Cpd. No. | $R^a$ | $R^2$ | $R^3$ | n | $R^4$ |
|---|---|---|---|---|---|
| 2-1 | H | — | tBu | 0 | 5-CH(OH)-cHx |
| 2-2 | H | — | tBu | 0 | 5-CH(OH)(CH$_2$)-cHx |
| 2-3 | H | — | tBu | 0 | 5-CH(OH)(CH$_2$)$_2$-cHx |
| 2-4 | H | — | tBu | 0 | 5-CH(OH)(CH$_2$)$_3$-cHx |
| 2-5 | H | — | tBu | 0 | 5-CH(OH)(CH$_2$)$_4$-cHx |
| 2-6 | H | — | tBu | 0 | 5-CH(OH)(CH$_2$)$_5$-cHx |
| 2-7 | H | H | tBu | 1 | 5-CH(OH)(CH$_2$)$_6$-cHp |
| 2-8 | 2-Br | — | tBu | 0 | 5-CH(OH)(CH$_2$)$_5$-cPn |
| 2-9 | 2-Br | H | tBu | 1 | 5-CH(OH)(CH$_2$)$_4$-cHp |
| 2-10 | 2-Cl | — | tBu | 0 | 5-CH(OH)(CH$_2$)$_3$-cHx |
| 2-11 | H | — | tBu | 0 | 5-CH(OH)(CH$_2$)$_2$-cPn |
| 2-12 | H | — | tBu | 0 | 5-(CH$_2$)CH(OH)-cHx |
| 2-13 | H | — | tBu | 0 | 5-(CH$_2$)CH(OH)(CH$_2$)-cHx |
| 2-14 | H | — | tBu | 0 | 5-(CH$_2$)CH(OH)(CH$_2$)$_2$-cHx |
| 2-15 | H | — | tBu | 0 | 5-(CH$_2$)CH(OH)(CH$_2$)$_3$-cHx |
| 2-16 | 2-Me | — | tBu | 0 | 5-(CH$_2$)CH(OH)(CH$_2$)$_4$-cHx |
| 2-17 | H | — | tBu | 0 | 5-(CH$_2$)$_2$CH(OH)(CH$_2$)-cHp |
| 2-18 | H | H | tBu | 1 | 5-(CH$_2$)$_2$CH(OH)(CH$_2$)$_2$-cPn |
| 2-19 | H | — | tBu | 0 | 5-(CH$_2$)$_2$CH(OH)(CH$_2$)-cHx |
| 2-20 | H | — | tBu | 0 | 5-(CH$_2$)$_2$CH(OH)-cHp |
| 2-21 | H | — | tBu | 0 | 5-(CH$_2$)$_3$CH(OH)-cHx |
| 2-22 | H | — | tBu | 0 | 5-(CH$_2$)$_3$CH(OH)(CH$_2$)-cHx |
| 2-23 | H | — | tBu | 0 | 5-(CH$_2$)$_3$CH(OH)(CH$_2$)$_2$-cHx |
| 2-24 | H | — | tBu | 0 | 5-(CH$_2$)$_3$CH(OH)(CH$_2$)$_3$-cHx |
| 2-25 | 2-Br | H | tBu | 1 | 5-(CH$_2$)$_3$CH(OH)(CH$_2$)$_2$-cHp |
| 2-26 | H | — | tBu | 0 | 5-(CH$_2$)$_3$CH(OH)(CH$_2$)-cPn |
| 2-27 | H | — | tBu | 0 | 5-(CH$_2$)$_3$CH(OH)-cHp |
| 2-28 | H | — | tBu | 0 | 5-(CH$_2$)$_4$CH(OH)-cHx |
| 2-29 | H | — | tBu | 0 | 5-(CH$_2$)$_4$CH(OH)(CH$_2$)-cHx |
| 2-30 | H | — | tBu | 0 | 5-(CH$_2$)$_4$CH(OH)(CH$_2$)$_2$-cHx |
| 2-31 | H | — | tBu | 0 | 5-(CH$_2$)$_4$CH(OH)(CH$_2$)-cHp |
| 2-32 | H | H | tBu | 1 | 5-(CH$_2$)$_4$CH(OH)-cPn |
| 2-33 | H | — | tBu | 0 | 5-CH(OH)Ph |
| 2-34 | H | — | tBu | 0 | 5-CH(OH)(CH$_2$)$_3$Ph |
| 2-35 | H | — | tBu | 0 | 5-(CH$_2$)CH(OH)(CH$_2$)$_2$Ph |
| 2-36 | H | — | tBu | 0 | 5-(CH$_2$)CH(OH)(CH$_2$)$_4$Ph |
| 2-37 | H | — | tBu | 0 | 5-(CH$_2$)$_2$CH(OH)Ph |
| 2-38 | H | — | tBu | 0 | 5-(CH$_2$)$_2$CH(OH)CH$_2$(4-MePh) |
| 2-39 | H | — | tBu | 0 | 5-(CH$_2$)$_2$CH(OH)(CH$_2$)$_3$Ph |
| 2-40 | H | — | tBu | 0 | 5-(CH$_2$)$_3$CH(OH)(4-MePh) |
| 2-41 | H | — | tBu | 0 | 5-(CH$_2$)$_4$CH(OH)(2-ClPh) |
| 2-42 | 2-Br | H | tBu | 1 | 5-(CH$_2$)$_5$CH(OH)(2-MePh) |
| 2-43 | H | — | tBu | 0 | 5-CH(OB$^2$)-cHx Na salt |
| 2-44 | H | — | tBu | 0 | 5-CH(OB$^2$)(CH$_2$)-cHx Na salt |
| 2-45 | H | — | tBu | 0 | 5-CH(OB$^2$)(CH$_2$)$_2$-cHx Na salt |
| 2-46 | 2-Br | — | tBu | 0 | 5-CH(OB$^2$)(CH$_2$)$_3$-cHx Na salt |
| 2-47 | H | — | tBu | 0 | 5-CH(OB$^2$)(CH$_2$)$_4$-cHx Na salt |
| 2-48 | H | — | tBu | 0 | 5-CH(OB$^2$)(CH$_2$)$_5$-cHp Na salt |
| 2-49 | H | — | tBu | 0 | 5-CH(OB$^2$)(CH$_2$)$_4$-Ph Na salt |
| 2-50 | H | — | tBu | 0 | 5-CH(OE$^1$)(CH$_2$)$_2$-cPn HCl salt |
| 2-51 | H | — | tBu | 0 | 5-CH(OE$^1$)-cHp HCl salt |
| 2-52 | H | — | tBu | 0 | 5-(CH$_2$)CH(OB$^2$)-cHx Na salt |
| 2-53 | H | — | tBu | 0 | 5-(CH$_2$)CH(OB$^2$)(CH$_2$)-cHx Na salt |
| 2-54 | H | — | tBu | 0 | 5-(CH$_2$)CH(OB$^2$)(CH$_2$)$_2$-cHx Na salt |
| 2-55 | H | — | tBu | 0 | 5-(CH$_2$)CH(OB$^2$)(CH$_2$)$_3$-cHx Na salt |
| 2-56 | H | — | tBu | 0 | 5-(CH$_2$)CH(OB$^2$)(CH$_2$)$_4$-cHx Na salt |
| 2-57 | H | — | tBu | 0 | 5-CH$_2$CH(OD$^1$)(CH$_2$)$_5$-cHx Na salt |
| 2-58 | H | — | tBu | 0 | 5-(CH$_2$)$_2$CH(OB$^2$)-cHx Na salt |
| 2-59 | H | — | tBu | 0 | 5-(CH$_2$)$_2$CH(OB$^2$)(CH$_2$)-cHx Na salt |
| 2-60 | H | — | tBu | 0 | 5-(CH$_2$)$_2$CH(OB$^2$)(CH$_2$)$_2$-cHx Na salt |
| 2-61 | H | — | tBu | 0 | 5-(CH$_2$)$_2$CH(OB$^2$)(CH$_2$)$_3$-cHx Na salt |
| 2-62 | 2-Cl | — | tBu | 0 | 5-(CH$_2$)$_2$CH(OB$^2$)(CH$_2$)$_4$-cHx Na salt |
| 2-63 | H | — | tBu | 0 | 5-(CH$_2$)$_2$CH(OB$^2$)(CH$_2$)$_3$-Ph Na salt |
| 2-64 | H | — | tBu | 0 | 5-(CH$_2$)$_2$CH(OB$^2$)(CH$_2$)$_2$-cHp Na salt |
| 2-65 | H | H | tBu | 1 | 5-(CH$_2$)$_2$CH(OD$^1$)(CH$_2$)$_2$-cHp Na salt |
| 2-66 | H | H | tBu | 1 | 5-(CH$_2$)$_2$CH(OE$^1$)-cPn HCl salt |
| 2-67 | H | H | tBu | 1 | 5-(CH$_2$)$_3$CH(OB$^2$)-cHx Na salt |
| 2-68 | H | H | tBu | 1 | 5-(CH$_2$)$_4$CH(OB$^2$)-cHx Na salt |
| 2-69 | H | H | tBu | 1 | 5-(CH$_2$)$_3$CH(OB$^3$)(CH$_2$)$_2$-cHx Na salt |
| 2-70 | H | H | tBu | 1 | 5-(CH$_2$)$_3$CH(OB$^2$)(CH$_2$)$_3$-cHx Na salt |
| 2-71 | H | — | tBu | 1 | 5-(CH$_2$)$_3$CH(OB$^2$)(CH$_2$)-cPn Na salt |
| 2-72 | H | — | tBu | 0 | 5-(CH$_2$)$_3$CH(OB$^2$)-Ph Na salt |
| 2-73 | H | — | tBu | 0 | 5-(CH$_2$)$_4$CH(OB$^2$)-cHx Na salt |
| 2-74 | 2-Br | — | tBu | 0 | 5-(CH$_2$)$_4$CH(OB$^2$)-cHp |
| 2-75 | H | — | iPr | 0 | 6-CH(OH)-cHx |
| 2-76 | H | — | iPr | 0 | 6-CH(OH)CH$_2$-cHp |
| 2-77 | H | — | iPr | 0 | 6-CH(OH)(CH$_2$)$_3$-cPn |
| 2-78 | H | — | iPr | 0 | 6-CH(OH)(CH$_2$)$_5$(2-ClPh) |
| 2-79 | H | — | iPr | 0 | 6-(CH$_2$)CH(OH)-cHx |
| 2-80 | H | — | iPr | 0 | 6-(CH$_2$)CH(OH)(CH$_2$)$_2$-cPn |
| 2-81 | 2-Br | — | iPr | 0 | 6-(CH$_2$)CH(OH)(CH$_2$)$_4$-cHp |
| 2-82 | H | — | iPr | 0 | 6-(CH$_2$)$_2$CH(OH)-cHx |
| 2-83 | H | — | iPr | 0 | 6-(CH$_2$)$_2$CH(OH)(CH$_2$)-cHp |
| 2-84 | H | — | iPr | 0 | 6-(CH$_2$)$_2$CH(OH)(CH$_2$)$_3$-cPn |
| 2-85 | H | — | iPr | 0 | 6-(CH$_2$)$_3$CH(OH)-cHx |
| 2-86 | H | — | iPr | 0 | 6-(CH$_2$)$_3$CH(OH)(CH$_2$)Ph |
| 2-87 | H | — | iPr | 0 | 6-(CH$_2$)$_3$CH(OH)(CH$_2$)$_3$-cHp |
| 2-88 | H | — | iPr | 0 | 6-(CH$_2$)$_4$CH(OH)-cHx |
| 2-89 | 2-MeO | H | iPr | 1 | 6-(CH$_2$)$_4$CH(OH)-cPn |
| 2-90 | H | — | iPr | 0 | 6-CH(OB$^2$)-cHx Na salt |
| 2-91 | H | — | iPr | 0 | 6-CH(OB$^2$)(CH$_2$)-cHx Na salt |
| 2-92 | H | — | iPr | 0 | 6-CH(OB$^2$)(CH$_2$)$_3$-cHx Na salt |
| 2-93 | H | — | iPr | 0 | 6-CH(OB$^2$)(CH$_2$)$_5$-cHx Na salt |
| 2-94 | H | — | iPr | 0 | 6-(CH$_2$)CH(OB$^2$)-cHx Na salt |
| 2-95 | H | — | iPr | 0 | 6-(CH$_2$)CH(OB$^2$)(CH$_2$)$_3$-cHx Na salt |
| 2-96 | H | — | iPr | 0 | 6-(CH$_2$)$_2$CH(OB$^2$)-cHx Na salt |
| 2-97 | H | — | iPr | 0 | 6-(CH$_2$)$_2$CH(OB$^2$)(CH$_2$)-cHx |

TABLE 2-continued

| Cpd. No. | R$^a$ | R$^2$ | R$^3$ | n | R$^4$ |
|---|---|---|---|---|---|
| 2-98 | H | — | iPr | 0 | 6-(CH$_2$)$_2$CH(OB$^2$)(CH$_2$)$_2$-cHx Na salt |
| 2-99 | H | — | iPr | 0 | 6-(CH$_2$)$_2$CH(OB$^2$)(CH$_2$)$_3$-cHx Na salt |
| 2-100 | H | — | iPr | 0 | 6-(CH$_2$)$_2$CH(OB$^2$)(CH$_2$)$_4$-cHx Na salt |
| 2-101 | H | — | iPr | 0 | 6-(CH$_2$)$_2$CH(OD$^1$)(CH$_2$)-cHp Na salt |
| 2-102 | H | — | iPr | 0 | 6-(CH$_2$)$_2$CH(OE$^1$)(CH$_2$)-cPn HCl salt |
| 2-103 | H | — | iPr | 0 | 6-(CH$_2$)$_3$CH(OB$^2$)-cHx Na salt |
| 2-104 | H | H | tBu | 1 | 6-(CH$_2$)$_3$CH(OB$^2$)-cHp Na salt |
| 2-105 | H | H | tBu | 1 | 6-(CH$_2$)$_4$CH(OB$^2$)-cHx Na salt |
| 2-106 | H | — | iPr | 0 | 6-CH$_2$O(CH$_2$)$_3$Imd HCl salt |
| 2-107 | H | — | iPr | 0 | 6-CH$_2$O(CH$_2$)$_4$Imd HCl salt |
| 2-108 | H | — | iPr | 0 | 6-CH$_2$O(CH$_2$)$_5$Imd HCl salt |
| 2-109 | H | H | iPr | 1 | 6-CH$_2$O(CH$_2$)$_3$Imd HCl salt |
| 2-110 | 2-Br | — | tBu | 0 | 5-CH$_2$O(CH$_2$)$_3$Imd HCl salt |
| 2-111 | H | — | tBu | 0 | 5-CH=CH—CH(OH)(CH$_2$)-cHx |
| 2-112 | H | — | iPr | 0 | 5-CH=CH—CH(OH)(CH$_2$)-cHx |
| 2-113 | H | — | tBu | 0 | 5-C(=O)(CH$_2$)-cHx |
| 2-114 | H | — | iPr | 0 | 6-(CH$_2$)$_2$C(=O)(CH$_2$)-cHx |
| 2-115 | H | — | tBu | 0 | 5-(CH$_2$)$_2$C(=O)(CH$_2$)-cHx |
| 2-116 | H | — | tBu | 0 | 6-C(=O)(CH$_2$)-cHx |
| 2-117 | H | — | S-Me | 0 | 6-(CH$_2$)O(CH$_2$)$_3$-Imd HCl |
| 2-118 | H | — | iPr | 0 | 6-(CH$_2$)O(CH$_2$)$_3$-Imd HCl |
| 2-119 | H | — | tBu | 0 | 6-(CH$_2$)O(CH$_2$)$_3$-Imd HCl |
| 2-120 | H | — | OtBu | 0 | 6-(CH$_2$)O(CH$_2$)$_3$-Imd HCl |

TABLE 3

| Cpd. No. | R$^a$ | n | m | R$^2$ | R$^3$ | R$^4$ |
|---|---|---|---|---|---|---|
| 3-1 | H | 0 | 2 | — | tBu | 5-CH(OH)-cHx |
| 3-2 | H | 0 | 2 | — | tBu | 5-CH(OH)(CH$_2$)-cHx |
| 3-3 | H | 0 | 2 | — | tBu | 5-CH(OH)(CH$_2$)$_2$-cHx |
| 3-4 | H | 0 | 2 | — | tBu | 5-CH(OH)(CH$_2$)$_3$-cHx |
| 3-5 | H | 0 | 2 | — | tBu | 5-CH(OH)(CH$_2$)$_4$-cHx |
| 3-6 | H | 0 | 2 | — | tBu | 5-CH(OH)(CH$_2$)$_5$-cHx |
| 3-7 | 2-Cl | 1 | 3 | H | tBu | 5-CH(OH)(CH$_2$)$_6$-cHp |
| 3-8 | H | 0 | 2 | — | tBu | 5-CH(OH)(CH$_2$)$_5$-cPn |
| 3-9 | H | 1 | 2 | H | tBu | 5-CH(OH)(CH$_2$)$_4$-cHp |
| 3-10 | H | 1 | 2 | H | tBu | 5-CH(OH)(CH$_2$)$_3$-cHx |
| 3-11 | H | 0 | 2 | — | tBu | 5-CH(OH)(CH$_2$)$_2$-cPn |
| 3-12 | H | 0 | 2 | — | tBu | 5-(CH$_2$)CH(OH)-cHx |
| 3-13 | H | 0 | 2 | — | tBu | 5-(CH$_2$)CH(OH)(CH$_2$)-cHx |
| 3-14 | H | 0 | 2 | — | tBu | 5-(CH$_2$)CH(OH)(CH$_2$)$_2$-cHx |
| 3-15 | H | 0 | 2 | — | tBu | 5-(CH$_2$)CH(OH)(CH$_2$)$_3$-cHx |
| 3-16 | H | 0 | 2 | — | tBu | 5-(CH$_2$)CH(OH)(CH$_2$)$_4$-cHx |
| 3-17 | H | 1 | 2 | Bu | iPr | 5-(CH$_2$)$_2$CH(OH)(CH$_2$)-cHp |
| 3-18 | H | 1 | 3 | Pn | tBu | 5-(CH$_2$)$_2$CH(OH)(CH$_2$)$_2$-cPn |
| 3-19 | H | 1 | 2 | H | tBu | 5-(CH$_2$)$_2$CH(OH)(CH$_2$)-cHx |
| 3-20 | H | 1 | 2 | Hp | tBu | 5-(CH$_2$)$_2$CH(OH)-cHp |
| 3-21 | 3-Cl | 1 | 2 | Hp | tBu | 5-(CH$_2$)$_3$CH(OH)-cHx |
| 3-22 | 3-Br | 1 | 2 | Hp | tBu | 5-(CH$_2$)$_3$CH(OH)(CH$_2$)-cHx |
| 3-23 | 3-OMe | 1 | 2 | Hp | tBu | 5-(CH$_2$)$_3$CH(OH)(CH$_2$)$_2$-cHx |
| 3-24 | 2-OMe | 1 | 2 | Hp | tBu | 5-(CH$_2$)$_3$CH(OH)(CH$_2$)$_3$-cHx |
| 3-25 | H | 0 | 2 | — | tBu | 5-(CH$_2$)$_3$CH(OH)(CH$_2$)$_2$-cHx |
| 3-26 | H | 0 | 2 | — | tBu | 5-(CH$_2$)$_3$CH(OH)(CH$_2$)-cPn |
| 3-27 | H | 0 | 2 | — | tBu | 5-(CH$_2$)$_3$CH(OH)-cHp |
| 3-28 | H | 0 | 2 | — | tBu | 5-(CH$_2$)$_4$CH(OH)-cHx |
| 3-29 | H | 0 | 2 | — | tBu | 5-(CH$_2$)$_4$CH(OH)(CH$_2$)-cHx |
| 3-30 | H | 0 | 2 | — | tBu | 5-(CH$_2$)$_4$CH(OH)(CH$_2$)$_2$-cHx |
| 3-31 | 3-Cl | 0 | 2 | — | tBu | 5-(CH$_2$)$_4$CH(OH)(CH$_2$)$_2$-cHp |
| 3-32 | H | 1 | 2 | — | tBu | 5-(CH$_2$)$_4$CH(OH)-cPn |
| 3-33 | H | 0 | 2 | — | tBu | 5-CH(OH)Ph |
| 3-34 | H | 0 | 2 | — | tBu | 5-CH(OH)(CH$_2$)$_3$Ph |
| 3-35 | H | 0 | 2 | — | tBu | 5-(CH$_2$)CH(OH)(CH$_2$)$_2$Ph |
| 3-36 | H | 0 | 2 | — | tBu | 5-(CH$_2$)CH(OH)(CH$_2$)$_4$Ph |
| 3-37 | H | 0 | 2 | — | tBu | 5-(CH$_2$)$_2$CH(OH)Ph |
| 3-38 | H | 0 | 2 | — | tBu | 5-(CH$_2$)$_2$CH(OH)CH$_2$(4-MePh) |
| 3-39 | H | 0 | 2 | — | tBu | 5-(CH$_2$)$_2$CH(OH)(CH$_2$)$_3$Ph |
| 3-40 | H | 0 | 2 | — | tBu | 5-(CH$_2$)$_3$CH(OH)(4-MePh) |
| 3-41 | H | 0 | 2 | — | tBu | 5-(CH$_2$)$_4$CH(OH)(2-ClPh) |
| 3-42 | H | 1 | 3 | — | tBu | 5-(CH$_2$)$_5$CH(OH)(2-MePh) |
| 3-43 | H | 0 | 2 | — | tBu | 5-CH(OB$^2$)-cHx Na salt |
| 3-44 | H | 0 | 2 | — | tBu | 5-CH(OB$^2$)(CH$_2$)-cHx Na salt |
| 3-45 | H | 0 | 2 | — | tBu | 5-CH(OB$^2$)(CH$_2$)$_2$-cHx Na salt |

TABLE 3-continued

| Cpd. No. | $R^a$ | n | m | $R^2$ | $R^3$ | $R^4$ |
|---|---|---|---|---|---|---|
| 3-46 | H | 0 | 2 | — | tBu | 5-CH(OB$^2$)(CH$_2$)$_3$-cHx Na salt |
| 3-47 | H | 0 | 2 | — | tBu | 5-CH(OB$^2$)(CH$_2$)$_4$-cHx Na salt |
| 3-48 | H | 0 | 2 | — | tBu | 5-CH(OB$^2$)(CH$_2$)$_5$-cHp Na salt |
| 3-49 | H | 0 | 2 | — | tBu | 5-CH(OB$^2$)(CH$_2$)$_4$-Ph Na salt |
| 3-50 | H | 0 | 2 | — | tBu | 5-CH(OE$^1$)(CH$_2$)$_2$-cPn HCl salt |
| 3-51 | H | 0 | 2 | — | tBu | 5-CH(OE$^1$)-cHp HCl salt |
| 3-52 | H | 0 | 2 | — | tBu | 5-(CH$_2$)CH(OB$^2$)-cHx Na salt |
| 3-53 | H | 0 | 2 | — | tBu | 5-(CH$_2$)CH(OB$^2$)(CH$_2$)-cHx Na salt |
| 3-54 | H | 0 | 2 | — | tBu | 5-(CH$_2$)CH(OB$^2$)(CH$_2$)$_2$-cHx Na salt |
| 3-55 | H | 0 | 2 | — | tBu | 5-(CH$_2$)CH(OB$^2$)(CH$_2$)$_3$-cHx Na salt |
| 3-56 | H | 0 | 2 | — | tBu | 5-(CH$_2$)CH(OB$^2$)(CH$_2$)$_4$-cHx Na salt |
| 3-57 | H | 0 | 2 | — | tBu | 5-CH$_2$CH(OD$^1$)(CH$_2$)$_5$-cHx Na salt |
| 3-58 | H | 0 | 2 | — | tBu | 5-(CH$_2$)$_2$CH(OB$^2$)-cHx Na salt |
| 3-59 | H | 0 | 2 | — | tBu | 5-(CH$_2$)$_2$CH(OB$^2$)(CH$_2$)-cHx Na salt |
| 3-60 | H | 0 | 2 | — | tBu | 5-(CH$_2$)$_2$CH(OB$^2$)(CH$_2$)$_2$-cHx Na salt |
| 3-61 | H | 0 | 2 | — | tBu | 5-(CH$_2$)$_2$CH(OB$^2$)(CH$_2$)$_3$-cHx Na salt |
| 3-62 | 2-Cl | 0 | 2 | — | tBu | 5-(CH$_2$)$_2$CH(OB$^2$)(CH$_2$)$_4$-cHx Na salt |
| 3-63 | H | 0 | 2 | — | tBu | 5-(CH$_2$)$_2$CH(OB$^2$)(CH$_2$)$_3$-Ph Na salt |
| 3-64 | H | 0 | 2 | — | tBu | 5-(CH$_2$)$_2$CH(OB$^2$)(CH$_2$)$_2$-cHp Na salt |
| 3-65 | H | 1 | 2 | H | tBu | 5-(CH$_2$)$_2$CH(OD$^1$)(CH$_2$)$_2$-cHp Na salt |
| 3-66 | H | 1 | 2 | H | tBu | 5-(CH$_2$)$_2$CH(OE$^1$)-cPn HCl salt |
| 3-67 | H | 1 | 2 | H | tBu | 5-(CH$_2$)$_3$CH(OB$^2$)-cHx Na salt |
| 3-68 | H | 1 | 3 | H | tBu | 5-(CH$_2$)$_3$CH(OB$^2$)-cHx Na salt |
| 3-69 | H | 1 | 2 | H | tBu | 5-(CH$_2$)$_3$CH(OB$^3$)(CH$_2$)$_2$-cHx Na salt |
| 3-70 | H | 1 | 2 | H | tBu | 5-(CH$_2$)$_3$CH(OB$^2$)(CH$_2$)$_3$-cHx Na salt |
| 3-71 | H | 0 | 2 | — | tBu | 5-(CH$_2$)$_3$CH(OB$^2$)(CH$_2$)-cPn Na salt |
| 3-72 | H | 0 | 2 | — | tBu | 5-(CH$_2$)$_3$CH(OB$^2$)-Ph Na salt |
| 3-73 | H | 0 | 2 | — | tBu | 5-(CH$_2$)$_4$CH(OB$^2$)-cHx Na salt |
| 3-74 | H | 0 | 2 | — | tBu | 5-(CH$_2$)$_4$CH(OB$^2$)-cHp |
| 3-75 | H | 0 | 2 | — | iPr | 6-CH(OH)-cHx |
| 3-76 | H | 0 | 2 | — | iPr | 6-CH(OH)CH$_2$-cHp |
| 3-77 | H | 0 | 2 | — | iPr | 6-CH(OH)(CH$_2$)$_3$-cPn |
| 3-78 | H | 0 | 2 | — | iPr | 6-CH(OH)(CH$_2$)$_5$-(2-ClPh) |
| 3-79 | 4-Me | 0 | 2 | — | iPr | 6-CH$_2$)CH(OH)-cHx |
| 3-80 | H | 0 | 2 | — | iPr | 6-(CH$_2$)CH(OH)(CH$_2$)$_2$-cPn |
| 3-81 | H | 0 | 2 | — | iPr | 6-(CH$_2$)CH(OH)(CH$_2$)$_4$-cHp |
| 3-82 | H | 0 | 2 | — | iPr | 6-(CH$_2$)$_2$CH(OH)-cHx |
| 3-83 | H | 0 | 2 | — | iPr | 6-(CH$_2$)$_2$CH(OH)(CH$_2$)-cHp |
| 3-84 | H | 0 | 2 | — | iPr | 6-(CH$_2$)$_2$CH(OH)(CH$_2$)$_3$-cPn |
| 3-85 | H | 0 | 2 | — | iPr | 6-(CH$_2$)$_3$CH(OH)-cHx |
| 3-86 | H | 0 | 2 | — | iPr | 6-(CH$_2$)$_3$CH(OH)(CH$_2$)Ph |
| 3-87 | H | 0 | 2 | — | iPr | 6-(CH$_2$)$_3$CH(OH)(CH$_2$)$_3$-cHp |
| 3-88 | H | 0 | 2 | — | iPr | 6-(CH$_2$)$_4$CH(OH)-cHx |
| 3-89 | H | 1 | 3 | H | iPr | 6-(CH$_2$)$_4$CH(OH)-cPn |
| 3-90 | H | 0 | 2 | — | iPr | 6-CH(OB$^2$)-cHx Na salt |
| 3-91 | H | 0 | 2 | — | iPr | 6-CH(OB$^2$)(CH$_2$)-cHx Na salt |
| 3-92 | H | 0 | 2 | — | iPr | 6-CH(OB$^2$)(CH$_2$)$_3$-cHx Na salt |

TABLE 3-continued

| Cpd. No. | R$^a$ | n | m | R$^2$ | R$^3$ | R$^4$ |
|---|---|---|---|---|---|---|
| 3-93 | H | 0 | 2 | — | iPr | 6-CH(OB$^2$)(CH$_2$)$_5$-cHx Na salt |
| 3-94 | H | 0 | 2 | — | iPr | 6-(CH$_2$)CH(OB$^2$)-cHx Na salt |
| 3-95 | H | 0 | 2 | — | iPr | 6-(CH$_2$)CH(OB$^2$)(CH$_2$)$_3$-cHx Na salt |
| 3-96 | H | 0 | 2 | — | iPr | 6-(CH$_2$)CH(OB$^2$)-cHx Na salt |
| 3-97 | H | 0 | 2 | — | iPr | 6-(CH$_2$)CH(OB$^2$)(CH$_2$)-cHx Na salt |
| 3-98 | H | 0 | 2 | — | iPr | 6-(CH$_2$)CH(OB$^2$)(CH$_2$)$_2$-cHx Na salt |
| 3-99 | H | 0 | 2 | — | iPr | 6-(CH$_2$)CH(OB$^2$)(CH$_2$)$_3$-cHx Na salt |
| 3-100 | H | 0 | 2 | — | iPr | 6-(CH$_2$)$_2$CH(OB$^2$)(CH$_2$)$_4$-cHx Na salt |
| 3-101 | H | 0 | 2 | — | i-Pr | 6-(CH$_2$)$_2$CH(OD$^1$)(CH$_2$)-cHp Na salt |
| 3-102 | H | 0 | 2 | — | iPr | 6-(CH$_2$)CH(OE$^1$)(CH$_2$)-cPn HCl salt |
| 3-103 | H | 0 | 2 | — | iPr | 6-(CH$_2$)CH(OB$^2$)-cHx Na salt |
| 3-104 | H | 1 | 2 | H | tBu | 6-(CH$_2$)$_4$CH(OB$^2$)-cHp Na salt |
| 3-105 | H | 1 | 2 | H | tBu | 6-(CH$_2$)$_4$CH(OB$^2$)-cHx Na salt |
| 3-106 | H | 0 | 2 | — | iPr | 6-CH$_2$O(CH$_2$)$_3$Imd HCl salt |
| 3-107 | H | 0 | 2 | — | iPr | 6-CH$_2$O(CH$_2$)$_4$Imd HCl salt |
| 3-108 | H | 0 | 2 | — | iPr | 6-CH$_2$O(CH$_2$)$_5$Imd HCl salt |
| 3-109 | H | 1 | 2 | H | iPr | 6-CH$_2$O(CH$_2$)$_3$Imd HCl salt |
| 3-110 | H | 0 | 2 | — | tBu | 6-CH$_2$O(CH$_2$)$_3$Imd |
| 3-111 | H | 0 | 2 | — | tBu | 5-CH=CH—CH(OH)(CH$_2$)-cHx |
| 3-112 | H | 0 | 2 | — | iPr | 6-CH=CH—CH(OH)(CH$_2$)-cHx |
| 3-113 | H | 0 | 2 | — | tBu | 5-C(=O)CH$_2$-cHx |
| 3-114 | H | 0 | 2 | — | iPr | 6-(CH$_2$)$_2$—C(=O)(CH$_2$)-cHx |
| 3-115 | H | 0 | 2 | — | tBu | 5-(CH$_2$)$_2$—C(=O)(CH$_2$)-cHx |
| 3-116 | H | 0 | 2 | — | tBu | 6-C(=O)—(CH$_2$)-cHx |
| 3-117 | H | 0 | 2 | — | tBu | 5-(CH$_2$)$_2$CH(OH)(CH$_2$)-cHx |
| 3-118 | H | 0 | 2 | — | SCH$_3$ | 6-(CH$_2$)O(CH$_2$)$_3$-Imd HCl |
| 3-119 | H | 0 | 2 | — | tBu | 5-(CH$_2$)$_2$CH(OE$^5$)(CH$_2$)$_2$-cHx HCl |
| 3-120 | H | 0 | 2 | — | tBu | 5-(CH$_2$)$_2$CH(OB$^4$)(CH$_2$)$_2$-cHx Na salt |
| 3-121 | H | 0 | 2 | — | tBu | 5-(CH$_2$)$_2$CH(OB$^{10}$)(CH$_2$)$_4$-cHx Na salt |
| 3-122 | H | 0 | 2 | — | tBu | 5-(CH$_2$)$_2$CH(OH)(CH$_2$)—O—cHx |
| 3-123 | H | 0 | 2 | — | tBu | 5-(CH$_2$)$_2$CH(OH)(CH$_2$)$_8$CH$_3$ |
| 3-124 | H | 0 | 2 | — | tBu | 5-(CH$_2$)CH(OH)(CH$_2$)$_8$CH$_3$ |
| 3-125 | H | 0 | 2 | — | tBu | 5-CH(OH)(CH$_2$)$_{10}$CH$_3$ |
| 3-126 | H | 0 | 2 | — | OtBu | 6-(CH$_2$)O(CH$_2$)$_3$-Imd HCl |

TABLE 4

| Cpd. No. | n | R$^2$ | R$^3$ | R$^4$ |
|---|---|---|---|---|
| 4-1 | 0 | — | tBu | 5-CH(OH)-cHx |
| 4-2 | 0 | — | tBu | 5-CH(OH)(CH$_2$)-cHx |
| 4-3 | 0 | — | tBu | 5-CH(OH)(CH$_2$)$_2$-cHx |
| 4-4 | 0 | — | tBu | 5-CH(OH)(CH$_2$)$_3$-cHx |
| 4-5 | 0 | — | tBu | 5-CH(OH)(CH$_2$)$_4$-cHx |
| 4-6 | 0 | — | tBu | 5-CH(OH)(CH$_2$)$_5$-cHx |
| 4-7 | 1 | H | tBu | 5-CH(OH)(CH$_2$)$_6$-cHp |
| 4-8 | 0 | — | tBu | 5-CH(OH)(CH$_2$)$_5$-cPn |
| 4-9 | 1 | H | tBu | 5-CH(OH)(CH$_2$)$_4$-cHp |
| 4-10 | 1 | H | tBu | 5-CH(OH)(CH$_2$)$_3$-cHx |
| 4-11 | 0 | — | tBu | 5-CH(OH)(CH$_2$)$_2$-cPn |
| 4-12 | 0 | — | tBu | 5-(CH$_2$)CH(OH)-cHx |
| 4-13 | 0 | — | tBu | 5-(CH$_2$)CH(OH)(CH$_2$)-cHx |
| 4-14 | 0 | — | tBu | 5-(CH$_2$)CH(OH)(CH$_2$)$_2$-cHx |
| 4-15 | 0 | — | tBu | 5-(CH$_2$)CH(OH)(CH$_2$)$_3$-cHx |
| 4-16 | 0 | — | tBu | 5-(CH$_2$)CH(OH)(CH$_2$)$_4$-cHx |
| 4-17 | 0 | — | tBu | 5-(CH$_2$)$_2$CH(OH)(CH$_2$)-cHp |
| 4-18 | 1 | H | tBu | 5-(CH$_2$)$_2$CH(OH)(CH$_2$)$_2$-cPn |
| 4-19 | 0 | — | tBu | 5-(CH$_2$)$_2$CH(OH)(CH$_2$)-cHx |
| 4-20 | 0 | — | tBu | 5-(CH$_2$)$_2$CH(OH)-cHp |
| 4-21 | 0 | — | tBu | 5-(CH$_2$)$_3$CH(OH)-cHx |
| 4-22 | 0 | — | tBu | 5-(CH$_2$)$_3$CH(OH)(CH$_2$)-cHx |
| 4-23 | 0 | — | tBu | 5-(CH$_2$)$_3$CH(OH)(CH$_2$)$_2$-cHx |
| 4-24 | 0 | — | tBu | 5-(CH$_2$)$_3$CH(OH)(CH$_2$)$_3$-cHx |
| 4-25 | 1 | H | tBu | 5-(CH$_2$)$_3$CH(OH)(CH$_2$)$_2$-cHp |
| 4-26 | 0 | — | tBu | 5-(CH$_2$)$_3$CH(OH)(CH$_2$)-cPn |
| 4-27 | 0 | — | tBu | 5-(CH$_2$)$_3$CH(OH)-cHp |
| 4-28 | 0 | — | tBu | 5-(CH$_2$)$_4$CH(OH)-cHx |
| 4-29 | 0 | — | tBu | 5-(CH$_2$)$_4$CH(OH)(CH$_2$)-cHx |
| 4-30 | 0 | — | tBu | 5-(CH$_2$)$_4$CH(OH)(CH$_2$)$_2$-cHx |

TABLE 4-continued

| Cpd. No. | n | R² | R³ | R⁴ |
|---|---|---|---|---|
| 4-31 | 0 | — | tBu | 5-(CH₂)₄CH(OH)(CH₂)-cHp |
| 4-32 | 1 | H | tBu | 5-(CH₂)₄CH(OH)-cPn |
| 4-33 | 0 | — | tBu | 5-CH(OH)Ph |
| 4-34 | 0 | — | tBu | 5-CH(OH)(CH₂)₃Ph |
| 4-35 | 0 | — | tBu | 5-(CH₂)CH(OH)(CH₂)₂Ph |
| 4-36 | 0 | — | tBu | 5-(CH₂)CH(OH)(CH₂)₄Ph |
| 4-37 | 0 | — | tBu | 5-(CH₂)CH(OH)Ph |
| 4-38 | 0 | — | tBu | 5-(CH₂)₂CH(OH)CH₂(4-MePh) |
| 4-39 | 0 | — | tBu | 5-(CH₂)₂CH(OH)(CH₂)₃Ph |
| 4-40 | 0 | — | tBu | 5-(CH₂)₃CH(OH)(4-MePh) |
| 4-41 | 0 | — | tBu | 5-(CH₂)₄CH(OH)(2-ClPh) |
| 4-42 | 1 | H | tBu | 5-(CH₂)₅CH(OH)(2-MePh) |
| 4-43 | 0 | — | tBu | 5-CH(OB²)-cHx Na salt |
| 4-44 | 0 | — | tBu | 5-CH(OB²)(CH₂)-cHx Na salt |
| 4-45 | 0 | — | tBu | 5-CH(OB²)(CH₂)₂-cHx Na salt |
| 4-46 | 0 | — | tBu | 5-CH(OB²)(CH₂)₃-cHx Na salt |
| 4-47 | 0 | — | tBu | 5-CH(OB²)(CH₂)₄-cHx Na salt |
| 4-48 | 0 | — | tBu | 5-CH(OB²)(CH₂)₅-cHp Na salt |
| 4-49 | 0 | — | tBu | 5-CH(OB²)(CH₂)₄-Ph Na salt |
| 4-50 | 0 | — | tBu | 5-CH(OE¹)(CH₂)₂-cPn HCl salt |
| 4-51 | 0 | — | tBu | 5-CH(OE¹)-cHp HCl salt |
| 4-52 | 0 | — | tBu | 5-(CH₂)CH(OB²)-cHx Na salt |
| 4-53 | 0 | — | tBu | 5-(CH₂)CH(OB²)(CH₂)-cHx Na salt |
| 4-54 | 0 | — | tBu | 5-(CH₂)CH(OB²)(CH₂)₂-cHx Na salt |
| 4-55 | 0 | — | tBu | 5-(CH₂)CH(OB²)(CH₂)₃-cHx Na salt |
| 4-56 | 0 | — | tBu | 5-(CH₂)CH(OB²)(CH₂)₄-cHx Na salt |
| 4-57 | 0 | — | tBu | 5-CH₂CH(OD¹)(CH₂)₅-cHx Na salt |
| 4-58 | 0 | — | tBu | 5-(CH₂)₂CH(OB²)-cHx Na salt |
| 4-59 | 0 | — | tBu | 5-(CH₂)₂CH(OB²)(CH₂)-cHx Na salt |
| 4-60 | 0 | — | tBu | 5-(CH₂)₂CH(OB²)(CH₂)₂-cHx Na salt |
| 4-61 | 0 | — | tBu | 5-(CH₂)₂CH(OB²)(CH₂)₃-cHx Na salt |
| 4-62 | 0 | — | tBu | 5-(CH₂)₂CH(OB²)(CH₂)₄-cHx Na salt |
| 4-63 | 0 | — | tBu | 5-(CH₂)₂CH(OB²)(CH₂)₃-Ph Na salt |
| 4-64 | 0 | — | tBu | 5-(CH₂)₂CH(OB²)(CH₂)₂-cHp Na salt |
| 4-65 | 1 | H | tBu | 5-(CH₂)₂CH(OD¹)(CH₂)-cHp Na salt |
| 4-66 | 1 | H | tBu | 5-(CH₂)₂CH(OE¹)-cPn HCl salt |
| 4-67 | 1 | H | tBu | 5-(CH₂)₃CH(OB²)-cHx Na salt |
| 4-68 | 1 | H | tBu | 5-(CH₂)₃CH(OB²)₅-cHx Na salt |
| 4-69 | 1 | H | tBu | 5-(CH₂)₃CH(OB³)(CH₂)₂-cHx Na salt |
| 4-70 | 1 | H | tBu | 5-(CH₂)₃CH(OB²)(CH₂)₃-cHx Na salt |
| 4-71 | 0 | — | tBu | 5-(CH₂)₃CH(OB²)(CH₂)-cPn Na salt |
| 4-72 | 0 | — | tBu | 5-(CH₂)₃CH(OB²)-Ph Na salt |
| 4-73 | 0 | — | tBu | 5-(CH₂)₄CH(OB²)-cHx Na salt |
| 4-74 | 0 | — | tBu | 5-(CH₂)₄CH(OB²)-cHp |
| 4-75 | 0 | — | iPr | 6-CH(OH)-cHx |
| 4-76 | 0 | — | iPr | 6-CH(OH)CH₂-cHp |
| 4-77 | 0 | — | iPr | 6-CH(OH)(CH₂)₃cPn |
| 4-78 | 0 | — | iPr | 6-CH(OH)(CH₂)₅(2-ClPh) |
| 4-79 | 0 | — | iPr | 6-(CH₂)CH(OH)-cHx |
| 4-80 | 0 | — | iPr | 6-(CH₂)CH(OH)(CH₂)₂-cPn |
| 4-81 | 0 | — | iPr | 6-(CH₂)CH(OH)(CH₂)₄-cHp |
| 4-82 | 0 | — | iPr | 6-(CH₂)₂CH(OH)-cHx |
| 4-83 | 0 | — | iPr | 6-(CH₂)₂CH(OH)(CH₂)-cHp |
| 4-84 | 0 | — | iPr | 6-(CH₂)₂CH(OH)(CH₂)₃-cPn |
| 4-85 | 0 | — | iPr | 6-(CH₂)₃CH(OH)-cHx |
| 4-86 | 0 | — | iPr | 6-(CH₂)₃CH(OH)(CH₂)Ph |
| 4-87 | 0 | — | iPr | 6-(CH₂)₃CH(OH)(CH₂)₃-cHp |
| 4-88 | 0 | — | iPr | 6-(CH₂)₄CH(OH)-cHx |
| 4-89 | 1 | H | iPr | 6-(CH₂)₄CH(OH)-cPn |
| 4-90 | 0 | — | iPr | 6-CH(OB²)-cHx Na salt |
| 4-91 | 0 | — | iPr | 6-CH(OB²)(CH₂)-cHx Na salt |
| 4-92 | 0 | — | iPr | 6-CH(OB²)(CH₂)₃-cHx Na salt |
| 4-93 | 0 | — | iPr | 6-CH(OB²)(CH₂)₅-cHx Na salt |
| 4-94 | 0 | — | iPr | 6-(CH₂)CH(OB²)-cHx Na salt |
| 4-95 | 0 | — | iPr | 6-(CH₂)CH(OB²)(CH₂)₃-cHx Na salt |
| 4-96 | 0 | — | iPr | 6-(CH₂)₂CH(OB²)-cHx Na salt |
| 4-97 | 0 | — | iPr | 6-(CH₂)₂CH(OB²)(CH₂)-cHx Na salt |
| 4-98 | 0 | — | iPr | 6-(CH₂)₂CH(OB²)(CH₂)₂-cHx Na salt |
| 4-99 | 0 | — | iPr | 6-(CH₂)₂CH(OB²)(CH₂)₃-cHx Na salt |
| 4-100 | 0 | — | iPr | 6-(CH₂)₂CH(OB²)(CH₂)₄-cHx Na salt |
| 4-101 | 0 | — | iPr | 6-(CH₂)₂CH(OD¹)(CH₂)-cHp Na salt |
| 4-102 | 0 | — | iPr | 6-(CH₂)₂CH(OE¹)(CH₂)-cPn HCl salt |
| 4-103 | 0 | — | iPr | 6-(CH₂)₃CH(OB²)-cHx Na salt |
| 4-104 | 1 | H | iPr | 6-(CH₂)₃CH(OB²)-cHp Na salt |
| 4-105 | 1 | H | tBu | 6-(CH₂)₄CH(OB²)-cHx Na salt |
| 4-106 | 0 | — | iPr | 6-CH₂O(CH₂)₃Imd HCl salt |
| 4-107 | 0 | — | iPr | 6-CH₂O(CH₂)₄Imd HCl salt |
| 4-108 | 0 | — | iPr | 6-CH₂O(CH₂)₅Imd HCl salt |
| 4-109 | 1 | H | iPr | 6-CH₂O(CH₂)₃Imd HCl salt |
| 4-110 | 1 | H | iPr | 5-CH₂O(CH₂)₃Imd |
| 4-111 | 0 | — | tBu | 5-CH=CH—CH(OH)(CH₂)-cHx |
| 4-112 | 0 | — | iPr | 6-CH=CH—CH(OH)(CH₂)-cHx |
| 4-113 | 0 | — | tBu | 5-(C=O)(CH₂)-cHx |
| 4-114 | 0 | — | iPr | 6-(CH₂)C(=O)(CH₂)-cHx |
| 4-115 | 0 | — | tBu | 5-(CH₂)₂C(=O)(CH₂)-cHx |
| 4-116 | 0 | — | tBu | 6-C(=O)—(CH₂)₂-cHx |
| 4-117 | 0 | — | tBu | 5-(CH₂)₂C(=O)(CH₂)-cHp |
| 4-118 | 0 | — | SCH₃ | 6-(CH₂)O(CH₂)₃-Imd HCl |
| 4-119 | 0 | — | tBu | 6-(CH₂)O(CH₂)₃-Imd HCl |

TABLE 5

| Cpd. No. | n | R¹ | R² | R³ | R⁴ |
|---|---|---|---|---|---|
| 5-1 | 0 | G | — | tBu | 5-CH(OH)-cHx |
| 5-2 | 0 | G | — | tBu | 5-CH(OH)(CH₂)-cHx |
| 5-3 | 0 | G | — | tBu | 5-CH(OH)(CH₂)₂-cHx |
| 5-4 | 0 | G | — | tBu | 5-CH(OH)(CH₂)₃-cHx |
| 5-5 | 0 | G | — | tBu | 5-CH(OH)(CH₂)₄-cHx |
| 5-6 | 0 | G | — | tBu | 5-CH(OH)(CH₂)₅-cHx |
| 5-7 | 1 | K | H | tBu | 5-CH(OH)(CH₂)₆-cHp |
| 5-8 | 0 | J | — | tBu | 5-CH(OH)(CH₂)₅-cPn |
| 5-9 | 1 | K | H | tBu | 5-CH(OH)(CH₂)₄-cHp |
| 5-10 | 0 | G | — | tBu | 5-CH(OH)(CH₂)₃-cHx |
| 5-11 | 0 | J | — | tBu | 5-CH(OH)(CH₂)₂-cPn |
| 5-12 | 0 | G | — | tBu | 5-(CH₂)CH(OH)-cHx |
| 5-13 | 0 | G | — | tBu | 5-(CH₂)CH(OH)(CH₂)-cHx |
| 5-14 | 0 | G | — | tBu | 5-(CH₂)CH(OH)(CH₂)₂-cHx |
| 5-15 | 0 | K | — | tBu | 5-(CH₂)CH(OH)(CH₂)₃-cHx |
| 5-16 | 0 | J | — | tBu | 5-(CH₂)CH(OH)(CH₂)₄-cHx |
| 5-17 | 0 | G | — | tBu | 5-(CH₂)₂CH(OH)(CH₂)-cHx |
| 5-18 | 1 | G | H | tBu | 5-(CH₂)₂CH(OH)(CH₂)₂-cPn |
| 5-19 | 0 | K | — | tBu | 5-(CH₂)₂CH(OH)(CH₂)₂-cHx |
| 5-20 | 0 | K | — | tBu | 5-(CH₂)₂CH(OH)-cHp |
| 5-21 | 0 | K | — | tBu | 5-(CH₂)₃CH(OH)-cHx |
| 5-22 | 0 | G | — | tBu | 5-(CH₂)₃CH(OH)(CH₂)-cHx |
| 5-23 | 0 | G | — | tBu | 5-(CH₂)₃CH(OH)(CH₂)₂-cHx |
| 5-24 | 0 | G | — | tBu | 5-(CH₂)₃CH(OH)(CH₂)₃-cHx |
| 5-25 | 1 | G | H | tBu | 5-(CH₂)₃CH(OH)(CH₂)₂-cHp |
| 5-26 | 0 | G | — | tBu | 5-(CH₂)₃CH(OH)-cPn |
| 5-27 | 0 | J | — | tBu | 5-(CH₂)₄CH(OH)-cHp |
| 5-28 | 0 | J | — | tBu | 5-(CH₂)₄CH(OH)-cHx |
| 5-29 | 0 | J | — | tBu | 5-(CH₂)₄CH(OH)(CH₂)-cHx |
| 5-30 | 0 | J | — | tBu | 5-(CH₂)₄CH(OH)(CH₂)₂-cHx |
| 5-31 | 0 | J | — | tBu | 5-(CH₂)₄CH(OH)(CH₂)₂-cHp |
| 5-32 | 1 | G | H | tBu | 5-(CH₂)₄CH(OH)-cPn |

TABLE 5-continued

| Cpd. No. | n | R¹ | R² | R³ | R⁴ |
|---|---|---|---|---|---|
| 5-33 | 0 | J | — | tBu | 5-CH(OH)Ph |
| 5-34 | 0 | G | — | tBu | 5-CH(OH)(CH₂)₃Ph |
| 5-35 | 0 | J | — | tBu | 5-(CH₂)CH(OH)(CH₂)₂Ph |
| 5-36 | 0 | G | — | tBu | 5-(CH₂)CH(OH)(CH₂)₄Ph |
| 5-37 | 0 | J | — | tBu | 5-(CH₂)₂CH(OH)Ph |
| 5-38 | 0 | J | — | tBu | 5-(CH₂)₂CH(OH)CH₂(4-MePh) |
| 5-39 | 0 | J | — | tBu | 5-(CH₂)₂CH(OH)(CH₂)₃Ph |
| 5-40 | 0 | J | — | tBu | 5-(CH₂)₃CH(OH)(4-MePh) |
| 5-41 | 0 | J | — | tBu | 5-(CH₂)₄CH(OH)(2-ClPh) |
| 5-42 | 1 | J | H | tBu | 5-(CH₂)₅CH(OH)(2-MePh) |
| 5-43 | 0 | G | — | tBu | 5-CH(OB²)-cHx Na salt |
| 5-44 | 0 | G | — | tBu | 5-CH(OB²)(CH₂)-cHx Na salt |
| 5-45 | 0 | G | — | tBu | 5-CH(OB²)(CH₂)₂-cHx Na salt |
| 5-46 | 0 | G | — | tBu | 5-CH(OB²)(CH₂)₃-cHx Na salt |
| 5-47 | 0 | G | — | tBu | 5-CH(OB²)(CH₂)₄-cHx Na salt |
| 5-48 | 0 | G | — | tBu | 5-CH(OB²)(CH₂)₅-cHx Na salt |
| 5-49 | 0 | J | — | tBu | 5-CH(OB²)(CH₂)₄-Ph Na salt |
| 5-50 | 0 | J | — | tBu | 5-CH(OE¹)(CH₂)₂-cPn HCl salt |
| 5-51 | 0 | J | — | tBu | 5-CH(OE¹)-cHp HCl salt |
| 5-52 | 0 | K | — | tBu | 5-(CH₂)CH(OB²)-cHx Na salt |
| 5-53 | 0 | G | — | tBu | 5-(CH₂)CH(OB²)(CH₂)-cHx Na salt |
| 5-54 | 0 | G | — | tBu | 5-(CH₂)CH(OB²)(CH₂)₂-cHx Na salt |
| 5-55 | 0 | G | — | tBu | 5-(CH₂)CH(OB²)(CH₂)₃-cHx Na salt |
| 5-56 | 0 | G | — | tBu | 5-(CH₂)CH(OB²)(CH₂)₄-cHx Na salt |
| 5-57 | 0 | J | — | tBu | 5-CH₂CH(OD¹)(CH₂)₅-cHx Na salt |
| 5-58 | 0 | G | — | tBu | 5-(CH₂)₂CH(OB²)-cHx Na salt |
| 5-59 | 0 | G | — | tBu | 5-(CH₂)₂CH(OB²)(CH₂)-cHx Na salt |
| 5-60 | 0 | G | — | tBu | 5-(CH₂)₂CH(OB²)(CH₂)₂-cHx Na salt |
| 5-61 | 0 | G | — | tBu | 5-(CH₂)₂CH(OB²)(CH₂)₃-cHx Na salt |
| 5-62 | 0 | J | — | tBu | 5-(CH₂)₂CH(OB²)(CH₂)₄-cHx Na salt |
| 5-63 | 0 | G | — | tBu | 5-(CH₂)₂CH(OB²)(CH₂)₃-Ph Na salt |
| 5-64 | 0 | G | — | tBu | 5-(CH₂)₂CH(OB²)(CH₂)₂-cHp Na salt |
| 5-65 | 1 | J | H | tBu | 5-(CH₂)₂CH(OD¹)(CH₂)-cHp Na salt |
| 5-66 | 1 | J | H | tBu | 5-(CH₂)₂CH(OE¹)-cPn HCl salt |
| 5-67 | 1 | G | H | tBu | 5-(CH₂)₃CH(OB²)-cHx Na salt |
| 5-68 | 1 | G | H | tBu | 5-(CH₂)₃CH(OB²)-cHx Na salt |
| 5-69 | 1 | G | H | tBu | 5-(CH₂)₃CH(OB³)(CH₂)₂-cHx Na salt |
| 5-70 | 1 | G | H | tBu | 5-(CH₂)₃CH(OB²)(CH₂)₃-cHx Na salt |
| 5-71 | 0 | G | — | tBu | 5-(CH₂)₃CH(OB²)(CH₂)-cPn Na salt |
| 5-72 | 0 | G | — | tBu | 5-(CH₂)₃CH(OB²)-Ph Na salt |
| 5-73 | 0 | G | — | tBu | 5-(CH₂)₄CH(OB²)-cHx Na salt |
| 5-74 | 0 | G | — | tBu | 5-(CH₂)₄CH(OB²)-cHp |
| 5-75 | 0 | G | — | iPr | 6-CH(OH)-cHx |
| 5-76 | 0 | J | — | iPr | 6-CH(OH)CH₂-cHp |
| 5-77 | 0 | K | — | iPr | 6-CH(OH)(CH₂)₃-cPn |
| 5-78 | 0 | K | — | iPr | 6-CH(OH)(CH₂)₅-(2-ClPh) |
| 5-79 | 0 | G | — | iPr | 6-(CH₂)CH(OH)-cHx |
| 5-80 | 0 | G | — | iPr | 6-(CH₂)CH(OH)(CH₂)₂-cPn |
| 5-81 | 0 | G | — | iPr | 6-(CH₂)CH(OH)(CH₂)₄-cHp |
| 5-82 | 0 | G | — | iPr | 6-(CH₂)₂CH(OH)-cHx |
| 5-83 | 0 | G | — | iPr | 6-(CH₂)₂CH(OH)(CH₂)-cHp |
| 5-84 | 0 | G | — | iPr | 6-(CH₂)₂CH(OH)(CH₂)₃-cPn |
| 5-85 | 0 | G | — | iPr | 6-(CH₂)₃CH(OH)-cHx |
| 5-86 | 0 | G | — | iPr | 6-(CH₂)₃CH(OH)(CH₂)Ph |
| 5-87 | 0 | G | — | iPr | 6-(CH₂)₃CH(OH)(CH₂)₃-cHp |
| 5-88 | 0 | G | — | iPr | 6-(CH₂)₄CH(OH)-cHx |
| 5-89 | 1 | J | H | iPr | 6-(CH₂)₄CH(OH)-cPn |
| 5-90 | 0 | J | — | iPr | 6-CH(OB²)-cHx Na salt |
| 5-91 | 0 | J | — | iPr | 6-CH(OB²)(CH₂)-cHx Na salt |
| 5-92 | 0 | G | — | iPr | 6-CH(OB²)(CH₂)₃-cHx Na salt |
| 5-93 | 0 | G | — | iPr | 6-CH(OB²)(CH₂)₅-cHx Na salt |
| 5-94 | 0 | K | — | iPr | 6-(CH₂)CH(OB²)-cHx Na salt |
| 5-95 | 0 | G | — | iPr | 6-(CH₂)CH(OB²)(CH₂)₃-cHx Na salt |
| 5-96 | 0 | G | — | iPr | 6-(CH₂)₂CH(OB²)-cHx Na salt |
| 5-97 | 0 | G | — | iPr | 6-(CH₂)₂CH(OB²)(CH₂)-cHx Na salt |
| 5-98 | 0 | G | — | iPr | 6-(CH₂)₂CH(OB²)(CH₂)₂-cHx Na salt |
| 5-99 | 0 | G | — | iPr | 6-(CH₂)₂CH(OB²)(CH₂)₃-cHx Na salt |
| 5-100 | 0 | G | — | iPr | 6-(CH₂)₂CH(OB²)(CH₂)₄-cHx Na salt |
| 5-101 | 0 | G | — | iPr | 6-(CH₂)₂CH(OD¹)(CH₂)-cHp Na salt |
| 5-102 | 0 | G | — | iPr | 6-(CH₂)₂CH(OE¹)(CH₂)-cPn HCl salt |
| 5-103 | 0 | G | — | iPr | 6-(CH₂)₃CH(OB²)-cHx Na salt |
| 5-104 | 1 | G | H | tBu | 6-(CH₂)₃CH(OB²)-cHp Na salt |
| 5-105 | 1 | G | H | tBu | 6-(CH₂)₄CH(OB²)-cHx Na salt |
| 5-106 | 0 | K | — | tBu | 5-CH=CH—CH(OH)(CH₂)-cHx |
| 5-107 | 0 | K | — | iPr | 6-CH=CH—CH(OH)(CH₂)-cHx |
| 5-108 | 0 | J | — | tBu | 5-C(=O)(CH₂)-cHx |
| 5-109 | 1 | G | H | iPr | 6-(CH₂)₂C(=O)(CH₂)-cHx |
| 5-110 | 1 | G | H | tBu | 5-(CH₂)₂C(=O)(CH₂)-cHx |
| 5-111 | 0 | G | — | tBu | 6-C(=O)—(CH₂)₂-cHx |
| 5-112 | 0 | tBu | — | tBu | 5-CH(OH)-cHx |
| 5-113 | 0 | tBu | — | tBu | 5-CH(OH)(CH₂)-cHx |
| 5-114 | 0 | tBu | — | tBu | 5-CH(OH)(CH₂)₂-cHx |
| 5-115 | 0 | tBu | — | tBu | 5-CH(OH)(CH₂)₃-cHx |
| 5-116 | 0 | tBu | — | tBu | 5-CH(OH)(CH₂)₄-cHx |
| 5-117 | 0 | tBu | — | tBu | 5-(CH₂)CH(OH)-cHx |
| 5-118 | 0 | tBu | — | tBu | 5-(CH₂)CH(OH)(CH₂)-cHx |
| 5-119 | 0 | tBu | — | tBu | 5-(CH₂)CH(OH)(CH₂)₂-cHx |
| 5-120 | 0 | tBu | — | tBu | 5-(CH₂)CH(OH)(CH₂)₃-cHx |
| 5-121 | 0 | tBu | — | tBu | 5-(CH₂)CH(OH)(CH₂)₄-cHx |
| 5-122 | 0 | tBuCH₂ | — | tBu | 5-CH(OH)-cHx |
| 5-123 | 0 | tBuCH₂ | — | tBu | 5-CH(OH)(CH₂)-cHx |
| 5-124 | 0 | tBuCH₂ | — | tBu | 5-CH(OH)(CH₂)₂-cHx |
| 5-125 | 0 | tBuCH₂ | — | tBu | 5-CH(OH)(CH₂)₃-cHx |
| 5-126 | 0 | tBuCH₂ | — | tBu | 5-CH(OH)(CH₂)₄-cHx |
| 5-127 | 0 | tBuCH₂ | — | tBu | 5-(CH₂)CH(OH)-cHx |
| 5-128 | 0 | tBuCH₂ | — | tBu | 5-(CH₂)CH(OH)(CH₂)-cHx |
| 5-129 | 0 | tBuCH₂ | — | tBu | 5-(CH₂)CH(OH)(CH₂)₂-cHx |
| 5-130 | 0 | tBuCH₂ | — | tBu | 5-(CH₂)CH(OH)(CH₂)₃-cHx |
| 5-131 | 0 | tBuCH₂ | — | tBu | 5-(CH₂)CH(OH)(CH₂)₄-cHx |
| 5-132 | 0 | Hp | — | tBu | 5-CH(OH)-cHx |
| 5-133 | 0 | Hp | — | tBu | 5-CH(OH)(CH₂)-cHx |
| 5-134 | 0 | Hp | — | tBu | 5-CH(OH)(CH₂)₂-cHx |
| 5-135 | 0 | Hp | — | tBu | 5-CH(OH)(CH₂)₃-cHx |
| 5-136 | 0 | Hp | — | tBu | 5-CH(OH)(CH₂)₄-cHx |
| 5-137 | 0 | Hp | — | tBu | 5-(CH₂)CH(OH)-cHx |
| 5-138 | 0 | Hp | — | tBu | 5-(CH₂)CH(OH)(CH₂)-cHx |
| 5-139 | 0 | Hp | — | tBu | 5-(CH₂)CH(OH)(CH₂)₂-cHx |
| 5-140 | 0 | Hp | — | tBu | 5-(CH₂)CH(OH)(CH₂)₃-cHx |
| 5-141 | 0 | Hp | — | tBu | 5-(CH₂)CH(OH)(CH₂)₄-cHx |

Of the compounds listed above, the preferred compounds are the following, that is to say Compounds No. 1-1, 1-2, 1-15, 1-25, 1-26, 1-30, 1-34, 1-36, 1-38, 1-39, 1-45, 1-49, 1-63, 1-73, 1-87, 1-97, 1-111, 1-120, 1-131, 1-145, 1-155, 1-169, 1-179, 1-193, 1-203, 1-217, 1-227, 1-241, 1-251, 1-265, 1-275, 1-286, 1-289, 1-299, 1-325, 1-349, 1-363, 1-373, 1-387, 1-397, 1-411, 1-421, 1-435, 1-445, 1-471, 1-485, 1-495, 1-519, 1-543, 1-557, 1-567, 1-577, 1-587, 1-597, 1-613, 1-617, 1-628, 1-642, 1-652, 1-661, 1-662, 1-670, 1-677, 1-684, 1-690, 1-696, 1-702, 1-703, 1-707, 1-713, 1-718, 1-723, 1-747, 1-761, 1-771, 1-783, 1-788, 1-799, 1-804, 1-810, 1-825, 1-831, 1-838, 1-839, 1-840, 1-841, 1-844, 1-845, 1-854, 1-864, 1-873, 1-881, 1-891, 1-897, 1-907, 1-915, 1-923, 1-929, 1-935, 1-943, 1-949, 1-959, 1-967, 1-976, 1-982, 1-986, 1-990, 1-996, 1-1002, 1-1009, 1-1011, 1-1013, 1-1015, 1-1016, 1-1019, 1-1021, 1-1022, 1-1023, 1-1026, 1-1030, 1-1037, 1-1046, 1-1054, 1-1057, 1-1064, 1-1065, 1-1068, 1-1078, 1-1079, 1-1084, 1-1088, 1-1089, 1-1090, 1-1093, 1-1095, 1-1100, 1-1102, 1-1103, 1-1104, 1-1105, 1-1106, 1-1107, 1-1108, 1-1109, 1-1111, 1-1112, 1-1113, 1-1114, 1-1115, 1-1117, 1-1118, 1-1120, 1-1121, 1-1122, 1-1124, 1-1127, 1-1129, 1-1131, 1-1132, 1-1136, 1-1137, 1-1141, 1-1142, 1-1143, 1-1144, 1-1145, 1-1149, 1-1151, 1-1153, 1-1155, 1-1156, 1-1157, 1-1158, 1-1159, 1-1160, 1-1163, 1-1164, 1-1165, 1-1166, 1-1167, 1-1168, 1-1172, 1-1176, 1-1183, 1-1184, 1-1185, 1-1186, 1-1188, 1-1191, 1-1192, 1-1193, 1-1194, 1-1197, 1-1199, 1-1200, 1-1203, 1-1204, 1-1205, 1-1206, 1-1207, 1-1208, 1-1209, 1-1212, 1-1213, 1-1214, 1-1215, 1-1216, 1-1219, 1-1220, 1-1221, 1-1222, 1-1223, 1-1224, 1-1234, 1-1235, 1-1240, 1-1241, 1-1262, 1-1263, 1-1264, 1-1265, 1-1266, 1-1267, 1-1268, 1-1269, 1-1271, 1-1278, 1-1279, 1-1283, 1-1290, 1-1291, 1-1300, 1-1301, 1-1302, 1-1303, 1-1304, 1-1309, 1-1310, 1-1311, 1-1312, 1-1314, 1-1319, 1-1325, 1-1326, 1-1327, 1-1331, 1-1332, 1-1336, 1-1337, 1-1342, 1-1343, 1-1344, 1-1348, 1-1355, 1-1357, 1-1364, 1-1367, 1-1369, 1-1384, 1-1385, 1-1386, 1-1387, 1-1397, 1-1409, 1-1418, 1-1425, 1-1434, 1-1442, 1-1461, 1-1462, 1-1463, 1-1467, 1-1474, 1-1475, 1-1476, 1-1477, 1-1480, 1-1481, 1-1522, 1-1552, 1-1565, 1-1567, 1-1862, 1-1875, 1-1877, 1-1890, 1-1903, 1-1905, 1-1918, 1-1933, 1-1977, 1-1979, 1-1982, 1-2144, 1-2147, 1-2186, 1-2276, 1-2361, 1-2387, 1-2388, 1-2389, 1-2390, 1-2657, 1-2659, 1-2660, 1-2711, 1-2713, 1-2714, 1-2765, 1-2767, 1-2768, 1-2819, 1-2821, 1-2822, 1-2855, 1-2910, 1-2911, 1-2914, 1-2915, 1-2918, 1-2920, 2-1, 2-2, 2-3, 2-4, 2-5, 2-8, 2-13, 2-15, 2-17, 2-19, 2-22, 2-24, 2-27, 2-28, 2-37, 2-38, 2-39, 2-43, 2-45, 2-48, 2-54, 2-58, 2-59, 2-60, 2-61, 2-62, 2-64, 2-67, 2-75, 2-77, 2-82, 2-83, 2-84, 2-90, 2-97, 2-106, 2-109, 2-113, 2-117, 2-119, 3-1, 3-2, 3-3, 3-4, 3-5, 3-8, 3-12, 3-13, 3-14, 3-16, 3-17, 3-19, 3-28, 3-37, 3-38, 3-44, 3-45, 3-46, 3-48, 3-51, 3-58, 3-59, 3-60, 3-61, 3-62, 3-64, 3-68, 3-76, 3-77, 3-19, 3-28, 3-37, 3-38, 3-44, 3-45, 3-46, 3-48, 3-51, 3-58, 3-59, 3-60, 3-61, 3-62, 3-64, 3-68, 3-76, 3-77, 3-82, 3-83, 3-84, 3-85, 3-90, 3-91, 3-93, 3-97, 3-99, 3-106, 3-109, 3-110, 3-114, 3-118, 3-119, 3-121, 3-123, 4-1, 4-2, 4-3, 4-4, 4-5, 4-13, 4-17, 4-18, 4-19, 4-20, 4-23, 4-27, 4-37, 4-43, 4-44, 4-45, 4-46, 4-47, 4-54, 4-58, 4-59, 4-60, 4-61, 4-62, 4-64, 4-75, 4-77, 4-82, 4-83, 4-84, 4-90, 4-97, 4-98, 4-99, 4-100, 4-106, 4-109, 4-115, 5-1, 5-2, 5-3, 5-4, 5-5, 5-8, 5-13, 5-17, 5-19, 5-26, 5-39, 5-44, 5-45, 5-46, 5-48, 5-52, 5-58, 5-59, 5-60, 5-61, 5-62, 5-63, 5-64, 5-68, 5-76, 5-77, 5-78, 5-82, 5-83, 5-84, 5-96, 5-97, 5-98, 5-99, 5-100, 5-106 and 5-111, of which Compounds No. 1-1, 1-15, 1-25, 1-26, 1-39, 1-49, 1-63, 1-73, 1-87, 1-97, 1-131, 1-145, 1-155, 1-169, 1-179, 1-203, 1-227, 1-251, 1-275, 1-325, 1-349, 1-373, 1-397, 1-421, 1-435, 1-471, 1-495, 1-543, 1-567, 5-587, 1-597, 1-613, 1-628, 1-652, 1-662, 1-670, 1-677, 1-684, 1-696, 1-702, 1-703, 1-707, 1-713, 1-718, 1-723, 1-747, 1-761, 1-771, 1-783, 1-788, 1-799, 1-804, 1-910, 1-825, 1-838, 1-839, 1-845, 1-854, 1-864, 1-873, 1-881, 1-891, 1-943, 1-949, 1-959, 1-967, 1-976, 1-982, 1-990, 1-996, 1-1002, 1-1021, 1-1022, 1-1023, 1-1026, 1-1037, 1-1046, 1-1057, 1-1064, 1-1065, 1-1068, 1-1078, 1-1079, 1-1084, 1-1088, 1-1089, 1-1093, 1-1100, 1-1102, 1-1103, 11104, 1-1105, 1-1106, 1-1107, 1-1108, 1-1109, 1-1111, 1-1112, 1-1113, 1-1114, 1-1115, 1-1117, 1-1118, 1-1120, 1-1121, 1-1122, 1-1124, 1-1127, 1-1129, 1-1131, 1-1132, 1-1136, 1-1137, 1-1142, 1-1143, 1-1155, 1-1156, 1-1157, 1-1158, 1-1159, 1-1160, 1-1163, 1-1164, 1-1167, 1-1172, 1-1176, 1-1183, 1-1184, 1-1185, 1-1194, 1-1203, 1-1204, 1-1205, 1-1206, 1-1207, 1-1208, 1-1219, 1-1220, 1-1221, 1-1222, 1-1223, 1-1224, 1-1263, 1-1264, 1-1278, 1-1281, 1-1282, 1-1357, 1-1364, 1-1384, 1-1385, 1-1386, 1-1387, 1-1397, 1-1409, 1-1425, 1-1461, 1-1462, 1-1463, 1-1467, 1-1474, 1-1475, 1-1476, 1-1477, 1-1480, 1-1481, 1-1522, 1-1552, 1-1565, 1-1567, 1-1862, 1-1875, 1-1877, 1-1890, 1-1903, 1-1905, 1-1918, 1-1933, 1-1977, 1-1979, 1-1982, 1-2144, 1-2147, 1-2186, 1-2276, 1-2361, 1-2387, 1-2388, 1-2389, 1-2390, 1-2657, 1-2659, 1-2660, 1-2711, 1-2713, 1-2714, 1-2765, 1-2767, 1-2768, 1-2819, 1-2821, 1-2822, 1-2855, 1-2910, 1-2911, 1-2914, 1-2915, 1-2918, 1-2920, 2-1, 2-2, 2-3, 2-4, 2-5, 2-8, 2-13, 2-15, 2-17, 2-19, 2-37, 2-38, 2-43, 2-45, 2-48, 2-58, 2-59, 2-60, 2-61, 2-62, 2-64, 2-75, 2-77, 2-82, 2-83, 2-84, 2-97, 2-106, 2-109, 2-117, 2-119, 3-1, 3-2, 3-3, 3-4, 3-5, 3-8, 3-13, 3-14, 3-19, 3-37, 3-44, 3-45, 3-46, 3-48, 3-58, 3-59, 3-60, 3-61, 3-62, 3-64, 3-68, 3-76, 3-82, 3-83, 3-84, 3-90, 3-91, 3-93, 3-97, 3-99, 3-106, 3-109, 3-110, 3-118, 3-119, 3-121, 3-123, 4-1, 4-2, 4-3, 4-4, 4-5, 4-17, 4-18, 4-19, 4-43, 4-44, 4-45, 4-46, 4-47, 4-58, 4-59, 4-60, 4-61, 4-62, 4-77, 4-82, 4-84, 4-97, 4-98, 4-99, 4-100, 4-106, 4-109, 5-1, 5-2, 5-3, 5-4, 5-5, 5-8, 5-17, 5-19, 5-39, 5-44, 5-45, 5-46, 5-48, 5-58, 5-59, 5-60, 5-61, 5-62, 5-63, 5-64, 5-68, 5-76, 5-77, 5-78, 5-82, 5-83, 5-84, 5-96, 5-97, 5-98, 5-99 and 5-100 are more preferred, Compounds No. 1-1, 1-25, 1-26, 1-49, 1-73, 1-131, 1-179, 1-203, 1-227, 1-251, 1-275, 1-325, 1-349, 1-373, 1-397, 1-421, 1-628, 1-652, 1-662, 1-670, 1-677, 1-684, 1-696, 1-702, 1-703, 1-713, 1-718, 1-123, 1-747, 1-771, 1-788, 1-799, 1-804, 1-943, 1-949, 1-959, 1-1023, 1-1046, 1-1065, 1-1093, 1-1102, 1-1111, 1-1120, 1-1129, 1-1183, 1-1263, 1-1385, 1-1387, 1-1474, 1-1475, 1-1480, 1-1481, 1-1522, 1-1552, 1-1565, 1-1567, 1-1862, 1-1875, 1-1877, 1-1890, 1-1903, 1-1905, 1-1918, 1-1933, 1-1977, 1-1979, 1-1982, 1-2144, 1-2147, 1-2186, 1-2276, 1-2361, 1-2387, 1-2388, 1-2389, 1-2390, 1-2657, 1-2659, 1-2660.1-2711, 1-2713, 1-2714, 1-2765, 1-2767, 1-2768, 1-2819, 1-2821, 1-2822, 1-2855, 1-2910, 1-2911, 1-2914, 1-2915, 1-2918 and 1-2920, are still more preferred, Compounds No. 1-1, 1-25, 1-49, 1-73, 1-131, 1-179, 1-275, 1-325, 1-349, 1-397, 1-421, 1-652, 1-662, 1-684, 1-696, 1-702, 1-718, 1-723, 1-747, 1-771, 1-788, 1-799, 1-804, 1-943, 1-1046, 1-1065, 1-1102, 1-1111, 1-1129, 1-1263, 1-1387, 1-1474, 1-1475, 1-1480, 1-1481, 1-1522, 1-1552, 1-1565, 1-1567, 1-1862, 1-1875, 1-1890, 1-1903, 1-1933, 1-1977, 1-2144, 1-2186, 1-2387, 1-2389, 1-2390, 1-2713, 1-2765, 1-2768, 1-2855, 1-2910, 1-2911, 1-2914, 1-2915, 1-2918 and 1-2920 are even more preferred.

The most preferred compounds are Compounds No.:

1-1. N-[2-t-Butyl-5-(5-cyclohexyl-3-hydroxypentyl)-phenyl]-2-(9H-xanthen-9-yl)acetamide;

1-25. N-[2-t-Butyl-5-(4-cyclohexyl-3-hydroxybutyl)phenyl]-2-(9H-xanthen-9-yl)acetamide;

1-49. N-[2-t-Butyl-5-(6-cyclohexyl-3-hydroxyhexyl)phenyl]-2-(9H-xanthen-9-yl)acetamide;

1-73. N-[2-t-Butyl-5-(7-cyclohexyl-3-hydroxyheptyl)phenyl]-2-(9H-xanthen-9-yl)acetamide;

1-131. N-[2-t-Butyl-5-(3-cyclohexyl-3-hydroxypropyl)phenyl]-2-(9H-xanthen-9-yl)acetamide;

1-179. N-[2-t-Butyl-5-(2-cyclohexyl-1-hydroxyethyl)phenyl]-2-(9H-xanthen-9-yl)acetamide;

1-684. N-[2-t-Butyl-5-(6-cyclopentyl-1-hydroxyhexyl)phenyl]-2-(9H-xanthen-9-yl)acetamide;

1-1102. 1-(2-{4-t-Butyl-3-[2-(9H-xanthen-9-yl)acetamido]phenyl}ethyl)-2-cyclohexylethyl sodium succinate;

1-1111. 1-(2-{4-t-Butyl-3-[2-(9H-xanthen-9-yl)acetamido]phenyl}ethyl)-3-cyclohexylpropyl sodium succinate;

1-1129. Sodium 1-(2-{4-t-butyl-3-[2-(9H-xanthen-9-yl)acetamido]phenyl}ethyl)-5-cyclohexylpentyl succinate;

1-1474. N-{2-[3-(1-Imidazolyl)propoxy]methyl-6-methylthiophenyl}-2-(9H-xanthen-9-yl)acetamide hydrochloride;

1-1475. N-{2-[3-(1-Imidazolyl)propoxy]methyl-6-methylthiophenyl}-2-(9H-xanthen-9-yl)acetamide;

1-1480. N-{2-[3-(1-Imidazolyl)propoxy]methyl-6-t-butylphenyl}-2-(9H-xanthen-9-yl)acetamide hydrochloride;

1-1552. Sodium salt of α-1-(2-{4-t-butyl-3-[2-9H-xanthen-9-yl)acetamido]phenyl}ethyl)-2-cyclohexylethyl carboxymethylthioacetate;

1-1565. N-(2-t-Butyl-5-{3-[2-(1-imidazolyl)acetoxy]-4-cyclohexylbutyl}phenyl)-2-(9H-xanthen-9-yl)acetamide hydrochloride;

1-1567. Sodium salt of N-(2-t-butyl-5-{3-[2-(carboxymethoxy)acetoxy]-4-cyclohexylbutyl}phenyl)-2-(9H-xanthen-9-yl)acetamide;

1-1933. Sodium salt of N-(2-t-butyl-5-{7-cyclohexyl-3-[2-(carboxymethoxy)acetoxy]heptyl}phenyl)-2-(9H-xanthen-9-yl)acetamide;

1-1977. N-[2-t-Butyl-5-(4-cyclohexyl-2-(hydroxymethyl)butyl]phenyl]-2-(9H-xanthen-9-yl)acetamide;

1-2389. N-{2-t-Butyl-5-[4-(2-cyclohexylethoxy)-3-hydroxybutyl]phenyl}-2-(9H-xanthen-9-yl)acetamide;

1-2390. N-[2-t-Butyl-5-(5-cyclohexyloxy-3-hydroxypentyl)phenyl]-2-(9H-xanthen-9-yl)acetamide;

1-2713. N-(2-t-Butyl-5-{4-(2-cyclohexylethoxy)-3-[2-(1-imidazolyl)acetoxy]butyl}phenyl)-2-(9H-xanthen-9-yl)acetamide hydrochloride;

1-2768. Sodium salt of N-{2-t-butyl-5-(3-[2-(carboxymethoxy)acetoxy]-5-cyclohexyloxypentyl}phenyl)-2-(9H-xanthen-9-yl)acetamide;

1-2920. N-{2-t-Butyl-5-[(2-ethyl-1-imidazolyl)methyl]phenyl}-2-(9H-xanthen-9-yl)acetamide;

and pharmaceutically acceptable salts thereof.

The compounds of the present invention can be prepared by a variety of well known methods, for example as illustrated by the following Reaction Schemes I to XXVI:

Reaction Scheme I

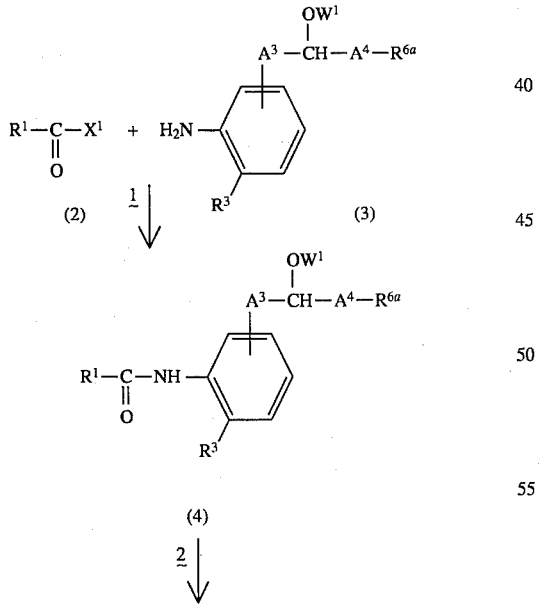

-continued
Reaction Scheme I

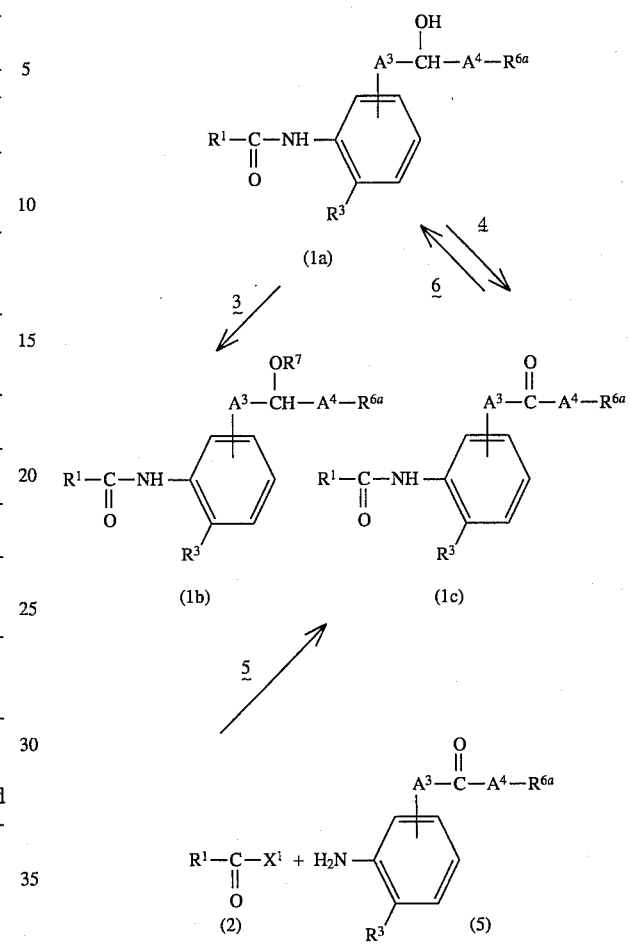

Reaction Scheme II

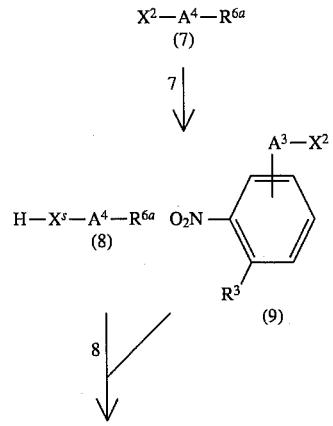

127
-continued
Reaction Scheme II
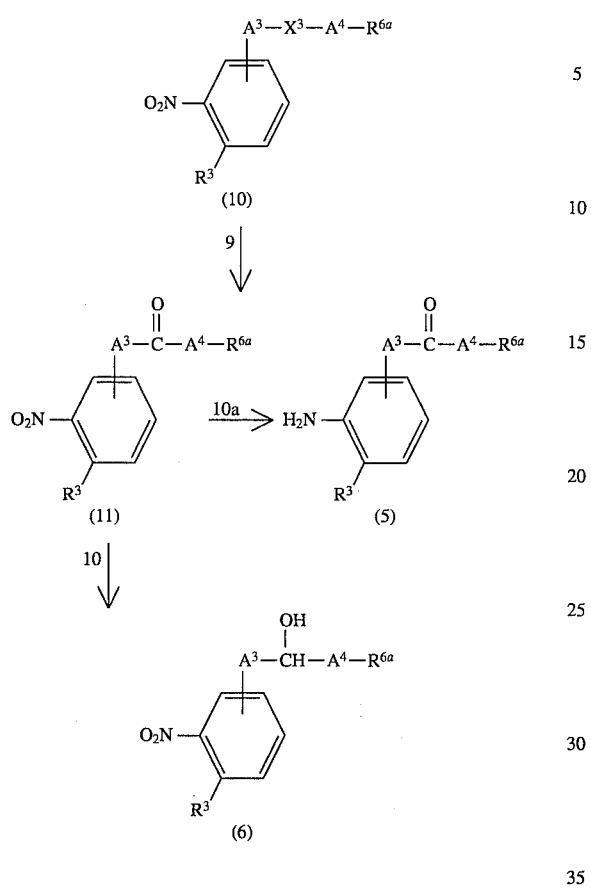
Reaction Scheme III
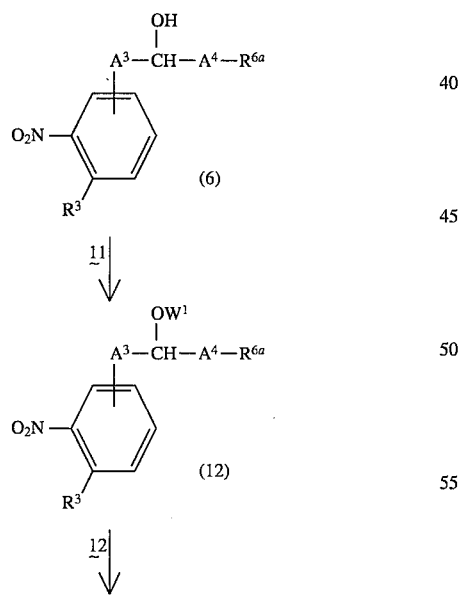
128
-continued
Reaction Scheme III
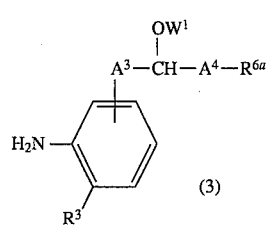
Reaction Scheme IV
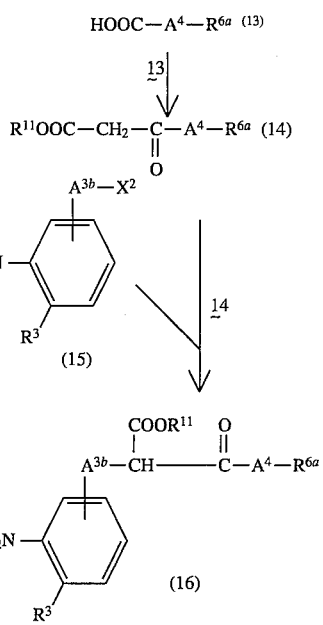
Reaction Scheme V
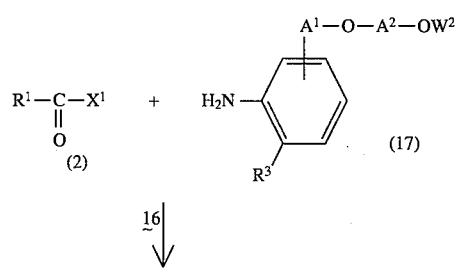

129
-continued
Reaction Scheme V
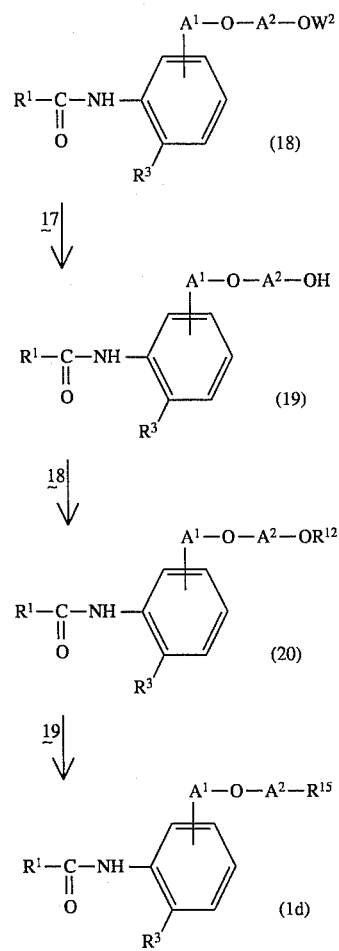
Reaction Scheme VI
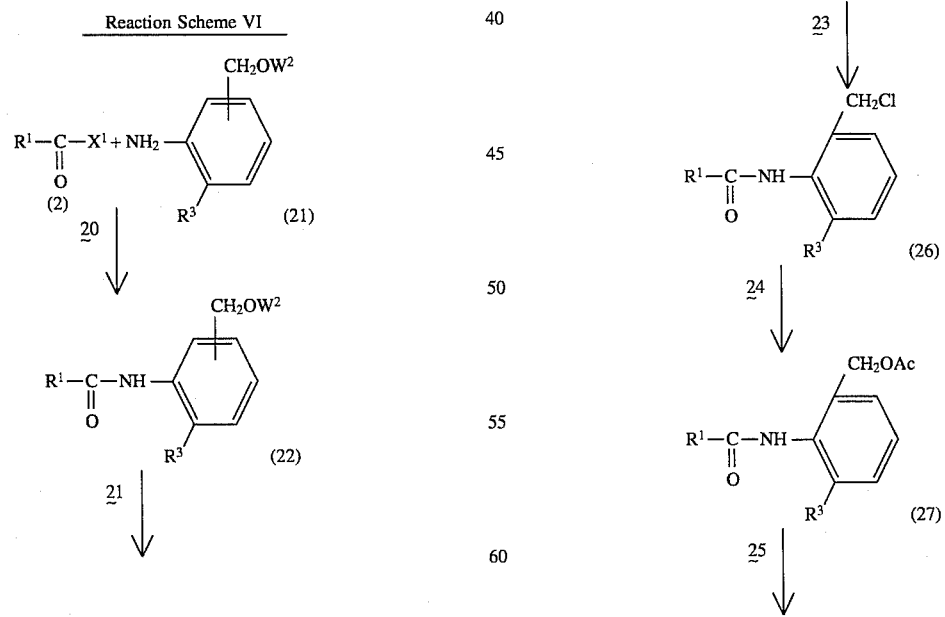
130
-continued
Reaction Scheme VI
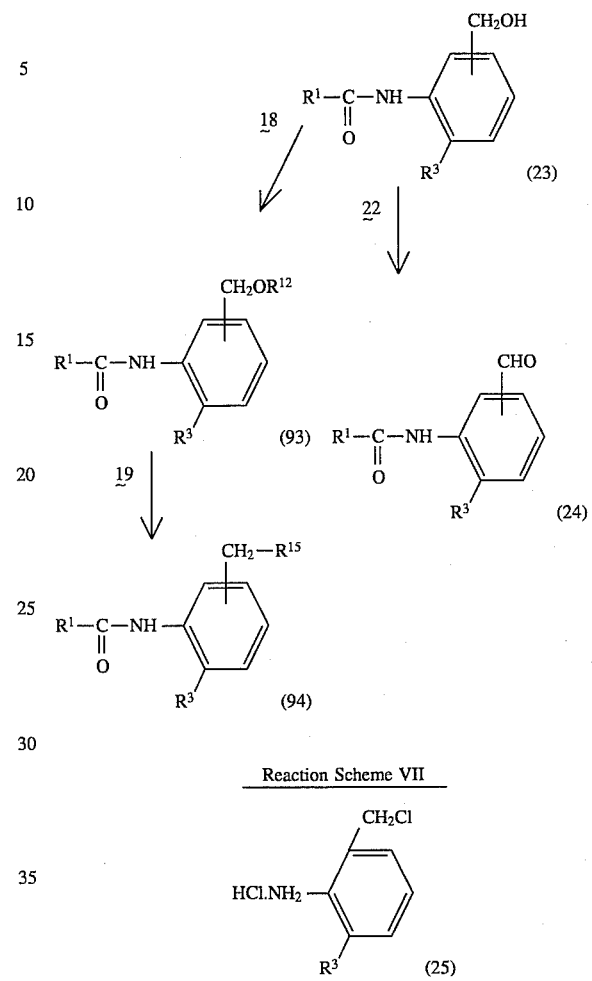
Reaction Scheme VII

131
-continued
Reaction Scheme VII
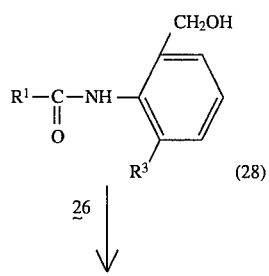
(28)
↓ 26
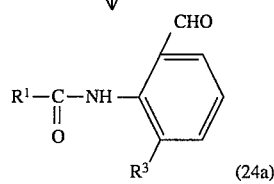
(24a)
Reaction Scheme VIII
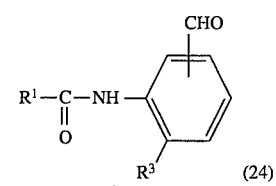
(24)
↓ 27
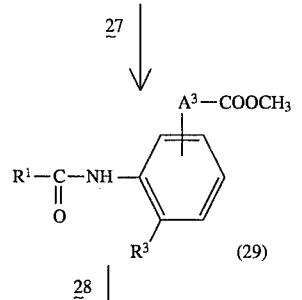
(29)
↓ 28
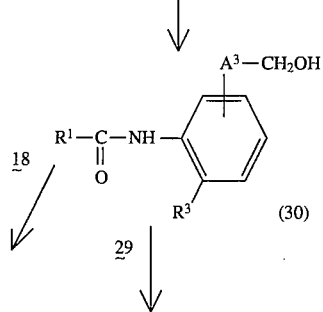
(30)
↙ 18 ↓ 29
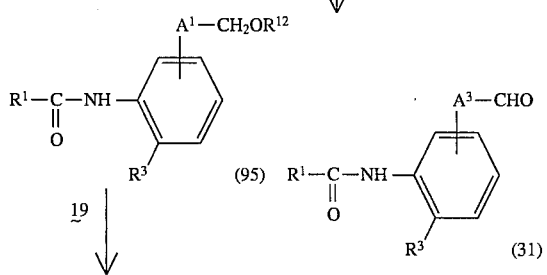
(95)    (31)
↓ 19
132
-continued
Reaction Scheme VIII
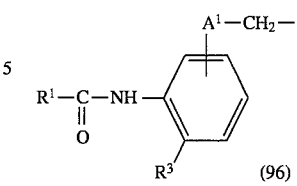
(96)
Reaction Scheme IX
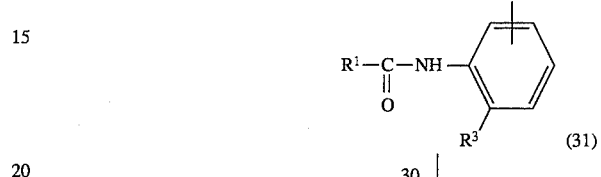
(31)
↓ 30
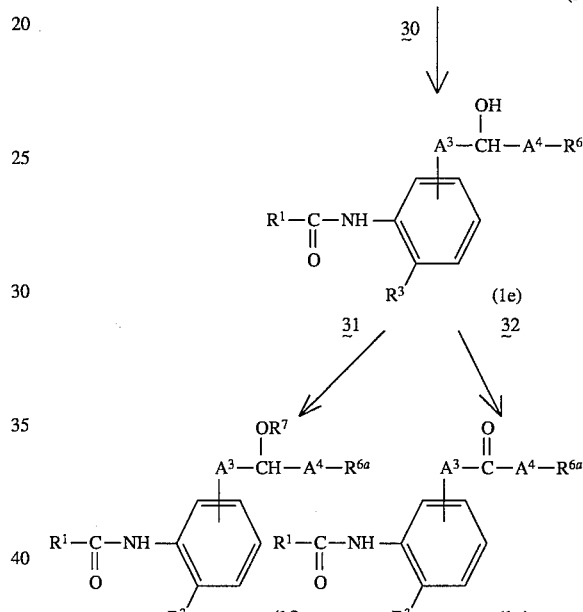
(1e)
31 ↙   ↘ 32
(1f)    (1g)
Reaction Scheme X
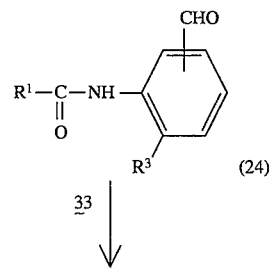
(24)
↓ 33

5,534,529
133
-continued
Reaction Scheme X
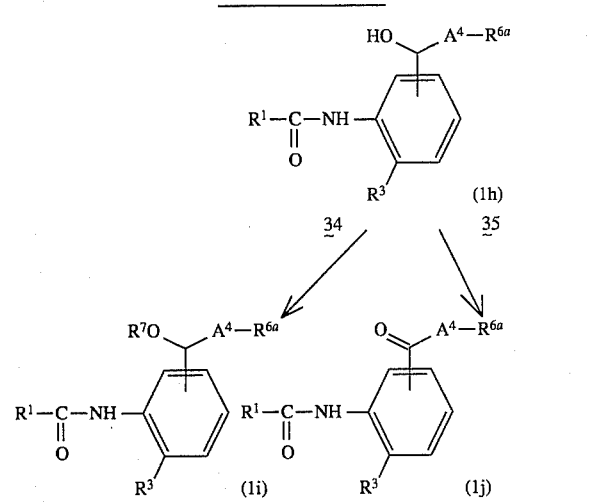
Reaction Scheme XI
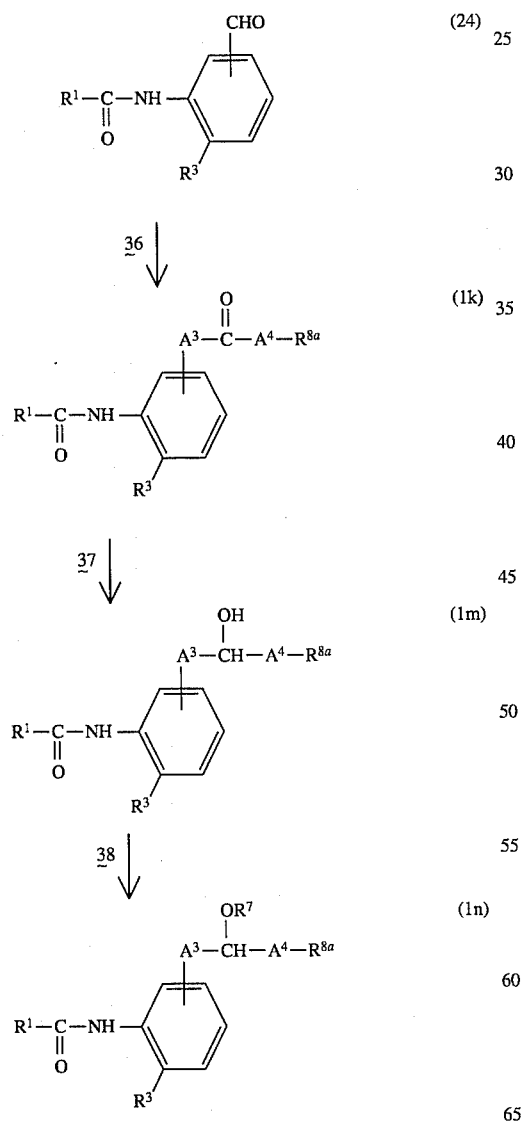
134
Reaction Scheme XII
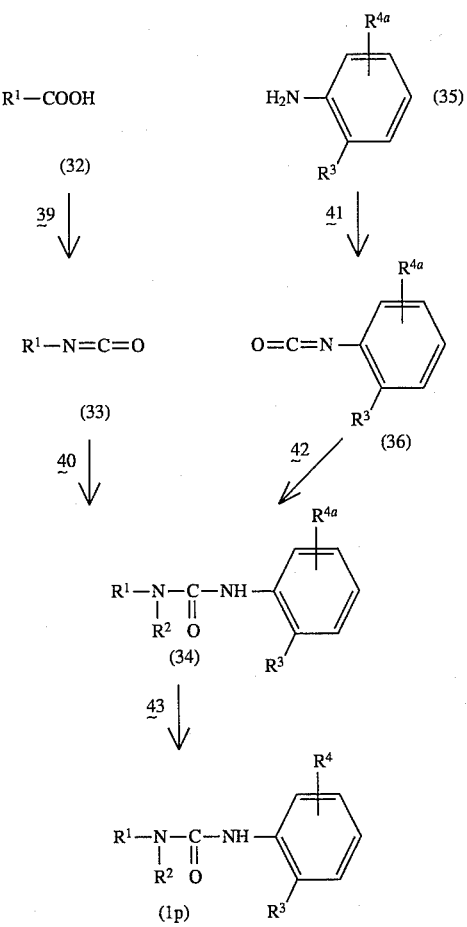
Reaction Scheme XIII
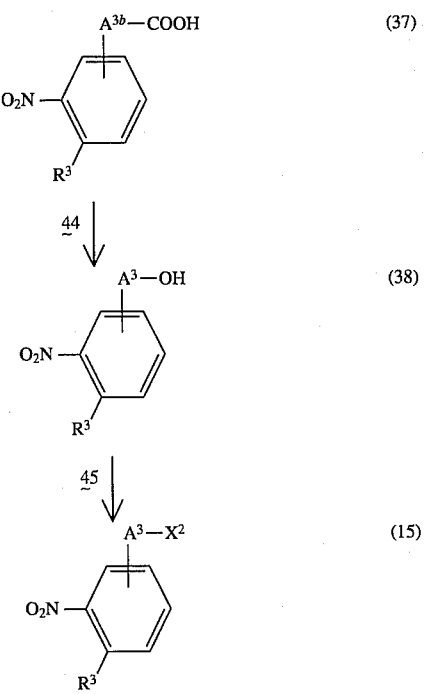

5,534,529
135
Reaction Scheme XIV
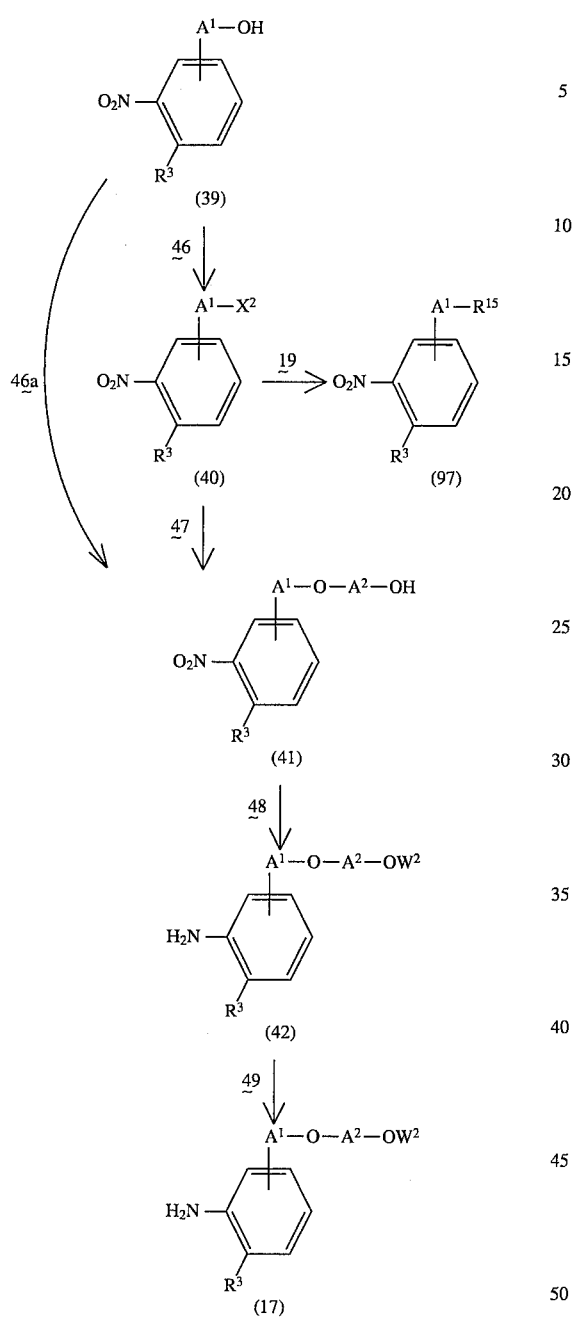
Reaction Scheme XV
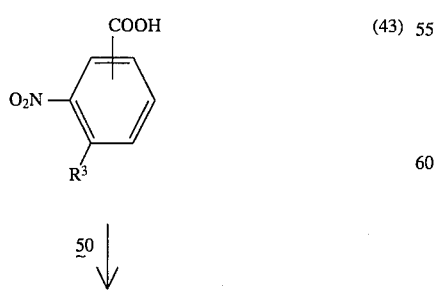
136
-continued
Reaction Scheme XV
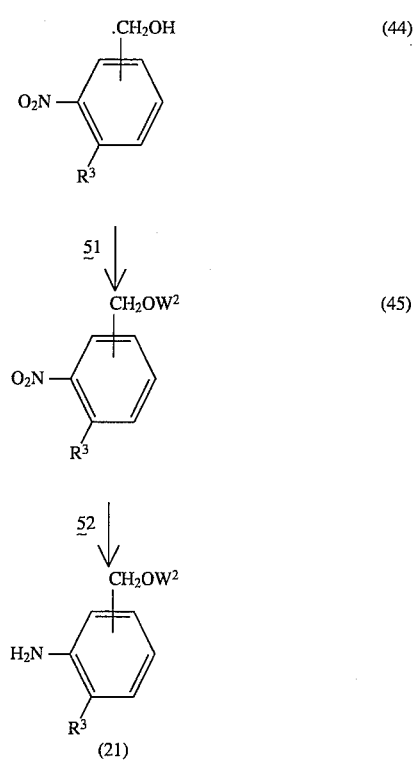
Reaction Scheme XVI
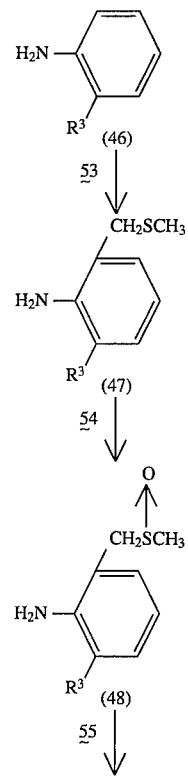

5,534,529
137
-continued
Reaction Scheme XVI
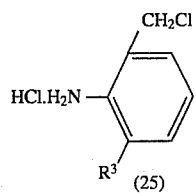
Reaction Scheme XVII
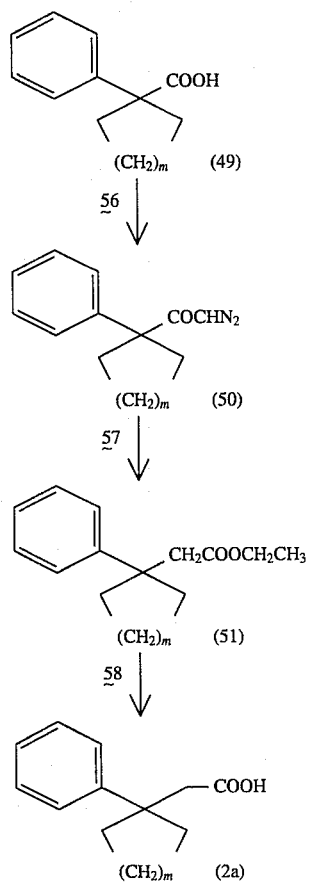
Reaction Scheme XVIII
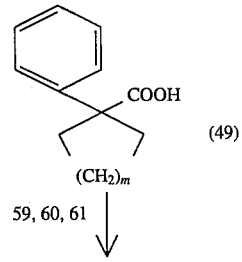
138
-continued
Reaction Scheme XVIII
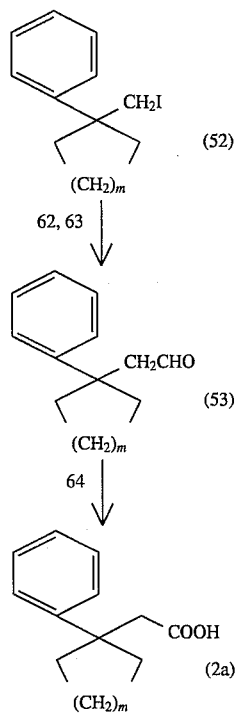
Reaction Scheme XIX
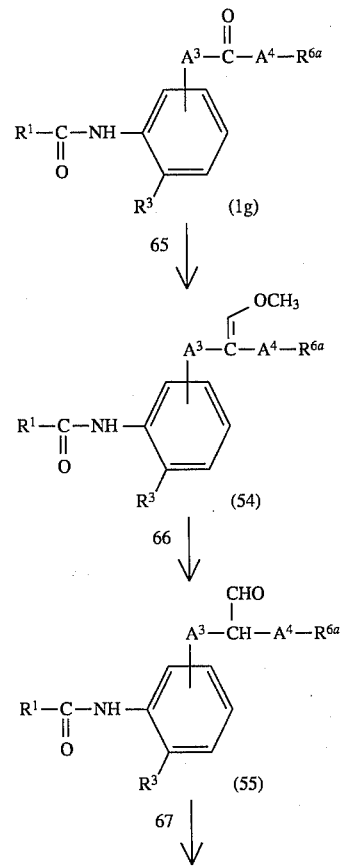

Reaction Scheme XIX (continued)
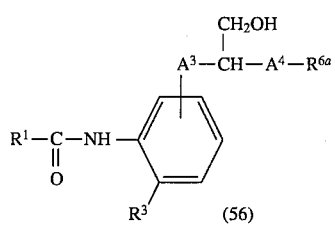
Reaction Scheme XX
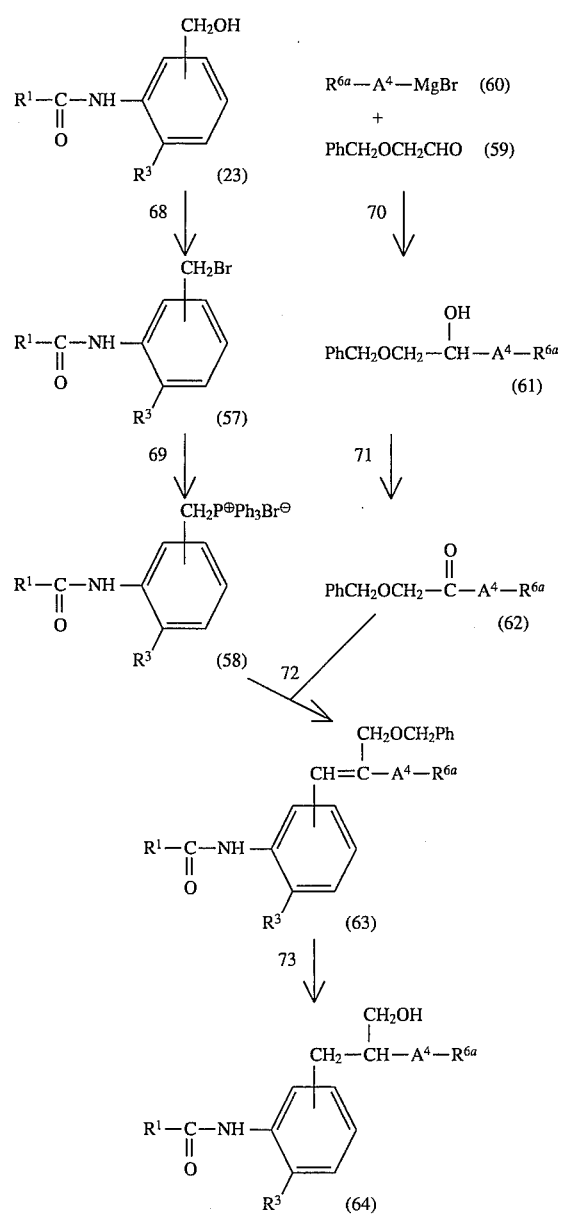
Reaction Scheme XXI
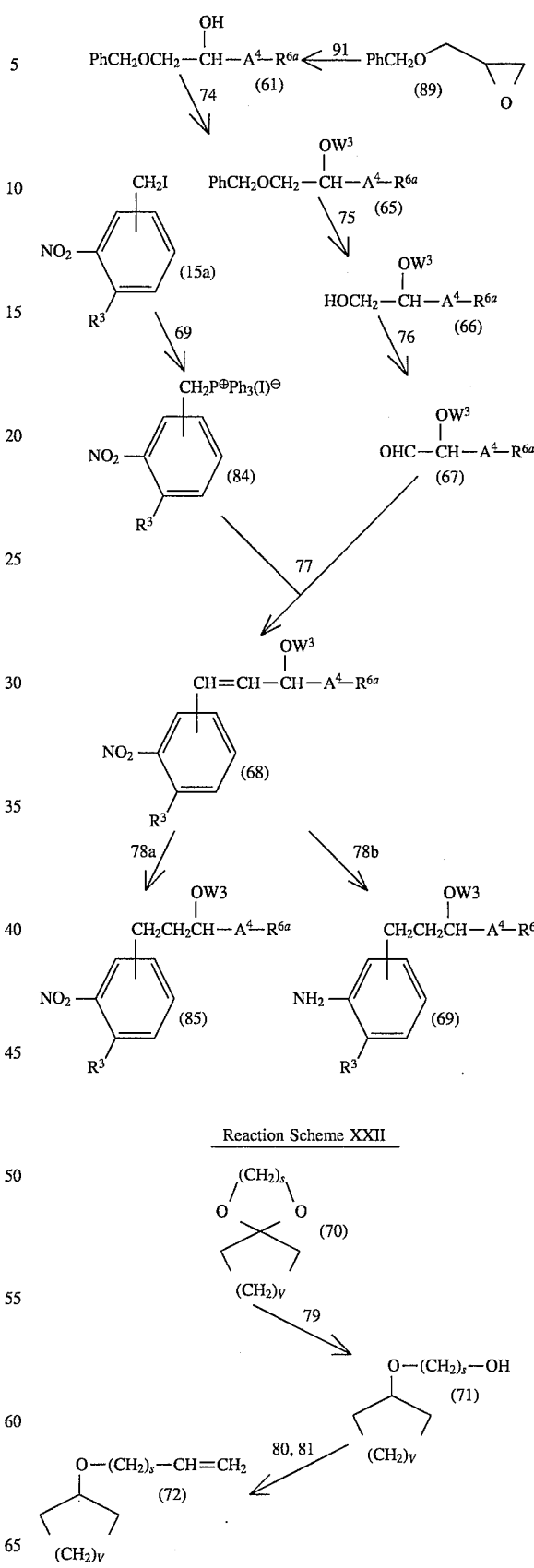
Reaction Scheme XXII

141
-continued
Reaction Scheme XXII
142
-continued
Reaction Scheme XXIV
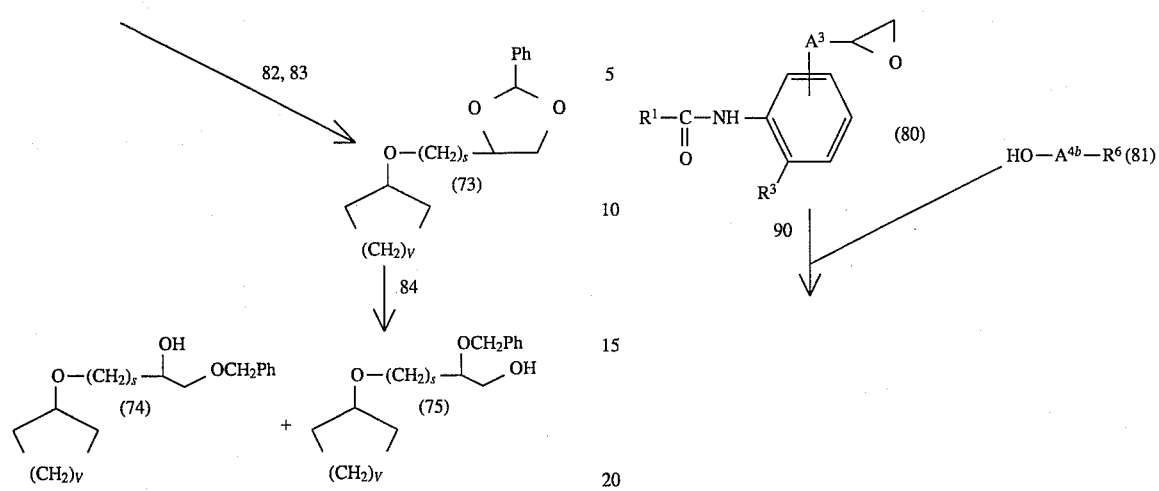
Reaction Scheme XXIII
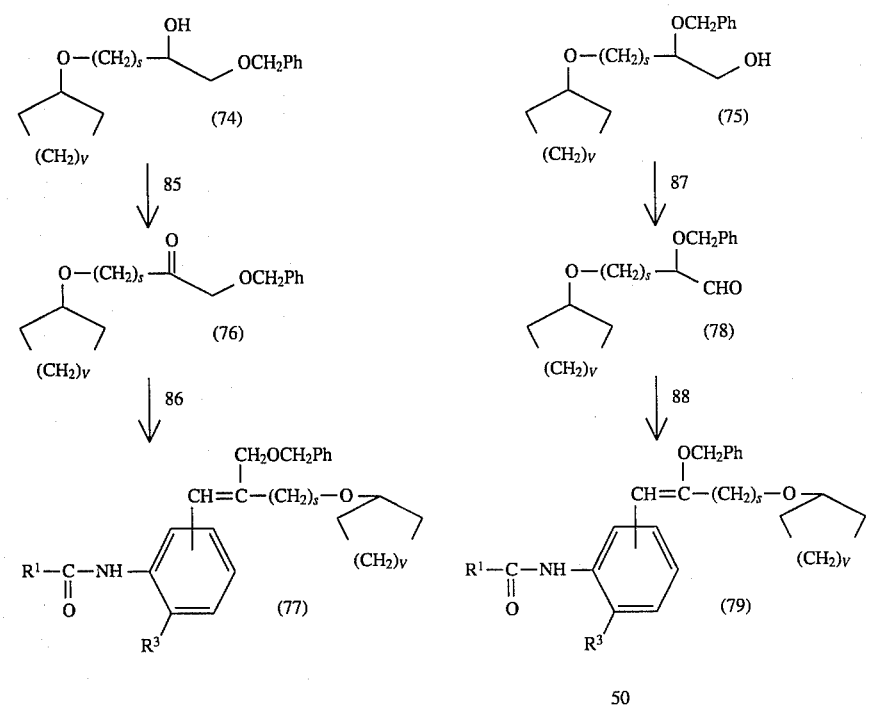
Reaction Scheme XXIV
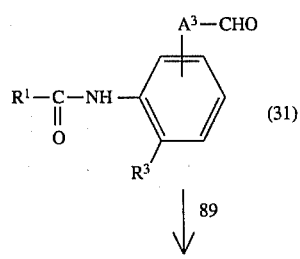
-continued
Reaction Scheme XXIV
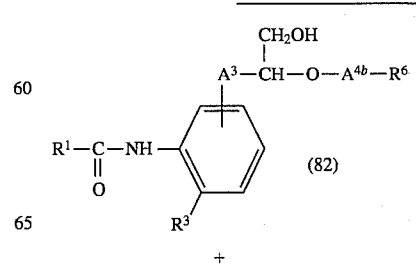
+

5,534,529
143
-continued
Reaction Scheme XXIV
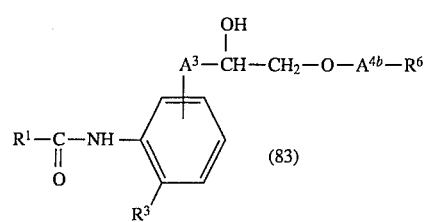
(83)
Reaction Scheme XXV
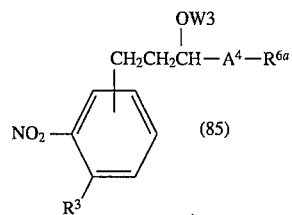
(85)
↓ 92
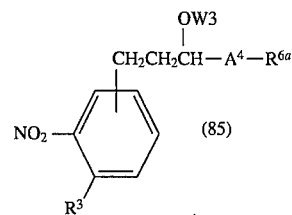
(86)
↓ 93
(87)
↓
(88)
↓ 94
144
-continued
Reaction Scheme XXV
(89)
Reaction Scheme XXVI
(41)
↓ 95
(90)
↓ 96
(91)
↓ 97
(92)
↓ 98
(1d)
In the above formulae:

$R^1$, $R^2$, $R^3$, $R^4$, $R^5$, $R^6$, $R^7$, $R^8$, $R^9$, $R^{10}$, $A^1$, $A^2$, $A^3$, $A^4$, $A^5$ and m are as defined above;

$R^{11}$ represents an alkyl group having from 1 to 6 carbon atoms (preferably a methyl or ethyl group);

$R^{12}$ represents an alkylsulfonyl or arylsulfonyl group in which the aryl group is as defined above and the alkyl group has from 1 to 6 carbon atoms (preferably a methanesulfonyl or p-toluenesulfonyl group);

$A^{3b}$ represents an alkylene group having from 1 to 8 carbon atoms (with a proviso that the number of carbon atoms in the carbon chain is less than that of $A^3$ by one carbon atom);

$R^{4a}$ has the same meaning as defined for $R^4$ (with a proviso that it may optionally have a protecting group);

$R^{4b}$ represents an alkylene group having from 1 to 10 carbon atoms which may be saturated or may include carbon-carbon double bonds (with the proviso that the number of carbon atoms in the carbon chain is less than that of $A^4$ by one carbon atom);

$X^1$ represents a hydroxy group or a halogen atom (preferably chlorine);

$X^2$ represents a halogen atom (preferably bromine or iodine), an alkylsulfonyloxy group having from 1 to 6 carbon atoms (preferably a methanesulfonyloxy group) or an alkylsulfonyloxy group in which the aryl part is as defined above;

$W^1$ represents a hydroxy-protecting group (preferably a trialkylsilyl group, particularly a t-butyldimethylsilyl group), a methoxymethyl group, an acyl group, an aralkyl group (particularly a benzyl group) or a tetrahydropyranyl group;

$W^2$ represents a hydroxy-protecting group (preferably a trialkylsilyl group, particularly a t-butyldimethylsilyl group), an aralkyl group (particularly a benzyl or trityl group), an acyl group (particularly an acetyl group) or a tetrahydropyranyl group;

$W^3$ represents a hydroxy protecting group (preferably a trialkylsilyl group, particularly a t-butyldimethylsilyl group; an alkoxyalkyl group, particularly a methoxymethyl group; or a tetrahydropyranyl group, most preferably a t-butyldimethylsilyl group);

$X^s$ represents a group of formula:

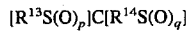

(wherein $R^{13}$ and $R^{14}$ are the same or different and each represents an alkyl group having from 1 to 6 carbon atoms or an aryl group as defined above, or $R^{13}$ and $R^{14}$ together represent an alkylene group having from 1 to 5 carbon atoms, and p and q are the same or different and each is 0, 1 or 2), preferably one of the following groups of formula (101), (102), (103), (104) or (105):

(101)

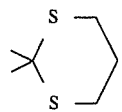

(102)

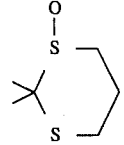

(103)

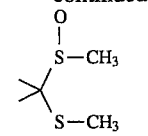

(104)

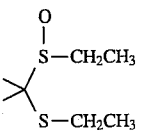

(105)

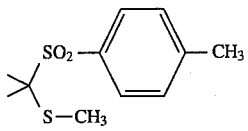

$R^{6a}$ represents $-(M)_n 2-A^5-R^6$, in which M, $n^2$, $A^5$ and $R^6$ are as defined above;

$R^{15}$ represents an imidazolyl or benzimidazolyl group substituted by at least one substituent selected from the group consisting of substituents β, defined above;

s represents 0 or an integer of from 1 to 7; and v represents an integer of from 1 to 10.

The reactions may be carried out as follows:

Reaction Scheme I

Step 1: Condensation

In this step, a compound of formula (4) is prepared by reacting a compound of formula (2) with a compound of formula (3) in an inert solvent. Where $X^1$ represents a hydroxy group, the reaction is conducted in the presence of a condensing agent and a base; and where $X^1$ represents a halogen atom, it is conducted in the presence of a base.

Where $X^1$ represents a hydroxy group (Step 1a), the reaction is normally and preferably effected in the presence of a suitable solvent. There is no particular limitation upon the nature of the solvent used, provided that it has no adverse effect upon the reaction and that it can dissolve the starting material at least to some extent. Examples of preferred solvents include: aromatic hydrocarbons, such as benzene, toluene or xylene; halogenated hydrocarbons, such as methylene chloride, chloroform, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone or methyl ethyl ketone; nitro compounds, such as nitroethane or nitrobenzene; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane; more preferably an aromatic hydrocarbon (particularly benzene), a halogenated hydrocarbon (particularly methylene chloride) or an ether (particularly tetrahydrofuran).

There is likewise no particular restriction on the nature of the condensing agent used, and examples of suitable such agents include: di(lower alkyl) azodicarboxylates-triphenylphosphine, such as diethyl azodicarboxylate-triphenylphosphine; N-(lower alkyl)-5-arylisoxazolium-3'-sulfonates, such as N-ethyl-5-phenylisoxazolium-3'-sulfonate; N,N'-dicycloalkylcarbodiimides, such as N,N'-dicyclohexylcarbodiimide (DCC); 2-halo-1-(lower alkyl)pyridinium halides, such as 2-chloro-1-methylpyridinium iodide; diarylphosphoryl azides, such as diphenylphosphoryl azide (DPPA); phosphoryl chlorides, such as diethyl phosphoryl chloride; imidazole derivatives, such as N,N'-carbonyldiimidazole (CDI); and carbodimide derivatives, such as 1-ethyl-3-(3-dimethylaminopropyl)carbodiimide (EDAPC); preferably N,N'-dicyclohexylcarbodiimide, 2-chloro-1-methylpyridinium iodide and diethyl phosphoryl chloride.

There is also no particular limitation on the nature of the base to be used, provided that it does not adversely affect the molecules of the reagents, and examples include organic bases, such as triethylamine, tributylamine, diisopropylethylamine, N-methylmorpholine, pyridine, 4-(N,N-dimethylamino)pyridine, 4-pyrrolidinopyridine, N,N-dimethylaniline, N,N-diethylaniline, 1,5-diazabicyclo [4.3.0]non-5-ene, 1,4-diazabicyclo[2.2.2]octane (DABCO) and 1,8-diazabicyclo[5.4.0]undec-7-ene (DBU). Of these, we prefer triethylamine, diisopropylethylamine or pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 120° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours, will usually suffice.

After completion of the reaction, the desired compound of formula (1) can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound can, if required, be further purified by such conventional means as recrystallization, reprecipitation or the various chromatography techniques, notably column chromatography.

Where $X^1$ represents a halogen atom (Step 1b), the reaction is normally and preferably effected in the presence of a suitable solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, dichloroethane, chlorobenzene or dichlorobenzene; esters, such as ethyl formate, ethyl acetate, propyl acetate, butyl acetate or diethyl carbonate; ethers, such as tetrahydrofuran, dioxane or dimethoxyethane; ketones, such as acetone or methyl ethyl ketone; and amides, such as formamide, dimethylformamide, dimethylacetamide or hexamethylphosphoric triamide. Of these, we prefer the aromatic hydrocarbons (particularly benzene) and halogenated hydrocarbons (particularly methylene chloride).

There is also no particular limitation on the nature of the base to be used, provided that it does not adversely affect the molecules of the reagents, and examples include organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]undec-7-ene (DBU). Of these, we prefer pyridine or N,N-dimethylaniline.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 50° C., more preferably from −40° to 25° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 24 hours, will usually suffice.

After completion of the reaction, the desired compound of formula (1) can be recovered from the reaction mixture by conventional means. For example, one suitable method comprises: properly neutralizing the reaction mixture; filtering off insoluble materials, if any; adding water and a water-immiscible organic solvent such as ethyl acetate; washing the organic phase with water; separating the organic phase containing the desired compound; drying the extract over a drying agent, such as anhydrous magnesium sulfate; and distilling off the solvent. The desired compound can, if required, be further purified by such conventional means as recrystallization, reprecipitation or the various chromatography techniques, notably column chromatography.

Step 2: Deprotection

In this step, a compound of formula (1a) is prepared by reacting a compound of formula (4) with a deprotecting agent in an inert solvent to remove a group represented by $W^1$.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; alcohols, such as methanol or ethanol; and nitriles, such as acetonitrile or isobutyronitrile. Of these, we prefer the aromatic hydrocarbons (particularly benzene), ethers (particularly tetrahydrofuran) and alcohols (particularly methanol).

Where the protecting group used is a silyl group, such as a t-butyldimethylsilyl group, it can be cleaved by using an inorganic acid, such as hydrochloric acid, or a reagent capable of forming a fluoride ion, such as tetrabutylammonium fluoride. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 70° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

Where the protecting group used is a methoxymethyl group, it can be removed by using an inorganic acid, such as hydrogen chloride in an organic solvent such as dioxane, methanol or ethyl acetate. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 70° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

Where the protecting group used is a tetrahydropyranyl group, it can be cleaved by using an inorganic acid, such as hydrochloric acid, or an organic acid, such as p-toluenesulfonic acid. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

Where the protecting group used is an acyl group, such as an acetyl group, it can be cleaved by using an alkali metal alkoxide, such as sodium methoxide or potassium methoxide, or an alkali metal hydroxide, such as sodium hydroxide or potassium hydroxide. The reaction can take place over a wide range of temperatures, and the precise reaction temperature is not critical to the invention. The preferred reaction temperature will depend upon such factors as the nature of the solvent, and the starting material or reagent used. However, in general, if, as is preferred, the reaction is carried out using methanol as the solvent, we find it convenient to carry out the reaction at a temperature of about 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the sovent. The desired compound, if required, can be further purified by such conventional means as recrystallization, reprecipitation or the various chromatography techniques, notably column chromatography.

Step 3: Esterification

In this step, a compound of formula (1b) is prepared by reacting a compound of formula (1a) with an acid anhydride, monoester, particularly benzyl-, t-butyl- or benzhydryl- ester, or monoester, particularly benzyl-, n-butyl- or benzhydryl- ester, monoacid halide of a dicarboxylic acid or a carboylic acid in an inert solvent. Where an acid anhydride of a dicarboxylic acid is used, the reaction is normally and preferably carried out in the presence of a base; where a monoester of a dicarboxylic or carboxylic acid is used, the reaction is normally and preferably carried out in the presence of a condensing agent and a base; and where a monoester monoacid halide of a dicarboxylic acid is used, the reaction is normally and preferably carried out in the presence of a base.

Where an acid anhydride is used (Step 3a), the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, dichloroethane, chlorobenzene or dichlorobenzene; esters, such as ethyl acetate, propyl acetate, butyl acetate or diethyl carbonate; ethers, such as tetrahydrofuran, dioxane, dimethoxyethane or diethylene glycol dimethyl ether; ketones, such as acetone or methyl ethyl ketone; nitriles, such as acetonitrile or isobutyronitrile; and pyridine or substituted derivatives thereof, such as pyridine or 2,6-lutidine. Of these, we prefer the aromatic hydrocarbons (particularly toluene or xylene) and pyridine or substituted derivatives thereof (particularly pyridine).

There is also no particular limitation on the nature of the base to be used, provided that it does not adversely affect the molecules of the reagents, and examples include organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), preferably triethylamine or pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C., preferably 70° to 120° C. The time required for the reaction may also vary widely, depending on many factors, notably the reaction temperature and the nature of the reagents and solvent employed. However, provided that the reaction is effected under the preferred conditions outlined above, a period of from 1 to 72 hours, preferably from 1 to 30 hours, will usually suffice.

After completion of the reaction, the desired compound can be recovered from the reaction mixture by conventional means. For example, one suitable method comprises: acidifying the the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Where a monoester of a dicarboxylic or carboxylic acid is used (Step 3b), the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, dichloroethane, chlorobenzene or dichlorobenzene; esters, such as ethyl acetate, propyl acetate, butyl acetate or diethyl carbonate; ethers, such as tetrahydrofuran, dioxane, dimethoxyethane or diethylene glycol dimethyl ether; ketones, such as acetone or methyl ethyl ketone; and nitriles, such as acetonitrile or isobutyronitrile. Of these, we prefer the aromatic hydrocarbons (particularly benzene), ethers (particularly tetrahydrofuran) and halogenated hydrocarbons (particularly methylene chloride).

There is no particular restriction on the nature of the condensing agent to be used, and suitable examples include di(lower alkyl) azodicarboxylates-triphenylphosphine, such as diethyl azodicarboxylate-triphenylphosphine; N-(lower alkyl)-5-arylisoxazolium-3'-sulfonates, such as N-ethyl-5-phenylisooxozolium-3'-sulfonate; N,N'-dicycloalkylcarbodiimides, such as N,N'-dicyclohexylcarbodiimide; 2-halo-1-(lower alkyl)pyridinium halides, such as 2-chloro-1-methylpyridinium iodide; diarylphosphoryl azides, such as diphenylphosphoryl azide (DPPA); imidazole derivatives, such as N,N'-carbodiimidazole (CDI); and carbodiimides, such as 1-ethyl-3-(3-dimethylaminopropyl)carbodiimide (EDAPC). Of these, we prefer N,N'-dicyclohexylcarbodiimide, 2-chloro-1-methylpyridinium iodide and 1-ethyl-3-(3-dimethylaminopropyl)carbodiimide.

There is also no particular limitation on the nature of the base to be used, provided that it does not adversely affect the molecules of the reagents, and examples include organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]undec-7-ene (DBU). Of these, we prefer triethylamine or N-diisopropyl-N-ethylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −60° to 120° C., more preferably from 0° to 70° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Debenzylation of the monobenzyl ester thus obtained may be carried out by catalytic reduction using a catalyst, such as palladium-on-charcoal or palladium black, in a stream of hydrogen or formic acid to produce a carboxylic acid compound.

Deprotection of the mono t-butyl ester thus obtained may be carried out by the use of an acid catalyst, such as hydrogen chloride/dioxane to produce a carboxylic acid compound.

Deprotection of the mono benzhydryl ester thus obtained may be carried out by the use of an acid catalyst, such as trifluoroacetic acid/anisole to produce a carboxylic acid compound.

Where a monoester monoacid halide is used (Step 3c), the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl acetate, propyl acetate, butyl acetate or diethyl carbonate; ethers, such as diethyl ether, tetrahydrofuran, dioxane or dimethoxyethane; ketones, such as acetone or methyl ethyl ketone; and nitriles, such as acetonitrile or isobutyronitrile. Of these, we prefer the aromatic hydrocarbons (particularly benzene) or halogenated hydrocarbons (particularly methylene chloride).

There is also no particular limitation on the nature of the base to be used, provided that it does not adversely affect the molecules of the reagents, and any which may be used in conventional reactions may equally be used here. Examples include organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo-[2.2.2]octane (DABCO) or 1,8-diazabicyclo [5.4.0]-undec-7-ene (DBU). Of these, we prefer triethylamine or pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −40° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Debenzylation of the monobenzyl ester thus obtained may be carried out by catalytic reduction using a catalyst, such as palladium-on-charcoal, in a stream of hydrogen to produce a carboxylic acid compound.

Deprotection of the mono t-butyl ester thus obtained may be carried out by the use of an acid catalyst, such as hydrogen chloride/dioxane to produce a carboxylic acid compound.

Deprotection of the mono benzhydryl ester thus obtained may be carried out by the use of an acid catalyst, such as trifluoroacetic acid/anisole to produce a carboxylic acid compound.

Where $R^7$ represents a group of formula: —C(=O)—CHR$^8$—NR$^9$R$^{10}$ (wherein $R^9$ and $R^{10}$ each independently represents an alkyl group), the desired compound of formula (1b) may be prepared by reacting the compound of formula (1a) with a compound of formula: HOC(=O)—CHR$^8$—NR$^9$R$^{10}$ in a similar manner to the procedure described in Step 3b. Where $R^7$ represents a group of formula: —C(=O)—CHR$^8$—NR$^9$R$^{10}$ (wherein $R^9$ represents a hydrogen atom), the desired compound of formula (1b) may be prepared by reacting the compound of formula (1a) with a compound of formula: HO—C(=O)—CHR$^8$—NR$^{10}$COOBu$^t$ in a similar manner to the procedure described in Step 3b and subsequently by eliminating the t-butoxycarbonyl group by using an acid, such as hydrogen chloride.

Where $R^7$ represents a group of formula: —P(=O)(OH)$_2$, the desired compound of formula (1b) can be prepared by reacting the compound of formula (1a) with a compound of formula: ClP(=O)(OCH$_2$Ph)$_2$ in a similar manner to the procedure described in Step 3c and subsequently by eliminating the benzyl group by catalytic reduction.

Step 4: Oxidation

In this step, a compound of formula (1c) can be prepared by reacting a compound of formula (1a) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl formate or ethyl acetate; ethers, such as tetrahydrofuran, dimethoxyethane or dioxane; ketones, such as acetone, methyl ethyl ketone or methyl isobutyl ketone; and nitriles, such as acetonitrile or isobutyronitrile. Of these, we prefer the halogenated hydrocarbons (particularly methylene chloride).

There is also no particular limitation upon the nature of the oxidizing agent used, and any such agent commonly used in conventional oxidation reaction may equally be used here. Examples of preferred oxidizing agents include: inorganic metal oxides including manganese oxides, such as potassium permanganate; chromic acid compounds, such as chromic acid-sulfuric acid, chromic anhyride-pyridine complex or pyridinium chlorochromate; and cerium compounds, such as ammonium cerium nitrate (CAN); and reagents usable in dimethyl sulfoxide oxidation (for example, dimethyl sulfoxide and dicyclohexylcarbodiimide, oxalyl chloride, acetic anhydride, phosphorus pentoxide or pyridine-sulfuric anhydride complex). Of these, we prefer pyridinium chlorochromate or dimethyl sulfoxide/oxalyl chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 50° C., more preferably from −60° to 25° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 12 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 5: Condensation

In this step, a compound of formula (1c) can be prepared by reacting a compound of formula (2) with a compound of formula (5) in an inert solvent. The reaction involved in this Step is essentially the same as that involved in Step 1 of Reaction Scheme I, and may be carried out using the same reagents and reaction conditions.

Step 6: Reduction

In this step, a compound of formula (1a) can be prepared by reacting a compound of formula (1c) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane or dimethoxyethane; and alcohols, such as methanol or ethanol. Of these, we prefer the alcohols (particularly methanol) and the ethers (particularly tetrahydrofuran).

There is likewise no particular restriction upon the nature of the reducing agent used, and any reducing agent commonly used in conventional reactions may equally be used here. Examples of suitable reducing agents include sodium borohydride and diisobutylaluminum hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 50° C., more preferably from −60° to 25° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, preferably 10 minutes to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Reaction Scheme II

Step 7: Alkylation

In this step, a compound of formula (8) can be prepared by alkylation of a compound of formula $X^sH_2$ with a compound of formula (7).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane or dimethoxyethane; nitro compounds, such as nitroethane; nitriles, such as acetonitrile; amides, such as dimethylformamide, dimethylacetamide or hexamethylphosphoric triamide; and sulfoxides, such as dimethyl sulfoxide or sulfolane. Of these, we prefer the amides (particularly dimethylformamide) and sulfoxides (particularly dimethyl sulfoxide).

There is likewise no particular restriction upon the nature of the base used, and any base commonly used in conventional reactions may equally be used here. Examples of suitable bases include alkali metal hydrides, such as lithium hydride, sodium hydride or potassium hydride; alkali metal alkoxides, such as sodium methoxide, sodium ethoxide, potassium t-butoxide or lithium methoxide; and organic metal bases, such as butyllithium or lithium diisopropylamide. Of these, we prefer the alkali metal hydrides (particularly sodium hydride) and organic metal bases (particularly butyllithium or lithium diisopropylamide).

Suitable compounds of formula $X^sH_2$ include such sulfur-containing compounds as 1,3-dithiane, (methylthio)methyl p-tolyl sulfone and (methylthio)methyl methyl sulfoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-20°$ to $100°$ C., more preferably from $0°$ to $50°$ C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 8: Alkylation

In this step, a compound of formula (10) can be prepared by reacting a compound of formula (8) with a compound of formula (9).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide or sulfolane. Of these, we prefer the ethers (particularly tetrahydrofuran or dimethoxyethane).

There is likewise no particular restriction upon the nature of the base used, and any base commonly used in conventional reactions may equally be used here. Examples of suitable bases include: alkali metal hydrides, such as lithium hydride, sodium hydride or potassium hydride; alkali metal alkoxides, such as sodium methoxide, sodium ethoxide, potassium t-butoxide or lithium methoxide; and organic metal bases, such as butyllithium or lithium diisopropylamide. Of these, we prefer the organic metal bases (particularly butyllithium).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-78°$ to $100°$ C., more preferably from $-60°$ to $50°$ C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

When the desired compound is labile, it can be used in the following reaction without purification.

Step 9: Desulfurization

In this step, a compound of formula (11) can be prepared by solvolysis of a compound of formula (10) in the presence of an acid catalyst, a mercury salt or a silver salt.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; ketones, such as acetone or methyl ethyl ketone; and water. Of these, we prefer the alcohols (particularly methanol) or ethers (particularly tetrahydrofuran).

There is likewise no particular restriction upon the nature of the acid catalyst used, and any acid catalyst commonly used in conventional reactions may equally be used here. Examples of suitable acid catalysts include: Bronsted acids, including inorganic acids, such as hydrochloric acid, hydrobromic acid, sulfuric acid, perchloric acid or phosphoric acid, and organic acids, such as methanesulfonic acid, p-toluenesulfonic acid, trifluoroacetic acid or trifluoromethanesulfonic acid. Of these, we prefer concentrated hydrochloric acid.

When 1,3-dithiane is used as the compound of formula $X^rH_2$, the solvolysis can be conducted in the presence of mercuric chloride or silver nitrate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 25° to 150° C., more preferably from 50° to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 10: Reduction of a keto group

In this step, a compound of formula (6) can be prepared by reacting a compound of formula (11) with a reducing agent in an inert solvent.

The reaction involved in this Step is essentially the same as that involved in Step 6 of Reaction Scheme I, and may be carried out using the same reagents and reaction conditions.

Step 10a: Reduction of a nitro group

This step involves the preparation of a compound of formula (5) by reacting a compound of formula (11) with a reducing agent in an inert solvent.

The reaction involved in this Step is essentially the same as that involved in Step 12 of Reaction Scheme III, and may be carried out using the same reagents and reaction conditions.

Reaction Scheme II

Step 11: Introduction of a protecting group

In this step, a compound of formula (12) can be prepared by reacting a compound of formula (6) with a protecting agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or dichloroethane; ethers, such as diethyl ether, tetrahydrofuran, dioxane or dimethoxyethane; and amides, such as formamide, dimethylformamide or dimethylacetamide. Of these, we prefer the halogenated hydrocarbons (particularly methylene chloride) or amides (particularly dimethylformamide).

There is likewise no particular restriction upon the nature of the protecting group used, and any protecting group commonly used in conventional reactions may equally be used here. Examples of suitable protecting agents include t-butyldimethylsilyl chloride, dihydropyrane or methoxymethyl chloride.

For example, protection using the above groups may be carried out as described in "Protective Groups in Organic Synthesis, Second Edition", T. W. Greene & P. G. M. Wut; John Wiley and Sons, Inc., New York (1991).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 30 minutes to 24 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 12: Reduction of a nitro group

This step involves the preparation of a compound of formula (3) by reacting a compound of formula (12) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and water. Of these, we prefer the alcohols.

There is likewise no particular restriction upon the nature of the reducing agent used, and any reducing agent commonly used in conventional reactions may equally be used here. Examples of suitable reducing agents include zinc/acetic acid, iron/hydrochloric acid or tin/hydrochloric acid, preferably zinc/acetic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 150° C., more preferably from 0° to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 20 minutes to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Reaction Scheme IV

Step 13: Formation of β-oxocarboxylate

In this step, a compound of formula (14) can be prepared by reacting a compound of formula (13), with carbonyldiimidazole, and then with potassium malonic acid monoester (preferably $R^{11}$ represents a methyl or ethyl group) in the presence of magnesium bromide-etherate.

Am activated compound of corresponding to the compound of formula (13) can be produced in a manner known per se, for example by analogy with the procedure described in Synthesis 478 (1978).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer diethyl ether, tetrahydrofuran or the nitriles, such as acetonitrile.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 60° C. Where the decarboxylation proceeds slowly, the reaction temperature can be allowed to increase further in the range of from 20° to 50° C. in order to promote the reaction. The time required for the reaction may also vary widely, depending on many factors, notably the reaction temperature and the nature of the reagents and solvent employed. However, provided that the reaction is effected under the preferred conditions outlined above, a period of about 12 hours will usually suffice at temperatures between room temperature and 60° C.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 14: Alkylation

In this step, a compound of formula (16) can be prepared by reacting a compound of formula (14) with a compound of formula (15) in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as dichloromethne; ethers, such as diethyl ether, tetrahydrofuran, dioxane or dimethoxyethane; alcohols, such as methanol, ethanol or t-butanol; nitro compounds, such as nitroethane; amides, such as formamide, dimethylformamide, dimethylacetamide or hexamethylphosphoric triamide; and sulfoxides, such as dimethyl sulfoxide or sulfolane. Of these, we prefer the ethers (particularly tetrahydrofuran), amides (particularly dimethylformamide) or alcohols.

There is likewise no particular restriction upon the nature of the base used, and any base commonly used in conventional reactions may equally be used here. Examples of suitable bases include: inorganic bases including alkali metal hydrides, such as lithium hydride, sodium hydride or potassium hydride; or alkali metal alkoxides, such as sodium methoxide, sodium ethoxide, potassium t-butoxide or lithium methoxide; more preferably alkali metal alkoxides (particularly sodium methoxide, sodium ethoxide or potassium t-butoxide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −30° to 100° C., more preferably from 0° to 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 1 to 10 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step 15: Decarboxylation

In this step, a compound of formula (11) can be prepared by subjecting a compound of formula (16) to hydrolysis in the presence of a base, followed by decarboxylation.

These reactions are normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran, dioxane or dimethoxyethane; alcohols, such as methanol or ethanol; and mixtures of alcohols and water. Of these, we prefer the alcohols or a mixture of an alcohol and water.

There is likewise no particular restriction upon the nature of the base used, and any base commonly used in conventional reactions may equally be used here. Examples of suitable bases include: alkali metal carbonates, such as sodium carbonate, potassium carbonate or lithium carbonate; and alkali metal hydroxides or alkali earth metal hydoxides, such as sodium hydroxide, potassium hydroxide, barium hydroxide or lithium hydroxide. Of these, we prefer sodium hydroxide or potassium hydroxide.

The reaction with the base can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, preferably 1 to 10 hours will usually suffice.

After completion of the hydrolysis, the pH of the reaction mixture is adjusted to a pH value of about 5 by the addition of an acid, such as concentrated hydrochloric acid or dilute sulfuric acid to effect decarboxylation.

The decarboxylation reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C., more preferably from 70° to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 4 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Reaction Scheme V

Step 16: Condensation

In this step, a compound of formula (18) can be prepared by reacting a compound of formula (2) with a compound of formula (17) in an inert solvent. The reaction involved in this Step is essentially the same as that involved in Step 1 of Reaction Scheme I, and may be carried out using the same reagents and reaction conditions.

Step 17: Deprotection

In this step, a compound of formula (19) can be prepared by reacting a compound of formula (18) with a deprotecting agent.

The method chosen for the deprotection will varies depending upon the nature of the protecting group, however, such methods are well known and the deprotection can be carried out by conventional means.

Where the protecting group is a t-butyldimethylsilyl group, it can be removed by reacting it with a deprotecting agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; and alcohols, such as methanol or ethanol.

There is likewise no particular restriction upon the nature of the deprotecting agent used, and any deprotecting agent commonly used in conventional reactions may equally be used here. Examples of suitable deprotecting agents include hydrochloric acid or tetrabutylammonium fluoride, preferably hydrochloric acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 1 to 48 hours, more preferably from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step 18: Introduction of a leaving group

In this step, a compound of formula (20), (93) or (95) can be prepared by reacting a compound of formula (19), (23) or (30) with a compound containing an alkylsulfonyl or arylsulfonyl group (preferably a methanesulfonyl or p-toluenesulfonyl group) in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; halogenated hydrocarbons, such as methylene chloride or chloroform; and ethers, such as diethyl ether, tetrahydrofuran, dioxane or dimethoxyethane. Of these, we prefer the halogenated hydrocarbons (particularly methylene chloride or dichloroethane).

There is likewise no particular restriction upon the nature of the base used, and any base commonly used in conventional reactions may equally be used here. Examples of suitable bases include organic bases, such as triethylamine, diisopropylamine, isopropylethylamine, N-methylmorpholine, pyridine, 4-(N,N-dimethylamino)pyridine, N,N-dimethylaniline or N,N-diethylaniline, of which we prefer triethylamine or diisopropylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 50° C., more preferably from 0° to 25° C. The time required for the reaction may also vary widely, depending on many factors, notably the reaction temperature and the nature of the reagents and solvent employed. However, provided that the reaction is effected under the preferred conditions outlined above, a period of from 5 minutes to 10 hours, more preferably from 10 minutes to 3 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step 19: Introduction of an imidazolyl group

In this step, a compound of formula (1d), (94), (96) or (97) can be prepared by reacting a compound of formula (20), (93), (95) or (40) with imidazole or benzimidazole.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran, dioxane, dimethoxyethane or diethylene glycol dimethyl ether; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the amides (particularly dimethylformamide) or sulfoxides (particularly dimethyl sulfoxide).

The reaction can sometimes be accelerated by carrying it out in the presence of sodium iodide or potassium iodide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 180° C., preferably 20° C. to 120° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 12 hours will usually suffice.

After completion of the reaction, the desired compound can be recovered from the reaction mixture by conventional means. For example, one suitable method comprises: adding water to the reaction mixture and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Scheme VI

Step 20: Condensation

In this step, a compound of formula (22) can be prepared by reacting a compound of formula (2) with a compound of formula (21). The reaction involved in this Step is essentially the same as that involved in Step 1 of Reaction Scheme I, and may be carried out using the same reagents and reaction conditions.

Step 21: Deprotection

In this step, a compound of formula (23) can be prepared by reacting a compound of formula (22) with a deprotecting agent.

Where the hydroxy-protecting group is a t-butyldimethylsilyl group, it can usually be removed by treatment with an inorganic acid, such as hydrochloric acid, or with a compound capable of producing a fluoride anion, such as tetrabutylammonium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol; and ethers, such as tetrahydrofuran or dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 70° C. The time required for the reaction may also vary widely, depending on many factors, notably the reaction temperature and the nature of the reagents and solvent employed. However, provided that the reaction is effected under the preferred conditions outlined above, a period of from 1 to 18 hours will usually suffice.

Where the hydroxy-protecting group is an aliphatic acyl group, such as an acetyl group, it can be removed by treatment with a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; organic solvents including alcohols, such as methanol, ethanol or propanol, and ethers, such as tetrahydrofuran or dioxane; or mixtures of water and one or more of these organic solvents.

There is likewise no particular restriction upon the nature of the base used, and any base commonly used in conventional reactions may equally be used here, provided that other parts of the compound are not affected when the protecting group is removed. Examples of suitable bases include: alkali metal alkoxides, such as sodium methoxide; alkali metal carbonates, such as sodium carbonate, potassium carbonate or lithium carbonate; alkali metal hydroxides, such as sodium hydroxide, potassium hydroxide or lithium hydroxide; and ammonia, which may be in various forms, such as aqueous ammonia or concentrated ammonia in methanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., in order to suppress side reactions. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

Where the hydroxy-protecting group is an alkoxymethyl, tetrahydropyranyl, tetrahydrothiopyranyl, tetrahydrofuranyl, tetrahydrothiofuranyl or substituted ethyl group, it can usually be removed by treatment with an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and mixtures of water and one or more of these organic solvents.

There is likewise no particular restriction upon the nature of the acid used, and any acid commonly used in conventional reactions may equally be used here. Examples of suitable acids include Bronsted acids, including inorganic acids, such as hydrochloric acid or sulfuric acid; organic acids, such as acetic acid or p-toluenesulfonic acid; and strongly acidic cationic ion-exchange resins, such as DOWEX (trade mark) 50W.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step 22: Oxidation

In this step, a compound of formula (24) can be prepared by reacting a compound of formula (23) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl formate, ethyl acetate or diethyl carbonate; ethers, such as diethyl ether, tetrahydrofuran, dioxane or dimethoxyethane; ketones, such as acetone or methyl ethyl ketone; and nitriles, such as acetonitrile or isobutyronitrile. Of these, we prefer the halogenated hydrocarbons (particularly methylene chloride) or ethers (particularly tetrahydrofuran).

There is likewise no particular restriction upon the nature of the oxidizing agent used, and any oxidizing agent commonly used in conventional reactions may equally be used here. Examples of suitable oxidizing agents include: manganese oxides, such as manganese dioxide; chromium oxides, such as chromic anhydride-pyridine complex; and reagents usable in dimethyl sulfoxide oxidation (such as complexes of dimethyl sulfoxide and dicyclohexylcarbodiimide, oxalyl chloride, acetic anhydride, phosphorous pentaoxide or pyridine-sulfuric anhydride).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −60° to 40° C. The time required for the reaction may also vary widely, depending on many factors, notably the reaction temperature and the nature of the reagents and solvent employed. However, provided that the reaction is effected under the preferred conditions outlined above, a period of from 1 to 16 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Reaction Scheme VII

Step 23: Condensation

In this step, a compound of formula (26) can be prepared by reacting a compound of formula (25) with the said compound of formula (2) in an inert solvent. The reaction involved in this Step is essentially the same as that involved in Step 1 of Reaction Scheme I, and may be carried out using the same reagents and reaction conditions.

Step 24: Substitution (X→AcO)

In this step, a compound of formula (27) can be prepared by reacting a compound of formula (26) with an acetic acid salt in the presence of sodium iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran, dioxane or dimethoxyethane; alcohols, such as t-butanol; ketones, such as acetone or methyl ethyl ketone; nitro compounds, such as nitromethane; amides, such as formamide, dimethylformamide, dimethylacetamide or hexamethylphosphoric triamide; sulfoxides, such as dimethyl sulfoxide or sulfolane; and organic acids, such as acetic acid. Of these, we prefer the amides (particularly dimethylformamide) or sulfoxides (particularly dimethyl sulfoxide).

Suitable acetates for use in this reaction include the alkali metal salts of acetic acid, such as sodium acetate or potassium acetate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step 25: Deprotection

In this step, a compound of formula (28) can be prepared by reacting a compound of formula (27) with a deacetylating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; and water. Of these, we prefer the alcohols (particularly methanol) or a mixture of water and one or more alcohols.

There is likewise no particular restriction upon the nature of the deacetylating agent used, and any deacetylating agent commonly used in conventional reactions may equally be used here. Examples of suitable deacetylating agents include inorganic bases including alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; and alkali metal hydroxides, such as sodium hydroxide, potassium hydroxide or lithium hydroxide; alkali earth metal hydroxides, such as barium hydroxide; or alkali metal alkoxides, such as sodium methoxide, sodium ethoxide, potassium t-butoxide or lithium methoxide. Of these, we prefer the alkali metal hydroxides (particularly sodium hydroxide or potassium hydroxide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 100° C., more preferably from 25° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, preferably 30 minutes to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or chromatography.

Step 26: Oxidation

In this step, a compound of formula (24a) can be prepared by reacting a compound of formula (28) with an oxidizing agent. The reaction involved in this Step is essentially the same as that involved in Step 22 of Reaction Scheme VI, and may be carried out using the same reagents and reaction conditions.

Reaction Scheme VIII

Step 27:

In this step, a compound of formula (29) can be prepared by reacting a compound of formula (24) with a Wittig-Horner reagent, such as ethyl diethoxyphosphorylacetate in the presence of base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; ethers, such as diethyl ether, tetrahydrofuran, dioxane or dimethoxyethane; amides, such as formamide, dimethylformamide, dimethylacetamide or hexamethylphosphoric triamide; and sulfoxides, such as dimethyl sulfoxide or sulfolane; more preferably ethers (particularly tetrahydrofuran) or amides (particularly dimethylformamide).

There is likewise no particular restriction upon the nature of the base used, and any base commonly used in conventional reactions may equally be used here. Examples of suitable bases include those bases used in step 7.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

A double bond formed in the product can, if desired, be catalytically reduced in a stream of hydrogen.

The reduction reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: esters, such as ethyl acetate; ethers, such as tetrahydrofuran, dioxane or dimethoxyethane; and alcohols, such as methanol or ethanol; more preferably alcohols, such as methanol or ethanol, ethers, such as tetrahydrofuran or dioxane, fatty acids, such as acetic acid, or mixtures of one or more of these organic solvents and water.

There is likewise no particular restriction upon the nature of the catalyst used, and any catalyst commonly used in conventional reactions may equally be used here. Examples of suitable catalysts include palladium-on-charcoal, platinum or Raney nickel.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° to 50° C., more preferably from 0° to 25° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 6 hours will usually suffice.

After completion of the reaction, the desired compound can be recovered from the reaction mixture by conventional means. For example, one suitable method comprises: filtering off the catalyst used; and distilling off the solvent. The desired product thus obtained can, if required, be further purified by such conventional means as recrystallization, reprecipitation or the various chromatography techniques, notably column chromatography.

Step 28: Reduction

In this step, a compound of formula (30) can be prepared by reacting a compound of formula (29) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; and alcohols, such as methanol or ethanol. Of these, we prefer the ethers (particularly tetrahydrofuran) or alcohols (particularly methanol).

There is likewise no particular restriction upon the nature of the reducing agent used, and any reducing agent commonly used in conventional reactions may equally be used here. Examples of suitable reducing agents include sodium borohydride or diisobutylaluminum hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 10 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or chromatography.

Step 29: Oxidation

In this step, a compound of formula (31) can be prepared by reacting a compound of formula (30) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; and ethers, such as tetrahydrofuran, dioxane or dimethoxyethane. Of these, we prefer the halogenated hydrocarbons (particularly methylene chloride).

There is likewise no particular restriction upon the nature of the oxidizing agent used, and any oxidizing agent commonly used in conventional reactions may equally be used here. Examples of suitable oxidizing agents include: chromium compounds, such as chromic anhydride-pyridine complex or pyridinium chlorochromate; and reagents usable in dimethyl sulfoxide oxidation (such as complexes of dimethyl sulfoxide and dicyclohexylcarbodiimide, oxalyl chloride, acetic anhydride, phosphorous pentaoxide or pyridine-sulfuric anhydride). Of these, we prefer pyridinium chlorochromate or dimethyl sulfoxide/oxalyl chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 40° C., more preferably from −60° to 25° C. The time required for the reaction may also vary widely, depending on many factors, notably the reaction temperature and the nature of the reagents and solvent employed. However, provided that the reaction is effected under the preferred conditions outlined above, a period of from 30 minutes to 6 hours, more preferably from 1 to 3 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Reaction Scheme IX

Step 30: Alkylation

In this step, a compound of formula (1e) can be prepared by reacting a compound of formula (31) with the desired Grignard reagent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; and ethers, such as diethyl ether, tetrahydrofuran, dioxane or dimethoxyethane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 50° C., more preferably from −60° to 25° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 1 hour, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step 31: Esterification

In this step, a compound of formula (1f) can be prepared by esterifying a compound of formula (1e) in an inert solvent. The reaction involved in this Step is essentially the same as that involved in Step 3 of Reaction Scheme I, and may be carried out using the same reagents and reaction conditions.

Step 32: Oxidation

In this step, a compound of formula (1g) can be prepared by reacting a compound of formula (1e) with an oxidizing agent in an inert solvent. The reaction involved in this Step is essentially the same as that involved in Step 29 of Reaction Scheme VIII, and may be carried out using the same reagents and reaction conditions.

Reaction Scheme X

Step 33: Alkylation

In this step, a compound of formula (1h) can be prepared by reacting a compound of formula (24) with a Grignard reagent in an inert solvent. The reaction involved in this Step is essentially the same as that involved in Step 30 of Reaction Scheme IX, and may be carried out using the same reagents and reaction conditions.

Step 34: Esterification

In this step, a compound of formula (1i) can be prepared by esterifying a compound of formula (1h) in an inert solvent. The reaction involved in this Step is essentially the same as that involved in Step 3 of Reaction Scheme I, and may be carried out using the same reagents and reaction conditions.

Step 35: Oxidation

In this step, a compound of formula (1j) can be prepared by reacting a compound of formula (1h) with an oxidizing agent in an inert solvent. The reaction involved in this Step is essentially the same as that involved in Step 22 of Reaction Scheme VI, and may be carried out using the same reagents and reaction conditions.

Reaction Scheme XI

Step 36:

In this step, a compound of formula (1k) can be prepared by reacting a compound of formula (24) with the desired Wittig or Wittig-Horner reagent in the presence of base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane, dimethoxyethane or diethylene glycol dimethyl ether; amides, such as dimethylformamide, dimethylacetamide or hexamethylphosphoric triamide; and sulfoxides, such as dimethyl sulfoxide or sulfolane. Of these, we prefer the ethers (particularly tetrahydrofuran) or amides (particularly dimethylformamide).

There is likewise no particular restriction upon the nature of the base used, and any base commonly used in conventional reactions may equally be used here. Examples of suitable bases include those bases used in Step 7.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 70° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 12 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

A double bond formed in the product can, if desired, be catalytically reduced in a stream of hydrogen.

The reduction reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: esters, such as ethylacetate; ethers, such as tetrahydrofuran, dioxane or dimethoxyethane; alcohols, such as methanol or ethanol; and fatty acids, such as acetic acid; water; more preferably alcohols, such as methanol or ethanol, ethers, such as tetrahydrofuran or dioxane, fatty acids, such as acetic acid, or mixtures of one or more of these organic solvents and water.

There is likewise no particular restriction upon the nature of the catalyst used, and any catalyst commonly used in conventional reactions may equally be used here. Examples of suitable catalysts include palladium-on-charcoal, platinum and Raney nickel.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° to 50° C., more preferably from 0° to 25° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 6 hours, will usually suffice.

After completion of the reaction, the desired compound can be recovered from the reaction mixture by conventional means. For example, one suitable method comprises: filtering off the catalyst used; and distilling off the solvent. The desired product thus obtained can, if required, be further purified by such conventional means as recrystallization, reprecipitation or the various chromatography techniques, notably column chromatography.

Step 37: Reduction

In this step, a compound of formula (1m) can be prepared by reacting a compound of formula (1k) with a reducing agent in an inert solvent. The reaction involved in this Step is essentially the same as that involved in Step 6 of Reaction Scheme I, and may be carried out using the same reagents and reaction conditions.

Step 38: Esterification

In this step, a compound of formula (1n) can be prepared by esterifying a compound of formula (1m) in an inert solvent. The reaction involved in this Step is essentially the same as that involved in Step 3 of Reaction Scheme I, and may be carried out using the same reagents and reaction conditions.

Reaction Scheme XII

Step 39: Isocyanation (of a carboxylic acid)

In this step, a compound of formula (33) can be prepared by reacting a compound of formula (32) with diphenylphosphoryl azide in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride or dichloroethane; ethers, such as diethyl ether, tetrahydrofuran, dioxane, dimethoxyethane or diethylene glycol dimethyl ether; nitriles, such as acetonitrile or iosbutyronitrile; and amides, such as formamide, dimethylformamide, dimethylacetamide or hexantethylphosphoric triamide. Of these, we prefer the aromatic hydrocarbons (particularly benzene or toluene) or ethers (particularly tetrahydrofuran).

There is likewise no particular restriction upon the nature of the base used, and any base commonly used in conventional reactions may equally be used here. Examples of suitable bases include organic bases, such as triethylamine, diisopropylethylamine, N-methylmorpholine, pyridine, 4-(N,N-dimethylamino)pyridine, N,N-dimethylaniline or N,N-diethylaniline. Of these, we prefer triethylamine or diisopropylethylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C., more preferably from 70° to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 12 hours, will usually suffice.

After completion of the reaction, the desired compound has so far been found to be too labile to purify and so it can be used in the following reaction without purification.

Step 40: Addition

In this step, a compound of formula (34) in which $R^2$ represents a hydrogen atom can be prepared by reacting a compound of formula (33) with said compound of formula (3), (5), (17) or (21).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride or dichloroethane; and ethers, such as tetrahydrofuran, dioxane or dimethoxyethane. Of these, we prefer the aromatic hydrocarbons (particularly benzene or toluene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 6 hours, will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent. The desired product thus obtained can, if required, be purified by such conventional means as recrystallization, reprecipitation or the various chromatography techniques, notably column chromatography.

Step 41: Isocyanation (of an amine)

In this step, a compound of formula (36) can be prepared by reacting a compound of formula (35) with phosgene, trichloromethyl chloroformate or bis(trichloromethyl) carbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or dichloroethane; and ethers, such as diethyl ether, tetrahydrofuran, dioxane or dimethoxyethane. Of these, we prefer methylene chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −40° to 50° C., more preferably from −20° to 0° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 6 hours will usually suffice.

After completion of the reaction, the desired product is preferably used in the following step without purification due to the lability of the compound.

Step 42: Addition

In this step, a compound of formula (34) can be prepared by reacting a compound of formula (36) with an amine of formula: $R^1R^2NH$ in an inert solvent. The reaction involved in this Step is essentially the same as that involved in Step 40 of Reaction Scheme XII, and may be carried out using the same reagents and reaction conditions.

Step 43: Deprotection

In this step, a compound of formula (1p) can be prepared by reacting a compound of formula (34) with a deprotecting agent in an inert solvent. The reaction involved in this Step is essentially the same as that involved in Step 2 of Reaction Scheme I, and may be carried out using the same reagents and reaction conditions. If desired, the secondary hydroxy group of the compound of formula (34) can be modified according to the procedure described in Step 3.

Methods for preparing the said starting compounds of formulae (15), (17), (21) and (25) will be explained as follows.

Reaction Scheme XIII

Step 44: Reduction

In this step, a compound of formula (38) can be prepared by reacting a compound of formula (37) with a reducing agent.

There is likewise no particular restriction upon the nature of the reducing agent used, and any reducing agent commonly used in conventional reactions may equally be used here. Examples of suitable reducing agents include diboranes, such as diborane or diborane-dimethyl sulfide complex.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran, dioxane or 1,2-dimethoxyethane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20° and 100° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

As an alternative to this reduction, a compound of formula (37) is reacted with a chloroformate, such as ethyl chloroformate, to produce a mixed anhydride and then the product can be reduced by sodium borohydride.

The solvent used in the synthesis of the mixed anhydride is preferably an ether, such as 1,2-dimethoxyethane or tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° and 30° C. The time required for the reaction may also vary widely, depending on many factors, notably the reaction temperature and the nature of the reagents and solvent employed. However, provided that the reaction is effected under the preferred conditions outlined above, a period of from 30 minutes to 6 hours will usually suffice.

After completion of the reaction, the anhydride may be recovered from the reaction mixture by a variety of well known techniques, for example by filtering the reaction mixture with the aid of a Celite (trade mark) filter aid. The filtrate is then added to a mixture of water and tetrahydrofuran containing sodium borohydride to effect reduction.

The reduction reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° and 50° C. The time required for the reaction may also vary widely, depending on many factors, notably the reaction temperature and the nature of the reagents and solvent employed. However, provided that the reaction is effected under the preferred conditions outlined above, a period of from 30 minutes to 3 hours will usually suffice.

Step 45: Introduction of a leaving group

In this step, a compound of formula (15) can be prepared by reacting a compound of formula (38) with an alkylsulfonyl or arylsulfonyl halide in an inert solvent in the presence of a base. The reaction involved in this Step is essentially the same as that involved in Step 18 of Reaction Scheme V, and may be carried out using the same reagents and reaction conditions.

The sulfonate obtained in this step can, if desired, be reacted with sodium iodide or potassium iodide to produce an iodide.

A suitable solvent for this reaction is a ketone, such as acetone or methyl ethyl ketone.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° and 80° C. The time required for the reaction may also vary widely, depending on many factors, notably the reaction temperature and the nature of the reagents and solvent employed. However, provided that the reaction is effected under the preferred conditions outlined above, a period of from 10 minutes to 8 hours will usually suffice.

Reaction Scheme XIV

Step 46: Introduction of a leaving group

In this step, a compound of formula (40) can be prepared by reacting a compound of formula (39) with an alkylsulfonyl or arylsulfonyl halide in an inert solvent. The reaction involved in this Step is essentially the same as that involved in Step 45 of Reaction Scheme XIII, and may be carried out using the same reagents and reaction conditions. This step is used for the preparation of a compound in which $A^1$ is other than a single bond.

Further the sulfonate thus obtained in this step can, if desired, be converted to the corresponding iodide in an analogous manner to the procedure described in Step 45.

Step 46(a): Preparation of an alcohol compound

In this step, a compound of formula (41) can be prepared by reacting a compound of formula (39) with the desired diol compound (HO—$A^2$—OH) or haloalcohol compound (hal—$A^2$—OH) in the presence of a base. This step is used for the preparation of a compound in which $A^1$ is a single bond.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran or 1,2-dimethoxyethane; and amides, such as dimethylformamide or dimethylacetamide.

There is likewise no particular restriction upon the nature of the base used, and any base commonly used in conventional reactions may equally be used here. Examples of suitable bases include alkali metal carbonates, such as potassium carbonate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20° to 100° C. The time required for the reaction may also vary widely, depending on many factors, notably the reaction temperature and the nature of the reagents and solvent employed. However, provided that the reaction is effected under the preferred conditions outlined above, a period of from 2 to 12 hours will usually suffice.

After completion of the reaction, the desired compound can be recovered from the reaction mixture by conventional means. For example, one suitable method comprises: distilling off the solvent; adding a water-immiscible solvent, such as diethyl ether; washing the organic phase with water; separating the organic phase containing the desired compound; drying the extract over a drying agent, such as anhydrous magnesium sulfate; and distilling off the solvent.

Step 47: Preparation of an alcoholic compound

In this step, a compound of formula (41) can be prepared by reacting a compound of formula (40) with the desired diol compound in the presence of a base. This step is used for the preparation of a compound in which $A^1$ is other than a single bond.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran or 1,2-dimethoxyethane; and amides, such as dimethylformamide or dimethylacetamide.

There is likewise no particular restriction upon the nature of the base used, and any base commonly used in conventional reactions may equally be used here. Examples of suitable bases include alkali metal hydrides, such as sodium hydride or lithium hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° and 60° C. (preferably at room temperature). The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent.

Step 48: Introduction of a protecting group

In this step, a compound of formula (42) can be prepared by reacting a compound of formula (41) with a protecting agent in an inert solvent. The reaction involved in this Step is essentially the same as that involved in Step 11 of Reaction Scheme III, and may be carried out using the same reagents (except methoxymethyl chloride) and reaction conditions.

Step 49: Reduction of a nitro group

In this step, a compound of formula (17) can be prepared by reacting a compound of formula (42) with a reducing agent in an inert solvent. The reaction involved in this Step is essentially the same as that involved in Step 12 of Reaction Scheme III, and may be carried out using the same reagents and reaction conditions.

Reaction Scheme XV

Step 50: Reduction

In this step, a compound of formula (44) can be prepared by reacting a compound of formula (43) with a reducing agent in an inert solvent. The reaction involved in this Step is essentially the same as that involved in Step 44 of Reaction Scheme XIII, and may be carried out using the same reagents and reaction conditions.

Step 51: Introduction of a protecting group

In this step, a compound of formula (45) can be prepared by reacting a compound of formula (44) with a protecting agent in an inert solvent. The reaction involved in this Step is essentially the same as that involved in Step 11 of Reaction Scheme III, and may be carried out using the same reagents (except methoxymethyl chloride) and reaction conditions.

Step 52: Reduction of a nitro group

In this step, a compound of formula (21) can be prepared by reacting a compound of formula (45) with a reducing agent in an inert solvent. The reaction involved in this Step is essentially the same as that involved in Step 12 of Reaction Scheme III, and may be carried out using the same reagents and reaction conditions.

Reaction Scheme XVI

Step 53: Alkylation

In this step, a compound of formula (47) can be prepared by reacting a compound of formula (46) with a dimethyl sulfide in the presence of N-chlorosuccinic imide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include halogenated hydrocarbons, such as methylene chloride or chloroform.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° and 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, one suitable method comprises: filtering off insoluble materials, if any; adding a halogenated hydrocarbon solvent, such as methylene chloride; washing the organic phase with a saturated aqueous solution of sodium hydrogencarbonate; separating the organic phase containing the desired compound; drying the extract over a drying agent, such as anhydrous magnesium sulfate; and distilling off the solvent.

Step 54: Oxidation

In this step, a compound of formula (48) can be prepared by reacting a compound of formula (47) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; and alcohols, such as methanol or ethanol.

There is likewise no particular restriction upon the nature of the oxidizing agent used, and any oxidizing agent commonly used in conventional reactions may equally be used here. Examples of suitable oxidizing agents include m-chloroperbenzoic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° and 60° C. (preferably at room temperature). The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, one suitable method comprises: filtering off insoluble materials, if any; adding water and a water-immiscible solvent, such as ethyl acetate; washing the organic phase with a saturated aqueous solution of sodium carbonate; and then separating the organic phase containing the desired compound; drying the extract over a drying agent, such as anhydrous magnesium sulfate; and distilling off the solvent.

Step 55: Halogenation

In this step, a compound of formula (25) can be prepared by reacting a compound of formula (48) with hydrogen halide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include halogenated hydrocarbons, such as methylene chloride, chloroform or 1,2-dichloroethane.

The hydrogen halide used may be, for example, hydrogen chloride or hydrogen bromide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-20°$ and $60°$ C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, the desired compound can be recovered by collecting the precipitates by filtration.

The starting compound of formula (2) used in the present invention can be prepared by preparing an acid halide from either a commercially available carboxylic acid or a carboxylic acid which can be produced by a manner known per se. In particular, a compound having a (9H-xanthen-9-yl)methyl group can be prepared by an analogous procedure to that disclosed in Japanese Patent Application No. Hei 4-243357. 6,11-dihydrobenz[b,e]-oxepine-11-carboxylic acid is known from EP Publication No. 0497201 (1992). Alternatively the starting compounds used in the present invention can be prepared as follows.

Reaction Scheme XVII

Step 56:

In this step, a compound of formula (50) can be prepared by reacting a compound of formula (49) with oxalyl chloride to produce an acid chloride and then reacting this product with diazomethane.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include diethyl ether or tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-20°$ and $60°$ C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent.

Step 57:

In this step, a compound of formula (51) can be prepared by heating a compound of formula (50) with an alcohol in the presence of a metal salt, such as silver benzoate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include alcohols, such as methanol or ethanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $40°$ and $100°$ C. The time required for the reaction may also vary widely, depending on many factors, notably the reaction temperature and the nature of the reagents and solvent employed. However, provided that the reaction is effected under the preferred conditions outlined above, a period of from 1 to 3 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible solvent, such as ethyl acetate; washing the organic phase with water; separating the organic phase containing the desired compound; drying the extract over a drying agent, such as anhydrous magnesium sulfate; and distilling off the solvent.

Step 58:

In this step, a compound of formula (2a) can be prepared by hydrolysis of a compound of formula (51) in an inert solvent. The reaction involved in this Step is essentially the same as that involved in Step 25 of Reaction Scheme VII, and may be carried out using the same reagents and reaction conditions.

Reaction Scheme XVIII

Step 59: Reduction by lithium aluminum hydride

This step involves the preparation of an alcohol compound by reacting a compound of formula (49) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane and diethylene glycol dimethyl ether (especially tetrahydrofuran).

There is likewise no particular restriction upon the nature of the reducing agent used, and any reducing agent commonly used in conventional reactions may equally be used here. Examples of suitable reducing agents include lithium aluminum hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 70° C., more preferably at a temperature of from 40° to 70° C. The time required for the reaction may also vary widely, depending on many factors, notably the reaction temperature and the nature of the reagents and solvent employed. However, provided that the reaction is effected under the preferred conditions outlined above, a period of from 15 minutes to 2 hours will usually suffice.

After completion of the reaction, the product can be recovered from the reaction mixture by conventional means. An example of such a technique is as follows: the reaction mixture is ice-cooled; water and an aqueous solution of sodium hydroxide are added, followed by a water-immiscible solvent, for example, diethyl ether; insoluble materials are filtered off; the filtrate is washed with water, an aqueous solution of sodium hydrogencarbonate and an aqueous solution of sodium chloride, in that order; and then the solvent is distilled off from the extract leaving the desired product as the residue. The product thus obtained can, if desired, be further purified by conventional menas, such as recrystallization or the various chromatography techniques, notably column chromatography.

Step 60: Introducing a leaving group

This step involves the preparation of an alkyl- or aryl-sulfonate compound by reacting an alcohol compound, prepared as described in Step 59, with a reagent used for introducing an alkyl- or aryl-sulfonyl group (preferably a methanesulfonyl group) in the presence of a base in an inert solvent.

The reaction involved in this Step is essentially the same as that involved in Step 18 of Reaction Scheme V, and may be carried out using the same reagents and reaction conditions.

Step 61: Iodination

This step involves the preparation of a compound of formula (52) by reacting an alkyl- or aryl-sulfonate compound, prepared as described in Step 60, with an iodinating reagent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ketones, such as acetone, methyl ethyl ketone or methyl isobutyl ketone (especially methyl isobutyl ketone).

There is likewise no particular restriction upon the nature of the iodinating agent used, and any iodinating agent commonly used in conventional reactions may equally be used here. Examples of suitable iodinating agents include sodium iodide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 30° to 150° C., more preferably at a temperature of from 60° to 100° C. The time required for the reaction may also vary widely, depending on many factors, notably the reaction temperature and the nature of the reagents and solvent employed. However, provided that the reaction is effected under the preferred conditions outlined above, a period of from 1 to 48 hours, more preferably from 5 to 20 hours, will usually suffice.

After completion of the reaction, the product can be recovered from the reaction mixture by conventional means. An example of such a technique is as follows: the reaction mixture is freed from the solvent by distillation; the residue is mixed with water; the aqueous mixture is extracted with a water-immiscible solvent, for example, benzene, diethyl ether, ethyl acetate or the like; and then the solvent is distilled off from the extract, leaving the desired product as the residue. The product thus obtained can, if desired, be further purified by conventional means, such as recrystallization or the various chromatography techniques, notably column chromatography.

Step 62: Synthesis of an aldehyde precursor

This step involves the preparation of an alkylated aldehyde precursor by reacting a compound of formula (52) with a compound of formula $X^3H_2$ in the presence of a base in an inert solvent.

The reaction involved in this Step is essentially the same as that involved in Step 7 of Reaction Scheme II, and may be carried out using the same reagents and reaction conditions.

Step 63: Hydrolysis

This step involves the preparation of a compound of formula (53) by hydrolizing an aldehyde precursor, prepared as described in Step 62, in the presence of a heavy metal compound.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: mixtures of water with a nitrile, such as acetonitrile, or an alcohol, such as ethanol.

The heavy metal compound used may be, for example, mercuric chloride or silver nitrate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 100° C. The time required for the reaction may also vary widely, depending on many factors, notably the reaction temperature and the nature of the reagents and solvent employed. However, provided that the reaction is effected under the preferred conditions outlined above, a period of from 1 to 5 hours will usually suffice.

After completion of the reaction, the product can be recovered from the reaction mixture by conventional means. An example of such a technique is as follows: the reaction mixture is cooled; a water-immiscible solvent, for example, benzene, diethyl ether, ethyl acetate or the like is added thereto; insoluble materials are filtered off; the filtrate is washed with an aqueous solution of sodium acetate, an aqueous solution of ammonium chloride and an aqueous solution of sodium chloride, in that order; and then the solvent is distilled off from the extract, leaving the desired product as the residue. The product thus obtained can, if desired, be further purified by conventional means, such as recrystallization or the various chromatography techniques, notably column chromatography.

Step 64: Oxidation (to produce a carboxyl group)

This step involves the preparation of a compound of formula (2a) by reacting a compound of formula (53) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. An example of a suitable solvent is a mixture of water and t-butanol.

There is likewise no particular restriction upon the nature of the oxidizing agent used, and any oxidizing agent commonly used in conventional reactions may equally be used here. Examples of suitable oxidizing agents include sodium chlorite.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 5 hours, more preferably from 1 to 3 hours, will usually suffice.

After completion of the reaction, the product can be recovered from the reaction mixture by conventional means. An example of such a technique is as follows: the reaction mixture is extracted with a water-immiscible solvent, for example, methylene chloride; the extract is washed with water; and then the solvent is distilled off from the extract, leaving the desired product as the residue. The product thus obtained can, if desired, be further purified by conventional means, such as recrystallization or the various chromatography techniques, notably column chromatography.

Reaction Scheme XIX

Step 65: Wittig reaction

This step involves the preparation of a compound of formula (54) by reacting a compound of formula (1g) with methoxymethyltriphenylphosphonium chloride in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetraphydrofuran, dioxane, dimethoxyethane and diethylene glycol dimethyl ether (especially tetrahydrofuran).

There is likewise no particular restriction upon the nature of the base used, and any base commonly used in conventional reactions may equally be used here. An Example of a suitable base is butyllithium.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 40° C., and, especially when butyllithium is used as the base, more preferably at a temperature of from 0° to 5° C. The time required for the reaction may also vary widely, depending on many factors, notably the reaction temperature and the nature of the reagents and solvent employed. However, provided that the reaction is effected under the preferred conditions outlined above, a period of from 1 to 5 hours will usually suffice.

After completion of the reaction, the product can be recovered from the reaction mixture by conventional means. An example of such a technique is as follows: the reaction mixture is poured into an aqueous solution of ammonium chloride; the aqueous mixture is extracted with a water-immiscible solvent, for example, benzene, diethyl ether, ethyl acetate or the like; and then the solvent is distilled off from the extract, leaving the desired product as the residue. The product thus obtained can, if desired, be further purified by conventional means, such as recrystallization or the various chromatography techniques, notably column chromatography.

Step 66: Hydrolysis

This step involves the preparation of a compound of formula (55) by reacting a compound of formula (54) with an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisoprophyl ether, tetrahydrofuran, dioxane, dimethoxyethane and diethylene glycol dimethyl ether (especially tetrahydrofuran).

There is likewise no particular restriction upon the nature of the acid used, and any acid commonly used in conventional reactions of this type may equally be used here. An example of a suitable acid is hydrochloric acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 100° C., more preferably at a temperature of from 30° to 80° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the product can be recovered from reaction mixture by conventional means. An example of such a technique is as follows: the reaction mixture is poured into water; the aqueous mixture is extracted with a water-immiscible solvent, for example, benzene, diethyl ether, ethyl acetate or the like; and then the solvent is distilled off from the extract, leaving the desired product as the residue. The product thus obtained can be used in the following reaction without purification or can, if desired, be purified by conventional means, such as recrystallization or the various chromatography techniques, notably column chromatography.

Step 67: Reduction

This step involves the preparation of a compound of formula (56) by reacting a compound of formula (55) with a reducing agent in an inert solvent.

The reaction involved in this Step is essentially the same as that involved in Step 10 of Reaction Scheme II, and may be carried out using the same reagents and reaction conditions.

Reaction Scheme XX

Step 68: Halogenation

This step involves the preparation of a compound of formula (57) by reacting a compound of formula (23) with a halogenating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride and chloroform (especially methylene chloride).

The halogenating agents used my be, for example, a combination of triphenylphosphine and carbon tetrabromide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 5 hours will usually suffice.

After completion of the reaction, the product can be recovered from the reaction mixture by conventional means, for example, the reaction mixture is washed with water and then the solvent is distilled off from the organic phase, leaving the desired product as the residue. The product thus obtained can, if desired, be further purified by conventional means, such as recrystallization or the various chromatography techniques, notably column chromatography.

Step 69: Formation of a phosphonium compound

This step involves the preparation of a compound of formula (58) by reacting a compound of formula (57) with triphenylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene and xylene (especially toluene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C. The time required for the reaction may also vary widely, depending on many factors, notably the reaction temperature and the nature of the reagents and solvent employed. However, provided that the reaction is effected under the preferred conditions outlined above, a period of from 5 to 24 hours will usually suffice.

After completion of the reaction, the product can be recovered from the reaction mixture by conventional means. An such a technique is as follows: the reaction temperature is reduced to room temperature; precipitates are collected by filtration and washed with toluene and hexane, and then dried. The product thus obtained can, if desired, be further purified by conventional means, such as recrystallization.

The same step is also involved in the preparation of a compound of formula (84) from a compound of formula (15a) (Reaction Scheme XXI).

Step 70: Grignard reaction

This step involves the preparation of a compound of formula (61) by a Grignard reaction between compounds of formulae (59) and (60).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane and diethylene glycol dimethyl ether (especially diethyl ether).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 40° C. The time required for the reaction may also vary widely, depending on many factors, notably the reaction temperature and the nature of the reagents and solvent employed. However, provided that the reaction is effected under the preferred conditions outlined above, a period of from 10 minutes to 2 hours will usually suffice.

After completion of the reaction, the product can be recovered from the reaction mixture by conventional means. An example of such a technique is as follows: an aqueous solution of ammonium chloride is added to the reaction temperature; the aqueous mixture is extracted with a water-immiscible solvent, for example, benzene, diethyl ether, ethyl acetate or the like; the extract is washed with water and dried; and then the solvent is distilled off from the extract, leaving the desired product as the residue. The product thus obtained can, if desired, be further purified by conventional means, such as recrystallization or the various chromatography techniques, notably column chromatography.

Step 71: Swern oxidation

This step involves the preparation of a compound of formula (62) by reacting a compound of formula (61) with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform and dichloroethane (especially methylene chloride).

The oxidizing agents used may be, for example, a combination of oxalyl chloride and dimethyl sulfoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° to −50° C. The time required for the reaction may also vary widely, depending on many factors, notably the reaction temperature and the nature of the reagents and solvent employed. However, provided that the reaction is effected under the preferred conditions outlined above, a period of from 10 minutes to 1 hour will usually suffice. After that, the reaction mixture is cooled to −78° C. and then a base (preferably triethylamine) is added, after which the temperature is allowed to rise to room temperature for a period of from 10 to 30 minutes.

After completion of the reaction, the product is recovered from the reaction mixture by conventional means. An example of such a technique is as follows: the reaction mixture is poured into water; the aqueous mixture is extracted with a water-immiscible solvent, for example, benzene, diethyl ether, ethyl acetate or the like; the extract is washed with dilute hydrochloric acid and water, in that order; and then the solvent is distilled off from the organic phase, leaving the desired product as the residue. The product thus obtained can normally be used in the following reaction without purification or can, if desired, be further purified by conventional means, such as recrystallization or the various chromatography techniques, notably column chromatography.

Step 72: Wittig reaction

This step involves the preparation of a compound of formula (63) by means of a Wittig reaction, using compounds of formulae (58) and (62) in an inert solvent.

The reaction involved in this Step is essentially the same as that involved in Step 65 of Reaction Scheme XIX, and may be carried out using the same reagents and reaction conditions.

Step 73: Debenzylation and reduction of a double bond

This step involves the preparation of a compound of formula (64) by reacting a compound of formula (63) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, isopropanol, butanol, isobutanol or t-butanol (especially ethanol); and ethers, such as diethyl ether or tetrahydrofuran.

There is likewise no particular restriction upon the nature of the reducing agent used, and any reducing agent commonly used in conventional reactions of this type may equally be used here. An examples of a suitable reducing agent is hydrogen in the presence of a palladium catalyst.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 40° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

After completion of the reaction, the product is recovered from the reaction mixture by conventional means, for example, the catalyst is filtered off and then the solvent is distilled off from the filtrate, leaving the desired product as the residue. The product thus obtained can, if desired, be further purified by conventional means, such as recrystallization or the various chromatography techniques, notably column chromatography.

Reaction Scheme XXI

Step 74: Protection of a hydroxy group

This step involves the preparation of a compound of formula (65) by reacting a compound of formula (61) with a reagent for protecting a hydroxy group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include dimethylformamide.

Examples of suitable protecting groups include the methoxymethyl and t-butyldimethylsilyl groups. The reaction conditions will depend on the nature of the protecting group to be introduced, for example as follows:

(i) Introduction of a methoxymethyl group

The desired compound can be prepared by reacting the compound of formula (61) with methoxymethyl chloride in the presence of an organic tertiary amine, such as triethylamine in a suitable solvent, for example dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 100° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

After completion of the reaction, the product may be recovered from the reaction mixture by conventional means. An example of such a technique is as follows: the reaction mixture is freed from the solvent by distillation; ice-water is added to the residue; the aqueous mixture is extracted with a water-immiscible solvent, such as benzene, diethyl ether, ethyl acetate or the like; the extract is washed with dilute hydrochloric acid and water, in that order; and then the solvent is distilled off from the extract, leaving the desired product as the residue. The product thus obtained can, if desired, be purified by conventional means, such as recrystallization or the various chromatography techniques, notably column chromatography.

(ii) Introduction of a t-butyldimethylsilyl group

The desired compound can be prepared by reacting the compound of formula (61) with t-butyldimethylsilyl chloride in the presence of an organic tertiary amine, such as triethylamine (if necessary, in the additional presence of 4-(N,N-dimethylamino)pyridine) in a suitable solvent, for example dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 5 hours will usually suffice.

After completion of the reaction, the product may be recovered from the reaction mixture by conventional means. An example of such a technique is as follows: the reaction mixture is freed from the solvent by distillation; ice-water is added to the residue; the aqueous mixture is extracted with a water-immiscible solvent, such as benzene, diethyl ether, ethyl acetate or the like; the extract is washed with dilute hydrochloric acid and water, in that order; and then the solvent is distilled off from the extract, leaving the desired product as the residue. The product thus obtained can, if desired, be further purified by conventional means, such as recrystallization or the various chromatography techniques, notably column chromatography.

Step 75: Debenzylation

This step involves the preparation of a compound of formula (66) by reacting a compound of formula (65) with a reducing agent in an inert solvent.

The reaction involved in this Step is essentially the same as that involved in Step 73 of Reaction Scheme XX, and may be carried out using the same reagents and reaction conditions.

Step 76: Swern oxidation

This step involves the preparation of a compound of formula (67) by reacting a compound of formula (66) with an oxidizing agent in an inert solvent.

The reaction involved in this Step is essentially the same as that involved in Step 71 of Reaction Scheme XX, and may be carried out using the same reagents and reaction conditions.

Step 77: Wittig reaction

This step involves the preparation of a compound of formula (68) by a Wittig reaction using compounds of formulae (67) and (84) in the presence of a base and in an inert solvent.

The reaction involved in this Step is essentially the same as that involved in Step 65 of Reaction Scheme XIX, and may be carried out using the same reagents and reaction conditions.

Steps 78a and 78b: Reduction

These steps involve the preparation of compounds of formulae (69) and (85) by reacting a compound of formula (68) with a reducing agent in an inert solvent.

The reaction involved in this Step is essentially the same as that involved in Step 73 of Reaction Scheme XX, and may be carried out using the same reagents and reaction conditions, except that the reaction of Step 78a is preferably conducted in diethyl ether at room temperature for a period of from 30 minutes to 1 hour, and that of Step 78b is preferably conducted in ethanol at room temperature for a period of from 5 to 10 hours.

Reaction Scheme XXII

Step 79: Reduction

This step involves the preparation of a compound of formula (71) by reacting a compound of formula (70) with a reducing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform, carbon tetrachloride, dichloroethane, chlorobenzene and dichlorobenzene (especially methylene chloride).

There is likewise no particular restriction upon the nature of the reducing agent used, and any reducing agent commonly used in conventional reactions of this type may equally be used here. An example of a suitable reducing agent is diisobutylaluminum hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 5 hours will usually suffice.

After completion of the reaction, the product can be recovered from the reaction mixture by conventional means. An example of such a technique is as follows: the reaction is quenched by adding methanol whilst ice-cooling; dilute hydrochloric acid is added to the reaction mixture, to dissolve insoluble materials; the mixture is extracted with a water-immiscible solvent, such as benzene, diethyl ether, ethyl acetate or the like; and then the solvent is distilled off from the extract, leaving the desired product as the residue. The product can, if desired, be further purified by conventional means, such as recrystallization or the various chromatography techniques, notably column chromatography.

Step 80: Swern oxidation

This step involves the preparation of an aldehyde compound by reacting a compound of formula (71) with an oxidizing agent in an inert solvent.

The reaction involved in this Step is essentially the same as that involved in Step 71 of Reaction Scheme XX, and may be carried out using the same reagents and reaction conditions.

Step 81: Wittig reaction

This step involves the preparation of a compound of formula (72) by reacting an aldehyde compound, prepared as described in Step 80, with a Wittig reagent using triphenylphosphoniumbromide in an inert solvent.

The reaction involved in this Step is essentially the same as that involved in Step 65 of Reaction Scheme XIX, and may be carried out using the same reagents and reaction conditions.

Step 82: Formation of a diol group

This step involves the preparation of a diol compound by reacting a compound of formula (72) with a reagent for forming a diol group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent.

An example of a suitable solvent is a mixture of acetonitrile and water.

An example of a suitable oxidizing agent which may be used is osmium tetraoxide (which may be used in association with morpholine-N-oxide as an auxiliary oxidizing agent).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 100° C., more preferably from 10° to 40° C. The time required for the reaction may also vary widely, depending on many factors, notably the reaction temperature and the nature of the reagents and solvent employed. However, provided that the reaction is effected under the preferred conditions outlined above, a period of from 5 to 12 hours, more preferably from 1 to 24 hours, will usually suffice.

After completion of the reaction, the product can be recovered from the reaction mixture by conventional means. An example of such a technique is as follows: the reaction mixture is poured into water; the aqueous mixture is extracted with a water-immiscible solvent, such as benzene, diethyl ether, ethyl acetate or the like; and then the solvent is distilling off from the extract, leaving the product as the residue. The product can, if desired, be further purified by conventional means, such as recrystallization or the various chromatography techniques, notably column chromatography.

Step 83: Formation of a benzylidene group

This step involves the preparation of a compound of formula (73) by reacting a diol compound, prepared as described in Step 82, with benzaldehyde dimethyl acetal in the presence of an acid catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform, carbon tetrachloride or dichloroethane (especially methylene chloride).

There is likewise no particular restriction upon the nature of the acid catalyst used, and any acid catalyst commonly used in conventional reactions of this type may equally be used here. An example of a suitable acid catalyst is p-toluenesulfonic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 40° C. The time required for the reaction may also vary widely, depending on many factors, notably the reaction temperature and the nature of the reagents and solvent employed. However, provided that the reaction is effected under the preferred conditions outlined above, a period of from 1 to 5 hours will usually suffice.

After completion of the reaction, the product can be recovered from the reaction mixture by conventional means. An example of such a technique is as follows: an aqueous solution of sodium hydrogencarbonate is added to the reaction mixture; the aqueous mixture is extracted with a water-immiscible solvent, such as benzene, diethyl ether, ethyl acetate or the like; the extract is washed with water; and then the solvent is distilled off from the extract, leaving the product as the residue. The product can be used in the following step without purification or can, if desired, be further purified by conventional means, such as recrystallization or the various chromatography techniques, notably column chromatography.

Step 84: Reduction

This step involves the preparation of compounds of formulae (74) and (75) by reacting a compound of formula (73) with a reducing agent in an inert solvent.

The reaction involved in this Step is essentially the same as that involved in Step 79 of Reaction Scheme XXII, and may be carried out using the same reagents and reaction conditions.

Reaction Scheme XXIII

Step 85: Swern oxidation

This step involves the preparation of a compound of formula (76) by reacting a compound of formula (74) with an oxidizing agent in an inert solvent.

The reaction involved in this Step is essentially the same as that involved in Step 71 of Reaction Scheme XX, and may be carried out using the same reagents and reaction conditions.

Step 86: Wittig reaction

This step involves the preparation of a compound of formula (77) by means of a Wittig reaction using compounds of formulae (76) and (58) (see Reaction Scheme XX) in the presence of a base in an inert solvent.

The reaction involved in this Step is essentially the same as that involved in Step 65 of Reaction Scheme XX, and may be carried out using the same reagents and reaction conditions.

Step 87: Swern Oxidation

This step involves the preparation of a compound of formula (78) by reacting a compound of formula (75) with an oxidizing agent in an inert solvent.

The reaction involved in this Step is essentially the same as that involved in Step 71 of Reaction Scheme XX, and may be carried out using the same reagents and reaction conditions.

Step 88: Wittig reaction

This step involves the preparation of a compound of formula (79) by means of a Wittig reaction using compounds of formulae (78) and (58) in the presence of a base in an inert solvent.

The reaction involved in this Step is essentially the same as that involved in Step 65 of Reaction Scheme XIX, and may be carried out using the same reagents and reaction conditions.

A desired compound of the invention can be prepared by reductive debenzylation and reduction of a double bond of the compound of formula (77) or (79) using the same procedure as described in Step 73.

Reaction Scheme XXIV

Step 89: Epoxidation

This step involves the preparation of a compound of formula (80) by reacting a compound of formula (31) with trimethylsulfoxonium iodide in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane or diethylene glycol dimethyl ether (especially tetrahydrofuran); and sulfoxides, such as dimethyl sulfoxide.

There is likewise no particular restriction upon the nature of the base used, and any base commonly used in conventional reactions of this type may equally be used here. An example of a suitable base is sodium hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20° to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 5 hours will usually suffice.

After completion of the reaction, the product can be recovered from the reaction mixture by conventional means. An example of such a technique is as follows: the reaction mixture is diluted with a water-immiscible solvent, such as benzene, diethyl ether, ethyl acetate or the like; the organic phase is washed with water; and then the solvent is distilled off, leaving the product as the residue. The product can, if desired, be further purified by conventional means, such as recrystallization or the various chromatography techniques, notably column chromatography.

Step 90: Cleavage of an epoxy group

This step involves the preparation of compounds (82) and (83) by reacting a compound of formula (80) with a compound of formula (81) in the presence of a Lewis acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform, carbon tetrachloride or dichloroethane (especially methylene chloride).

There is likewise no particular restriction upon the nature of the Lewis acid used, and any Lewis acid commonly used in conventional reactions of this type may equally be used here. An example of a suitable Lewis acid is boron trifluoride etherate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 60° C. The time required for the reaction may also vary widely, depending on many factors, notably the reaction temperature and the nature of the reagents and solvent employed. However, provided that the reaction is effected under the preferred conditions outlined above, a period of from 5 to 15 hours will usually suffice.

After completion of the reaction, the product can be recovered from the reaction mixture by conventional means. An example of such a technique is as follows: the reaction mixture is freed from the solvent by distillation; the concentrate is poured into water; the aqueous mixture is extracted with a water-immiscible solvent, such as benzene, diethyl ether, ethyl acetate or the like; and then the solvent is distilled off from the extract, leaving the products of formulae (82) and (83) as the residue. The products can, if desired, be further purified by conventional means, such as recrystallization or the various chromatography techniques, notably column chromatography.

If necessary, the hydroxy group of the compounds of formulae (82) and (83) can be acetylated and each of the resulting acetylated compounds may be separated by chromatography followed by deacetylation to produce the compounds (82) and (83) individually.

Reaction Scheme XXI

Step 91: Grignard reaction

This step involves the preparation of a compound of formula (61) by reacting a compound of formula (89) with a Grignard reagent ($R^6A^{4b}MgBr$) in the presence of cuprous iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxythane or diethylene glycol dimethyl ether (especially tetrahydrofuran).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-100°$ to $-50°$ C. The time required for the reaction may also vary widely, depending on many factors, notably the reaction temperature and the nature of the reagents and solvent employed. However, provided that the reaction is effected under the preferred conditions outlined above, a period of from 1 to 5 hours will usually suffice. However, if the rate of reaction is sluggish, the reaction may require a further 1 to 2 hours at 0°.

After completion of the reaction, the product can be recovered from the reaction mixture by conventional means. An example of such a technique is as follows: the reaction mixture is ice-cooled; an aqueous solution of ammonium chloride and concentrated aqueous ammonia are added, and then the mixture is stirred; the mixture is then extracted with a water-immiscible solvent, such as diethyl ether; the extract is washed with an aqueous solution of sodium hydrogencarbonate and with a saturated aqueous solution of sodium chloride, in that order; and then the solvent is distilled off from the extract, leaving the product as the residue. The product can, if desired, be further purified by conventional means, such as recrystallization or the various chromatography techniques, notably column chromatography.

Reaction Scheme XXV

Step 92: Deprotection

Where the hydroxy-protecting group is a t-butyldimethylsilyl group, it can be removed by treatment with a compound capable of generating a fluorine anion, such as tetrabutyl-ammonium fluoride or hydrochloric acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran, or alcohols, such as methanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at from about 0° to 60° C. The time required for the reaction may also vary widely, depending on many factors, notably the reaction temperature and the nature of the reagents and solvent employed. However, provided that the reaction is effected under the preferred conditions outlined above, a period of from 10 to 18 hours will usually suffice.

Where the hydroxy-protecting group is a methoxymethyl group, it can normally be removed by treatment with an acid.

There is likewise no particular restriction upon the nature of the acid used, and any acid commonly used in conventional reactions of this type may equally be used here. Examples of suitable acids include: Bronsted acids, including halogenated hydroacids, such as hydrogen chloride or hydrogen bromide, and organic acids, such as acetic acid or p-toluenesulfonic acid; and strongly acidic cation ion-exchange resins, such as Dowex (trade mark) 50W.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and mixtures of one or more of these organic solvents and water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

After completion of the reaction, the product can be recovered from the reaction mixture by conventional means. An example of such a technique is as follows: the reaction mixture is poured into water; the aqueous mixture is extracted with a water-immiscible solvent, such as benzene, diethyl ether, ethyl acetate or the like; and then the solvent is distilled off from the extract, leaving the product as the residue. The product can normally be used in the following step without purification or can, if desired, be purified by conventional means, such as recrystallization or the various chromatography techniques, notably column chromatography.

Step 93: Mitsunobu inversion reaction

This step involves the preparation of a compound of formula (87) by reacting a compound of formula (86) with benzoic acid in the presence of triphenylphosphine and diethyl azodicarboxylate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane or diethylene glycol dimethyl ether (especially tetrahydrofuran).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 40° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the product can be recovered from the reaction mixture by conventional means. An example of such a technique is as follows: the reaction mixture is diluted with a water-immiscible solvent, such as benzene, diethyl ether, ethyl acetate or the like; the diluted mixture is washed with an aqueous solution of sodium hydrogencarbonate; and then the solvent is distilled off from the organic phase, leaving the product as the residue. The product can, if desired, be further purified by conventional means, such as recrystallization or the various chromatography techniques, notably column chromatography.

In a further step, the compound of formula (88) can be prepared from the compound of formula (87) by the same procedure as that described in Step 12 (Reaction Scheme III), followed by a procedure similar to that described in Step 1 (Reaction Scheme I).

Step 94:

This step involves the preparation of a compound of formula (89) by reacting a compound of formula (88) with a base.

There is likewise no particular restriction upon the nature of the base used, and any base commonly used in conventional reactions of this type may equally be used here. Examples of suitable bases include alkali metal alkoxides, such as sodium methoxide, sodium ethoxide, potassium t-butoxide or lithium methoxide, preferably sodium ethoxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, isopropanol, butanol, isobutanol, t-butanol or isoamyl alcohol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to the boiling point of the solvent used. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the product can be recovered from the reaction mixture by conventional means.

An example of such a technique is as follows: the reaction mixture is poured into water and then neutralized; the mixture is extracted with a water-immiscible solvent, such as benzene, diethyl ether, ethyl acetate or the like; and then the solvent is distilled off from the extract, leaving the product as the residue. The product can, if desired, be further purified by conventional means, such as recrystallization or the various chromatography techniques, notably column chromatography.

Reaction Scheme XXVI

Step 95: Introduction of a leaving group

This step involves the preparation of a compound of formula (90) by reacting a compound of formula (41) with an alkylsulfonyl halide or arylsulfonyl halide (preferably methanesulfonyl chloride) in an inert solvent in the presence of a base.

The reaction involved in this Step is essentially the same as that involved in Step 18 of Reaction Scheme V, and may be carried out using the same reagents and reaction conditions.

Step 96: Introduction of an imidazolyl group

This step involves the preparation of a compound of formula (91) by reacting a compound of formula (90) with imidazole in an inert solvent.

The reaction involved in this Step is essentially the same as that involved in Step 19 of Reaction Scheme V, and may be carried out using the same reagents and reaction conditions.

Step 97: Reduction of a nitro group

This step involves the preparation of a compound of formula (92) by reacting a compound of formula (91) with a reducing agent in an inert solvent.

The reaction involved in this Step is essentially the same as that involved in Step 12 of Reaction Scheme III, and may be carried out using the same reagents and reaction conditions.

Step 98: Condensation

This step involves the preparation of a compound of formula (1d) by reacting a compound of formula (92) with a compound of formula (2) (see Reaction Scheme I), in an inert solvent.

The reaction involved in this Step is essentially the same as that involved in Step 1 of Reaction Scheme I, and may be carried out using the same reagents and reaction conditions.

Those compounds containing a group represented by $R^7$ in accordance with the present invention can be prepared by using a compound obtained by reductive debenzylation and reduction of a double bond of a compound of formula (77) or (79) or by using the compounds of formulae (56), (64), (82), (83) and (89), which may be obtained by the steps described above, in the same procedure as that described in Step 3.

Where $R^7$ includes an oxycarbonyl group, the reaction can be carried out as follows:

That is, a solution of trichloromethyl chloroformate in tetrahydrofuran is added, whilst ice-cooling, to a tetrahydrofuran solution containing pyridine, and the resulting mixture is stirred at room temperature for a suit6able period, for example, 1 hour. The mixture is again ice-cooled and a solution of a compound of formula (1a), (1e), (1h), (1m), (56), (64), (82), (83) or (89) in tetrahydrofuran is added, and the mixture is again stirred, e.g. for 1 hour. The tetrahydrofuran is removed by distillation, and the residue is dissolved in methylene chloride. A solution of the desired alcohol in methylene chloride is then added thereto. 4-(N,N-dimethylamino)pyridine is then added to the mixture thus obtained, and the resulting mixture is stirred at room temperature, e.g. for an hour.

After completion of the reaction, the reaction mixture may be diluted with a water-immiscible solvent, such as benzene, diethyl ether, ethyl acetate or the like. The diluted mixture is then washed with water and with a saturated aqueous solution of sodium chloride, in that order, and the solvent is distilled off from the organic phase to produce the product. The product can, if desired, be further purified by chromatography or recrystallization.

A compound, wherein a carboxylic acid group represented by $R^7$ is an alkali metal salt, can be prepared as follows:

That is, a base is added to a solution of a carboxylic acid derivative in a solvent. The amount of base is preferably from 0.9 to 1 moles per mole of the carboxylic acid derivative. There is likewise no particular restriction upon the nature of the base used, and any base commonly used in conventional reactions of this type may equally be used here. Examples of suitable bases include: alkali metal hydrogencarbonates, such as sodium hydrogencarbonate, potassium hydrogencarbonate or lithium hydrogencarbonate; alkali metal carbonates, such as sodium carbonate, potassium carbonate or lithium carbonatre; alkali metal hydroxides, such as sodium hydroxide, potassium hydroxide or lithium hydroxide; and alkali metal alkoxides, such as sodium methoxide, sodium ethoxide, potassium t-butoxide or lithium methoxide. If desired, the base may be added as an aqueous or alcohol solution thereof. All of the resulting mixture is dissolved to form a solution (by the application of ultrasonic if needed), after which the solvent is distilled off to give the desired alkali metal salt.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol, ethanol or isopropyl alchol; esters, such as ethyl acetate or methyl acetate; halogenated hydrocarbons, such as methylene chloride or chloroform; water; and also mixtures of water and one or more watersoluble organic solvents (for example, dioxane, dimethoxyethane, methanol and isopropyl alcohol). When an aqueous solvent mixture is used, it is lyophilized, as such or after distilling off the organic solvent, to give the desired alkali metal salt.

A salt of an inorganic acid, such as hydrochloric acid, or of an organic acid, such as maleic acid, of a compound of the present invention having an amino group or an heterocyclic group containing a basic nitrogen atom, such as an imidazole group, can be prepared as follows:

That is, such a compound is dissolved in a suitable solvent, and then from 1 to 10 equivalents of the desired acid are added. The resulting precipitate is collected by filtration to give the desired salt. If there is no precipitation, the solvent is distilled off to give the desired salt. If the salt is obtained in the form of a glassy material, the salt is again dissolved in water or in a mixture of water and a watersoluble organic solvent, such as dioxane, dimethoxyethane, methanol or isopropyl alcohol, and the solution is then lyophilized as such or the solution is lyophilized after removal by distillation of the water-soluble organic solvent. Consequently, the purified compound can be obtained as a salt in the form or a powder or foam. The product can, if necessary, be further purified by recrystallization.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol, ethanol, isopropyl alcohol; esters, such as ethyl acetate or methyl acetate; halogenated hydrocarbons, such as methylene chloride or chloroform.

The compounds of the present invention exhibit an excellent inhibitory activity against acyl-CoA: cholesterol acyl transferase, are well absorbed after oral administration and are less toxic than prior compounds. They are, therefore, useful for the therapy and prevention of arteriosclerosis.

The activity of the compounds of the present invention is illustrated by the following tests.

β-Very low density lipoprotein (β-VLDL)

Blood was obtained [using the anticoagulant ethylene diamine tetraacetic acid (5 mM)] from Japanese White rabbits which had been fed a 2% w/w cholesterol diet for 2 weeks and then fasted overnight prior to removing the blood. β-VLDL (d<1.006 g/ml) was isolated by ultracentrifugation from the plasma according to the method of Hatch and Lees [Hatch, F. T. and Lees, R. S., Adv. Lipid Res., 6, 1–68 (1968)] and dialyzed against 10 mM of a sodium phosphate buffer (pH 7.4) containing 150 mM sodium chloride at 4° C.

Preparation of Mouse Macrophages (Mφ)

Peritoneal cells were harvested from unstimulated female DDY mice (body weight 20–30 g) in phosphate buffer saline (PBS) as described by Edelson and Cohn [Edelson, P. J. and Cohn, Z. A., 1976, IN VITRO Methods in Cell-Mediated and Tumor Immunity, eds, Bloon, B.R and David, J. R., (Academic, New York), 333–340.]. The fluid from the mice was pooled and the cells were collected by centrifugation at 400×g, for 10 minutes at 4° C., and washed once with PBS. The cells were resuspended in Dulbecco's modified Eagle's medium (DMEM) containing 10% (vol/vol) fetal calf serum (FCS), penicillin (100 units/ml), and streptomycin (100 μg/ml) at a final concentration of $3\times10^6$ cells per ml. Aliquots (1 ml) of this cell suspension were dispersed onto plastic Petri dishes (35×10 mm) and then incubated in a $CO_2$ incubator (5% $CO_2$/95% air) at 37° C. for 2 hours. Each dish was washed twice with PBS without serum to remove nonadherent cells. The cells were washed twice with 2 ml of PBS and used for the experiment.

Inhibition of ACAT in Mφ

Inhibition of ACAT in Mφ was determined according to the method described by Brown et al. [Brown, M. S., Goldstein J. L., Krieger, M., Ho, Y. K. and Anderson, R. G. W. (1979) J. Cell Biol., 82, 597–613.]. Cholesterol reacylation was initiated by adding β-VLDL (final concentration 50 μg/ml cholesterol), [$^{14}$C]oleate-albumin complex (final concentrations: 0.2 mM oleate and 0.6 mg/ml albumin) and a test compound dissolved in ethanol into the Mφ monolayer, and the preparation was incubated at 37° C. for 3 hours in a $CO_2$ incubator. Cells were washed three times with PBS and cellular lipid was extracted with 1 ml hexane/isopropanol (3:2, vol/vol). A lipid extract was evaporated in a stream of nitrogen. Cholesterol [$^{14}$C]oleated was seperated by thin layer chromatography through silica gel using a 85:15:1 by volume mixture of hexane, diethyl ether and acetic acid as developing solvents. The ACAT activity in Mφ was determined by measuring the radioactivity and an inhibition rate (%) was calculated by comparing a control activity with those of the test compound at given concentrations. The results are shown in the following Table.

TABLE

| Compound of Example No. | Inhibition of ACAT* (%) |
| --- | --- |
| 13 | 80 |
| 26 | 77 |
| 44 | 89 |
| 98 | 81 |
| 125 | 85 |
| 217 | 74 |
| 219 | 86 |
| Compound A | 51 |

*at a dose of 300 mg/ml
Compound A is a prior art compound having the formula (A):

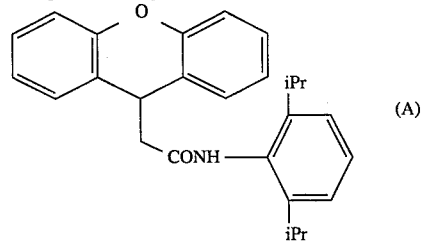

It is disclosed in WO 93/06096.

The compounds of the present invention may be administed by any known route, as is well known for prior art compounds having the same type of activity. For example, they may be administered orally, suitably in the form of tablets, capsules, granules, powders or syrups. These drug formulations can be prepared by conventional means by adding suitable additives, such as vehicles, binders, disintegrators, lubricants, stabilizers and corrigents. The dosage may be vary, depending upon patient's symptoms and age; however, a daily dose of from 1 to 500 mg per kg of body weight, preferably from 1 to 100 mg per kg of body weight, may, in general, be given to a human adult patient, and this may be administered in a single dose or in divided doses.

The present invention is further illustrated by the following non-limiting Examples. In these Examples, the Compound Nos. given are those assigned in the foregoing Tables 1 to 5. Preparation of certain of the starting materials used in some of these Examples is illustrated by the subsequent Preparations. Some pharmaceutical preparations incorporating the compounds of the present invention are then illustrated in the subsequent Formulations.

EXAMPLE 1

N-{2-[3-(1-Imidazolyl)propoxy]methyl-6-methylthiophenyl}-2-(9H-xanthen-9-yl)acetamide (Compound No. 1-1475)

1(i) N-{2-[3-(Mesyloxy)propoxy]methyl-6-methylthiophenyl}-2-(9H-Xanthen-9-yl)acetamide 212 mg (0.48 mmol) of N-[2-(3-hydroxypropoxy)methyl-6-methylthiophenyl]-2-(9H-xanthen-9-yl)acetamide (prepared as described in Preparation 4) were suspended in 15 ml of methylene chloride. The suspension was cooled on an ice bath, and then 102 mg (0.89 mmol) of methanesulfonyl chloride were added, followed by 94 mg (0.90 mmol) of triethylamine. The temperature of the reaction mixture was allowed to rise to room temperature, after which the mixture was stirred for an additional 1 hour. At the end of this time, the reaction was stopped by the addition of water. The mixture was then diluted with methylene chloride, after which the organic layer was washed with dilute aqueous hydrochloric acid and then with water. The solvent was then removed by distillation under reduced pressure, to obtain 251 mg (a quantitative yield) of the title compound as crystals. These crystals were used for the next step without purification.

1(ii)  N-{2-[3-(1-Imidazolyl)propoxy]methyl-6-methylthiophenyl}-2-(9H-xanthen-9-yl)acetamide 251 mg of the crude crystals of N-{2-[3-(mesyloxy)propoxy]methyl-6-methylthiophenyl}-2-(9H-xanthen-9-yl)acetamide [prepared as described in step (i) above] were suspended in 3 ml of dimethylformamide. 162 mg (2.39 mmol) of imidazole were added to the suspension, and the mixture was stirred for 5.5 hours at 90° C. At the end of this time, the reaction mixture was allowed to return to room temperature, after which it was diluted with ethyl acetate and washed several times with water. The solvent was then removed by distillation under reduced pressure, and the resulting residue was subjected to column chromatography through 15 g of silica gel. Fractions eluted with mixtures of methylene chloride and methanol ranging from 100:2 to 100:7 by volume were collected. Recrystallization from a mixture of methylene chloride and methanol afforded 162 mg (yield 68%) of the title compound as crystals, melting at 176.5°–177° C.

Infrared Absorption Spectrum (KBr), $v_{max}$ cm$^{-1}$: 3267, 1649, 1515, 1481, 1260, 757.

Nuclear Magnetic Resonance Spectrum (CDCl$_3$, 60 MHz), δ ppm:

1.88 (2H, quintet, J=6.5 Hz);
2.28 (3H, singlet);
2.73 (2H, doublet, J=6.5 Hz);
3.17 (2H, triplet, J=6.5 Hz);
3.93 (2H, triplet, J=6.5 Hz);
4.10 (2H, singlet);
4.68 (1H, triplet, J=6.5 Hz);
6.7–7.7 (14H, multiplet).

EXAMPLE 2

N-{2-[3-(1-Imidazolyl)propoxy]methyl-6-methylthiophenyl}-2-(9H-xanthen-9-yl)acetamide hydrochloride (Compound No. 1-1474)

100 mg of N-{2-[3-(1-imidazolyl)propoxy]methyl-6-methylthiophenyl}-2-(9H-xanthen-9-yl)acetamide (prepared as described in Example 1) were dissolved in a mixture of methanol and methylene chloride. An excess of concentrated aqueous hydrochloric acid was added to the solution, and then the solvent was removed by distillation under reduced pressure. The resulting residue was dissolved in methanol, and diethyl ether was added to produce 85 mg of the title compound as crystals, melting at 175°–184° C.

Infrared Absorption Spectrum (KBr), $v_{max}$ cm$^{-1}$: 3405, 3269, 1649, 1516, 1482, 1261, 758.

Elemental analysis:

Calculated for $C_{29}H_{29}N_3O_3S \cdot HCl \cdot \frac{1}{2}H_2O$: C, 63.90%; H, 5.73%; N, 7.71%; Cl, 6.50%.

Found: C, 63.86%; H, 5.78%; N, 7.69%; Cl, 6.35%.

EXAMPLE 3

N-{5-[3-(1-Imidazolyl)propoxy]methyl-2-methylthiophenyl}-2-(9H-xanthen-9-yl)acetamide (Compound No. 1-1477)

Following a procedure similar to that described in Example 1, but using N-[5-(3-hydroxypropoxy)methyl-2-methylthiophenyl]-2-(9H-xanthen-9-yl)acetamide (prepared by a procedure similar to that described in Preparation 4) as a starting material, in a relative amount similar to that used in that Example, the title compound was obtained as an oily substance.

Infrared Absorption Spectrum (liquid film), $v_{max}$ cm$^{-1}$: 2923, 1679, 1574, 1480, 1254, 757.

Nuclear Magnetic Resonance Spectrum (CDCl$_3$, 60 MHz), δ ppm:

1.8–2.4 (2H, multiplet);
2.05 (3H, singlet);
2.75 (2H, doublet, J=7 Hz);
3.43 (2H, triplet, J=6 Hz);
3.9–4.3 (2H, multiplet);
4.45 (2H, singlet);
4.70 (1H, triplet, J=7 Hz);
6.8–7.6 (12H, multiplet);
8.0–8.2 (1H, broad singlet);
8.3–8.5 (1H, broad singlet).

EXAMPLE 4

N-{5-[3-(1-Imidazolyl)propoxy]methyl-2-methylthiophenyl}-2-(9H-xanthen-9-yl)acetamide hydrochloride (Compound No. 1-1476)

Following a procedure similar to that described in Example 2, but using N-{5-[3-(1-imidazolyl)propoxy]-methyl-2-methylthiophenyl}-2-(9H-xanthen-9-yl)acetamide (prepared as described in Example 3) as a starting material, the title compound was obtained as crystals, melting at 85°–86° C. (after recrystallization from a mixture of methylene chloride and ethyl acetate).

Infrared Absorption Spectrum (KBr) $v_{max}$ cm$^{-1}$: 3036, 1660, 1526, 1479, 1458, 1258, 760.

Nuclear Magnetic Resonance Spectrum (CDCl$_3$, 270 MHz), δ ppm:

2.1–2.35 (2H, broad singlet);
2.12 (3H, singlet);
2.80 (2H, doublet, J=7 Hz);
3.49 (2H, broad singlet);
4.3–4.6 (2H, broad singlet);
4.47 (2H, singlet);
4.69 (1H, triplet, J=7 Hz);
6.9–7.4 (12H, multiplet);
8.11 (1H, singlet);
8.27 (1H, singlet);
9.0–9.15 (1H, broad singlet).

EXAMPLE 5

N-[2-Ethyl-6-(1-hydroxypropyl)phenyl]-2-(9H-xanthen-9-yl)acetamide (Compound No. 1-1434)

9.6 mg (0.18 mmol) of sodium methoxide were added to 3 ml of a methanolic solution containing 37 mg (0.060 mmol) of N-(2-ethyl-6-{1-[2-(9H-xanthen-9-yl)acetoxy]propyl}phenyl)-2-(9H-xanthen-9-yl)acetamide (prepared as described in Preparation 55). The mixture was then stirred for 4 hours at 60° C. At the end of this time, the reaction solution was diluted with diethyl ether. Water was then added to the reaction mixture, and the title compound was distributed between the organic solvent and the water. The organic layer was then separated and washed with water 3 times. The solvent was removed by distillation under reduced pressure, and the resulting residue was subjected to column chromatography through 5 g of silica gel. Elution with mixtures of methylene chloride and ethyl acetate ranging from 10:1 to 5:1 by volume afforded 21 mg (yield 89%) of the title compound as crystals, melting at 167°–168° C. (after recrystallization from a mixture of diethyl ether and hexane).

Infrared Absorption Spectrum (KBr), $v_{max}$ cm$^{-1}$: 1655, 1635, 1520, 1482, 1460, 1260, 756.

Nuclear Magnetic Resonance Spectrum (CDCl$_3$, 270 MHz), δ ppm:

0.78 (3H, triplet, J=7 Hz);
1.06 (3H, triplet, J=7.5 Hz);
1.55–1.8 (2H, multiplet);
2.33 (2H, quartet, J=7 Hz);
2.79 (2H, doublet, J=7 Hz);
4.34 (1H, triplet, J=7 Hz);
4.72 (2H, triplet, J=7 Hz);
6.95–7.5 (11H, multiplet).

EXAMPLE 6

N-[2-(3-Hydroxy-3-phenyl-1-propenyl)-6-methoxymethylphenyl]-2-(9H-xanthen-9-yl)acetamide (Compound No. 1-1443)

10 ml of a tetrahydrofuran suspension containing 152 mg (0.392 mmol) of N-(2-formyl-6-methoxymethylphenyl)-2-(9H-xanthen-9-yl)acetamide (prepared as described in Preparation 53), 199 mg (0.432 mmol) of phenacyltriphenylphosphonium bromide and 48 mg (0.471 mmol) of triethylamine was heated for 6 hours under reflux. At the end of this time, the mixture was allowed to return to room temperature. 4 ml of methanol were added, and then 155 mg (4.10 mmol) of sodium borohydride were gradually added to the mixture, which was then stirred for 1 hour. The reaction solution was then diluted with ethyl acetate, and washed several times with water. The solvent was removed by distillation under reduced pressure. The residue was subjected to column chromatography through 20 g of silica gel. Elution with a 4:1 by volume mixture of methylene chloride and ethyl acetate afforded 126 mg (yield 66%) of the title compound as crystals, melting at 204.5°–206.5° C. (after recrystallization from methanol).

Infrared Absorption Spectrum (KBr), $v_{max}$ cm$^{-1}$: 3258, 1652, 1482, 1457, 1263, 752.

Nuclear Magnetic Resonance Spectrum (CDCl$_3$, 270 MHz), δ ppm:

2.73 (2H, doublet, J=7 Hz);
3.10 (3H, singlet);
3.94 (2H, singlet);
4.70 (1H, triplet, J=7 Hz);
5.34 (1H, doublet, J=7 Hz);
6.32 (1H, doublet of doublets, J=16 & 7 Hz);
6.53 (1H, doublet, J=16 Hz);
7.1–7.6 (16H, multiplet).

EXAMPLE 7

N-[2-(3-Hydroxy-3-phenylpropyl)-6-methoxymethylphenyl]-2-(9H-xanthen-9-yl]acetamide Compound No. 1-1444)

35 mg of 10% w/w palladium-on-carbon were added to 15 ml of a tetrahydrofuran solution containing 111 mg (0.226 mmol) of N-[2-(3-hydroxy-3-phenyl-1-propenyl)-6-methoxymethylphenyl]-2-(9H-xanthen-9-yl)acetamide (prepared as described in Example 6), and the mixture was stirred vigorously for 15 hours in a stream of hydrogen. The reaction solution was then filtered with the help of a Celite (trade mark) filter aid, and the catalyst was washed with tetrahydrofuran. The filtrate and the washings were combined, and the solvent was removed from the combined solution by distillation under reduced pressure. The resulting residue was subjected to column chromatography through 15 g of silica gel. Elution with a 4:1 by volume mixture of methylene chloride and ethyl acetate afforded 86 mg (yield 77%) of the title compound as crystals, melting at 143.5°–146° C. (after recrystallization from a mixture of methanol and hexane).

Infrared Absorption Spectrum (KBr), $v_{max}$ cm$^{-1}$: 3370, 3280, 1652, 1515, 1480, 1457, 1260, 757.

Nuclear Magnetic Resonance Spectrum (CDCl$_3$, 60 MHz), δ ppm:

1.7–2.1 (2H, multiplet);
2.2–2.6 (2H, multiplet);
2.53 (2H, doublet, J=7 Hz);
3.07 (3H, singlet);
3.96 (2H, singlet);
4.2–4.6 (1H, multiplet);
4.59 (1H, triplet, J=7 Hz);
6.9–7.7 (16H, multiplet).

EXAMPLE 8

N-[2-Ethyl-6-(3-oxo-6-phenylhexyl)phenyl]-2-(9H-xanthen-9-yl)acetamide (8a) (Compound No. 1-1445) and
N-[2-Ethyl-6-(3-hydroxy-6-phenylhexyl)phenyl]-2-(9H-xanthen-9-yl)acetamide (8b) (Compound No. 1-1446)

93 mg of 10% w/w palladium-on-carbon were added to 5 ml of a methanolic solution containing 154 mg of N-[2-ethyl-6-(3-oxo-6-phenyl-1-hexenyl)phenyl]-2-(9H-xanthen-9-yl)acetamide (prepared as described in Example 68), and the mixture was stirred vigorously for 3 hours in a stream of hydrogen. At the end of this time, the reaction solution was filtered using a Celite (trade mark) filter aid, and the catalyst was washed with ethyl acetate several times. The filtrate and the washings were combined, and the solvent was removed from the combined solution by distillation under reduced pressure. The resulting residue was subjected to column chromatography through 10 g of silica gel. Elution with a 2:1 by volume mixture of diethyl ether and hexane afforded 87 mg (yield 56%) of the 3-oxo compound (8a) and 53 mg (yield 34%) of the 3-hydroxy compound (8b) both as crystals.

(8a) N-[2-Ethyl-6-(3-oxo-6-phenylhexyl)phenyl]-2-(9H-xanthen-9-yl)acetamite:

melting at 113°–114° C. (after recrystallization from a mixture of methylene chloride and diethyl ether).

Infrared Absorption Spectrum (KBr), $v_{max}$ cm$^{-1}$: 3246, 1709, 1653, 1528, 1480, 1459, 1262, 758.

Nuclear Magnetic Resonance Spectrum (CDCl$_3$, 270 MHz), δ ppm:

1.09 (3H, triplet, J=7.5 Hz);
1.78 (2H, quartet, J=7 Hz);
2.26 (2H, triplet, J=7.5 Hz);
2.38–2.55 (6H, multiplet);
2.62 (2H, triplet, J=6 Hz);
2.84 (2H, doublet, J=7 Hz);
4.73 (1H, triplet, J=7 Hz);
6.91–7.43 (16H, multiplet).

(8b) N-[2-Ethyl-6-(3-hydroxy-6-phenylhexyl)phenyl]-2-(9H-xanthen-9-yl)acetamide:

melting at 131°–132° C. (after recrystallization from a mixture of diethyl ether and hexane).

Infrared Absorption Spectrum (KBr), $v_{max}$ cm$^{-1}$: 3274, 1648, 1522, 1480, 1459, 1260, 754.

Nuclear Magnetic Resonance Spectrum (CDCl$_3$, 270 MHz), δ ppm:

1.09 (3H, triplet, J=7.5 Hz);
1.31–1.79 (6H, multiplet);
2.18–2.47 (4H, multiplet);
2.56 (2H, triplet, J=7.5 Hz);
2.71 (1H, doublet of doublets, J=7 & 14.5 Hz);
2.76 (1H, doublet of doublets, J=7 & 14.5 Hz);
3.18–3.30 (1H, multiplet);
4.70 (1H, triplet, J=7 Hz);
6.97–7.42 (16H, multiplet).

EXAMPLE 9

N-{2-t-butyl-5-[5-(4-fluorophenyl)-3-hydroxy-1-pentenyl]phenyl}-2-(9H-xanthen-9-yl)acetamide (Compound No. 1-1319)

Following a procedure similar to that described in Example 6, but using N-{2-t-butyl-5-[5-(4-fluorophenyl)-3-oxo-1-pentenyl]phenyl}-2-(9H-xanthen-9-yl)acetamide as a starting material, the title compound was obtained as an oily substance. The starting material was prepared following a similar procedure to that described in Example 68, but using 4-fluoro-1-(4-diethoxyphosphoryl-3-oxobutyl)benzene and N-(2-t-butyl-5-formylphenyl)-2-(9H-xanthen-9-yl)acetamide (prepared as described in Preparation 15).

Infrared Absorption Spectrum (CHCl$_3$), $v_{max}$ cm$^{-1}$: 3450, 1673, 1600, 1573, 1508, 1477, 1456.

Nuclear Magnetic Resonance Spectrum (CDCl$_3$, 270 MHz), δ ppm:

1.17 (9H, singlet);
1.85–2.0 (2H, multiplet);
2.4–2.5 (1/3H, multiplet);
2.65–2.8 (2H, multiplet);
2.72 (5/3H, doublet, J=7 Hz);
4.2–4.35 (1H, multiplet);
4.77 (1H, triplet, J=7 Hz);
6.22 (1H, doublet of doublets, J=7 & 16 Hz);
6.53 (1H, doublet, J=16 Hz);
6.9–7.6 (15H, multiplet).

EXAMPLE 10

N-{2-t-Butyl-5-[5-(4-fluorophenyl)-3-hydroxypentyl]phenyl}-2-(9H-xanthen-9-yl)acetamide (Compound No. 1-1318)

Following a procedure similar to that described in Example 7, but subjecting N-{2-t-butyl-5-[5-(4-fluorophenyl)-3-hydroxy-1-pentenyl]phenyl}-2-(9H-xanthen-9-yl)acetamide (prepared as described in Example 9) to catalytic reduction, the title compound was obtained as a foam-like substance.

Infrared Absorption Spectrum (CHCl$_3$), $v_{max}$ cm$^{-1}$: 3450, 1677, 1600, 1575, 1509, 1479, 1456.

Nuclear Magnetic Resonance Spectrum (CDCl$_3$, 270 MHz), δ ppm:

1.17 (9H, singlet);
1.4–1.65 (2H, multiplet);
1.7–1.9 (2H, multiplet);
2.3–2.9 (6H, multiplet);
3.4–3.7 (1H, multiplet);
4.74 (1H, triplet, J=7 Hz);
6.9–7.5 (15H, multiplet).

EXAMPLE 11

N-[2-Ethyl-6-(3-hydroxy-3-phenylpropyl)phenyl]-2-(9H-xanthen-9-yl)acetamide (Compound No. 1-1440)

Following a procedure similar to that described in Example 8, but using N-[2-ethyl-6-(3-oxo-3-phenyl-1-propenyl)phenyl]-2-(9H-xanthen-9-yl)acetamide as a starting material, in a relative amount similar to that used in that Example, the title compound was obtained as crystals, melting at 192°–193° C. (after recrystallization from a mixture of ethyl acetate and hexane). The starting material was prepared following a similar procedure to that described in Example 6, but using N-(2-ethyl-6-formylphenyl)-2-(9H-xanthen-9-yl)acetamide (prepared by a procedure similar to that described in Preparation 29).

Infrared Absorption Spectrum (KBr), $v_{max}$ cm$^{-1}$: 3242, 1657, 1522, 1480, 1459, 1254, 760.

Nuclear Magnetic Resonance Spectrum (CDCl$_3$, 270 MHz), δ ppm:

1.09 (3H, triplet, J=7.5 Hz);
1.82–1.93 (2H, multiplet);
2.23–2.48 (4H, multiplet);
2.68 (2H, doublet, J=7 Hz);
4.36 (1H, triplet, J=6 Hz);
4.69 (1H, triplet, J=7 Hz);
6.96–7.44 (16H, multiplet).

EXAMPLE 12

N-[2-t-Butyl-5-(4-cyclohexyl-3-hydroxybutyl)phenyl]-2-(9H-xanthen-9-yl)acetamide (Compound No. 1-25)

0.18 ml of a 1M solution of cyclohexylmethylmagnesium bromide in diethyl ether was added to 2 ml of tetrahydrofuran, and the mixture was cooled to −78° C. 2 ml of a tetrahydrofuran solution containing 50 mg (0.12 mmol) of N-[2-t-butyl-5-(3-oxopropyl)phenyl]-2-(9H-xanthen-9-yl)acetamide (prepared as described in Preparation 19) was then added dropwise to this solution, over a period of 5 minutes. The mixture was then stirred for 40 minutes at this temperature, after which the temperature was allowed to return gradually to 0° C. The reaction was then stopped by the addition of a saturated aqueous solution of ammonium chloride. Diethyl ether was added, which caused the title compound to be distributed between the organic solvent and water. The organic layer was separated and washed with water, after which the solvent was removed by distillation under reduced pressure. The resulting residue was subjected to column chromatography through 10 g of silica gel. Elution with a 100:15 by volume mixture of methylene chloride and ethyl acetate afforded 41 mg (yield 67%) of the title compound as crystals, melting at 145°–146° C. (after recrystallization from a mixture of methylene chloride and diethyl ether).

Infrared Absorption Spectrum (KBr), $v_{max}$ cm$^{-1}$: 3343, 3244, 1654, 1529, 1478, 1458, 1253, 760, 749.

Nuclear Magnetic Resonance Spectrum (CDCl$_3$, 270 MHz), δ ppm:

0.76–1.87 (15H, multiplet);

1.16 (9H, singlet);

2.20–2.84 (4H, multiplet);

3.55–3.83 (1H, multiplet);

4.74 (1H, triplet, J=7 Hz);

6.92–7.45 (11H, multiplet).

EXAMPLE 13

N-[2-t-Butyl-5-(4-cyclohexyl-3-oxobutyl)phenyl]-2-(9H-xanthen-9-yl)acetamide (Compound No. 1-1263)

1 ml of a methylene chloride solution containing 16 mg (0.13 mmol) of oxalyl chloride was cooled to −78° C. 1.5 ml of a methylene chloride solution containing 20 mg (0.25 mmol) of dimethyl sulfoxide were then added to this solution. The resulting mixture was then stirred for 5 minutes, after which 1 ml of a methylene chloride solution containing 56 mg (0.11 mmol) of N-[2-t-butyl-5-(4-cyclohexyl-3-hydroxybutyl)phenyl]-2-(9H-xanthen-9-yl)acetamide (prepared as described in Example 12) was added dropwise over a period of 5 minutes at the same temperature. The mixture was then stirred for 15 minutes, and then 1 ml of a methylene chloride solution containing 64 mg (0.64 mmol) of triethylamine was added dropwise to it. The mixture was stirred for 10 minutes, and then the reaction mixture was allowed to return to room temperature. The reaction solution was diluted with diethyl ether, and washed with dilute aqueous hydrochloric acid and then with water. The solvent was then removed by distillation under reduced pressure. The resulting residue was subjected to column chromatography through 10 g of silica gel. Elution with a 100:8 by volume mixture of methylene chloride and ethyl acetate afforded 51 mg (yield 91%) of the title compound as crystals, melting at 154°–155° C. (after recrystallization from a mixture of diethyl ether and hexane).

Infrared Absorption Spectrum (KBr), $v_{max}$ cm$^{-1}$: 3233, 1711, 1637, 1529, 1481, 1456, 1261, 758.

Nuclear Magnetic Resonance Spectrum (CDCl$_3$, 270 MHz), δ ppm:

0.80–1.91 (11H, multiplet);

1.15 (9H, singlet);

2.29 (2H, doublet, J=6.5 Hz);

2.36–2.90 (6H, multiplet);

4.74 (1H, triplet, J=7 Hz);

6.91–7.45 (11H, multiplet).

EXAMPLE 14

N-[2-t-Butyl-5-(2-cyclohexyl-1-hydroxyethyl)phenyl]-2-(9H-xanthen-9-yl)acetamide (Compound No. 1-179)

8 ml of a tetrahydrofuran solution containing 100 mg (0.25 mmol) of N-(2-t-butyl-5-formylphenyl)-2-(9H-xanthen-9-yl)acetamide (prepared as described in Preparation 15) were cooled in an ice bath. 0.38 ml (0.38 mmol) of a 1M solution of cyclohexylmethylmagnesium bromide in diethyl ether was then added dropwise to the solution. The resulting mixture was stirred for 20 minutes at this temperature. It was then diluted with diethyl ether, and washed with dilute aqueous hydrochloric acid and then with water. The solvent was then removed by distillation under reduced pressure. The resulting residue was subjected to column chromatography through 20 g of silica gel. Elution with mixtures of methylene chloride and ethyl acetate ranging from 7:1 to 2:1 by volume afforded 95 mg (yield 76%) of the title compound as a foam-like substance.

Infrared Absorption Spectrum (CHCl$_3$), $v_{max}$ cm$^{-1}$: 3425, 1678, 1508, 1479, 1458, 1250.

Nuclear Magnetic Resonance Spectrum (CDCl$_3$, 270 MHz), δ ppm:

0.80–1.95 (13H, multiplet);

1.18 (9H, singlet);

2.32–2.54 (0.5H, multiplet);

2.70 (1.5H, doublet, J=7 Hz);

4.41–4.54 (0.25H, multiplet);

4.67–4.83 (0.75H, multiplet);

4.73 (1H, triplet, J=7 Hz);

7.01–7.49 (11H, multiplet).

EXAMPLE 15

N-[2-Ethyl-6-(1-hydroxy-3-phenylpropyl)phenyl]-2-(9H-xanthen-9-yl)acetamide (Compound No. 1-1441)

Following a procedure similar to that described in Example 14, but using N-(2-ethyl-6-formylphenyl)-2-(9H-xanthen-9-yl)acetamide (prepared by a procedure similar to that described in Preparation 29) and phenethylmagnesium bromide as starting materials, in relative proportions similar to those used in that Example, the title compound was obtained as crystals, melting at 128°–129° C. (after recrystallization from a mixture of ethyl acetate and hexane).

Infrared Absorption Spectrum (KBr), $v_{max}$ cm$^{-1}$: 3240, 1648, 1524, 1480, 1459, 1260, 754.

Nuclear Magnetic Resonance Spectrum (CDCl$_3$, 270 MHz), δ ppm:

1.03 (3H, triplet, J=7.5 Hz);

1.81–1.96 (1H, multiplet);

2.07–2.23 (1H, multiplet);

2.28 (2H, quartet, J=7.5 Hz);

2.54 (2H, triplet, J=7.5 Hz);

2.56 (1H, doublet of doublets, J=7 & 15 Hz);

2.62 (1H, doublet of doublets, J=7 & 15 Hz);

4.42 (1H, triplet, J=7 Hz);
4.67 (1H, triplet, J=7 Hz);
7.01–7.42 (16H, multiplet).

EXAMPLE 16

N-[2-t-Butyl-5-(6-phenyl-1-hydroxyhexyl)phenyl-2-(9H-xanthen-9-yl)acetamide (Compound No. 1-1283)

Following a procedure similar to that described in Example 12, but using 5-phenylpentylmagnesium iodide and N-(2-t-butyl-5-formylphenyl)-2-(9H-xanthen-9-yl)acetamide (prepared as described in Preparation 15) as starting materials, in relative proportions similar to those used in that Example, the title compound was obtained as a foam-like substance.

Infrared Absorption Spectrum (film), $\nu_{max}$ cm$^{-1}$: 3395, 3280, 1653, 1522, 1480, 1459, 1256, 758.

Nuclear Magnetic Resonance Spectrum (CDCl$_3$, 270 MHz), δ ppm:

1.17 (9H, multiplet);
1.25–1.85 (8H, multiplet);
2.42 (0.4H, doublet, J=7 Hz);
2.61 (2H, triplet, J=8 Hz);
2.69 (1.6H, doublet, J=7 Hz);
4.26–4.34 (0.2H, multiplet);
4.63 (0.8H, triplet, J=6.5 Hz);
4.73 (1H, triplet, J=7 Hz);
6.97–7.45 (16H, multiplet).

EXAMPLE 17

N-[2-t-Butyl-5-(4-cyclohexyl-1-hydroxybutyl)phenyl]-2-(9H-xanthen-9-yl)acetamide (Compound No. 1-227)

Following a procedure similar to that described in Example 14, but using 3-cyclohexylpropylmagnesium iodide and N-(2-t-butyl-5-formylphenyl)-2-(9H-xanthen-9-yl)acetamide (prepared as described in Preparation 15) as starting materials, in relative proportions similar to those used in that Example, the title compound was obtained as a foam-like substance.

Infrared Absorption Spectrum (film), $\nu_{max}$ cm$^{-1}$: 3395, 3280, 1655, 1522, 1480, 1459, 1256, 758.

Nuclear Magnetic Resonance Spectrum (CDCl$_3$, 270 MHz), δ ppm:

0.80–0.94 (2H, multiplet);
1.11–1.80 (15H, multiplet);
1.17 (9H, singlet);
2.43 (0.4H, doublet, J=7 Hz);
2.70 (1.6H, doublet, J=7 Hz);
4.28–4.34 (0.2H, multiplet);
4.60–4.68 (0.8H, multiplet);
4.73 (1H, triplet, J=7 Hz);
6.97–7.46 (11H, multiplet).

EXAMPLE 18

N-[2-t-Butyl-5-(6-cyclohexyl-1-hydroxyhexyl)phenyl]-2-(9H-xanthen-9-yl)acetamide (Compound No. 1-275)

Following a procedure similar to that described in Example 14, but using 5-cyclohexylpentylmagnesium iodide and N-(2-t-butyl-5-formylphenyl)-2-(9H-xanthen-9-yl)acetamide (prepared as described in Preparation 15) as starting materials, in relative proportions similar to those used in that Example, the title compound was obtained as a foam-like substance.

Infrared Absorption Spectrum (film), $\nu_{max}$ cm$^{-1}$: 3395, 3290, 1653, 1522, 1480, 1459, 1256, 756.

Nuclear Magnetic Resonance Spectrum (CDCl$_3$, 270 MHz), δ ppm:

0.77–0.94 (2H, multiplet);
1.06–1.80 (19H, multiplet);
1.17 (9H, singlet);
2.43 (0.4H, doublet, J=7 Hz);
2.70 (1.6H, doublet, J=7 Hz);
4.28–4.35 (0.2H, multiplet);
4.63 (0.8H, triplet, J=6.5 Hz);
4.74 (1H, triplet, J=7 Hz);
6.95–7.46 (11H, multiplet).

EXAMPLE 19

N-[2-t-Butyl-5-(1-oxo-6-phenylhexyl)phenyl]-2-(9H-xanthen-9-yl)acetamide (Compound No. 1-1325)

Following a procedure similar to that described in Example 13, but using N-[2-t-butyl-5-(6-phenyl-1-hydroxyhexyl)phenyl- 2-(9H-xanthen-9-yl)acetamide (prepared as described in Example 16) as a starting material, in a relative amount similar to that used in that Example, the title compound was obtained as crystals, melting at 119°–120° C. (after recrystallization from a mixture of hexane and ethyl acetate).

Infrared Absorption Spectrum (KBr) $\nu_{max}$ cm$^{-1}$: 3240, 1686, 1646, 1524, 1482, 1459, 1258, 758.

Nuclear Magnetic Resonance Spectrum (CDCl$_3$, 270 MHz), δ ppm:

1.19 (9H, singlet);
1.45 (2H, quintet, J=7.5 Hz);
1.70 (2H, quintet, J=7.5 Hz);
1.78 (2H, quintet, J=8 Hz);
2.40–2.45 (0.2H, multiplet);
2.60–2.80 (0.2H, multiplet);
2.65 (2H, triplet, J=7.5 Hz);
2.74 (1.8H, doublet, J=7 Hz);
2.94 (1.8H, triplet, J=7 Hz);
4.74 (1H, triplet, J=7 Hz);
7.05–7.43 (14.1H, multiplet);
7.72 (1H, doublet of doublets, J=2 & 8 Hz);
8.05 (0.9H, doublet, J=2 Hz).

EXAMPLE 20

N-[2-t-Butyl-5-(6-cyclohexyl-1-oxohexyl)phenyl]-2-(9H-xanthen-9-yl)acetamide (Compound No. 1-1262)

Following a procedure similar to that described in Example 13, but using N-[2-t-butyl-5-(6-cyclohexyl-1-hydroxyhexyl)phenyl]-2-(9H-xanthen-9-yl)acetamide (prepared as described in Example 18) as a starting material, in a relative amount similar to that used in that Example, the title compound was obtained as crystals, melting at 133.5°–134° C. (after recrystallization from a mixture of hexane and diisopropyl ether).

Infrared Absorption Spectrum (film), $v_{max}$ cm$^{-1}$: 3235, 1686, 1644, 1524, 1482, 1459, 1258, 758.

Nuclear Magnetic Resonance Spectrum (CDCl$_3$, 270 MHz), δ ppm.

0.80–0.96 (2H, multiplet);
1.06–1.78 (17H, multiplet);
1.20 (9H, singlet);
2.33–2.47 (0.2H, multiplet);
2.65–2.75 (0.2H, multiplet);
2.74 (1.8H, doublet, J=7 Hz);
2.93 (1.8H, triplet, J=7 Hz);
4.75 (1H, triplet, J=7 Hz);
7.07–7.43 (9.1H, multiplet);
7.73 (1H, doublet of doublets, J=2 & 8 Hz);
8.06 (0.9H, singlet).

EXAMPLE 21

N-[2-t-Butyl-5-(6-cyclohexyl-5-oxohexyl)phenyl]-2-(9H-xanthen-9-yl)acetamide (Compound No. 1-1268)

0.66 ml (7.65 mmol) of oxalyl chloride and 30 mg of N,N-dimethylformamide were added, in turn, to 10 ml of a methylene chloride suspension containing 368 mg (1.53 mmol) of 2-(9H-xanthen-9-yl)acetic acid. The suspension was stirred in an ice bath for 30 minutes and then at room temperature for 1 hour. At the end of this time, the solvent and excess reagents were removed by distillation under reduced pressure. The residue was again dissolved in 10 ml of methylene chloride, and the resulting solution was placed in an ice bath. 2 ml of a methylene chloride solution containing 458 mg (1.39 mmol) of 2-t-butyl-5-(6-cyclohexyl-5-oxohexyl)aniline and 0.56 ml of pyridine were then added to the solution, and the mixture was stirred for 10 minutes. The reaction solution was then diluted with diethyl ether, washed with a dilute aqueous solution of sodium hydroxide, with dilute aqueous hydrochloric acid and with water, in that order. The solvent was then removed by distillation under reduced pressure. The resulting residue was subjected to column chromatography through 40 g of silica gel. Elution with a 100:20 by volume mixture of hexane and ethyl acetate afforded 663 mg (yield 86%) of the title compound as crystals, melting at 126°–127° C. (after recrystallization from a mixture of diethyl ether and hexane).

Infrared Absorption Spectrum (KBr), $v_{max}$ cm$^{-1}$: 1709, 1663, 1518, 1478, 1459, 1256, 762.

Nuclear Magnetic Resonance Spectrum (CDCl$_3$, 270 MHz), δ ppm:

0.81–1.02 (2H, multiplet);
1.05–1.93 (13H, multiplet);
1.18 (9H, singlet);
2.27 (2H, doublet, J=7 Hz);
2.28–2.75 (6H, multiplet);
4.74 (1H, triplet, J=7 Hz);
6.88–7.45 (11H, multiplet).

EXAMPLE 22

N-[2-t-Butyl-5-(6-hexyl-5-hydroxyhexyl)phenyl]-2-(9H-xanthen-9-yl)acetamide (Compound No. 1-587)

37 mg (0.99 mmol) of sodium borohydride were added to 10 ml of a methanolic suspension containing 544 mg (0.986 mmol) of N-[2-t-butyl-5-(6-cyclohexyl-5-oxohexyl)phenyl]-2-(9H-xanthen-9-yl)acetamide (prepared as described in Example 21), in an ice bath. The ice bath was then removed, and the reaction mixture was stirred for 1 hour at room temperature. At the end of this time, the reaction solution was diluted with diethyl ether, washed with a saturated aqueous solution of ammonium chloride and then with water several times. The solvent was then removed by distillation under reduced pressure, to obtain 532 mg (yield 97%) of the title compound as a foam-like substance.

Infrared Absorption Spectrum (CHCl$_3$), $v_{max}$ cm$^{-1}$: 3450, 1678, 1509, 1479, 1458, 1250.

Nuclear Magnetic Resonance Spectrum (CDCl$_3$, 270 MHz), δ ppm:

0.77–1.85 (19H, multiplet);
1.16 (9H, singlet);
2.23–2.37 (0.5H, multiplet);
2.45 (0.5H, doublet, J=7 Hz);
2.60 (1.5H, triplet, J=7 Hz);
2.70 (1.5H, doublet, J=7 Hz);
3.63–3.79 (1H, multiplet);
4.74 (1H, triplet, J=7 Hz);
6.89–7.45 (11H, multiplet).

EXAMPLE 23

N-[2-t-Butyl-5-(4-cyclohexyl-2-oxobutyl)phenyl]-2-(9H-xanthen-9-yl)acetamide (Compound No. 1-1265)

Following a procedure similar to that described in Example 21, but using 2-t-butyl-5-(4-cyclohexyl-2-oxobutyl)aniline as a starting material, in a relative amount similar to that used in that Example, the title compound was obtained as crystals, melting at 134°–135° C. (after recrystallization from a mixture of ethyl acetate and hexane).

Infrared Absorption Spectrum (KBr), $v_{max}$ cm$^{-1}$: 3379, 2922, 1701, 1663, 1480, 1458, 1258, 761.

Nuclear Magnetic Resonance Spectrum (CDCl$_3$, 270 MHz), δ ppm:

0.7–1.0 (2H, multiplet);
1.0–1.3 (3H, multiplet);
1.16 (9H, singlet);
1.3–1.7 (8H, multiplet);
2.2–2.75 (4H, multiplet);
3.39 (2/5H, singlet);
3.66 (8/5H, singlet);
4.73 (1H, triplet, J=7 Hz);
6.9–7.45 (11H, multiplet).

EXAMPLE 24

N-[2-t-Butyl-5-(4-cyclohexyl-2-hydroxybutyl)phenyl]-2-(9H-xanthen-9-yl)acetamide (Compound No. 1-373)

Following a procedure similar to that described in Example 22, but using N-[2-t-butyl-5-(4-cyclohexyl-2-oxobutyl)phenyl]-2-(9H-xanthen-9-yl)acetamide (prepared as described in Example 23) as a starting material, in a relative amount similar to that used in that Example, the title compound was obtained as a foam-like substance.

Infrared Absorption Spectrum (CHCl$_3$), $\nu_{max}$ cm$^{-1}$: 3430, 1678, 1600, 1575, 1480, 1457.

Nuclear Magnetic Resonance Spectrum (CDCl$_3$, 270 MHz), δ ppm:
 0.8–1.0 (2H, multiplet);
 1.0–1.8 (13H, multiplet);
 1.70 (9H, singlet);
 2.3–2.9 (4H, multiplet);
 3.7–3.85 (1H, multiplet);
 4.74 (1H, triplet, J=7 Hz);
 6.9–7.5 (11H, multiplet).

EXAMPLE 25

N-[2-t-Butyl-5-(5-cyclohexyl-3-oxopentyl)phenyl]-2-(9H-xanthen-9-yl)acetamide (Compound No. 1-1264)

Following a procedure similar to that described in Example 21, but using 2-t-butyl-5-(5-cyclohexyl-3-oxopentyl)aniline (prepared by a procedure similar to that described in Preparation 7) as a starting material, in a relative amount similar to that used in that Example, the title compound was obtained as a foam-like substance.

Infrared Absorption Spectrum (CHCl$_3$), $\nu_{max}$ cm$^{-1}$: 3460, 1708, 1678, 1480, 1458.

Nuclear Magnetic Resonance Spectrum (CDCl$_3$, 270 MHz), δ ppm:
 0.7–1.0 (2H, multiplet);
 1.1–1.8 (11H, multiplet);
 1.15 (9H, singlet);
 2.3–2.9 (8H, multiplet);
 4.74 (1H, triplet, J=7 Hz);
 6.9–7.5 (11H, multiplet).

EXAMPLE 26

N-[2-t-Butyl-5-(5-cyclohexyl-3-hydroxypentyl)phenyl]-2-(9H-xanthen-9-yl)acetamide (Compound No. 1-1)

Following a procedure similar to that described in Example 22, but using N-[2-t-butyl-5-(5-cyclohexyl-3-oxopentyl)phenyl]-2-(9H-xanthen-9-yl)acetamide (prepared as described in Example 25) as a starting material, in a relative amount similar to that used in that Example, the title compound was obtained as crystals, melting at 148°–149° C. (after recrystallization from a mixture of ethyl acetate and hexane).

Infrared Absorption Spectrum (KBr), $\nu_{max}$ cm$^{-1}$: 3371, 2921, 2849, 1658, 1518, 1480, 1458, 1259, 761.

Nuclear Magnetic Resonance Spectrum (CDCl$_3$, 270 MHz), δ ppm:
 0.7–1.0 (2H, multiplet);
 1.0–1.85 (15H, multiplet);
 1.16 (9H, singlet);
 2.3–2.9 (4H, multiplet);
 3.4–3.7 (1H, multiplet);
 4.74 (1H, triplet, J=7 Hz);
 6.9–7.5 (11H, multiplet).

EXAMPLE 27

N-[2-t-Butyl-5-(5-cyclohexyl-4-oxopentyl)phenyl]-2-(9H-xanthen-9-yl)acetamide (Compound No. 1-1269)

Following a procedure similar to that described in Example 21, but using 2-t-butyl-5-(5-cyclohexyl-4-oxopentyl)aniline as a starting material, in a relative amount similar to that used in that Example, the title compound was obtained as crystals, melting at 193°–194.5° C. (after recrystallization from a mixture of methylene chloride and diethyl ether). The starting material was prepared following a similar procedure to that described in Preparation 7, but using 2-t-butyl-5-(5-cyclohexyl-4-oxopentyl)-1-nitrobenzene (prepared by a procedure similar to that described in Preparation 9).

Infrared Absorption Spectrum (KBr), $\nu_{max}$ cm$^{-1}$: 3233, 1703, 1640, 1536, 1480, 1459, 1258, 756.

Nuclear Magnetic Resonance Spectrum (CDCl$_3$, 270 MHz), δ ppm:
 0.8–1.0 (2H, multiplet);
 1.05–1.4 (3H, multiplet);
 1.17 (9H, singlet);
 1.6–2.0 (8H, multiplet);
 2.2–2.75 (8H, multiplet);
 4.74 (1H, triplet, J=7 Hz);
 6.9–7.45 (11H, multiplet).

EXAMPLE 28

N-[2-t-Butyl-5-(5-cyclohexyl-4-hydroxypentyl)phenyl]-2-(9H-xanthen-9-yl)acetamide (Compound No. 1-495)

Following a procedure similar to that described in Example 22, but using N-[2-t-butyl-5-(5-cyclohexyl-4-oxopentyl)phenyl]-2-(9H-xanthen-9-yl)acetamide (prepared as described in Example 27) as a starting material, in a relative amount similar to that used in that Example, the title compound was obtained as crystals, melting at 157°–158° C. (after recrystallization from a mixture of diethyl ether and hexane).

Infrared Absorption Spectrum (KBr), $\nu_{max}$ cm$^{-1}$: 3238, 1639, 1531, 1482, 1459, 1257, 756.

Nuclear Magnetic Resonance Spectrum (CDCl$_3$, 270 MHz), δ ppm:
 0.75–1.05 (2H, multiplet);
 1.1–1.9 (15H, multiplet);
 1.16 (9H, singlet);
 2.25–2.4 (1/2H, multiplet);
 2.45 (1/2H, broad doublets, J=8 Hz);
 2.61 (3/2H, triplet, J=7 Hz);
 2.70 (3/2H, doublet, J=7 Hz);
 3.65–3.75 (1H, broad singlet);
 4.75 (1H, triplet, J=7 Hz);
 6.9–7.45 (11H, multiplet).

EXAMPLE 29

N-[2-t-Butyl-5-(5-cyclohexyl-2-oxopentyl)phenyl]-2-(9H-xanthen-9-yl)acetamide (Compound No. 1-1266)

Following a procedure similar to that described in Example 21, but using 2-t-butyl-5-(5-cyclohexyl-2-oxopentyl)aniline as a starting material, in a relative amount similar to that used in that Example, the title compound was obtained as crystals, melting at 146°–147° C. (after recrystallization from a mixture of diisopropyl ether and hexane). The starting material was prepared following a similar procedure to that described in Preparation 7, but using 2-t-butyl-5-(5-cyclohexyl-2-oxopentyl)-1-nitrobenzene (prepared by a procedure similar to that described in Preparation 9).

Infrared Absorption Spectrum (KBr), $v_{max}$ cm$^{-1}$: 3386, 1711, 1663, 1519, 1480, 1458, 1259, 764.

Nuclear Magnetic Resonance Spectrum (CDCl$_3$, 270 MHz), δ ppm:

0.77–0.94 (2H, multiplet);
1.08–1.28 (6H, multiplet);
1.16 (9H, singlet);
1.50–2.72 (7H, multiplet);
2.28–2.40 (0.4H, multiplet);
2.45 (2H, triplet, J=7 Hz);
2.70 (1.6H, doublet, J=7 Hz);
3.38 (0.4H, singlet);
3.65 (1.6H, singlet);
4.73 (1H, triplet, J=7 Hz);
6.94–7.40 (11H, multiplet).

EXAMPLE 30

N-[2-t-Butyl-5-(5-cyclohexyl-2-hydroxypentyl)phenyl]-2-(9H-xanthen-9-yl)acetamide (Compound No. 1-397)

Following a procedure similar to that described in Example 22, but using N-[2-t-butyl-5-(5-cyclohexyl-2-oxopentyl)phenyl]-2-(9H-xanthen-9-yl)acetamide (prepared as described in Example 29) as a starting material, in a relative amount similar to that used in that Example, the title compound was obtained as crystals, melting at 109°–111° C. (after recrystallization from diisopropyl ether).

Infrared Absorption Spectrum (KBr), $v_{max}$ cm$^{-1}$: 3246, 1643, 1527, 1482, 1458, 1259, 760.

Nuclear Magnetic Resonance Spectrum (CDCl$_3$, 270 MHz), δ ppm:

0.80–0.97 (2H, multiplet);
1.12–1.77 (15H, multiplet);
1.17 (9H, multiplet);
2.35–2.55 (0.8H, multiplet);
2.60 (0.8H, doublet of doublets, J=9 & 14 Hz);
2.70 (1.6H, doublet, J=7 Hz);
2.80 (0.8H, doublet of doublets, J=4 & 14 Hz);
3.55–3.87 (1H, multiplet);
4.74 (1H, triplet, J=7 Hz);
6.97–7.41 (11H, multiplet).

EXAMPLE 31

N-[2-t-Butyl-5-(6-cyclohexyl-2-oxohexyl)phenyl]-2-(9H-xanthen-9-yl)acetamide (Compound No. 1-1267)

Following a procedure similar to that described in Example 21, but using 2-t-butyl-5-(6-cyclohexyl-2-oxohexyl)aniline as a starting material, in a relative amount similar to that used in that Example, the title compound was obtained as a foam-like substance. The starting material was prepared following a similar procedure to that described in Preparation 7, but using 2-t-butyl-5-(6-cyclohexyl-2-oxohexyl)-1-nitrobenzene (prepared by a procedure similar to that described in Preparation 9).

Infrared Absorption Spectrum (film), $v_{max}$ cm$^{-1}$: 3280, 1713, 1655, 1518, 1480, 1459, 1256, 758.

Nuclear Magnetic Resonance Spectrum (CDCl$_3$, 270 MHz), δ ppm:

0.75–0.90 (2H, multiplet);
1.10–1.30 (8H, multiplet);
1.17 (9H, singlet);
1.50–2.70 (7H, multiplet);
2.31–2.42 (0.4H, multiplet);
2.47 (2H, triplet, J=7 Hz);
2.70 (1.6H, doublet, J=7 Hz);
3.38 (0.4H, singlet);
3.65 (1.6H, singlet);
4.73 (1H, triplet, J=7 Hz);
6.94–7.40 (11H, multiplet).

EXAMPLE 32

N-[2-t-Butyl-5-(6-cyclohexyl-2-hydroxyhexyl)phenyl]-2-(9H-xanthen-9-yl)acetamide (Compound No. 1-421)

Following a procedure similar to that described in Example 22, but using N-[2-t-butyl-5-(6-cyclohexyl-2-oxohexyl)phenyl]-2-(9H-xanthen-9-yl)acetamide (prepared as described in Example 31) as a starting material, in a relative amount similar to that used in that Example, the title compound was obtained as a foam-like substance.

Infrared Absorption Spectrum (film), $v_{max}$ cm$^{-1}$: 3380, 3275, 1655, 1522, 1480, 1459, 1256, 758.

Nuclear Magnetic Resonance Spectrum (CDCl$_3$, 270 MHz), δ ppm:

0.80–0.94 (2H, multiplet);
1.12–1.75 (17H, multiplet);
1.17 (9H, singlet);
2.33–2.55 (0.8H, multiplet);
2.60 (0.8H, doublet of doublets, J=9 & 14 Hz);
2.70 (1.6H, doublet, J=7 Hz);
2.80 (0.8H, doublet of doublets, J=3 & 14 Hz);
3.52–3.88 (1H, multiplet);
4.74 (1H, triplet, J=7 Hz);
6.97–7.41 (11H, multiplet).

EXAMPLE 33

N-[2-t-Butyl-5-(4-cycloheptyl-3-oxobutyl)phenyl]-4-decyloxybenzamide (Compound No. 4-117)

Following a procedure similar to that described in Example 21, but using 4-decyloxybenzoic acid and 2-t-butyl-5-(4-cycloheptyl-3-oxobutyl)aniline as starting materials, in relative proportions similar to those used in that Example, the title compound was obtained as crystals, melting at 98°–99° C. (after recrystallization from a mixture of ethyl acetate and hexane). The 2-t-butyl-5-(4-cycloheptyl-3-oxobutyl)aniline used as a starting material was prepared following a similar procedure to that described in Preparation 7, but using 2-t-butyl-5-(4-cycloheptyl-3-oxobutyl)-1-nitrobenzene (prepared by a procedure similar to that described in Preparation 6).

Infrared Absorption Spectrum (KBr), $v_{max}$ cm$^{-1}$: 3314, 1715, 1640, 1502, 1251, 766.

Nuclear Magnetic Resonance Spectrum (CDCl$_3$, 270 MHz), δ ppm:

0.88 (3H, triplet, J=7 Hz);
1.05–1.7 (26H, multiplet);
1.43 (9H, singlet);
1.75–1.9 (2H, multiplet);
1.9–2.1 (1H, multiplet);
2.31 (2H, doublet, J=7 Hz);
2.7–2.8 (2H, multiplet);
2.8–2.9 (2H, multiplet);
4.03 (2H, triplet, J=7 Hz);
6.95–7.05 (3H, multiplet);
7.32 (1H, doublet, J=8 Hz);
7.60 (1H, singlet);
7.78 (1H, singlet);
7.85 (2H, doublet, J=8 Hz).

EXAMPLE 34

N-[2-t-Butyl-5-(4-cycloheptyl-3-hydroxybutyl)phenyl]-4-decyloxybenzamide (Compound No. 4-17)

Following a procedure similar to that described in Example 22, but using N-[2-t-butyl-5-(4-cycloheptyl-3-oxobutyl)phenyl]-4-decyloxybenzamide (prepared as described in Example 33) as a starting material, in a relative amount similar to that used in that Example, the title compound was obtained as a foam-like substance.

Infrared Absorption Spectrum (CHCl$_3$), $v_{max}$ cm$^{-1}$: 3480, 1664, 1607, 1503, 1468.

Nuclear Magnetic Resonance Spectrum (CDCl$_3$, 270 MHz), δ ppm:

0.88 (3H, triplet, J=7 Hz);
1.05–1.9 (33H, multiplet);
1.43 (9H, singlet);
2.6–2.9 (2H, multiplet);
3.65–3.8 (1H, multiplet);
4.02 (2H, triplet, J=7 Hz);
6.98 (2H, doublet, J=8 Hz);
7.02 (1H, doublet, J=8 Hz);
7.33 (1H, doublet, J=8 Hz);
7.61 (1H, singlet);
7.78 (1H, singlet);
7.85 (2H, doublet, J=8 Hz).

EXAMPLE 35

N-[2-t-Butyl-5-(3-phenyl-3-oxopropyl)phenyl]-2-(9H-xanthen-9-yl)acetamide (Compound No. 1-1326)

0.58 ml (4.20 mmol) of triethylamine and 0.31 ml (2.10 mmol) of diethylphosphoryl chloride were added to 20 ml of a benzene suspension containing 505 mg (2.10 mmol) of 2-(9H-xanthen-9-yl)acetic acid, and then the mixture was stirred for 1 hour. At the end of this time, 5 ml of a benzene solution containing 587 mg (2.09 mmol) of 2-t-butyl-5-(3-phenyl-3-oxopropyl)aniline (prepared by a procedure similar to that described in Preparation 7), followed by 10 mg of 4-pyrrolidinopyridine, were added to the reaction suspension, and the resulting mixture was heated under reflux for 4.5 hours. The reaction mixture was then diluted with ethyl acetate, washed with dilute aqueous hydrochloric acid, with water, with a saturated aqueous solution of sodium hydrogen carbonate solution and with a saturated aqueous solution of sodium chloride, in that order. The solvent was then removed by distillation under reduced pressure, and the resulting residue was subjected to column chromatography through silica gel. Elution with a 4:1 by volume mixture of methylene chloride and cyclohexane yielded 934 mg (yield 86%) of the title compound as crystals, melting at 116°–118° C. (after crystallization from diisopropyl ether).

Infrared Absorption Spectrum (KBr), $v_{max}$ cm$^{-1}$: 3216, 1686, 1640, 1481, 1457, 1254.

Nuclear Magnetic Resonance Spectrum (CDCl$_3$, 270 MHz), δ ppm:

1.17 (27/4H, singlet);
1.22 (9/4H, singlet);
2.46 (9/4H, doublet, J=7 Hz);
2.65–2.85 (1/2H, multiplet);
2.71 (3/2H, doublet, J=7 Hz);
3.04 (3/2H, triplet, J=7 Hz);
3.05–3.2 (1/2H, multiplet);
3.32 (3/2H, triplet, J=7 Hz);
4.74 (1H, triplet, J=7 Hz);
6.7–6.9 (14H, multiplet);
7.99 (2H, doublet, J=7 Hz).

EXAMPLE 36

N-[2-t-Butyl-5-(3-hydroxy-3-phenylpropyl)phenyl]-2-(9H-xanthen-9-yl)acetamide (Compound No. 1-1300)

Following a procedure similar to that described in Example 22, but using N-[2-t-butyl-5-(3-phenyl-3-oxopropyl)phenyl]-2-(9H-xanthen-9-yl)acetamide (prepared as described in Example 35) as a starting material, in a relative amount similar to that used in that Example, the title compound was obtained as crystals, melting an 136°–137° C. (after recrystallization from diisopropyl ether).

Infrared Absorption Spectrum (KBr), $v_{max}$ cm$^{-1}$: 3267, 1658, 1525, 1479, 1255.

Nuclear Magnetic Resonance Spectrum (CDCl$_3$, 270 MHz), δ ppm:

1.16 (15/2H, singlet);
1.18 (3/2H, singlet);
1.8–2.8 (6H, multiplet);
4.5–4.8 (2H, multiplet);
6.9–7.5 (16H, multiplet).

EXAMPLE 37

N-[2-t-Butyl-5-(3-oxo-4-phenylbutyl)phenyl]-2-(9H-xanthen-9-yl)acetamide (Compound No. 1-1327)

Following a procedure similar to that described in Example 35, but using 2-t-butyl-5-(3-oxo-4-phenylbutyl)aniline (prepared by a procedure similar to that described in Preparation 7) as a starting material, in a relative amount similar to that used in that Example, the title compound was obtained as crystals, melting at 122°–123° C. (after recrystallization from diisopropyl ether).

Infrared Absorption Spectrum (KBr), $v_{max}$ cm$^{-1}$: 3224, 1716, 1640, 1480, 1456, 1257.

Nuclear Magnetic Resonance Spectrum (CDCl$_3$, 270 MHz), δ ppm:

1.15 (27/4H, singlet);
1.18 (9/4H, singlet);
2.41 (1/2H, doublet, J=7 Hz);
2.5–2.6 (1/2H, multiplet);
2.69 (3/2H, doublet, J=7 Hz);
2.7–2.9 (3/2H, multiplet);
3.67 (1/2H, singlet);
3.71 (3/2H, singlet);
4.74 (1H, triplet, J=7 Hz);
6.85–7.4 (16H, multiplet).

EXAMPLE 38

N-[2-t-Butyl-5-(3-hydroxy-4-phenylbutyl)phenyl]-2-(9H-xanthen-9-yl)acetamide (Compound No. 1-1301)

Following a procedure similar to that described in Example 22, but using the compound obtained in Example 37, the title compound was obtained as a foam-like substance.

Infrared Absorption Spectrum (KBr), $v_{max}$ cm$^{-1}$: 3403, 3278, 1655, 1458, 1416, 1256.

Nuclear Magnetic Resonance Spectrum (CDCl$_3$, 270 MHz), δ ppm:

1.16 (27/4H, singlet);
1.20 (9/4H, singlet);
1.75–2.0 (2H, multiplet);
2.3–2.95 (6H, multiplet);
3.7–4.0 (1H, multiplet);
4.74 (1H, triplet, J=7 Hz);
6.9–7.45 (16H, multiplet).

EXAMPLE 39

N-[2-t-Butyl-5-(4-cycloheptyl-3-hydroxybutyl)phenyl]-2-(9H-xanthen-9-yl)acetamide (Compound No. 1-949)

Following a procedure similar to that described hereafter in Example 40, but using N-[2-t-butyl-5-(4-cycloheptyl-3-t-butyldimethylsilyloxybutyl)phenyl]-2-(9H-xanthen-9-yl)acetamide (prepared by a procedure similar to that described in Preparation 11) as a starting material, in a relative amount similar to that used in that Example, the title compound was obtained as a foam-like substance.

Infrared Absorption Spectrum CHCl$_3$), $v_{max}$ cm$^{-1}$: 3400, 1668, 1596, 1475, 1458.

Nuclear Magnetic Resonance Spectrum (CDCl$_3$, 270 MHz), δ ppm:

1.0–1.8 (17H, multiplet);
1.16 (9H, singlet);
2.3–2.9 (4H, multiplet);
3.6–3.8 (1H, multiplet);
4.74 (1H, triplet, J=7 Hz);
7.5–7.9 (11H, multiplet).

EXAMPLE 40

N-[2-t-Butyl-5-(3-cyclohexyl-2-hydroxypropyl)phenyl]-2-(9H-xanthen-9-yl)acetamide (Compound No. 1-349)

1.5 ml of 2N aqueous hydrochloric acid were added to 15 ml of a tetrahydrofuran solution containing 813 mg (1.30 mmol) of N-[2-t-butyl-5-(3-cyclohexyl-2-t-butyl-dimethyl-silyloxypropyl)phenyl]-2-(9H-xanthen-9-yl)-acetamide (prepared by a procedure similar to that described in Preparation 11), and the mixture was stirred for 2.5 hours at 50° C. The reaction mixture was then allowed to return to room temperature. Addition of a mixture of ethyl acetate and water caused the title compound to be distributed between the organic solvent and water. The organic layer was separated and washed with a saturated aqueous solution of sodium hydrogen carbonate, and then with a saturated aqueous solution of sodium chloride. The solvent was removed by distillation under reduced pressure. The resulting residue was subjected to column chromatography through 50 g of silica gel. Elution with mixtures of ethyl acetate and hexane ranging from 1:2 to 2:3 by volume afforded 650 mg (yield 98%) of the title compound as crystals, melting at 177°–178° C. (after recrystallization from diisopropyl ether).

Infrared Absorption Spectrum (KBr), $v_{max}$ cm$^{-1}$: 3393, 3223, 1641, 1537, 1482, 1457, 1257, 760.

Nuclear Magnetic Resonance Spectrum (CDCl$_3$, 270 MHz), δ ppm:

0.82–1.04 (2H, multiplet);
1.12–1.87 (11H, multiplet);
1.17 (9H, multiplet);
2.35–2.50 (0.8H, multiplet);
2.57 (0.8H, doublet of doublets, J=8 & 14 Hz);
2.70 (1.6H, doublet, J=7 Hz);
2.79 (0.8H, doublet of doublets, J=4 & 8 Hz);
3.67–3.99 (1H, multiplet);
4.74 (1H, triplet, J=7 Hz);
6.97–7.41 (11H, multiplet).

EXAMPLE 41

N-[5-(4-Cyclohexyl-3-hydroxybutyl]-2-isopropylphenyl]-2-(9H-xanthen-9-yl)acetamide (Compound No. 1-26)

Following a procedure similar to that described in Example 40, but using N-[5-(4-cyclohexyl-3-t-butyl-dimethylsilyloxybutyl)-2-isopropylphenyl]-2-(9H-xanthen-9-yl)acetamide (prepared by a procedure similar to that described in Preparation 11) as a starting material, in a relative amount similar to that used in that Example, the title compound was obtained as crystals, melting at 144°–145° C. (after recrystallization from a mixture of ethyl acetate and hexane).

Infrared Absorption Spectrum (KBr), $v_{max}$ cm$^{-1}$: 3282, 2919, 1644, 1528, 1481, 1260, 757.

Nuclear Magnetic Resonance Spectrum (CDCl$_3$, 270 MHz), δ ppm:

0.8–1.9 (15H, multiplet);
1.05 (6H, doublet, J=7 Hz);
2.5–2.9 (5H, multiplet);
3.65–3.85 (1H, multiplet);

4.69 (1H, triplet, J=7 Hz);
7.0–7.5 (11H, multiplet).

EXAMPLE 42

N-[2-t-Butyl-5-(3-cyclohexyl-3-hydroxypropyl)phenyl]-2-(9H-xanthen-9-yl)acetamide (Compound No. 1-131)

Following a procedure similar to that described in Example 40, but using N-[2-t-butyl-5-(3-cyclohexyl-3-t-butyldimethylsilyloxypropyl)phenyl]-2-(9H-xanthen-9-yl)acetamide (prepared by a procedure similar to that described in Preparation 11) as a starting material, in a relative amount similar to that used in that Example, the title compound was obtained as a foam-like substance.

Infrared Absorption Spectrum (film), $v_{max}$ cm$^{-1}$: 3400, 3270, 1653, 1522, 1480, 1457, 1256, 758.

Nuclear Magnetic Resonance Spectrum (CDCl$_3$, 270 MHz), δ ppm:
0.90–1.89 (13H, multiplet);
1.16 (9H, singlet);
2.30–2.87 (4H, multiplet);
3.28–3.45 (1H, multiplet);
4.74 (1H, triplet, J=7 Hz);
6.95–7.42 (11H, multiplet).

EXAMPLE 43

N-[2-t-Butyl-5-(6-cyclohexyl-3-hydroxyhexyl)phenyl]-2-(9H-xanthen-9-yl)acetamide (Compound No. 1-49)

Following a procedure similar to that described in Example 40, but using N-[2-t-butyl-5-(6-cyclohexyl-3-t-butyldimethylsilyloxyhexyl)phenyl]-2-(9H-xanthen-9-yl)acetamide (prepared by a procedure similar to that described in Preparation 11) as a starting material, in a relative amount similar to that used in that Example, the title compound was obtained as a foam-like substance.

Infrared Absorption Spectrum (film), $v_{max}$ cm$^{-1}$: 3390, 3280, 1655, 1522, 1480, 1459, 1256, 758.

Nuclear Magnetic Resonance Spectrum (CDCl$_3$, 270 MHz), δ ppm:
0.80–0.95 (2H, multiplet);
1.10–1.82 (17H, multiplet);
1.16 (9H, singlet);
2.30–2.82 (4H, multiplet);
3.50–3.69 (1H, multiplet);
4.74 (1H, triplet, J=7 Hz);
6.95–7.41 (11H, multiplet).

EXAMPLE 44

N-[2-t-Butyl-5-(7-cyclohexyl-3-hydroxyheptyl)phenyl]-2-(9H-xanthen-9-yl)acetamide (Compound No. 1-73)

Following a procedure similar to that described in Example 40, but using N-[2-t-butyl-5-(7-cyclohexyl-3-t-butyldimethylsilyloxyheptyl)phenyl]-2-(9H-xanthen-9-yl)acetamide (prepared by a procedure similar to that described in Preparation 11) as a starting material, in a relative amount similar to that used in that Example, the title compound was obtained as a foam-like substance.

Infrared Absorption Spectrum (film), $v_{max}$ cm$^{-1}$: 3390, 3270, 1653, 1522, 1480, 1459, 1256, 758.

Nuclear Magnetic Resonance Spectrum (CDCl$_3$, 270 MHz), δ ppm:
0.77–0.93 (2H, multiplet);
1.10–1.81 (19H, multiplet);
1.16 (9H, singlet);
2.30–2.83 (4H, multiplet);
3.47–3.69 (1H, multiplet);
4.74 (1H, triplet, J=7 Hz);
6.95–7.42 (11H, multiplet).

EXAMPLE 45

N-[2-t-Butyl-5-(6-cyclohexyl-4-hydroxyhexyl)phenyl]-2-(9H-xanthen-9-yl)acetamide (Compound No. 1-519)

Following a procedure similar to that described in Example 40, but using N-[2-t-butyl-5-(6-cyclohexyl-4-t-butyldimethylsilyloxyhexyl)phenyl]-2-(9H-xanthen-9-yl)acetamide (prepared by a procedure similar to that described in Preparation 11) as a starting material, in a relative amount similar to that used in that Example, the title compound was obtained as a foam-like substance.

Infrared Absorption Spectrum (CHCl$_3$), $v_{max}$ cm$^{-1}$: 3450, 1659 (broad), 1600, 1575, 1478, 1453.

Nuclear Magnetic Resonance Spectrum (CDCl$_3$, 270 MHz), δ ppm:
0.7–1.0 (2H, multiplet);
1.0–1.9 (17H, multiplet);
1.17 (9H, singlet);
2.2–2.8 (4H, multiplet);
3.5–3.7 (1H, multiplet);
4.76 (1H, triplet, J=7 Hz);
6.9–7.5 (11H, multiplet).

EXAMPLE 46

N-[2-t-Butyl-5-(5-cyclohexyl-5-hydroxypentyl)phenyl]-2-(9H-xanthen-9-yl)acetamide (Compound No. 1-577)

Following a procedure similar to that described in Example 40, but using N-[2-t-butyl-5-(5-cyclohexyl-5-t-butyldimethylsilyloxypentyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 147°–148° C. (after recrystallization from a mixture of methylene chloride and diisopropyl ether).

Infrared Absorption Spectrum (KBr), $v_{max}$ cm$^{-1}$: 3336, 1657, 1519, 1480, 1458, 1260, 761.

Nuclear Magnetic Resonance Spectrum (CDCl$_3$, 270 MHz), δ ppm:
0.93–1.86 (17H, multiplet);
1.16 (9H, singlet);
2.27–2.35 (0.4H, multiplet);
2.45 (0.4H, doublet, J=7 Hz);
2.60 (1.6H, triplet, J=7 Hz);
2.70 (1.6H, doublet, J=7 Hz);
3.32–3.41 (1H, multiplet);

4.74 (1H, triplet, J=7 Hz);
6.93–7.41 (11H, multiplet).

EXAMPLE 47

N-[2-t-Butyl-5-(4-cyclopentyl-3-hydroxybutyl)phenyl]-2-(9H-xanthen-9-yl)acetamide (Compound No. 1-747)

Following a procedure similar to that described in Example 40, but using N-[2-t-butyl-5-(4-cyclopentyl-3-t-butyldimethylsilyloxybutyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 142°–143° C. (after recrystallization from a mixture of ethyl acetate and hexane).

Infrared Absorption Spectrum (KBr), $v_{max}$ cm$^{-1}$: 2951, 1654, 1529, 1478, 1458, 1253, 760.

Nuclear Magnetic Resonance Spectrum (CDCl$_3$, 270 MHz), δ ppm:

1.0–1.3 (2H, multiplet);
1.16 (9H, singlet);
1.3–2.0 (11H, multiplet);
2.2–2.9 (4H, multiplet);
3.5–3.8 (1H, multiplet);
4.74 (1H, triplet, J=7 Hz);
6.9–7.5 (11H, multiplet).

EXAMPLE 48

N-[2-t-Butyl-5-(6-cyclopentyl-5-hydroxyhexyl)phenyl]-2-(9H-xanthen-9-yl)acetamide (Compound No. 1-839)

Following a procedure similar to that described in Example 40, but using N-[2-t-butyl-5-(6-cyclopentyl-5-t-butyldimethylsilyloxyhexyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 132°–133° C. (after recrystallization from a mixture of ethyl acetate and hexane).

Infrared Absorption Spectrum (KBr), $v_{max}$ cm$^{-1}$: 2949, 1649, 1523, 1479, 1458, 1258, 760.

Nuclear Magnetic Resonance Spectrum (CDCl$_3$, 270 MHz), δ ppm:

1.0–1.3 (2H, multiplet);
1.17 (9H, singlet);
1.3–2.0 (15H, multiplet);
2.25–2.35 (2/5H, multiplet);
2.45 (2/5H, doublet, J=7 Hz);
2.60 (8/5H, triplet, J=7 Hz);
2.69 (8/5H, doublet, J=7 Hz);
3.6–3.7 (1H, multiplet);
4.74 (1H, triplet, J=7 Hz);
6.9–7.5 (11H, multiplet).

EXAMPLE 49

N-[2-t-Butylthio-6-(3-hydroxy-3-phenylpropyl)phenyl]-2-(9H-xanthen-9-yl)acetamide (Compound No. 1-1442)

Following a procedure similar to that described in Example 40, but using N-[2-t-butylthio-6-(3-t-butyldimethylsilyloxy-3-phenylpropyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 145°–147° C. (after recrystallization from a mixture of ethyl acetate and hexane).

Infrared Absorption Spectrum (KBr), $v_{max}$ cm$^{-1}$: 2959, 1662, 1481, 1456, 1259, 762.

Nuclear Magnetic Resonance Spectrum (CDCl$_3$, 270 MHz), δ ppm:

1.13 (9H, singlet);
1.99 (2H, quartet, J=7 Hz);
2.60 (2H, triplet, J=7 Hz);
2.75 (2H, doublet, J=7 Hz);
4.51 (1H, triplet, J=6 Hz);
4.70 (1H, triplet, J=7 Hz);
7.0–7.5 (16H, multiplet).

EXAMPLE 50

N-[2-Methyl-6-(3-hydroxy-3-phenylpropyl)phenyl]-2-(9H-xanthen-9-yl)acetamide (Compound No. 1-1438)

Following a procedure similar to that described in Example 40, but using N-[2-methyl-6-(3-t-butyldimethylsilyloxy-3-phenylpropyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 193°–194° C. (after recrystallization from a mixture of methylene chloride, methanol and hexane).

Infrared Absorption Spectrum (KBr), $v_{max}$ cm$^{-1}$: 3235, 1648, 1523, 1479, 1458, 754.

Nuclear Magnetic Resonance Spectrum (CDCl$_3$, 60 MHz), δ ppm:

1.5–2.8 (6H, multiplet);
2.05 (3H, singlet);
4.2–4.5 (1H, multiplet);
4.68 (1H, triplet, J=7 Hz);
6.9–7.6 (11H, multiplet).

EXAMPLE 51

N-[2-Methyl-6-(3-oxo-3-phenylpropyl)phenyl]-2-(9H-xanthen-9-yl)acetamide (Compound No. 1-1437)

Following a procedure similar to that described in Example 13, but using N-[2-methyl-6-(3-hydroxy-3-phenylpropyl)phenyl]-2-(9H-xanthen-9-yl)acetamide (prepared as described in Example 50) as a starting material, in a relative amount similar to that used in that Example, the title compound was obtained, melting at 175°–176° C. (after recrystallization from a mixture of ethyl acetate and hexane).

Infrared Absorption Spectrum (KBr), $v_{max}$ cm$^{-1}$: 3280, 1684, 1653, 1480, 1457, 1259, 762.

Nuclear Magnetic Resonance Spectrum (CDCl$_3$, 60 MHz), δ ppm:

2.10 (3H, singlet);
2.62 (2H, triplet, J=7 Hz);
2.85 (2H, doublet, J=7 Hz);

3.23 (2H, triplet, J=7 Hz);
4.75 (1H, triplet, J=7 Hz);
6.9–8.05 (16H, multiplet);
8.1–8.3 (1H, broad singlet).

EXAMPLE 52

N-[2-Methyl-6-(3-hydroxybutyl)phenyl]-2-(9H-xanthen-9-yl)acetamide (Compound No. 1-1435)

Following a procedure similar to that described in Example 40, but using N-[2-methyl-6-(3-t-butyldimethylsilyloxybutyl)phenyl]-2-(9H-xanthen-9-yl)acetamide (prepared by a procedure similar to that described in Preparation 11) as a starting material, in a relative amount similar to that used in that Example, the title compound was obtained as crystals, melting at 167°–168° C. (after recrystallization from a mixture of ethyl acetate and hexane).

Infrared Absorption Spectrum (KBr), $v_{max}$ cm$^{-1}$: 3244, 1653, 1530, 1481, 1457, 1260, 758.

Nuclear Magnetic Resonance Spectrum (CDCl$_3$, 60 MHz), δ ppm:
  1.05 (3H, doublet, J=7 Hz);
  1.4–1.9 (2H, multiplet);
  2.06 (3H, singlet);
  2.32 (2H, triplet, J=7 Hz);
  2.70 (2H, doublet, J=7 Hz);
  3.1–3.6 (1H, multiplet);
  4.68 (1H, triplet, J=7 Hz);
  6.8–7.9 (11H, multiplet).

EXAMPLE 53

N-[2-Methyl-6-(3-oxobutyl)phenyl]-2-(9H-xanthen-9-yl)acetamide (Compound No. 1-1436)

Following a procedure similar to that described in Example 13, but using N-[2-methyl-6-(3-hydroxybutyl)phenyl]-2-(9H-xanthen-9-yl)acetamide (prepared as described in Example 52) as a starting material, in a relative amount similar to that used in that Example, the title compound was obtained as crystals, melting at 179°–180° C. (after recrystallization from a mixture of ethyl acetate and hexane).

Infrared Absorption Spectrum (KBr), $v_{max}$ cm$^{-1}$: 3281, 1711, 1648, 1480, 1260, 754.

Nuclear Magnetic Resonance Spectrum (CDCl$_3$, 60 MHz), δ ppm:
  1.95 (3H, singlet);
  2.03 (3H, singlet);
  2.1–2.9 (4H, multiplet);
  2.75 (2H, doublet, J=7 Hz);
  4.68 (1H, triplet, J=7 Hz);
  6.75–7.5 (11H, multiplet);
  8.0–8.3 (1H, broad singlet).

EXAMPLE 54

1-{4-t-Butyl-3-[2-(9H-xanthen-9-yl)acetamido]phenyl}-6-phenylhexyl Hydrogen Succinate (Compound No. 1-1337)

1 ml of a pyridine solution containing 276 mg (0.504 mmol) of N-[2-t-butyl-5-(6-phenyl-1-hydroxyhexyl)phenyl-2-(9H-xanthen-9-yl)acetamide (prepared as described in Example 16), 58 mg (0.58 mmol) of succinic anhydride and 64 mg (0.52 mmol) of 4-(N,N-dimethylamino)pyridine was stirred for 1 hour at 100° C. At the end of this time, the reaction solution was diluted with ethyl acetate, washed with 2N aqueous hydrochloric acid once, with water twice and with a saturated aqueous solution of sodium chloride once. The solvent was then removed by distillation under reduced pressure. The resulting residue was subjected to silica gel column chromatography. Elution with a 9:1 by volume mixture of methylene chloride and methanol afforded 294 mg (yield 90%) of the title compound as a foam-like substance.

Infrared Absorption Spectrum (liquid film), $v_{max}$ cm$^{-1}$: 3260, 1734, 1715, 1651, 1480, 1459, 1254, 760.

Nuclear Magnetic Resonance Spectrum (CDCl$_3$, 270 MHz), δ ppm:
  1.10–1.44 (4H, multiplet);
  1.16 (9H, singlet);
  1.53–1.98 (4H, multiplet);
  2.38–2.80 (8H, multiplet);
  4.74 (1H, triplet, J=7 Hz);
  5.67 (1H, triplet, J=7 Hz);
  7.04–7.51 (16H, multiplet).

EXAMPLE 55

1-{4-t-Butyl-3-[2-(9H-xanthen-9-yl)acetamido]phenyl}-6-phenylhexyl Sodium Succinate (Compound No. 1-1336)

4 ml of a methanolic solution containing 165 mg (0.255 mmol) of 1-{4-t-butyl-3-[2-(9H-xanthen-9-yl)acetamido]phenyl}-6-phenylhexyl hydrogen succinate (prepared as described in Example 54) were cooled in an ice bath, and then 2.42 ml (0.242 mmol) of a 0.1N aqueous solution of sodium hydroxide was added dropwise. The reaction solution was condensed by evaporation under reduced pressure, whilst keeping its temperature below 15° C. 20 ml of toluene were added to the residue, and then sufficient ethanol was added until the solution became homogenous. The solvent was then was removed by distillation under reduced pressure. In order to remove any remaining water, toluene was added to the residue and the mixture was distilled again. This procedure was repeated several times, and gave 170 mg (a quantitative yield) of the title compound as a foam-like substance.

Nuclear Magnetic Resonance Spectrum (CDCl$_3$, 270 MHz), δ ppm:
  1.03–1.80 (8H, multiplet);
  1.06 (9H, multiplet);
  2.10–2.59 (7.2H, multiplet);
  2.80–2.98 (0.8H, multiplet);
  4.61 (0.8H, triplet, J=7 Hz);
  4.60–4.70 (0.2H, multiplet);
  5.27–5.33 (0.2H, multiplet);
  5.53 (0.8H, triplet, J=7 Hz);
  6.85–7.32 (16H, multiplet).

EXAMPLE 56

1-(2-{4-t-Butyl-3-[2-(9H-xanthen-9-yl)acetamido]phenyl}ethyl)-2-cyclohexylethyl Hydrogen Succinate (Compound No. 1-1109)

5 ml of a xylene solution containing 74 mg (0.14 mmol) of N-[2-t-butyl-5-(4-cyclohexyl-3-hydroxybutyl)phenyl]-2-

(9H-xanthen-9-yl)acetamide (prepared as described in Example 12), 15 mg (0.15 mmol) of succinic anhydride, 18 mg (0.15 mmol) of 4-(N,N-dimethylamino)pyridine and 112 mg (1.41 mmol) of pyridine were stirred for 9 hours at 125° C. At the end of this time, the reaction mixture was allowed to return to room temperature. The reaction solution was then diluted with diethyl ether, and washed with dilute aqueous hydrochloric acid and then with water. The solvent was then removed by distillation under reduced pressure. The resulting residue was subjected to column chromatography through 20 g of silica gel. Elution using a gradient elution method, with mixtures of methylene chloride and methanol in ratios ranging from 100:5 to 10:1 by volume as the eluent, afforded 73 mg (yield 84%) of the title compound as a foam-like substance.

Infrared Absorption Spectrum (CHCl$_3$), $\nu_{max}$ cm$^{-1}$: 1722, 1671, 1479, 1458, 1250.

Nuclear Magnetic Resonance Spectrum (CDCl$_3$, 270 MHz), δ ppm:

0.75–2.00 (15H, multiplet);

1.14 (9H, singlet);

2.19–2.80 (8H, multiplet);

4.72 (1H, triplet, J=7 Hz);

4.92–5.20 (1H, multiplet);

6.87–7.47 (11H, multiplet).

EXAMPLE 57

1-(2-{4-t-Butyl-3-[2-(9H-xanthen-9-yl)acetamido]phenyl}ethyl)-2-cyclohexylethyl Sodium Succinate (Compound No. 1-1102)

Following a procedure similar to that described in Example 55, but using 1-(2-{4-t-butyl-3-[2-(9H-xanthen-9-yl)acetamido]phenyl}ethyl)-2-cyclohexylethyl hydrogen succinate (prepared as described in Example 56) as a starting material, in a relative amount similar to that used in that Example, the title compound was obtained as a foam-like substance.

Infrared Absorption Spectrum (KBr), $\nu_{max}$ cm$^{-1}$: 1720, 1655, 1578, 1524, 1480, 1459, 1414, 1255, 758.

Nuclear Magnetic Resonance Spectrum (CDCl$_3$, 270 MHz), δ ppm:

0.68–1.86 (15H, multiplet);

1.09 (9H, singlet);

2.14–2.74 (8H, multiplet);

4.70 (1H, triplet, J=7 Hz);

4.73–5.05 (1H, multiplet);

6.79–7.43 (11H, multiplet).

EXAMPLE 58

1-(2-{4-t-Butyl-3-[2-(9H-xanthen-9-yl)acetamido]phenyl}ethyl)-3-cyclohexylpropyl Hydrogen Succinate (Compound No. 1-1118)

Following a procedure similar to that described in Example 56, but using N-[2-t-butyl-5-(5-cyclohexyl-3-hydroxypentyl)phenyl]-2-(9H-xanthen-9-yl)acetamide (prepared as described in Example 26) as a starting material, in a relative amount similar to that used in that Example, the title compound was obtained as a foam-like substance.

Infrared Absorption Spectrum (CHCl$_3$), $\nu_{max}$ cm$^{-1}$: 1728, 1672, 1479, 1457, 1418.

Nuclear Magnetic Resonance Spectrum (CDCl$_3$, 270 MHz), δ ppm:

0.7–1.0 (2H, multiplet);

1.0–2.0 (15H, multiplet);

1.15 (9H, singlet);

2.3–2.8 (8H, multiplet);

4.73 (1H, triplet, J=7 Hz);

4.9–5.0 (1H, multiplet);

6.9–7.5 (11H, multiplet).

EXAMPLE 59

1-(2-{4-t-Butyl-3-[2-(9H-xanthen-9-yl)acetamido]phenyl}ethyl)-3-cyclohexylpropyl Sodium Succinate (Compound No. 1-1111)

Following a procedure similar to that described in Example 55, but using 1-(2-{4-t-butyl-3-[2-(9H-xanthen-9-yl)acetamido]phenyl}ethyl)-3-cyclohexylpropyl hydrogen succinate (prepared as described in Example 58) as a starting material, in a relative amount similar to that used in that Example, the title compound was obtained as a foam-like substance.

Infrared Absorption Spectrum (CHCl$_3$), $\nu_{max}$ cm$^{-1}$: 3100–3500 (broad), 1716, 1672, 1573, 1455, 1412.

Nuclear Magnetic Resonance Spectrum (CDCl$_3$, 270 MHz), δ ppm:

0.65–0.9 (2H, multiplet);

0.9–1.85 (15H, multiplet);

1.10 (9H, singlet);

2.0–2.75 (8H, multiplet);

4.69 (1H, triplet, J=7 Hz);

4.8–4.9 (1H, multiplet);

6.9–7.4 (11H, multiplet).

EXAMPLE 60

1-(2-{4-t-Butyl-3-[2-(9H-xanthen-9-yl)acetamido]phenyl}ethyl)-2-cyclopentylethyl Hydrogen Succinate (Compound No. 1-1183)

Following a procedure similar to that described in Example 56, but using N-[2-t-butyl-5-(4-cyclopentyl-3-hydroxybutyl)phenyl]-2-(9H-xanthen-9-yl)acetamide (prepared as described in Preparation 47) as a starting material, in a relative amount similar to that used in that Example, the title compound was obtained as a foam-like substance.

Infrared Absorption Spectrum (CHCl$_3$), $\nu_{max}$ cm$^{-1}$: 1725, 1671, 1478, 1456, 1417.

Nuclear Magnetic Resonance Spectrum (CDCl$_3$, 270 MHz), δ ppm:

0.9–1.2 (2H, multiplet);

1.14 (9H, singlet);

1.3–2.0 (11H, multiplet);

2.0–3.8 (8H, multiplet);

4.72 (1H, triplet, J=7 Hz);

5.0–5.15 (1H, multiplet);

6.9–7.5 (11H, multiplet).

EXAMPLE 61

1-(2-{4-t-Butyl-3-[2-(9H-xanthen-9-yl)acetamido]
phenyl}ethyl)-2-cyclopentylethyl Sodium Succinate
(Compound No. 1-1176)

Following a procedure similar to that described in Example 55, but using 1-(2-{4-t-butyl-3-[2-(9H-xanthen-9-yl)acetamido]phenyl}ethyl)-2-cyclopentylethyl hydrogen succinate (prepared as described in Example 60) as a starting material, in a relative amount similar to that used in that Example, the title compound was obtained as a powder.

Infrared Absorption Spectrum (CHCl$_3$), $v_{max}$ cm$^{-1}$: 3100–3500 (broad), 1711, 1672, 1576, 1478, 1454.

Nuclear Magnetic Resonance Spectrum (CDCl$_3$, 270 MHz), δ ppm:

0.9–1.15 (2H, multiplet);
1.09 (9H, singlet);
1.3–1.8 (11H, multiplet);
2.2–3.15 (8H, multiplet);
4.68 (1H, triplet, J=7 Hz);
4.7–5.0 (1H, multiplet);
6.8–7.4 (11H, multiplet).

EXAMPLE 62

N-{5-[3-(1-Imidazolyl)propoxy]-2-methylthiophenyl}-
2-(9H-xanthen-9-yl)acetamide (Compound
No. 1-1479)

Following a procedure similar to that described in Example 1, but using N-[5-(3-hydroxypropoxy)-2-methylthiophenyl]-2-(9H-xanthen-9-yl)acetamide (prepared as described in Preparation 54) as a starting material, in a relative amount similar to that used in that Example, the title compound was obtained as crystals, melting at 127°–129° C. (after recrystallization from a mixture of ethyl acetate and hexane).

Infrared Absorption Spectrum (KBr), $v_{max}$ cm$^{-1}$: 3297, 1658, 1576, 1480, 1456, 1257, 756.

Nuclear Magnetic Resonance Spectrum (CDCl$_3$, 60 MHz), δ ppm:

1.95 (3H, singlet);
2.0–2.5 (2H, multiplet);
2.75 (2H, doublet, J=7 Hz);
3.95 (2H, triplet, J=5 Hz);
4.18 (2H, triplet, J=6 Hz);
4.70 (1H, triplet, J=7 Hz);
6.51 (0.6H, doublet, J=2 Hz);
6.65 (0.4H, doublet, J=2 Hz);
7.6–7.9 (11H, multiplet);
8.0–8.4 (2H, multiplet).

EXAMPLE 63

N-{5-[3-(1-Imidazolyl)propoxy]-2-methylthiophenyl}-
2-(9H-xanthen-9-yl)acetamide Hydrochloride
(Compound No. 1-1478)

Following a procedure similar to that described in Example 2, but using N-{5-[3-(1-imidazolyl)propoxy]-2-methylthiophenyl}-2-(9H-xanthen-9-yl)acetamide (prepared as described in Example 62) as a starting material, in a relative amount similar to that used in that Example, the title compound was obtained as crystals, melting at 155°–159° C. (after recrystallization from a mixture of methanol and diethyl ether).

Infrared Absorption Spectrum (KBr), $v_{max}$ cm$^{-1}$: 3262, 2921, 1658, 1574, 1482, 1259, 751.

Nuclear Magnetic Resonance Spectrum (CDCl$_3$, 270 MHz), δ ppm:

1.98 (3H, singlet);
2.3–2.6 (2H, broad singlet);
2.75 (2H, doublet, J=7 Hz);
4.0–4.2 (2H, broad singlet);
4.5–4.8 (3H, multiplet);
6.55 (1H, broad singlet);
7.0–7.5 (11H, multiplet);
8.11 (1H, broad singlet);
8.22 (1H, broad singlet);
9.60 (1H, broad singlet).

EXAMPLE 64

N-[2-t-Butyl-5-(5-cycloheptyl-3-oxopentyl)phenyl]-
2-(9H-xanthen-9-yl)acetamide (Compound. No.
1-1271)

Following a procedure similar to that described in Example 21, but using 2-t-butyl-5-[5-cycloheptyl-3-oxopentyl)aniline (prepared as described in Preparation 6) as a starting material, in a relative amount similar to that used in that Example, the title compound was obtained as crystals, melting at 136°–137° C. (after recrystallization from a mixture of methylene chloride, diethyl ether and hexane).

Infrared Absorption Spectrum (KBr), $v_{max}$ cm$^{-1}$: 1701, 1665, 1520, 1480, 1458, 1300.

Nuclear Magnetic Resonance Spectrum (CDCl$_3$, 270 MHz), δ ppm:

1.06–1.73 (15H, multiplet);
1.16 (9H, singlet);
2.38–2.59 (8H, multiplet);
4.74 (1H, triplet, J=7 Hz);
6.91–7.44 (11H, multiplet).

EXAMPLE 65

N-[2-t-Butyl-5-(5-cycloheptyl-3-hydroxypentyl)
phenyl]-2-(9H-xanthen-9-yl)acetamide (Compound
No. 1-959)

Following a procedure similar to that described in Example 22, but using N-[2-t-butyl-5-(5-cycloheptyl-3-oxopentyl)phenyl]-2-(9H-xanthen-9-yl)acetamide (prepared as described in Example 64) as a starting material, in a relative amount similar to that used in that Example, the title compound was obtained as crystals, melting at 146°–147° C. (after recrystallization from a mixture of diethyl ether and hexane).

Infrared Absorption Spectrum (KBr), $v_{max}$ cm$^{-1}$: 3380, 1659, 1518, 1480, 1459, 1260, 760.

Nuclear Magnetic Resonance Spectrum (CDCl$_3$, 270 MHz), δ ppm:

1.09–1.86 (19H, multiplet);
1.16 (9H, singlet);
2.30–2.85 (4H, multiplet);
3.46–3.67 (1H, multiplet);

4.74 (1H, triplet, J=7 Hz);
6.95–7.42 (11H, multiplet).

EXAMPLE 66

1-(2-{4-t-Butyl-3-[2-(9H-xanthen-9-yl)acetamido]phenyl} ethyl)-2-cycloheptylethyl Hydrogen Succinate (Compound No. 1-1221)

Following a procedure similar to that described in Example 56, but using N-[2-t-butyl-5-(4-cycloheptyl-3-hydroxybutyl)phenyl]-2-(9H-xanthen-9-yl)acetamide (prepared as described in Example 39) as a starting material, in a relative amount similar to that used in that Example, the title compound was obtained as a foam-like substance.

Infrared Absorption Spectrum (CHCl$_3$), $v_{max}$ cm$^{-1}$: 1726, 1670, 1575, 1478, 1458.

Nuclear Magnetic Resonance Spectrum (CDCl$_3$, 270 MHz), δ ppm:

1.05–2.0 (17H, multiplet);
1.14 (9H, singlet);
2.2–2.8 (8H, multiplet);
4.73 (1H, triplet, J=7 Hz);
4.9–5.2 (1H, multiplet);
6.9–7.5 (11H, multiplet).

EXAMPLE 67

1-(2-{4-t-Butyl-3-[2-(9H-xanthen-9-yl)acetamido] phenyl]ethyl]-2-cycloheptylethyl Sodium Succinate (Compound No. 1-1220)

Following a procedure similar to that described in Example 55, but using 1-(2-{4-t-butyl-3-[2-(9H-xanthen-9-yl)acetamido]phenyl}ethyl)-2-cycloheptylethyl hydrogen succinate (prepared as described in Example 66) as a starting material, in a relative amount similar to that used in that Example, the title compound was obtained as a foam-like substance.

Infrared Absorption Spectrum (CHCl$_3$), $v_{max}$ cm$^{-1}$: 3100–3500 (broad), 1711, 1674, 1652, 1576, 1480, 1457.

Nuclear Magnetic Resonance Spectrum (CDCl$_3$, 270 MHz), δ ppm:

1.0–1.9 (17H, multiplet);
1.09 (9H, singlet);
2.2–2.7 (8H, multiplet);
4.70 (1H, triplet, J=7 Hz);
4.70–5.0 (1H, multiplet);
6.8–7.5 (11H, multiplet).

EXAMPLE 68

N-[2-Ethyl-6-(3-oxo-6-phenyl-1-hexenyl)phenyl]-2-(9H-xanthen-9-yl)acetamide (Compound No. 1-1447)

49 mg (1.13 mmol) of sodium hydride (as a 55% w/w suspension in mineral oil) were washed twice, each time with hexane, and were suspended in 6 ml of dimethylformamide. 2 ml of a dimethylformamide solution containing 289 mg (0.97 mmol) of 5-diethoxyphosphoryl-1-(4-oxopentyl)benzene were added to the suspension, whilst ice-cooling. The reaction mixture was then immediately allowed to return to room temperature, after which it was stirred for 30 minutes. 300 mg (0.808 mmol) of N-(2-ethyl-6-formylphenyl)-2-(9H-xanthen-9-yl)acetamide were then added to the reaction mixture, once again whilst ice-cooling. The mixture was then stirred for 1 hour at the ice-cooling temperature and then for 3 hours at room temperature. At the end of this time, the reaction solution was poured into ice-water and extracted with diethyl ether. The organic extract was washed with water. The solvent was removed by distillation under reduced pressure, and the resulting residue was recrystallized from a mixture of methylene chloride and diethyl ether, to give 220 mg (yield 53%) of the title compound as crystals, melting at 168°–170° C.

Infrared Absorption Spectrum (KBr), $v_{max}$ cm$^{-1}$: 3287, 1651, 1518, 1480, 1459, 1260.

Nuclear Magnetic Resonance Spectrum (CDCl$_3$, 270 MHz), δ ppm:

0.92 (1/2H, triplet, J=7 Hz);
1.02 (5/2H, triplet, J=7 Hz);
1.98 (2H, quintet, J=7 Hz);
2.15 (1/3H, doublet, J=7 Hz);
2.23 (2H, quartet, J=7 Hz);
2.56 (2H, triplet, J=7 Hz);
2.66 (2H, triplet, J=7 Hz);
2.77 (5/3H, doublet, J=7 Hz);
4.70 (1H, triplet, J=7 Hz);
6.5–6.7 (2H, multiplet);
6.9–7.5 (16H, multiplet).

EXAMPLE 69

3-[4-t-Butyl-3-[2-(9H-xanthen-9-yl)acetamido]phenyl]-1-cyclohexylpropyl Hydrogen Succinate (Compound No. 1-1100)

Following a procedure similar to that described in Example 56, but using N-[2-t-butyl-5-(3-cyclohexyl-3-hydroxypropyl)phenyl]-2-(9H-xanthen-9-yl)acetamide (prepared as described in Example 42) as a starting material, in a relative amount similar to that used in that Example, the title compound was obtained as a foam-like material.

Infrared Absorption Spectrum (KBr), $v_{max}$ cm$^{-1}$: 2930, 1732, 1713, 1481, 1458, 1254, 761.

EXAMPLE 70

Sodium 3-{4-t-butyl-3-[2-(9H-xanthen-9-yl)acetamido] phenyl}-1-cyclohexylpropyl Succinate (Compound No. 1-1093)

Following a procedure similar to that described in Example 55, but using 3-{4-t-butyl-3-[2-(9H-xanthen-9-yl)acetamido]phenyl}-1-cyclohexylpropyl hydrogen succinate (prepared as described in Example 69) as a starting material, in a relative amount similar to that used in that Example, and using ethylene glycol dimethyl ether as the solvent, the title compound was obtained as a foam-like material.

Infrared Absorption Spectrum (KBr), $v_{max}$ cm$^{-1}$: 2929, 1726, 1657, 1578, 1481, 1457, 1255, 759.

EXAMPLE 71

1-(2-(4-t-Butyl-3-[2-(9H-xanthen-9-yl)acetamido] phenyl}ethyl)-5-cyclohexylpentyl Hydrogen Succinate (Compound No. 1-1136)

Following a procedure similar to that described in Example 56, but using N-[2-t-butyl-5-(7-cyclohexyl-3-hydroxyheptyl)phenyl]-2-(9H-xanthen-9-yl)acetamide (prepared as described in Example 44) as a starting material, in a relative amount similar to that used in that Example, the title compound was obtained as a foam-like material.

Infrared Absorption Spectrum (KBr), $v_{max}$ cm$^{-1}$: 2923, 1733, 1713, 1481, 1458, 1253, 760.

EXAMPLE 72

Sodium 1-(2-{4-t-butyl-3-[2-(9H-xanthen-9-yl)acetamido] phenyl}ethyl)-5-cyclohexylpentyl Succinate (Compound No. 1-1129)

Following a procedure similar to that described in Example 70, but using 1-(2-{4-t-butyl-3-[2-(9H-xanthen-9-yl)acetamido]phenyl}ethyl)-5-cyclohexylpentyl hydrogen succinate (prepared as described in Example 71) as a starting material, in a relative amount similar to that used in that Example, the title compound was obtained as a foam-like material.

Infrared Absorption Spectrum (KBr), $v_{max}$ cm$^{-1}$: 2923, 1726, 1656, 1578, 1524, 1481, 1458, 1415, 1364, 1300, 1255, 759.

EXAMPLE 73

1-{4-t-Butyl-3-[2-(9H-xanthen-9-yl)acetamido] phenyl}-2-cyclohexylethyl Hydrogen Succinate (Compound No. 1-1022)

Following a procedure similar to that described in Example 56, but using N-[2-t-butyl-5-(2-cyclohexyl-1-hydroxyethyl)phenyl]-2-(9H-xanthen-9-yl)acetamide (prepared as described in Example 14) as a starting material, in a relative amount similar to that used in that Example, the title compound was obtained as a foam-like material.

Infrared Absorption Spectrum (KBr) $v_{max}$ cm$^{-1}$: 2924, 1736, 1714, 1481, 1458, 1255, 761.

EXAMPLE 74

Sodium 1-{4-t-butyl-3-[2-(9H-xanthen-9-yl)acetamido] phenyl}-2-cyclohexylethyl Succinate (Compound No. 1-1023)

Following a procedure similar to that described in Example 70, but using 1-{4-t-butyl-3-[2-(9H-xanthen-9-yl)acetamido]phenyl}-2-cyclohexylethyl hydrogen succinate (prepared as described in Example 73) as a starting material, in a relative amount similar to that used in that Example, the title compound was obtained as a foam-like material.

Infrared Absorption Spectrum (KBr) $v_{max}$ cm$^{-1}$: 2923, 1728, 1658, 1578, 1481, 1458, 1256, 758.

EXAMPLE 75

1-{4-t-Butyl-3-[2-(9H-xanthen-9-yl)acetamido] phenyl}-3-cyclohexylpropyl Hydrogen Succinate (Compound No. 1-2865)

Following a procedure similar to that described in Example 56, but using N-[2-t-butyl-5-(3-cyclohexyl-1-hydroxypropyl)phenyl]-2-(9H-xanthen-9-yl)acetamide (prepared as described in Example 99) as a starting material, in a relative amount similar to that used in that Example, the title compound was obtained as a foam-like material.

Infrared Absorption Spectrum (KBr) $v_{max}$ cm$^{-1}$: 2923, 1736, 1714, 1481, 1458, 1255, 759.

EXAMPLE 76

Sodium 1-{4-t-butyl-3-[2-(9H-xanthen-9-yl)acetamido] phenyl}-3-cyclohexylpropyl Succinate (Compound No. 1-1026)

Following a procedure similar to that described in Example 70, but using 1-{4-t-butyl-3-[2-(9H-xanthen-9-yl)acetamido]phenyl}-3-cyclohexylpropyl hydrogen succinate (prepared as described in Example 75) as a starting material, in a relative amount similar to that used in that Example, the title compound was obtained as a foam-like material.

Infrared Absorption Spectrum (KBr) $v_{max}$ cm$^{-1}$: 2923, 1728, 1658, 1578, 1481, 1458, 1255, 758.

EXAMPLE 77

1-{4-t-Butyl-3-[2-(9H-xanthen-9H-yl)acetamido] phenyl}-6-cyclohexylhexyl Hydrogen Succinate (Compound No. 1-1053)

Following a procedure similar to that described in Example 56, but using N-[2-t-butyl-5-(6-cyclohexyl-1-hydroxyhexyl)phenyl]-2-(9H-xanthen-9-yl)acetamide (prepared as described in Example 18) as a starting material, in a relative amount similar to that used in that Example, the title compound was obtained as a foam-like material.

Infrared Absorption Spectrum (KBr) $v_{max}$ cm$^{-1}$: 2923, 2852, 1736, 1713, 1652, 1480, 1458, 1254, 1165, 759.

EXAMPLE 78

Sodium 1-{4-t-butyl-3-[2-(9H-xanthen-9-yl)acetamido] phenyl}-6-cyclohexylhexyl Succinate (Compound No. 1-1046)

Following a procedure similar to that described in Example 70, but using 1-{4-t-butyl-3-[2-(9H-xanthen-9-yl)acetamido]phenyl}-6-cyclohexylhexyl hydrogen succinate (prepared as described in Preparation 77) as a starting material, in a relative amount similar to that used in that Example, the title compound was obtained as a foam-like material.

Infrared Absorption Spectrum (KBr) $v_{max}$ cm$^{-1}$: 2923, 2852, 1728, 1656, 1577, 1480, 1458, 1416, 1255, 757.

EXAMPLE 79

(R)-1-(2-{4-t-Butyl-3-[2-(9H-xanthen-9-yl)acetamido] phenyl}ethyl)-2-cyclohexylethyl Hydrogen Succinate (Compound No. 1-1109)

A solution of 337 mg (0.471 mmol) of (R)-1-(2-{4-t-butyl-3-[2-(9H-xanthen-9-yl)acetamido]phenyl}ethyl)-2-cyclohexylethyl benzyl succinate (prepared as described in Preparation 25) in 10 ml of ethyl acetate was vigorously stirred in a stream of hydrogen in the presence of 173 mg of 10% w/w palladium-on-charcoal. The reaction mixture was then filtered, and the catalyst was washed with ethyl acetate. The filtrate and the washings were combined, and the solvent was removed by distillation under reduced pressure.

The residue was purified by column chromatography through 15 g of silica gel, using a 1:19 by volume mixture of methanol and methylene chloride as the eluent, to give the title compound as a foam-like material.

$[\alpha]_D^{22} = -5.3°$ (c=1.16, CHCl$_3$).

EXAMPLE 80

Sodium
(R)-1-(2-{4-t-butyl-3-[2-(9H-xanthen-9-yl)acetamido]phenyl}ethyl)-2-cyclohexylethyl Succinate (Compound No. 1-1102)

Following a procedure similar to that described in Example 70, but using (R)-1-(2-{4-t-butyl-3-[2-(9H-xanthen-9-yl)acetamido]phenyl}ethyl)-2-cyclohexylethyl hydrogen succinate (prepared as described in Example 79) as a starting material, in a relative amount similar to that used in that Example, the title compound was obtained as a foam-like material.

Infrared Absorption Spectrum (KBr) $v_{max}$ cm$^{-1}$: 1721, 1655, 1576, 1526, 1482, 1459, 1416, 1256, 760.

$[\alpha]_D^{26} = -6.1°$ (c=1.05, methanol).

EXAMPLE 81

(S)-1-(2-{4-t-Butyl-3-[2-(9H-xanthen-9-yl)acetamido]phenyl}ethyl)-2-cyclohexylethyl Hydrogen Succinate (Compound No. 1-1109)

Following a procedure similar to that described in Example 54, but using (S)-N-[2-t-butyl-5-(4-cyclohexyl-3-hydroxybutyl)phenyl]-2-(9H-xanthen-9-yl)acetamide (prepared as described in Example 102) as a starting material, in a relative amount similar to that used in that Example, the title compound was obtained as a foam-like material.

$[\alpha]_D^{23} = +4.9°$ (c=1.14, CHCl$_3$).

EXAMPLE 82

Sodium
(S)-1-(2-{4-t-butyl-3-[2-(9H-xanthen-9-yl)acetamido]phenyl}ethyl)-2-cyclohexylethyl Succinate (Compound No. 1-1102)

Following a procedure similar to that described in Example 70, but using (S)-1-(2-{4-t-butyl-3-[2-(9H-xanthen-9-yl)acetamido]phenyl}ethyl)-2-cyclohexylethyl hydrogen succinate (prepared as described in Example 81) as a starting material, in a relative amount similar to that used in that Example, the title compound was obtained as a foam-like material.

Infrared Absorption Spectrum (KBr) $v_{max}$ cm$^{-1}$: 1721, 1655, 1578, 1524, 1482, 1459, 1416, 1256, 760.

$[\alpha]_D^{26} = +5.4°$ (c=1.10, methanol).

EXAMPLE 83

1-(2-{4-t-Butyl-3-[2-(9H-xanthen-9-yl)acetamido]phenyl}ethyl)-4-cyclohexylbutyl Hydrogen Succinate (Compound No. 1-1127)

Following a procedure similar to that described in Example 56, but using N-[2-t-butyl-5-(6-cyclohexyl-3-hydroxyhexyl)phenyl]-2-(9H-xanthen-9-yl)acetamide (prepared as described in Example 43) as a starting material, in a relative amount similar to that used in that Example, the title compound was obtained as a foam-like material.

Infrared Absorption Spectrum (KBr) $v_{max}$ cm$^{-1}$: 2923, 1733, 1713, 1481, 1458, 1254, 760.

EXAMPLE 84

Sodium 1-(2-{4-t-butyl-3-[2-(9H-xanthen-9-yl)acetamido]phenyl}ethyl)-4-cyclohexylbutyl Succinate (Compound No. 1-1120)

Following a procedure similar to that described in Example 70, but using 1-(2-{4-t-butyl-3-[2-(9H-xanthen-9-yl)acetamido]phenyl}ethyl)-4-cyclohexylbutyl hydrogen succinate (prepared as described in Example 83) as a starting material, in a relative amount similar to that used in that Example, the title compound was obtained as a foam-like material.

Infrared Absorption Spectrum (KBr) $v_{max}$ cm$^{-1}$: 2923, 1727, 1656, 1578, 1481, 1458, 1255, 759.

EXAMPLE 85

3-{4-t-Butyl-3-[2-(9H-xanthen-9-yl)acetamido]phenyl}-1-(cyclohexyloxymethyl)propyl Hydrogen Succinate (Compound No. 1-2441)

Following a procedure similar to that described in Example 56, but using N-[2-t-butyl-5-(4-cyclohexyloxy-3-hydroxybutyl)phenyl]-2-(9H-xanthen-9-yl)acetamide (prepared as described in Example 215) as a starting material, in a relative amount similar to that used in that Example, the title compound was obtained as a foam-like material.

Infrared Absorption Spectrum (KBr) $v_{max}$ cm$^{-1}$: 2933, 1736, 1481, 1458, 1254, 761.

EXAMPLE 86

Sodium 3-{4-t-Butyl-3-[2-(9H-xanthen-9-yl)acetamido]phenyl}-1-[(cyclohexyloxy)methyl]propyl Succinate (Compound No. 1-2657)

Following a procedure similar to that described in Example 70, but using 3-{4-t-butyl-3-[2-(9H-xanthen-9-yl)acetamido]phenyl}-1-(cyclohexyloxymethyl)propyl hydrogen succinate (prepared as described in Example 85) as a starting material, in a relative amount similar to that used in that Example, the title compound was obtained as a foam-like material.

Infrared Absorption Spectrum (KBr) $v_{max}$ cm$^{-1}$: 2932, 1728, 1656, 1578, 1481, 1458, 1256, 760.

EXAMPLE 87

(S)-1-(2-{4-t-Butyl-3-[2-(9H-xanthen-9-yl)acetamido]phenyl}ethyl)-3-cyclohexylpropyl Hydrogen Succinate (Compound No. 1-1118)

Following a procedure similar to that described in Example 56, but using (S)-N-[2-t-butyl-5-(5-cyclohexyl-3-hydroxypentyl)phenyl]-2-(9H-xanthen-9-yl)acetamide (prepared as described in Example 114) as a starting material, in a relative amount similar to that used in that Example, the title compound was obtained as a foam-like material.

Infrared Absorption Spectrum (KBr) $v_{max}$ cm$^{-1}$: 2923, 2851, 1733, 1713, 1652, 1480, 1458, 1414, 1253, 760.

EXAMPLE 88

Sodium (S)-1-(2-{4-t-Butyl-3-[2-(9H-xanthen-9-yl)acetamido]phenyl}ethyl)-3-cyclohexylpropyl Succinate (Compound No. 1-1111)

Following a procedure similar to that described in Example 70, but using (S)-1-(2-{4-t-butyl-3-[2-(9H-xanthen-9-yl)acetamido]phenyl}ethyl)-3-cyclohexylpropyl hydrogen succinate (prepared as described in Example 87) as a starting material, in a relative amount similar to that used in that Example, the title compound was obtained as a foam-like material.

Infrared Absorption Spectrum (KBr) $v_{max}$ cm$^{-1}$: 2923, 2851, 1726, 1656, 1577, 1480, 1458, 1414, 1254, 759.

$[\alpha]_D^{22} = -6.79°$ (c=3.80, CHCl$_3$).

EXAMPLE 89

(R)-1-(2-{4-t-Butyl-3-[2-(9H-xanthen-9-yl)acetamido]phenyl}ethyl)-3-cyclohexylpropyl Hydrogen Succinate (Compound No. 1-1118)

Following a procedure similar to that described in Example 56, but using (R)-N-[2-t-butyl-5-(5-cyclohexyl-3-hydroxypentyl)phenyl]-2-(9H-xanthen-9-yl)acetamide (prepared as described in Example 115) as a starting material, in a relative amount similar to that used in that Example, the title compound was obtained as a foam-like material.

Infrared Absorption Spectrum (KBr) $v_{max}$ cm$^{-1}$: 2923, 2851, 1733, 1713, 1652, 1480, 1458, 1414, 1253, 760.

EXAMPLE 90

Sodium (R)-1-(2-{4-t-Butyl-3-[2-(9H-xanthen-9-yl)acetamido]phenyl}ethyl)-3-cyclohexylpropyl Succinate (Compound No. 1-1111)

Following a procedure similar to that described in Example 70, but using (g)-1-(2-{4-t-butyl-3-[2-(9H-xanthen-9-yl)acetamido]phenyl}ethyl)-3-cyclohexylpropyl hydrogen succinate (prepared as described in Example 89) as a starting material, in a relative amount similar to that used in that Example, the title compound was obtained as a foam-like material.

Infrared Absorption Spectrum (KBr) $v_{max}$ cm$^{-1}$: 2923, 2851, 1726, 1656, 1577, 1480, 1458, 1414, 1254, 759.

$[\alpha]_D^{22} = +6.71°$ (c=3.80, CHCl$_3$).

EXAMPLE 91

1-(2-{3-Isopropyl-2-[2-(9H-xanthen-9-yl)acetamido]phenyl}ethyl)-4-cyclohexylbutyl Hydrogen Succinate (Compound No. 1-2866)

Following a procedure similar to that described in Preparation 25, but using N-[2-isopropyl-6-(6-cyclohexyl-3-hydroxyhexyl)phenyl]-2-(9H-xanthen-9-yl)acetamide (prepared as described in Example 125) as a starting material, in a relative amount similar to that used in that Preparation, a benzyl ester of the title compound was obtained. This was then debenzylated in a similar manner to that described in Example 79, to give the title compound as a foam-like material.

Infrared Absorption Spectrum (KBr) $v_{max}$ cm$^{-1}$: 2924, 2851, 1718, 1655, 1578, 1479, 1458, 1406, 1255.

EXAMPLE 92

Sodium 1-(2-{3-Isopropyl-2-[2-(9H-xanthen-9-yl)acetamido]phenyl}ethyl)-4-cyclohexylbutyl Succinate (Compound No. 1-2867)

Following a procedure similar to that described in Example 70, but using 1-(2-{3-isopropyl-2-[2-(9H-xanthen-9-yl)acetamido]phenyl}ethyl)-4-cyclohexylbutyl hydrogen succinate (prepared as described in Example 91) as a starting material, in a relative amount similar to that used in that Example, the title compound was obtained as a foam-like material.

Infrared Absorption Spectrum (KBr) $v_{max}$ cm$^{-1}$: 2924, 2851, 1732, 1655, 1578, 1479, 1458, 1255.

EXAMPLE 93

2-(2-{4-t-Butyl-3-[2-(9H-xanthen-9-yl)acetamido]phenyl}ethyl)-3-cyclohexylpropyl Hydrogen Succinate (Compound No. 1-2349)

Following a procedure similar to that described in Preparation 25, but using N-[2-t-butyl-5-[4-cyclohexyl-3-(hydroxymethyl)butyl]phenyl]-2-(9H-xanthen-9-yl)acetamide (prepared as described in Example 207) as a starting material, in a relative amount similar to that used in that Preparation, a benzyl ester of the title compound was obtained. This was then debenzylated in a similar manner to that described in Example 79, to give the title compound as a foam-like material.

Infrared Absorption Spectrum (KBr) $v_{max}$ cm$^{-1}$: 2924, 2851, 1732, 1655, 1649, 1639, 1524, 1479, 1458, 1255.

EXAMPLE 94

Sodium 2-(2-{4-t-butyl-3-[2-(9H-xanthen-9-yl)acetamido]phenyl}ethyl)-3-cyclohexylpropyl Succinate (Compound No. 1-2367)

Following a procedure similar to that described in Example 70, but using 2-(2-{4-t-butyl-3-[2-(9H-xanthen-9-yl)acetamido]phenyl}ethyl)-3-cyclohexylpropyl hydrogen succinate (prepared as described in Example 93) as a starting material, in a relative amount similar to that used in that Example, the title compound was obtained as a foam-like material.

Infrared Absorption Spectrum (KBr) $v_{max}$ cm$^{-1}$: 2922, 2851, 1724, 1655, 1578, 1479, 1458, 1414, 1255.

EXAMPLE 95

N-[2-t-Butyl-5-(7-cycloheptyl-5-oxoheptyl)phenyl]-2-(9H-xanthen-9-yl)acetamide (Compound No 1-2868)

Following a procedure similar to that described in Example 21, but using 2-t-butyl-5-(7-cycloheptyl-5-oxoheptyl)aniline (prepared by a procedure similar to that described in Preparation 7) as a starting material, in a relative amount similar to that used in that Example, the title compound was obtained as a foam-like material.

Infrared Absorption Spectrum (KBr) $v_{max}$ cm$^{-1}$: 2922, 2855, 1711, 1657, 1576, 1520, 1479, 1458, 1414, 1363, 1255.

EXAMPLE 96

N-[2-t-Butyl-5-(7-cycloheptyl-5-hydroxyheptyl)
phenyl]-2-(9H-xanthen-9-yl)acetamide (Compound
No. 1-1013)

Following a procedure similar to that described in Example 22, but using N-[2-t-butyl-5-(7-cycloheptyl-5-oxoheptyl)phenyl]-2-(9H-xanthen-9-yl)acetamide (prepared as described in Example 95) as a starting material, in a relative amount similar to that used in that Example, the title compound was obtained as a foam-like material.

Infrared Absorption Spectrum (KBr) $v_{max}$ cm$^{-1}$: 2924, 2855, 1655, 1576, 1524, 1479, 1458, 1414, 1363, 1300, 1255.

EXAMPLE 97

N-[2-t-Butyl-5-(3-cycloheptyl-3-oxopropyl)phenyl]-
2-(9H-xanthen-9-yl)acetamide (Compound No.
1-2869)

Following a procedure similar to that described in Example 21, but using 2-t-butyl-5-(3-cycloheptyl-3-oxopropyl)aniline (prepared by a procedure similar to that described in Preparation 7) as a starting material, in a relative amount similar to that used in that Example, the title compound was obtained as crystals, melting at 155°–156° C. (after recrystallization from a mixture of methylene chloride and hexane).

Infrared Absorption Spectrum (KBr) $v_{max}$ cm$^{-1}$: 3187, 2927, 2857, 1703, 1649, 1520, 1479, 1458, 1255, 759.

EXAMPLE 98

N-[2-t-Butyl-5-(3-cycloheptyl-3-hydroxypropyl)
phenyl]-2-(9H-xanthen-9-yl)acetamide (Compound
No. 1-943)

Following a procedure similar to that described in Example 22, but using N-[2-t-butyl-5-(3-cycloheptyl-3-oxopropyl)phenyl]-2-(9H-xanthen-9-yl)acetamide (prepared as described in Example 97) as a starting material, in a relative amount similar to that used in that Example, the title compound was obtained as a foam-like material.

Infrared Absorption Spectrum (KBr) $v_{max}$ cm$^{-1}$: 3400, 3272, 2922, 2855, 1655, 1577, 1522, 1480, 1458, 1255, 759.

EXAMPLE 99

N-[2-t-Butyl-5-(3-cyclohexyl-1-hydroxypropyl)
phenyl]-2-(9H-xanthen-9-yl)acetamide (Compound
No. 1-203)

Following a procedure similar to that described in Example 14, but using 2-cyclohexylethylmagnesium iodide as a starting material, in a relative amount similar to that used in that Example, the title compound was obtained as a foam-like material.

Infrared Absorption Spectrum (KBr) $v_{max}$ cm$^{-1}$: 3390, 3284, 2923, 1656, 1577, 1520, 1481, 1458, 1256, 758.

EXAMPLE 100

(R)-N-[2-t-Butyl-5-(4-cyclohexyl-3-hydroxybutyl)
phenyl]-2-(9H-xanthen-9-yl)acetamide (Compound
No. 1-25)

Following a procedure similar to that described in Example 40, but using (R)-N-{2-t-butyl-5-[4-cyclohexyl-3-(t-butyldimethylsilyloxy)butyl]phenyl}-2-(9H-xanthen-9-yl)acetamide (prepared as described in Preparation 23) as a starting material, in a relative amount similar to that used in that Example, the title compound was obtained as crystals, melting at 140°–141° C. (after recrystallization from diisopropyl ether).

Infrared Absorption Spectrum (KBr) $v_{max}$ cm$^{-1}$: 3340, 3230, 1655. 1532, 1478, 1459, 1254, 760.

$[\alpha]_D^{23}$=−1.5° (c=1.03, CHCl$_3$).

EXAMPLE 101

(S)-N-[2-t-Butyl-5-(4-cyclohexyl-3-benzoyloxybutyl)
phenyl]-2-(9H-xanthen-9-yl)acetamide
(Compound No. 1-1547)

Following a procedure similar to that described in Example 21, but using (S)-[2-t-butyl-5-(4-cyclohexyl-3-benzoyloxybutyl)aniline (prepared as described in Preparation 24) as a starting material, in a relative amount similar to that used in that Example, the title compound was obtained as a glassy material.

Infrared Absorption Spectrum (film), $v_{max}$ cm$^{-1}$: 3280, 1715, 1655, 1520, 1480, 1457, 1275, 1258, 1115, 909

$[\alpha]_D^{23}$=+8.4° (c=1.18, CHCl$_3$).

EXAMPLE 102

(S)-N-[2-t-Butyl-5-(4-cyclohexyl-3-hydroxybutyl)
phenyl]-2-(9H-xanthen-9-yl)acetamide (Compound
No. 1-25)

13.3 ml of a 0.58M ethanolic solution of sodium ethoxide were added to 1.62 g (2.57 mmol) of (S)-N-[2-t-butyl-5-(4-cyclohexyl-3-benzoyloxybutyl)phenyl]-2-(9H-xanthen-9-yl)acetamide (prepared as described in Example 101), and the resulting mixture was stirred at room temperature for 8 hours, after which it was heated under reflux for 2 hours. At the end of this time, the solvent was removed by distillation under reduced pressure, and the resulting residue was mixed with water and then extracted with ethyl acetate. The extract was washed with water and with a saturated aqueous solution of sodium chloride, in that order. The organic phase was dried over anhydrous magnesium sulfate, and the solvent was removed by distillation under reduced pressure. The residue was purified by column chromatography through 150 g of silica gel, using a 2:8 by volume mixture of acetonitrile and benzene as the eluent. The concentrated eluate was recrystallized from diisopropyl ether, to give 1.14 g (yield 85%) of the title compound, melting at 141°–142° C.

Infrared Absorption Spectrum (KBr) $v_{max}$ cm$^{-1}$: 3350, 3240, 1655, 1532, 1478, 1459, 1254, 760.

$[\alpha]_D^{23}$=+2.0° (c=1.09, CHCl$_3$).

EXAMPLE 103

N-[(9H-Xanthen-9-yl)methyl]-N'-[2-t-butyl-5-(4-cyclohexyl-3-hydroxybutyl)phenyl]urea (Compound No. 1-39)

Following a procedure similar to that described in Example 40, but using N-[(9H-xanthen-9-yl)methyl]-N'-[2-t-butyl-5-[4-cyclohexyl-3-(t-butyldimethylsilyloxy)butyl]phenyl]urea (prepared as described in Preparation 20) as a starting material, in a relative amount similar to that used in that Example, the title compound was obtained as crystals, melting at 156°–157° C. (after recrystallization from a mixture of methylene chloride and hexane).

Infrared Absorption Spectrum (KBr) $v_{max}$ cm$^{-1}$: 3343, 2923, 2851, 1641, 1558, 1481, 1458, 1297, 1256, 1188, 756.

EXAMPLE 104

N-[2-t-Butyl-5-(4-cyclohexyl-3-hydroxybutyl)phenyl]-2,2-dimethyldodecanamide (Compound No. 5-19)

Following a procedure similar to that described in Example 40, but using N-[2-t-butyl-5-[4-cyclohexyl-3-(t-butyldimethylsilyloxy)butyl]phenyl]-2,2-dimethyldodecanamide (prepared as described in Preparation 46) as a starting material, in a relative amount similar to that used in that Example, the title compound was obtained as a foam-like material.

Infrared Absorption Spectrum (KBr) $v_{max}$ cm$^{-1}$: 3395, 3304, 2923, 2853, 1651, 1509, 1479, 1448, 1363, 823.

EXAMPLE 105

N-[2-t-Butyl-5-(5-cyclohexyl-1-hydroxypentyl)phenyl-2-(9H-xanthen-9-yl)acetamide (Compound No 1-251)

Following a procedure similar to that described in Example 14, but using 4-cyclohexylbutylmagnesium bromide as a starting material, in a relative amount similar to that used in that Example, the title compound was obtained as crystals, melting at 121°–122° C. (after recrystallization from a mixture of methylene chloride, diethyl ether and hexane).

Infrared Absorption Spectrum (KBr) $v_{max}$ cm$^{-1}$: 2922, 2851, 1655, 1643, 1578, 1527, 1481, 1458, 1410, 1257.

EXAMPLE 106

N-[2-t-Butyl-5-(4-cyclohexyl-3-hydroxybutyl)phenyl]-6,11-dihydrodibenzene[b.e]oxepine-11-carboxemide (Compound No. 2-19)

Following a procedure similar to that described in Example 40, but using N-[2-t-butyl-5-[4-cyclohexyl-3-(t-butyldimethylsilyloxy)butyl]phenyl]-6,11-dihydrodibenz[b.e]oxepine-11-carboxamide (prepared as described in Preparation 47) as a starting material, in a relative amount similar to that used in that Example, the title compound was obtained as a foam-like material.

Infrared Absorption Spectrum (KBr) $v_{max}$ cm$^{-1}$: 3430, 2922, 1679, 1522, 1488, 1447, 1419, 1244, 1203, 757.

EXAMPLE 107

N-[2-t-Butyl-5-(4-cyclohexyl-3-hydroxybutyl)phenyl]-2-(1-phenylcyclopentyl)acetamide (Compound No. 3-13)

Following a procedure similar to that described in Example 40, but using N-{2-t-butyl-5-[4-cyclohexyl-3-(t-butyldimethylsilyloxy)butyl]phenyl}-2-(1-phenylcyclopentyl)acetamide (prepared as described in Preparation 48) as a starting material, in a relative amount similar to that used in that Example, the title compound was obtained as a foam-like material.

Infrared Absorption Spectrum (KBr) $v_{max}$ cm$^{-1}$: 3407, 3278, 2922, 2872, 2851, 1655, 1519, 1497, 1448, 699.

EXAMPLE 108

N-[2-(1,1-Dimethyl-2-methoxyethyl)-6-(4-cyclohexyl-3-hydroxybutyl)phenyl]-2-(9H-xanthen-9-yl)acetamide (Compound No. 1-2870)

Following a procedure similar to that described in Example 14, but using cyclohexylmethylmagnesium bromide and N-[2-(1,1-dimethyl-2-methoxy)ethyl-6-(3-oxopropyl)phenyl]-2-(9H-xanthen-9-yl)acetamide (prepared as described in Preparation 26) as starting materials, in relative proportions similar to those used in that Example, the title compound was obtained as a foam-like material.

Infrared Absorption Spectrum (film), $v_{max}$ cm$^{-1}$: 3260, 1667, 1509, 1480, 1459, 1254, 1096, 963, 758.

EXAMPLE 109

(S)-1-(2-{4-t-Butyl-3-[2-(9H-xanthen-9-yl)acetamido]phenyl}ethyl)-2-cyclohexylethyl Dihydrogenphosphate (Compound No. 1-2871)

Following a procedure similar to that described in Example 79, but using (S)-1-(2-{4-t-butyl-3-[2-(9H-xanthen-9-yl)acetamido]phenyl}ethyl-2-cyclohexylethyl)dibenzyl phosphate (prepared as described in Preparation 49) as a starting material, in a relative amount similar to that used in that Example, the starting material was debenzylated, to give the title compound as a glassy material.

Infrared Absorption Spectrum (film), $v_{max}$ cm$^{-1}$: 3260, 1659, 1526, 1480, 1459, 1254, 1188, 1096, 988, 758.

EXAMPLE 110

Sodium (S)-1-(2-{4-t-butyl-3-[2-(9H-xanthen-9-yl)acetamido]phenyl}ethyl)-2-cyclohexylethyl Hydrogenphosphate (Compound No. 1-1099)

Following a procedure similar to that described in Example 70, but using (S)-1-(2-{4-t-butyl-3-[2-(9H-xanthen-9-yl)acetamido]phenyl}ethyl)-2-cyclohexylethyl dihydrogenphosphate (prepared as described in Example 109) as a starting material, in a relative amount similar to that used in that Example, the title compound was obtained as a foam-like material.

Infrared Absorption Spectrum (KBr) $v_{max}$ cm$^{-1}$: 3440, 1655, 1524, 1482, 1459, 1420, 1256, 1096, 758.

EXAMPLE 111

(S)-1-(2-{4-t-Butyl-3-[2-(9H-xanthen-9-yl)
acetamido]phenyl}ethyl)-2-cyclohexylethyl
Hydrogen Phthalate (Compound No. 1-2872)

Following a procedure similar to that described in Example 54, but using (S)-N-[2-t-butyl-5-(4-cyclohexyl-3-hydroxybutyl)phenyl]-2-(9H-xanthen-9-yl)acetamide (prepared as described in Example 102) and phthalic anhydride as starting materials, in relative proportions similar to those used in that Example, the title compound was obtained as a foam-like material.

Infrared Absorption Spectrum (film), $v_{max}$ cm$^{-1}$: 1717, 1651, 1576, 1480, 1459, 1404, 1256, 1134, 1077, 909, 760.

EXAMPLE 112

Sodium (S)-1-(2-{4-t-butyl-3-[2-(9H-xanthen-9-yl)
acetamido]phenyl}ethyl)-2-cyclohexylethyl
Phthalate (Compound No. 1-1104)

Following a procedure similar to that described in Example 70, but using (S)-1-(2-{4-t-butyl-3-[2-(9H-xanthen-9-yl)acetamido]phenyl}ethyl)-2-cyclohexylethyl hydrogen phthalate (prepared as described in Example 111) as a starting material, in a relative amount similar to that used in that Example, the title compound was obtained as a foam-like material.

Infrared Absorption Spectrum (film), $v_{max}$ cm$^{-1}$: 3260, 1705, 1653, 1574, 1480, 1459, 1397, 1258, 1079, 909, 758.

EXAMPLE 113

(S)-N-[2-t-Butyl-5-(5-cyclohexyl-3-
benzoyloxypentyl)phenyl]-2-(9H-xanthen-9-yl)
acetamide (Compound No. 1-1857)

Following a procedure similar to that described in Example 21, but using (S)-2-t-butyl-5-(5-cyclohexyl-3-benzoyloxypentyl)aniline as a starting material, in a relative amount similar to that used in that Example, the title compound was obtained as a foam-like material.

Infrared Absorption Spectrum (KBr) $v_{max}$ cm$^{-1}$: 3260, 2923, 2851, 1717, 1653, 1519, 1481, 1457, 1275, 1257, 1115, 759, 712.

$[\alpha]_D^{23}$=+1.89° (c=0.95, CHCl$_3$).

EXAMPLE 114

(S)-N-[2-t-Butyl-5-(5-cyclohexyl-3-hydroxypentyl)
phenyl]-2-(9H-xanthen-9-yl)acetamide (Compound
No. 1-1)

Following a procedure similar to that described in Example 102, but using (S)-N-[2-t-butyl-5-(5-cyclohexyl-3-benzoyloxypentyl)phenyl]-2-(9H-xanthen-9-yl)acetamide (prepared as described in Example 113) as a starting material, in a relative amount similar to that used in that Example, the title compound was obtained as crystals, melting at 136°–137° C. (after recrystallization from a mixture of ethyl acetate and hexane).

Infrared Absorption Spectrum (KBr) $v_{max}$ cm$^{-1}$: 3377, 2921, 2849, 1660, 1516, 1481, 1458, 1423, 1412, 1260, 756.

$[\alpha]_D^{25}$=+0.55° (c=1.09, CHCl$_3$).

EXAMPLE 115

(R)-N-[2-t-Butyl-5-(5-cyclohexyl-3-hydroxypentyl)
phenyl]-2-(9H-xanthen-9-yl)acetamide (Compound
No. 1-1)

Following a procedure similar to that described in Example 40, but using (R)-N-{2-t-butyl-5-[5-cyclohexyl-3-(t-butyldimethylsilyloxy)pentyl]phenyl}-2-(9H-xanthen-9-yl)acetamide (prepared by a procedure similar to that described in Preparation 11) as a starting material, in a relative amount similar to that used in that Example, the title compound was obtained as crystals, melting at 136°–137° C. (after recrystallization from a mixture of ethyl acetate and hexane).

Infrared Absorption Spectrum (KBr) $v_{max}$ cm$^{-1}$: 3377, 2921, 2849, 1660, 1516, 1481, 1458, 1423, 1412, 1260, 756.

$[\alpha]_D^{25}$=−0.75° (c=1.07, CHCl$_3$).

EXAMPLE 116

(S)-1-(2-{4-t-Butyl-3-[2-(9H-xanthen-9-yl)acetamido]
phenyl}ethyl)-2-cyclohexylethyl Hydrogen
Malonate (Compound No. 1-2873)

Following a procedure similar to that described in Example 79, but using (S)-[1-(2-{4-t-butyl-3-[2-(9H-xanthen-9-yl)acetamido]phenyl}ethyl)-2-cyclohexylethyl]benzyl malonate (prepared as described in Preparation 27) as a starting material, in a relative amount similar to that used in that Example, the title compound was obtained as a foam-like material.

Infrared Absorption Spectrum (film), $v_{max}$ cm$^{-1}$: 3260, 1729, 1632, 1480, 1459, 1302, 1254, 1156, 910, 760.

EXAMPLE 117

Sodium
(S)-1-(2-{4-t-Butyl-3-[2-(9H-xanthen-9-yl)acetamido]
phenyl}ethyl)-2-cyclohexylethyl Malonate
(Compound No. 1-1101)

Following a procedure similar to that described in Example 70, but using (S)-1-(2-{4-t-butyl-3-[2-(9H-xanthen-9-yl)acetamido]phenyl}ethyl)-2-cyclohexylethyl hydrogen malonate (prepared as described in Example 116) as a starting material, in a relative amount similar to that used in that Example, the title compound was obtained as a foam-like material.

Infrared Absorption Spectrum (film), $v_{max}$ cm$^{-1}$: 3250, 1717, 1653, 1605, 1480, 1459, 1300, 1256, 1156, 909, 758.

Nuclear Magnetic Resonance Spectrum (CDCl$_3$, 270 MHz), δ ppm:
0.70–0.90 (2H, multiplet);
1.13–1.80 (13H, multiplet);
1.08 (9H, singlet);
2.26–2.67 (4H, multiplet);
3.03 (0.2H, doublet, J=16 Hz);
3.20 (0.2H, doublet, J=16 Hz);
3.23 (1.6H, singlet);
4.70 (1H, triplet, J=7 Hz);
4.80–4.84 (0.2H, multiplet);
4.92–5.00 (0.8H, multiplet);
6.82 (11H, multiplet).

EXAMPLE 118

N-[(1-Phenylcyclopentyl)methyl]-N'-[2-t-butyl-5-(4-cyclohexyl-3-hydroxybutyl)phenyl]urea (Compound No. 3-19)

Following a procedure similar to that described in Example 40, but using N-[2-(1-phenylcyclopentyl)methyl]-N'-[2-t-butyl-5-(3-t-butyldimethylsilyloxy-4-cyclohexylbutyl)phenyl]urea (prepared as described in Preparation 22) as a starting material, in a relative amount similar to that used in that Example, the title compound was obtained as a foam-like material.

Infrared Absorption Spectrum (KBr) $v_{max}$ cm$^{-1}$: 3344, 2922, 2852, 1641, 1558, 1448, 1418, 1364, 1253, 1073, 763, 701.

EXAMPLE 119

Glycine (S)-1-(2-{4-t-butyl-3-[2-(9H-xanthen-9-yl)acetamido]phenyl}ethyl)-2-cyclohexyl Ethyl Ester Hydrochloride (Compound No. 1-1105)

0.21 ml of a 4N solution of hydrogen chloride in dioxane was added to 374 mg (0.547 mmol) of N-t-butoxycarbonylglycine (S)-1-(2-{4-t-butyl-3-[2-(9H-xanthen-9-yl)acetamido]phenyl}ethyl)-2-cyclohexylethyl ester, and the resulting mixture was stirred overnight. The reaction mixture was then diluted with diethyl ether, after which a saturated aqueous solution of sodium hydrogencarbonate was added. The mixture was stirred, and the organic phase was separated and then washed with water; the solvent was then removed by distillation under reduced pressure. The resulting residue was purified by column chromatography through 15 g of silica gel, using a gradient elution method, with mixtures of ethyl acetate and methanol ranging from 100:0 to 100:3 by volume as the eluent, to give 277 mg of the free base corresponding to the title compound as a foam-like material. 3 ml of a 4N solution of hydrogen chloride in dioxane were added to the free base, and the mixture was freed from the solvent by distillation under reduced pressure, to give the title compound as a foam-like material.

Infrared Absorption Spectrum (KBr) $v_{max}$ cm$^{-1}$: 2924, 2853, 1747, 1655, 1576, 1522, 1481, 1458, 1365, 1254.

EXAMPLE 120

N,N-Dimethylglycine (S)-1-(2-{4-t-butyl-3-[2-(9H-xanthen-9-yl)acetamido]phenyl}ethyl)-2-cyclohexylethyl Ester (Compound No. 1-2874)

Following a procedure similar to that described in Preparation 25, but using (S)-N-[2-t-butyl-5-(4-cyclohexyl-3-hydroxybutyl)phenyl]-2-(9H-xanthen-9-yl)acetamide (prepared as described in Example 102) and N,N-dimethylglycine hydrochloride as starting materials, in relative proportions similar to those used in that Preparation, the title compound was obtained as a foam-like material.

Infrared Absorption Spectrum (KBr) $v_{max}$ cm$^{-1}$: 2924, 2853, 1736, 1655, 1578, 1522, 1479, 1458, 1255, 1194.

EXAMPLE 121

N,N-Dimethylglycine (S)-1-(2-{4-t-butyl-3-[2-(9H-xanthen-9-yl)acetamido]phenyl]ethyl]-2-cyclohexylethylethyl Ester Hydrochloride (Compound No. 1-1106)

Following a procedure similar to that described in Example 119, but using N,N-dimethylglycine (S)-1-(2-{4-t-butyl-3-[2-(9H-xanthen-9-yl)acetamido]phenyl}ethyl)-2-cyclohexylethyl ester (prepared as described in Example 120) and a 4N solution of hydrogen chloride in dioxane as starting materials, in relative proportions similar to those used in that Example, the title compound was obtained as a foam-like material.

Infrared Absorption Spectrum (KBr) $v_{max}$ cm$^{-1}$: 2924, 2853, 1743, 1655, 1576, 1522, 1481, 1458, 1414, 1363, 1255.

EXAMPLE 122

(S)-1-(2-{4-t-Butyl-3-[2-(9H-xanthen-9-yl)acetamido]phenyl}ethyl)-2-cyclohexylethyl Hydrogen Glutarate (Compound No. 1-2875)

Following a procedure similar to that described in Example 56, but using (S)-N-[2-t-butyl-5-(4-cyclohexyl-3-hydroxybutyl)phenyl]-2-(9H-xanthen-9-yl)acetamide (prepared as described in Example 102) and glutaric anhydride as starting materials, in relative proportions similar to those used in that Example, the title compound was obtained as a foam-like material.

Infrared Absorption Spectrum (KBr) $v_{max}$ cm$^{-1}$: 2924, 2853, 1730, 1709, 1655, 1649, 1641, 1578, 1524, 1479, 1458, 1254.

EXAMPLE 123

Sodium (S)-1-(2-{4-t-butyl-3-[2-(9H-xanthen-9-yl)acetamido]phenyl}ethyl)-2-cyclohexylethyl Glutarate (Compound No. 1-1103)

Following a procedure similar to that described in Example 70, but using (S)-1-(2-{4-t-butyl-3-[2-(9H-xanthen-9-yl)acetamido]phenyl}ethyl)-2-cyclohexylethyl hydrogen glutarate (prepared as described in Example 122) as a starting material, in a relative amount similar to that used in that Example, the title compound was obtained as a foam-like material.

Infrared Absorption Spectrum (KBr) $v_{max}$ cm$^{-1}$: 2924, 2853, 1720, 1655, 1576, 1526, 1479, 1458, 1410, 1302, 1254.

EXAMPLE 124

N-[2-Isopropyl-6-(6-cyclohexyl-3-oxo-2-hexenyl)phenyl]-2-(9H-xanthen-9-yl)acetamide (Compound No. 1-2876)

A suspension comprising 239 mg (0,620 mmol) of N-(2-isopropyl-6-formylphenyl)-2-(9H-xanthen-9-yl)acetamide (prepared as described in Preparation 29), 347 mg (0.682 mmol) of (5-cyclohexyl-2-oxopentyl)triphenylphosphonium bromide and 66 mg (0.652 mmol) of triethylamine in 10 ml of tetrahydrofuran was heated under reflux for 4 hours. At the end of this time, the reaction mixture was cooled to room temperature and then diluted with diethyl ether; the diluted mixture was then washed with dilute hydrochloric acid. The organic phase was separated and washed with water until it was neutral, after which it was dried and then the solvent was removed by distillation under reduced pressure. The resulting residue was purified by column chromatography through 25 g of silica gel, using a 4:1:1 by volume mixture of hexane, methylene chloride and ethyl acetate as the eluent, to give 223 mg (yield 67%) of the title compound as crystals, melting at 190°–191° C. (after recrystallization from a mixture of methylene chloride and hexane).

Infrared Absorption Spectrum (KBr) $v_{max}$ cm$^{-1}$: 2924, 2851, 1655, 1634, 1578, 1518, 1479, 1458, 1300, 1255.

EXAMPLE 125

N-[2-Isopropyl-6-(6-cyclohexyl-3-hydroxyhexyl) phenyl]-2-(9H-xanthen-9-yl)acetamide (Compound No. 1-1387)

Following a procedure similar to that described in Example 8, but using N-[2-isopropyl-6-(6-cyclohexyl-3-oxo-2-hexenyl)phenyl]-2-(9H-xanthen-9-yl)acetamide (prepared as described in Example 124) as a starting material, in a relative amount similar to that used in that Example, the starting material was catalytically hydrogenated, after which the keto group was reduced to a hydroxyl group in a similar manner to that described in Example 9, to give the title compound as crystals, melting at 142°–143° C. (after recrystallization from a mixture of diethyl ether and hexane).

Infrared Absorption Spectrum (KBr) $v_{max}$ cm$^{-1}$: 2924, 2851, 1655, 1634, 1578, 1518, 1479, 1458, 1300, 1255.

EXAMPLES 126 TO 152

The procedure described in Example 35 or 21 was repeated, except that the corresponding aniline derivative was used as a starting material, in a relative amount similar to that used in that Example, to afford the compounds defined in the following Table 6. The Compound Nos. (Cpd. No.) referred to in this Table are the numbers assigned to the compounds in the foregoing Tables 1 to 5. In this and subsequent Tables, the following abbreviations are used:

| | |
|---|---|
| Ether | diethyl ether |
| IR spectrum | Infrared Absorption Spectrum |
| ML | methylene chloride |
| iPr$_2$O | diisopropyl ether |
| Hxa | hexane |
| AcOEt | ethyl acetate |
| AT | acetone |

Other abbreviations are as defined hitherto in connection with Tables 1 to 5.

Under the column "m.p.", where the product was not a crystalline solid, its physical form is indicated, e.g. "oil".

TABLE 6

| Ex. No. (Cpd. No.) | m | n | R | m.p.(solvents) °C. | IR spectrum (KBr) (cm$^{-1}$) |
|---|---|---|---|---|---|
| 126 (1-2877) | 2 | 3 | Ph | oil | 1713, 1657, 1480, 1458, 1255, 760, 700[1] |
| 127 (1-2878) | 1 | 2 | Ph | 108–109 (ML-iPr$_2$O) | 1713, 1652, 1456, 1252, 758, 699[2] |
| 128 (1-2879) | 2 | 2 | cPn | 108–109 (iPr$_2$O) | 1713, 1658, 1519, 1480, 1458, 1259, 761 |
| 129 (1-2880) | 4 | 2 | cPn | 102–104 (iPr$_2$O) | 1709, 1660, 1519, 1480, 1457, 1260, 760, 754 |
| 130 (1-2881) | 1 | 3 | cPn | 127–128 (hexane) | 1701, 1662, 1518, 1480, 1458, 1259, 757 |
| 131 (1-2882) | 2 | 0 | cPn | 163–165 (iPr$_2$O) | 1711, 1640, 1537, 1480, 1457, 1256, 760 |
| 132 (1-2883) | 1 | 2 | cPn | 159–161 (iPr$_2$O) | 1718, 1635, 1530, 1481, 1458, 1258, 764, 756 |
| 133 (1-2884) | 4 | 0 | cPn | 120–122 (iPr$_2$O) | 1708, 1640, 1533, 1481, 1457, 1260, 760 |
| 134 (1-2885) | 3 | 2 | cPn | 139–141 (iPr$_2$O) | 1706, 1637, 1537, 1481, 1456, 1259, 757 |
| 135 (1-2886) | 3 | 1 | cPn | 184–186 (iPr$_2$O) | 1705, 1637, 1536, 1481, 1458, 1258, 761, 756 |
| 136 (1-2887) | 3 | 3 | cPn | 83–85 (iPr$_2$O) | 1706, 1661, 1519, 1478, 1457, 1256, 761, 753 |
| 137 (1-2888) | 1 | 0 | cPn | 132–135 (iPr$_2$O) | 1659, 1520, 1479, 1458, 1257, 760 |
| 138 (1-2889) | 2 | 3 | cPn | 108–110 (Hxa-iPr$_2$O) | 1715, 1639, 1537, 1481, 1456, 1260, 758 |
| 139 (1-2890) | 4 | 3 | cPn | 99–101 (Hxa-iPr$_2$O) | 1708, 1663, 1517, 1477, 1457, 1255, 763, 751 |
| 140 (1-2891) | 1 | 1 | cPn | 136–138 (iPr$_2$O) | 1716, 1637, 1526, 1480, 1459, 1257, 766, 755 |
| 141 (1-2892) | 2 | 4 | cPn | 99–101 (hexane) | 1713, 1640, 1533, 1481, 1457, 1261, 761, 753 |
| 142 (1-2893) | 4 | 4 | cPn | 83–85 (hexane) | 1713, 1641, 1540, 1481, 1457, 1260, 760 |
| 143 (1-2894) | 3 | 0 | cPn | 179–181 (iPr$_2$O) | 1704, 1638, 1534, 1481, 1458, 1259, 763, 755 |
| 144 (1-2895) | 1 | 5 | cPn | 99–101 (iPr$_2$O) | 1715, 1640, 1534, 1481, 1457, 1262, 761 |
| 145 (1-2896) | 3 | 4 | cPn | 72–74 (iPr$_2$O) | 1713, 1640, 1541, 1529, 1481, 1457, 1261, 1254, 760 |
| 146 (1-2897) | 2 | 5 | cPn | 94–96 (Hxa-iPr$_2$O) | 1711, 1639, 1537, 1481, 1457, 1262, 1254, 761, 753 |
| 147 (1-2898) | 3 | 5 | cPn | 74–76 (iPr$_2$O) | 1713, 1642, 1527, 1480, 1457, 1255, 760 |
| 148 (1-1492) | 2 | 1 | SO$_2$-cHx | 135–137 (iPr$_2$O) | 1720, 1664, 1516, 1481, 1458, 1311, 1255, 1138, 762 |
| 149 (1-2899) | 1 | 4 | cPn | 124–126 (iPr$_2$O) | 1715, 1638, 1532, 1481, 1456, 1258, 763, 755 |
| 150 (1-1493) | 2 | 2 | SO$_2$-cHx | 161–163 (AcOEt) | 1715, 1663, 1518, 1481, 1457, 1309, 1299, 1261, 1135, 1128, 761, 753 |
| 151 (1-2900) | 4 | 5 | cPn | 63–66 (hexane) | 1713, 1640, 1538, 1481, 1457, 1262, 1254, 761, 752 |
| 152 (1-1498) | 2 | 1 | SO$_2$—CH$_2$ cHx | 120–122 (iPr$_2$O) | 1710, 1668, 1513, 1480, 1458, 1301, 1250, 1138, 761 |

[1]Determined using liquid film
[2]Determined by the Nujol (trade mark) method

EXAMPLES 153 to 158

The procedure described in Example 14 was repeated, except that N-(2-t-butyl-5-formylphenyl)-2-(9H-xanthen-9-yl)acetamide was used as a starting material, in a relative amount similar to that used in that Example, to give the compounds defined in the following Table 7.

TABLE 7

| Cpd. (Ex.) No. | R³ | R⁴ | m.p.(solvents) °C. | IR spectrum (KBr) cm$^{-1}$ |
|---|---|---|---|---|
| 153 (1-628) | tBu | 5-CH(OH)-cPn | Powder | 1656, 1519, 1480, 1458, 1255, 757 |
| 154 (1-670) | tBu | 5-CH(OH)(CH₂)₃-cPn | 137–138 (iPr₂O) | 1658, 1516, 1480, 1458, 1256, 757 |
| 155 (1-662) | tBu | 5-CH(OH)(CH₂)₂-cPn | 153–154 (iPr₂O) | 1655, 1480, 1458, 1256, 760 |
| 156 (1-677) | tBu | 5-CH(OH)(CH₂)₄-cPn | 111–113 (iPr₂O) | 1653, 1480, 1458, 1256, 759 |
| 157 (1-684) | tBu | 5-CH(OH)(CH₂)₅-cPn | 118–120 (iPr₂O) | 1642, 1480, 1457, 1258, 760 |
| 158 (1-652) | tBu | 5-CH(OH)CH₂-cPn | 160–161 (i-Pr₂O) | 1643, 1480, 1458, 1257, 760 |

EXAMPLES 159 to 161

The procedure described in Example 14 was repeated, except that N-(2-isopropyl-6-formylphenyl)-2-(9H-xanthen-9-yl)acetamide was used as a starting material, in a relative amount similar to that used in that Example, to give the compounds defined in the following Table 8.

TABLE 8

| Cpd. (Ex.) No. | R³ | R⁴ | m.p. (solvents) °C. | IR spectrum (KBr) (cm$^{-1}$) |
|---|---|---|---|---|
| 159 (1-1358) | iPr | 6-CH(OH)CH₂-cHx | 204 (AT-ML-Hxa) | 3419, 3246, 1640, 1525, 1482, 1457, 1301, 1265, 1047, 752 |
| 160 (1-1364) | iPr | 6-CH(OH)—(CH₂)₃-cHx | 145–146 (iPr₂O) | 3251, 1641, 1523, 1481, 1458, 1301, 1257, 801, 757 |
| 161 (1-1370) | iPr | 6-CH(OH)—(CH₂)₅-cHx | 128–130 (Ether-Hxa) | 3229, 1655, 1527, 1480, 1457, 1253, 988, 808, 758 |

EXAMPLES 162 to 188

The procedure described in Example 22 was repeated, except that the compound prepared in the respective one of Examples 126 to 152 was used as a starting material, in a relative amount similar to that used in that Example, to give the compounds defined in the following Table 9 by reduction of a keto group.

TABLE 9

| Ex. No. (Cpd. No.) | m | n | R | m.p.(solvents) °C. | IR spectrum (KBr) (cm$^{-1}$) |
|---|---|---|---|---|---|
| 162 (1-1303) | 2 | 3 | Ph | Powder | 1655, 1513, 1480, 1458, 1254, 760, 699[1] |
| 163 (1-2901) | 1 | 2 | Ph | Foam | 1652, 1479, 1456, 1253, 758, 700[1] |
| 164 (1-771) | 2 | 2 | cPn | 127–129 (iPr₂O) | 1656, 1519, 1480, 1458, 1259, 761 |
| 165 (1-2902) | 4 | 2 | cPn | 108–110 (iPr₂O) | 1658, 1520, 1478, 1457, 1257, 759 |
| 166 (1-707) | 1 | 3 | cPn | 103–105 (hexane) | 1653, 1522, 1480, 1458, 1256, 760 |
| 167 (1-723) | 2 | 0 | cPn | 88–91 (iPr₂O) | 1659, 1519, 1480, 1458, 1256, 757 |
| 168 (1-703) | 1 | 2 | cPn | 140–142 (hexane) | 1636, 1533, 1480, 1458, 1258, 757 |
| 169 (1-838) | 4 | 0 | cPn | 137–139 (iPr₂O) | 1655, 1517, 1480, 1458, 1259, 761 |
| 170 (1-825) | 3 | 2 | cPn | Foam | 1655, 1522, 1480, 1458, 1255, 758 |
| 171 (1-819) | 3 | 1 | cPn | 137–140 (iPr₂O) | 1638, 1534, 1480, 1457, 1258, 756 |
| 172 (1-831) | 3 | 3 | cPn | Foam | 1655, 1522, 1480, 1255, 758[1] |
| 173 (1-696) | 1 | 0 | cPn | 137–138[2] (iPr₂O) | 1660, 1519, 1479, 1457, 1259, 760 |
| 173 (1-696) | 1 | 0 | cPn | 175–177[2] (iPr₂O) | 1657, 1481, 1458, 1260, 1250, 754 |
| 174 (1-788) | 2 | 3 | cPn | 104–105 (iPr₂O) | 1656, 1529, 1477, 1458, 1252, 760 |
| 175 (1-841) | 4 | 3 | cPn | 67–69 (iPr₂O) | 1640, 1534, 1481, 1457, 1255, 760 |
| 176 (1-702) | 1 | 1 | cPn | 154–156 (iPr₂O) | 1636, 1481, 1458, 1250, 760 |
| 177 (1-799) | 2 | 4 | cPn | 114–116 (ML-Hxa) | 1653, 1529, 1478, 1458, 1255, 759 |
| 178 (1-2903) | 4 | 4 | cPn | 104–105.5 (hexane) | 1652, 1524, 1480, 1458, 1257, 758 |
| 179 (1-810) | 3 | 0 | cPn | 78–80 (hexane) | 1639, 1534, 1481, 1457, 1255, 760 |
| 180 (1-718) | 1 | 5 | cPn | 101–103 | 1643, 1527, 1481, 1458, 1258, 760 |
| 181 (1-836) | 3 | 4 | cPn | 122–124 (iPr₂O) | 1655, 1526, 1479, 1458, 1259, 1250, 759 |
| 182 (1-804) | 2 | 5 | cPn | 104–106 (hexane) | 1652, 1529, 1479, 1458, 1255, 758 |
| 183 (1-2904) | 3 | 5 | cPn | 81–83 (iPr₂O) | 1640, 1530, 1481, 1457, 1256, 760 |
| 184 (1-1516) | 2 | 1 | SO₂-cHx | 149–151 (iPr₂O) | 1658, 1516, 1479, 1457, 1299, 1257, 1126, 761, 752 |
| 185 (1-713) | 1 | 4 | cPn | 99–101 (iPr₂O) | 1652, 1523, 1480, 1458, 1256, 759 |
| 186 (1-1517) | 2 | 2 | SO₂-cHx | 147–148 (AcOEt) | 1664, 1518, 1479, 1457, 1295, 1256, 1158, 761, 752 |
| 187 (1-2905) | 4 | 5 | cPn | Foam | 1655, 1522, 1480, 1458, 1255, 758 |
| 188 (1-1522) | 2 | 1 | SO₂-cHx | 170–171 (ML-iPr₂O) | 1661, 1522, 1478, 1457, 1290, 1252, 1115, 763, 752 |

[1] determined by the Nujol method
[2] due to polymorphism

EXAMPLE 189

(S)-N-[2-t-Butyl-5-(6-cyclohexyl-3-hydroxyhexyl)-phenyl]-2-(9H-xanthen-9-yl) acetamide (Compound No. 1-49)

Following a procedure similar to that described in Example 40, but using (S)-N-{2-t-butyl-5-[6-cyclohexyl-3-(t-butyldimethylsilyloxy)hexyl]phenyl}-2-(9-H-xanthen-9-yl)acetamide as a starting material, in a relative amount similar to that used in that Example, the title compound was obtained as crystals, melting at 125°–127° C. (after recrystallization from diisopropyl ether).

Infrared Absorption Spectrum (KBr) νmax cm-1: 1658, 1518, 1480, 1458, 1256, 763, 756.

$[\alpha]_D^{25}$=+1.9° (c=1.0, CHCl₃).

EXAMPLE 190

(R)-N-[2-t-Butyl-5-(6-cyclohexyl-3-hydroxyhexyl)-phenyl]-2-(9H-xanthen-9-yl)acetamide (Compound No. 1-49)

190(i) (R)-N-[2-t-Butyl-5-(6-cyclohexyl-3-benzoyloxy-hexyl)phenyl]-2-(9H-xanthen-9-yl)acetamide Following a procedure similar to that described in Preparation 24(ii), but using (S)-N-[2-t-butyl-5-(6-cyclohexyl-3-hydroxyhexyl)phenyl]-2-(9H-xanthen-9-yl)-acetamide (prepared as described in Example 189) as a starting material, in a relative amount similar to that used in that Example, the title compound was obtained as a foam-like material.

190 (ii) (R)-N-[2-t-Butyl-5-(6-cyclohexyl-3-hydroxyhexyl)phenyl]-2-(9H-xanthen-9-yl)acetamide 5 ml of a 1N aqueous solution of sodium hydroxide were added to a solution of 460 mg (0.70 mmol) of (R)-N-[2-t-butyl-5-(6-cyclohexyl-3-benzoyloxyhexyl)-phenyl]-2-(9H-xanthen-9-yl)acetamide [prepared as described in step (i) above] in 40 ml of ethanol, and the resulting mixture was heated under reflux for 2 hours. At the end of this time, the reaction mixture was freed from the solvent by distillation under reduced pressure, and the residue was first diluted with ethyl acetate and then acidified with 2N aqueous hydrochloric acid. The organic phase was separated and then washed with a saturated aqueous solution of sodium hydrogen-carbonate and with a saturated aqueous solution of sodium chloride, in that order. The mixture was dried over anhydrous sodium sulfate, and then the solvent was removed by distillation under reduced pressure. The resulting residue was recrystallized from diisopropyl ether, to give 180 mg (yield 47%) of the title compound as crystals, melting at 128°–129° C.

Infrared Absorption Spectrum (KBr) νmax cm-1: 1658, 1515, 1480, 1458, 1255, 758.

$[\alpha]_D^{25} = -1.2°$ (c=1.0, CHCl$_3$).

EXAMPLE 191

(S)-N-[2-t-Butyl-5-(7-cyclohexyl-3-hydroxyheptyl)-phenyl]-2-(9H-xanthen-9-yl)acetamide (Compound No. 1-73)

A mixture of 1.20 g (1.96 mmol) of (S)-N-{2-t-butyl-5-[7-cyclohexyl-3-(methoxymethoxy)heptyl]phenyl}-2-(9H-xanthen-9-yl)acetamide (prepared as described in Preparation 43) in 12 ml of a 4N solution of hydrogen chloride in dioxane was stirred for 30 minutes and then the solvent was removed by distillation under reduced pressure. The pH of the residue was brought to 7 by adding an aqueous solution of sodium hydrogencarbonate, and the resulting mixture was extracted twice with ethyl acetate. The combined extracts were washed with a saturated aqueous solution of sodium chloride. The washed extracts were dried, and the solvent was removed by distillation under reduced pressure. The resulting residue was purified by column chromatography through silica gel, using a 4:1 by volume mixture of hexane and ethyl acetate as the eluent, to give 0.9 g of the title compound as an oil. This oil was triturated with hexane and the resulting crystallized product was collected, to give 0.83 9 (yield 75%) of the title compound as crystals.

Infrared Absorption Spectrum (KBr) νmax cm-1: 1656, 1524, 1479, 1458, 1255, 759.

$[\alpha]_D^{25} = +0.97°$ (c=1.03, CHCl$_3$).

EXAMPLE 192

(R)-N-[2-t-Butyl-5-(7-cyclohexyl-3-hydroxyheptyl)-phenyl]-2-(9H-xanthen-9-yl)acetamide (Compound No. 1-73)

Following a procedure similar to that described in Example 190(i), but using (S)-N-[2-t-butyl-5-(7-cyclohexyl-3-hydroxyheptyl)phenyl]-2-(9H-xanthen-9-yl)acetamide (prepared as described in Example 191) as a starting material, in a relative amount similar to that used in that Example, an (R)-benzoyl derivative of the starting material was obtained. This was hydrolyzed in a similar manner to that described in Example 190(ii), to give the title compound as crystals, melting at 100°–102° C. (after recrystallization from hexane).

Infrared Absorption Spectrum (KBr) νmax cm-1: 1655, 1523, 1480, 1458, 1255, 759.

$[\alpha]_D^{25} = -1.12°$ (c=1.07, CHCl$_3$).

EXAMPLE 193

N-{2-[3-(2-Ethyl-1-imidazolyl)propyl]oxymethyl-6-methylthiophenyl}-2-(9H-xanthen-9-yl) acetamide (Compound No. 1-2906)

Following a procedure similar to that described in Example 1, but using 2-ethylimidazole as a starting material, in a relative amount similar to that used in that Example, the title compound was obtained as crystals, melting at 159°–160° C. (after recrystallization from a mixture of hexane and methylene chloride).

Infrared Absorption Spectrum (KBr) νmax cm-1: 3266, 1676, 1649, 1600, 1576, 1518, 1493, 1481, 1457, 1433, 1366, 1258.

EXAMPLE 194

N-{2-[3-(1-Imidazolyl)propyl]oxymethyl-6-methyl-sulfonylphenyl}-2-(9H-xanthen-9-yl)acetamide (Compound No. 1-1989) and N-{2-[3-(1-imidazolyl)propyl]oxymethyl-6-methyl-sulfinylphenyl}-2-(9H-xanthen-9-yl)acetamide (Compound No. 1-1990)

224 mg (0.71 mmol) of m-chloroperoxybenzoic acid (55% purity) were added over the course of 3 minutes to a solution of 200 mg (0.40 mmol) of N-{2-[3-(1-imidazolyl)propoxyl]methyl-6-methylthiophenyl}-2-(9H-xanthen-9-yl)acetamide (prepared as described in Example 1) in 15 ml of methylene chloride, and the resulting mixture was stirred for 2.5 hours. At the end of this time, the solvent was removed by distillation under reduced pressure, and the resulting residue was diluted with ethyl acetate. The diluted solution was washed with a saturated aqueous solution of sodium hydrogen-carbonate and with water, in that order. The organic phase was dried and the solvent was removed by distillation under reduced pressure. The residue was purified by column chromatography through 12 g of silica gel, using a gradient elution method, with mixtures of methylene chloride and methanol in ratios ranging from 100:1 to 100:6 by volume as the eluent, to give 114 mg (yield 54%) of a less polar sulfone derivative (Compound No. 1-1989) and 87 mg (yield 42%) of a more polar sulfinyl derivative (Compound No. 1-1990), respectively, both as foam-like materials.

Infrared Absorption Spectrum (KBr) νmax cm$^{-1}$:

(Compound No. 1-1989).

3249, 1679, 1600, 1577, 1507, 1480, 1458, 1309, 1255, 1127, 961, 760;

(Compound No. 1-1990)

3222, 3165, 3108, 1680, 1600, 1576, 1509, 1480, 1457, 1256, 1110, 1096, 1080, 1052, 1034.

EXAMPLE 195

N-{2-[3-(1-Imidazolyl)propyl]oxymethyl-6-isopropyl-phenyl}-2-(9H-xanthen-9-yl) acetamide (Compound No. 1-2907)

Following a procedure similar to that described in Example 1, but using N-[2-isopropyl-6-[(3-hydroxy-propyl)oxymethyl]phenyl]-2-(9-H-xanthen-9-yl)acetamide (prepared as described in Preparation 31) as a starting material, in a relative amount similar to that used in that Example, the title compound was obtained as crystals, melting at 131°–132° C. (after recrystallization from a mixture of methylene chloride, diethyl ether and hexane).

Infrared Absorption Spectrum (KBr) νmax cm-1: 2960, 1670, 1480, 1460, 1250, 1080.

EXAMPLE 196

N-{2-[3-(1-Imidazolyl)propyl]oxymethyl-6-isopropyl-phenyl}-2-(9H-xanthen-9-yl)acetamide hydrochloride (Compound No. 1-1481)

0.39 ml of a 4N solution of hydrogen chloride in dioxane was added to a solution of 192 mg (0.39 mmol) of N-{2-[3-(1-imidazolyl)propyl]oxymethyl-6-isopropyl-phenyl}-2-(9H-xanthen-9-yl)acetamide (prepared as described in Example 195) in 2 ml of methylene chloride, and the resulting mixture was freed from the solvent by distillation under reduced pressure. The resulting residue was dissolved in a small amount of dioxane and, after water had been added, the resulting mixture was lyophilized, to give 206 mg of the title compound as a powder.

Infrared Absorption Spectrum (CHCl$_3$) ν$_{max}$ cm$^{-1}$: 2960, 1670, 1480, 1460, 1250, 1090.

EXAMPLE 197

N-{2-Isopropyl-6-[3-(1-imidazolyl)propyl]phenyl}-2-(9H-xanthen-9-yl)acetamide (Compound No. 1-2028)

Following a procedure similar to that described in Example 1, but using N-[2-isopropyl-6-(3-hydroxypropyl)-phenyl]-2-(9H-xanthen-9-yl)acetamide (prepared as described in Preparation 30) as a starting material, in a relative amount similar to that used in that Example, the title compound was obtained as crystals, melting at 194°–195° C. (after recrystallization from a mixture of diethyl ether, methylene chloride and hexane).

Infrared Absorption Spectrum (KBr) νmax cm-1: 3272, 2963, 1645, 1525, 1480, 1457, 1257, 757.

EXAMPLE 198

N-{2-Isopropyl-6-[3-(1-imidazoyl)propyl]phenyl}-2-(9H-xanthen-9-yl)acetamide hydrochloride Compound No. 1-2027)

Following a procedure similar to that described in Example 196, but using N-{2-isopropyl-6-[3-(1-imidazolyl)propyl]phenyl}-2-(9-H-xanthen-9-yl)acetamide (prepared as described in Example 197) as a starting material, in a relative amount similar to that used in that Example, the title compound was obtained as a foam-like material.

Infrared Absorption Spectrum (CHCl$_3$), ν$_{max}$ cm$^{-1}$: 2960, 1660, 1570, 1480, 1458, 1250.

EXAMPLE 199

N-{2-Isopropyl-6-[2-(1-imidazolyl)ethyl]oxymethyl-phenyl}-2-(9H-xanthen-9-yl)acetamide (Compound No. 1-2908)

Following a procedure similar to that described in Example 1, but using N-[2-isopropyl-6-(2-hydroxyethyl)-oxymethylphenyl]-2-(9H-xanthen-9-yl)acetamide (prepared as described in Preparation 32) as a starting material, in a relative amount similar to that used in that Example, the title compound was obtained as a foam-like material.

Infrared Absorption Spectrum (CHCl$_3$), ν$_{max}$ cm$^{-1}$: 2960, 1675, 1480, 1460, 1250, 1150, 1080.

EXAMPLE 200

N-{2-Isopropyl-6-[2-(1-imidazolyl)ethyl]oxymethyl-phenyl}-2-(9H-xanthen-9-yl)acetamide hydrochloride (Compound No. 1-1484)

Following a procedure similar to that described in Example 196, but using a N-{2-isopropyl-6-[2-(1-imidazolyl)ethyl]oxymethylphenyl}-2-(9H-xanthen-9-yl)-acetamide (prepared as described in Example 199) as a starting material, in a relative amount similar to that used in that Example, the title compound was obtained as a foam-like material.

Infrared Absorption Spectrum (CHCl$_3$), ν$_{max}$cm$^{-1}$: 2960, 1670, 1480, 1458, 1250, 1120, 1090.

EXAMPLE 201

N-[2-Isopropyl-6-(1-imidazolylmethyl)phenyl]-2-(9H-xanthen-9-yl)acetamide (Compound No. 1-2024)

A suspension of 500 mg (1.23 mmol) of N-(2-isopropyl-6-chloromethylphenyl)-2-(9H-xanthen-9-yl)acetamide [prepared as described in Preparation 28(iv)], 847 mg (12.3 mmol) of imidazole and 277 mg (1.9 mmol) of sodium iodide in 10 ml of N,N-dimethylformamide was stirred at 90° C. for 2 hours and then the temperature was lowered to room temperature. The resulting mixture was diluted with ethyl acetate. The diluted mixture was washed several times with water and once with a saturated aqueous solution of sodium chloride. The organic phase was dried over anhydrous sodium sulfate, and then the solvent was removed by distillation under reduced pressure. The resulting residue was triturated with a mixture of diethyl ether and hexane, and the resulting crystallized product was collected to give 471 mg (yield 88%) of the title compound as crystals, melting at 193°–195° C. (after recrystallization from a mixture of methanol, diethyl ether and hexane).

Infrared Absorption Spectrum (KBr) νmax cm-1: 2961, 1671, 1508, 1475, 1458, 1250, 1236, 758.

EXAMPLE 202

N-[2-Isopropyl-6-(1-imidazolylmethyl)phenyl]-2-(9H-xanthen-9-yl)acetamide hydrochloride (Compound No. 1-2023)

Following a procedure similar to that described in Example 196, but using N-[2-isopropyl-6-(1-imidazolylmethyl)phenyl]-2-(9H-xanthen-9-yl)acetamide (prepared as described in Example 201) as a starting material, in a relative amount similar to that used in that Example, the title compound was obtained as a foam-like material.

Infrared Absorption Spectrum (CHCl$_3$) $v_{max}$ cm$^{-1}$: 2960, 1670, 1576, 1510, 1480, 1458, 1250.

EXAMPLE 203

N-[2-Isopropyl-6-(1-benzimidazolylmethyl)phenyl]-2-(9H-xanthen-9-yl)acetamide (Compound No. 1-2001)

Following a procedure similar to that described in Example 201, but using benzimidazole as a starting material, in a relative amount similar to that used in that Example, the title compound was obtained as crystals, melting at 244°–245° C. (after recrystallization from a mixture of ethyl acetate and hexane).

Infrared Absorption Spectrum (KBr) vmax cm-1: 2961, 1677, 1499, 1480, 1458, 1258, 753, 737.

EXAMPLE 204

N-[2-Isopropyl-6-(1-benzimidazolylmethyl)phenyl]-2-(9H-xanthen-9-yl)acetamide hydrochloride (Compound No. 1-2002)

Following a procedure similar to that described in Example 196, but using N-[2-isopropyl-6-(1-benzimidazolylmethyl)phenyl]-2-(9H-xanthen-9-yl)acetamide (prepared as described in Example 203) as a starting material, in a relative amount similar to that used in that Example, the title compound was obtained as a powder.

Infrared Absorption Spectrum (CHCl$_3$), $v_{max}$ cm$^{-1}$: 2960, 1670, 1480, 1458, 1250, 1120, 870.

EXAMPLE 205

N-{2-Methyl-6-[3-(1-imidazolyl)propyl]oxymethyl-phenyl}-2-(9H-xanthen-9-yl)acetamide hydrochloride (Compound No. 1-2909)

Following a procedure similar to that described in Example 35, but using 2-methyl-6-{[3-(1-imidazolyl)-propyl]oxymethyl}aniline (prepared as described in Preparation 45) as a starting material, in a relative amount similar to that used in that Example, acylation was carried out to give an amide derivative of the starting material, which was then converted to the title hydrochloride by conventional means, to give the title compound in the form of crystals, melting at 109°–110° C. (after recrystallization from a mixture of ethanol and diethyl ether).

Infrared Absorption Spectrum (KBr) vmax cm-1: 1652, 1632, 1576, 1520, 1481, 1458, 1258, 1086, 763.

EXAMPLE 206

N-[2-Isopropyl-6-(4-Cyclohexyl-3-hydroxybutyl)phenyl]-2-(9H-xanthen-9-yl)acetamide (Compound No. 1-1385)

Following a procedure similar to that described in Preparation 19, N-[2-isopropyl-6-(3-hydroxypropyl)-phenyl]-2-(9M-xanthen-9-yl)acetamide (prepared as described in Preparation 30) was oxidized, to give N-[2-isopropyl-6-(3-oxopropyl)phenyl]-2-(9-H-xanthen-9-yl) acetamide, which was then reacted with a Grignard reagent in a similar manner to that described in Example 14, to give the title compound as crystals, melting at 148° C. (after recrystallization from a mixture of diethyl ether and hexane).

Infrared Absorption Spectrum (KBr) vmax cm-1: 3262, 2923, 1648, 1523, 1481, 1457, 1259, 757.

EXAMPLE 207

N-{2-t-Butyl-5-[4-cyclohexyl-3-(hydroxymethyl)-butyl]phenyl}-2-(9H-xanthen-9-yl)acetamide (Compound No. 1-1984)

Following a procedure similar to that described in Example 22, N-[2-t-butyl-5-(4-cyclohexyl-3-formylbutyl)-phenyl]-2-(9M-xanthen-9-yl)acetamide (prepared as described in Preparation 33) was reduced, to give the title compound as crystals, melting at 130°–131° C. (after recrystallization from a mixture of diethyl ether and hexane).

Infrared Absorption Spectrum (KBr) vmax cm-1: 2922, 2851, 1736, 1655, 1603, 1578, 1524, 1479, 1458, 1416, 1363, 1255.

EXAMPLE 208

N-[2-t-Butyl-5-(5-cyclohexyl-2-benzylomethyl-1-pentenyl)phenyl]-2-(9H-xanthen-9-yl)acetamide (Compound No. 1-1955)

A suspension of 1.36 g (1.87 mmol) of [4-t-butyl-3-[2-(9H-xanthen-9-yl)acetamido]phenyl]methyltriphenyl-phosphonium bromide (prepared as described in Preparation 34) in 15 ml of tetrahydrofuran was ice-cooled, and 2.10 ml (2.10 mmol) of a 1.0M tetrahydrofuran solution of sodium hexamethyldisilazide were added dropwise thereto over the course of 3 minutes. After 35 minutes, a solution of 511 mg (1.86 mmol) of 1-benzyloxy-5-cyclohexyl-2-pentanone (prepared as described in Preparation 35) in 5 ml of tetrahydrofuran was added to the mixture. The resulting mixture was stirred for 10 minutes whilst ice-cooling, at room temperature for 35 minutes and finally at 50° C. for 4.5 hours. At the end of this time, the temperature of the reaction mixture was lowered to room temperature, and then a saturated aqueous solution of ammonium chloride was added, in order to stop the reaction. The reaction mixture was then diluted with ethyl acetate and the diluted mixture was washed with water and with a saturated aqueous solution of sodium chloride, in that order. The organic phase was dried over anhydrous sodium sulfate, and the solvent was removed by distillation under reduced pressure. The resulting residue was purified by column chromatography through 100 g of silica gel, using a 1:4 by volume mixture of ethyl acetate and hexane as the eluent, to give 781 mg (yield 65%) of the title compound as a foam-like material.

Infrared Absorption Spectrum (film), $v_{max}$ cm$^{-1}$: 3260, 1651, 1518, 1480, 1457, 1364, 1256, 1096, 1071, 754.

EXAMPLE 209

N-{2-t-Butyl-5-[5-cyclohexyl-2-(hydroxymethyl)-pentyl]phenyl}-2-(9H-xanthen-9-yl)acetamide (Compound No. 1-1979)

A solution of 1.54 g (2.30 mmol) of N-[2-t-butyl-5-(5-cyclohexyl-2-benzyloxymethyl-1-pentenyl)phenyl]-2-(9H-xanthen-9-yl)acetamide (prepared as described in Example 208) in 15 ml of ethanol was vigorously stirred in a stream of hydrogen in the presence of 1.54 g of 10% w/w palladium-on-charcoal at room temperature for 4 hours and 20 minutes and then at 40° C. for 2 hours. At the end of this time, the reaction mixture was filtered, and the filtrate was concentrated by distillation under reduced pressure. The concentrate was purified by column chromatography through 75 g of silica gel, using a 2:3 by volume mixture of ethyl acetate and hexane as the eluent. Fractions containing the desired compound together with a small amount of impurities were combined and concentrated by distillation under reduced pressure. The concentrate was again purified by column chromatography under the same conditions as above, to give 1.19 g (yield 90%) of the title compound as a foam-like material.

Infrared Absorption Spectrum (film), $v_{max}$ cm$^{-1}$: 3400, 3270, 1653, 1522, 1480, 1459, 1256, 1032, 909, 758.

EXAMPLE 210

N-[2-t-Butyl-5-(7-cyclohexyl-2-benzyloxymethyl-1-heptenyl)phenyl]-2-(9H-xanthen-9-yl)acetamide (Compound No. 1-1957)

Following a procedure similar to that described in Example 208, but using 1-benzyloxy-7-cyclohexyl-2-heptanone as a starting material, in a relative amount similar to that used in that Example, the title compound was obtained as crystals, melting at 110° C. (after recrystallization from a mixture of ethyl acetate and hexane).

Infrared Absorption Spectrum (KBr) vmax cm-1: 3222, 2925, 2853, 1641, 1536, 1481, 1457, 1258, 964, 759, 753.

EXAMPLE 211

N-{2-t-Butyl-5-[7-cyclohexyl-2-(hydroxymethyl)-heptyl]phenyl}-2-(9H-xanthen-9-yl)acetamide (Compound No. 1-1982)

Following a procedure similar to that described in Example 209, but using N-[2-t-butyl-5-(7-cyclohexyl-2-benzyloxymethyl-1-heptenyl)phenyl]-2-(9-H-xanthen-9-yl)-acetamide (prepared as described in Example 210) as a starting material, in a relative amount similar to that used in that Example, the title compound was obtained as a foam-like material.

Infrared Absorption Spectrum (KBr) vmax cm-1: 3396, 3269, 2923, 2851, 1655, 1523, 1481, 1458, 1256, 758.

EXAMPLE 212

N-[2-t-Butyl-5-(4-cyclohexyl-2-benzyloxymethyl-1-butenyl)phenyl]-2-(9H-xanthen-9-yl)acetamide (Compound No. 1-1954)

Following a procedure similar to that described in Example 208, but using 1-benzyloxy-4-cyclohexyl-2-butanone as a starting material, in a relative amount similar to that used in that Example, the title compound was obtained as an oil.

Infrared Absorption Spectrum (liquid film), $v_{max}$ cm$^{-1}$: 2922, 2851, 1643, 1576, 1514, 1479, 1456, 1410, 1365, 1255.

EXAMPLE 213

N-[2-t-Butyl-5-(4-cyclohexyl-2-(hydroxymethyl) butyl]-phenyl]-2-(9H-xanthen-9-yl)acetamide (Compound No. 1-1977)

Following a procedure similar to that described in Example 209, but using N-[2-t-butyl-5-(4-cyclohexyl-2-benzyloxymethyl-1-butenyl)phenyl]-2-(9-H-xanthen-9-yl)- acetamide (prepared as described in Example 212) as a starting material, in a relative amount similar to that used in that Example, the title compound was obtained as a foam-like material.

Infrared Absorption Spectrum (KBr) vmax cm-1: 2922, 2851, 1655, 1578, 1560, 1524, 1479, 1458, 1419, 1363, 1255.

EXAMPLE 214

N-{2-t-Butyl-5-[4-cyclohexyloxy-2-(hydroxymethyl)-butyl]phenyl}-2-(9H-xanthen-9-yl)acetamide (Compound No. 1-2186)

Following a procedure similar to that described in Example 208, 1-benzyloxy-4-cyclohexyloxy-2-butanone (prepared as described in Preparation 37) was subjected to Wittig reaction. The resulting product was then reacted in a similar manner to that described in Example 209, to give the title compound as a foam-like material.

Infrared Absorption Spectrum (film), $v_{max}$ cm$^{-1}$: 3260, 1653, 1522, 1480, 1459, 1364, 1256, 1096, 1034, 760.

EXAMPLE 215

N-[2-t-Butyl-5-(4-cyclohexyloxy-3-hydroxybutyl) phenyl]-2-(9H-xanthen-9-yl)acetamide (Compound No. 1-2387)

Following a procedure similar to that described in Example 40, but using N-[2-t-butyl-5-(4-cyclohexyloxy-3-t-butyldimethylsilyloxybutyl)phenyl]-2-(9H-xanthen-9-yl)acetamide (prepared by a procedure similar to that described in Preparation 11) as a starting material, in a relative amount similar to that used in that Example, the title compound was obtained as a foam-like material.

Infrared Absorption Spectrum (KBr) vmax cm-1: 3270, 2932, 1655, 1522, 1481, 1458, 1256, 1118, 1096, 760.

EXAMPLE 216

N-[2-t-Butyl-5-(5-cyclohexyloxy-3-benzyloxy-1-pentenyl)phenyl]-2-(9H-xanthen-9-yl)acetamide (Compound No. 1-1945)

Following a procedure similar to that described in Example 208, but using 1-benzyloxy-4-cyclohexyloxy-butanal (prepared as described in Preparation 38) as a starting material, in a relative amount similar to that used in that Example, the title compound was obtained as a foam-like material.

Infrared Absorption Spectrum (film), $v_{max}$ cm$^{-1}$: 1655, 1520, 1480, 1459, 1364, 1256, 1096, 758.

EXAMPLE 217

N-[2-t-Butyl-5-(5-cyclohexyloxy-3-hydroxypentyl)-phenyl]-2-(9H-xanthen-9-yl)acetamide (Compound No. 1-2390)

Following a procedure similar to that described in Example 209, [-[2-t-butyl-5-(5-cyclohexyloxy-3-benzyl-oxy-1-pentenyl)phenyl]-2-(9H-xanthen-9-yl)acetamide (prepared as described in Example 216) was reduced, to give the title compound as a foam-like material.

Infrared Absorption Spectrum (film), $v_{max}$ cm$^{-1}$: 3250, 1655, 1522, 1480, 1459, 1364, 1256, 1190, 1094, 758.

EXAMPLE 218

N-[2-t-Butyl-5-(4-cyclohexylmethyloxy-3-hydroxybutyl)-phenyl]-2-(9H-xanthen-9-yl)acetamide (Compound No. 1-2388) and N-{2-t-butyl-5-[3-cyclohexylmethyloxy-3-(hydroxy-methyl)propyl]phenyl}-2-(9H-xanthen-9-yl) acetamide (Compound No. 1-2189)

(i) 4 μl of boron trifluoride etherate were added to a solution of 73 mg (0,165 mmol) of N-[2-t-butyl-5-[2-(oxiran-2-yl)ethyl]-2-(9H-xanthen-9-yl)acetamide (prepared as described in Preparation 39) and 41 mg (0.359 mmol) of cyclohexylmethanol in 2 ml of methylene chloride, and the resulting mixture was stirred for 4 hours and 40 minutes. At the end of this time, it was concentrated by evaporation under reduced pressure. The colorless oil thus obtained as a residue was dissolved in 2 ml of ethyl acetate. 0.2 ml of pyridine and 0.1 ml of acetic anhydride were added to the solution, and the resulting mixture was allowed to stand for 45 minutes. The reaction mixture was then diluted with ethyl acetate, and the diluted mixture was washed with 2N aqueous hydrochloric acid, with water, with a saturated aqueous solution of sodium hydrogencarbonate and with a saturated aqueous solution of sodium chloride, in that order. The organic phase was dried over anhydrous magnesium sulfate, and the solvent was removed by distillation under reduced pressure. The resulting residue was purified by column chromatography through 10 g of silica gel, using a 1:3 by volume mixture of ethyl acetate and hexane as the eluent, to give 62 mg (yield 63%) of an acetyl derivative mixture comprising Compound No. 1-2388 and Compound No. 1-2189 as a gummy material.

(ii) 15 mg (0.28 mmol) of sodium methoxide were added to a solution of 72 mg (0.12 mmol) of the product mixture obtained as described in step (i) above in 2 ml of methanol, and the resulting mixture was stirred at 50° C. for 70 minutes. At the end of this time, the reaction mixture was concentrated by evaporation under reduced pressure, and the concentrate was diluted with ethyl acetate. The diluted mixture was washed with a saturated aqueous solution of ammonium chloride and with a saturated aqueous solution of sodium chloride, in that order. The organic phase was dried over anhydrous magnesium sulfate, and the solvent was removed by distillation under reduced pressure. The resulting residue was purified by column chromatography through 40 g of silica gel, using a 2:3 by volume mixture of ethyl acetate and hexane as the eluent, to give a mixture comprising a less polar compound which was Compound No. 1-2388 and a more polar compound which was Compound No. 1-2189. The mixture was separated and purified by column chromatography under the same conditions as above, to give 44 mg (yield 66%) of Compound No. 1-2388 and 20 mg (yield 30%) of Compound No. 1-2189, respectively, both as gummy materials.

Infrared Absorption Spectrum (liquid film), $v_{max}$ cm$^{-1}$:

(Compound No. 1-2388)

3390, 3270, 1653, 1522, 1480, 1458, 1256, 1121, 909, 758;

(Compound No. 1-2189)

3400, 3270, 1653, 1522, 1480, 1458, 1256, 1117, 909, 758.

EXAMPLE 219

N-{2-t-Butyl-5-[4-(2-cyclohexylethoxy)-3-hydroxybutyl]-phenyl}-2-(9H-xanthen-9-yl)acetamide (Compound No. 1-2389)

Following a procedure similar to that described in Example 218, but using 2-cyclohexylethanol as a starting material, in a relative amount similar to that used in that Example, the title compound was obtained as a glassy material.

Infrared Absorption Spectrum (film), $v_{max}$ cm$^{-1}$: 3270, 1655, 1522, 1480, 1459, 1256, 1094, 758.

EXAMPLE 220

α-(S)-1-(2-{4-t-Butyl-3-[2-(9H-xanthen-9-yl)-acetamido]phenyl}ethyl)-2-cyclohexylethyl L-aspartate hydrochloride (Compound No. 1-1548)

Following a procedure similar to that described in Preparation 25, but using the dichlorohexylamine salt of α-t-butyl N-t-butoxycarbonyl-L-aspartate and (S)-N-[2-t-butyl-5-(4-cyclohexyl-3-hydroxybutyl)phenyl]-2-(9H-xanthen-9-yl)acetamide (prepared as described in Example 102) as starting materials, in relative proportions similar to those used in that Example, the free base corresponding to the title compound was obtained. 3 ml of a 4N solution of hydrogen chloride in dioxane were added to 292 mg (0.366 mmol) of the free base, and the resulting mixture was allowed to stand at room temperature for 20 hours. At the end of this time, the solvent was removed by distillation under reduced pressure, and 198 mg of the title compound were obtained as a foam-like material.

Infrared Absorption Spectrum (film), $v_{max}$ cm$^{-1}$: 3240, 1746, 1651, 1518, 1482, 1459, 1254, 909, 760.

EXAMPLE 221

L-Lysine α-(S)-1-(2-{4-t-butyl-3-[2-(9H-xanthen-9-yl) aceramido]phenyl}ethyl)-2-cyclohexylethyl ester dihydrochloride (Compound No 1-1549)

Following a procedure similar to that described in Preparation 25, but using the dicyclohexylamine salt of N,N'-di-t-butoxycarbonyl-L-lysine and (S)-N-[2-t-butyl-5-(4-cyclohexyl-3-hydroxybutyl)phenyl]-2-(9-H-xanthen-9-yl)acetamide (prepared as described in Example 102) as starting materials, in relative proportions similar to those used in that Example, an L-lysine ester derivative was obtained. This was deprotected in a similar manner to that described in Example 220, to give the title compound as a foam-like material.

Infrared Absorption Spectrum (film), $v_{max}$ cm$^{-1}$: 3420, 1740, 1642, 1526, 1482, 1457, 1256, 760.

EXAMPLE 222

∪-L-Glutamine α-(S)-1-(2-{4-t-butyl-3-[2-(9H-xanthen-9-yl) acetamido]phenyl}ethyl)-2-cyclohexylethyl ester hydrochloride (Compound No. 1-1550)

Following a procedure similar to that described in Preparation 25, but using N-[2-t-butyl-5-(4-cyclohexyl-3-hydroxybutyl)phenyl]-2-(9H-xanthen-9-yl)acetamide (prepared as described in Example 12) and α-benzyl N-benzyloxycarbonyl-L-glutamate, a glutamate derivative was obtained. 293 mg (0.333 mmol) of this glutate derivative were dissolved in 10 ml of methanol, and then 0.88 ml of a solution prepared by diluting a 4N solution of hydrogen chloride in dioxane with methanol to ten times its original volume. The resulting mixture was vigorously stirred in an atmosphere of hydrogen and in the presence of 60 mg of 10% w/w palladium-on-charcoal for 1 hour. At the end of

EXAMPLE 223

α-1-(2-{4-t-Butyl-3-[2-(9H-xanthen-9-yl)-acetamido]phenyl}ethyl)-2-cyclohexylethyl carboxymethylthioacetate (Compound No. 1-1551)

A solution of 200 mg of N-[2-t-butyl-5-(4-cyclohexyl-3-{9-[(benzyloxycarbonyl)methylthio]acetoxy}butyl)-phenyl]-2-(9H-xanthen-9-yl)acetamide (prepared as described in Preparation 40) in 10 ml of methanol was mixed with 0.44 ml of formic acid, and the resulting mixture was vigorously stirred whilst heating at 50° C. for 3 hours in the presence of 200 mg of palladium black. At the end of this time, the reaction mixture was allowed to cool to room temperature. The reaction mixture was then filtered using a Celite (trade mark) filter aid and the catalyst was washed with methanol. The filtrate and the washings were combined and the solvent was removed by distillation under reduced pressure. The resulting residue was purified by column chromatography through 10 g of silica gel, using a gradient elution method, with mixtures of methylene chloride and methanol ranging from 100:5 to 100:15 by volume as the eluent, to give 121 mg (yield 69%) of the title compound as a foam-like material.

Infrared Absorption Spectrum (KBr) $v_{max}$ cm$^{-1}$: 2923, 1726, 1652, 1602, 1577, 1481, 1458, 1416, 1256, 760.

EXAMPLE 224

Sodium salt of α-1-(2-{4-t-butyl-3-[2-9H-xanthen-9-yl)acetamido]phenyl}ethyl)-2-cyclohexyl-ethyl carboxymethylthioacetate (Compound No. 1-1552)

Following a procedure similar to that described in Example 70, but using α-1-(2-{4-t-butyl-3-[2-(9H-xanthen-9-yl)acetamido]phenyl}ethyl)-2-cyclohexylethyl carboxymethylthioacetate (prepared as described in Example 223) as a starting material, in a relative proportion similar to that used in that Example, the title compound was obtained.

Infrared Absorption Spectrum (KBr) $v_{max}$ cm$^{-1}$: 2923, 1722, 1641, 1602, 1481, 1457, 1393, 1292, 1257, 760.

EXAMPLE 225

α-1-(2-{4-t-Butyl-3-[2-(9H-xanthen-9-yl)-acetamido]phenyl}ethyl)-2-cyclohexylethyl carboxymethylsulfonylacetate (Compound No. 1-1553)

Following a procedure similar to that described in Example 223, but using N-[2-t-butyl-5-(4-cyclohexyl-3-{2-[(benzyloxycarbonyl)methylsulfonyl]acetoxy}butyl)-phenyl]-2-(9H-xanthen-9-yl)acetamide (prepared as described in Preparation 41), the title compound was obtained as a foam-like material.

Infrared Absorption Spectrum (KBr) $v_{max}$ cm$^{-1}$: 2925, 1733, 1633, 1480, 1458, 1398, 1320, 1255, 760.

EXAMPLE 226

Sodium salt of α-1-(2-{4-t-butyl-3-[2-(9H-xanthen-9-yl)acetamido]phenyl}ethyl)-2-cyclohexyl-ethyl carboxymethylsulfonylacetate (Compound No. 1-1554)

Following a procedure similar to that described in Example 70, but using α-1-(2-{4-t-butyl-3-[2-(9H-xanthen-9-yl)acetamido]phenyl}ethyl)-2-cyclohexyl-ethyl carboxymethylsulfonylacetate (prepared as described in Example 225) as a starting material, in a relative proportion similar to that used in that Example, the title compound was obtained as a foam-like material.

Infrared Absorption Spectrum (KBr) $v_{max}$ cm$^{-1}$: 2924, 1732, 1641, 1480, 1458, 1383, 1318, 1256, 760.

EXAMPLE 227

α-1-(2-{4-t-Butyl-3-[2-(9H-xanthen-9-yl)-acetamido]phenyl}ethyl)-2-cyclohexylethyl carboxymethylsulfinylacetate (Compound No. 1-1555)

Following a procedure similar to that described in Example 223, but using N-[2-t-butyl-5-(4-cyclohexyl-3-{2-[(benzyloxycarbonyl)methylsulfinyl]acetoxy}butyl)-phenyl]-2-(9H-xanthen-9-yl)acetamide (prepared as described in Preparation 41) as a starting material, in a relative proportion similar to that used in that Example, the title compound was obtained as a foam-like material.

Infrared Absorption Spectrum (KBr) $v_{max}$ cm$^{-1}$: 2923, 1729, 1605, 1481, 1458, 1414, 1385, 1298, 1256, 1034, 760.

EXAMPLE 228

Sodium salt of α-1-(2-{4-t-butyl-3-[2-(9H-xanthen-9-yl)acetamido]phenyl)ethyl)-2-cyclohexyl-ethyl carboxymethylsulfinylacetate (Compound No. 1-1556)

Following a procedure similar to that described in Example 70, but using α-1-(2-{4-t-butyl-3-[2-(9H-xanthen-9-yl)acetamido]phenyl}ethyl)-2-cyclohexyl-ethyl carboxymethylsulfinylacetate (prepared as described in Example 227), the title compound was obtained as a foam-like material.

Infrared Absorption Spectrum (KBr) $v_{max}$ cm$^{-1}$: 2852, 1727, 1640, 1615, 1481, 1458, 1384, 1295, 1257, 1033, 760.

EXAMPLE 229

α-1-(2-{4-t-Butyl-3-[2-(9H-xanthen-9-yl)-acetamido]phenyl}ethyl)-2-cyclohexylethyl 4-(morpholinomethyl)benzoate (Compound No. 1-1557)

Following a procedure similar to that described in Preparation 25, but using N-[2-t-butyl-5-(4-cyclohexyl-3-hydroxybutyl)phenyl]-2-(9H-xanthen-9-yl)acetamide (prepared as described in Example 12) and 4-morpholinomethylbenzoic acid as starting materials, in relative proportions similar to those used in that Example, the title compound was obtained as crystals, melting at 123°–125° C. (after recrystallisation from diisopropyl ether).

Infrared Absorption Spectrum (KBr) $v_{max}$ cm$^{-1}$: 1713, 1650, 1480, 1457, 1274, 1258, 1116, 1097, 869, 758.

--- this time, the catalyst was filtered off and washed with methanol. The filtrate and the washings were combined and the solvent was removed by distillation under reduced pressure, to give 220 mg of the title compound as a foam-like material.

Infrared Absorption Spectrum (film), $v_{max}$ cm$^{-1}$: 3230, 1732, 1651, 1520, 1480, 1458, 1418, 1256, 758.

EXAMPLE 230

N-[2-t-Butyl-5-(3-carboxymethoxycarbonyloxy-4-cyclohexylbutyl)phenyl]-2-(9H-xanthen-9-yl)acetamide (Compound No. 1-1558)

Following a procedure similar to that described in Example 79, N-{2-t-butyl-5-[3-(benzyloxycarbonyl)-methoxycarbonyloxy-4-cyclohexylbutyl)phenyl]-2-(9H-xanthen-9-yl)acetamide (prepared as described in Preparation 42) was debenzylated, to give the title compound as crystals, melting at 143°–145° C. (after recrystallisation from a mixture of ethyl acetate and hexane).

Infrared Absorption Spectrum (KBr) $v_{max}$ cm$^{-1}$: 2924, 2852, 1745, 1629, 1481, 1458, 1366, 1255, 1118, 1097, 760.

EXAMPLE 231

Sodium salt of N-[2-t-butyl-5-(3-carboxymethoxy-carbonyloxy-4-cyclohexylbutyl)phenyl]-2-(9H-xanthen-9-yl)acetamide (Compound No. 1-1559)

Following a procedure similar to that described in Example 70, but using N-[2-t-butyl-5-(3-carboxy-methoxycarbonyloxy-4-cyclohexylbutyl)phenyl]-2-(9H-xanthen-9-yl)acetamide (prepared as described in Example 230) as a starting material, in a relative proportion similar to that used in that Example, the title compound was obtained as a powder.

Infrared Absorption Spectrum (KBr) $v_{max}$ cm$^{-1}$: 2924, 2852, 1742, 1626, 1577, 1518, 1481, 1458, 1423, 1257, 760.

EXAMPLE 232

N-{2-t-Butyl-5-[3-(4-carboxymethylphenoxy)carbonyl-oxy-4-cyclohexylbutyl)phenyl]-2-(9H-xanthen-9yl)-acetamide (Compound No. 1-1560)

Following a procedure similar to that described in Preparation 42, but using 4-(benzyloxycarbonyl)methyl-phenol and N-[2-t-butyl-5-(4-cyclohexyl-3-hydroxybutyl)-phenyl]-2-(9H-xanthen-9-yl)acetamide (prepared as described in Example 12) as starting materials, in relative proportions similar to those used in that Example, a carbonate derivative was obtained. This was then debenzylated in a similar manner to that described in Example 79, to give the title compound as a foam-like material.

Infrared Absorption Spectrum (KBr) $v_{max}$ cm$^{-1}$: 2924, 2853, 1757, 1710, 1509, 1481, 1458, 1255, 1218, 1193.

EXAMPLE 233

Sodium salt of N-{2-t-butyl-5-[3-(4-carboxymethyl-phenoxy)carbonyloxy-4-cyclohexylbutyl)phenyl]-2-(9H-xanthen-9-yl) acetamide (Compound No. 1-1561)

Following a procedure similar to that described in Example 70, but using N-{2-t-butyl-5-[3-(4-carboxy-methylphenoxy) carbonyloxy-4-cyclohexylbutyl)phenyl]-2-(9H-xanthen-9-yl)acetamide (prepared as described in Example 232) as a starting material, in a relative proportion similar to that used in that Example, the title compound was obtained as a powder.

Infrared Absorption Spectrum (KBr) $v_{max}$ cm$^{-1}$: 2924, 2852, 1756, 1657, 1600, 1577, 1509, 1481, 1458, 1256, 1217, 1198.

EXAMPLE 234

N-{2-t-Butyl-5-[3-(1-carboxyethoxy)carbonyloxy-4-cyclohexylbutyl]phenyl}-2-(9H-xanthen-9-yl)acetamide (Compound No. 1-1562)

Following a procedure similar to that described in Preparation 42, but using benzyl L-lactate and N-[2-t-butyl-5-(4-cyclohexyl-3-hydroxybutyl)phenyl]-2-(9H-xanthen-9-yl)acetamide (prepared as described in Example 12) as starting materials, in relative proportions similar to those used in that Example, a carbonate derivative was obtained. This was then debenzylated in a similar manner to that described in Example 79, to give the title compound as a foam-like material.

Infrared Absorption Spectrum (KBr) $v_{max}$ cm$^{-1}$: 1744, 1480, 1458, 1259, 761.

EXAMPLE 235

Sodium salt of N-{2-t-butyl-5-[3-(1-carboxyethoxy)-carbonyloxy-4-cyclohexylbutyl]phenyl}-2-(9H-xanthen-9-yl)acetamide (Compound No. 1-1563)

Following a procedure similar to that described in Example 70, but using N-{2-t-butyl-5-[3-(1-carboxyethoxy)carbonyloxy-4-cyclohexylbutyl]phenyl}-2-(9H-xanthen-9-yl)acetamide (prepared as described in Example 234) as a starting material, in a relative proportion similar to that used in that Example, the title compound was obtained as a powder.

Infrared Absorption Spectrum (KBr) $v_{max}$ cm$^{-1}$: 3270, 1728, 1614, 1577, 1522, 1481, 1458, 1415, 1366, 1259.

EXAMPLE 236

N-{2-5-Butyl-5-[3-(5-methyl-2-oxo-1,3-dioxolen-4-yl)-methoxycarbonyloxy-4-cyclohexylbutyl]phenyl}-2-(9H-xanthen-9-yl)acetamide (Compound No. 1-1564)

Following a procedure similar to that described in Preparation 42, but using (5-methyl-2-oxo-1,3-dioxolen-4-yl)methyl alcohol and N-[2-t-butyl-5-(4-cyclohexyl-3-hydroxybutyl)phenyl]-2-(9H-xanthen-9-yl)acetamide (prepared as described in Example 12) as starting materials, in relative proportions similar to those used in that Example, the title compound was obtained as a foam-like material.

Infrared Absorption Spectrum (KBr) $v_{max}$ cm$^{-1}$: 1822, 1745, 1657, 1480, 1458, 1257, 1226, 788, 761.

EXAMPLE 237

N-(2-t-Butyl-5-{3-[2-(1-imidazolyl)acetoxy]-4-cyclo-hexylbutyl}phenyl)-2-(9H-xanthen-9-yl)acetamide hydrochloride (Compound No. 1-1565)

237(i) N-(2-t-Butyl-5-{3-[2-(1-imidazolyl)acetoxy]-4-cyclohexylbutyl}phenyl)-2-(9H-xanthen-9-yl)acetamide A suspension comprising 422 mg (0.80 mmol) of N-[2-t-butyl-5-(4-cyclohexyl-3-hydroxybutyl)phenyl]-2-(9H-xanthen-9-yl)acetamide (prepared as described in Example 12), 311 mg (1.51 mmol) of dicyclohexyl-carbodiimide, 142

μl (1.76 mmol) of pyridine, 20 mg (0.16 mmol) of 4-(N,N-dimethylamino)pyridine and 156 mg (0.96 mmol) of 2-(1-imidazolyl)acetic acid hydrochloride in 10 ml of methylene chloride was stirred for 3 days. At the end of this time, insoluble materials were filtered off, and the filtrate was washed with water and with a saturated aqueous solution of sodium chloride, in that order, after which it was dried over anhydrous sodium sulfate. The solvent was then removed by distillation under reduced pressure. The resulting residue was purified by column chromatography through 75 g of silica gel, using a 1: 4 by volume mixture of ethyl acetate and hexane as the eluent, to give 507 mg (a quantitative yield) of the title compound as a colorless foam-like material.

Infrared Absorption Spectrum (KBr) $v_{max}$ cm$^{-1}$: 2926, 2853, 1748, 1655, 1510, 1480, 1458, 1256, 1080, 758, 731.

237(ii) N-(2-t-Butyl-5-{3-[2-(1-imidazolyl)acetoxy]-4-cyclohexylbutyl}phenyl)-2-(9H-xanthen-9-yl)acetamide hydrochloride 200 μl of a 4N dioxane solution of hydrogen chloride were added to a solution of 339 mg (0.54 mmol) of N-(2-t-butyl-5-{3-[2-(1-imidazolyl)acetoxy]-4-cyclohexylbutyl}phenyl)-2-(9H-xanthen-9-yl)acetamide [prepared as described in step (i) above] in 3 ml of diethyl ether, and the crystals which precipitated were collected by filtration and washed with diethyl ether. The crystals were purified by high performance liquid chromatography through ODS (120 A, ɸ 30 mm×250 mm) using a 3:1 by volume mixture of acetonitrile and water as the eluent, to give a gel. This gel was crystallized by trituration with diethyl ether, to give 170 mg (yield 85%) of the title compound as colorless crystals, melting at 125°–133° C.

Infrared Absorption Spectrum (KBr) $v_{max}$ cm$^{-1}$: 2924, 2853, 1746, 1655, 1576, 1522, 1482, 1459, 1258, 1230, 758.

EXAMPLES 238 to 243

The procedure described in Preparation 25 was repeated, except that the corresponding compound prepared as described in Example 213, 209 or 211 was used as a starting material, in a relative amount similar to that used in that Preparation, to obtain the corresponding benzyl ester derivative, which was then debenzylated in a similar manner to that described in Example 79, to afford the compounds of Examples 238, 240 and 242). The compounds of Examples 238, 240 and 242 were then converted to their sodium salts following a procedure similar to that described in Example 70 (Examples 239, 241 and 243). Details are as given in the following Table 10. The abbreviations are as previously explained.

TABLE 10

| Ex.No. (Cpd. No.) | n | R$^3$ | R | m.p.(solvents) °C. | IR spectrum (KBr) (cm$^{-1}$) |
|---|---|---|---|---|---|
| 238 (1-2344) | 2 | tBu | H | Foam | 2924, 2851, 1736, 1718, 1655, 1608, 1524, 1479, 1458, 1419, 1254, 1165 |
| 239 (1-2359) | 2 | tBu | Na | Foam | 2922, 2851, 1726, 1656, 1578, 1524, 1479, 1458, 1416, 1362, 1300, 1255, 1167 |
| 240 (1-2345) | 3 | tBu | H | Foam | 3270, 1734, 1715, 1636, 1480, 1459, 1254, 1167, 760, 733 |
| 241 (1-2363) | 3 | tBu | Na | Foam | 3245, 1723, 1655, 1576, 1482, 1459, 1414, 1256, 1175, 758 |
| 242 (1-2347) | 5 | tBu | H | Foam | 2924, 2852, 1737, 1713, 1651, 1481, 1458, 1254, 1166, 760 |
| 243 (1-2365) | 5 | tBu | Na | Foam | 2923, 2852, 1729, 1657, 1578, 1481, 1458, 1417, 1255, 1189, 1167, 759 |

EXAMPLE 244

N-(2-t-Butyl-5-{3-[2-(carboxymethoxy)acetoxy]-4-cyclohexylbutyl}phenyl)-2-(9H-xanthen-9-yl)acetamide (Compound No. 1-1566)

Following a procedure similar to that described in Preparation 25, but using [-[2-t-butyl-5-(4-cyclohexyl-3-hydroxy-butyl)phenyl]-2-(9H-xanthen-9-yl)acetamide (prepared as described in Example 12) and 2-(benzyl-oxycarbonyl-methoxy)acetic acid as starting materials, in relative proportions similar to those used in that Example, a benzyl ester derivative was obtained. This was then debenzylated in a similar manner to that described in Example 79, to give the title compound as a foam-like material.

Infrared Absorption Spectrum (KBr) $v_{max}$ cm$^{-1}$: 1744, 1652, 1480, 1458, 1253, 1217, 1142, 760.

EXAMPLE 245

Sodium salt of N-(2-t-butyl-5-{3-[2-(carboxymethoxy)-acetoxyl]-4-cyclohexylbutyl}phenyl)-2-(9H-xanthen-9-yl)acetamide (Compound No. 1-1567)

Following a procedure similar to that described in Example 70, but using N-(2-t-butyl-5-{3-[2-(carboxy-methoxy)acetoxy]-4-cyclohexylbutyl}phenyl)-2-(9H-xanthen-9-yl)acetamide (prepared as described in Example 244) as a starting material, in a relative proportion similar to that used in that Preparation, the title compound was obtained as a powder.

Infrared Absorption Spectrum (KBr) $v_{max}$ cm$^{-1}$: 3249, 1741, 1642, 1615, 1577, 1523, 1481, 1458, 1421, 1365, 1338, 1300, 1255, 1137.

EXAMPLE 246

(S)-1-(2-{4-t-Butyl-3-[2-(9H-xanthen-9yl) acetamido]-phenyl}ethyl)-4- cyclohexylbutyl hydrogen succinate (Compound No. 1-1127)

Following a procedure similar to that described in Preparation 25, but using (S)-N-[2-t-butyl-5-(6-cyclo-hexyl-3-hydroxyhexyl)phenyl]-2-(9-H-xanthen-9-yl)acetamide (prepared as described in Example 189) as a starting material, in a relative proportion similar to that used in that Example, a benzyl ester derivative was obtained. This was debenzylated in a similar manner to that described in Example 79, to give the title compound as a foam-like material.

Infrared Absorption Spectrum (KBr) $v_{max}$ cm$^{-1}$: 1732, 1713, 1656, 1480, 1458, 1253, 1167, 760.

EXAMPLE 247

Sodium (S)-1-(2-{4-t-butyl-3-[2-(9H-xanthen-9-yl)-acetamido]phenyl}ethyl)-4-cyclohexylbutyl succinate (Compound No. 1-1120)

Following a procedure similar to that described in Example 70, but using (S)-1-(2-{4-t-butyl-3-[2-(9H-xanthen-9-yl)acetamido]phenyl}ethyl]-4-cyclohexylbutyl hydrogen succinate (prepared as described in Example 246) as a starting material, in a relative proportion similar to that used in that Example, the title compound was obtained as a powder.

Infrared Absorption Spectrum (KBr) $v_{max}$ cm$^{-1}$: 3270, 1726, 1656, 1578, 1524, 1481, 1458, 1415, 1365, 1301, 1256.

EXAMPLE 248

(R)-1-(2-{4-t-Butyl-3-[2-(9H-xanthen-9-yl)acetamido]-phenyl}ethyl)-4-cyclohexylbutyl hydrogen succinate (Compound No. 1-1127)

Following a procedure similar to that described in Example 79, (R)-1-(2-{4-t-butyl-3-[2-(9H-xanthen-9-yl)acetamido]phenyl}ethyl)-2-cyclohexylethyl benzyl succinate (prepared as described in Preparation 25) was debenzylated, to give the title compound as a foam-like material.

Infrared Absorption Spectrum (KBr) $v_{max}$ cm$^{-1}$: 1733, 1713, 1655, 1480, 1458, 1253, 1166, 760.

EXAMPLE 249

Sodium (R)-1-(2-{4-t-butyl-3-[2-(9H-xanthen-9-yl)-acetamido]phenyl}ethyl)-4-cyclohexylbutyl succinate (Compound No. 1-1120)

Following a procedure similar to that described in Example 70, but using (R)-1-(2-{4-t-butyl-3-[2-(9H-xanthen-9-yl)acetamido]phenyl}ethyl]-4-cyclohexylbutyl hydrogen succinate (prepared as described in Example 248) as a starting material, in a relative proportion similar to that used in that Example, the title compound was obtained as a powder.

Infrared Absorption Spectrum (KBr) $v_{max}$ cm$^{-1}$: 3270, 1728, 1656, 1577, 1523, 1481, 1458, 1416, 1365, 1301, 1255.

EXAMPLE 250

(S)-1-(2-{4-t-Butyl-3-[2-(9H-xanthen-9-yl)acetamido]-phenyl}ethyl)-5-cyclohexylpentyl hydrogen succinate (Compound No. 1-1136)

Following a procedure similar to that described in Preparation 25, but using (S)-N-[2-t-butyl-5-(7-cyclo-hexyl-3-hydroxyheptyl)phenyl]-2-(9H-xanthen-9-yl)acetamide (prepared as described in Example 191) as a starting material, in a relative proportion similar to that used in that Example, a benzyl ester derivative was obtained. This was then debenzylated in a similar manner to that described in Example 79, to give the title compound as crystals, melting at 93°–95° C. (after recrystallisation from hexane).

Infrared Absorption Spectrum (KBr) $v_{max}$ cm$^{-1}$: 1732, 1713, 1610, 1480, 1458, 1252, 1166, 760.

EXAMPLE 251

Sodium (S)-1-(2-{4-t-butyl-3-[2-(9H-xanthen-9-yl)-acetamido]phenyl}ethyl)-5-cyclohexylphentyl succinate (Compound No. 1-1129)

Following a procedure similar to that described in Example 70, but using (S)-1-(2-{4-t-butyl-3-[2-(9H-xanthen-9-yl)acetamido]phenyl}ethyl)-5-cyclohexylpentyl hydrogen succinate (prepared as described in Example 250) as a starting material, in a relative proportion similar to that used in that Example, the title compound was obtained as a powder.

Infrared Absorption Spectrum (KBr) $v_{max}$ cm$^{-1}$: 3274, 1726, 1656, 1578, 1523, 1481, 1458, 1416, 1365, 1300, 1256.

EXAMPLE 252

(R)-1-(2-{4-t-Butyl-3-[2-(9H-xanthen-9-yl)acetamido]-phenyl}ethyl)-5-cyclohexylpentyl hydrogen succinate (Compound No. 1-1136)

Following a procedure similar to that described in Preparation 25, but using (R)-N-[2-t-butyl-5-(7-cyclo-hexyl-3-hydroxyheptyl)phenyl]-2-(9H-xanthen-9-yl)acetamide (prepared as described in Example 192) as a starting material, in a relative proportion similar to that used in that Preparation, a benzyl ester derivative was obtained. This was debenzylated in a similar manner to that described in Example 79, to give the title compound as crystals, melting at 95°–97° C. (after recrystallisation from hexane).

Infrared Absorption Spectrum (KBr) $v_{max}$ cm$^{-1}$: 1732, 1712, 1627, 1480, 1457, 1251, 1221, 1165, 752.

EXAMPLE 253

Sodium (R)-1-(2-{4-t-butyl-3-[2-(9H-xanthen-9-yl)-acetamido]phenyl}ethyl)-5-cyclohexylpentyl succinate (Compound No. 1-1129)

Following a procedure similar to that described in Example 70, but using (R)-1-(2-{4-t-butyl-3-[2-(9H-xanthen-9-yl)acetamido]phenyl}ethyl)-5-cyclohexylpentyl hydrogen succinate (prepared as described in Example 252) as a starting material, in a relative proportion similar to that used in that Example, the title compound was obtained as a powder.

Infrared Absorption Spectrum (KBr) $v_{max}$ cm$^{-1}$: 3273, 1727, 1656, 1578, 1523, 1481, 1458, 1416, 1365, 1300, 1255.

EXAMPLE 254

N-{2-t-Butyl-5-[3-(4-carboxymethylbenzoyloxy)-4-cyclohexylbutyl]phenyl}-2-(9H-xanthen-9-yl)acetamide (Compound No. 1-1568)

Following a procedure similar to that described in Example 79, N-(2-t-butyl-5-{3-[(4-benzyloxycarbonyl-methyl)benzoyloxy]-4-cyclohexylbutyl}phenyl)-2-(9H-xanthen-9-yl)acetamide (prepared as described in Preparation 44) was debenzylated, to give the title compound as a foam-like material.

Infrared Absorption Spectrum (KBr) $v_{max}$ cm$^{-1}$: 2924, 2853, 1713, 1639, 1612, 1578, 1522, 1458, 1418, 1365, 1275, 1255, 1180, 1117.

Nuclear Magnetic Resonance Spectrum (CDCl$_3$, 270 MHz), δ ppm:

0.81–2.06 (15H, multiplet);
1.13 (9H, singlet);
2.29–2.45 (4/3H, multiplet);
2.58–2.76 (8/3H, multiplet);
3.72 (2H, singlet);
4.72 (1H, triplet, J=7 Hz);
5.23–5.38 (1H, multiplet);
6.88–7.45 (13H, multiplet);
8.00 (2H, doublet, J=8 Hz).

EXAMPLE 255

Sodium salt of
N-{2-t-Butyl-5-[3-(4-carboxymethyl-benzoyloxy)-4-cyclohexylbutyl]phenyl}-2-(9H-xanthen-9-yl)acetamide (Compound No. 1-1569)

Following a procedure similar to that described in Example 70, but using N-{2-t-butyl-5-[3-(4-carboxy-methylbenzoyloxy)-4-cyclohexylbutyl]phenyl}-2-(9H-xanthen-9-yl)acetamide (prepared as described in Example 254) as a starting material, in a relative proportion similar to that used in that Example, the title compound was obtained as a foam-like material.

Infrared Absorption Spectrum (KBr) ν$_{max}$ cm$^{-1}$: 2923, 2852, 1713, 1657, 1602,. 1577, 1480, 1458, 1387, 1274, 1256, 1117, 1107, 1097.

Nuclear Magnetic Resonance Spectrum (CDCl$_3$, 270 MHz), δ ppm:

0.67–2.68 (19H, multiplet);
1.03 (3H, singlet);
1.08 (6H, singlet);
3.37 (2H, singlet);
4.60 (1H, triplet, J=7 Hz);
5.10–5.26 (1H, multiplet);
6.76–7.33 (13H, multiplet);
7.66 (2/3H, doublet, J=8 Hz);
7.84 (4/3H, doublet, J=8 Hz).

EXAMPLE 256

N-{2-t-Butyl-5-[3-(4-carboxyphenyloxycarbonyloxy)-4-cyclohexylbutyl]phenyl}-2-(9H-xanthen-9-yl)acetamide (Compound No. 1-1570)

Following a procedure similar to that described in Preparation 42, N-[2-t-butyl-5-(4-cyclohexyl-3-hydroxy-butyl)phenyl]-2-(9H-xanthen-9-yl)acetamide (prepared as described in Example 12) was reacted with diphenylmethyl 4-hydroxybenzoate, to obtain a carbonate derivative. 624 mg of the derivative thus obtained were dissolved in ml of methylene chloride, and 1 ml of anisole and 5 ml of trifluoroacetic acid were added to the resulting solution. The mixture thus obtained was then allowed to stand for 1 hour, after which the solvent was removed by distillation under reduced pressure. The resulting residue was crystallized by trituration with a mixture of hexane and diisopropyl ether. The crystals were collected by filtration and then recrystallized from diisopropyl ether, to give 403 mg (yield 80%) of the title compound, melting at 139°–141° C.

Infrared Absorption Spectrum (KBr) ν$_{max}$ cm$^{-1}$: 1759, 1715, 1694, 1641, 1605, 1577, 1508, 1481, 1458, 1422, 1366, 1257, 1215.

EXAMPLE 257

Sodium salt of
N-{2-t-Butyl-5-[3-(4-carboxyphenyl-oxycarbonyloxy)-4-cyclohexylbutyl]phenyl}-2-(9H-xanthen-9-yl)acetamide (Compound No. 1-1571)

Following a procedure similar to that described in Example 70, but using N-{2-t-butyl-5-[3-(4-carboxy-phenyloxycarbonyloxy)-4-cyclohexylbutyl]phenyl}-2-(9H-xanthen-9-yl)acetamide (prepared as described in Example 256) as a starting material, in a relative proportion similar to that used in that Example, the title compound was obtained as a powder.

Infrared Absorption Spectrum (KBr) ν$_{max}$ cm$^{-1}$: 3404, 1758, 1658, 1608, 1566, 1481, 1458, 1397, 1212, 1162, 1096.

EXAMPLE 258

N-[2-t-Butyl-5-(4-cyclohexyl-3-carbamoyloxybutyl)-phenyl]-2-(9H-xanthen-9-yl)acetamide
(Compound No. 1-1572)

64 μl (0.54 mmol) of trichloroacetyl isocyanate, were added to a solution of 272 mg (0.52 mmol) of N-[2-t-butyl-5-(4-cyclohexyl-3-hydroxybutyl)phenyl]-2-(9H-xanthen-9-yl) acetamide (prepared as described in Example 12) in 6 ml of benzene, and the resulting mixture was stirred for 10 minutes. At the end of this time, a methanolic solution of calcium carbonate was then added, whilst stirring. The reaction mixture was then mixed with water, and the organic phase was separated and dried. The solvent was then removed by distillation under reduced pressure. The resulting residue was purified by column chromatography through 50 g of silica gel, using a 15:85 by volume mixture of ethyl acetate and methylene chloride as the eluent, to give 135 mg (yield 46%) of the title compound as a foam-like material.

Infrared Absorption Spectrum (KBr) ν$_{max}$ cm$^{-1}$: 3389, 2924, 1715, 1575, 1480, 1458, 1333, 1256, 760, 733.

EXAMPLE 259

N-[2-t-Butyl-5-(3-hydroxydodecyl)phenyl]-2-(9H-xanthen-9-yl)acetamide (Compound No. 1-2910)

Following a procedure similar to that described in Example 40, but using N-[2-t-butyl-5-(3-(t-butyl-dimethyl-silyloxydodecyl)phenyl]-2-(9H-xanthen-9-yl)-acetamide (prepared by a procedure similar to that described in Preparation 11) as a starting material, in a relative proportion similar to that used in that Example, the title compound was obtained as an amorphous solid.

Infrared Absorption Spectrum (KBr) ν$_{max}$ cm$^{-1}$: 2953, 2926, 2855, 1655, 1578, 1524, 1479, 1458, 1414, 1363, 1300, 1255.

EXAMPLE 260

N-[2-t-Butyl-5-(4-cyclohexyl-3-hydroxybutyl)phenyl]-2,2-dimethylpropanamide (Compound No. 5-118)

Following a procedure similar to that described in Example 40, but using N-[2-t-butyl-5-(3-t-butyldimethylsilyloxy-4-cyclohexyl)phenyl]-2,2-dimethylpropanamide (prepared by a procedure similar to that described in Preparation 11) as a starting material, in a relative proportion similar to that used in that Example, the title compound was obtained as a foam.

Infrared Absorption Spectrum (KBr) $v_{max}$ cm$^{-1}$: 2957, 2922, 2853, 1655, 1508, 1481, 1448, 1416, 1363, 1200, 1165.

EXAMPLE 261

N-(2-t-Butyl,5-{4-cyclohexyl-3-[(4-carboxyphenyl)-carbonyloxy]butyl}phenyl)-2-(9H-xanthen-9-yl)-acetamide (Compound No. 1-1573)

Following a procedure similar to that described in Example 79, but using N-(2-t-butyl-5-{4-cyclohexyl-3-[(4-benzyloxycarbonylphenyl)carbonyloxy]butyl}-phenyl)-2-(9H-xanthen-9-yl)acetamide (prepared by a procedure similar to that described in Preparation 25) as a starting material, in a relative proportion similar to that used in that Example, the title compound was obtained as a foam.

Infrared Absorption Spectrum (KBr) $v_{max}$ cm$^{-1}$: 2923, 1718, 1699, 1650, 1481, 1458, 1410, 1256, 1118, 760.

EXAMPLE 262

Sodium salt of N-(2-t-Butyl-5-{4-cyclohexyl-3-[(4-carboxyphenyl)carbonyloxy]butyl}phenyl)-2-(9H-xanthen-9-yl)acetamide (Compound No. 1-1574)

Following a procedure similar to that described in Example 70, but using N-(2-t-butyl-5-{4-cyclohexyl-3-[(4-carboxyphenyl)carbonyloxy]butyl}phenyl)-2-(9H-xanthen-9-yl)acetamide (prepared as described in Example 261) as a starting material, in a relative proportion similar to that used in that Example, the title compound was obtained as a powder.

Infrared Absorption Spectrum (KBr) $v_{max}$ cm$^{-1}$: 2923, 1715, 1602, 1481, 1458, 1397, 1273, 1259, 1117, 760, 742.

EXAMPLE 263

N-(2-t-Butyl-5-{7-cyclohexyl-3-[2-(carboxymethoxy)-acetoxy]heptyl}phenyl)-2-(9H-xanthen-9-yl)acetamide (Compound No. 1-1932)

Following a procedure similar to that described in Example 79, but using N-(2-t-butyl-5-{7-cyclohexyl-3-2-(benzyloxycarbonylmethoxy)acetoxy]heptyl}phenyl)-2-(9H-xanthen-9-yl)acetamide (prepared by a procedure similar to that described in Preparation 25) as a starting material, in a relative proportion similar to that used in that Example, the title compound was obtained as a powder.

Infrared Absorption Spectrum (KBr) $v_{max}$ cm$^{-1}$: 1727, 1655, 1649, 1578, 1522, 1482, 1459, 1420, 1256, 1138, 758.

EXAMPLE 264

Sodium salt of N-(2-t-Butyl-5-{7-cyclohexyl-3-[2-carboxymethoxy)acetoxy]heptyl}phenyl)-2-(9H-xanthen-9-yl)acetamide (Compound No. 1-1933)

Following a procedure similar to that described in Example 70, but using N-(2-t-butyl-5-{7-cyclohexyl-3-[2-(carboxymethoxy)acetoxy]heptyl}phenyl)-2-(9H-xanthen-9-yl)acetamide (prepared as described in Example 263) as a starting material, in a relative proportion similar to that used in that Example, the title compound was obtained as a powder.

Infrared Absorption Spectrum (KBr) $v_{max}$ cm$^{-1}$: 1740, 1651, 1611, 1518, 1256, 1140, 876, 759.

EXAMPLE 265

N-{2-[3-(1-Imidazolyl)propoxymethyl]-6-methoxy-phenyl}-2-(1 9H- xanthen-9-yl)acetamide (Compound No. 1-2077)

Following a procedure similar to that described in Example 35, but using 2-[3-(1-imidazolyl)propoxymethyl]-6-methoxyaniline (prepared by a procedure similar to that described in Preparation 45) as a starting material, in a relative proportion similar to that used in that Example, the title compound was obtained as crystals, melting at 155°–156° C. (after recrystallisation from ethyl acetate).

Infrared Absorption Spectrum (KBr) $v_{max}$ cm$^{-1}$: 1676, 1553, 1479, 1471, 1462, 1367, 1261, 1246, 1081, 760.

EXAMPLE 266

N-{2-[3-(1-Imidazolyl)propoxymethyl]-6-methoxy-phenyl}-2-(9H-xanthen-9-yl)acetamide hydrogen chloride (Compound No. 1-2076).

Following a procedure similar to that described in Example 2, but using N-{2-[3-(1-imidazolyl)propoxy-methyl]-6-methoxyphenyl}-2-(9H-xanthen-9-yl)acetamide (prepared as described in Example 265) as a starting material, in a relative proportion similar to that used in that Example, the title compound was obtained as a powder.

Infrared Absorption Spectrum (KBr) $v_{max}$ cm$^{-1}$: 3397, 3274, 1652, 1527, 1483, 1458, 1286, 1260, 1080, 761.

EXAMPLE 267

N-(2-t-Butyl-5-{3-cyclohexyl-3-[2-(carboxymethoxy)-acetoxy]propyl}phenyl)-2-(9H-xanthen-9-yl)acetamide (Compound No. 1-1848)

Following a procedure similar to that described in Example 79, but using N-(2-t-butyl-5-{3-cyclohexyl-3-[2-(benzyloxycarbonylmethoxy)acetoxy]propyl}phenyl)-2-(9H-xanthen-9-yl)acetamide (prepared by a procedure similar to that described in Preparation 25) as a starting material, in a relative proportion similar to that used in that Example, the title compound was obtained as crystals, melting at 128°–129° C. (after recrystallisation from diisopropyl ether).

Infrared Absorption Spectrum (KBr) $v_{max}$ cm$^{-1}$: 3292, 1750, 1656, 1481, 1458, 1255, 1215, 1139, 760.

EXAMPLE 268

Sodium salt of
N-(2-t-Butyl-5-{3-cyclohexyl-3-[2-(carboxymethoxy)acetoxy]propyl}phenyl)-2-(9H-xanthen-9-yl)acetamide (Compound No. 1-1849)

Following a procedure similar to that described in Example 70, but using N-(2-t-butyl-5-{3-cyclohexyl-3-[2-(carboxymethoxy)acetoxy]propyl}phenyl]-2-(9H-xanthen-9-yl)acetamide (prepared as described in Example 267) as a starting material, in a relative proportion similar to that used in that Example, the title compound was obtained as a foam.

Infrared Absorption Spectrum (KBr) $v_{max}$ cm$^{-1}$: 3419, 3278, 1741, 1651, 1614, 1481, 1458, 1421, 1256, 1222, 1138, 760.

EXAMPLE 269

N-[2-t-Butyl-5-(1-imidazolylmethyl)phenyl]-2-(9H-xanthen-9-yl)acetamide (Compound No. 1-2922)

Following a procedure similar to that described in Preparation 21(ii), but using N-(2-t-butyl-5-hydroxy-methylphenyl)-2-(9H-xanthen-9-yl)acetamide (prepared as described in Preparation 14) as a starting material, in a relative amount similar to that used in that Preparation, a methanesulfonyl derivative was obtained. This was then converted to the title compound, in the form of crystals melting at 222°–223° C. (after recrystallization from a mixture of methanol, methylene chloride and hexane), following a procedure similar to that described in Example 1(ii).

Nuclear Magnetic Resonance Spectrum (CDCl$_3$, 270 MHz), δ ppm:
- 1.16 (9H, singlet);
- 2.70 (2H, doublet, J=7 Hz);
- 4.69–4.80 (1H, multiplet);
- 5.09 (2H, singlet);
- 6.79–7.57 (15H, multiplet).

EXAMPLE 270

N-[2-t-Butyl-5-(1-imidazolylmethyl)phenyl]-2-(9H-xanthen-9-yl)acetamide hydrochloride (Compound No. 1-2919)

Following a procedure similar to that described in Example 196, but using N-[2-t-butyl-5-(1-imidazolyl-methyl)phenyl]-2-(9H-xanthen-9-yl)acetamide (prepared as described in Example 269) as a starting material, in a relative amount similar to that used in that Example, the title compound was obtained as a powder.

Nuclear Magnetic Resonance Spectrum (CDCl$_3$, 270 MHz), δ ppm:
- 1.16 (9H, singlet);
- 2.75 (2H, doublet, J=7 Hz);
- 4.68–4.73 (1H, multiplet);
- 5.35 (2H, singlet);
- 7.01–7.46 (13H, multiplet);
- 7.62 (1H, broad singlet);
- 9.01 (1H, broad singlet).

EXAMPLE 271

N-{2-t-Butyl-5-[(2-ethyl-1-imidazolyl)methyl]-phenyl}-2-(9H-xanthen-9-yl) acetamide (Compound No. 1-2921)

Following a procedure similar to that described in Example 269, but using 2ethylimidazole in place of the imidazole in a similar relative amount, the title compound was obtained as an amorphous solid.

Nuclear Magnetic Resonance Spectrum (CDCl$_3$, 270 MHz), δ ppm:
- 1.16 (9H, singlet);
- 1.21–1.37 (3H, multiplet);
- 2.52–2.71 (4H, multiplet);
- 4.70–4.80 (1H, multiplet);
- 5.03 (2H, singlet);
- 6.72–7.43 (14H, multiplet).

EXAMPLE 272

N-{2-t-Butyl-5-[(2-ethyl-1-imidazolyl)methyl]-phenyl}-2-(9H-xanthen-9-yl)acetamide hydrochloride (Compound No. 1-2920)

Following a procedure similar to that described in Example 196, but using N-[2-t-butyl-5-(2-ethyl-1-imidazolylmethyl)phenyl]-2-(9H-xanthen-9-yl)acetamide (prepared as described in Example 271) as a starting material, in a relative amount similar to that used in that Example, the title compound was obtained as a powder.

Nuclear Magnetic Resonance Spectrum (CDCl$_3$, 270 MHz), δ ppm:
- 1.15 (9H, singlet);
- 1.48 (3H, triplet, J=7.5 Hz);
- 2.75 (2H, doublet, J=7 Hz);
- 3.07–3.16 (2H, multiplet);
- 4.70 (1H, triplet, J=7 Hz);
- 5.16 (2H, singlet);
- 6.81 (1H, doublet, J=7.5 Hz);
- 6.93–7.42 (12H, multiplet);
- 7.56 (1H, broad singlet).

PREPARATION 1

2-[(3-Hydroxypropoxy)methyl]-6-methylthio-1-nitrobenzene

1(i) 2-Mesyloxymethyl-6-methylthio-1-nitrobenzene 76 mg (0.66 mmol) of mesyl chloride and then 69 mg (0.68 mmol) of triethylamine were added to 5 ml of a methylene chloride solution containing 100 mg (0.50 mmol) of 2-hydroxymethyl-6-methylthio-1-nitro-benzene, in an ice bath. The mixture was stirred at the temperature of the ice bath for 1 hour and 15 minutes. At the end of this time, water was added to the reaction mixture, and the mixture was extracted with ethyl acetate. The organic extract was separated and washed with 2N aqueous hydrochloric acid and then with water. The solvent was then removed by distillation under reduced pressure, to obtain the title compound. This product was used for the next step without purification.

1(ii) 2-[(3-Hydroxypropoxy)methyl]-6-methylthio-1-nitrobenzene 33 mg (0.76 mmol) of sodium hydride (as a 55% w/w suspension in mineral oil) were washed twice with hexane, and then 1 ml of dimethylformamide was added to the suspension. The resulting suspension was cooled in an ice bath, and then 0.8 ml (11 mmol) of 1,3-propane-diol was added. The mixture was then stirred for 30 minutes at this temperature and then for 30 minutes at room temperature. 1 ml of a dimethylformamide solution containing the whole of the 2-mesyloxymethyl-6-methyl-thio-1-nitrobenzene prepared as described in step (i) above was then added to the resulting solution, whilst ice-cooling, and the mixture was stirred for 2 hours at the ice-cooling temperature and then for 1.5 hours at room temperature. At the end of this time, water was added to the reaction solution, and the mixture was extracted with ethyl acetate. The organic extract was washed with water several times, and then the solvent was removed by distillation under reduced pressure. The resulting residue was subjected to column chromatography through 10 g of silica gel using mixtures of methylene chloride and ethyl acetate in ratios ranging from 10:1 to 8:1 by volume as the eluent, to obtain 95 mg (yield 74%) of the title compound as an oily substance.

Infrared Absorption Spectrum (CHCl$_3$, $\nu_{max}$ cm$^{-1}$: 3530, 1590, 1525, 1357.

Nuclear Magnetic Resonance Spectrum (CDCl$_3$, 60 MHz), δ ppm:

1.83 (2H, quintet, J=6 Hz);
2.46 (3H, singlet);
3.61 (2H, triplet, J=6 Hz);
3.73 (2H, triplet, J=6 Hz);
4.57 (2H, singlet);
7.25–7.6 (3H, multiplet).

PREPARATION 2

2-[(3-t-Butyldimethylsilyloxypropoxy)methyl]-2-methylthio-1-nitrobenzene 927 mg (6.15 mmol) of t-butyldimethylsilyl chloride, 622 mg (6.15 mmol) of triethylamine and 60 mg (0.49 mmol) of 4-(N,N-dimethylamino)pyridine were added to 20 ml of a methylene chloride solution containing 1.044 g (4.06 mmol) of 2-[(3-hydroxypropoxy)methyl]-6-methylthio-1-nitrobenzene (prepared as described in Preparation 1). The mixture was then stirred overnight at ambient temperature. At the end of this time, the reaction solution was diluted with methylene chloride, and washed with dilute aqueous hydrochloric acid and then with water. The solvent was then removed by distillation under reduced pressure. The resulting residue was subjected to column chromatography through 40 g of silica gel. Elution with mixtures of methylene chloride and hexane ranging from 1:1.5 to 1:1 by volume afforded 1.26 g (yield 83%) of the title compound as an oily substance.

Infrared Absorption Spectrum (CHCl$_3$), $\nu_{max}$ cm$^{-1}$: 1590, 1527, 1358.

Nuclear Magnetic Resonance Spectrum (CDCl$_3$, 60 MHz), δ ppm:

0.04 (6H, singlet);
0.88 (9H, singlet);
1.78 (2H, quintet, J=6 Hz);
2.46 (3H, singlet);
3.53 (2H, triplet, J=6 Hz);
3.68 (2H, triplet, J=6 Hz);
4.54 (2H, singlet);
7.25–7.5 (3H, multiplet).

PREPARATION 3

N-{2-[(3-t-Butyldimethylsilyloxypropoxy)methyl]-6-methylthiophenyl]-2-(9H, xanthen-9-yl)acetamide 3(i) 2-[(3-t-Butyldimethylsilyloxypropoxy)methyl]-6-methylthioaniline 3.53 g (54 mmol) of zinc and 0.5 ml of acetic acid were added to 20 ml of a methanolic solution containing 1.25 g (3.37 mmol) of 2-[(3-t-butyldimethylsilyloxy-propoxy)methyl]-2-methylthio-1-nitrobenzene (prepared as described in Preparation 2), in an ice bath. The mixture was then stirred for 50 minutes, after which it was diluted with ethyl acetate. The mixture was then filtered using a Celite (trade mark) filter aid. The insoluble material was washed with ethyl acetate. The filtrate and the washings were combined, condensed by evaporation under reduced pressure to about 5 ml, and diluted again with ethyl acetate; a saturated solution of sodium hydrogen carbonate was then added. The desired compound was distributed between the organic solvent and the sodium hydrogen carbonate solution. The organic layer containing a precipitate and the aqueous layer were filtered, again using a Celite filter aid, and the insoluble material was washed with ethyl acetate. The organic layers were combined and washed with water. The solvent was then removed by distillation under reduced pressure, to obtain 1.10 g (yield 96%) of the title compound as an oily substance.

Nuclear Magnetic Resonance Spectrum (CDCl$_3$, 60 MHz), δ ppm:

0.04 (6H, singlet);
0.88 (9H, singlet);
1.89 (2H, quintet, J=6 Hz);
2.31 (3H, singlet);
3.51 (2H, triplet, J=6 Hz);
3.68 (2H, triplet, J=6 Hz);
4.48 (2H, singlet);
4.9 (2H, broad singlet);
6.60 (1H, triplet, J=7.5 Hz);
6.98 (1H, doublet of doublets, J=7.5 & 1.5 Hz);
7.35 (1H, doublet of doublets, J=7.5 & 1.5 Hz).

3(ii) N-{2-[(3-t-Butyldimethylsilyloxypropoxy)-methyl]-6-methylthiophenyl]-2-(9H-xanthen-9-yl)acetamide Following a procedure similar to that described in Example 21, the whole of the 2-[(3-t-butyldimethyl-silyloxypropoxy)methyl]-6-methylthioaniline prepared as described in step (i) above was acylated, to give the title compound as crystals, melting at 185.5°–186° C. (after recrystallization from a mixture of methylene chloride and methanol), in a yield of 77%.

Infrared Absorption Spectrum (KBr), $\nu_{max}$ cm$^{-1}$: 3263, 1648, 1517, 1260, 1097.

Nuclear Magnetic Resonance Spectrum (CDCl$_3$, 60 MHz), δ ppm:

0.01 (6H, singlet);
0.84 (9H, singlet);
1.67 (2H, quintet, J=6 Hz);
2.30 (3H, singlet);
2.85 (2H, doublet, J=7 Hz);
3.28 (2H, triplet, J=6 Hz);

3.63 (2H, triplet, J=6 Hz);
4.09 (2H, singlet);
4.72 (1H, triplet, J=7 Hz);
6.9–7.5 (11H, multiplet).

PREPARATION 4

N-[2-[(3-Hydroxypropoxy)methyl]-6-methylthiophenyl]-2(9H-xanthen-9-yl)acetamide

Following a procedure similar to that described in Example 40, N-{2-[(3-t-butyldimethylsilyloxypropoxy)-methyl]-6-methylthiophenyl]-2-(9H-xanthen-9-yl)acetamide (prepared as described in Preparation 3) was desilylated, to give the title compound as crystals, melting at 207°–208° C. (after recrystallization from acetone), in a quantitative yield.

Infrared Absorption Spectrum (KBr), $v_{max}$ cm$^{-1}$: 3398, 1649, 1514, 1482, 1259.

Nuclear Magnetic Resonance Spectrum (CDCl$_3$, 270 MHz), δ ppm:
 1.71 (2H, quintet, J=5.5 Hz);
 1.86 (1H, triplet, J=5.5 Hz);
 2.37 (3H, singlet);
 2.80 (2H, doublet, J=7 Hz);
 3.32 (2H, triplet, J=5.5 Hz);
 3.69 (2H, quartet, J=5.5 Hz);
 4.09 (2H, singlet);
 4.73 (1H, triplet, J=7 Hz);
 7.0–7.5 (11H, multiplet).

PREPARATION 5

Ethyl 5-cycloheptyl-3-oxovalerate 343 mg (2.12 mmol) of carbonyldiimidazole were added to 4 ml of an acetonitrile solution containing 300 mg (1.76 mmol) of 3-cycloheptylpropionic acid. The mixture was then stirred for 1 hour at 40° C., to prepare an active ester.

Separately, 273 mg (1.06 mmol) of a complex of magnesium bromide with diethyl ether was added to 4 ml of a tetrahydrofuran suspension containing 360 mg (2.12 mmol) of ethyl potassiummalonate, in an ice bath. The mixture was then stirred for 1 hour at the temperature of the ice bath and then for 1 hour at room temperature. At the end of this time, the acetonitrile solution containing the active ester which had been prepared as described above was added dropwise at room temperature over a period of 5 minutes to the resulting suspension which contained the magnesium salt of the malonic acid mono-ester. When the dropwise addition was complete, the mixture was stirred for a further 1 hour at 60° C. The reaction solution was then diluted with diethyl ether, and washed with a saturated aqueous solution of sodium hydrogen carbonate, with dilute aqueous hydrochloric acid, with water and with a saturated aqueous solution of sodium chloride, in that order. The solvent was then removed by distillation under reduced pressure. The resulting residue was subjected to column chromatography through 20 g of silica gel. Elution with methylene chloride alone afforded 367 mg (yield 87%) of the title compound as an oily substance.

Infrared Absorption Spectrum (neat), $v_{max}$ cm$^{-1}$: 1733, 1710, 1305, 1230, 1030.

Nuclear Magnetic Resonance Spectrum (CDCl$_3$, 270 MHz), δ ppm:
 1.06–1.73 (15H, multiplet);
 1.28 (3H, triplet, J=7 Hz);
 2.54 (2H, triplet, J=7.5 Hz);
 3.44 (2H, singlet);
 4.20 (2H, quartet, J=7 Hz).

PREPARATION 6

2-t-Butyl-5-(5-cycloheptyl-3-oxopentyl)-1-nitrobenzene 454 mg (4.06 mmol) of potassium-t-butoxide were added to 10 ml of a tetrahydrofuran solution containing 1.00 g (4.16 mmol) of ethyl 5-cycloheptyl-3-oxovalerate (prepared as described in Preparation 5). The mixture was then stirred for 10 minutes to prepare the corresponding potassium salt. 1.11 g (3.47 mmol) of 2-t-butyl-5-iodomethyl-1-nitrobenzene (prepared as described in Preparation 51) were added to the mixture in an ice bath, and the mixture was stirred for 2 hours at the temperature of the ice bath. The reaction solution was diluted with diethyl ether and washed with water. The solvent was removed by distillation under reduced pressure, and the resulting residue was dissolved in 10 ml of ethanol. 1.73 ml of a 2N aqueous solution of sodium hydroxide were added, and the mixture was heated for 4 hours under reflux. The reaction mixture was then cooled in an ice bath, sufficient concentrated aqueous hydrochloric acid was added to adjust its pH to a value of 5.0, and the mixture was heated for a further 2 hours under reflux. At the end of this time, the reaction solution was diluted with diethyl ether and washed with water. The solvent was then removed by distillation under reduced pressure. The resulting residue was subjected to column chromatography through 70 g of silica gel. Elution with a 2:1 by volume mixture of methylene chloride and hexane afforded 850 mg (yield 68%) of the title compound as an oily substance.

Infrared Absorption Spectrum (neat), $v_{max}$ cm$^{-1}$: 1703, 1525, 1362.

Nuclear Magnetic Resonance Spectrum (CDCl$_3$, 270 MHz), δ ppm:
 1.06–1.23 (2H, multiplet);
 1.25–1.71 (13H, multiplet);
 1.38 (9H, singlet);
 2.39 (2H, triplet, J=7.5 Hz);
 2.73 (2H, triplet, J=7 Hz);
 2.88 (2H, triplet, J=7 Hz);
 7.12 (1H, doublet, J=2 Hz);
 7.26 (1H, doublet of doublets, J=2 & 8 Hz);
 7.44 (1H, doublet, J=8 Hz).

PREPARATION 7

2-t-Butyl-5-(5-cycloheptyl,3-oxopentyl)aniline 3.08 g (47.1 mmol) of zinc powder and then 0.32 ml of acetic acid were added to 16 ml of a methanolic solution containing 847 mg (2.36 mmol) of 2-t-butyl-5-(5-cycloheptyl-3-oxopentyl)-1-nitrobenzene (prepared as described in Preparation 6), in an ice bath. The mixture was then stirred for 1 hour. At the end of this time, a further 0.32 ml of acetic acid was added, and the mixture was stirred for a further 1 hour. The reaction mixture was then filtered using a Celite filter aid. The insoluble material was washed with ethyl acetate. The filtrate and the washings were combined, condensed to about 10 ml by evaporation under reduced pressure, and diluted with ethyl acetate to distribute the desired compound between the organic solvent and water. In order to remove the insoluble material, the solution was filtered again using a Celite filter aid and the insoluble material was washed again with ethyl acetate. The organic layer was combined with the washings and washed with a saturated aqueous solution of sodium hydrogen carbonate and then with water. The solvent was then removed by distillation under reduced pressure, to obtain 789 mg (a quantitative yield) of the title compound as an oily substance.

Infrared Absorption Spectrum (neat), $v_{max}$ cm$^{-1}$: 3490, 3375, 1702, 1618, 1419.

Nuclear Magnetic Resonance Spectrum (CDCl$_3$, 270 MHz), δ ppm:

1.05–1.22 (2H, multiplet);
1.23–1.71 (13H, multiplet);
1.39 (9H, singlet);
2.39 (2H, triplet, J=7.5 Hz);
2.65–2.81 (4H, multiplet);
3.65–3.83 (2H, broad singlet);
6.47 (1H, doublet, J=2 Hz);
6.55 (1H, doublet of doublets, J=2 & 8 Hz);
7.14 (1H, doublet, J=8 Hz).

PREPARATION 8

1-[2-(4-Methylphenyl)sulfonyl-2-methylthioethyl]hexane 990 mg (22.7 mmol) of sodium hydride (as a 55% w/w suspension in mineral oil) were washed twice with hexane, and suspended in 40 ml of dimethylformamide. 4.35 g (20.1 mmol) of methylthiomethyl p-tolyl sulfone were added to this suspension and, after 5 minutes, 3.1 ml (22.2 mmol) of cyclohexylmethyl bromide were added. The mixture was allowed to return to room temperature, after which it was stirred for 5 hours. At the end of this time, a dilute aqueous solution of ammonium chloride was added to stop the reaction. The reaction mixture was then extracted with diethyl ether, and the extract was washed with a saturated aqueous solution of sodium chloride. The solvent was then removed by distillation under reduced pressure. The resulting residue was subjected to column chromatography through 100 g of silica gel. Elution with a 1:3 by volume mixture of ethyl acetate and hexane afforded 5.57 g (yield 89%) of the title compound as crystals, melting at 65°–66° C. (after recrystallization from a mixture of diisopropyl ether and hexane)

Infrared Absorption Spectrum (KBr), $v_{max}$ cm$^{-1}$: 1595, 1445, 1300, 1146, 1084, 961, 816, 760.

Nuclear Magnetic Resonance Spectrum (CDCl$_3$, 270 MHz), δ ppm:

0.74–1.34 (5H, multiplet);
1.46 (1H, doublet of doublets of doublets, J=3 & 12 & 13 Hz);
1.50–1.74 (6H, multiplet);
1.92 (1H, doublet of doublets of doublets, J=3 & 9 & 13 Hz);
2.23 (3H, singlet);
2.46 (3H, singlet);
3.75 (1H, doublet of doublets, J=3 & 12 Hz);
7.35 (2H, doublet, J=8 Hz);
7.82 (2H, doublet, J=8 Hz).

PREPARATION 9

2-t-Butyl-5-(3-cyclohexyl-2-oxopropyl)-1-nitrobenzene

9(i) 2-t-Butyl-5-[3-cyclohexyl-2-(4-methylphenyl)-sulfonyl-2-methylthiopropyl]-1-nitrobenzene 3.45 ml (5.52 mmol) of a 1.6M hexane solution of butyllithium was added dropwise over a period of 5 minutes to 10 ml of a tetrahydrofuran solution containing 1.73 g (5.52 mmol) of 1-[2-(4-methylphenyl)-sulfonyl-2-methylthioethyl]hexane (prepared as described in Preparation 8), maintained at −78° C. After 15 minutes, 12 ml of a dimethylformamide solution containing 1.68 g (5.26 mmol) of 5-iodomethyl-2-t-butyl-1-nitrobenzene (prepared as described in Preparation 51) was added dropwise. The reaction mixture was allowed to return to room temperature, after which it was stirred for 1 hour and 20 minutes. At the end of this time, a dilute aqueous solution of ammonium chloride was added, to stop the reaction. Water and diethyl ether were added, and the product was distributed between the organic solvent and water. The organic layer was separated and washed with a saturated aqueous solution of sodium chloride. The solvent was removed by distillation under reduced pressure, to obtain the title compound. Since this compound was unstable, however, it was used for the next step without purification.

9(ii) 2-t-Butyl-5-(3-cyclohexyl-2-oxopropyl)-1-nitrobenzene

The whole of the 2-t-butyl-5-[3-cyclohexyl-2-(4-methylphenyl)sulfonyl-2-methylthiopropyl]-1-nitrobenzene prepared as described in step (i) above was dissolved in 50 ml of methanol. 5 ml of concentrated aqueous hydrochloric acid were added, and the resulting solution was heated for 2 hours under reflux. At the end of this time, the solvent was removed by distillation under reduced pressure. The resulting residue was dissolved in diethyl ether, and the solution was washed with water, with a saturated aqueous solution of sodium hydrogen carbonate, with water and with a saturated aqueous solution of sodium chloride, in that order. The solvent was then removed by distillation under reduced pressure. The resulting residue was subjected to column chromatography through 150 g of silica gel. Elution with a 1:5 by volume mixture of ethyl acetate and hexane afforded 1.20 g (yield 73%) of the title compound as an oily substance.

Infrared Absorption Spectrum (liquid film), $v_{max}$ cm$^{-1}$: 1717, 1532, 1449, 1370, 814.

Nuclear Magnetic Resonance Spectrum (CDCl$_3$, 270 MHz), δ ppm:

0.83–0.98 (2H, multiplet);
1.04–1.46 (3H, multiplet);
1.39 (9H, singlet);
1.59–1.73 (5H, multiplet);
1.76–1.92 (1H, multiplet);
2.35 (2H, doublet, J=7 Hz);
3.67 (2H, singlet);
7.14 (1H, doublet, J=2 Hz);
7.26 (1H, doublet of doublets, J=2 & 8 Hz);
7.50 (1H, doublet, J=8 Hz).

PREPARATION 10

5-(3-cyclohexyl-2-t-butyldimethylsilyloxypropyl)-2-t-butyl-1-nitrobenzene

10(i) 5-(3-Cyclohexyl-2-hydroxypropyl)-2-t-butyl-1-nitrobenzene

Following a procedure similar to that described in Example 22, but using 1.70 g (5.36 mmol) of 2-t-butyl-5-(3-cyclohexyl-2-oxopropyl)-1-nitrobenzene (prepared as described in Preparation 9), 1.74 g of the title compound was obtained as an oily substance. The product was used for the next step without purification.

Infrared Absorption Spectrum (liquid film), $v_{max}$ cm$^{-1}$: 3560, 3410, 1532, 1449, 1368, 812.

Nuclear Magnetic Resonance Spectrum (CDCl$_3$, 270 MHz), δ ppm:
- 0.80–1.04 (2H, multiplet);
- 1.07–1.55 (6H, multiplet);
- 1.39 (9H, singlet);
- 1.61–1.83 (5H, multiplet);
- 2.64 (1H, doublet of doublets, J=8 & 14 Hz);
- 2.78 (1H, doublet of doublets, J=4 & 14 Hz);
- 3.89–4.00 (1H, multiplet);
- 7.18 (1H, doublet, J=2 Hz);
- 7.30 (1H, doublet of doublets, J=2 & 8 Hz);
- 7.47 (1H, doublet, J=8 Hz).

10(ii) 5-(3-Cyclohexyl-2-t-butyldimethylsilyloxypropyl)-2t-butyl-1-nitrobenzene 973 mg (6.46 mmol) of t-butyldimethylsilyl chloride, 0.90 ml (6.46 mmol) of triethylamine and 67 mg (0.55 mmol) of 4-(N,N-dimethylamino)pyridine were added to 10 ml of a dimethylformamide solution containing 1.74 g of 5-(3-cyclohexyl-2-hydroxypropyl)-2-t-butyl-1-nitrobenzene [prepared as described in step (i) above]. The mixture was then stirred for 1 hour and 20 minutes at room temperature, and then for 2.5 hours at 40° C. At the end of this time, the reaction solution was poured in water and extracted with a 3:1 by volume mixture of hexane and ethyl acetate. The organic layer was washed with dilute aqueous hydrochloric acid, with water, with a saturated aqueous solution of sodium hydrogen carbonate and with a saturated aqueous solution of sodium chloride, in that order. The solvent was then removed by distillation under reduced pressure. The resulting residue was subjected to column chromatography through 75 g of silica gel. Elution with a 1:9 by volume mixture of diethyl ether and hexane afforded 2.22 g (yield 96% over the 2 steps) of the title compound as an oily substance.

Infrared Absorption Spectrum (liquid film), $v_{max}$ cm$^{-1}$: 1534, 1368, 1254, 1067, 835.

Nuclear Magnetic Resonance Spectrum (CDCl$_3$, 270 MHz), δ ppm:
- −0.26 (3H, singlet);
- −0.05 (3H, singlet);
- 0.78–0.97 (2H, multiplet);
- 0.81 (9H, singlet);
- 1.10–1.40 (6H, multiplet);
- 1.38 (9H, singlet);
- 1.62–1.75 (5H, multiplet);
- 2.60 (1H, doublet of doublets, J=7 & 13 Hz);
- 2.78 (1H, doublet of doublets, J=5 & 13 Hz);
- 3.85–3.94 (1H, multiplet);
- 7.12 (1H, doublet, J=2 Hz);
- 7.23 (1H, doublet of doublets, J=2 & 8 Hz);
- 7.42 (1H, doublet, J=8 Hz).

PREPARATION 11

N-[2-t-Butyl-5-(3-cyclohexyl-2-t-butyldimethyl-silyloxypropyl)phenyl]-2-(9H-xanthen-9-yl)acetamide 11(i) 2-t-Butyl-5-(3-cyclohexyl-2-t-butyldimethyl-silyloxypropyl)aniline Following a procedure similar to that described in Preparation 7, but using 5-(3-cyclohexyl-2-t-butyl-dimethylsilyloxypropyl)-2-t-butyl-1-nitrobenzene (prepared as described in Preparation 10) as a starting material, in a relative amount similar to that used in that Preparation, the title compound was obtained as an oily substance.

11(ii) N-[2-t-Butyl-5-(3-cyclohexyl-2-t-butyldimethyl-silyloxypropyl)phenyl]-2-(9H-xanthen-9-yl)acetamide Following an acylation procedure similar to that described in Example 21, but using 2-t-butyl-5-(3-cyclo-hexyl-2-t-butyldimethylsilyloxypropyl)aniline [prepared as described in step (i) above] as a starting material, in a relative amount similar to that used in that Example, the title compound was obtained as crystals, melting at 148°–150° C. (after recrystallization from a mixture of diisopropyl ether and hexane). The yield in both steps was quantitative.

Infrared Absorption Spectrum (KBr), $v_{max}$ cm$^{-1}$: 3232, 1641, 1533, 1482, 1458, 1256, 759.

Nuclear Magnetic Resonance Spectrum (CDCl$_3$, 270 MHz), δ ppm:
- −0.37 (0.6H, singlet);
- −0.20 (2.4H, singlet);
- −0.10 (0.6H, singlet);
- −0.02 (2.4H, singlet);
- 0.75–0.97 (2H, multiplet);
- 0.78 (1.8H, singlet);
- 0.82 (7.2H, singlet);
- 1.06–1.47 (6H, multiplet);
- 1.16 (9H, singlet);
- 1.60–1.77 (SH, multiplet);
- 2.37–2.76 (4H, multiplet);
- 3.68–2.76 (0.2H, multiplet);
- 3.92 (0.8H, quintet, J=6 Hz);
- 4.75 (1H, triplet, J=7 Hz);
- 6.90–7.41 (11H, multiplet).

PREPARATION 12

2-t-Butyl-5-hydroxymethyl-1-nitrobenzene 10 ml of a tetrahydrofuran solution containing 3.12 g (28.8 mol) of ethyl chloroformate were added dropwise over a period of 10 minutes to 60 ml of a tetrahydrofuran solution containing 6.0 g (26.9 mmol) of 4-t-butyl-3-nitrobenzoic acid and 3.12 g (30.9 mmol) of triethylamine, whilst ice-cooling. The reaction solution was stirred for 45 minutes at this temperature, after which it was filtered using a Celite filter aid. The precipitate was washed with tetrahydrofuran, and the filtrate and the washings were combined. The combined solution was then added dropwise to a mixed solution which was composed of 40 ml of tetrahydrofuran and 40 ml of water containing 3.76 g (9.95 mmol) of sodium borohydride, over a period of 25 minutes, on an ice bath. The reaction mixture was then stirred for 2 hours at the temperature of the ice bath, after which it was condensed by evaporation under reduced pressure. As much as possible of the tetrahydrofuran was then removed by distillation under reduced pressure, and the residue was distributed between diethyl ether and water. The product was extracted from the aqueous layer with diethyl ether. The organic layers were combined and washed twice with water and then once with a saturated aqueous solution of sodium chloride. The solvent was then removed by distillation under reduced pressure.

The resulting residue was subjected to column chromatography through 100 g of silica gel. Elution with mixtures of ethyl acetate and hexane ranging from 20:80 to 30:70 by volume afforded 5.24 g (yield 93%) of the title compound as an oily substance.

Nuclear Magnetic Resonance Spectrum (CDCl$_3$, 270 MHz), δ ppm:

1.40 (9H, singlet);
4.69 (2H, doublet, J=5 Hz);
7.33 (1H, singlet);
7.41 (1H, doublet, J=9.5 Hz);
7.53 (1H, doublet, J=9.5 Hz).

PREPARATION 13

2-t-Butyl-5-(2-t-butyldimethylsilyloxymethyl)-1-nitrobenzene 4.15 g (27.5 mmol) of t-butyldimethylsilyl chloride, 3.85 ml (27.6 mmol) of triethylamine and 815 mg (0.503 mmol) of 4-(N,N-dimethylamino)pyridine were added to 50 ml of a methylene chloride solution containing 5.24 g (25.0 mmol) of 2-t-butyl-5-hydroxymethyl-1-nitro-benzene (prepared as described in Preparation 12), in an ice bath. The reaction mixture was allowed to return to room temperature, after which it was stirred for 40 minutes. At the end of this time, the reaction solution was diluted with a 1:1 by volume mixture of hexane and diethyl ether, and washed with water, with dilute aqueous hydrochloric acid, again with water, with a saturated aqueous solution of sodium hydrogen carbonate and with a saturated aqueous solution of sodium chloride, in that order. The solvent was then removed by distillation under reduced pressure. The resulting residue was subjected to column chromatography through 100 g of silica gel. Elution with a 1:1 by volume mixture of methylene chloride and hexane afforded 8.04 g (yield 99%) of the title compound as an oily substance.

Nuclear Magnetic Resonance Spectrum (CDCl$_3$, 270 MHz), δ ppm:

0.09 (6H, singlet);
0.93 (9H, singlet);
1.38 (9H, singlet);
4.69 (2H, singlet);
7.2–7.6 (3H, multiplet).

PREPARATION 14

N-(2-t-Butyl-5-hydroxymethylphenyl)-2-(9H-xanthen-9-yl)acetamide

14(i) 2-t-Butyl-5-(t-butyldimethylsilylomethyl)-aniline

Following a procedure similar to that described in Preparation 7, but using 2-t-butyl-5-(2-t-butyldimethyl-silyloxymethyl)-1-nitrobenzene (prepared as described in Preparation 13) as a starting material, in a relative amount similar to that used in that Preparation, the title compound was obtained as an oily substance in a quantitative yield.

14(ii) N-[2-t-Butyl-5-(2-t-butyldimethylsilyloxymethyl)-phenyl]-2-(9H-xanthen-9-yl)acetamide Following a procedure similar to that described in Example 21, but using 2-t-butyl-5-(t-butyldimethylsilyloxymethyl)aniline [prepared as described in step (i) above] as a starting material, in a relative amount similar to that used in that Example, the title compound was obtained as crystals in an 84% yield.

14(iii) N-(2-t-Butyl-5-hydroxymethylphenyl)-2-(9H-xanthen-9-yl)acetamide

Following a procedure similar to that described in Example 40, but using N-[2-t-butyl-5-(2-t-butyldimethyl-silyloxymethyl)phenyl]-2-(9H-xanthen-9-yl)acetamide [prepared as described in step (ii) above] as a starting material, in a relative amount similar to that used in that Example, the title compound was obtained as crystals, melting at 137°–138° C. (after recrystallization from a mixture of ethyl acetate and hexane) in a quantitative yield.

Infrared Absorption Spectrum (KBr), $v_{max}$ cm$^{-1}$: 1664, 1541, 1478, 1460, 1250.

Nuclear Magnetic Resonance Spectrum (CDCl$_3$, 270 MHz), δ ppm:

1.17 (9H, singlet);
2.41 (2/5H, broad doublet, J=7 Hz);
2.71 (8/5H, doublet, J=7 Hz);
4.35–4.45 (2/5H, broad singlet);
4.66 (8/5H, singlet);
4.73 (1H, triplet, J=7 Hz);
7.05–7.55 (11H, multiplet).

PREPARATION 15

N-(2-t-Butyl-5-formylphenyl)-2-(9H-xanthen-9-yl)acetamide 1.24 g (3.08 mmol) of N-(2-t-butyl-5-hydroxymethyl-phenyl)-2-(9H-xanthen-9-yl)acetamide (prepared as described in Preparation 14) were added to 12 ml of a methylene chloride suspension containing 1.06 g (4.92 mmol) of pyridinium chlorochromate. The mixture was then stirred for 1.75 hours. At the end of this time, the reaction suspension was diluted with diethyl ether, filtered through a column using 50 ml of Florisil (trade mark) absorbent, and eluted with a 1:1 by volume mixture of methylene chloride and diethyl ether. The solvent was then removed by distillation under reduced pressure. The resulting residue was subjected to column chromatography through 50 g of silica gel. Elution with a 1:9 by volume mixture of diethyl ether and methylene chloride afforded the title compound containing a small amount of impurities. Recrystallization of this from a mixture of ethyl acetate and hexane afforded 442 mg of the title compound as crystals, melting at 172.5°–174° C. (after recrystallization from a mixture of ethyl acetate and hexane). The mother liquors were condensed and subjected to column chromatography through 100 g of silica gel. Elution with a 4:6 by volume mixture of ethyl acetate and hexane afforded a further 643 mg of the title compound. The total yield was 88%.

Infrared Absorption Spectrum (KBr), $v_{max}$ cm$^{-1}$: 1702, 1642, 1482, 1459, 1260, 760.

Nuclear Magnetic Resonance Spectrum (CDCl$_3$, 270 MHz), δ ppm:

1.21 (9H, singlet);
2.74 (2H, doublet, J=7 Hz);
4.75 (1H, triplet, J=7 Hz);
7.07–7.15 (4H, multiplet);
7.21–7.29 (2H, multiplet);
7.39 (2H, doublet of doublets, J=2 & 8 Hz);
7.49 (1H, doublet, J=8 Hz);
7.66 (1H, doublet of doublets, J=2 & 8 Hz);
8.08 (1H, broad singlet);

9.98 (1H, singlet).

PREPARATION 16

N-[2-t-Butyl-5-(2-ethoxycarbonylethenyl)phenyl]-2-(9H-xanthen-9-yl)acetamide 153 mg (3.51 mmol) of sodium hydride (as a 55% w/w suspension in mineral oil) were washed twice with hexane; 5 ml of dimethylformamide were then added. The suspension was cooled in an ice bath, and then 1 ml of a dimethylformamide solution containing 673 mg (3.00 mmol) of ethyl 2-diethoxyphosphorylacetate was added. When the foaming had finished, the reaction mixture was stirred for a further 40 minutes at room temperature. The mixture was then cooled again on an ice bath, and 1.0 g (2.5 mmol) of N-[2-t-butyl-5-formylphenyl-2-(9H-xanthen-9-yl)acetamide (prepared as described in Preparation 15) was added over a period of 5 minutes. The mixture was stirred for 20 minutes at the temperature of the ice bath and for 10 minutes at room temperature. At the end of this time, the reaction mixture was diluted with diethyl ether, and washed with dilute aqueous hydrochloric acid and with water, after which the solvent was removed by distillation under reduced pressure. The resulting residue was recrystallized from a mixture of methylene chloride, diethyl ether and hexane, to afford 804 mg of the title compound as crystals, melting at 180°–181° C. The mother liquors were condensed and recrystallization from the same solvent mixture afforded a further 263 mg of the title compound. Altogether, 1.067 g (yield 90%) of the title compound were obtained.

Infrared Absorption Spectrum (KBr), $v_{max}$ cm$^{-1}$: 3235, 1711, 1645, 1523, 1480, 1458, 1257, 1176, 756.

Nuclear Magnetic Resonance Spectrum (CDCl$_3$, 270 MHz), δ ppm:

1.18 (9H, singlet);
1.36 (3H, triplet, J=7 Hz);
2.33–2.46 (0.4H, multiplet);
2.72 (1.6H, doublet, J=7 Hz);
4.28 (2H, quartet, J=7 Hz);
4.74 (1H, triplet, J=7 Hz);
6.42 (1H, doublet, J=16 Hz);
7.03–7.45 (10H, multiplet);
7.63 (1H, doublet, J=16 Hz);
7.70 (1H, singlet).

PREPARATION 17

N-[2-t-Butyl-5-(2-ethoxycarbonylethyl)phenyl]-2-(9H-xanthen-9-yl)acetamide

Following a catalytic reduction procedure similar to that described in Example 8, but using N-[2-t-butyl-5-(2-ethoxycarbonylethenyl)phenyl]-2-(9H-xanthen-9-yl)-acetamide (prepared as described in Preparation 16) as a starting material, in a relative amount similar to that used in that Example, the title compound was obtained in a yield of 95% as crystals, melting at 160.5°–161.5° C. (after recrystallization from a mixture of methylene chloride and diethyl ether).

Infrared Absorption Spectrum (KBr), $v_{max}$ cm$^{-1}$: 3223, 1736, 1640, 1539, 1481, 1261, 1192, 760.

Nuclear Magnetic Resonance Spectrum (CDCl$_3$, 270 MHz), δ ppm:

1.16 (9H, singlet);
1.26 (3H, triplet, J=7 Hz);
2.35–2.50 (1H, multiplet);
2.58–2.75 (3.5H, multiplet);
2.86–2.98 (1.5H, multiplet);
4.16 (2H, quartet, J=7 Hz);
4.74 (1H, triplet, J=7 Hz);
6.91–7.45 (11H, multiplet).

PREPARATION 18

N-[2-t-Butyl-5-(3-hydroxypropyl)phenyl]-2-(9H-xanthen-9-yl)acetamide 5.96 ml (5.96 mmol) of a 1.0M hexane solution of diisobutylaluminum hydride were added dropwise, over a period of 10 minutes, to 14 ml of a tetrahydrofuran solution containing 702 mg (1.49 mmol) of N-[2-t-butyl-5-(2-ethoxycarbonylethyl)phenyl]-2-(9H-xanthen-9-yl)-acetamide (prepared as described in Preparation 17) which had previously been cooled at −78° C. The mixture was stirred for 75 minutes at this temperature and then for 45 minutes at room temperature. At the end of this time, the reaction solution was poured into a mixture of dilute aqueous hydrochloric acid and ice, and was then extracted with diethyl ether. The organic extract was washed with water, and then the solvent was removed by distillation under reduced pressure. The resulting residue was subjected to column chromatography through 30 g of silica gel. Elution with a 5:4 by-volume mixture of methylene chloride and ethyl acetate afforded 427 mg (yield 67%) of the title compound as crystals, melting at 185°–186° C. (after recrystallization from a mixture of methylene chloride and diethyl ether).

Infrared Absorption Spectrum (KBr), $v_{max}$ cm$^{-1}$: 3417, 3212, 1659, 1530, 1481, 1457, 1254, 765, 757.

Nuclear Magnetic Resonance Spectrum (CDCl$_3$, 270 MHz), δ ppm:

1.16 (9H, singlet);
1.67–1.98 (2H, multiplet);
2.33–2.53 (1H, multiplet);
2.61–2.76 (3H, multiplet);
3.53–3.75 (2H, multiplet);
4.74 (1H, triplet, J=7 Hz);
6.92–7.46 (11H, multiplet).

PREPARATION 19

N-[2-t-Butyl-5-(3-oxopropyl)phenyl]-2-(9H-xanthen-9-yl)acetamide 2 ml of a methylene chloride solution containing 155 mg (1.98 mmol) of dimethyl sulfoxide were added dropwise over a period of 5 minutes to 2 ml of a methylene chloride solution containing 126 mg (0.99 mmol) of oxalyl chloride which had previously been cooled at −78° C. The mixture was then stirred for 5 minutes at this temperature, after which 15 ml of a methylene chloride solution containing 354 mg (0.825 mmol) of N-[2-t-butyl-5-(3-hydroxypropyl)phenyl]-2-(9H-xanthen-9-yl)acetamide (prepared as described in Preparation 18) were added, and the mixture was stirred for a further 15 minutes at this temperature. 501 mg (4.95 mmol) of triethylamine were then added to the reaction mixture, which was then stirred for 5 minutes at the same temperature. The reaction mixture was then allowed to return to room temperature, after which it was diluted with diethyl ether, and washed with dilute aqueous hydrochloric acid and then with water. The solvent was then removed by distillation under reduced pressure. The resulting residue was subjected to column chromatography through 20 g of silica gel. Elution with a 100:5 by volume mixture of methylene chloride and ethyl acetate afforded 310 mg (yield 88%) of the title compound as crystals, melting at 176°–177° C. (after recrystallization from a mixture of methylene chloride and diethyl ether).

Infrared Absorption Spectrum (KBr), $v_{max}$ cm$^{-1}$: 3230, 1729, 1641, 1534, 1481, 1458, 1260, 759.

Nuclear Magnetic Resonance Spectrum (CDCl$_3$, 270 MHz), δ ppm:

1.16 (9H, singlet);
2.36–3.00 (6H, multiplet);
4.74 (1H, triplet, J=7 Hz);
6.92–7.45 (11H, multiplet);
9.84 (1H, singlet).

PREPARATION 20

N-[(9H-Xanthen-9-yl)methyl]-N'-{2-t-butyl-5-[4-cyclohexyl-3-(t-butyldimethylsilyloxy)butyl]phenyl}urea A solution of 240 mg (1.00 mmol) of 2-(9H-xanthen-9-yl)acetic acid, 275 mg (1.00 mmol) of diphenylphosphoryl azide and 139 µl (1.00 mmol) of triethylamine in 3 ml of benzene was heated under reflux, with stirring, for 2.5 hours, after which a solution of 459 mg (1.10 mmol) of 2-t-butyl-5-[4-cyclohexyl-3-(t-butyldimethylsilyl-oxy)butyl]aniline in 0.5 ml of benzene was added. The resulting mixture was heated under reflux for 3 hours. At the end of this time, the reaction mixture was diluted with ethyl acetate, and the diluted mixture was washed with dilute aqueous hydrochloric acid, with water, with a saturated aqueous solution of sodium hydrogencarbonate and with a saturated aqueous solution of sodium chloride, in that order. The organic phase was dried over anhydrous sodium sulfate, and the solvent was removed by distillation under reduced pressure. The resulting residue was purified by column chromatography through 25 g of silica gel, using a 95:5 by volume mixture of methylene chloride and ethyl acetate as the eluent, to give 414 mg (yield 65%) of the title compound as a foam-like material.

Infrared Absorption Spectrum (KBr) $v_{max}$ cm$^{-1}$: 3341, 2953, 2926, 2854, 1637, 1561, 1481, 1458, 1256, 1075, 835, 755.

PREPARATION 21

2-(1-Phenylcyclopentyl)acetic acid

21(i) (1-Phenylcylopentyl)methanol

A solution of 1.15 g (6.04 mmol) of (1-phenylcyclopentyl)carboxylic acid in 10 ml of tetrahydrofuran was added dropwise over a period of 20 minutes to a suspension of 344 mg (9.06 mmol) of lithium aluminum hydride in 20 ml of tetrahydrofuran, whilst ice-cooling, and the resulting mixture was stirred for 30 minutes at 60° C. At the end of this time, the reaction mixture was again ice-cooled, and then 0.3 ml of water, 10 ml of a 2N aqueous solution of sodium hydroxide and 1 ml of water were added, in that order, and the resulting mixture was diluted with diethyl ether. The white gel material which appeared was filtered off, and then the filtrate was washed with water, with a saturated aqueous solution of sodium hydrogen carbonate and with a saturated aqueous solution of sodium chloride, in that order. The organic phase was dried over anhydrous sodium sulfate, and the solvent was removed by distillation under reduced pressure. The resulting residue was purified by column chromatography through 50 g of silica gel, using methylene chloride as the eluent, to give 1.06 g (yield 99%) of the title compound as colorless crystals.

Infrared Absorption Spectrum (KBr) $v_{max}$ cm$^{-1}$: 3310, 2952, 2929, 2873, 1496, 1446, 1059, 1032, 766, 699, 567.

21(ii) (1-Phenylcyclopentyl)methyl methanesulfonate 659 mg (6.07 mmol) of methanesulfonyl chloride and then 838 µl (6.01 mmol) of triethylamine were added, whilst cooling in an ice-salt bath, to a solution of 1.00 g (5.67 mmol) of (1-phenylcyclopentyl)methanol [prepared as described in step (i) above] in 18 ml of methylene chloride, and the resulting mixture was stirred for 1 hour. At the end of this time, the reaction mixture was diluted with diethyl ether, and the diluted mixture was washed with 2N aqueous hydrochloric acid, with water, with a saturated aqueous solution of sodium hydrogencarbonate and with a saturated aqueous solution of sodium chloride, in that order. The organic phase was dried over anhydrous sodium sulfate, and the solvent was distilled off to give 1.44 g (a quantitative yield) of the title compound as colorless crystals.

Infrared Absorption Spectrum (KBr) $v_{max}$ cm$^{-1}$: 2959, 2943, 2874, 1337, 1180, 1166, 975, 960, 853, 845, 770, 750, 702, 526, 505.

21(iii) (1-Phenylcyclopentyl)methyl iodide 5.00 g (33.3 mmol) of sodium iodide were added to a solution of 1.00 g (3.93 mmol) of (1-phenylcyclopentyl)-methylmethanesulfonate [prepared as described in step (ii) above] in 10 ml of methyl isobutyl ketone, and the resulting mixture was heated under reflux for 18 hours. At the end of this time, the solvent was removed by distillation under reduced pressure, and the resulting residue was partitioned between diethyl ether and water. The organic phase was washed with water, with a saturated aqueous solution of sodium hydrogencarbonate and with a saturated aqueous solution of sodium chloride, in that order. The organic phase was dried over anhydrous sodium sulfate, and the solvent was removed by distillation under reduced pressure. The resulting residue was purified by column chromatography through 50 g of silica gel, using a 1: 1 by volume mixture of methylene chloride and hexane as the eluent, to give 504 mg (yield 45%) of the title compound as an oil.

Infrared Absorption Spectrum (liquid film), $v_{max}$ cm$^{-1}$: 2956, 2872, 1496, 1446, 1210, 1188, 760, 699, 546.

21(iv) 2-(1-Phenylcyclopentyl)methyl-1,3-dithiane

720 µl of a 1.6M hexane solution of butyllithium were added dropwise at −78° C. to a solution of 126 mg (1.05 mmol) of 1,3-dithiane in a mixture of 1.5 ml of tetrahydrofuran and 720 µl of hexamethylphosphoric triamide, whilst stirring, and the resulting mixture was stirred for 10 minutes whilst cooling in an ice-salt bath. At the end of this time, a solution of 200 mg (0.699 mmol) of 2-(1-phenylcyclopentyl)methyl iodide [prepared as described in step (iii) above] in 1 ml of tetrahydrofuran was added dropwise to the mixture at −78° C. The resulting mixture was then stirred for 20 minutes, whilst cooling in an ice-salt bath. In order to stop the reaction, a saturated aqueous solution of ammonium chloride was then added to the reaction mixture, which was then extracted with diethyl ether. The extract was washed with a saturated aqueous solution of sodium chloride. The organic phase was dried over anhydrous sodium sulfate, and the solvent was removed by distillation under reduced pressure. The resulting residue was purified by column chromatography through 15 g of silica gel, using a 3:2 by volume mixture of hexane and methylene chloride as the eluent, to give 100 mg (yield 51%) of the title compound as a colorless foam-like material.

Nuclear Magnetic Resonance Spectrum (CDCl$_3$, 270 MHz), δ ppm:

1.57–2.10 (12H, multiplet);
2.61–2.85 (4H, multiplet);
3.58 (1H, triplet, J=5.9 Hz);
7.18–7.37 (5H, multiplet).

21(v) 2-(1-Phenylcyclopentyl)acetaldehyde 263 mg (0.969 mmol) of mercuric chloride and 129 mg (1.29 mmol) of calcium carbonate were added to a suspension of 90 mg (0.323 mmol) of 2-(1-phenylcyclopentyl)methyl-1,3-dithiane [prepared as described in step (iv) above] in a mixture of 4 ml of acetonitrile and 0.6 ml of water, and the resulting mixture was stirred for 3 hours at 90° C. At the end of this time, the reaction mixture was cooled and then diluted with ethyl acetate. The insoluble materials were filtered off from the diluted mixture with the help of Celite (trade mark) filter aid. The filtrate was then washed with a 1M aqueous solution of sodium acetate, with a saturated aqueous solution of ammonium chloride and with a saturated aqueous solution of sodium chloride, in that order. The organic phase was dried over anhydrous sodium sulfate, and the solvent was removed by distillation under reduced pressure. The resulting residue was purified by column chromatography through 5 g of silica gel, using methylene chloride as the eluent, to give 58.4 mg (yield 96%) of the title compound as a foam-like material.

Nuclear Magnetic Resonance Spectrum (CDCl$_3$, 270 MHz), δ ppm:

1.76–1.99 (8H, multiplet);
2.64 (2H, doublet, J=3.3 Hz);
7.18–7.34 (5H, multiplet);
9.43 (1H, triplet, J=3.3 Hz).

21(vi) 2-(1-Phenylcyclopentyl)acetic acid 1 ml of an aqueous solution of 39 mg (0.402 mmol) of sulfamic acid and then 1 ml of an aqueous solution of 37.6 mg (0.416 mmol) of sodium chlorite were added dropwise to a solution of 58.4 mg (0.310 mmol) of 2-(1-phenylcyclopentyl)acetaldehyde [prepared as described in step (v) above] in 1 ml of t-butanol at room temperature, and the resulting mixture was stirred for 1 hour at room temperature, after which it was extracted with methylene chloride. The extract was washed with water and then dried over anhydrous sodium sulfate. The solvent was removed by distillation under reduced pressure, to give colorless crystals. These were recrystallized from a mixture of ethyl acetate and hexane, to give 57 mg (yield 90%) of the title compound as plate-like crystals.

Infrared Absorption Spectrum (KBr) ν$_{max}$ cm$^{-1}$: 2967, 2945, 2869, 1706, 1426, 1400, 1204, 1195, 924, 911, 773, 698.

PREPARATION 22

N-[(1-Phenylcyclopentyl)methyl]-N'-[2-t-butyl-5-(3-t-butyldimethylsilyloxy-4-cyclohexylbutyl)phenyl] urea Following a procedure similar to that described in Preparation 20, but using 2-(1-phenylcyclopentyl)acetic acid (prepared as described in Preparation 21) as a starting material, in a relative proportion similar to that used in that Preparation, the title compound was obtained as a colorless foam-like material.

Nuclear Magnetic Resonance Spectrum (CDCl$_3$, 270 MHz), δ ppm:

0.59 (6H, singlet);
0.92 (9H, singlet);
1.17–1.93 (23H, multiplet);
1.27 (9H, singlet);
2.39–2.62 (2H, multiplet);
3.31 (2H, doublet, J=5 Hz);
3.80–3.82 (1H, multiplet);
5.74 (1H, singlet);
6.84–7.28 (8H, multiplet).

PREPARATION 23

(R)-N-{2-t-Butyl-5-[4-cyclohexyl-3-(t-butyldimethylsilyloxy)butyl]phenyl}-2-(9H-xanthen-9-yl)acetamide 23(i) (S)-2-Cyclohexyl-1-(benzyloxymethyl)ethyl alcohol A solution of a Grignard reagent, prepared from 9.79 g (60.0 mmol) of cyclohexyl bromide and 1.46 g (60.0 mmol) of magnesium, in 85 ml of tetrahydrofuran was added dropwise over a period of 10 minutes to a suspension of 1.90 g (9.98 mmol) of cuprous iodide in 50 ml of tetrahydrofuran at −75° C. The mixture was allowed to stand for 10 minutes, and then a solution of 8.21 g (50.0 mmol) of (S)-benzyloxymethyloxirane, [α]$_D$=+4.82° (c=1, toluene), in 20 ml of tetrahydrofuran was added dropwise over a period of 15 minutes. The resulting mixture was stirred for 3 hours at the same temperature and then for 30 minutes at 0° C. At the end of this time, the reaction was stopped by adding a saturated aqueous solution of ammonium chloride. The reaction mixture was then mixed with 20 ml of concentrated aqueous ammonia, after which it was extracted with diethyl ether. The extract was washed with a saturated aqueous solution of ammonium chloride, with a saturated aqueous solution of sodium hydrogencarbonate and with a saturated aqueous solution of sodium chloride, in that order. The organic phase was then dried over anhydrous sodium sulfate, and the solvent was removed by distillation under reduced pressure. The resulting residue was purified by column chromatography through 250 g of silica gel, using a 1:4 by volume mixture of ethyl acetate and methylene chloride as the eluent, to give 10.0 g (yield 82%) of the title alcohol derivative as a colorless oil.

Infrared Absorption Spectrum (liquid film), ν$_{max}$ cm$^{-1}$: 3460, 1451, 1364, 1102, 1048, 1028, 737, 699.

[α]$_D^{25}$=−0.84° (c=1.78, CHCl$_3$).

23(ii) (S)-[3-Benzyloxy-2-(t-butyldimethylsilyloxypropyl)cyclohexane

Following a procedure similar to that described in Preparation 10(ii), but using (S)-2-cyclohexyl-1-(benzyloxymethyl)ethyl alcohol [prepared as described in step (i) above] as a starting material, in a relative proportion similar to that used in that Preparation, the title silyl compound was obtained as an oil in a quantitative yield.

Infrared Absorption Spectrum (liquid film), ν$_{max}$ cm$^{-1}$: 1451, 1362, 1252, 1125, 1028, 970, 835, 776.

[α]$_D^{25}$=−17.4° (c=1.22, CHCl$_3$).

23(iii) (S)-2-t-Butyldimethylsilyloxy-3-cyclohexylpropyl alcohol

A solution of 3.46 g (9.55 mmol) of (S)-[3-benzyloxy-2-(t-butyldimethylsilyloxypropyl)cyclohexane [prepared as described in step (ii) above] in 50 ml of ethanol was vigorously stirred for 5 hours and 20 minutes in a stream of hydrogen and in the presence of 580 mg of 10% w/w palladium-on-charcoal. At the end of this time, the reaction mixture was filtered, and the catalyst was washed with ethanol. The filtrate and the washings were combined and the solvent was removed by distillation under reduced pressure. The resulting residue was purified by column chromatography through 180 g of silica gel, using a 1:4 by volume mixture of ethyl acetate and hexane as the eluent, to give 2.54 g (yield 98%) of the title alcohol derivative as a colorless oil.

Infrared Absorption Spectrum (liquid film), $v_{max}$ cm$^{-1}$: 3400, 1449, 1254, 1080, 969, 837, 776.

$[\alpha]_D^{25}$=+3.6° (C=1.02, CHCl$_3$).

23(iv) (S)-2-t-Butyldimethylsilyloxy-3-cyclohexylpropanal 1.5 ml (21.1 mmol) of dimethyl sulfoxide were added dropwise over a period of 2 minutes to a solution of 1.0 ml (11.5 mmol) of oxalyl chloride in 20 ml of methylene chloride at −78° C. The mixture was allowed to stand for 10 minutes, after which a solution of 2.54 g (9.32 mmol) of (S)-2-t-butyldimethylsilyloxy-3-cyclohexylpropyl alcohol [prepared as described in step (iii) above] in 12 ml of methylene chloride was added dropwise over a period of 5 minutes. The resulting mixture was then stirred for 20 minutes at the same temperature, after which 6.5 ml (46.6 mmol) of triethylamine were added. The mixture was then allowed to stand for 7 minutes, and the cooling bath was removed. After a further 10 minutes, the reaction was stopped by adding an aqueous solution of ammonium chloride. The reaction mixture was then extracted with diethyl ether. The extract was washed twice with water and once with a saturated aqueous solution of sodium chloride. The organic phase was dried over anhydrous magnesium sulfate, and the solvent was then removed by distillation under reduced pressure, to give 2.55 g (a quantitative yield) of the title aldehyde compound as a colorless oil.

Infrared Absorption Spectrum (liquid film), $v_{max}$ cm$^{-1}$: 1738, 1472, 1449, 1256, 1115, 1007, 940, 839, 778.

23(v) (S)-2-t-Butyl-5-(3-t-butyldimethylsilyloxy-4-cyclohexyl-1-butenyl)-1-nitrobenzene 8.6 ml (8.6 mmol) of a 1.0M tetrahydrofuran solution of sodium hexamethyldisilazide were added dropwise over a period of 20 minutes to a suspension of 5.04 g (8.67 mmol) of (4-t-butyl-3-nitrophenyl)methyltriphenylphosphonium iodide (prepared as described in Preparation 52) in 80 ml of tetrahydrofuran at −78° C., and the mixture was allowed to stand for 1 hour. A solution of 2.33 g (8.61 mmol) of (S)-2-t-butyldimethylsilyloxy-3-cyclohexylpropanol [prepared as described in step (iv) above] in 7 ml of tetrahydrofuran was then added all at once, and the resulting mixture was stirred for 1 hour at the same temperature. The cooling bath was then removed, and the mixture was stirred for a further 4 hours. The reaction was then stopped by adding a saturated aqueous solution of ammonium chloride, after which the reaction mixture was extracted with a 1:3 by volume mixture of ethyl acetate and hexane. The extract was washed with water and with a saturated aqueous solution of sodium chloride, in that order, after which it was dried over anhydrous magnesium sulfate. The solvent was then removed by distillation under reduced pressure, and the resulting residue was purified by column chromatography through 150 g of silica gel, using a 1:19 by volume mixture of diethyl ether and hexane as the eluent, to give fractions containing small amounts of impurities. These fractions were again purified by column chromatography through 150 g of silica gel, using a 1:4 by volume mixture of methylene chloride and hexane as the eluent, to give 2.78 g (yield 72%) of the title olefin derivative as a colorless oil.

Infrared Absorption Spectrum (liquid film), $v_{max}$ cm$^{-1}$: 1534, 1368, 1254, 1096, 1073, 1003, 970, 938, 837, 776.

23(vi) (R)-2-t-Butyl-5-(3-t-butyldimethylsilyloxy-4-cyclohexylbutyl)-1-nitrobenzene A solution of 2.75 g (6.17 mmol) of (S)-2-t-butyl-5-(3-t-butyldimethylsilyloxy-4-cyclohexyl-1-butenyl)-1-nitrobenzene [prepared as described in step (v) above] in 30 ml of diethyl ether was vigorously stirred for 20 minutes at 0° C. in a stream of hydrogen and in the presence of 303 mg of 10% w/w palladium-on-charcoal. The reaction mixture was then worked up in a similar manner to that described in step (iii) above, to give 2.65 g (yield 96%) of the title nitrobenzene derivative as a colorless oil.

Infrared Absorption Spectrum (liquid film), $v_{max}$ cm$^{-1}$: 1532, 1472, 1449, 1368, 1254, 1077, 1024, 1005, 978, 835, 774.

$[\alpha]_D^{22}$=−4.4° (c=1.46, CHCl$_3$).

23(vii) (R)-N-{2-t-Butyl-5-[4-cyclohexyl-3-(t-butyl-dimethylsilyloxy)butyl]phenyl}-2-(9H-xanthen-9-yl)-acetamide Following a procedure similar to that described in Preparation 3, (R)-2-t-butyl-5-(3-t-butyldimethylsilyloxy-4-cyclohexylbutyl)-1-nitrobenzene [prepared as described in step (vi) above] was converted to an aniline derivative. This was acylated in a similar manner to that described in Example 21, to give the title compound in a 94% yield as crystals, melting at 173°–174.5° C. (after recrystallisation from a mixture of ethyl acetate and hexane).

Infrared Absorption Spectrum (KBr) $v_{max}$ cm$^{-1}$: 3460, 1640, 1538, 1482, 1459, 1256, 1079, 835, 758.

$[\alpha]_D^{25}$=−5.9° (c=1.14, CHCl$_3$).

PREPARATION 24

(S)-2-t-Butyl-5-(3-benzoyloxy-4-cyclohexylbutyl)aniline

24(i) (R)-2-t-Butyl-5-(3-hydroxy-4-cyclohexylbutyl)-1-nitrobenzene

Following a procedure similar to that described in Example 40, but using (R)-2-t-butyl-5-(3-t-butyldimethylsilyloxy-4-cyclohexylbutyl)-1-nitrobenzene [prepared as described in Preparation 23(vi)] as a starting material, in a relative proportion similar to that used in that Example, the title alcohol derivative was obtained in a 98% yield as a colorless oil.

Infrared Absorption Spectrum (liquid film), $v_{max}$ cm$^{-1}$: 3360, 1532, 1449, 1368, 1254, 1063, 1048, 834, 810.

$[\alpha]_D^{25}$=+5.0° (c=1.19, CHCl$_3$).

24(ii) (S)-2-t-Butyl-5-(3-benzoyloxy-4-cyclohexylbutyl)-1-nitrobenzene

A solution of 734 mg (4.21 mmol) of diethyl azodicarboxylate in 5 ml of tetrahydrofuran was added dropwise over a period of 5 minutes to a solution of 1.16 g (3.48 mmol) of (R)-2-t-butyl-5-(3-hydroxy-4-cyclohexylbutyl)-1-nitrobenzene [prepared as described in step (i) above], 1.10 g (4.21 mmol) of triphenylphosphine and 512 mg (4.19 mmol) of benzoic acid in 12 ml of tetrahydrofuran, whilst ice-cooling. The temperature of the reaction mixture was allowed to rise gradually to room temperature, after which the resulting mixture was stirred for 12 hours. At the end of this time, the reaction mixture was diluted with ethyl acetate. The diluted mixture was then washed with a saturated aqueous solution of sodium hydrogencarbonate and with a saturated aqueous solution of sodium chloride, in that order. The organic phase was dried over anhydrous magnesium sulfate, and then the solvent was removed by distillation under reduced pressure. The resulting residue was purified by column chromatography through 150 g of silica gel, using a 1:9 by volume mixture of diethyl ether and hexane as the eluent, to give 1.19 g (yield 78% yield) of the title benzoyl derivative as an oil.

Infrared Absorption Spectrum (liquid film), $v_{max}$ cm$^{-1}$: 1715, 1532, 1451, 1368, 1273, 1113, 1069, 1026, 712.

$[\alpha]_D^{22}$=+8.1° (c=1.54, CHCl$_3$).

24(iii) (S)-2-t-Butyl-5-(3-benzoyloxy-4-cyclohexylbutyl)aniline

Following a procedure similar to that described in Preparation 3, but using (S)-2-t-butyl-5-(3-benzoyloxy-4-cyclohexylbutyl)-1-nitrobenzene [prepared as described in step (ii) above] as a starting material, in a relative proportion similar to that used in that Example, the title compound was obtained as a crude product. The product was used in the following reaction without further purification.

PREPARATION 25

(R)-1-(2-{4-t-Butyl-3-[2-(9H-xanthen-9-yl) acetamido]-phenyl}ethyl)-2-cyclohexylethyl benzyl succinate A suspension of 249 mg (0.474 mmol) of (R)-N-[2-t-butyl- 5-(4-cyclohexyl-3-hydroxybutyl)phenyl]-2-(9H-xanthen-9-yl)acetamide (prepared as described in Example 100), 218 mg (1.05 mmol) of benzyl hydrogen succinate, 76 mg (0.62 mmol) of 4-(N,N-dimethylamino)pyridine and 256 mg (1.34 mmol) of 1-ethyl-3-(3'-dimethylaminopropyl)carbodiimide hydrochloride in 5 ml of tetrahydrofuran was stirred for 17 hours at room temperature. At the end of this time, the reaction mixture was diluted with ethyl acetate, and the diluted mixture was washed with 2N aqueous hydrochloric acid, with water, with a saturated aqueous solution of sodium hydrogencarbonate and with a saturated aqueous solution of sodium chloride, in that order. The organic phase was then dried over anhydrous magnesium sulfate, and the solvent was removed by distillation under reduced pressure. The resulting residue was purified by column chromatography through 20 g of silica gel, using a 1:9 by volume mixture of ethyl acetate and hexane as the eluent, to give 352 mg (a quantitative yield) of the title compound as a glassy material.

Infrared Absorption Spectrum (film), $v_{max}$ cm$^{-1}$: 1734, 1659, 1480, 1459, 1416, 1256, 1215, 1158, 870, 758.

PREPARATION 26

N-[2-(1,1-Dimethyl-2-methoxy)ethyl-6-(3-oxopropyl)-phenyl]-2-(9H-xanthen-9-yl)acetamide 26(i) N-[2-(1,1-Dimethyl-2-methoxy)ethyl-6-[3-t-butyldimethylsilyloxy)propyl]phenyl]-2-19H-xanthen-9-yl)-acetamide Following a procedure similar to that described in Example 21, but using 2-(1,1-dimethyl-2-methoxy)ethyl-6-[3-(t-butyldimethylsilyloxy)propyl]aniline as a starting material, in a relative proportion similar to that used in that Example, the title amide derivative was obtained as colorless crystals.

Infrared Absorption Spectrum (KBr) $v_{max}$ cm$^{-1}$: 3249, 1649, 1526, 1480, 1459, 1258, 1102, 837, 754.

26(ii) N-[2-(1,1-Dimethyl-2-methoxy)ethyl-6-(3-oxopropyl)phenyl]-2-(9H-xanthen-9-yl)acetamide Following a procedure similar to that described in Example 40, N-[2-(1,1-dimethyl-2-methoxy)ethyl-6-[3-t-butyldimethylsilyloxy)propyl]phenyl]-2-(9H-xanthen-9-yl)-acetamide [prepared as described in step (i) above] was desilylated, after which it was oxidized in a similar manner to that described in Preparation 19, to give the title compound as colorless crystals, melting at 112°–113.5° C.

Infrared Absorption Spectrum (KBr) $v_{max}$ cm$^{-1}$: 3225, 1725, 1648, 1534, 1482, 1459, 1262, 1107, 756.

PREPARATION 27

(S)-1-(2-{4-t-Butyl-3-[2-(9H-xanthen-9-yl)acetamido]-phenyl}ethyl)-2-cyclohexylethyl benzyl succinate Following a procedure similar to that described in Preparation 25, but using (S)-N-[2-t-butyl-5-(4-cyclohexyl-3-hydroxybutyl)phenyl]-2-(9H-xanthen-9-yl)acetamide (prepared as described in Example 102) and benzyl hydrogen malonate as starting materials, in relative proportions similar to those used in that Preparation, the title compound was obtained as a foam-like material.

Nuclear Magnetic Resonance Spectrum (CDCl$_3$, 270 MHz), δ ppm:

0.78–1.02 (2H, multiplet);

1.10–1.90 (13H, multiplet);

1.16 (9H, singlet);

2.40–2.71 (4H, multiplet);

3.38 (2H, singlet);

4.74 (1H, triplet, J=7 Hz);

5.05–5.16 (1H, multiplet);

5.19 (2H, singlet);

6.90–7.40 (16H, multiplet).

PREPARATION 28

N-(2-Isopropyl-6-hydroxymethylphenyl)-2-(9H-xanthen-9-yl)acetamide

Method A

28(i) 2-Isopropyl-6-methylthiomethylaniline 15.51 g (116 mmol) of N-chlorosuccinimide were added over a period of 20 minutes to a solution of 11.2 g (82.9 mmol) of 2-isopropylaniline and 7.22 g (116 mmol) of dimethyl sulfide in 200 ml of methylene chloride, whilst maintaining the internal temperature at between 15° and 20° C. After 15 minutes, 11.73 g (116 mmol) of triethylamine were added to the mixture, which was then heated under reflux for 9 hours. At the end of this time, the solvent was removed by distillation under reduced pressure. The resulting residue was mixed with diethyl ether and insoluble materials which appeared were filtered off. The filtrate was concentrated by evaporation under reduced pressure, and the concentrate was purified by column chromatography through 300 g of silica gel, using a gradient elution method, with mixtures of hexane and methylene chloride ranging from 4:1 to 0:1 as the eluent, to give 10.45 g (yield 65%) of the title sulfide derivative as an oil.

Infrared Absorption Spectrum (liquid film), $v_{max}$ cm$^{-1}$: 3447, 3354, 1623, 1460, 1447, 1280, 1268, 1242, 1049, 747.

28(ii) 2-Isopropyl-6-methylsulfinylmethylaniline 12.9 g (52.3 mmol) of m-chloroperbenzoic acid (70% purity) were added over a period of 15 minutes to a suspension of 10.21 g (52.3 mmol) of 2-isopropyl-6-methylthiomethylaniline [prepared as described in step (i) above] and 5.31 g (50 mmol) of sodium carbonate in 200 ml of methylene chloride, whilst ice-cooling. The reaction mixture was stirred for 1.5 hours at the same temperature, after which it was diluted with methylene chloride, and the diluted mixture was washed with a saturated aqueous solution of sodium hydrogencarbonate, with an aqueous solution of sodium sulfite and with water, in that order. The solvent was then removed by distillation under reduced pressure, and the resulting residue was recrystallized from a mixture of diethyl ether and diisopropyl ether, to give 7.74 g of the title compound as a first crop. The mother liquor was then concentrated by evaporation under reduced pressure, and the concentrate was repeatedly recrystallized from the same solvent to give a further 0.75 g of the title S-oxide derivative. The total yield was 8.49 g (yield 77%). The title compound melted at 91°–91.5° (after recrystallisation from a mixture of methylene chloride and diisopropyl ether).

Infrared Absorption Spectrum (KBr) $v_{max}$ cm$^{-1}$: 3465, 3367, 1644, 1461, 1437, 1417, 1018, 948, 752.

28(iii) 2-Isopropyl-6-chloromethylaniline hydrochloride

Hydrogen chloride gas was introduced for 35 minutes into a solution of 7.74 g of 2-isopropyl-6-methylsulfinylmethylaniline [prepared as described in step (ii) above] in 80 ml of 1,2-dichloroethane warmed at 50° C., with the aid of a gas-inlet tube. The reaction mixture was then cooled to room temperature and 50 ml of hexane were added thereto. The crystals which precipitated were collected by filtration and washed with hexane to give 7.78 g (yield 96%) of the title aniline hydrochloride as a powder.

28(iv) N-(2-Isopropyl-6-chloromethylphenyl)-2-(9H-xanthen-9-yl)acetamide

Following a procedure similar to that described in Example 21, but using 1.0 g (4.17 mmol) of 2-(9H-xanthen-9-yl)acetic acid, the acid chloride was obtained. The whole of this acid chloride was dissolved in 30 ml of methylene chloride, and then 917 mg (4.17 mmol) of 2-isopropyl-6-chloromethylaniline hydrochloride [prepared as described in step (iii) above] were added, and the resulting mixture was cooled to −78° C. A solution of 1.18 g (9.17 mmol) of N-diisopropyl-N-ethylamine in 5 ml of methylene chloride was then added dropwise to the mixture. The temperature of the mixture was allowed to rise gradually to 0° C. over a period of 2 hours, after which a solution of 0.30 g (2.32 mmol) of N-diisopropyl-N-ethylamine in 1 ml of methylene chloride was added. The mixture was then stirred for 20 minutes at the same temperature. At the end of this time, the reaction mixture was diluted with methylene chloride, and the diluted mixture was washed twice with 2N aqueous hydrochloric acid, once with a saturated aqueous solution of sodium hydrogencarbonate and then once with a saturated aqueous solution of sodium chloride. The organic phase was concentrated by evaporation under reduced pressure to a volume of about 10 ml, and the concentrate was diluted with 10 ml of diethyl ether. The crystals which precipitated were collected by filtration to give 0.73 g of the title compound as a first crop. The mother liquor was then concentrated by evaporation under reduced pressure, and the concentrate was mixed with diethyl ether to precipitate 0.46 g of a second crop. The concentrate, obtained from the mother liquor of the second crop, was purified by column chromatography through 15 g of silica gel, using a 50:1 by volume mixture of methylene chloride and ethyl acetate as the eluent, to give a further 0.19 g of the title compound as crystals. The total yield was 1.38 g (yield 82%). The title compound melted at 199.5°–202° C. (after recrystallisation from a mixture of ethyl acetate and diethyl ether).

Infrared Absorption Spectrum (KBr) $v_{max}$ cm$^{-1}$: 3218, 1656, 1598, 1576, 1530, 1482, 1456, 1409, 1359, 1262.

28(v) N-(2-Isopropyl-6-acetoxymethylphenyl)-2-(9H-xanthen-9-yl)acetamide

A suspension of 189 mg (0.467 mmol) of N-(2-isopropyl-6-chloromethylphenyl)-2-(9H-xanthen-9-yl)acetamide [prepared as described in step (iv) above], 153 mg (1.86 mmol) of sodium acetate and 105 mg (0.70 mmol) of sodium iodide in 2 ml of N,N-dimethylformamide was stirred for 3 hours at 50° C. The reaction mixture was then diluted with ethyl acetate, and the diluted mixture was washed several times with water. The organic phase was dried over anhydrous sodium sulfate, and the solvent was removed by distillation under reduced pressure. The resulting residue was purified by column chromatography through 7 g of silica gel, using a gradient elution method, with mixtures of methylene chloride and ethyl acetate ranging from 50:1 to 12:1 as the eluent, to give 126 mg (yield 63%) of the title acetyl derivative as crystals, melting at 159°–160° C. (after recrystallization from a mixture of ethyl acetate and hexane).

Infrared Absorption Spectrum (KBr) $v_{max}$ cm$^{-1}$: 3249, 1746, 1647, 1600, 1577, 1525, 1480, 1458, 1261, 1217.

28(vi) N-(2-Isopropyl-6-hydromethylphenyl)-2-xanthen-9-yl)acetamide

A solution of 79 mg (1.98 mmol) of sodium hydroxide in 1 ml of water was added to a solution of 567 mg (1.32 mmol) of N-(2-isopropyl-6-acetoxymethylphenyl)-2-(9H-xanthen-9-yl)acetamide [prepared as described in step (v) above] in 15 ml of methanol, and the resulting mixture was stirred for 1 hour at room temperature. At the end of this time, the reaction mixture was concentrated by evaporation under reduced pressure, and the concentrate was partitioned between ethyl acetate and water. The organic phase was washed with a saturated aqueous solution of sodium chloride, and the solvent was removed by distillation under reduced pressure, to give 511 mg (a quantitative yield) of the title compound, melting at 155°–156° C. (after recrystallization from a mixture of ethyl acetate and hexane).

Infrared Absorption Spectrum (KBr) $v_{max}$ cm$^{-1}$: 3248, 1660, 1646, 1528, 1480, 1457, 1255, 1045.

Method B

28(vii) N-(2-Isopropyl-6-hydroxymethylphenyl)-2-(9H-xanthen-9-yl)acetamide 4.24 g (25 mmol) of silver nitrate were added to a solution of 10.14 g (25.0 mmol) N-(2-isopropyl-6-chloromethylphenyl)-2-(9H-xanthen-9-yl)acetamide [prepared as described in step (iv) above] in a mixture of 500 ml of acetone, 100 ml of tetrahydrofuran and 200 ml of water, and the resulting mixture was stirred for 7 hours at 60° C. At the end of this time, the reaction mixture was concentrated by evaporation under reduced pressure, and the concentrate was diluted with ethyl acetate. The diluted mixture was washed with water and with a saturated aqueous solution of sodium chloride, in that order. The organic phase was then dried over anhydrous sodium sulfate, and the solvent was removed by distillation under reduced pressure. The resulting residue was purified by column chromatography through silica gel, using a 3:1 by volume mixture of methylene chloride and ethyl acetate as the eluent, to give 6.41 g (yield 66%) of the title compound as crystals.

PREPARATION 29

N-(2-Isopropyl-6-formylphenyl)-2-(9H-xanthen-9-yl)acetamide

Method A

Following a procedure similar to that described in Preparation 19, but using N-(2-isopropyl-6-hydroxymethylphenyl)-2-(9H-xanthen-9-yl)acetamide (prepared as described in Preparation 28) as a starting material, in a relative amount similar to that used in that Example, the title compound was obtained as crystals, melting at 201°–202° C. (after recrystallization from a mixture of methylene chloride, diethyl ether and hexane).

Infrared Absorption Spectrum (KBr) $v_{max}$ cm$^{-1}$: 3263, 2966, 1695, 1647, 1585, 1516, 1481, 1458, 1408, 1396, 1363, 1257.

Method B

300 mg (4.0 mmol) of trimethylamine N-oxide were added, whilst ice-cooling, to a solution of 406 mg (1.0 mmol) of N-(2-isopropyl-6-chloromethylphenyl)-2-(9H-xanthen-9-yl)acetamide [prepared as described in Preparation 28(iv)] in a mixture of 6 ml of dimethyl sulfoxide and 2 ml of methylene chloride. After the addition was complete, the temperature of the mixture was allowed to rise gradually to room temperature, and then the resulting mixture was stirred for 15 hours at room temperature. At the end of this time, the reaction mixture was diluted with ethyl acetate, and the diluted mixture was washed with water and then with a saturated aqueous solution of sodium chloride. The organic phase was dried over anhydrous sodium sulfate, and the solvent was removed by distillation under reduced pressure. The resulting residue was purified by column chromatography through silica gel, using methylene chloride as the eluent, to give 173 mg (yield 45%) of the title compound as crystals.

PREPARATION 30

N-[2-Isopropyl-6-(3-hydroxypropyl)phenyl]-2-(9H-xanthen-9-yl)acetamide

30(i) N-[2-Isopropyl-6-(2-ethoxycarbonylethenyl)phenyl]-2-(9H-xanthen-9-yl)acetamide Following a procedure similar to that described in Preparation 16, but using N-(2-isopropyl-6-formylphenyl)-2-(9H-xanthen-9-yl)acetamide (prepared as described in Preparation 29) as a starting material, in a relative amount similar to that used in that Example, the title ester derivative was obtained as crystals, melting at 217°–218° C. (after recrystallization from a mixture of ethyl acetate and hexane).

Infrared Absorption Spectrum (KBr) $v_{max}$ cm$^{-1}$: 3275, 2969, 1709, 1666, 1638, 1517, 1480, 1460, 1313, 1253, 1178, 761.

30(ii) N-[2-Isopropyl-6-(3-hydroxy-1-propenyl)phenyl]-(9H-xanthen-9-yl)acetamide 68 μl (0.60 mmol) of boron trifluoride etherate were added at −78° C. to a solution of 228 mg (0.5 mmol) of N-[2-isopropyl-6-(2-ethoxycarbonylethenyl)phenyl]-2-(9H-xanthen-9-yl)acetamide [prepared as described in step (i) above] in 6 ml of methylene chloride. The resulting mixture was stirred for 30 minutes, after which 2.0 ml of a 1.0M solution of diisobutylaluminum hydride were added dropwise over a period of 5 minutes. The temperature of the mixture was allowed to rise to room temperature, and then 10 ml of a 10% w/v aqueous solution of tartaric acid were added to the reaction mixture in order to stop the reaction. The reaction mixture was then diluted with methylene chloride. The diluted mixture was washed with a saturated aqueous solution of sodium hydrogencarbonate and then with a saturated aqueous solution of sodium chloride. The organic phase was dried over anhydrous sodium sulfate, and the solvent was removed by distillation under reduced pressure. The resulting residue was triturated with a mixture of diethyl ether and hexane to cause crystallization. The crystals were collected by filtration to give 185 mg (yield 85%) of the title alcohol derivative, melting at 225°–227° C. (after recrystallization from a mixture of acetonitrile and diisopropyl ether).

Infrared Absorption Spectrum (KBr) $v_{max}$ cm$^{-1}$: 3285, 2962, 1653, 1480, 1458, 1256, 756.

30(iii) N-[2-Isopropyl-6-(3-hydroxypropyl)phentil]-2-(9H-xanthen-9-yl) acetamide Following a procedure similar to that described in Example 8, but using N-[2-isopropyl-6-(3-hydroxy-1-propenyl)phenyl]-2-(9H-xanthen-9-yl)acetamide [prepared as described in step (ii) above] as a starting material, in a relative amount similar to that used in that Example, the title compound was obtained as crystals, melting at 218°–219° C. (after recrystallization from a mixture of diethyl ether and hexane).

Infrared Absorption Spectrum (KBr) $v_{max}$ cm$^{-1}$: 3405, 3236, 2963, 1652, 1518, 1482, 1458, 1260, 758.

PREPARATION 31

N-(2-Isopropyl-6-[(3-hydroxypropyl)oxymethyl]phenyl}-2-(9H-xanthen-9-yl)acetamide Following a procedure similar to that described in Preparation 1, but using N-(2-isopropyl-6-hydroxymethylphenyl)-2-(9H-xanthen-9-yl)acetamide (prepared as described in Preparation 28) as a starting material, in a relative amount similar to that used in that Preparation, the title compound was obtained as crystals, melting at 150°–151° C. (after recrystallization from a mixture of diethyl ether and hexane).

Infrared Absorption Spectrum (KBr) $v_{max}$ cm$^{-1}$: 3238, 2960, 2867, 1651, 1527, 1480, 1457, 1260, 754.

PREPARATION 32

N-[2-Isopropyl-6-(2-hydroxyethyl)oxymethylphenyl]-2-(9H-xanthen-9-yl)acetamide Following a procedure similar to that described in Preparation 1(ii), but using N-(2-isopropyl-6-chloromethylphenyl)-2-(9H-xanthen-9-yl)acetamide [prepared as described in Preparation 28(iv)] and ethylene glycol as starting materials, in relative amounts similar to those used in that Preparation, the title compound melting at 153°–154° C. (after recrystallization from a mixture of diethyl ether and hexane), was obtained in a 52% yield.

Infrared Absorption Spectrum (KBr) $v_{max}$ cm$^{-1}$: 3384, 3255, 2962, 2869, 1650, 1522, 1478, 1457, 1258, 1116, 752.

PREPARATION 33

N-[2-t-Butyl-5-(4-cyclohexyl-3-formylbutyl)phenyl]-2-(9H-xanthen-9-yl)acetamide 33(i) N-[2-t-Butyl-5-(4-cyclohexyl-3-(methoxyvinylidene)butylphenyl]-2-(9H-xanthen-9-yl)acetamide 1.51 ml (2.42 mmol) of a 1.6M hexane solution of butyllithium were added dropwise over a period of 3 minutes to a suspension of 828 mg (2.42 mmol) of methoxymethyltriphenylphosphonium chloride in 10 ml of tetrahydrofuran, whilst ice-cooling. The resulting mixture was then stirred for 30 minutes at the same temperature, after which 422 mg (0.805 mmol) of N-[2-t-butyl-5-(4-cyclohexyl-3-oxobutyl)phenyl]-2-(9H-xanthen-9-yl)acetamide (prepared as described in Example 13) were added to the mixture. The temperature of the mixture was allowed to rise to room temperature, and then the reaction mixture was stirred for a further 1 hour. In order to stop the reaction, a saturated aqueous solution of ammonium chloride was added to the reaction mixture, after which it was extracted with diethyl ether. The extract was washed twice with water and once with a saturated aqueous solution of sodium chloride. The organic phase was then dried over anhydrous sodium sulfate, and the solvent was removed by distillation under reduced pressure. The resulting residue was purified by column chromatography through 25 g of silica gel, using a gradient elution method, with mixtures of methylene chloride and ethyl acetate ranging from 100:3 to 100:5 by volume as the eluent. The combined eluates were concentrated by evaporation under reduced pressure and the concentrate was recrystallized from a mixture of diethyl ether and hexane to give 278 mg (yield 62%) of the title vinyl ether derivative as crystals melting at 117°–118° C.

Infrared Absorption Spectrum (KBr) $v_{max}$ cm$^{-1}$: 2924, 2847, 1670, 1639, 1578, 1541, 1529, 1481, 1458, 1257, 1213.

33(ii) N-[2-t-Butyl-5-(4-cyclohexyl-3-formylbutyl)-phenyl]-2-(9H-xanthen-9-yl) acetamide 2 ml of 2N aqueous hydrochloric acid were added to a solution of 278 mg (0.503 mmol) of N-[2-t-butyl-5-(4-cyclohexyl-3-(methoxyvinylidene)butylphenyl]-2-(9H-xanthen-9-yl)acetamide [prepared as described in step (i) above] in 8 ml of tetrahydrofuran, and the resulting mixture was stirred for 4 hours at 50° C. At the end of this time, the reaction mixture was allowed to cool to room temperature, after which it was diluted with diethyl ether. The diluted mixture was washed with water until it was neutral and then washed with a saturated aqueous solution of sodium chloride. The organic phase was then dried over anhydrous sodium sulfate, and the solvent was removed by distillation under reduced pressure. The resulting residue was purified by column chromatography through 15 g of silica gel, using a gradient elution method, with mixtures of methylene chloride and ethyl acetate in ratios ranging from 100:3 to 100:5 by volume as the eluent. The combined eluates were concentrated by evaporation under reduced pressure, and the concentrate was recrystallized from a mixture of diethyl ether and hexane, to give 227 mg (yield 83%) of the title compound, melting at 121°–122° C.

Infrared Absorption Spectrum (KBr) $v_{max}$ cm$^{-1}$: 2924, 2851, 1726, 1655, 1639, 1576, 1527, 1479, 1458, 1419, 1363, 1298, 1257.

PREPARATION 34

{4-t-Butyl-3-[2-(9H-xanthen-9-yl)acetamido]phenyl}-methyltriphenylphosphonium bromide 34(i)  N-[2-t-Butyl-5-bromomethylphenyl]-2-(9H-xanthen-9)-yl)acetamide 3.19 g (9.63 mmol) of carbon tetrabromide were added to a solution of 2.57 g (6.40 mmol) of N-(2-t-butyl-5-hydroxymethylphenyl)-2-(9H-xanthen-9-yl)acetamide (prepared as described in Preparation 14) and 2.04 g (7.77 mmol) of triphenylphosphine in 20 ml of methylene chloride, and the resulting mixture was stirred for 4 hours at room temperature. At the end of this time, the reaction mixture was placed on a column containing 100 g of silica gel and the column was eluted with a 1:9 by volume mixture of diethyl ether and methylene chloride. The eluates were combined and concentrated by evaporation under reduced pressure, to give 2.52 g (yield 85%) of the title bromide as crystals, melting at 229°–231° C. (after recrystallization from ethyl acetate).

Infrared Absorption Spectrum (KBr) $v_{max}$ cm$^{-1}$: 3216, 1640, 1535, 1487, 1457, 1414, 1366, 1262, 1236, 763.

34(ii)  {4-t-Butyl-3-[2-(9H-xanthen-9-yl)acetamido]-phenyl}methyltriphenylphosphonium bromide A solution of 2.52 g (5.42 mmol) of N-[2-t-butyl-5-bromomethylphenyl]-2-(9H-xanthen-9-yl)acetamide [prepared as described in step (i) above] and 1.58 g (6.02 mmol) of triphenylphosphine in 25 ml of toluene was heated under reflux for 5 hours whilst vigorously stirring. At the end of this time, it was cooled to room temperature, and the resulting precipitate was collected by filtration and pulverized. This precipitate was then washed with toluene and with hexane, in that order, and dried over anhydrous sodium sulfate, to give 3.71 g (yield 90%) of the title compound as a powder.

Infrared Absorption Spectrum (KBr) $v_{max}$ cm$^{-1}$: 3420, 1669, 1482, 1459, 1439, 1256, 1111, 834, 753, 691.

PREPARATION 35

1-Benzyloxy-5-cyclohexyl-2-pentanone

35(i) 4-Cyclohexyl-1-(benzyloxymethyl)butanol

A solution of 1.01 g (6.73 mmol) of 2-benzyloxyacetaldehyde in 6 ml of diethyl ether was added dropwise over a period of 3 minutes to 14 ml (8.6 mmol) of a 0.6M diethyl ether solution of 3-cyclohexylpropylmagnesium bromide, whilst ice-cooling, and the resulting mixture was stirred for 30 minutes at the same temperature and then for 10 minutes at room temperature. In order to stop the reaction, a saturated aqueous solution of ammonium chloride was added to the reaction mixture. The reaction mixture was then diluted with diethyl ether, and the diluted mixture was washed with water and with a saturated aqueous solution of sodium chloride, in that order. The organic phase was dried over anhydrous magnesium sulfate, and the solvent was removed by distillation under reduced pressure. The resulting residue was purified by column chromatography through 150 g of silica gel, using a 1:3 by volume mixture of ethyl acetate and hexane as the eluent, to give 1.27 g (yield 68%) of the title alcohol derivative as an oil.

Infrared Absorption Spectrum (liquid film), $v_{max}$ cm$^{-1}$: 3470, 3031, 1497, 1451, 1364, 1206, 1100, 1028, 735, 699.

35(ii) 1-Benzyloxy-5-cyclohexyl-2-pentanone

Following a procedure similar to that described in Preparation 19, but using 4-cyclohexyl-1-(benzyloxymethyl)butanol [prepared as described in step (i) above] as a starting material, in a relative amount similar to that used in that Preparation, the title compound was obtained as an oil.

Infrared Absorption Spectrum (liquid film), $v_{max}$ cm$^{-1}$: 3032, 1721, 1497, 1451, 1260, 1210, 1102, 1028, 737, 699.

PREPARATION 36

3-Cyclohexyloxy-1-(benzyloxymethyl)propyl alcohol and 4-cyclohexyloxy-2-benzyloxybutyl alcohol

36(i) 3-Cyclohexyloxypropyl alcohol 14.0 ml (14.0 mmol) of a 1M hexane solution of diisobutylaluminum hydride were added dropwise over a period of 5 minutes to a solution of 1.01 g (647 mmol) of 1,5-dioxaspiro[5.5]-undecane in 5 ml of methylene chloride, and the resulting mixture was stirred for 1 hour at room temperature. At the end of this time, the reaction mixture was ice-cooled and 20 ml of methanol were added dropwise over a period of 5 minutes in order to stop the reaction. The mixture was stirred for 20 minutes at room temperature, and then 2N aqueous hydrochloric acid was added to dissolve the precipitate. The mixture was then extracted with diethyl ether. The extract was washed with water, with a saturated aqueous solution of sodium hydrogencarbonate and with a saturated aqueous solution of sodium chloride, in that order. The organic phase was dried over anhydrous magnesium sulfate, and the solvent was removed by distillation under reduced pressure. The resulting residue was purified by column chromatography through 25 g of silica gel, using a 3:1 by volume mixture of diethyl ether and hexane as the eluent, to give 774 mg (yield 76%) of the title alcohol derivative as an oil.

Infrared Absorption Spectrum (liquid film), $v_{max}$ cm$^{-1}$: 3390, 1451, 1366, 1258, 1092, 984, 967, 930, 889.

36(ii) 3-Cyclohexyloxypropanal

Following a procedure similar to that described in Preparation 19, but using 3-cyclohexyloxypropyl alcohol [prepared as described in step (i) above] as a starting material, in a relative amount similar to that used in that Example, the title aldehyde derivative was obtained as an oil.

Infrared Absorption Spectrum (liquid film), $v_{max}$ cm$^{-1}$: 2728, 1727, 1451, 1364, 1258, 1212, 1100, 1025, 984, 889.

36(iii) 4-Cyclohexyloxy-1-butene 3.3 ml of a 1.6M hexane solution of butyllithium were added dropwise over a period of 4 minutes to a suspension of 1.88 g (5.26 mmol) of methyltripherlylphosphonium bromide in 19 ml of tetrahydrofuran at −20° C. The reaction mixture was allowed to stand for 25 minutes, after which a solution of 747 mg (4.75 mmol) of 3-cyclohexyloxypropanal [prepared as described in step (ii) above] in 5 ml of tetrahydrofuran was added dropwise over a period of 3 minutes. The reaction mixture was then stirred for 30 minutes at the same temperature and then for 30 minutes at room temperature. In order to stop the reaction, a saturated aqueous solution of ammonium chloride was added to the reaction mixture, which was then extracted with diethyl ether. The extract was washed with water and with a saturated aqueous solution of sodium chloride, in that order. The organic phase was dried over anhydrous magnesium sulfate, and then the solvent was removed by distillation under reduced pressure. The resulting residue was purified by column chromatography through 25 g of silica gel, using a 1:1 by volume mixture of methylene chloride and hexane as the eluent, to give 462 mg (yield 63%) of the title olefin derivative as an oil.

Infrared Absorption Spectrum (liquid film), $v_{max}$ cm$^{-1}$: 3079, 1642, 1451, 1364, 1258, 1107, 992, 957, 913.

36(iv) 4-Cyclohexyloxy-2-hydroxybutyl alcohol 1.9 ml (0.15 mmol) of a 2% w/v aqueous solution of osmium tetraoxide were added to a solution of 462 mg (3.00 mmol) of 4-Cyclohexyloxy-1-butene [prepared as described in step (iii) above] and 702 mg (5.99 mmol) of N-methylmorpholine N-oxide in a mixture of 20 ml of acetonitrile and 5 ml of water, and the resulting mixture was stirred for 12 hours at room temperature. In order to stop the reaction, an aqueous solution of sodium sulfite was added to the reaction mixture, which was then extracted with ethyl acetate. The extract was washed with water, with 2N aqueous hydrochloric acid with a saturated aqueous solution of sodium hydrogen-carbonate and with a saturated aqueous solution of sodium chloride, in that order. The organic phase was dried over anhydrous magnesium sulfate, and the solvent was removed by distillation under reduced pressure. The resulting residue was purified by column chromatography through 15 g of silica gel, using ethyl acetate as the eluent, to give 443 mg (yield 78%) of the title diol derivative as an oil.

Infrared Absorption Spectrum (liquid film), $v_{max}$ cm$^{-1}$: 3990, 1451, 1366, 1258, 1092, 994, 951, 872, 791.

36(v) 2-Phenyl-4-(2-cyclohexylethyl)-1,3-dioxolane 43 mg (0.23 mmol) of p-toluenesulfonic acid monohydrate were added, whilst ice-cooling, to a solution of 473 mg (2.51 mmol) of 4-cyclohexyloxy-2-hydroxybutyl alcohol [prepared as described in step (iv) above] and 1.14 ml (7.56 mmol) of benzaldehyde dimethyl acetal in 10 ml of methylene chloride, and the resulting mixture was stirred for 2.5 hours at room temperature. In order to stop the reaction, a saturated aqueous solution of sodium hydrogencarbonate was added to the reaction mixture, which was then extracted with diethyl ether. The extract was washed with a saturated aqueous solution of sodium chloride. The organic phase was dried over anhydrous magnesium sulfate, and the solvent was removed by distillation under reduced pressure. The resulting residue was purified by column chromatography through 50 g of silica gel, using a 1:9 by volume mixture of diethyl ether and methylene chloride as the eluent, to give 578 mg (yield 83%) of the title 1,3-dioxolane derivative as an oil.

Infrared Absorption Spectrum (liquid film), $v_{max}$ cm$^{-1}$: 1453, 1403, 1366, 1219, 1096, 1026, 914, 758, 699.

36(vi) 3-Cyclohexyloxy-1-(benzyloxymethyl)propyl alcohol and 4-cyclohexyloxy-2-benzyloxybutyl alcohol 4.5 ml (4.5 mmol) of a 1M hexane solution of diisobutyl aluminum hydride were added dropwise over a period of 5 minutes to a solution of 560 mg (2.03 mmol) of 2-phenyl-4-(2-cyclohexylethyl)-1,3-dioxolane [prepared as described in step (v) above] in 5 ml of methylene chloride, and the resulting mixture was stirred for 50 minutes. In order to stop the reaction, 0.8 ml of methanol was added the reaction mixture, and the precipitate which appeared was dissolved by adding 2N aqueous hydrochloric acid, after which it was extracted with diethyl ether. The extract was washed with water, with a saturated aqueous solution of sodium hydrogencarbonate and with a saturated aqueous solution of sodium chloride, in that order. The organic phase was dried over anhydrous magnesium sulfate, and the solvent was removed by distillation under reduced pressure. The resulting residue was purified by column chromatography through 60 g of silica gel, using a 1:4 by volume mixture of ethyl acetate and methylene chloride as the eluent, to give 409 mg (yield 72%) of a less polar secondary alcohol, 3-cyclohexyloxy-1-(benzyloxymethyl)-propyl alcohol, and 133 mg (yield 24%) of a more polar primary alcohol, 4-cyclohexyloxy-2-benzyloxybutyl alcohol, respectively, both as oils.

Infrared Absorption Spectrum (liquid film), $v_{max}$ cm$^{-1}$: 3-Cyclohexyloxy-1-(benzyloxymethyl)propyl alcohol:

3450, 1453, 1364, 1206, 1100, 1026, 737, 699: and 4-cyclohexloxy-2-benzyloxybutyl alcohol: 3440, 1453, 1364, 1208, 1092, 1028, 737, 699.

PREPARATION 37

1-Benzyloxy-4-cyclohexyloxy-2-butanone

Following a procedure similar to that described in Preparation 19, but using 3-cyclohexyloxy-1-(benzyloxymethyl)propyl alcohol (prepared as described in Preparation 36) as a starting material, in a relative amount similar to that used in that Preparation, the title compound was obtained as an oil.

Infrared Absorption Spectrum (liquid film), $v_{max}$ cm$^{-1}$: 3032, 1725, 1453, 1366, 1258, 1209, 1105, 1026, 739, 698.

PREPARATION 38

2-Benzyloxy-4-cyclohexyloxybutanal

Following a procedure similar to that described in Preparation 19, but using 4-cyclohexyloxy-2-benzyloxybutyl alcohol (prepared as described in Preparation 36) as a starting material, in a relative amount similar to that used in that Preparation, the title compound was obtained as an oil.

Infrared Absorption Spectrum (liquid film), $v_{max}$ cm$^{-1}$: 3032, 1734, 1453, 1366, 1209, 1104, 1026, 951, 739, 699.

PREPARATION 39

N-{2-t-Butyl-5-[2-(oxiran-2-yl)ethyl]phenyl}-2-(9H-xanthen-9-yl)acetamide

A suspension of 690 mg (15.8 mmol) of sodium hydride (as a 55% w/w dispersion in mineral oil, which had previously been washed with hexane) in 10 ml of dimethyl sulfoxide was stirred for 30 minutes, after which 2.66 g (12.1 mmol) of trimethylsulfoxonium iodide were added. The resulting mixture was stirred for 1 hour at 40° C., and then a solution of 4.50 g (10.5 mmol) of N-[2-t-butyl-5-(3-oxopropyl)phenyl]-2-(9H-xanthen-9-yl)acetamide (prepared as described in Preparation 19) in 25 ml of tetrahydrofuran was added dropwise over a period of 5 minutes. The reaction mixture was then stirred for 1 hour, after which the reaction mixture was cooled to room temperature and then diluted with ethyl acetate. The diluted mixture was washed several times with water and once with a saturated aqueous solution of sodium chloride. The organic phase was dried over anhydrous magnesium sulfate, and the solvent was removed by distillation under reduced pressure. The resulting residue was purified by column chromatography through 250 g of silica gel, using a 9:1 by volume mixture of methylene chloride and ethyl acetate as the eluent, to give 3.00 g (yield 65%) of the title compound as crystals, melting at 156°–157° C. (after recrystallization from a mixture of ethyl acetate and hexane).

Infrared Absorption Spectrum (KBr) $v_{max}$ cm$^{-1}$: 3266, 2965, 1655, 1611, 1576, 1481, 1458, 1404, 1302, 1254, 829, 756.

PREPARATION 40

N-(2-t-Butyl-5-{4-cyclohexyl-3-[2-(benzyloxycarbonylmethylthio)acetoxy]butyl}phenyl)-2-(9H-xanthen-9-yl)acetamide Following a procedure similar to that described in Preparation 25, but using N-[2-t-butyl-5-(4-cyclohexyl-3-hydroxybutyl)phenyl]-2-(9H-xanthen-9-yl)acetamide (prepared as described in Example 12) and 2-(benzyloxycarbonylmethylthio)acetic acid as starting materials, in relative proportions similar to those used in that Preparation, the title compound was obtained as a foam-like material.

Infrared Absorption Spectrum (KBr) $v_{max}$ cm$^{-1}$: 3275, 2923, 1733, 1660, 1481, 1457, 1256, 1153, 1119, 760.

PREPARATION 41

N(2-t-Butyl-5-{4-cyclohexyl-3-[2-(benzyloxycarbonylmethylsulfonyl)acetoxy]butyl}phenyl)-2-(9H-xanthen-9-yl)acetamide and

N-(2-t-butyl-5-{4-cyclohexyl-3-[2-(benzyloxycarbonylmethylsulfinyl)acetoxy]butyl}phenyl)-2-(9H-xanthen-9-yl)acetamide Following a procedure similar to that described in Example 194, but using N-(2-t-butyl-5-{4-cyclohexyl-3-[2-(benzyloxycarbonylmethylthio)acetoxy]butyl}phenyl)-2-(9H-xanthen-9-yl)acetamide (prepared as described in Preparation 40) as a starting material, in a relative amount similar to that used in that Example, the title compounds were obtained, both as foam-like materials.

Infrared Absorption Spectrum (KBr), $v_{max}$ cm$^{-1}$:

N-(2-t-Butyl-5-{4-cyclohexyl-3-[2-(benzyloxycarbonylmethylsulfonyl)acetoxy]butyl}phenyl)-2-(9H-xanthen-9-yl)acetamide: 3274, 2924, 1738, 1660, 1481, 1458, 1340, 1294, 1256, 1117, 760; and N-(2-t-butyl-5-{4-cyclohexyl-3-[2-(benzyloxycarbonylmethylsulfinyl)acetoxy]butyl}phenyl)-2-(9H-xanthen-9-yl)acetamide: 3271, 2923, 1732, 1660, 1481, 1457, 1257, 1118, 1058, 759.

PREPARATION 42

N-{2-t-Butyl-5-[3-(benzyloxycarbonylmethoxycarbonyloxy)-4-cyclohexylbutyl]phenyl}-2-(9H-xanthen-9-yl) acetamide A solution of 55 μl (0.46 mmol) of trichloromethyl chloroformate in 1 ml of tetrahydrofuran was added dropwise to a solution of 74 μl (0.91 mmol) of pyridine in 1 ml of tetrahydrofuran, whilst ice-cooling, and then the temperature of the resulting mixture was allowed to rise gradually to room temperature. The mixture was stirred for 1 hour at room temperature, after which it was again cooled, and a solution of 400 mg (0.76 mmol) of N-[2-t-butyl-5-(4-cyclohexyl-3-hydroxybutyl)phenyl]-2-(9H-xanthen-9-yl)acetamide (prepared as described in Example 12) in 3 ml of tetrahydrofuran was added dropwise. The mixture was stirred for 1 hour at the same temperature, and then the solvent was removed by distillation under reduced pressure, to give a colorless foam-like material as a residue. This residue was dissolved in 1 ml of methylene chloride, and a solution of 151 mg (0.91 mmol) of benzyl α-hydroxyacetate in 1.5 ml of methylene chloride and then 110 mg (0.91 mmol) of 4-(N,N-dimethylamino)pyridine were added dropwise, whilst ice-cooling. The mixture was stirred at room temperature for 1 hour, and then the reaction mixture was diluted with methylene chloride, after which it was washed with water and with a saturated aqueous solution of sodium chloride, in that order. The organic phase was dried over anhydrous sodium sulfate, and the solvent was removed by distillation under reduced pressure. The resulting residue was purified by column chromatography through 75 g of silica gel, using a 1:9 by volume mixture of methylene chloride and ethyl acetate as the eluent, to give 522 mg (yield 96%) of the title compound as a colorless foam-like material.

Infrared Absorption Spectrum (KBr) $v_{max}$ cm$^{-1}$: 3274, 2924, 2853, 1750, 1655, 1480, 1458, 1422, 1256, 1194, 758.

PREPARATION 43

(S)-N-{2-t-Butyl-5-[7-cyclohexyl-3-(methoxymethoxy)heptyl]phenyl}-2-(9H-xanthen-9-yl) acetamide 43(i) (S)-[6-Benzyloxy-5-(methoxymethoxy)hexyl]cyclohexane 25.6 ml (184 mmol) of triethylamine and 9.3 ml (122 mmol) of methoxymethyl chloride were added to a solution of 10 g (34.4 mmol) of (S)-(1-benzyloxymethyl-5-cyclohexyl)pentyl alcohol [prepared in a similar manner to that described in Preparation 23(i), but using cyclohexylpropylmagnesium bromide] in 200 ml of N,N-dimethylformamide, and the resulting mixture was stirred at 80° C. for 5.5 hours. At the end of this time, the reaction mixture was concentrated by evaporation under reduced pressure, and the concentrate was mixed with ice-water, after which it was extracted three times with ethyl acetate. The combined extracts were washed with a saturated aqueous solution of sodium chloride. The organic phase was dried over anhydrous sodium sulfate, and the solvent was removed by distillation under reduced pressure. The resulting residue was purified by column chromatography through silica gel, using a 9:1 by volume mixture of hexane and ethyl acetate as the eluent, to give 10.2 g (yield 89%) of the title methoxymethyl derivative as an oil.

Nuclear Magnetic Resonance Spectrum (CDCl$_3$, 270 MHz), δ ppm:

0.73–1.80 (19H, multiplet);
3.39 (3H, singlet);
3.51 (2H, doublet, J=5 Hz);
3.69–3.85 (1H, multiplet);
4.56 (2H, singlet);
4.68 (1H, doublet, J=7 Hz);
4.79 (1H, doublet, J=7 Hz);
7.23–7.42 (5H, multiplet).

43(ii) (S)-6-Cyclohexyl-2-(methoxymethloxy)hexyl alcohol

Following a procedure similar to that described in Preparation 23(iii), but using (S)-[6-benzyloxy-5-(methoxymethoxy)hexyl]cyclohexane [prepared as described in step (i) above] as a starting material, in a relative amount similar to that used in that Preparation, the title compound was obtained as an oil.

Nuclear Magnetic Resonance Spectrum (CDCl$_3$, 270 MHz), δ ppm:

0.75–1.8 (19H, multiplet);
2.9–3.2 (1H, broad singlet);
3.43 (3H, singlet);
3.45–3.65 (3H, multiplet);
4.68 (1H, doublet, J=7 Hz);
4.74 (1H, doublet, J=7 Hz).

43(iii) (S)-2-t-Butyl-5-(3-methoxymethyloxy-7-cyclohexyl-1-heptenyl)-1-nitrobenzene (S)-6-Cyclohexyl-2-(methoxymethyloxy)hexyl alcohol [prepared as described in step (ii) above] was oxidized by a procedure similar to that described in Preparation 23(iv), to give an aldehyde derivative. This was subjected to the Witrig reaction by a procedure similar to that described in Preparation 23(v), to give the title olefin derivative as an oil.

43(iv) (S)-2-t-Butyl-5-(3-methoxymethyloxy-7-cyclohexylheptyl)aniline

A solution of 2.2 g (5.27 mmol) of (S)-2-t-butyl-5-(3-methoxymethyloxy-7-cyclohexyl-1-heptenyl)-1-nitrobenzene [prepared as described in step (iii) above] in 40 ml of ethanol was vigorously stirred in a stream of hydrogen for 6 hours in the presence of 1.5 g of 10% w/w palladium-on-charcoal. The catalyst was then filtered off and washed with ethanol. The filtrate and the washings were combined, and the solvent was removed by distillation under reduced pressure. The resulting residue was purified by column chromatography through silica gel, using a 9:1 by volume mixture of hexane and ethyl acetate as the eluent, to give 1.16 g (yield 57%) of the title aniline derivative as an oil.

Nuclear Magnetic Resonance Spectrum (CDCl$_3$, 270 MHz), δ ppm:

0.75–1.9 (21H, multiplet);
1.40 (9H, singlet);
2.43–2.70 (2H, multiplet);
3.41 (3H, singlet);
3.59 (1H, quintet, J=6 Hz);
4.68 (2H, singlet);
6.51 (1H, singlet);
6.58 (1H, doublet, J=8 Hz);
7.13 (1H, doublet, J=8 Hz).

43(v) (S)-N-{2-t-Butyl-5-[7-cyclohexyl-3-(methoxymethoxy)heptyl]phenyl}-2-(9H-xanthen-9-yl)acetamide Following a procedure similar to that described in Example 35, but using (S)-2-t-butyl-5-(3-methoxymethyloxy-7-cyclohexylheptyl)aniline [prepared as described in step (iv) above] as a starting material, in a relative amount similar to that used in that Example, the title compound was obtained as crystals, melting at 71°–73° C. (after recrystallization from from hexane).

Infrared Absorption Spectrum (KBr) $v_{max}$ cm$^{-1}$: 3221, 1639, 1577, 1535, 1482, 1456, 1263, 1255, 1034.

Nuclear Magnetic Resonance Spectrum (CDCl$_3$, 270 MHz), δ ppm:

0.75–1.90 (21H, multiplet);
2.25–3.80 (4H, multiplet);
3.42 (3H, singlet);
3.45–3.70 (1H, multiplet);
4.60–4.82 (3H, multiplet);
6.90–7.46 (11H, multiplet).

PREPARATION 44

N-{2-t-Butyl-5-[3-(4-benzyloxycarbonylmethylbenzoyloxy)-4-cyclohexylbutyl]phenyl}-2-(9H-xanthen-9-yl)acetamide 44(i) 4-Hydroxymethylphenylacetic acid A solution of 9.00 g (39.3 mmol) of p-bromomethylphenylacetic acid, 3.14 g (78.6 mmol) of sodium hydroxide and 3.54 g (43.2 mmol) of sodium acetate in 40 ml of water was stirred for 4 hours at 100° C. At the end of this time, it was cooled to room temperature and then acidified with 2N aqueous hydrochloric acid. It was then extracted with ethyl acetate. The extract was washed with a saturated aqueous solution of sodium chloride. The organic phase was dried over anhydrous sodium sulfate, and the solvent was removed by distillation under reduced pressure. The resulting residue was recrystallized from a mixture of ethyl acetate and methylene chloride to give 3.60 g (yield 55%) of the title compound, melting at 136°–137° C.

Infrared Absorption Spectrum (KBr) $v_{max}$ cm$^{-1}$: 3304, 1703, 1520, 1421, 1408, 1360, 1288, 1234, 1200, 1188, 1009.

44(ii) Benzyl 4-hydroxymethylphenylacetate 2.52 g (23.8 mmol) of sodium carbonate and 8.13 g (47.6 mmol) of benzyl bromide were added to a solution of 3.95 g (23.8 mmol) of 4-Hydroxymethylphenylacetic acid [prepared as described in step (i) above] in 40 ml of N,N-dimethylformamide, and the resulting mixture was stirred for 3.5 hours. At the end of this time, the reaction mixture was diluted with diethyl ether, and the diluted mixture was washed with water and then with a saturated aqueous solution of sodium chloride. The organic phase was dried over anhydrous sodium sulfate, and the solvent was distilled off. The resulting residue was purified by column chromatography through 200 g of silica gel, using a gradient elution method, with mixtures of methylene chloride and ethyl acetate in ratios ranging from 100:5 to 100:10 by volume as the eluent, to give 5.03 g (yield 82%) of the title compound as an oil.

Infrared Absorption Spectrum (liquid film), $v_{max}$ cm$^{-1}$: 2941, 2876, 1734, 1516, 1499, 1456, 1423, 1377, 1336, 1259, 1221, 1149.

44(iii) Benzyl 4-formylphenylacetate

Following a procedure similar to that described in Preparation 19, but using benzyl 4-hydroxymethylphenylacetate [prepared as described in step (ii) above] as a starting material, in a relative amount similar to that used in that Example, the title compound was obtained as crystals, melting at 54°–55° C. (after recrystallization from a mixture of diethyl ether and hexane).

Infrared Absorption Spectrum (KBr) $v_{max}$ cm$^{-1}$: 1726, 1689, 1607, 1578, 1458, 1425, 1383, 1338, 1225, 1192, 1169.

44(iv) Benzyl 4-carboxyphenylacetate

Following a procedure similar to that described in Preparation 21(vi), but using benzyl 4-formylphenylacetate [prepared as described in step (iii) above] as a starting material, in a relative amount similar to that used in that Preparation, the title compound was obtained as crystals, melting at 123°–124° C. (after recrystallization from a mixture of methylene chloride and ethyl acetate).

Infrared Absorption Spectrum (KBr) $v_{max}$ cm$^{-1}$: 1718, 1703, 1685, 1610, 1450, 1429, 1323, 1292, 1271, 1182, 1151.

44(v) N-[2-t-Butyl-5-[3-(4-benzyloxycarbonylmethylbenzoyloxy)-4-cyclohexylbutyl]phenyl}-2-(9H-xanthen-9-yl)acetamide Following a procedure similar to that described in Preparation 25, but using benzyl 4-carboxyphenylacetate [prepared as described in step (iv) above] and N-[2-t-butyl-5-(4-cyclohexyl-3-hydroxybutyl)phenyl]-2-(9H-xanthen-9-yl)acetamide (prepared as described in Example 12) as starting materials, in relative proportions similar to those used in that Preparation, the title compound was obtained as a foam-like material.

Infrared Absorption Spectrum (KBr) $v_{max}$ cm$^{-1}$: 2924, 2851, 1736, 1715, 1686, 1655, 1612, 1578, 1522, 1479, 1458, 1273, 1257.

PREPARATION 45

2-Methyl-6-{[3-(1-imidazolyl)propyl]oxymethyl}-aniline

45(i) 2-Methyl-6-mesyloxymethyl-1-nitrobenzene

Following a procedure similar to that described in Preparation 1(i), but using 2-methyl-6-hydroxymethyl-1-nitrobenzene as a starting material, in a relative amount similar to that used in that Preparation, the title methanesulfonyl derivative was obtained as crystals, melting at 48°–50° C.

45(ii) 2-Methyl-6-[(3-hydroxypropyl)oxymethyl]-1-nitrobenzene

Following a procedure similar to that described in Preparation 1(ii), but using 2-methyl-6-mesyloxymethyl-1-nitrobenzene [prepared as described in step (i) above] as a starting material, in a relative amount similar to that used in that Example, the title alcohol derivative was obtained as an oil.

Nuclear Magnetic Resonance Spectrum (CDCl$_3$, 270 MHz), δ ppm:

1.84 (2H, quintet, J=6 Hz);

2.35 (3H, singlet);

3.62 (2H, triplet, J=6 Hz);

3.75 (2H, broad singlet);

4.56 (2H, singlet);

7.2–7.43 (3H, multiplet).

45(iii) 2-Methyl-6-[(3-mesyloxypropyl)oxymethyl]-1-nitrobenzene

Following a procedure similar to that described in Example 1(i), but using 2-methyl-6-[(3-hydroxypropyl)oxymethyl]-1-nitrobenzene [prepared as described in step (ii) above] as a starting material, in a relative amount similar to that used in that Example, the title methanesulfonyl derivative was obtained as an oil.

Nuclear Magnetic Resonance Spectrum (CDCl$_3$, 270 MHz), δ ppm:

2.01 (2H, quintet, J=6 Hz);

2.35 (3H, singlet);

3.03 (3H, singlet);

3.56 (2H, triplet, J=6 Hz);

4.32 (2H, triplet, J=6 Hz);

4.56 (2H, singlet);

7.20–7.42 (3H, multiplet).

45(iv) 2-Methyl-6-{[3-(1-imidazolyl)propyl]oxymethyl}-1-nitrobenzene

Following a procedure similar to that described in Example 1(ii), but using 2-methyl-6-[(3-mesyloxypropyl)oxymethyl]-1-nitrobenzene [prepared as described in step (iii) above] as a starting material, in a relative amount similar to that used in that Example, the title imidazolyl derivative was obtained as an oil.

Nuclear Magnetic Resonance Spectrum (CDCl$_3$, 270 MHz), δ ppm:

1.99 (2H, quintet, J=6 Hz);

2.37 (3H, singlet);

3.38 (2H, triplet, J=6 Hz);
4.04 (2H, triplet, J=6 Hz);
4.54 (2H, singlet);
6.91 (1H, singlet);
7.05 (1H, singlet);
7.2–7.42 (3H, multiplet);
7.48 (1H, singlet).

45(v) 2-Methyl-6-{[3-(1-imidazolyl)propyl]oxymethyl}aniline

Following a procedure similar to that described in Preparation 43(iv), but using 2-methyl-6-{[3-(1-imidazolyl)propyl]oxymethyl}-1-nitrobenzene [prepared as described in step (iv) above] as a starting material, in a relative amount similar to that used in that Preparation, the title aniline derivative was obtained as an oil.

Nuclear Magnetic Resonance Spectrum (CDCl$_3$, 270 MHz), δ ppm:

2.01 (2H, quintet, J=6 Hz);
2.19 (3H, singlet);
3.38 (2H, triplet, J=6 Hz);
4.04 (2H, triplet, J=6 Hz);
4.11 (2H, broad singlet);
4.52 (2H, singlet);
6.65 (1H, triplet, J=7 Hz);
6.85 (1H, singlet);
6.93 (1H, doublet, J=7 Hz);
7.04 (1H, singlet);
7.06 (1H, doublet, J=7 Hz);
7.40 (1H, singlet).

PREPARATION 46

N-{2-t-Butyl-5-[4-cyclohexyl-3-(t-butyldimethylsilyloxy)butyl]phenyl}-2,2-dimethyldodecanamide Following a procedure similar to that described in Example 21, but using 2,2-dimethyldodecanoic acid and 2-t-butyl-5-[4-cyclohexyl-3-(t-butyldimethylsilyloxy)butyl]aniline [prepared by a procedure similar to that described in Preparation 11(i)] as starting materials, in relative proportions similar to those used in that Example, the title compound was obtained as a foam-like material.

Nuclear Magnetic Resonance Spectrum (CDCl$_3$, 270 MHz), δ ppm:

0.05 (6H, singlet);
0.83 (9H, singlet);
0.85–0.96 (6H, multiplet);
1.11–1.35 (30H, multiplet);
1.40 (9H, singlet);
1.58–1.78 (6H, multiplet);
2.53–2.67 (2H, multiplet);
3.80 (1H, triplet, J=5 Hz);
6.94 (1H, doublet, J=8 Hz);
7.29 (1H, doublet, J=8 Hz);
7.38 (1H, singlet);
7.56 (1H, singlet).

PREPARATION 47

N-{2-t-Butyl-5-[4-cyclohexyl-3-(t-butyldimethylsilyloxy)butyl]phenyl}-6,11-dihydrobenz-[b.e]oxepine-11-carboxamide Following a procedure similar to that described in Example 21, but using 6,11-dihydrobenz[b.e]oxepine-11-carboxylic acid and 2-t-butyl-5-[4-cyclohexyl-3-(t-butyldimethylsilyloxy)butyl]aniline [prepared by a procedure similar to that described in Preparation 11(i)] as starting materials, in relative proportions similar to those used in that Example, the title compound was obtained as colorless crystals.

Infrared Absorption Spectrum (KBr) ν$_{max}$ cm$^{-1}$: 3276, 2925, 1648, 1520, 1447, 1256, 1075, 835, 774, 759.

PREPARATION 48

N-{2-t-Butyl-5-[4-cyclohexyl-3-(t-butyldimethylsilyloxy)butyl]phenyl}-2-(1-phenylcyclopentyl)acetamide Following a procedure similar to that described in Example 21, but using 2-(1-phenylcyclopentyl)acetic acid [prepared as described in Preparation 21] and 2-t-butyl-5-[4-cyclohexyl-3-(t-butyldimethylsilyloxy)butyl]aniline [prepared by a procedure similar to that described in Preparation 11(i)] as starting materials, in relative proportions similar to those used in that Example, the title compound was obtained as a foam-like material.

Nuclear Magnetic Resonance Spectrum (CDCl$_3$, 270 MHz), δ ppm:

0.06 (6H, singlet);
0.85–0.96 (6H, multiplet);
0.91 (9H, singlet);
1.07 (9H, singlet);
1.18–1.41 (12H, multiplet);
1.57–2.19 (5H, multiplet);
2.55–2.60 (2H, multiplet);
2.70 (1H, singlet);
3.02 (1H, singlet);
3.78 (1H, triplet, J=6 Hz);
6.33 (1H, singlet);
6.88–7.45 (8H, multiplet).

PREPARATION 49

(S)-1-(2-{4-t-butyl-3-[2-(9H-xanthen-9-yl)acetamido]phenyl}ethyl)-2-cyclohexylethyl dibenzyl phosphate 0.86 ml (1.72 mmol) of a 2M tetrahydrofuran solution of t-butylmagnesium chloride was added over a period of 2 minutes to a solution of 420 mg (0.799 mmol) of (S)-N-[2-t-butyl-5-(4-cyclohexyl-3-hydroxybutyl)phenyl]-2-(9H-xanthen-9-yl)acetamide (prepared as described in Example 102) in 5 ml of tetrahydrofuran, and the resulting mixture was sifted for a further 10 minutes. A solution of 556 mg (1.87 mmol) of dibenzyl phosphoryl chloride in 2 ml of tetrahydrofuran was then added, after which the mixture was stirred for 1 hour. In order to stop the reaction, a saturated aqueous solution of ammonium chloride was added to the reaction mixture, which was then diluted with water. The diluted mixture was extracted with ethyl acetate. The extract was washed with a saturated aqueous solution of sodium chloride. The organic phase was dried over anhydrous magnesium sulfate, and the solvent was removed by distillation under reduced pressure. The resulting residue was purified by column chromatography through 50 g of silica gel, using a 1:9 by volume mixture of ethyl acetate and methylene chloride as the eluent, to give 505 mg (yield 80%) of the title compound as a gummy material.

PREPARATION 50

(R)-1-(2-{4-t-Butyl-3-[2-(9H-xanthen-9-yl)acetamido]-phenyl}ethyl]-4-cyclohexylbutyl benzyl succinate 0.09 ml of diethyl azodicarboxylate was added, whilst ice-cooling, to a solution of 260 mg (0.47 mmol) of (S)-N-[2-t-Butyl-5-(6-cyclohexyl-3-hydroxyhexyl)-phenyl]-2-(9H-xanthen-9-yl)acetamide (prepared as described in Example 189), 117 mg (0.56 mmol) of benzyl hydrogen succinate and 148 mg (0.56 mmol) of triphenylphosphine in 5 ml of tetrahydrofuran, and the resulting mixture was stirred for 1 hour at room temperature. At the end of this time, the reaction mixture was mixed with a saturated aqueous solution of sodium hydrogencarbonate, after which it was extracted with ethyl acetate. The extract was washed with a saturated aqueous solution of sodium chloride and then dried over anhydrous sodium sulfate. The solvent was removed by distillation under reduced pressure, and the resulting residue was purified by column chromatography through silica gel using a gradient elution method, with mixtures of ethyl acetate and hexane in ratios ranging from 1:10 to 1:5 by volume as the eluent, to give fractions containing small amounts of impurities. The chromatography was repeated under the same conditions, and there were obtained 258 mg (yield 74%) of the title compounds as a foam-like material.

$[\alpha]_D = +5.05°$ (c=1.11, $CHCl_3$).

PREPARATION 51

2-t-Butyl-5-(iodomethyl)-1-nitrobenzene

51(i) 2-t-Butyl-5-(methanesulfonyloxymethyl)-1-nitrobenzene

Following a procedure similar to that described in Preparation 21(ii), but using 2-t-butyl-3-hydroxymethyl-1-nitrobenzene (prepared as described in Preparation 12) as a starting material, in a relative amount similar to that used in that Preparation, a methanesulfonyl derivative was obtained.

51(ii) 2-t-Butyl-5-(iodomethyl)-1-nitrobenzene 1.65 g (11 mmol) of sodium iodide were added to a solution of 2.00 g (6.96 mmol) of 2-t-butyl-5-(methanesulfonyloxymethyl)-1-nitrobenzene [prepared as described in step (i) above] in 40 ml of acetone, and the mixture was stirred at 50° C. for 20 minutes. At the end of this time, the reaction mixture was cooled to room temperature, and filtered. The precipitate was washed with ethyl acetate, and the combined filtrate and washings were concentrated by evaporation under reduced pressure. The concentrate was dissolved in ethyl acetate, and the resulting solution was washed with water, with an aqueous solution of sodium thiosulfate, and with a saturated aqueous solution of sodium chloride, in that order. The organic phase was dried over anhydrous sodium sulfate, and the solvent was removed by distillation under reduced pressure, to give 2.18 g (yield 98%) of the title compound as crystals, melting at 98°–99° C. (after recrystallization from a mixture of methylene chloride, diethyl ether and hexane).

Infrared Absorption Spectrum (KBr), $v_{max}$ $cm^{-1}$: 1530, 1370, 1250, 1169, 1061, 886, 839, 807, 627.

Nuclear Magnetic Resonance Spectrum ($CDCl_3$, 270 MHz), δ ppm:

1.39 (9H, singlet);
4.39 (2H, singlet);
7.32 (1H, doublet, J=2 Hz);
7.44 (1H, doublet of doublets, J=2 & 8 Hz);
7.48 (1H, doublet, J=8 Hz).

PREPARATION 52

(4-t-Butyl-3-nitrophenyl)methyltriphenylphosphonium iodide

Following a procedure similar to that described in Preparation 34(ii), but using 2-t-butyl-5-(iodomethyl)nitrobenzene (prepared as described in Preparation 51) as a starting material, in a relative amount similar to that used in that Preparation, the title compound was obtained as powder. The product was used in the following step without any further purification.

PREPARATION 53

N-[2-Methoxymethyl-6-formylphenyl]-2-(9H-xanthen-(9-yl)acetamide

53(i) N-[2-Methoxymethyl-6-(hydroxymethyl)phenyl]-2-(9H-xanthen-9-yl)acetamide

Following a procedure similar to that described in Preparation 14, but using 2-methoxymethyl-6-(t-butyldimethylsilyloxymethyl)-1-nitrobenzene as a starting material, in a relative amount similar to that used in that Preparation, the title amide derivative was obtained as crystals, melting at 194°–194.5° C. (after recrystallization from a mixture of methylene chloride and ethyl acetate).

Infrared Absorption Spectrum (KBr), $v_{max}$ $cm^{-1}$: 3256, 1647, 1596, 1577, 1523, 1482, 1457, 1362, 1301, 1263, 1098, 1066, 751.

53(ii) N-[2-Methoxymethyl-6-formylphenyl]-2-(9H-xanthen-9-yl)acetamide

Following a procedure similar to that described in Preparation 19, but using N-[2-methoxymethyl-6-(hydroxymethyl)phenyl]-2-(9H-xanthen-9-yl)acetamide [prepared as described in step (i) above] as a starting material, in a relative amount similar to that used in that Preparation, the title compound was obtained as crystals, melting at 202.5°–203° C. (after recrystallization from a mixture of methylene chloride and acetone).

Infrared Absorption Spectrum (KBr), $v_{max}$ $cm^{-1}$: 3270, 1698, 1645, 1592, 1578, 1518, 1482, 1456, 1264, 1250, 1112, 755.

PREPARATION 54

N-[5-(3-Hydroxypropoxy)-2-methylthiophenyl]-2-(9H-xanthen-9-yl)acetamide

Following a procedure similar to that described in Preparation 14, but using 5-(3-t-butyldimethylsilyloxypropyl)oxy-2-methylthio-1-nitrobenzene as a starting material, in a relative amount similar to that used in that Preparation, the title compound was obtained as crystals, melting at 136°–137° C. (after recrystallization from a mixture of ethyl acetate, diethyl ether and hexane).

Infrared Absorption Spectrum (KBr), $v_{max}$ $cm^{-1}$: 3297, 1657, 1600, 1574, 1530, 1481, 1457, 1299, 1260, 1237, 1189.

Infrared Absorption Spectrum (film), $v_{max}$ $cm^{-1}$: 3255, 1655, 1522, 1480, 1459, 1256, 999, 758, 696.

PREPARATION 55

N-(2-Ethyl-6-{1-[2-(9H-xanthen-9-yl)acetoxy]propyl}-phenyl)-2-(9H-xanthen-9-yl)acetamide Following a procedure similar to that described in Example 21, but using 2.2 equivalents of 2-(9H-xanthen-yl)acetyl chloride and one equivalent of 2-ethyl-6-(1-hydroxypropyl)aniline, the title compound was obtained as a foam-like material.

Infrared Absorption Spectrum (KBr), $v_{max}$ cm$^{-1}$: 2968, 2932, 2876, 1726, 1657, 1601, 1576, 1479, 1458, 1363, 1342, 1255.

FORMULATION 1

Hard Capsule Preparation 100 mg of one of the following active compounds, 150 mg of lactose, 50 mg of cellulose and 6 mg of magnesium stearate were charged into a hard gelatin capsule of the standard separate type, and the capsules were washed and then dried. The active compounds used were those prepared as described in Examples 2, 4, 12, 26, 57 or 59.

FORMULATION 2

Soft Capsule Preparation

A mixture of one of the compounds prepared as described in Example 2, 4, 12, 26, 57 or 59 with soy bean oil was prepared. The mixture was poured into gelatin using a substitution pump to obtain soft capsules each containing 100 mg of the active ingredient. The capsules were washed and then dried. Other capsules were prepared using cotton seed oil or olive oil in place of the soy bean oil. If desired, other digestible oils may also be used.

FORMULATION 3

Tablet Preparation 100 mg of an active compound, 0.2 mg of colloidal silicon dioxide, 5 mg of magnesium stearate, 275 mg of fine crystalline cellulose, 11 mg of starch and 98.8 mg of lactose were mixed and then formed into tablets using conventional means. The active compounds used were those prepared as described in Examples 2, 4, 12, 26, 57 and 59. Coating was conducted, where desired.

We claim:

1. A compound of formula (I):

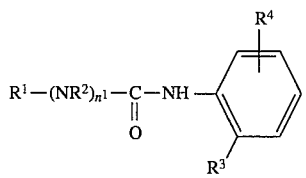

wherein:

$R^1$ represents an alkyl group having from 1 to 20 carbon atoms, or a group of formula (II):

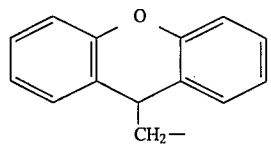

wherein any aromatic ring in said group represented by $R^1$ is unsubstituted or is substituted by one or more substituents selected from the group consisting of substituents α, defined below;

$R^2$ represents a hydrogen atom or an alkyl group having from 1 to 10 carbon atoms;

$R^3$ represents
an alkyl group having from 1 to 10 carbon atoms,
an alkoxy group having from 1 to 10 carbon atoms,
an alkylthio group having from 1 to 10 carbon atoms,
an alkylsulfinyl group having from 1 to 10 carbon atoms,
an alkylsulfonyl group having from 1 to 10 carbon atoms,
a phenylthio group in which the phenyl part is unsubstituted or is substituted by one or more substituents selected from the group consisting of substituents α, defined below;
a phenylsulfinyl group in which the phenyl part is unsubstituted or is substituted by one or more substituents selected from the group consisting of substituents α, defined below;
a phenylsulfonyl group in which the phenyl part is unsubstituted or is substituted by one or more substituents selected from the group substituents α, defined below, or
an alkoxyalkyl group in which the alkoxy part has from 1 to 6 carbon atoms and the alkyl part has from 1 to 4 carbon atoms;

$R^4$ represents a group of formula (VI), (VII), (VIII), (IX), (X) or (XI):

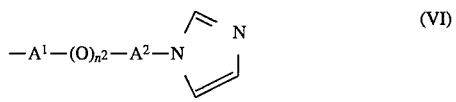

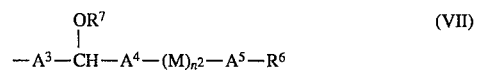

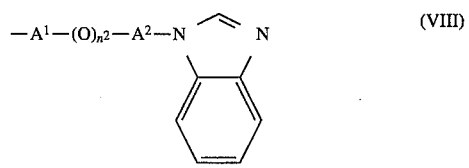

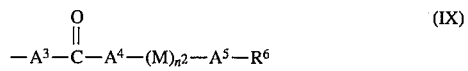

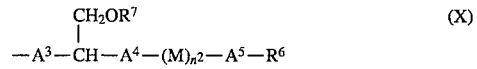

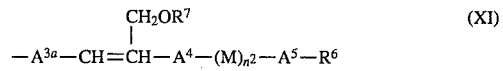

where
$A^1$ represents a single bond or an alkylene group having from 1 to 4 carbon atoms, $A^2$ represents a single bond or an alkylene group having from 1 to 6 carbon atoms, $A^3$, $A^{3a}$, $A^4$ and $A^5$ are independently selected from the group consisting of single bonds and alkylene groups having from 1 to 10 carbon atoms which is saturated or includes a carbon—carbon double bond, provided that the total number of carbon atoms in $A^3$, $A^4$ and $A^5$ and that in $A^{3a}$, $A^4$ and $A^5$ does not exceed 10;

$R^6$ represents an alkyl group having from 1 to 6 carbon atoms, a cycloalkyl group having from 3 to 9 carbon atoms in one or more aliphatic carbocyclic rings, said rings being unsubstituted or being substituted by one or more substituents selected from the group consisting of substituents α, defined below, or an aryl group, as defined below; and in the groups of formulae (VI) and (VIII), the imidazolyl and benzimidazolyl groups are unsubstituted or are substituted by one or more substituents selected from the group consisting of substituents β, defined below;

$R^7$ represents a hydrogen atom, a benzyl group, a phosphono group or a group of formula (XII):

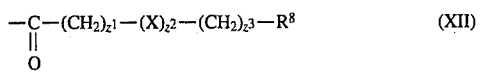

where:
$z^1$ is 0 or 1;
$z^2$ is 0, 1 or 2;
X is an oxygen or sulfur atom or a sulfinyl, sulfonyl or phenylene group, provided that, when $z^2$ is 2, at least one X is a phenylene group;
$z^3$ is 0 or an integer from 1 to 4; and
$R^8$ is a carboxy group, a phenyl group, a group of formula $-NR^9R^{10}$,
where $R^9$ and $R^{10}$ are independently selected from the group consisting of hydrogen atoms and alkyl groups having from 1 to 4 carbon atoms,
or a heterocyclic group having 5 or 6 ring atoms of which 1 or 2 are hetero-atoms selected from the group consisting of oxygen and nitrogen atoms, said heterocyclic group being unsubstituted or being substituted on a carbon atom by an oxygen atom or by an alkyl group having from 1 to 4 carbon atoms; and
said groups of formula $(CH_2)_z1$ and $(CH_2)_z3$ being unsubstituted or being substituted on a carbon atom by an alkyl group having from 1 to 4 carbon atoms or by a group of formula $-NR^9R^{10}$, where $R^9$ and $R^{10}$ are as defined above;

$n^1$ is 0,
$n^2$ is 0 or 1;
M represents an oxygen atom, a sulfur atom, a sulfinyl group or a sulfonyl group;
said substituents α are selected from the group consisting of alkyl groups having from 1 to 4 carbon atoms, alkoxy groups having from 1 to 4 carbon atoms and halogen atoms; and
said substituents β are selected from the group consisting of alkyl groups having from 1 to 4 carbon atoms and phenyl groups which are unsubstituted or are substituted by one or more substituents selected from the group consisting of said substituents α;
said aryl groups are aromatic carbocyclic groups having from 6 to 10 ring carbon atoms and are unsubstituted or are substituted by one or more substituents selected from the group consisting of said substituents α; defined above;

PROVIDED THAT, where $R^4$ represents said group of formula (VII), (IX), (X) or (XI), $R^1$ does not represent said alkyl group and that, where $n^2$ is 1, $A^4$ does not represent a single bond, and that, where $n^1$ is 0, $R^3$ is ethyl and $R^4$ is 2-acetyl, $R^1$ does not represent a methyl group;

or a pharmaceutically acceptable salt thereof.

2. A compound of formula (I) or salts thereof, as defined in claim 1, in which $R^1$ represents a group of formula (II), wherein the aromatic rings are unsubstituted and $R^3$ represents an alkyl group having from 1 to 10 carbon atoms, an alkylthio group having from 1 to 10 carbon atoms or an alkoxy group having from 1 to 10 carbon atoms.

3. A compound of formula (I) or salts thereof, as defined in claim 1, in which $R^1$ represents a group of formula (II), wherein the aromatic rings are unsubstituted and $R^3$ represents an alkyl group having from 1 to 6 carbon atoms, an alkylthio group having from 1 to 6 carbon atoms or an alkoxy group having from 1 to 6 carbon atoms.

4. A compound of formula (I) or salts thereof, as defined in claim 1, in which:
$R^1$ represents a group of formula (II) and the aromatic rings are unsubstituted;
$R^3$ represents an alkyl group having from 1 to 6 carbon atoms, an alkylthio group having from 1 to 6 carbon atoms or an alkoxy group having from 1 to 6 carbon atoms; and
$R^4$ represents a group of formula (VI), (VII) or (X), as defined in claim 1, in which M represents an oxygen atom.

5. A compound of formula (I) or salts thereof, as defined in claim 1, in which:
$R^1$ represents a group of formula (II) and the aromatic rings are unsubstituted;
$R^3$ represents an alkyl group having from 1 to 6 carbon atoms, an alkylthio group having from 1 to 6 carbon atoms or an alkoxy group having from 1 to 6 carbon atoms;
$R^4$ represents a group of formula (VI), (VII) or (X), as defined in claim 1, in which M represents an oxygen atom; and
in the case where $n^2$ is 1, $R^4$ represents a group of formula (VI), as defined in claim 1, in which the total number of carbon atoms in $A^1$ and $A^2$ is from 2 to 4.

6. A compound of formula (I) or salts thereof, as defined in claim 1, in which:
$R^1$ represents a group of formula (II), wherein the aromatic rings are unsubstituted;
$R^3$ represents an alkyl group having from 1 to 6 carbon atoms, an alkylthio group having from 1 to 6 carbon atoms or an alkoxy group having from 1 to 6 carbon atoms;
$R^4$ represents a group of formula (VI), (VII) or (X), as defined in claim 1, in which M represents an oxygen atom; and
in the case where $n^2$ is 0, $R^4$ represents a group of formula (VI), as defined in claim 1, in which the total number of carbon atoms in $A^1$ and $A^2$ is from 1 to 3.

7. A compound of formula (I) or salts thereof, as defined in claim 1, in which:
$R^1$ represents a group of formula (II), wherein the aromatic rings are unsubstituted;
$R^3$ represents an alkyl group having from 1 to 6 carbon atoms, an alkylthio group having from 1 to 6 carbon atoms or an alkoxy group having from 1 to 6 carbon atoms; and
$R^4$ represents a group of formula (VII) as defined in claim 1, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

8. A compound of formula (I) or salts thereof, as defined in claim 1, in which:
$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 1, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

9. A compound of formula (I) or salts thereof, defined in claim 1, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII) as defined in claim 1, in which the total number of carbon atoms in $A^3$, $A^4$ and $A^5$ is from 1 to 6, and $R^7$ represents a hydrogen atom or a group of formula (XVI), (XXIV), (XXV) or (XXX):

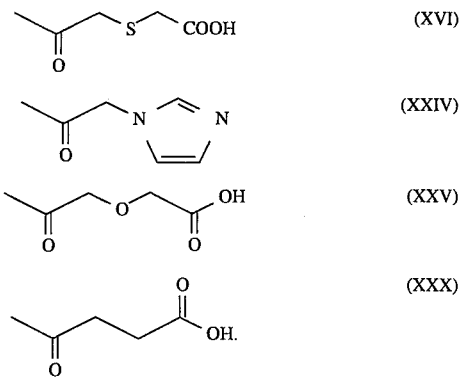

10. A compound of formula (I) or salts thereof, as defined in claim 1, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X) as defined in claim 1, in which the total number of carbon atoms in $A^3$, $A^4$ and $A^5$ is from 1 to 6, and $R^7$ represents a hydrogen atom or a group of formula (XVI), (XXIV), (XXV) or (XXX):

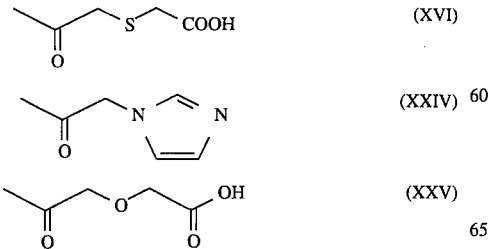

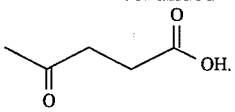

11. A compound of formula (I) or salts thereof, as defined in claim 1, in which:

$R^1$ represents a group of formula (II), wherein, and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII), as defined in claim 1, in which the total number of carbon atoms in $A^3$, $A^4$ and $A^5$ is from 1 to 6, and $R^6$ represents an unsubstituted cyclohexyl group.

12. A compound of formula (I) or salts thereof, as defined in claim 1, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 1, in which the total number of carbon atoms in $A^3$, $A^4$ and $A^5$ is from 1 to 6, and $R^6$ represents an unsubstituted cyclohexyl group.

13. A compound of formula (I) and salts thereof, as defined in claim 1, in which:

$R^1$ represents a (9H-xanthen-9-yl)methyl group;

$n^1$ is 0;

$R^3$ represents a methylthio isopropylthio, isopropyl or t-butyl group;

$R^4$ represents a group of formula (VIa), (VIIa) or

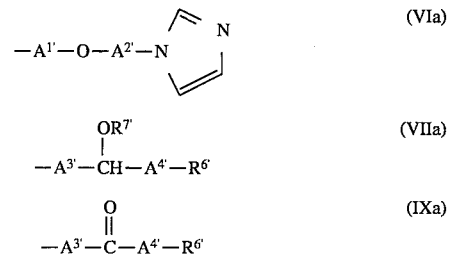

in which $R^{6'}$ represents a cyclopentyl group, a cyclohexyl group, a cycloheptyl group, a phenyl group, a 2-methylphenyl group, a 2-chlorophenyl group or a 4-chlorophenyl group;

$R^{7'}$ represents a 3-carboxypropionyl group, a 2-carboxybenzoyl group or an aminoacetyl group;

$A^{1'}$ represents a methylene group;

$A^{2'}$ represents an alkylene group having from 2 to 4 carbon atoms;

$A^{3'}$ represents a single bond or an alkylene group having from 1 to 3 carbon atoms which is uninterrupted or is interrupted by a double bond;

$A^{4'}$ represents a single bond or an alkylene group having from 1 to 5 carbon atoms which is uninterrupted or is interrupted by a double bond;

the bonding site of $R^4$ on the benzene ring in the compound of formula (I) is the ortho-position with respect to the amino group and the meta-position with respect to $R^3$, or the recta-position with respect to the antino group and the para-position with respect to $R^3$.

14. A compound as defined in claim 1, selected from the group consisting of N-[2-t-butyl-5-(5-cyclohexyl-3-hydroxypentyl)phenyl]-2-(9H-xanthen-9-yl)acetamide and pharmaceutically acceptable salts thereof.

15. A compound as defined in claim 1, selected from the group consisting of N-[2-t-butyl-5-(4-cyclohexyl-3-hydroxybutyl)phenyl]-2-(9H-xanthen-9-yl)acetamide and pharmaceutically acceptable salts thereof.

16. A compound as defined in claim 1, selected from the group consisting of N-[2-t-butyl-5-(6-cyclohexyl-3-hydroxyhexyl)phenyl]-2-(9H-xanthen-9-yl)acetamide and pharmaceutically acceptable salts thereof.

17. A compound as defined in claim 1, selected from the group consisting of N-[2-t-butyl-5-(7-cyclohexyl-3-hydroxyheptyl)phenyl]-2-(9H-xanthen-9-yl)acetamide and pharmaceutically acceptable salts thereof.

18. A compound as defined in claim 1, selected from the group consisting of N-[2-t-butyl-5-(3-cyclohexyl-3-hydroxypropyl)phenyl] -2-(9H-xanthen-9-yl)acetamide and pharmaceutically acceptable salts thereof.

19. A compound as defined in claim 1, selected from the group consisting of N-[2-t-butyl-5-(2-cyclohexyl-1-hydroxyethyl)phenyl]-2-(9H-xanthen-9-yl)acetamide and pharmaceutically acceptable salts thereof.

20. A compound as defined in claim 1, selected from the group consisting of N-[2-t-butyl-5-(6-cyclopentyl-1-hydroxyhexyl)phenyl]-2-(9H-xanthen-9-yl)acetamide and pharmaceutically acceptable salts thereof.

21. A compound as defined in claim 1, which is 1-(2-{4-t-butyl-3-[2-(9H-xanthen-9-yl)acetamido]-phenyl}ethyl)-2-cyclohexylethyl sodium succinate.

22. A compound as defined in claim 1, which is 1-(2-{4-t-butyl-3-[2-(9H-xanthen-9-yl)acetamido]-phenyl}ethyl)-3-cyclohexyl-propyl sodium succinate.

23. A compound as defined in claim 1, selected from the group consisting of sodium 1-(2-{4-t-butyl-3-[2-(9H-xanthen-9-yl )acetamido]phenyl}ethyl)-5-cyclohexylpentyl succinate and pharmaceutically acceptable salts thereof.

24. A compound as defined in claim 1, selected from the group consisting of N-{2-[3-(1-imidazolyl)propoxy]-methyl-6-methylthiophenyl}-2-(9H-xanthen-9-yl)acetamide hydrochloride and pharmaceutically acceptable salts thereof.

25. A compound as defined in claim 1, selected from the group consisting of N-{2-[3-(1-imidazolyl)propoxy]-methyl-6-methylthiophenyl}-2-(9H-xanthen-9-yl)acetamide and pharmaceutically acceptable salts thereof.

26. A compound as defined in claim 1, selected from the group consisting of N-{2-[3-(1-imidazolyl)propoxy]-methyl-6-t-butylphenyl}-2-(9H-xanthen-9-yl)acetamide hydrochloride and pharmaceutically acceptable salts thereof.

27. A compound as defined in claim 1, which is the sodium salt of α-1-(2-{4-t-butyl-3-[2-9H-xanthen-9-yl)acetamido]phenyl}ethyl)-2-cyclohexylethyl carboxymethylthioacetate.

28. A compound as defined in claim 1, selected from the group consisting of N-(2-t-butyl-5-{3-[2-(1-imidazolyl)acetoxy]-4-cyclohexylbutyl}phenyl)-2-(9H-xanthen-9-yl)acetamide hydrochloride and pharmaceutically acceptable salts thereof.

29. A compound as defined in claim 1, which is the sodium salt of N-(2-t-butyl-5-{3-[2-(carboxy-methoxy)acetoxy]-4-cyclo-hexylbutyl}phenyl)-2-(9H-xanthen-9-yl)acetamide.

30. A compound as defined in claim 1, which is the sodium salt of N-(2-t-butyl-5-{7-cyclohexyl-3-[2-(carboxymethoxy)acetoxy]heptyl}phenyl)-2-(9H-xanthen-9-yl)acetamide.

31. A compound as defined in claim 1, selected from the group consisting of N-[2-t-butyl-5-(4-cyclohexyl-2-(hydroxymethyl)butyl]phenyl]-2-(9H-xanthen-9-yl)acetamide and pharmaceutically acceptable salts thereof.

32. A compound as defined in claim 1, selected from the group consisting of N-{2-t-butyl-5-[4-(2-cyclohexylethoxy)-3-hydroxybutyl]phenyl}-2-(9H-xanthen-9-yl)-acetamide and pharmaceutically acceptable salts thereof.

33. A compound as defined in claim 1, selected from the group consisting of N-[2-t-butyl-5-(5-cyclohexyloxy-3-hydroxypentyl)phenyl]-2-(9H-xanthen-9-yl)acetamide and pharmaceutically acceptable salts thereof.

34. A compound as defined in claim 1, selected from the group consisting of N-(2-t-butyl-5-{4-(2-cyclohexylethoxy)-3-[2-(1-imidazolyl)acetoxy]butyl}phenyl)-2-(9H-xanthen-9-yl)acetamide hydrochloride and pharmaceutically accepable salts thereof.

35. A compound as defined in claim 1, which is the sodium salt of N-{2-t-butyl-5-(3-[2-(carboxymethoxy)acetoxy]-5-cyclohexyloxypentyl}phenyl)-2-(9H-xanthen-9-yl)acetamide.

36. A compound as defined in claim 1, selected from the group consisting of N-{2-t-butyl-5-[(2-ethyl-1-imidazolyl)methyl]phenyl}-2-(9H-xanthen-9-yl)acetamide and pharmaceutically acceptable salts thereof.

37. A composition for the treatment and prophylaxis of hypercholesteremia or arteriosclerosis, which comprises an effective amount of a compound of formula (I), as defined in claim 1, or a pharmaceutically acceptable salt thereof, in admixture with a pharmaceutically acceptable carrier or diluent, $n^1$ is 0; and $R^3$ represents an alkyl group having from 1 to 10 carbon atoms, an alkylthio group having from 1 to 10 carbon atoms or an alkoxy group having from 1 to 10 carbon atoms.

38. The composition of claim 37, in which $R^1$ represents a group of formula (II), wherein and the aromatic rings are unsubstituted; and $R^3$ represents an alkyl group having from 1 to 10 carbon atoms, an alkylthio group having from 1 to 10 carbon atoms or an alkoxy group having from 1 to 10 carbon atoms.

39. The composition of claim 37, in which $R^1$ represents a group of formula (II), wherein and the aromatic rings are unsubstituted; and $R^3$ represents an alkyl group having from 1 to 6 carbon atoms, an alkylthio group having from 1 to 6 carbon atoms or an alkoxy group having from 1 to 6 carbon atoms.

40. The composition of claim 37, in which $R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VI), (VII) or (X), as defined in claim 37, in which M represents an oxygen atom.

41. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms;

$R^4$ represents a group of formula (VI), (VII) or (X), as defined in claim 37, in which M represents an oxygen atom; and in the case wherein $n^2$ is 1, $R^4$ represents a group of formula (VI), as defined in claim 37, in which the total number of carbon atoms in $A^1$ and $A^2$ is from 2 to 4.

42. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms;

$R^4$ represents a group of formula (VI), (VII) or (X), as defined in claim 37, in which M represents an oxygen atom; and in the case where $n^2$ is 0, $R^4$ represents a group of formula (VI), as defined in claim 37, in which the total number of carbon atoms in $A^1$ and $A^2$ is from 1 to 3.

43. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII) as defined in claim 37, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

44. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 37, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

45. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII) as defined in claim 37, in which the total number of carbon atoms in $A^3$, $A^4$ and $A^5$ is from 1 to 6, and $R^7$ represents a hydrogen atom or a group of formula (XVI), (XXIV), (XXV) or (XXX):

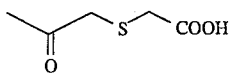

(XVI)

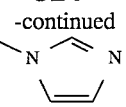

(XXIV)

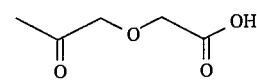

(XXV)

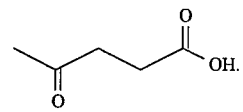

(XXX)

46. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X) as defined in claim 37, in which the total number of carbon atoms in $A^3$, $A^4$ and $A^5$ is from 1 to 6, and $R^7$ represents a hydrogen atom or a group of formula (XVI), (XXIV), (XXV) or (XXX):

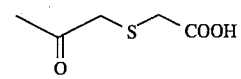

(XVI)

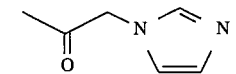

(XXIV)

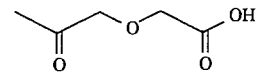

(XXV)

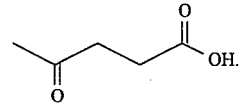

(XXX)

47. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII), as defined in claim 37, in which the total number of carbon atoms in $A^3$, $A^4$ and $A^5$ is from 1 to 6, and $R^6$ represents an unsubstituted cyclohexyl group.

48. The composition of claim 37, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 37, in which the total number of carbon atoms in $A^3$, $A^4$ and $A^5$ is from 1 to 6, and $R^6$ represents an unsubstituted cyclohexyl group.

49. The composition of claim 37, in which:

$R^1$ represents a (9H-xanthen-9-yl)methyl group;

$n^1$ is 0;

$R^3$ represents a methylthio isopropylthio, isopropyl or t-butyl group;

$R^4$ represents a group of formula (VIa), (VIIa) or (IXa):

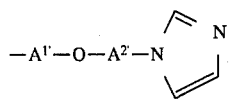
(VIa)

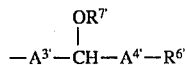
(VIIa)

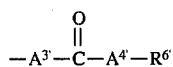
(IXa)

in which
  $R^{6'}$ represents a cyclopentyl group, a cyclohexyl group, a cycloheptyl group, a phenyl group, a 2-methylphenyl group, a 2-chlorophenyl group or a 4-chlorophenyl group;
  $R^{7'}$ represents a 3-carboxypropionyl group, a 2-carboxybenzoyl group or an aminoacetyl group;
  $A^{1'}$ represents a methylene group;
  $A^{2'}$ represents an alkylene group having from 2 to 4 carbon atoms;
  $A^{3'}$ represents a single bond or an alkylene group having from 1 to 3 carbon atoms which is uninterrupted or is interrupted by a double bond;
  $A^{4'}$ represents a single bond or an alkylene group having from 1 to 5 carbon atoms which is uninterrupted or is interrupted by a double bond;
  the bonding site of $R^4$ on the benzene ring in the compound of formula (I) is the ortho-position with respect to the amino group and the meta-position with respect to $R^3$, or the meta-position with respect to the antino group and the para-position with respect to $R^3$.

50. The composition of claim 37, in which the compound of formula (I) is selected from the group consisting of:

N-[2-t'-butyl-5-(5-cyclohexyl-3-hydroxypentyl)-phenyl]-2-(9H-xanthen-9-yl)acetamide;

N-[2-t-butyl-5-(4-cyclohexyl-3-hydroxybutyl)-phenyl]-2-(9H-xanthen-9-yl)acetamide;

N-[2-t-butyl-5-(6-cyclohexyl-3-hydroxyhexyl)-phenyl]-2-(9H-xanthen-9 -yl)acetamide;

N-[2-t-butyl-5-(7-cyclohexyl-3-hydroxyheptyl)-phenyl]-2-(9H-xanthen-9-yl)acetamide;

N-[2-t-butyl-5-(3-cyclohexyl-3-hydroxypropyl)-phenyl]-2-(9H-xanthen-9-yl)acetamide;

N-[2-t-butyl-5-(2-cyclohexyl-1-hydroxyethyl)-phenyl]-2-(9H-xanthen-9-yl)acetamide;

N-[2-t-butyl-5-(6-cyclopentyl-1-hydroxyhexyl)-phenyl]-2-(9H-xanthen-9-yl)acetamide;

1-(2-{4-t-butyl-3-[2-(9H-xanthen-9-yl)-acetamido]phenyl}ethyl)-2-cyclohexylethyl sodium succinate;

1-(2-{4-t-butyl-3-[2-(9H-xanthen-9-yl)-acetamido]phenyl}ethyl)-3-cyclohexylpropyl sodium succinate;

sodium 1-(2-{4-t-butyl-3-[2-(9H-xanthen-9-yl)acetamido]phenyl}ethyl)-5 -cyclohexylpentyl succinate;

N-{2-[3-(1-imidazolyl)propoxy]methyl-6-methylthiophenyl}-2-(9H-xanthen-9-yl)acetamide hydrochloride;

N-{2-[3-(1-imidazolyl)propoxy]methyl-6-methylthiophenyl}-2-(9H-xanthen-9-yl)acetamide;

N-{2-[3-(1-imidazolyl)propoxy]methyl-6-t-butylphenyl}-2-(9H-xanthen-9-yl)acetamide hydrochloride;

sodium salt of α-1-(2-{4-t-butyl-3-[2-9H-xanthen-9-yl)acetamido]phenyl}ethyl)-2-cyclohexylethyl carboxymethylthioacetate;

N-(2-t-butyl-5-{3-[2-(1-imidazolyl)acetoxy]-4-cyclohexylbutyl}phenyl)-2-(9H-xanthen-9-yl)acetamide hydrochloride;

sodium salt of N-(2-t-butyl-5-{3-[2-(carboxymethoxy)acetoxy]-4-cyclohexylbutyl}phenyl)-2-(9H-xanthen-9-yl)acetamide;

sodium salt of N-(2-t-butyl-5-{7-cyclohexyl-3-[2-(carboxymethoxy)acetoxy]heptyl}phenyl)-2-(9H-xanthen-9-yl)acetamide;

N-[2-t-butyl-5-(4-cyclohexyl-2-(hydroxymethyl)-butyl]phenyl]-2-(9H-xanthen-9-yl)acetamide;

N-{2-t-butyl-5-[4-(2-cyclohexylethoxy)-3-hydroxybutyl]phenyl}-2-(9H-xanthen-9-yl)acetamide;

N-[2-t-butyl-5-(5-cyclohexyloxy-3-hydroxypentyl)phenyl]-2-(9H-xanthen-9-yl)acetamide;

N-(2-t-butyl-5-{4-(2-cyclohexylethoxy)-3-[2-(1-imidazolyl)acetoxy]butyl}phenyl)-2-(9H-xanthen-9-yl)acetamide hydrochloride;

sodium salt of N-{2-t-butyl-5-(3-[2-(carboxymethoxy)acetoxy]-5-cyclohexyloxypentyl}phenyl)-2-(9H-xanthen-9-yl) acetamide;

N-{2-t-butyl-5-[(2-ethyl-1-imidazolyl)methyl]-phenyl}-2-(9H-xanthen-9-yl)acetamide;

and pharmaceutically acceptable salts thereof.

51. A method for the treatment and prophylaxis of hypercholesteremia or arteriosclerosis in a mammal, which may be human, which comprises administering to said mammal an effective amount of a compound of formula (I), as defined in claim 1, or a pharmaceutically acceptable salt thereof.

52. The method of claim 51, in which
  $R^1$ represents a group of formula (II), wherein and the aromatic rings are unsubstituted; and
  $R^3$ represents an alkyl group having from 1to 10 carbon atoms, an alkylthio group having from 1to 10 carbon atoms or an alkoxy group having from 1to 10 carbon atoms.

53. The method of claim 51, in which
  $R^1$ represents a group of formula (II), wherein and the aromatic rings are unsubstituted; and
  $R^3$ represents an alkyl group having from 1to 6 carbon atoms, an alkylthio group having from 1 to 6 carbon atoms or an alkoxy group having from 1 to 6 carbon atoms.

54. The method of claim 51, wherein
  $R^1$ represents a group of formula (II), wherein and the aromatic rings are unsubstituted;
  $R^3$ represents an alkyl group having from 1 to 6 carbon atoms, an alkylthio group having from 1 to 6 carbon atoms or an alkoxy group having from 1 to 6 carbon atoms; and
  $R^4$ represents a group of formula (VI), (VII) or (X), as defined in claim 51, in which M represents an oxygen atom.

55. The method of claim 51, in which:
  $R^1$ represents a group of formula (II), wherein and the aromatic rings are unsubstituted;
  $R^3$ represents an alkyl group having from 1 to 6 carbon atoms, an alkylthio group having from 1 to 6 carbon atoms or an alkoxy group having from 1 to 6 carbon atoms;
  $R^4$ represents a group of formula (VI), (VII) or (X), as defined in claim 51, in which M represents an oxygen atom; and
  in the case where $n^2$ is 1, $R^4$ represents a group of formula (VI), as defined in claim 51, in which the total number of carbon atoms in $A^1$ and $A^2$ is from 2 to 4.

56. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms;

$R^4$ represents a group of formula (VI), (VII) or (X), as defined in claim 51, in which M represents an oxygen atom; and in the case where $n^2$ is 0, $R^4$ represents a group of formula (VI) as defined in claim 51, in which the total number of carbon atoms in $A^1$ and $A^2$ is from 1 to 3.

57. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII) as defined in claim 51, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

58. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 51, in which the total number of carbon atoms in $A^3$, $A^4$ and $A^5$ is from 1 to 6, and $R^6$ represents an alkyl group having from 1 to 6 carbon atoms or a cycloalkyl group having from 3 to 7 carbon atoms.

59. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII) as defined in claim 51, in which the total number of carbon atoms in $A^3$, $A^4$ and $A^5$ is from 1 to 6, and $R^7$ represents a hydrogen atom or a group of formula (XVI), (XXIV), (XXV) or (XXX):

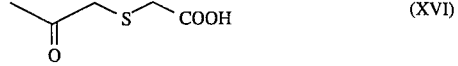 (XVI)

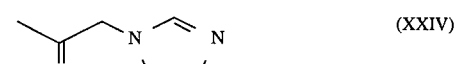 (XXIV)

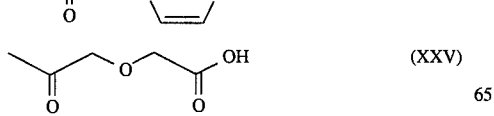 (XXV)

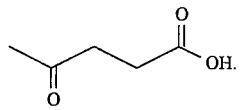 (XXX)

60. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X) as defined in claim 37, in which the total number of carbon atoms in $A^3$, $A^4$ and $A^5$ is from 1 to 6, and $R^7$ represents a hydrogen atom or a group of formula (XVI), (XXIV), (XXV) or (XXX):

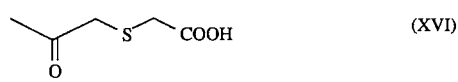 (XVI)

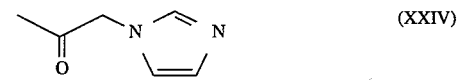 (XXIV)

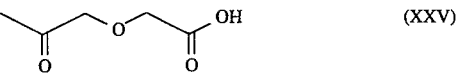 (XXV)

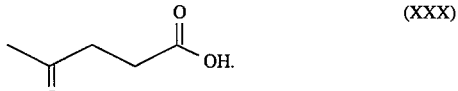 (XXX)

61. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (VII), as defined in claim 51, in which the total number of carbon atoms in $A^3$, $A^4$ and $A^5$ is from 1 to 6 and $R^6$ represents an unsubstituted cyclohexyl group.

62. The method of claim 51, in which:

$R^1$ represents a group of formula (II), wherein and the aromatic rings are unsubstituted;

$R^3$ represents an alkyl group having from 1 to 6 carbon atoms, an alkylthio group having from 1 to 6 carbon atoms or an alkoxy group having from 1 to 6 carbon atoms; and $R^4$ represents a group of formula (X), as defined in claim 51, in which the total number of carbon atoms in $A^3$, $A^4$ and $A^5$ is from 1 to 6, and $R^6$ represents an unsubstituted cyclohexyl group.

63. The method of claim 51, in which $R^1$ represents a (9H-xanthen-9-yl)methyl group;

$R^3$ represents a methylthio isopropylthio, isopropyl or t-butyl group;

$R^4$ represents a group of formula (VIa), (VIIa) or (IXa):

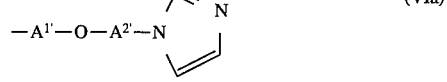 (VIa)

-continued $$-A^{3'}-CH-A^{4'}-R^{6'} \quad \text{(VIIa)}$$
$$\phantom{-A^{3'}-}OR^{7'}$$

$$-A^{3'}-\overset{O}{\underset{\|}{C}}-A^{4'}-R^{6'} \quad \text{(IXa)}$$

in which
R⁶' represents a cyclopentyl group, a cyclohexyl group, a cycloheptyl group, a phenyl group, a 2-methylphenyl group, a 2-chlorophenyl group or a 4-chlorophenyl group;
R⁷' represents a 3-carboxypropionyl group, a 2-carboxybenzoyl group or an aminoacetyl group;
A¹' represents a methylene group;
A²' represents an alkylene group having from 2 to 4 carbon atoms;
A³' represents a single bond or an alkylene group having from 1 to 3 carbon atoms which is uninterrupted or is interrupted by a double bond;
A⁴' represents a single bond or an alkylene group having from 1 to 5 carbon atoms which is uninterrupted or is interrupted by a double bond;
the bonding site of R⁴ on the benzene ring in the compound of formula (I) is the ortho-position with respect to the amino group and the meta-position with respect to R³, or the meta-position with respect to the amino group and the para-position with respect to R³.

64. The method of claim 51, in which the compound of formula (I) is selected from the group consisting of:

N-[2-t-butyl-5-(5-cyclohexyl-3-hydroxypentyl)-phenyl]-2-(9H-xanthen-9-yl)acetamide;

N-[2-t-butyl-5-(4-cyclohexyl-3-hydroxybutyl)-phenyl]-2-(9H-xanthen-9-yl)acetamide;

N-[2-t-butyl-5-(6-cyclohexyl-3-hydroxyhexyl)-phenyl]-2-(9H-xanthen-9-yl)acetamide;

N-[2-t-butyl-5-(7-cyclohexyl-3-hydroxyheptyl)-phenyl]-2-(9H-xanthen-9-yl)acetamide;

N-[2-t-butyl-5-(3-cyclohexyl-3-hydroxypropyl)-phenyl]-2-(9H-xanthen-9-yl)acetamide;

N-[2-t-butyl-5-(2-cyclohexyl-1-hydroxyethyl)-phenyl]-2-(9H-xanthen-9-yl)acetamide;

N-[2-t-butyl-5-(6-cyclopentyl-1-hydroxyhexyl)-phenyl]-2-(9H-xanthen-9-yl) acetamide;

1-(2-{4-t-butyl-3-[2-(9H-xanthen-9-yl)-acetamido]phenyl}ethyl)-2-cyclohexylethyl sodium succinate;

1-(2-{4-t-butyl-3-[2-(9H-xanthen-9-yl)-acetamido]phenyl}ethyl)-3-cyclohexylpropyl sodium succinate;

sodium 1-(2-{4-t-butyl-3-[2-(9H-xanthen-9-yl)acetamido]phenyl}ethyl)-5-cyclohexylpentyl succinate;

N-{2-[3-(1-imidazolyl)propoxy]methyl-6-methylthiophenyl}-2-(9H-xanthen-9-yl)acetamide hydrochloride;

N-{2-[3-(1-imidazolyl)propoxy]methyl-6-methylthiophenyl}-2-(9H-xanthen-9-yl)acetamide;

N-{2-[3-(1-imidazolyl)propoxy]methyl-6-t-butylphenyl}-2-(9H-xanthen-9-yl)acetamide hydrochloride;

sodium salt of α-1-(2-{4-t-butyl-3-[2-9H-xanthen-9-yl)acetamido]phenyl}ethyl)-2-cyclohexylethyl carboxymethylthioacetate;

N-(2-t-butyl-5-{3-[2-(1-imidazolyl)acetoxy]-4-cyclohexylbutyl}phenyl)-2-(9H-xanthen-9-yl) acetamide hydrochloride;

sodium salt of N-(2-t-butyl-5-{3-[2-(carboxymethoxy)acetoxy]-4-cyclohexylbutyl}phenyl)-2-(9H-xanthen-9-yl) acetamide;

sodium salt of N-(2-t-butyl-5-{7-cyclohexyl-3-[2-(carboxymethoxy)acetoxy]heptyl}phenyl)-2-(9H-xanthen-9-yl)acetamide;

N-[2-t-butyl-5-(4-cyclohexyl-2-(hydroxymethyl)-butyl]phenyl]-2-(9H-xanthen-9-yl)acetamide;

N-{2-t-butyl-5-[4-(2-cyclohexylethoxy)-3-hydroxybutyl]phenyl}-2-(9H-xanthen-9-yl)acetamide;

N-[2-t-butyl-5-(5-cyclohexyloxy-3-hydroxypentyl)phenyl]-2-(9H-xanthen-9-yl)acetamide;

N-(2-t-butyl-5-{4-(2-cyclohexylethoxy)-3-[2-(1-imidazolyl)acetoxy]butyl}phenyl)-2-(9H-xanthen-9-yl)acetamide hydrochloride;

sodium salt of N-{2-t-butyl-5-(3-[2-(carboxymethoxy)acetoxy]-5-cyclohexyloxypentyl}phenyl)-2-(9H-xanthen-9-yl)acetamide;

N-{2-t-butyl-5-[(2-ethyl-1-imidazolyl)methyl]-phenyl}-2-(9H-xanthen-9-yl) acetamide;

and pharmaceutically acceptable salts thereof.

65. The composition of claim 49 in which A³' is a methylene group or a ethylene group.

66. The composition of claim 63 in which A³' is a methylene group or a ethylene group.

* * * * *

UNITED STATES PATENT AND TRADEMARK OFFICE
CERTIFICATE OF CORRECTION

PATENT NO. : 5,534,529
DATED : July 9, 1996
INVENTOR(S) : Yoshida et al

It is certified that error appears in the above-identified patent and that said Letters Patent is hereby corrected as shown below:

Column 318, line 66, (Claim 8) after "wherein" delete "and".

Column 319, line 14, (Claim 9) after "wherein" delete "and".

Column 319, line 44, (Claim 10) after "wherein" delete "and".

Column 320, line 8, (Claim 11) after "wherein" delete "and".

Column 320, line 21, (Claim 12) after "wherein" delete "and".

Column 322, lines 34-39, (Claim 37) delete in entirety.

Column 322, line 41, (Claim 38) after "wherein" delete "and".

Column 322, line 48, (Claim 39) after "wherein" delete "and".

UNITED STATES PATENT AND TRADEMARK OFFICE
CERTIFICATE OF CORRECTION

PATENT NO.  : 5,534,529
DATED       : July 9, 1996
INVENTOR(S) : Yoshida et al

It is certified that error appears in the above-identified patent and that said Letters Patent is hereby corrected as shown below:

Column 322, line 55, (Claim 40) after "wherein" delete "and".

Column 322, line 66, (Claim 41) after "wherein" delete "and".

Column 323, line 13, (Claim 42) after "wherein" delete "and".

Column 323, line 26, (Claim 43) after "wherein" delete "and".

Column 323, line 39, (Claim 44) after "wherein" delete "and".

Column 323, line 52, (Claim 45) after "wherein" delete "and".

Column 324, line 14, (Claim 46) after "wherein" delete "and".

Column 326, line 31, (Claim 52) after "wherein" delete "and".

UNITED STATES PATENT AND TRADEMARK OFFICE
CERTIFICATE OF CORRECTION

PATENT NO. : 5,534,529
DATED : July 9, 1996
INVENTOR(S) : Yoshida et al

Page 3 of 4

It is certified that error appears in the above-identified patent and that said Letters Patent is hereby corrected as shown below:

Column 326, line 38, (Claim 53) after "wherein" delete "and".

Column 326, line 46, (Claim 54) after "wherein" delete "and".

Column 326, line 56, (Claim 55) after "wherein" delete "and".

Column 327, line 2, (Claim 56) after "wherein" delete "and".

Column 327, line 17, (Claim 57) after "wherein" delete "and".

Column 327, line 31, (Claim 58) after "wherein" delete "and".

Column 327, line 44, (Claim 59) after "wherein" delete "and".

Column 328, line 8, (Claim 60) after "wherein" delete "and".

Column 328, line 35, (Claim 61) after "wherein" delete "and".

UNITED STATES PATENT AND TRADEMARK OFFICE
CERTIFICATE OF CORRECTION

PATENT NO. : 5,534,529
DATED : July 9, 1996
INVENTOR(S) : Yoshida, et. al.

It is certified that error appears in the above-indentified patent and that said Letters Patent is hereby corrected as shown below:

Column 328, line 47, (Claim 62) after "wherein" delete "and".

Signed and Sealed this

Twenty-eighth Day of July, 1998

*Attest:*

BRUCE LEHMAN

*Attesting Officer*  *Commissioner of Patents and Trademarks*